United States Patent
Ravina et al.

(10) Patent No.: US 12,319,929 B2
(45) Date of Patent: *Jun. 3, 2025

(54) COMPOSITIONS AND METHODS FOR THE TREATMENT OF PARKINSON'S DISEASE

(71) Applicant: VOYAGER THERAPEUTICS, INC., Cambridge, MA (US)

(72) Inventors: Bernard Ravina, Newton, MA (US); Adrian Philip Kells, Upper Arlington, OH (US)

(73) Assignee: Voyager Therapeutics, Inc., Cambridge, MA (US)

( * ) Notice: Subject to any disclaimer, the term of this patent is extended or adjusted under 35 U.S.C. 154(b) by 1147 days.

This patent is subject to a terminal disclaimer.

(21) Appl. No.: 17/055,378

(22) PCT Filed: May 15, 2019

(86) PCT No.: PCT/US2019/032384
§ 371 (c)(1),
(2) Date: Nov. 13, 2020

(87) PCT Pub. No.: WO2019/222328
PCT Pub. Date: Nov. 21, 2019

(65) Prior Publication Data
US 2021/0198691 A1  Jul. 1, 2021

Related U.S. Application Data

(60) Provisional application No. 62/831,400, filed on Apr. 9, 2019, provisional application No. 62/789,909, filed
(Continued)

(51) Int. Cl.
*C12N 15/86* (2006.01)
*A61K 38/51* (2006.01)

(52) U.S. Cl.
CPC ............ *C12N 15/86* (2013.01); *A61K 38/51* (2013.01); *C12N 2750/14143* (2013.01); *C12Y 401/01028* (2013.01)

(58) Field of Classification Search
CPC .......... C12N 15/86; C12N 2750/14143; C12N 15/62; A61K 38/51; A61K 48/005; C12Y 401/01028; A61P 25/16
See application file for complete search history.

(56) References Cited

U.S. PATENT DOCUMENTS 5,064,764 A   11/1991   Besnainon
5,474,935 A   12/1995   Chatterjee
(Continued)

FOREIGN PATENT DOCUMENTS

EP   1015619 A1   7/2000
EP   1046711 A2   10/2000
(Continued)

OTHER PUBLICATIONS

Ernst et al. 1999. Abstract: High Presynaptic Dopaminergic Activity in Children With Tourette's Disorder. J. Am. Acad. Child Adolescent Psychi. 38[1]:86-94, Abstract only (Year: 1999).*
(Continued)

*Primary Examiner* — Kimberly Chong
*Assistant Examiner* — Ruth Sophia Arieti
(74) *Attorney, Agent, or Firm* — McCarter & English, LLP; Maria Laccotripe Zacharakis; Yu Lu

(57) ABSTRACT

The present disclosure relates to methods, formulations and devices for the delivery and therapeutic administration of polynucleotides encoding AADC. The present disclosure relates to methods, formulations and devices for the delivery and therapeutic administration of AAV vectors which include polynucleotides encoding AADC. The present disclosure relates to methods, formulations and devices for the
(Continued)

delivery and therapeutic administration of polynucleotides encoding AADC in the treatment of neurological diseases, disorders and conditions, including Parkinson's Disease.

19 Claims, 19 Drawing Sheets

Specification includes a Sequence Listing.

Related U.S. Application Data on Jan. 8, 2019, provisional application No. 62/756,897, filed on Nov. 7, 2018, provisional application No. 62/748,119, filed on Oct. 19, 2018, provisional application No. 62/741,021, filed on Oct. 4, 2018, provisional application No. 62/703,137, filed on Jul. 25, 2018, provisional application No. 62/698,419, filed on Jul. 16, 2018, provisional application No. 62/691,748, filed on Jun. 29, 2018, provisional application No. 62/684,384, filed on Jun. 13, 2018, provisional application No. 62/681,891, filed on Jun. 7, 2018, provisional application No. 62/671,944, filed on May 15, 2018.

(56) References Cited

U.S. PATENT DOCUMENTS

| | | | |
|---|---|---|---|
| 5,538,885 A | 7/1996 | Hollis et al. |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | O'Riordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |
| 6,194,191 B1 | 2/2001 | Zhang et al. |
| 6,200,560 B1 | 3/2001 | Couto |
| 6,204,059 B1 | 3/2001 | Samulski |
| 6,211,163 B1 | 4/2001 | Podsakoff |
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,309,634 B1 | 10/2001 | Bankiewicz |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson et al. |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,841,357 B1 | 1/2005 | Vaillancourt et al. |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,943,019 B2 | 9/2005 | Wilson |
| 6,953,575 B2 | 10/2005 | Bankiewicz |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | O'Riordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,169,612 B2 | 1/2007 | Kostenis |
| 7,182,944 B2 | 2/2007 | Bankiewicz |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,259,015 B2 | 8/2007 | Kingsman |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,319,002 B2 | 1/2008 | Wilson |
| 7,326,555 B2 | 2/2008 | Konz |
| 7,344,872 B2 | 3/2008 | Gao |
| 7,419,817 B2 | 9/2008 | Chiorini |
| 7,419,956 B2 | 9/2008 | Ohtaki |
| 7,445,930 B2 | 11/2008 | Zhang |
| 7,479,554 B2 | 1/2009 | Chiorini |
| 7,491,508 B2 | 2/2009 | Roy |
| 7,510,872 B2 | 3/2009 | Clark |
| 7,510,875 B2 | 3/2009 | Zhang |
| 7,534,613 B2 | 5/2009 | Bankiewicz |
| 7,579,181 B2 | 8/2009 | O'Riordan |
| 7,588,757 B2 | 9/2009 | Ozawa |
| 7,588,772 B2 | 9/2009 | Kay et al. |
| 7,625,570 B1 | 12/2009 | Schaffer |
| 7,638,120 B2 | 12/2009 | Liu |
| 7,662,627 B2 | 2/2010 | Johnson |
| 7,704,492 B2 | 4/2010 | Podsakoff |

(56) References Cited

U.S. PATENT DOCUMENTS

| | | |
|---|---|---|
| 7,704,721 B2 | 4/2010 | Wright |
| 7,732,129 B1 | 6/2010 | Zhang |
| 7,790,449 B2 | 9/2010 | Gao |
| 7,803,622 B2 | 9/2010 | Engelhardt |
| 7,838,277 B2 | 11/2010 | Gao |
| 7,888,096 B2 | 2/2011 | Wu |
| 7,901,921 B2 | 3/2011 | Coffey |
| 7,906,111 B2 | 3/2011 | Wilson et al. |
| 7,968,333 B2 | 6/2011 | Yu |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,309,355 B2 | 11/2012 | Bankiewicz |
| 8,318,480 B2 | 11/2012 | Gao |
| 8,318,687 B2 | 11/2012 | Tabira |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Herm |
| 8,524,219 B2 | 9/2013 | Roy |
| 8,524,446 B2 | 9/2013 | Gao |
| 8,603,459 B2 | 12/2013 | Wilson |
| 8,614,101 B2 | 12/2013 | VanDine |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Fontanellas Roma et al. |
| 8,834,863 B2 | 9/2014 | Roy |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,034,836 B2 | 5/2015 | Dodge |
| 9,050,299 B2 | 6/2015 | Bankiewicz |
| 9,051,542 B2 | 6/2015 | Wright |
| 9,056,892 B2 | 6/2015 | Pun |
| 9,066,966 B2 | 6/2015 | Puccio |
| 9,080,183 B2 | 7/2015 | Klein |
| 9,089,667 B2 | 7/2015 | Bankiewicz |
| 9,102,943 B2 | 8/2015 | Shinmura |
| 9,102,949 B2 | 8/2015 | Gao |
| 9,107,884 B2 | 8/2015 | Chedotal |
| 9,115,373 B2 | 8/2015 | Herm |
| 9,116,157 B2 | 8/2015 | Ringe |
| 9,163,260 B2 | 10/2015 | Wilson |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,283,357 B2 | 3/2016 | Stedman |
| 9,415,119 B2 | 8/2016 | Passini |
| 9,415,121 B2 | 8/2016 | Kaspar |
| 9,434,776 B2 | 9/2016 | Ando |
| 9,434,928 B2 | 9/2016 | Mendell |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,486,541 B2 | 11/2016 | Hutton |
| 9,492,415 B2 | 11/2016 | Bankiewicz |
| 9,493,788 B2 | 11/2016 | Gao et al. |
| 9,504,762 B2 | 11/2016 | Colosi |
| 9,506,052 B2 | 11/2016 | Samulski |
| 9,506,083 B2 | 11/2016 | Arbetman |
| 9,528,126 B2 | 12/2016 | Qu |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,616,090 B2 | 4/2017 | Conway et al. |
| 9,617,561 B2 | 4/2017 | Roy |
| 9,623,120 B2 | 4/2017 | Chatterjee |
| 9,624,274 B2 | 4/2017 | Lux |
| 9,629,930 B2 | 4/2017 | Gregory |
| 9,636,370 B2 | 5/2017 | McCown |
| 9,670,507 B2 | 6/2017 | Xiao |
| 9,677,088 B2 | 6/2017 | Nakai |
| 9,677,089 B2 | 6/2017 | Gao |
| 9,682,193 B2 | 6/2017 | Anand |
| 9,695,220 B2 | 7/2017 | Vandenberghe |
| 9,701,984 B2 | 7/2017 | Gao |
| 9,708,627 B2 | 7/2017 | Hermens |
| 9,719,070 B2 | 8/2017 | Vandenberghe |
| 9,719,106 B2 | 8/2017 | Wilson |
| 9,725,485 B2 | 8/2017 | Srivastava |
| 9,732,345 B2 | 8/2017 | Martin |
| 9,733,237 B2 | 8/2017 | Wichterle et al. |
| 9,737,618 B2 | 8/2017 | Wilson |
| 9,745,590 B2 | 8/2017 | Kay |
| 9,775,918 B2 | 10/2017 | Zhong |
| 9,777,291 B2 | 10/2017 | Chatterjee |
| 9,783,824 B2 | 10/2017 | Kay |
| 9,783,825 B2 | 10/2017 | Chatterjee |
| 9,790,472 B2 | 10/2017 | Gao |
| 9,803,218 B2 | 10/2017 | Chatterjee |
| 10,041,090 B2 | 8/2018 | Gao et al. |
| 10,335,466 B2 | 7/2019 | Kotin et al. |
| 11,027,000 B2 | 6/2021 | Kotin et al. |
| 11,759,506 B2 * | 9/2023 | Scheel ............ A61P 25/16 424/93.2 |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0096264 A1 | 5/2003 | Altar et al. |
| 2003/0100115 A1 | 5/2003 | Raj |
| 2003/0119191 A1 | 6/2003 | Gao |
| 2003/0138772 A1 | 7/2003 | Gao |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0261218 A1 | 11/2005 | Esau |
| 2006/0003451 A1 | 1/2006 | Gao |
| 2006/0204479 A1 | 9/2006 | Wilson |
| 2007/0004042 A1 | 1/2007 | Gao et al. |
| 2007/0148132 A1 | 6/2007 | Bohn et al. |
| 2008/0008684 A1 | 1/2008 | Wilson |
| 2008/0050343 A1 | 2/2008 | Wilson |

(56) References Cited

U.S. PATENT DOCUMENTS

| | | |
|---|---|---|
| 2008/0050345 A1 | 2/2008 | Wilson |
| 2008/0075737 A1 | 3/2008 | Gao |
| 2009/0215871 A1 | 8/2009 | Wilson |
| 2009/0275107 A1 | 11/2009 | Lock |
| 2009/0317417 A1 | 12/2009 | Vandenberghe |
| 2010/0247490 A1 | 9/2010 | Roy |
| 2010/0278791 A1 | 11/2010 | Wilson |
| 2011/0136227 A1 | 6/2011 | Bakker |
| 2011/0171262 A1 | 7/2011 | Bakker |
| 2011/0206616 A1 | 8/2011 | Ichtchenko |
| 2011/0223135 A1 | 9/2011 | Roy |
| 2011/0229971 A1 | 9/2011 | Knop et al. |
| 2011/0263001 A1 | 10/2011 | Lakshmipathy |
| 2011/0288160 A1 | 11/2011 | During et al. |
| 2012/0046349 A1 | 2/2012 | Bell |
| 2012/0058102 A1 | 3/2012 | Wilson |
| 2012/0064115 A1 | 3/2012 | John |
| 2012/0093853 A1 | 4/2012 | Wilson |
| 2012/0137379 A1 | 5/2012 | Gao |
| 2012/0220648 A1 | 8/2012 | Hwu |
| 2012/0258046 A1 | 10/2012 | Mutzke |
| 2012/0295960 A1 | 11/2012 | Palfi et al. |
| 2013/0023033 A1 | 1/2013 | Wilson |
| 2013/0045186 A1 | 2/2013 | Gao |
| 2013/0101558 A1 | 4/2013 | Gao |
| 2013/0195801 A1 | 8/2013 | Gao et al. |
| 2013/0296532 A1 | 11/2013 | Herm |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia et al. |
| 2014/0336245 A1 | 11/2014 | Mingozzi |
| 2014/0341852 A1 | 11/2014 | Srivastava |
| 2014/0342434 A1 | 11/2014 | Herm |
| 2015/0005369 A1 | 1/2015 | Muzyczka |
| 2015/0023924 A1 | 1/2015 | High |
| 2015/0065562 A1 | 3/2015 | Yazicioglu |
| 2015/0118287 A1 | 4/2015 | Hammond |
| 2015/0139952 A1 | 5/2015 | Webster |
| 2015/0151007 A1 | 6/2015 | Dodge |
| 2015/0152127 A1 | 6/2015 | Selnick |
| 2015/0159173 A1 | 6/2015 | Vandenberghe |
| 2015/0184197 A1 | 7/2015 | Davidson |
| 2015/0196671 A1 | 7/2015 | Byrne |
| 2015/0203553 A1 | 7/2015 | Chiorini |
| 2015/0238610 A1 | 8/2015 | Sista |
| 2015/0307898 A2 | 10/2015 | Herm |
| 2015/0315610 A1 | 11/2015 | Nishie et al. |
| 2015/0374803 A1 | 12/2015 | Wolfe |
| 2016/0032319 A1 | 2/2016 | Wright |
| 2016/0108373 A1 | 4/2016 | Bennett et al. |
| 2016/0153992 A1 | 6/2016 | Buening |
| 2016/0166709 A1 | 6/2016 | Davidson |
| 2016/0256534 A1 | 9/2016 | Bankiewicz |
| 2016/0271192 A1 | 9/2016 | Roy |
| 2016/0273058 A1 | 9/2016 | Akashika |
| 2016/0289275 A1 | 10/2016 | Chiorini |
| 2016/0296694 A1 | 10/2016 | Bankiewicz |
| 2016/0319278 A1 | 11/2016 | Khvorova et al. |
| 2016/0326524 A1 | 11/2016 | Flotte et al. |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0334417 A1 | 11/2016 | Rouillon |
| 2016/0340393 A1 | 11/2016 | Schaffer |
| 2016/0340692 A1 | 11/2016 | Wang |
| 2016/0346359 A1 | 12/2016 | Buchlis |
| 2016/0347822 A1 | 12/2016 | Crystal |
| 2016/0354487 A1 | 12/2016 | Zhang et al. |
| 2016/0355577 A1 | 12/2016 | Kelley |
| 2016/0355796 A1 | 12/2016 | Davidson et al. |
| 2016/0361439 A1 | 12/2016 | Agbandje-Mckenna |
| 2016/0367661 A1 | 12/2016 | Flavell |
| 2016/0369297 A1 | 12/2016 | Byrne |
| 2016/0369298 A1 | 12/2016 | Marsic |
| 2016/0369299 A1 | 12/2016 | Boye |
| 2016/0375110 A1 | 12/2016 | High et al. |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007645 A1 | 1/2017 | Handa |
| 2017/0007669 A1 | 1/2017 | Sarkar |
| 2017/0007720 A1 | 1/2017 | Boye |
| 2017/0008939 A1 | 1/2017 | Khanna |
| 2017/0021037 A1 | 1/2017 | Wang |
| 2017/0022507 A1 | 1/2017 | Reyon et al. |
| 2017/0028082 A1 | 2/2017 | Wilson |
| 2017/0043037 A1 | 2/2017 | Kariko |
| 2017/0044504 A1 | 2/2017 | Schaffer |
| 2017/0051259 A1 | 2/2017 | Wang |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0087219 A1 | 3/2017 | Bunting |
| 2017/0088819 A1 | 3/2017 | Vandendriessche |
| 2017/0088858 A1 | 3/2017 | Gao |
| 2017/0095538 A1 | 4/2017 | Colosi |
| 2017/0096646 A1 | 4/2017 | Roy |
| 2017/0105927 A1 | 4/2017 | Thorne |
| 2017/0107536 A1 | 4/2017 | Zhang et al. |
| 2017/0112946 A1 | 4/2017 | Ikeda |
| 2017/0121734 A1 | 5/2017 | Cairns |
| 2017/0128581 A1 | 5/2017 | Freskgard |
| 2017/0128594 A1 | 5/2017 | Wright |
| 2017/0130208 A1 | 5/2017 | Potter |
| 2017/0130245 A1 | 5/2017 | Kotin et al. |
| 2017/0145440 A1 | 5/2017 | Herm |
| 2017/0151348 A1 | 6/2017 | Kasper |
| 2017/0151416 A1 | 6/2017 | Kutikov |
| 2017/0152525 A1 | 6/2017 | Herm |
| 2017/0157213 A1 | 6/2017 | Dickson |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0183636 A1 | 6/2017 | Roy |
| 2017/0191039 A1 | 7/2017 | Gao |
| 2017/0191079 A1 | 7/2017 | Vandenberghe |
| 2017/0198304 A1 | 7/2017 | Wilson |
| 2017/0204144 A1 | 7/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |
| 2017/0218395 A1 | 8/2017 | Byrne |
| 2017/0226160 A1 | 8/2017 | Sonntag |
| 2017/0232072 A1 | 8/2017 | Ikeda |
| 2017/0232117 A1 | 8/2017 | Arbetman |
| 2017/0240885 A1 | 8/2017 | Deverman |
| 2017/0240921 A1 | 8/2017 | Gao |
| 2017/0246322 A1 | 8/2017 | Mendell |
| 2017/0247664 A1 | 8/2017 | Wright |
| 2017/0258996 A1 | 9/2017 | Anand |
| 2017/0260545 A1 | 9/2017 | Qu |
| 2017/0274024 A1 | 9/2017 | McCown |
| 2017/0275337 A1 | 9/2017 | Srivastava |
| 2017/0298323 A1 | 10/2017 | Vandenberghe |
| 2017/0304464 A1 | 10/2017 | Kugler |
| 2017/0306354 A1 | 10/2017 | Gao |
| 2017/0306355 A1 | 10/2017 | Davidson |
| 2017/0321290 A1 | 11/2017 | Lubelski |
| 2017/0333538 A1 | 11/2017 | Kotin et al. |

(56) References Cited

U.S. PATENT DOCUMENTS

| | | | |
|---|---|---|---|
| 2018/0339065 A1 | 11/2018 | Wilson | |
| 2019/0000940 A1 | 1/2019 | Kotin | |
| 2019/0000991 A1 | 1/2019 | Pykett | |
| 2019/0008931 A1 | 1/2019 | Kotin et al. | |
| 2019/0008932 A1 | 1/2019 | Kotin et al. | |
| 2019/0008933 A1 | 1/2019 | Kotin et al. | |
| 2019/0060425 A1 | 2/2019 | Scheel et al. | |
| 2019/0343937 A1 | 11/2019 | Scheel et al. | |
| 2021/0238630 A1* | 8/2021 | Drouin | C12N 9/88 |
| 2023/0242939 A1* | 8/2023 | Mathur | C12N 15/86 435/320.1 |

FOREIGN PATENT DOCUMENTS

| | | |
|---|---|---|
| EP | 1078096 A1 | 2/2001 |
| EP | 1164195 A2 | 12/2001 |
| EP | 1183380 A1 | 3/2002 |
| EP | 1218035 A2 | 7/2002 |
| EP | 1240345 A2 | 9/2002 |
| EP | 1279740 A1 | 1/2003 |
| EP | 1453547 A2 | 9/2004 |
| EP | 1578253 A2 | 9/2005 |
| EP | 1621625 A2 | 2/2006 |
| EP | 1696036 A1 | 8/2006 |
| EP | 1847614 A1 | 10/2007 |
| EP | 1849872 A1 | 10/2007 |
| EP | 1857552 A1 | 11/2007 |
| EP | 1944043 A1 | 7/2008 |
| EP | 2007795 A2 | 12/2008 |
| EP | 2176283 A2 | 4/2010 |
| EP | 2186283 A2 | 5/2010 |
| EP | 2198016 A1 | 6/2010 |
| EP | 2212348 A1 | 8/2010 |
| EP | 2220241 A2 | 8/2010 |
| EP | 2220242 A2 | 8/2010 |
| EP | 2250256 A1 | 11/2010 |
| EP | 2292779 A2 | 3/2011 |
| EP | 2292780 A2 | 3/2011 |
| EP | 2301582 A1 | 3/2011 |
| EP | 2311967 A2 | 4/2011 |
| EP | 2325298 A2 | 5/2011 |
| EP | 2348119 A2 | 7/2011 |
| EP | 2359866 A1 | 8/2011 |
| EP | 2383346 A1 | 11/2011 |
| EP | 2524037 A1 | 11/2012 |
| EP | 2531604 A2 | 12/2012 |
| EP | 2660325 A2 | 11/2013 |
| EP | 2699270 A2 | 2/2014 |
| EP | 2737071 A2 | 6/2014 |
| EP | 2771471 A1 | 9/2014 |
| EP | 2814958 A1 | 12/2014 |
| EP | 2871239 A1 | 5/2015 |
| EP | 2879719 A1 | 6/2015 |
| EP | 2933336 A2 | 10/2015 |
| EP | 2943567 A1 | 11/2015 |
| EP | 3058959 A1 | 8/2016 |
| EP | 3067417 A2 | 9/2016 |
| EP | 3108000 A1 | 12/2016 |
| EP | 3117005 A1 | 1/2017 |
| EP | 3126506 A1 | 2/2017 |
| EP | 3134431 A1 | 3/2017 |
| EP | 3168298 A1 | 5/2017 |
| EP | 3209311 A1 | 8/2017 |
| EP | 3215191 A2 | 9/2017 |
| EP | 3215602 A1 | 9/2017 |
| EP | 3219801 A1 | 9/2017 |
| EP | 3221349 A1 | 9/2017 |
| EP | 3221453 A1 | 9/2017 |
| EP | 3221456 A2 | 9/2017 |
| EP | 3224376 A1 | 10/2017 |
| EP | 3230441 A1 | 10/2017 |
| EP | 3235827 A2 | 10/2017 |
| JP | 2002-516295 A | 6/2002 |
| JP | 2007-524386 A | 8/2007 |
| JP | 2014-511180 A | 5/2014 |
| WO | WO-1993/009239 A1 | 5/1993 |
| WO | WO-1995/034670 A2 | 12/1995 |
| WO | WO-1996/023810 A1 | 8/1996 |
| WO | WO-1996/030540 A2 | 10/1996 |
| WO | WO-1998/010088 A1 | 3/1998 |
| WO | WO-1999/027110 A1 | 6/1999 |
| WO | WO-1999/043360 A1 | 9/1999 |
| WO | WO-1999/058700 A1 | 11/1999 |
| WO | WO-1999/060146 A1 | 11/1999 |
| WO | WO-1999/061066 A2 | 12/1999 |
| WO | WO-1999/061595 A2 | 12/1999 |
| WO | WO-2000/23116 A1 | 4/2000 |
| WO | WO-2000/024916 A1 | 5/2000 |
| WO | WO-2000/066780 A2 | 11/2000 |
| WO | WO-2000/075353 A1 | 12/2000 |
| WO | WO-2001/014539 A2 | 3/2001 |
| WO | WO-2001/023001 A2 | 4/2001 |
| WO | WO-2001/025465 A1 | 4/2001 |
| WO | WO-2001/032711 A2 | 5/2001 |
| WO | WO-2001/036623 A2 | 5/2001 |
| WO | WO-2001/042444 A2 | 6/2001 |
| WO | WO-2001/068888 A2 | 9/2001 |
| WO | WO-2001/089583 A2 | 11/2001 |
| WO | WO-2001/096587 A2 | 12/2001 |
| WO | WO-2002/012525 A2 | 2/2002 |
| WO | WO-2002/014487 A2 | 2/2002 |
| WO | WO-2002/020748 A2 | 3/2002 |
| WO | WO-2002/070719 A2 | 9/2002 |
| WO | WO-2002/071843 A1 | 9/2002 |
| WO | WO-2003/010320 A2 | 2/2003 |
| WO | WO-2003/024502 A2 | 3/2003 |
| WO | WO-2003/042397 A2 | 5/2003 |
| WO | WO-2003/087382 A1 | 10/2003 |
| WO | WO-2003/087383 A1 | 10/2003 |
| WO | WO-2004/044003 A2 | 5/2004 |
| WO | WO-2004/083441 A2 | 9/2004 |
| WO | WO-2004/108922 A2 | 12/2004 |
| WO | WO-2004/111248 A2 | 12/2004 |
| WO | WO-2004/112727 A2 | 12/2004 |
| WO | WO-2005/005610 A2 | 1/2005 |
| WO | WO-2005/012537 A2 | 2/2005 |
| WO | WO-2005/111220 A2 | 11/2005 |
| WO | WO-2006/063247 A2 | 6/2006 |
| WO | WO-2006/102072 A2 | 9/2006 |
| WO | WO-2007/130519 A2 | 11/2007 |
| WO | WO-2007/148971 A2 | 12/2007 |
| WO | WO-2009/134681 A2 | 11/2009 |
| WO | WO-2010/109053 A1 | 9/2010 |
| WO | WO-2011/038187 A1 | 3/2011 |
| WO | WO-2011/054976 A2 | 5/2011 |
| WO | WO-2011/122950 A1 | 10/2011 |
| WO | WO-2012/007458 A1 | 1/2012 |
| WO | WO-2012/057363 A1 | 5/2012 |
| WO | WO-2012/109570 A1 | 8/2012 |
| WO | WO-2012/114090 A1 | 8/2012 |
| WO | WO-2012/144446 A1 | 10/2012 |
| WO | WO-2013/078199 A2 | 5/2013 |
| WO | WO-2013/164793 A2 | 11/2013 |
| WO | WO-2013/170078 A1 | 11/2013 |
| WO | WO-2014/160092 A1 | 10/2014 |
| WO | WO-2014/168953 A1 | 10/2014 |
| WO | WO-2014/170470 A1 | 10/2014 |
| WO | WO-2014/170480 A1 | 10/2014 |
| WO | WO-2014/172669 A1 | 10/2014 |
| WO | WO-2014/186579 A1 | 11/2014 |
| WO | WO-2014/186746 A1 | 11/2014 |
| WO | WO-2014/194132 A1 | 12/2014 |
| WO | WO-2014/201252 A2 | 12/2014 |
| WO | WO-2015/012924 A2 | 1/2015 |
| WO | WO-2015/013148 A2 | 1/2015 |
| WO | WO-2015/018503 A1 | 2/2015 |
| WO | WO-2015/031686 A1 | 3/2015 |
| WO | WO-2015/038625 A1 | 3/2015 |
| WO | WO-2015/044292 A1 | 4/2015 |
| WO | WO-2015/060722 A1 | 4/2015 |
| WO | WO-2015/106273 A2 | 7/2015 |
| WO | WO-2015/108610 A1 | 7/2015 |
| WO | WO-2015/114365 A1 | 8/2015 |

(56) References Cited

FOREIGN PATENT DOCUMENTS

| | | |
|---|---|---|
| WO | WO-2015/121501 A1 | 8/2015 |
| WO | WO-2015/124546 A1 | 8/2015 |
| WO | WO-2015/127128 A2 | 8/2015 |
| WO | WO-2015/137802 A1 | 9/2015 |
| WO | WO-2015/152813 A1 | 10/2015 |
| WO | WO-2015/196179 A1 | 12/2015 |
| WO | WO-2016/019364 A1 | 2/2016 |
| WO | WO-2016/054554 A1 | 4/2016 |
| WO | WO-2016/054557 A1 | 4/2016 |
| WO | WO-2016/065001 A1 | 4/2016 |
| WO | WO-2016/073693 A2 | 5/2016 |
| WO | WO-2016/081811 A1 | 5/2016 |
| WO | WO-2016/081927 A2 | 5/2016 |
| WO | WO-2016/115382 A1 | 7/2016 |
| WO | WO-2016/122791 A1 | 8/2016 |
| WO | WO-2016/126857 A1 | 8/2016 |
| WO | WO-2016/130591 A2 | 8/2016 |
| WO | WO-2016/137949 A1 | 9/2016 |
| WO | WO-2016/145217 A1 | 9/2016 |
| WO | WO-2016/154055 A1 | 9/2016 |
| WO | WO-2016/154344 A1 | 9/2016 |
| WO | WO-2016/164609 A2 | 10/2016 |
| WO | WO-2016/168728 A2 | 10/2016 |
| WO | WO-2016/172008 A1 | 10/2016 |
| WO | WO-2016/172155 A1 | 10/2016 |
| WO | WO-2016/179496 A1 | 11/2016 |
| WO | WO-2016/183297 A1 | 11/2016 |
| WO | WO-2016/191418 A1 | 12/2016 |
| WO | WO-2016/196328 A1 | 12/2016 |
| WO | WO-2016/196507 A1 | 12/2016 |
| WO | WO-2017/004514 A1 | 1/2017 |
| WO | WO-2017/005806 A1 | 1/2017 |
| WO | WO-2017/015102 A1 | 1/2017 |
| WO | WO-2017/019876 A1 | 2/2017 |
| WO | WO-2017/019994 A2 | 2/2017 |
| WO | WO-2017/024198 A1 | 2/2017 |
| WO | WO-2017023724 A1 * | 2/2017 ............. A61K 38/51 |
| WO | WO-2017/058892 A2 | 4/2017 |
| WO | WO-2017/070476 A2 | 4/2017 |
| WO | WO-2017/070516 A1 | 4/2017 |
| WO | WO-2017/070525 A1 | 4/2017 |
| WO | WO-2017/070678 A1 | 4/2017 |
| WO | WO-2017/075335 A1 | 5/2017 |
| WO | WO-2017/079768 A1 | 5/2017 |
| WO | WO-2017/083423 A1 | 5/2017 |
| WO | WO-2017/093330 A1 | 6/2017 |
| WO | WO-2017/096039 A1 | 6/2017 |
| WO | WO-2017/100671 A1 | 6/2017 |
| WO | WO-2017/100674 A1 | 6/2017 |
| WO | WO-2017/100676 A1 | 6/2017 |
| WO | WO-2017/100704 A1 | 6/2017 |
| WO | WO-2017/106236 A1 | 6/2017 |
| WO | WO-2017/112948 A1 | 6/2017 |
| WO | WO-2017/122789 A1 | 7/2017 |
| WO | WO-2017/123934 A1 | 7/2017 |
| WO | WO-2017/136202 A1 | 8/2017 |
| WO | WO-2017/136536 A1 | 8/2017 |
| WO | WO-2017/139381 A1 | 8/2017 |
| WO | WO-2017/143100 A1 | 8/2017 |
| WO | WO-2017/147477 A1 | 8/2017 |
| WO | WO-2017/151884 A1 | 9/2017 |
| WO | WO-2017/152149 A1 | 9/2017 |
| WO | WO-2017/155973 A1 | 9/2017 |
| WO | WO-2017/160360 A2 | 9/2017 |
| WO | WO-2017/165167 A1 | 9/2017 |
| WO | WO-2017/165859 A1 | 9/2017 |
| WO | WO-2017/172733 A1 | 10/2017 |
| WO | WO-2017/172772 A1 | 10/2017 |
| WO | WO-2017/173043 A1 | 10/2017 |
| WO | WO-2017/173283 A1 | 10/2017 |
| WO | WO-2017/180854 A1 | 10/2017 |
| WO | WO-2017/181162 A1 | 10/2017 |
| WO | WO-2017/184879 A1 | 10/2017 |
| WO | WO-2017/190031 A1 | 11/2017 |
| WO | WO-2017/192699 A1 | 11/2017 |
| WO | WO-2017/192750 A1 | 11/2017 |
| WO | WO-2018/191450 A2 | 10/2018 |
| WO | 2018232055 A1 | 12/2018 |

OTHER PUBLICATIONS

Da Luz et al. 2015. Dopamine induces the accumulation of insoluble prion protein and affects autophagic flux. Front. Cell. Neurosci. 9:12 (Year: 2015).*

Pena et al. 2020. Gene therapy for neurological disorders: challenges and recent advancements. J. Drug Targeting 28[2]:111-128 (Year: 2020).*

Martier and Konstantinova. 2020. Gene Therapy for Neurodegenerative Diseases: Slowing Down the Ticking Clock. Frontiers. Neurosci. 14:580179 (Year: 2020).*

Jhu. Brain Tumor Types. Available at https://www.hopkinsmedicine.org/health/conditions-and-diseases/brain-tumor/brain-tumor-types. Accessed Dec. 20, 2023 (Year: 2023).*

Mount Sinai. Multiple Sclerosis. Available at https://www.mountsinai.org/health-library. Accessed Dec. 20, 2023 (Year: 2023).*

International Search Report received in corresponding PCT application No. PCT/US2019/032384 dated Aug. 27, 2019.

U.S. Appl. No. 15/524,986, filed May 5, 2014, U.S. Pat. No. 10,335,466, Issued.

U.S. Appl. No. 16/136,926, filed Sep. 20, 2018, 2019-0008931, Abandoned.

U.S. Appl. No. 16/137,028, filed Sep. 20, 2018, 2019-0008932, Abandoned.

U.S. Appl. No. 16/137,049, filed Sep. 20, 2018, 2019-0008933, Abandoned.

U.S. Appl. No. 16/540,375, filed Aug. 14, 2019, U.S. Pat. No. 11,027,000, Issued.

U.S. Appl. No. 17/306,376, filed May 5, 2021, Pending.

U.S. Appl. No. 16/184,466, filed Nov. 8, 2018, 2019-00060425, Abandoned.

U.S. Appl. No. 16/523,567, filed Jul. 26, 2019, 2019-0343937, Published.

Adachi et al., Drawing a high-resolution functional map of adeno-associated virus capsid by massively parallel sequencing. Nat Commun. 2014;5:3075.

Adamson-Small et al., Sodium Chloride Enhances Recombinant Adeno-Associated Virus Production in a Serum-Free Suspension Manufacturing Platform Using the Herpes Simplex Virus System. Hum Gene Ther Methods. Feb. 2017;28(1):1-14. pre-publication edition.

Afione et al., Identification and mutagenesis of the adeno-associated virus 5 sialic acid binding region. J Virol. Feb. 2015;89(3):1660-72.

Ahmad et al., Engineered Expression of Broadly Neutralizing Antibodies Against Human Immunodeficiency Virus. Annu Rev Virol. Sep. 29, 2017;4(1):491-510.

Ahmed et al., rAAV Gene Therapy in a Canavan's Disease Mouse Model Reveals Immune Impairments and an Extended Pathology Beyond the Central Nervous System. Mol Ther. Jun. 2016;24(6):1030-1041. pre-publication edition.

Ai et al., A Scalable and Accurate Method for Quantifying Vector Genomes of Recombinant Adeno-Associated Viruses in Crude Lysate. Hum Gene Ther Methods. Jun. 2017;28(3):139-147. pre-publication edition.

Ai et al., Adeno-associated virus serotype rh. 10 displays strong muscle tropism following intraperitoneal delivery. Sci Rep. Jan. 9, 2017;7:40336, 6 pages.

Alton et al., Repeated nebulisation of non-viral CFTR gene therapy in patients with cystic fibrosis: a randomised, double-blind, placebo-controlled, phase 2b trial. Lancet Respir Med. Sep. 2015;3(9):684-691.

Altschul et al., Basic local alignment search tool. J Mol Biol. Oct. 5, 1990;215(3):403-10.

Alves et al., Ultramicroscopy as a novel tool to unravel the tropism of AAV gene therapy vectors in the brain. Sci Rep. Jun. 20, 2016;6:28272, 12 pages.

(56) References Cited

OTHER PUBLICATIONS

Andersson et al., Striatal vol. changes in the rat following long-term administration of typical and atypical antipsychotic drugs. Neuropsychopharmacology. Aug. 2002;27(2):143-51.
Aoyama et al., Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Armbruster et al., Efficacy and biodistribution analysis of intracerebroventricular administration of an optimized scAAV9-SMN1 vector in a mouse model of spinal muscular atrophy. Mol Ther Methods Clin Dev. Sep. 14, 2016;3:16060, 8 pages.
Arrigo et al., Visual System Involvement in Patients with Newly Diagnosed Parkinson Disease. Radiology. Dec. 2017;285(3):885-895.
Arruda et al., Obstacles and future of gene therapy for hemophilia. Expert Opin Orphan Drugs. 2015;3(9):997-1010.
Athauda et al., Exenatide once weekly versus placebo in Parkinson's disease: a randomised, double-blind, placebo-controlled trial. Lancet. Oct. 7, 2017;390(10103):1664-1675.
Aubourg, Gene Therapy for Rare Central Nervous System Diseases Comes to Age. Endocr Dev. 2016;30:141-6.
Aydemir et al., Mutants at the 2-Fold Interface of Adeno-associated Virus Type 2 (AAV2) Structural Proteins Suggest a Role in Viral Transcription for AAV Capsids. J Virol. Jul. 27, 2016;90(16):7196-7204. pre-publicaton edition.
Ayuso et al., High AAV vector purity results in serotype- and tissue-independent enhancement of transduction efficiency. Gene Ther. Apr. 2010;17(4):503-10.
Bankiewicz et al., AAV viral vector delivery to the brain by shape-conforming MR-guided infusions. J Control Release. Oct. 28, 2016;240:434-442. pre-publication edition.
Bankiewicz et al., Convection-enhanced delivery of AAV vector in parkinsonian monkeys; in vivo detection of gene expression and restoration of dopaminergic function using pro-drug approach. Exp Neurol. Jul. 2000;164(1):2-14.
Bankiewicz et al., Long-term clinical improvement in MPTP-lesioned primates after gene therapy with AAV-hAADC. Mol Ther. Oct. 2006;14(4):564-70.
Bantel-Schaal et al., Human adeno-associated virus type 5 is only distantly related to other known primate helper-dependent parvoviruses. J Virol. Feb. 1999;73(2):939-47.
Bartus et al., Parkinson's disease gene therapy: success by design meets failure by efficacy. Mol Ther. Mar. 2014;22(3):487-497.
Bartus et al., Safety/feasibility of targeting the substantia nigra with AAV2-neurturin in Parkinson patients. Neurology. Apr. 30, 2013;80(18):1698-701.
Bassil et al., Viral-mediated oligodendroglial alpha-synuclein expression models multiple system atrophy. Mov Disord. Aug. 2017;32(8):1230-1239.
Baum et al., Advances in salivary gland gene therapy—oral and systemic implications. Expert Opin Biol Ther. 2015;15(10):1443-54.
Baum et al., Early responses to adenoviral-mediated transfer of the aquaporin-1 cDNA for radiation-induced salivary hypofunction. Proc Natl Acad Sci U S A. Nov. 20, 2012;109(47):19403-7.
Bell et al., Effects of Self-Complementarity, Codon Optimization, Transgene, and Dose on Liver Transduction with AAV8. Hum Gene Ther Methods. Dec. 2016;27(6):228-237. pre-publication edition.
Bennett et al., Thermal Stability as a Determinant of AAV Serotype Identity. Mol Ther Methods Clin Dev. Jul. 24, 2017;6:171-182.
Bennett et al., Understanding capsid assembly and genome packaging for adeno-associated viruses. Future Virology. Jun. 8, 2017;12(6):283-297.
Benskey et al., Targeted gene delivery to the enteric nervous system using AAV: a comparison across serotypes and capsid mutants. Mol Ther. Mar. 2015;23(3):488-500.
Berge et al., Pharmaceutical salts. J Pharm Sci. Jan. 1977;66(1):1-19.
Berry et al., Cellular transduction mechanisms of adeno-associated viral vectors. Curr Opin Virol. Dec. 2016;21:54-60.
Bey et al., Efficient CNS targeting in adult mice by intrathecal infusion of single-stranded AAV9-GFP for gene therapy of neurological disorders. Gene Ther. May 2017;24(5):325-332.
Blesa et al., Classic and new animal models of Parkinson's disease. J Biomed Biotechnol. 2012;2012:845618.
Blits et al., Perspective on the Road toward Gene Therapy for Parkinson's Disease. Front Neuroanat. Jan. 9, 2017;10:128, 8 pages.
Boone et al., Effects of AAV-mediated knockdown of nNOS and GPx-1 gene expression in rat hippocampus after traumatic brain injury. PLoS One. Oct. 10, 2017;12(10):e0185943, 22 pages.
Bosch et al., Self-Complementary AAV9 Gene Delivery Partially Corrects Pathology Associated with Juvenile Neuronal Ceroid Lipofuscinosis (CLN3). J Neurosci. Sep. 14, 2016;36(37):9669-82.
Braak et al., Staging of brain pathology related to sporadic Parkinson's disease. Neurobiol Aging. Mar.-Apr. 2003;24(2):197-211.
Bradbury et al., Biomarkers for disease progression and AAV therapeutic efficacy in feline Sandhoff disease. Exp Neurol. Jan. 2015;263:102-12.
Brady et al., Antibody gene transfer with adeno-associated viral vectors as a method for HIV prevention. Immunol Rev. Jan. 2017;275(1):324-333.
Brodsky et al., Effects of a dopamine agonist on the pharmacodynamics of levodopa in Parkinson disease. Arch Neurol. Jan. 2010;67(1):27-32.
Brown et al., Adeno-Associated Virus Vectors and Stem Cells: Friends or Foes? Hum Gene Ther. Jun. 2017;28(6):450-463.
Brulet et al., NEUROD1 Instructs Neuronal Conversion in Non-Reactive Astrocytes. Stem Cell Reports. Jun. 6, 2017;8(6):1506-1515.
Brun et al., Clinical and biochemical features of aromatic L-amino acid decarboxylase deficiency. Neurology. Jul. 6, 2010;75(1):64-71.
Buclez et al., Rapid, scalable, and low-cost purification of recombinant adeno-associated virus produced by baculovirus expression vector system. Mol Ther Methods Clin Dev. May 11, 2016;3:16035, 10 pages.
Buning et al., Capsid Modifications for Targeting and Improving the Efficacy of AAV Vectors. Mol Ther Methods Clin Dev. Jan. 26, 2019;12:248-265.
Burbulla et al., Dopamine oxidation mediates mitochondrial and lysosomal dysfunction in Parkinson's disease. Science. Sep. 22, 2017;357(6357):1255-1261.
Burnham et al., Analytical Ultracentrifugation as an Approach to Characterize Recombinant Adeno-Associated Viral Vectors. Hum Gene Ther Methods. Dec. 2015;26(6):228-42.
Cabral-Miranda et al., rAAV8-733-Mediated Gene Transfer of CHIP/Stub-1 Prevents Hippocampal Neuronal Death in Experimental Brain Ischemia. Mol Ther. Feb. 1, 2017;25(2):392-400.
Carrillo et al., The Multiple Sequence Alignment Problem in Biology. SIAM J Appl Math. Oct. 1988;48(5):1073-1082.
Carter et al., Adeno-associated virus and the development of adeno-associated virus vectors: a historical perspective. Mol Ther. Dec. 2004;10(6):981-9.
Carvalho et al., Evaluating Efficiencies of Dual AAV Approaches for Retinal Targeting. Front Neurosci. Sep. 8, 2017;11:503, 8 pages.
Castle et al., Controlling AAV Tropism in the Nervous System with Natural and Engineered Capsids. Methods Mol Biol. 2016;1382:133-49.
Cell Biolabs. Product Data Sheet: pAAVS-MCS Expression Vector. Retrieved online at: https://www.cellbiolabs.com/sites/default/files/VPK-410-aav-expression-ve-ctor.pdf. 10 pages, (2010).
Chai et al., Application of polyploid adeno-associated virus vectors for transduction enhancement and neutralizing antibody evasion. J Control Release. Sep. 2, 20178;262:348-356. pre-publication edition.
Chali et al., Inhibiting cholesterol degradation induces neuronal sclerosis and epileptic activity in mouse hippocampus. Eur J Neurosci. May 2015;41(10):1345-55.
Chamberlain et al., Expressing Transgenes That Exceed the Packaging Capacity of Adeno-Associated Virus Capsids. Hum Gene Ther Methods. Feb. 2016;27(1):1-12. pre- publication edition.

(56) References Cited

OTHER PUBLICATIONS

Chan et al., Engineered AAVs for efficient noninvasive gene delivery to the central and peripheral nervous systems. Nat Neurosci. Aug. 2017;20(8):1172-1179.

Chan et al., Modeling the short- and long-duration responses to exogenous levodopa and to endogenous levodopa production in Parkinson's disease. J Pharmacokinet Pharmacodyn. Jun. 2004;31(3):243-68.

Chan et al., Pharmacokinetic and pharmacodynamic changes during the first four years of levodopa treatment in Parkinson's disease. J Pharmacokinet Pharmacodyn. Aug. 2005;32(3-4):459-84.

Chandler et al., Recombinant Adeno-Associated Viral Integration and Genotoxicity: Insights from Animal Models. Hum Gene Ther. Apr. 2017;28(4):314-322.

Chandler et al., Systemic AAV9 gene therapy improves the lifespan of mice with Niemann-Pick disease, type C1. Hum Mol Genet. Jan. 1, 2017;26(1):52-64.

Chandran et al., Gene Therapy in the Nervous System: Failures and Successes. Adv Exp Med Biol. 2017;1007:241-257.

Chandran et al., Site Specific Modification of Adeno-Associated Virus Enables Both Fluorescent Imaging of Viral Particles and Characterization of the Capsid Interactome. Sci Rep. Nov. 7, 2017;7(1):14766, 17 pages.

Chansel-Debordeaux et al., In utero delivery of rAAV2/9 induces neuronal expression of the transgene in the brain: towards new models of Parkinson's disease. Gene Ther. Dec. 2017;24(12):801-809. pre-publication edition.

Chen et al., Efficient Gene Delivery and Expression in Pancreas and Pancreatic Tumors by Capsid-Optimized AAV8 Vectors. Hum Gene Ther Methods. Feb. 2017;28(1):49-59. pre-publication edition.

Chen et al., Viral Vectors for Gene Transfer. Curr Protoc Mouse Biol. Dec. 2018;8(4):e58, 7 pages.

Chien et al., Efficacy and safety of AAV2 gene therapy in children with aromatic L-amino acid decarboxylase deficiency: an open-label, phase 1/2 trial. Lancet Child Adolesc Health. Dec. 2017;1(4):265-273.

Chiorini et al., Adeno-associated virus (AAV) type 5 Rep protein cleaves a unique terminal resolution site compared with other AAV serotypes. J Virol. May 1999;73(5):4293-8.

Chiorini et al., Cloning and characterization of adeno-associated virus type 5. J Virol. Feb. 1999;73(2):1309-19.

Chiorini et al., Cloning of adeno-associated virus type 4 (AAV4) and generation of recombinant AAV4 particles. J Virol. Sep. 1997;71(9):6823-33.

Chiuchiolo et al., Gene Therapy for Alpha-1 Antitrypsin Deficiency Lung Disease. Ann Am Thorac Soc. Aug. 2016;13(Suppl 4):S352-69.

Choudhury et al., In Vivo Selection Yields AAV-B1 Capsid for Central Nervous System and Muscle Gene Therapy. Mol Ther. Aug. 2016;24(7):1247-57. pre-publication edition.

Choudhury et al., Widespread Central Nervous System Gene Transfer and Silencing After Systemic Delivery of Novel AAV-AS Vector. Mol Ther. Apr. 2016;24(4):726-35.

Christine et al., Magnetic resonance imaging-guided phase 1 trial of putaminal AADC gene therapy for Parkinson's disease. Ann Neurol. May 2019;85(5):704-714.

Christine et al., Safety and tolerability of putaminal AADC gene therapy for Parkinson disease. Neurology. Nov. 17, 2009;73(20):1662-9.

Ciesielska et al., Carbidopa-based modulation of the functional effect of the AAV2-hAADC gene therapy in 6-OHDA lesioned rats. PLoS One. Apr. 10, 2015;10(4):e0122708, 14 pages.

Ciesielska et al., Depletion of AADC activity in caudate nucleus and putamen of Parkinson's disease patients; implications for ongoing AAV2-AADC gene therapy trial. PLoS One. Feb. 6, 2017;12(2):e0169965, 13 pages.

Ciurleo et al., Assessment of Duodopa® effects on quality of life of patients with advanced Parkinson's disease and their caregivers. J Neurol. Sep. 2018;265(9):2005-2014.

Clement et al., Manufacturing of recombinant adeno-associated viral vectors for clinical trials. Mol Ther Methods Clin Dev. Mar. 16, 2016;3:16002, 7 pages.

Clift et al., A Method for the Acute and Rapid Degradation of Endogenous Proteins. Cell. Dec. 14, 2017;171(7):1692-1706.e18. 33 pages.

Coleman et al., Validity and Efficacy of Screening Algorithms for Assessing Deep Brain Stimulation Candidacy in Parkinson Disease. Mov Disord Clin Pract. Dec. 1, 2014;1(4):342-347.

Conlon et al., Transfer of Therapeutic Genes into Fetal Rhesus Monkeys Using Recombinant Adeno-Associated Type I Viral Vectors. Hum Gene Ther Clin Dev. Dec. 2016;27(4):152-159. pre-publication edition.

Corti et al., Evaluation of Readministration of a Recombinant Adeno-Associated Virus Vector Expressing Acid Alpha-Glucosidase in Pompe Disease: Preclinical to Clinical Planning. Hum Gene Ther Clin Dev. Sep. 2015;26(3):185-93.

Cuende et al., Cell, tissue and gene products with marketing authorization in 2018 worldwide. Cytotherapy. Nov. 2018;20(11):1401-1413.

Cunningham et al., Biodistribution of adeno-associated virus type-2 in nonhuman primates after convection-enhanced delivery to brain. Mol Ther. Jul. 2008;16(7):1267-75.

D'Costa et al., Practical utilization of recombinant AAV vector reference standards: focus on vector genomes titration by free ITR qPCR. Mol Ther Methods Clin Dev. Mar. 30, 2016;5:16019, 9 pages.

Daher et al., Leucine-rich Repeat Kinase 2 (LRRK2) Pharmacological Inhibition Abates alpha-Synuclein Gene-induced Neurodegeneration. J Biol Chem. Aug. 7, 2015;290(32):19433-44.

Dang et al., In vivo dynamics of AAV-mediated gene delivery to sensory neurons of the trigeminal ganglia. Sci Rep. Apr. 19, 2017;7(1):927, 13 pages.

Dashkoff et al., Tailored transgene expression to specific cell types in the central nervous system after peripheral injection with AAV9. Mol Ther Methods Clin Dev. Dec. 7, 2016;3:16081, 9 pages.

Davidsson et al., A novel process of viral vector barcoding and library preparation enables high-diversity library generation and recombination-free paired-end sequencing. Sci Rep. Nov. 22, 2016;6:37563, 18 pages.

Davis et al., Rational design and engineering of a modified adeno-associated virus (AAV1)-based vector system for enhanced retrograde gene delivery. Neurosurgery. Feb. 2015;76(2):216-25.

De La Manza et al., Molecular structure of adeno-associated virus variant DNA. J Biol Chem. Apr. 10, 1980;255(7):3194-203.

De Leeuw et al., rAAV-compatible MiniPromoters for restricted expression in the brain and eye. Mol Brain. May 10, 2016;9(1):52, 13 pages.

De Silva et al., Single residue AAV capsid mutation improves transduction of photoreceptors in the Abca4−/− mouse and bipolar cells in the rd1 mouse and human retina ex vivo. Gene Ther. Nov. 2016;23(11):767-774.

Delenclos et al., Neonatal AAV delivery of alpha-synuclein induces pathology in the adult mouse brain. Acta Neuropathol Commun. Jun. 23, 2017;5(1):51, 14 pages.

Deng et al., Replication of an Autonomous Human Parvovirus in Non-dividing Human Airway Epithelium Is Facilitated through the DNA Damage and Repair Pathways. PLoS Pathog. Jan. 14, 2016;12(1):e1005399, 25 pages.

Devereux et al., A comprehensive set of sequence analysis programs for the VAX. Nucleic Acids Res. Jan. 11, 1984;12(1 Pt 1):387-95.

Deverman et al., Cre-dependent selection yields AAV variants for widespread gene transfer to the adult brain. Nat Biotechnol. Feb. 2016;34(2):204-9.

Dewey, Autonomic dysfunction in Parkinson's disease. Neurol Clin. Oct. 2004;22(3 Suppl):S127-39.

Deyaert et al., A homologue of the Parkinson's disease-associated protein LRRK2 undergoes a monomer-dimer transition during GTP turnover. Nat Commun. Oct. 18, 2017;8(1):1008, 12 pages.

Dhawan et al., Comparative analysis of striatal FDOPA uptake in Parkinson's disease: ratio method versus graphical approach. J Nucl Med. Oct. 2002;43(10):1324-30.

(56) References Cited

OTHER PUBLICATIONS

Di Maio et al., A Central Role for LRRK2 activation in idiopathic Parkinson's disease. Sci Transl Med. Jul. 25, 2018;10(451):eaar5429, 23 pages.
Dickson, Neuropathology of Parkinson disease. Parkinsonism Relat Disord. Jan. 2018;46 Suppl 1 (Suppl 1):S30-S33.
Dimidschstein et al., A viral strategy for targeting and manipulating interneurons across vertebrate species. Nat Neurosci. Dec. 2016;19(12):1743-1749.
Dinculescu et al., AAV-Mediated Clarin-1 Expression in the Mouse Retina: Implications for USH3A Gene Therapy. PLoS One. Feb. 16, 2016;11(2):e0148874, 15 pages.
Ding et al., Biochemical characterization of Junonia coenia densovirus nonstructural protein NS-1. J Virol. Jan. 2002;76(1):338-45.
Doerfler et al., Copackaged AAV9 Vectors Promote Simultaneous Immune Tolerance and Phenotypic Correction of Pompe Disease. Hum Gene Ther. Jan. 2016;27(1):43-59.
Donsante et al., Intracerebroventricular delivery of self-complementary adeno-associated virus serotype 9 to the adult rat brain. Gene Ther. May 2016;23(5):401-7. pre-publication edition.
Doroudchi et al., AAV Gene Transfer of aadc protects dopaminergic and striatal neurons from toxicity of L-DOPA in a primary cultur model. 33rd Annual Meeting of the Society of Neuroscience. Abstract No. 733.4, 2 pages, Nov. 8-12, 2003.
Doroudchi et al., Adeno-associated virus-mediated gene transfer of human aromatic L-amino acid decarboxylase protects mixed striatal primary cultures from L-DOPA toxicity. J Neurochem. 2005;93:634-40.
Dorsey et al., The Emerging Evidence of the Parkinson Pandemic. J Parkinsons Dis. 2018;8(s1):S3-S8.
Douglas et al., Gene therapy for Parkinson's disease: state-of-the-art treatments for neurodegenerative disease. Expert Rev Neurother. Jun. 2013;13(6):695-705.
Drouin et al., Cryo-electron Microscopy Reconstruction and Stability Studies of the Wild Type and the R432A Variant of Adeno-associated Virus Type 2 Reveal that Capsid Structural Stability Is a Major Factor in Genome Packaging. J Virol. Sep. 12, 2016;90(19):8542-51. pre-publication edition.
Durost et al., Gene Therapy with an Adeno-Associated Viral Vector Expressing Human Interleukin-2 Alters Immune System Homeostasis in Humanized Mice. Hum Gene Ther. Mar. 2018;29(3):352-365. pre-publication edition.
Earley et al., Adeno-associated Virus (AAV) Assembly-Activating Protein Is Not an Essential Requirement for Capsid Assembly of AAV Serotypes 4, 5, and 11. J Virol. Jan. 18, 2017;91(3):e01980-16. pre-publication edition.
Earley et al., Identification and characterization of nuclear and nucleolar localization signals in the adeno-associated virus serotype 2 assembly-activating protein. J Virol. Mar. 2015;89(6):3038-48.
Eichler et al., Hematopoietic Stem-Cell Gene Therapy for Cerebral Adrenoleukodystrophy. N Engl J Med. Oct. 26, 2017;377(17):1630-1638.
Eichler et al., The complete connectome of a learning and memory centre in an insect brain. Nature. Aug. 9, 2017;548(7666):175-182.
El-Shamayleh et al., Strategies for targeting primate neural circuits with viral vectors. J Neurophysiol. Jul. 1, 2016;116(1):122-34.
Espay et al., Optimizing extended-release carbidopa/levodopa in Parkinson disease: Consensus on conversion from standard therapy. Neurol Clin Pract. Feb. 2017;7(1):86-93.
Fahn et al., Levodopa and the progression of Parkinson's disease. N Engl J Med. Dec. 9, 2004;351(24):2498-508.
Fahn, The medical treatment of Parkinson disease from James Parkinson to George Cotzias. Mov Disord. Jan. 2015;30(1):4-18.
Fan et al., Behavioral recovery in 6-hydroxydopamine-lesioned rats by cotransduction of striatum with tyrosine hydroxylase and aromatic L-amino acid decarboxylase genes using two separate adeno-associated virus vectors. Hum Gene Ther. Nov. 20, 1998;9(17):2527-35.
Fargnoli et al., Liquid jet delivery method featuring S100A1 gene therapy in the rodent model following acute myocardial infarction. Gene Ther. Feb. 2016;23(2):151-7.
Feng et al., Gene therapy in Parkinson's disease: rationale and current status. CNS Drugs. Mar. 2010;24(3):177-92.
Ferla et al., Prevalence of anti-adeno-associated virus serotype 8 neutralizing antibodies and arylsulfatase B cross-reactive immunologic material in mucopolysaccharidosis VI patient candidates for a gene therapy trial. Hum Gene Ther. Mar. 2015;26(3):145-52.
Fluri et al., Adeno-associated viral vectors engineered for macrolide-adjustable transgene expression in mammalian cells and mice. BMC Biotechnol. Nov. 6, 2007;7:75, 15 pages.
Fol et al., Viral gene transfer of APPsa rescues synaptic failure in an Alzheimer's disease mouse model. Acta Neuropathol. Feb. 2016;131(2):247-266.
Foley et al., Intra-arterial delivery of AAV vectors to the mouse brain after mannitol mediated blood brain barrier disruption. J Control Release. Dec. 28, 2014;196:71-78.
Forsayeth et al., A dose-ranging study of AAV-hAADC therapy in Parkinsonian monkeys. Mol Ther. Oct. 2006;14(4):571-7.
Forsayeth et al., Transduction of antigen-presenting cells in the brain by AAV9 warrants caution in preclinical studies. Mol Ther. Apr. 2015;23(4):612.
Foust et al., Intravascular AAV9 preferentially targets neonatal neurons and adult astrocytes. Nat Biotechnol. Jan. 2009;27(1):59-65.
Francis et al., N-acetylaspartate supports the energetic demands of developmental myelination via oligodendroglial aspartoacylase. Neurobiol Dis. Dec. 2016;96:323-334.
Fu et al., Differential Prevalence of Antibodies Against Adeno-Associated Virus in Healthy Children and Patients with Mucopolysaccharidosis III: Perspective for AAV-Mediated Gene Therapy. Hum Gene Ther Clin Dev. Dec. 2017;28(4):187-196.
Fu et al., Functional correction of neurological and somatic disorders at later stages of disease in MPS IIIa mice by systemic scAAV9-hSGSH gene delivery. Mol Ther Methods Clin Dev. Jun. 8, 2016;3:16036, 12 pages.
Gadalla et al., Development of a Novel AAV Gene Therapy Cassette with Improved Safety Features and Efficacy in a Mouse Model of Rett Syndrome. Mol Ther Methods Clin Dev. Apr. 22, 2017;5:180-190.
Galli et al., Strategies to optimize capsid protein expression and single-stranded DNA formation of adeno-associated virus in Saccharomyces cerevisiae. J Appl Microbiol. Aug. 2017;123(2):414-428.
Gant et al., Reversal of Aging-Related Neuronal Ca2+ Dysregulation and Cognitive Impairment by Delivery of a Transgene Encoding FK506-Binding Protein 12.6/1b to the Hippocampus. J Neurosci. Jul. 29, 2015;35(30):10878-87.
GenBank Accession No. AF396260, Cloning vector pAAV-MCS, complete sequence. 2 pages, dated Aug. 13, 2001.
GenBank Accession No. AH002785, Adeno-associated virus-2 *Homo sapiens* DNA fragment containing the 5' cellular/adeno-associated viral junction. 2 pages, Aug. 25, 2016.
GenBank Accession No. JX445134, Insertion vector scAAV-CMV-GFP, complete sequence. 3 pages, Sep. 30, 2012.
George et al., Gene therapy for hemophilia: past, present and future. Semin Hematol. Jan. 2016;53(1):46-54.
Gessler et al., Gene Therapy for the Treatment of Neurological Disorders: Metabolic Disorders. Methods Mol Biol. 2016;1382:429-65.
Gessler et al., Redirecting N-acetylaspartate metabolism in the central nervous system normalizes myelination and rescues Canavan disease. JCI Insight. Feb. 9, 2017;2(3):e90807, 16 pages.
Gil-Farina et al., Recombinant AAV Integration Is Not Associated With Hepatic Genotoxicity in Nonhuman Primates and Patients. Mol Ther. Jun. 2016;24(6):1100-1105.
Gilkes et al., Mucopolysaccharidosis IIIB confers enhanced neonatal intracranial transduction by AAV8 but not by 5, 9 or rh10. Gene Ther. Mar. 2016;23(3):263-71.
Gilkes et al., Preferred transduction with AAV8 and AAV9 via thalamic administration in the MPS IIIb model: A comparison of four rAAV serotypes. Mol Genet Metab Rep. Dec. 7, 2015;6:48-54.

(56) References Cited

OTHER PUBLICATIONS

Globe Newswire, Voyager Therapeutics Announces Positive Interim Results from Phase 1b Trial of VY-AADC01 for Advanced Parkinson's Disease. Press Release, 6 pages, Dec. 7, 2016.
Golebiowski et al., Direct Intracranial Injection of AAVrh8 Encoding Monkey beta-N-Acetylhexosaminidase Causes Neurotoxicity in the Primate Brain. Hum Gene Ther. Jun. 2017;28(6):510-522.
Gombash et al., Systemic gene delivery transduces the enteric nervous system of guinea pigs and cynomolgus macaques. Gene Ther. Oct. 2017;24(10):640-648. pre-publication edition.
Gombash et al., Systemic Gene Therapy for Targeting the CNS. Methods Mol Biol. 2016;1382:231-7.
Gray-Edwards et al., Adeno-Associated Virus Gene Therapy in a Sheep Model of Tay-Sachs Disease. Hum Gene Ther. Mar. 2018;29(3):312-326. pre-publication edition.
Greig et al., Impact of intravenous infusion time on AAV8 vector pharmacokinetics, safety, and liver transduction in cynomolgus macaques. Mol Ther Methods Clin Dev. Dec. 7, 2016;3:16079, 7 pages.
Greig et al., Intramuscular administration of AAV overcomes pre-existing neutralizing antibodies in rhesus macaques. Vaccine. Dec. 7, 2016;34(50):6323-6329. pre-publication edition.
Gribskov, The A, B, C of Molecular Grammar, Sequence Analysis Primer. Cell. Mar. 6, 1992;68:827-828.
Grieger et al., Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-297.
Griesenbach et al., Cystic Fibrosis Gene Therapy in the UK and Elsewhere. Hum Gene Ther. May 2015;26(5):266-75.
Grimm et al., E Pluribus Unum: 50 Years of Research, Millions of Viruses, and One Goal—Tailored Acceleration of AAV Evolution. Mol Ther. Dec. 2015;23(12):1819-31.
Grimm et al., In vitro and in vivo gene therapy vector evolution via multispecies interbreeding and retargeting of adeno-associated viruses. J Virol. Jun. 2008;82(12):5887-911.
Grimm et al., Progress in adeno-associated virus type 2 vector production: promises and prospects for clinical use. Hum Gene Ther. Oct. 10, 1999;10(15):2445-50.
Grimm et al., Small But Increasingly Mighty: Latest Advances in AAV Vector Research, Design, and Evolution. Hum Gene Ther. Nov. 2017;28(11):1075-1086. pre-publication edition.
Grimm et al., Titration of AAV-2 particles via a novel capsid ELISA: packaging of genomes can limit production of recombinant AAV-2. Gene Ther. Jul. 1999;6(7):1322-30.
Grimson et al., MicroRNA targeting specificity in mammals: determinants beyond seed pairing. Mol Cell. Jul. 6, 2007;27(1):91-105.
Grosse et al., Relevance of Assembly-Activating Protein for Adeno-associated Virus Vector Production and Capsid Protein Stability in Mammalian and Insect Cells. J Virol. Sep. 27, 2017;91(20):e01198-17. pre-publication edition.
Gruntman et al., Delivery of Adeno-Associated Virus Gene Therapy by Intravascular Limb Infusion Methods. Hum Gene Ther Clin Dev. Sep. 2015;26(3):159-64.
Gruntman et al., Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Gruntman et al., Stability and compatibility of recombinant adeno-associated virus under conditions commonly encountered in human gene therapy trials. Hum Gene Ther Methods. Apr. 2015;26(2):71-6.
GTEx Consortium et al., Genetic effects on gene expression across human tissues. Nature. Oct. 11, 2017;550(7675):204-213.
Guggino et al., A Preclinical Study in Rhesus Macaques for Cystic Fibrosis to Assess Gene Transfer and Transduction by AAV1 and AAV5 with a Dual-Luciferase Reporter System. Hum Gene Ther Clin Dev. Sep. 2017;28(3):145-156. pre-publication edition.
Gurda et al., Evaluation of AAV-mediated Gene Therapy for Central Nervous System Disease in Canine Mucopolysaccharidosis VII. Mol Ther. Feb. 2016;24(2):206-216.
Hacker et al., Effects of deep brain stimulation on rest tremor progression in early stage Parkinson disease. Neurology. Jul. 31, 2018;91(5):e463-e471.
Hadaczek et al., Eight years of clinical improvement in MPTP-lesioned primates after gene therapy with AAV2-hAADC. Mol Ther. Aug. 2010;18(8):1458-61.
Hadaczek et al., GDNF signaling implemented by GM1 ganglioside; failure in Parkinson's disease and GM1-deficient murine model. Exp Neurol. Jan. 2015;263:177-89.
Hagedorn et al., S/MAR Element Facilitates Episomal Long-Term Persistence of Adeno-Associated Virus Vector Genomes in Proliferating Cells. Hum Gene Ther. Dec. 2017;28(12):1169-1179. pre-publication edition.
Hagg et al., Using AAV vectors expressing the beta2-adrenoceptor or associated Ga proteins to modulate skeletal muscle mass and muscle fibre size. Sci Rep. Mar. 14, 2016;6:23042, 10 pages.
Hai et al., Long-term transduction of miniature pig parotid glands using serotype 2 adeno-associated viral vectors. J Gene Med. Jun. 2009;11(6):506-14.
Halder et al., Structure of neurotropic adeno-associated virus AAVrh.8. J Struct Biol. Oct. 2015;192(1):21-36.
Han et al., Enhanced efficacy from gene therapy in Pompe disease using coreceptor blockade. Hum Gene Ther. Jan. 2015;26(1):26-35.
Harrington et al., Neutralizing Antibodies Against Adeno-Associated Viral Capsids in Patients with mut Methylmalonic Acidemia. Hum Gene Ther. May 2016;27(5):345-53.
Hastie et al., Adeno-associated virus at 50: a golden anniversary of discovery, research, and gene therapy success—a personal perspective. Hum Gene Ther. May 2015;26(5):257-65.
Hastie et al., Recombinant adeno-associated virus vectors in the treatment of rare diseases. Expert Opin Orphan Drugs. 2015;3(6):675-689.
Hauser et al., A home diary to assess functional status in patients with Parkinson's disease with motor fluctuations and dyskinesia. Clin Neuropharmacol. Mar.-Apr. 2000;23(2):75-81.
Heim et al., Engineering green fluorescent protein for improved brightness, longer wavelengths and fluorescence resonance energy transfer. Curr Biol. Feb. 1, 1996;6(2):178-82.
Heim et al., Improved green fluorescence. Nature. Feb. 23, 1995;373(6516):663-4.
Heim et al., Wavelength mutations and posttranslational autoxidation of green fluorescent protein. Proc Natl Acad Sci U S A. Dec. 20, 1994;91(26):12501-4.
Heller et al., Human a7 Integrin Gene (ITGA7) Delivered by Adeno-Associated Virus Extends Survival of Severely Affected Dystrophin/Utrophin-Deficient Mice. Hum Gene Ther. Oct. 2015;26(10):647-56.
Hemphill et al., Adeno-associated virus gene therapy vector scAAVIGF-I for transduction of equine articular chondrocytes and RNA-seq analysis. Osteoarthritis Cartilage. May 2016;24(5):902-11.
Herrera-Carrillo et al., Improving miRNA Delivery by Optimizing miRNA Expression Cassettes in Diverse Virus Vectors. Hum Gene Ther Methods. Aug. 2017;28(4):177-190.
Herzog et al., Long-term correction of canine hemophilia B by gene transfer of blood coagulation factor IX mediated by adeno-associated viral vector. Nat Med. Jan. 1999;5(1):56-63.
Hickey et al., Tropism of engineered and evolved recombinant AAV serotypes in the rd1 mouse and ex vivo primate retina. Gene Ther. Dec. 2017;24(12):787-800. pre-publication edition.
Hinderer et al., Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915.
Hinderer et al., Evaluation of Intrathecal Routes of Administration for Adeno-Associated Viral Vectors in Large Animals. Hum Gene Ther. Jan. 2018;29(1):15-24. pre-publication edition.
Hinderer et al., Neonatal Systemic AAV Induces Tolerance to CNS Gene Therapy in MPS I Dogs and Nonhuman Primates. Mol Ther. Aug. 2015;23(8):1298-1307.
Hirsch et al., Delivering Transgenic DNA Exceeding the Carrying Capacity of AAV Vectors. Methods Mol Biol. 2016;1382:21-39.

(56) References Cited

OTHER PUBLICATIONS

Hocquemiller et al., Adeno-Associated Virus-Based Gene Therapy for CNS Diseases. Hum Gene Ther. Jul. 2016;27(7):478-96. pre-publication edition.

Hordeaux et al., Efficient central nervous system AAVrh10-mediated intrathecal gene transfer in adult and neonate rats. Gene Ther. Apr. 2015;22(4):316-24.

Hordeaux et al., Long-term neurologic and cardiac correction by intrathecal gene therapy in Pompe disease. Acta Neuropathol Commun. Sep. 6, 2017;5(1):66, 19 pages.

Hu et al., Opposing effects of viral mediated brain expression of apolipoprotein E2 (apoE2) and apoE4 on apoE lipidation and Aβ metabolism in apoE4-targeted replacement mice. Mol Neurodegener. Mar. 5, 2015;10:6, 11 pages.

Huang et al., Characterization of the Adeno-Associated Virus 1 and 6 Sialic Acid Binding Site. J Virol. May 12, 2016;90(11):5219-5230. pre-publication edition.

Huang et al., Targeting Visceral Fat by Intraperitoneal Delivery of Novel AAV Serotype Vector Restricting Off-Target Transduction in Liver. Mol Ther Methods Clin Dev. Jun. 19, 2017;6:68-78.

Hudry et al., Efficient Gene Transfer to the Central Nervous System by Single-Stranded Anc80L65. Mol Ther Methods Clin Dev. Jul. 23, 2018;10:197-209.

Hudry et al., Exosome-associated AAV vector as a robust and convenient neuroscience tool. Gene Ther. Apr. 2016;23(4):380-92. pre-publication edition.

Hudry et al., Therapeutic AAV Gene Transfer to the Nervous System: A Clinical Reality. Neuron. Mar. 6, 2019;101(5):839-862.

Hwu et al., AADC deficiency: occurring in humans, modeled in rodents. Adv Pharmacol. 2013;68:273-84.

Hwu et al., Gene therapy for aromatic L-amino acid decarboxylase deficiency. Sci Transl Med. May 16, 2012;4(134):134ra61, 8 pages.

Ibrahim et al., Stable liver-specific expression of human IDOL in humanized mice raises plasma cholesterol. Cardiovasc Res. May 1, 2016;110(1):23-9.

Ito et al., HMGB1 facilitates repair of mitochondrial DNA damage and extends the lifespan of mutant ataxin-1 knock-in mice. EMBO Mol Med. Jan. 2015;7(1):78-101.

Ito et al., In utero gene therapy rescues microcephaly caused by Pqbp1-hypofunction in neural stem progenitor cells. Mol Psychiatry. Apr. 2015;20(4):459-71.

Iwamoto et al., Control of phosphorothioate stereochemistry substantially increases the efficacy of antisense oligonucleotides. Nat Biotechnol. Sep. 2017;35(9):845-851. pre-publication edition.

Iwayama et al., Adeno Associated Virus 9-Based Gene Therapy Delivers a Functional Monocarboxylate Transporter 8, Improving Thyroid Hormone Availability to the Brain of Mct8-Deficient Mice. Thyroid. Sep. 2016;26(9):1311-9.

Jackson et al., Better Targeting, Better Efficiency for Wide-Scale Neuronal Transduction with the Synapsin Promoter and AAV-PHP.B. Front Mol Neurosci. Nov. 4, 2016;9:116, 11 pages.

Jankovic et al., Safety and Tolerability of Multiple Ascending Doses of PRX002/RG7935, an Anti-α-Synuclein Monoclonal Antibody, in Patients With Parkinson Disease: A Randomized Clinical Trial. JAMA Neurol. Oct. 1, 2018;75(10):1206-1214.

Jeong et al., Matricellular Protein CCN5 Reverses Established Cardiac Fibrosis. J Am Coll Cardiol. Apr. 5, 2016;67(13):1556-1568.

Jin et al., Direct Liquid Chromatography/Mass Spectrometry Analysis for Complete Characterization of Recombinant Adeno-Associated Virus Capsid Proteins. Hum Gene Ther Methods. Oct. 2017;28(5):255-267.

Jolesz, Intraoperative imaging in neurosurgery: where will the future take us? Acta Neurochir Suppl. 2011;109:21-5.

Jungmann et al., Protocol for Efficient Generation and Characterization of Adeno-Associated Viral Vectors. Human Gene Therapy Methods. Oct. 1, 2017;28(5):235-246. pre-publication edition.

Kailasan et al., Parvovirus Family Conundrum: What Makes a Killer? Annu Rev Virol. Nov. 2015;2(1):425-50.

Kailasan et al., Structure of an enteric pathogen, bovine parvovirus. J Virol. Mar. 2015;89(5):2603-14.

Kajigaya et al., Self-assembled B19 parvovirus capsids, produced in a baculovirus system, are antigenically and immunogenically similar to native virions. Proc Natl Acad Sci U S A. Jun. 1, 1991;88(11):4646-50.

Kanaan et al., Rationally Engineered AAV Capsids Improve Transduction and Volumetric Spread in the CNS. Mol Ther Nucleic Acids. Sep. 15, 2017;8:184-197. Supplemental Material.

Kao et al., Effect of naltrexone on neuropathic pain in mice locally transfected with the mutant μ-opioid receptor gene in spinal cord. Br J Pharmacol. Jan. 2015;172(2):630-41.

Karumuthil-Melethil et al., Novel Vector Design and Hexosaminidase Variant Enabling Self-Complementary Adeno-Associated Virus for the Treatment of Tay-Sachs Disease. Hum Gene Ther. Jul. 2016;27(7):509-21. pre-publication edition.

Katz et al., AAV gene transfer delays disease onset in a TPP1-deficient canine model of the late infantile form of Batten disease. Sci Transl Med. Nov. 11, 2015;7(313):313ra180, 23 pages.

Katz et al., Use of Adeno-Associated Virus Vector for Cardiac Gene Delivery in Large-Animal Surgical Models of Heart Failure. Hum Gene Ther Clin Dev. Sep. 2017;28(3):157-164. pre-publication edition.

Kells et al., Efficient gene therapy-based method for the delivery of therapeutics to primate cortex. Proc Natl Acad Sci U S A. Feb. 17, 2009;106(7):2407-11.

Keravala et al., Evaluating AAV Hybrid Variants for Improved Tropism after Intravitreal Gene Delivery to the Retina. Molecular Therapy. May 2015;23:S127-S128, Abstract No. 316.

Kern et al., Identification of a heparin-binding motif on adeno-associated virus type 2 capsids. J Virol. Oct. 2003;77(20):11072-81.

Kikuchi et al., Human iPS cell-derived dopaminergic neurons function in a primate Parkinson's disease model. Nature. Aug. 30, 2017;548(7669):592-596.

Kim et al., Mutagenic Analysis of an Adeno-Associated Virus Variant Capable of Simultaneously Promoting Immune Resistance and Robust Gene Delivery. Hum Gene Ther. Jan. 2018;29(1):25-41. pre-publication edition.

Kim et al., RNA Interference of Human alpha-Synuclein in Mouse. Front Neurol. Jan. 31, 2017;8:13, 10 pages.

Kirik et al., Gene therapy for Parkinson's disease: Disease modification by GDNF family of ligands. Neurobiol Dis. Jan. 2017;97(Pt B):179-188.

Kirnbauer et al., Virus-like particles of bovine papillomavirus type 4 in prophylactic and therapeutic immunization. Virology. May 1, 1996;219(1):37-44.

Knezevic et al., Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.

Ko et al., AAV8-mediated expression of N-acetylglucosamine-1-phosphate transferase attenuates bone loss in a mouse model of mucolipidosis II. Mol Genet Metab. Apr. 2016;117(4):447-55. pre-publication edition.

Kohlbrenner et al., Production and Characterization of Vectors Based on the Cardiotropic AAV Serotype 9. Methods Mol Biol. 2017;1521:91-107.

Kojima et al., Gene therapy improves motor and mental function of aromatic l-amino acid decarboxylase deficiency. Brain. Feb. 1, 2019;142(2):322-333.

Kondratov et al., Direct Head-to-Head Evaluation of Recombinant Adeno-associated Viral Vectors Manufactured in Human versus Insect Cells. Molecular Therapy. Dec. 6, 2017;25(12):2661-2675. pre-publication edition.

Kordower et al., Disease duration and the integrity of the nigrostriatal system in Parkinson's disease. Brain. Aug. 2013;136(Pt 8):2419-31.

Kothari et al., Iodine-124 Labeled Adeno-Associated Virus: A Promising Tool for Tracking Gene Therapy. The Journal of Nuclear Medicine. 2015;15(Suppl 3):Abstract 494.

Kothari et al., Radioiodinated Capsids Facilitate In Vivo Non-Invasive Tracking of Adeno-Associated Gene Transfer Vectors. Sci Rep. Jan. 6, 2017;7:39594, 10 pages.

(56) References Cited

OTHER PUBLICATIONS

Kotin et al., Manufacturing Clinical Grade Recombinant Adeno-Associated Virus Using Invertebrate Cell Lines. Hum Gene Ther. Apr. 2017;28(4):350-360. pre-publication edition.
Kotin et al., Organization of adeno-associated virus DNA in latently infected Detroit 6 cells. Virology. Jun. 1989;170(2):460-7.
Kotin, Large-scale recombinant adeno-associated virus production. Hum Mol Genet. Apr. 15, 2011;20(R1):R2-6.
Kotterman et al., Antibody neutralization poses a barrier to intravitreal adeno-associated viral vector gene delivery to non-human primates. Gene Ther. Feb. 2015;22(2):116-26.
Kotterman et al., Enhanced cellular secretion of AAV2 by expression of foreign viral envelope proteins. Biochemical Engineering Journal. Jan. 15, 2015;93:108-114.
Kozak, Interpreting cDNA sequences: some insights from studies on translation. Mamm Genome. Aug. 1996;7(8):563-74.
Kozak, Point mutations define a sequence flanking the AUG initiator codon that modulates translation by eukaryotic ribosomes. Cell. Jan. 31, 1986;44(2):283-92.
Kozak, The scanning model for translation: an update. J Cell Biol. Feb. 1989;108(2):229-41.
Kubu et al., Patients' shifting goals for deep brain stimulation and informed consent. Neurology. Jul. 31, 2018;91(5):e472-e478.
Kurosaki et al., Optimization of adeno-associated virus vector-mediated gene transfer to the respiratory tract. Gene Ther. May 2017;24(5):290-297.
Lai et al., Aquaporin gene therapy corrects Sjogren's syndrome phenotype in mice. Proc Natl Acad Sci U S A. May 17, 2016;113(20):5694-9.
Landau et al., In Vivo Zinc Finger Nuclease-mediated Targeted Integration of a Glucose-6-phosphatase Transgene Promotes Survival in Mice With Glycogen Storage Disease Type IA. Mol Ther. Apr. 2016;24(4):697-706.
Landeck et al., Toxic effects of human and rodent variants of alpha-synuclein in vivo. Eur J Neurosci. Feb. 2017;45(4):536-547.
Landegger et al., A synthetic AAV vector enables safe and efficient gene transfer to the mammalian inner ear. Nat Biotechnol. Mar. 2017;35(3):280-284. pre-publication edition.
Latourelle et al., Large-scale identification of clinical and genetic predictors of motor progression in patients with newly diagnosed Parkinson's disease: a longitudinal cohort study and validation. Lancet Neurol. Nov. 2017;16(11):908-916.
Le Pichon et al., Loss of dual leucine zipper kinase signaling is protective in animal models of neurodegenerative disease. Sci Transl Med. Aug. 16, 2017;9(403):eaag0394, 14 pages.
Lee et al., A Neuron-Specific Gene Therapy Relieves Motor Deficits in Pompe Disease Mice. Mol Neurobiol. Jun. 2018;55(6):5299-5309.
Lee et al., Benefits of Neuronal Preferential Systemic Gene Therapy for Neurotransmitter Deficiency. Mol Ther. Oct. 2015;23(10):1572-81.
Lee et al., Mutation-adapted U1 snRNA corrects a splicing error of the dopa decarboxylase gene. Hum Mol Genet. Dec. 1, 2016;25(23):5142-5147. pre-publication edition.
Lee et al., Regulation of the dopaminergic system in a murine model of aromatic L-amino acid decarboxylase deficiency. Neurobiol Dis. Apr. 2013;52:177-90.
Lee et al., Treatment of congenital neurotransmitter deficiencies by intracerebral ventricular injection of an adeno-associated virus serotype 9 vector. Hum Gene Ther. Mar. 2014;25(3):189-98.
Lentz et al., Insight into the mechanism of inhibition of adeno-associated virus by the Mre11/Rad50/Nbs1 complex. J Virol. Jan. 2015;89(1):181-94.
Levacic et al., Minicircle Versus Plasmid DNA Delivery by Receptor-Targeted Polyplexes. Hum Gene Ther. Oct. 2017;28(10):862-874.
Li et al., Efficient and Targeted Transduction of Nonhuman Primate Liver With Systemically Delivered Optimized AAV3B Vectors. Mol Ther. Dec. 2015;23(12):1867-76.

Li et al., Production and characterization of novel recombinant adeno-associated virus replicative-form genomes: a eukaryotic source of DNA for gene transfer. PLoS One. Aug. 1, 2013;8(8):e69879, 14 pages.
Li et al., Site-Directed Mutagenesis of Surface-Exposed Lysine Residues Leads to Improved Transduction by AAV2, But Not AAV8, Vectors in Murine Hepatocytes In Vivo. Hum Gene Ther Methods. Dec. 2015;26(6):211-20.
Li et al., The impact of rare variation on gene expression across tissues. Nature. Oct. 11, 2017;550(7675):239-243.
Lidstone, Great expectations: the placebo effect in Parkinson's disease. Handb Exp Pharmacol. 2014;225:139-47.
Ling et al., Development of Optimized AAV Serotype Vectors for High-Efficiency Transduction at Further Reduced Doses. Hum Gene Ther Methods. Aug. 2016;27(4):143-9. pre-publication edition.
Ling et al., Enhanced transgene expression from recombinant single-stranded D-sequence-substituted adeno-associated virus vectors in human cell lines in vitro and in murine hepatocytes in vivo. J Virol. Jan. 15, 2015;89(2):952-61.
Ling et al., High-Efficiency Transduction of Primary Human Hematopoietic Stem/Progenitor Cells by AAV6 Vectors: Strategies for Overcoming Donor-Variation and Implications in Genome Editing. Sci Rep. Oct. 19, 2016;6:35495.
Ling et al., Strategies to generate high-titer, high-potency recombinant AAV3 serotype vectors. Mol Ther Methods Clin Dev. May 4, 2016;3:16029, 8 pages.
Liu et al., Single-cell transcriptomics reconstructs fate conversion from fibroblast to cardiomyocyte. Nature. Nov. 2, 2017;551(7678):100-104.
Lloyd et al., The neurochemistry of Parkinson's disease: effect of L-dopa therapy. J Pharmacol Exp Ther. Dec. 1975;195(3):453-64.
Logan et al., Identification of liver-specific enhancer-promoter activity in the 3' untranslated region of the wild-type AAV2 genome. Nat Genet. Aug. 2017;49(8):1267-1273. pre-publication edition.
Loring et al., Development of rAAV2-CFTR: History of the First rAAV Vector Product to be Used in Humans. Hum Gene Ther Methods. Apr. 2016;27(2):49-58.
Low et al., Direct and retrograde transduction of nigral neurons with AAV6, 8, and 9 and intraneuronal persistence of viral particles. Hum Gene Ther. Jun. 2013;24(6):613-29.
Lu et al., A 5' Noncoding Exon Containing Engineered Intron Enhances Transgene Expression from Recombinant AAV Vectors in vivo. Hum Gene Ther. Jan. 2017;28(1):125-134.
Lu et al., Therapeutic Benefit of TH-engineered mesenchymal stem cells for Parkinson's disease. Brain Research Protocols. 2005;15:46-51.
Lukashchuk et al., AAV9-mediated central nervous system-targeted gene delivery via cisterna magna route in mice. Mol Ther Methods Clin Dev. Feb. 17, 2016;3:15055, 10 pages.
Luo et al., AAVS1-Targeted Plasmid Integration in AAV Producer Cell Lines. Hum Gene Ther Methods. Jun. 2017;28(3):124-138. pre-publication edition.
Mack et al., Minimally Effective Dose of Systemic AAV8-MTM1 Needed to Prolong Survival and Correct Severe Muscle Pathology in a Canine Model of X-Linked Myotubular Myopathy. Molecular Therapy. May 1, 2015;23(Suppl. 1):S201. Abstract No. 503.
Mack et al., Systemic AAV8-Mediated Gene Therapy Drives Whole-Body Correction of Myotubular Myopathy in Dogs. Mol Ther. Apr. 5, 2017;25(4):839-854.
Maclullich et al., Enlarged perivascular spaces are associated with cognitive function in healthy elderly men. J Neurol Neurosurg Psychiatry. Nov. 2004;75(11):1519-23.
Magnani et al., Dengue Virus Evades AAV-Mediated Neutralizing Antibody Prophylaxis in Rhesus Monkeys. Mol Ther. Oct. 4, 2017;25(10):2323-2331.
Majowicz et al., Successful Repeated Hepatic Gene Delivery in Mice and Non-human Primates Achieved by Sequential Administration of AAV5ch and AAV1. Mol Ther. Aug. 2, 2017;25(8):1831-1842.
Man et al., Cell reprogramming approaches in gene- and cell-based therapies for Parkinson's disease. J Control Release. Sep. 28, 2018;286:114-124.

(56) References Cited

OTHER PUBLICATIONS

Mandel et al., Novel oligodendroglial alpha synuclein viral vector models of multiple system atrophy: studies in rodents and nonhuman primates. Acta Neuropathol Commun. Jun. 16, 2017;5(1):47, 15 pages.
Manfredsson, Methods in Molecular Biology. Gene Therapy for Neurological Disorders, Methods and Protocols. Humana Press, NJ. 488 pages, (2016).
Mao et al., Single point mutation in adeno-associated viral vectors -DJ capsid leads to improvement for gene delivery in vivo. BMC Biotechnol. Jan. 5, 2016;16:1, 8 pages.
Maramatsu et al., A phase I study of aromatic L-amino acid decarboxylase gene therapy for Parkinson's disease. Mol Ther. Sep. 2010;18(9):1731-5.
Marcos-Contreras et al., Sustained correction of FVII deficiency in dogs using AAV-mediated expression of zymogen FVII. Blood. Feb. 4, 2016;127(5):565-71.
Marks et al., Long-Term Safety of Patients with Parkinson's Disease Receiving rAAV2-Neurturin (CERE-120) Gene Transfer. Hum Gene Ther. Jul. 2016;27(7):522-7.
Marongiu et al., Gene therapy blockade of dorsal striatal p11 improves motor function and dyskinesia in parkinsonian mice. Proc Natl Acad Sci U S A. Feb. 2, 2016;113(5):1423-8.
Marsic et al., Altering Tropism of rAAV by Directed Evolution. Methods Mol Biol. 2016;1382:151-73.
Mason et al., Delivery and evaluation of recombinant adeno-associated viral vectors in the equine distal extremity for the treatment of laminitis. Equine Vet J. Jan. 2017;49(1):79-86.
Matsushita et al., Adeno-associated virus vectors can be efficiently produced without helper virus. Gene Ther. Jul. 1998;5(7):938-45.
Matsuura et al., Human herpesvirus 6 major immediate early promoter has strong activity in T cells and is useful for heterologous gene expression. Virol J. Jan. 11, 2011;8:9, 9 pages.
Matsuzaki et al., Intravenous administration of the adeno-associated virus-PHP.B capsid fails to upregulate transduction efficiency in the marmoset brain. Neurosci Lett. Feb. 5, 2018;665:182-188.
McClements et al., A fragmented adeno-associated viral dual vector strategy for treatment of diseases caused by mutations in large genes leads to expression of hybrid transcripts. J Genet Syndr Gene Ther. Nov. 14, 2016;7(5):311, 8 pages.
Meadows et al., A GLP-Compliant Toxicology and Biodistribution Study: Systemic Delivery of an rAAV9 Vector for the Treatment of Mucopolysaccharidosis IIIB. Hum Gene Ther Clin Dev. Dec. 2015;26(4):228-42.
Mendell et al., Follistatin Gene Therapy for Sporadic Inclusion Body Myositis Improves Functional Outcomes. Mol Ther. Apr. 5, 2017;25(4):870-879.
Mendoza et al., AAV-mediated delivery of optogenetic constructs to the macaque brain triggers humoral immune responses. J Neurophysiol. May 1, 2017;117(5):2004-2013. pre-publication edition.
Merkel et al., Trafficking of AAV Vectors Across a Model of the Blood-Brain Barrier; a Comaparative Study of Transcytosis and Transduction Using Primary Human Brain Endothelial Cells. J Neurochem. Jan. 2017;140(2):216-230. pre-publication edition.
Merkel et al., Trafficking of adeno-associated virus vectors across a model of the blood-brain barrier; a comparative study of transcytosis and transduction using primary human brain endothelial cells. Journal of Neurochemistry. 2017;140:216-230.
Merten et al., Viral vectors for gene therapy and gene modification approaches. Biochemical Engineering Journal. Apr. 15, 2016;108:98-115.
Meyer et al., Improving single injection CSF delivery of AAV9-mediated gene therapy for SMA: a dose-response study in mice and nonhuman primates. Mol Ther. Mar. 2015;23(3):477-87.
Mietzsch et al., OneBac 2.0: Sf9 Cell Lines for Production of AAV1, AAV2, and AAV8 Vectors with Minimal Encapsidation of Foreign DNA. Hum Gene Ther Methods. Feb. 2017;28(1):15-22. pre-publication edition.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. pre-publication edition.
Mingozzi et al., Adeno-Associated Viral Vectors at the Frontier between Tolerance and Immunity. Front Immunol. Mar. 17, 2015;6:120, 13 pages.
Mingozzi et al., Overcoming the Host Immune Response to Adeno-Associated Virus Gene Delivery Vectors: The Race Between Clearance, Tolerance, Neutralization, and Escape. Annu Rev Virol. Sep. 29, 2017;4(1):511-534.
Mittal et al., beta2-Adrenoreceptor is a regulator of the a-synuclein gene driving risk of Parkinson's disease. Science. Sep. 1, 2017;357(6354):891-898.
Mittermeyer et al., Long-term evaluation of a phase 1 study of AADC gene therapy for Parkinson's disease. Hum Gene Ther. Apr. 2012;23(4):377-81.
Miyanohara et al., Potent spinal parenchymal AAV9-mediated gene delivery by subpial injection in adult rats and pigs. Mol Ther Methods Clin Dev. Jul. 13, 2016;3:16046, 10 pages.
Moffett et al., Hit-and-run programming of therapeutic cytoreagents using mRNA nanocarriers. Nat Commun. Aug. 30, 2017;8(1):389, 13 pages.
Morabito et al., AAV-PHP.B-Mediated Global-Scale Expression in the Mouse Nervous System Enables GBA1 Gene Therapy for Wide Protection from Synucleinopathy. Molecular Therapy. Dec. 6, 2017;25(12):2727-2742. pre-publication edition.
Morizane et al., MHC matching improves engraftment of iPSC-derived neurons in non-human primates. Nat Commun. Aug. 30, 2017;8(1):385, 12 pages.
Moser et al., AAV Vectorization of DSB-mediated Gene Editing Technologies. Current Gene Therapy. 2016;26:207-219.
Muramatsu et al., A phase I study of aromatic L-amino acid decarboxylase gene therapy for Parkinson's disease. Mol Ther. Sep. 2010;18(9):1731-5.
Muramatsu et al., Behavioral recovery in a primate model of Parkinson's disease by triple transduction of striatal cells with adeno-associated viral vectors expressing dopamine-synthesizing enzymes. Hum Gene Ther. Feb. 10, 2002;13(3):345-54.
Murlidharan et al., Glymphatic fluid transport controls paravascular clearance of AAV vectors from the brain. JCI Insight. Sep. 8, 2016;1(14):e88034, 11 pages.
Murlidharan et al., Unique glycan signatures regulate adeno-associated virus tropism in the developing brain. J Virol. Apr. 2015;89(7):3976-87. pre-publication edition.
Muzyczka et al., AAV's Golden Jubilee. Mol Ther. May 2015;23(5):807-808.
Myers et al., Optimal alignments in linear space. Comput Appl Biosci. Mar. 1988;4(1):11-7.
Nagatsu et al., Biochemistry of postmortem brains in Parkinson's disease: historical overview and future prospects. J Neural Transm Suppl. 2007;(72):113-20.
Naidoo et al., Extensive Transduction and Enhanced Spread of a Modified AAV2 Capsid in the Non-human Primate CNS. Mol Ther. Oct. 3, 2018;26(10):2418-2430.
Nambiar et al., Characteristics of Minimally Oversized Adeno-Associated Virus Vectors Encoding Human Factor VIII Generated Using Producer Cell Lines and Triple Transfection. Hum Gene Ther Methods. Feb. 2017;28(1):23-38. pre-publication edition.
Nery et al., New methods for investigation of neuronal migration in embryonic brain explants. J Neurosci Methods. Jan. 15, 2015;239:80-4.
Neuberger et al., Establishment of two quantitative nested qPCR assays targeting the human EPO transgene. Gene Ther. Apr. 2016;23(4):330-9.
Ng et al., Clinical features and pharmacotherapy of childhood monoamine neurotransmitter disorders. Paediatr Drugs. Aug. 2014;16(4):275-91.
Nicolson et al., Identification and Validation of Small Molecules That Enhance Recombinant Adeno-associated Virus Transduction following High-Throughput Screens. J Virol. Jul. 27, 2016;90(16):7019-7031. pre-publication edition.

(56) References Cited

OTHER PUBLICATIONS

Nutt et al., The response to levodopa in Parkinson's disease: imposing pharmacological law and order. Ann Neurol. May 1996;39(5):561-73.
Nygaard et al., A universal system to select gene-modified hepatocytes in vivo. Sci Transl Med. Jun. 8, 2016;8(342):342ra79, 10 pages.
Ojala et al., Adeno-associated virus vectors and neurological gene therapy. Neuroscientist. Feb. 2015;21(1):84-98.
Ojala et al., In Vivo Selection of a Computationally Designed SCHEMA AAV Library Yields a Novel Variant for Infection of Adult Neural Stem Cells in the SVZ. Mol Ther. Jan. 3, 2018;26(1):304-319. pre-publication edition.
Olanow et al., Gene delivery of neurturin to putamen and substantia nigra in Parkinson disease: A double-blind, randomized, controlled trial. Ann Neurol. Aug. 2015;78(2):248-57.
Olanow et al., Risk of dyskinesia in Parkinsons's disease patients who already have developed wearing-off: A secondary analysis of STRIDE-PD study. J Neurol Sci. 2013;333:e65-e66.
Oliva et al., An automated classification of the structure of protein loops. J Mol Biol. Mar. 7, 1997;266(4):814-30.
Osmon et al., Systemic Gene Transfer of a Hexosaminidase Variant Using an scAAV9.47 Vector Corrects GM2 Gangliosidosis in Sandhoff Mice. Hum Gene Ther. Jul. 2016;27(7):497-508. pre-publication edition.
Ossig et al., Treatment of Parkinson's disease in the advanced stage. J Neural Transm (Vienna). Apr. 2013;120(4):523-9.
Pacouret et al., AAV-ID: A Rapid and Robust Assay for Batch-to-Batch Consistency Evaluation of AAV Preparations. Mol Ther. Jun. 7, 2017;25(6):1375-1386.
Palfi et al., Long-Term Follow-Up of a Phase I/II Study of ProSavin, a Lentiviral Vector Gene Therapy for Parkinson's Disease. Hum Gene Ther Clin Dev. Sep. 2018;29(3):148-155.
Pan et al., Gene therapy restores auditory and vestibular function in a mouse model of Usher syndrome type 1c. Nat Biotechnol. Mar. 2017;35(3):264-272. pre-publication edition.
Parr et al., Tumor-selective transgene expression in vivo mediated by an E2F-responsive adenoviral vector. Nat Med. Oct. 1997;3(10):1145-9.
Paul et al., Safety and tolerability of intracerebroventricular PDGF-BB in Parkinson's disease patients. J Clin Invest. Mar. 2, 2015;125(3):1339-46.
Paulk et al., Bioengineered AAV Capsids with Combined High Human Liver Transduction In Vivo and Unique Humoral Seroreactivity. Mol Ther. Jan. 3, 2018;26(1):289-303. pre-publication edition.
PD Med Collaborative Group et al., Long-term effectiveness of dopamine agonists and monoamine oxidase B inhibitors compared with levodopa as initial treatment for Parkinson's disease (Pd Med): a large, open-label, pragmatic randomised trial. Lancet. Sep. 27, 2014;384(9949):1196-205.
Penaud-Budloo et al., Accurate Identification and Quantification of DNA Species by Next-Generation Sequencing in Adeno-Associated Viral Vectors Produced in Insect Cells. Hum Gene Ther Methods. Jun. 2017;28(3):148-162. pre-publication edition.
Petit et al., Rod Outer Segment Development Influences AAV-Mediated Photoreceptor Transduction After Subretinal Injection. Hum Gene Ther. Jun. 2017;28(6):464-481.
Pierce et al., The Status of RPE65 Gene Therapy Trials: Safety and Efficacy. Cold Spring Harb Perspect Med. Jan. 29, 2015;5(9):a017285, 15 pages.
Pierson et al., Resolving Adeno-Associated Viral Particle Diversity With Charge Detection Mass Spectrometry. Anal Chem. Jul. 5, 2016;88(13):6718-25. pre-publication edition.
Piguet et al., Clinical Gene Therapy for Neurodegenerative Diseases: Past, Present, and Future. Hum Gene Ther. Nov. 2017;28(11):988-1003.
Pillay et al., Adeno-associated Virus (AAV) Serotypes Have Distinctive Interactions with Domains of the Cellular AAV Receptor. J Virol. Aug. 24, 2017;91(18):e00391-17. pre-publication edition.
Pillay et al., An essential receptor for adeno-associated virus infection. Nature. Feb. 4, 2016;530(7588):108-12.
Pillay et al., Corrigendum: An essential receptor for adeno-associated virus infection. Nature. Nov. 17, 2016;539(7629):456.
Pillay et al., Host determinants of adeno-associated viral vector entry. Curr Opin Virol. Jun. 2017;24:124-131.
Platt et al., Embryonic disruption of the candidate dyslexia susceptibility gene homolog Kiaa0319-like results in neuronal migration disorders. Neuroscience. Sep. 17, 2013;248:585-93.
Ponder et al., Intrathecal injection of lentiviral vector results in high expression in the brain of mucopolysaccharidosis VII dogs but the pattern of expression is different than for AAV9 or AAV-rh10. Molecular Genetics and Metabolism. Feb. 2015;114(2):S95-S96, Abstract 210.
Poon et al., Distribution of Kiaa0319-like immunoreactivity in the adult mouse brain—a novel protein encoded by the putative dyslexia susceptibility gene KIAA0319-like. Histol Histopathol. Aug. 2011;26(8):953-63.
Poon et al., Dyslexia-associated kiaa0319-like protein interacts with axon guidance receptor nogo receptor 1. Cell Mol Neurobiol. Jan. 2011;31(1):27-35.
Porras et al., Modeling Parkinson's Disease in Primates: The MPTP Model. Cold Spring Harb Perspect Med. Mar. 2012;2(3):a009308, 10 pages.
Potter et al., Cerebral perivascular spaces visible on magnetic resonance imaging: development of a qualitative rating scale and its observer reliability. Cerebrovasc Dis. 2015;39(3-4):224-31.
Potter et al., Enlarged perivascular spaces (EPVS): a visual rating scale and user guide. Edinburgh University. Retrieved online at: https://www.ed.ac/uk. 48 pages.
Potter et al., Systemic Delivery of Dysferlin Overlap Vectors Provides Long-Term Gene Expression and Functional Improvement for Dysferlinopathy. Hum Gene Ther. Jul. 2018;29(7):749-762. Pre-publication edition.
Powell et al., Characterization of a novel adeno-associated viral vector with preferential oligodendrocyte tropism. Gene Ther. Nov. 2016;23(11):807-814.
Powell et al., Viral expression cassette elements to enhance transgene target specificity and expression in gene therapy. Discov Med. Jan. 2015;19(102):49-57.
Pozsgai et al., beta-Sarcoglycan gene transfer decreases fibrosis and restores force in LGMD2E mice. Gene Ther. Jan. 2016;23(1):57-66.
Quattrochi et al., Dose-related suppression of REM sleep and PGO waves by the serotonin-1 agonist eltoprazine. Neuropsychopharmacology. Jan. 1993;8(1):7-13.
Racette et al., [18F]FDOPA Pet as an endophenotype for Parkinson's Disease linkage studies. Am J Med Genet B Neuropsychiatr Genet. Apr. 5, 2006;141B(3):245-9.
Ramos et al., Gene Therapy for Duchenne muscular dystrophy. Expert Opin Orphan Drugs. 2015;3(11):1255-1266.
Rashnonejad et al., Large-Scale Production of Adeno-Associated Viral Vector Serotype-9 Carrying the Human Survival Motor Neuron Gene. Mol Biotechnol. Jan. 2016;58(1):30-6.
Reichel et al., AAV8 Can Induce Innate and Adaptive Immune Response in the Primate Eye. Mol Ther. Dec. 6, 2017;25(12):2648-2660. pre-publication edition.
Reid et al., miRNA-mediated post-transcriptional silencing of transgenes leads to increased adeno-associated viral vector yield and targeting specificity. Gene Ther. Aug. 2017;24(8):462-469. pre-publication edition.
Ren et al., Adeno-associated virus-mediated BMP-7 and SOX9 in vitro co-transfection of human degenerative intervertebral disc cells. Genet Mol Res. Apr. 22, 2015;14(2):3736-44.
Ren et al., Noninvasive tracking of gene transcript and neuroprotection after gene therapy. Gene Ther. Jan. 2016;23(1):1-9.
Richardson et al., Interventional MRI-guided putaminal delivery of AAV2-GDNF for a planned clinical trial in Parkinson's disease. Mol Ther. Jun. 2011;19(6):1048-57.
Richardson et al., Novel platform for MRI-guided convection-enhanced delivery of therapeutics: preclinical validation in nonhuman primate brain. Stereotact Funct Neurosurg. 2011;89(3):141-51.
Rocha et al., Glucocerebrosidase gene therapy prevents alpha-synucleinopathy of midbrain dopamine neurons. Neurobiol Dis. Oct. 2015;82:495-503.

(56) References Cited

OTHER PUBLICATIONS

Rockwell et al., AAV-mediated gene delivery in a feline model of Sandhoff disease corrects lysosomal storage in the central nervous system. ASN Neuro. Apr. 13, 2015;7(2):1759091415569908, 13 pages.
Rolston et al., An unexpectedly high rate of revisions and removals in deep brain stimulation surgery: Analysis of multiple databases. Parkinsonism Relat Disord. Dec. 2016;33:72-77.
Ronzitti et al., A translationally optimized AAV-UGT1A1 vector drives safe and long-lasting correction of Crigler-Najjar syndrome. Mol Ther Methods Clin Dev. Jul. 20, 2016;3:16049, 10 pages.
Rosario et al., Microglia-specific targeting by novel capsid-modified AAV6 vectors. Mol Ther Methods Clin Dev. Apr. 13, 2016;3:16026, 9 pages.
Rosas et al., Patterns of scAAV vector insertion associated with oncogenic events in a mouse model for genotoxicity. Mol Ther. Nov. 2012;20(11):2098-110.
Rosenberg et al., Gene therapy for metachromatic leukodystrophy. J Neurosci Res. Nov. 2016;94(11):1169-79.
Ruffing et al., Assembly of viruslike particles by recombinant structural proteins of adeno- associated virus type 2 in insect cells. J Virol. Dec. 1992;66(12):6922-30.
Rutledge et al., Infectious clones and vectors derived from adeno-associated virus (AAV) serotypes other than AAV type 2. J Virol. Jan. 1998;72(1):309-19.
Salegio et al., Axonal transport of adeno-associated viral vectors is serotype-dependent. Gene Ther. Mar. 2013;20(3):348-52.
Salegio et al., MRI-Guided Delivery of Viral Vectors. Methods Mol Biol. 2016;1382:217-30.
Samaranch et al., Cerebellomedullary Cistern Delivery for AAV-Based Gene Therapy: A Technical Note for Nonhuman Primates. Hum Gene Ther Methods. Feb. 2016;27(1):13-6. pre-publication edition.
Samaranch et al., MR-guided parenchymal delivery of adeno-associated viral vector serotype 5 in non-human primate brain. Gene Ther. Apr. 2017;24(4):253-261.
Samulski et al., Helper-free stocks of recombinant adeno-associated viruses: normal integration does not require viral gene expression. J Virol. Sep. 1989;63(9):3822-8.
San Sebastian et al., Safety and tolerability of magnetic resonance imaging-guided convection-enhanced delivery of AAV2-hAADC with a novel delivery platform in nonhuman primate striatum. Hum Gene Ther. Feb. 2012;23(2):210-7.
San Sebastian et al., Safety and tolerability of MRI-guided infusion of AAV2-hAADC into the mid-brain of nonhuman primate. Mol Ther Methods Clin Dev. Oct. 15, 2014;3:14049, 10 pages.
Sanchez-Pernaute et al., Functional effect of adeno-associated virus mediated gene transfer of aromatic L-amino acid decarboxylase into the striatum of 6-OHDA-lesioned rats. Mol Ther. Oct. 2001;4(4):324-30.
Saraiva et al., Gene therapy for the CNS using AAVs: The impact of systemic delivery by AAV9. J Control Release. Nov. 10, 2016;241:94-109.
Savy et al., Impact of Inverted Terminal Repeat Integrity on rAAV8 Production Using the Baculovirus/Sf9 Cells System. Hum Gene Ther Methods. Oct. 2017;28(5):277-289. pre-publication edition.
Sawada et al., Inflammation-induced reversible switch of the neuron-specific enolase promoter from Purkinje neurons to Bergmann glia. Sci Rep. Jun. 13, 2016;6:27758, 12 pages.
Schnepp et al., Recombinant Adeno-Associated Virus Vector Genomes Take the Form of Long-Lived, Transcriptionally Competent Episomes in Human Muscle. Hum Gene Ther. Jan. 2016;27(1):32-42.
Sehara et al., Persistent Expression of Dopamine-Synthesizing Enzymes 15 Years After Gene Transfer in a Primate Model of Parkinson's Disease. Hum Gene Ther Clin Dev. Jun. 2017;28(2):74-79.
Shen et al., Analysis of cis and trans Requirements for DNA Replication at the Right-End Hairpin of the Human Bocavirus 1 Genome. J Virol. Aug. 12, 2016;90(17):7761-77.
Shen et al., Functional analysis of the putative integrin recognition motif on adeno-associated virus 9. J Biol Chem. Jan. 16, 2015;290(3):1496-504.
Shen et al., Inhibition of pathological brain angiogenesis through systemic delivery of AAV vector expressing soluble FLT1. Gene Ther. Nov. 2015;22(11):893-900.
Shulman et al., The clinically important difference on the unified Parkinson's disease rating scale. Arch Neurol. Jan. 2010;67(1):64-70.
Singh et al., Therapeutic Value of Adeno Associated Virus as a Gene Therapy Vector for Parkinson's Disease—A Focused Review. Curr Gene Ther. 2016;16(4):278-286.
Sinnett et al., Improved MECP2 Gene Therapy Extends the Survival of MeCP2-Null Mice without Apparent Toxicity after Intracisternal Delivery. Mol Ther Methods Clin Dev. Apr. 19, 2017;5:106-115.
Siu et al., Improved gene delivery to adult mouse spinal cord through the use of engineered hybrid adeno-associated viral serotypes. Gene Ther. Jun. 2017;24(6):361-369. pre-publication edition.
Smith et al., A simplified baculovirus-AAV expression vector system coupled with one-step affinity purification yields high-titer rAAV stocks from insect cells. Mol Ther. Nov. 2009;17(11):1888-96.
Smith et al., Gene transfer properties and structural modeling of human stem cell-derived AAV. Mol Ther. Sep. 2014;22(9):1625-34.
Smith et al., Germline viral "fossils" guide in silico reconstruction of a mid-Cenozoic era marsupial adeno-associated virus. Sci Rep. Jul. 5, 2016;6:28965, 17 pages.
Sondhi et al., Genetic Modification of the Lung Directed Toward Treatment of Human Disease. Hum Gene Ther. Jan. 2017;28(1):3-84.
Srivastava et al., Nucleotide sequence and organization of the adeno-associated virus 2 genome. J Virol. Feb. 1983;45(2):555-64.
Srivastava, Adeno-Associated Virus: The Naturally Occurring Virus Versus the Recombinant Vector. Hum Gene Ther. Jan. 2016;27(1):1-6.
Srivastava, In vivo tissue-tropism of adeno-associated viral vectors. Curr Opin Virol. Dec. 2016;21:75-80.
Stavarache et al., The tumor suppressor PTEN regulates motor responses to striatal dopamine in normal and Parkinsonian animals. Neurobiol Dis. Oct. 2015;82:487-494.
Steines et al., CFTR gene transfer with AAV improves early cystic fibrosis pig phenotypes. JCI Insight. Sep. 8, 2016;1(14):e88728, 14 pages.
Stoker et al., Regenerative Therapies for Parkinson's Disease: An Update. BioDrugs. Aug. 2018;32(4):357-366.
Su et al., Real-time MR imaging with Gadoteridol predicts distribution of transgenes after convection-enhanced delivery of AAV2 vectors. Mol Ther. Aug. 2010;18(8):1490-5.
Su et al., Recombinant adeno-associated viral (rAAV) vectors mediate efficient gene transduction in cultured neonatal and adult microglia. J Neurochem. Jan. 2016;136 Suppl 1(01):49-62.
Su et al., Safety evaluation of AAV2-GDNF gene transfer into the dopaminergic nigrostriatal pathway in aged and parkinsonian rhesus monkeys. Hum Gene Ther. Dec. 2009;20(12):1627-40.
Summerford et al., AAVR: A Multi-Serotype Receptor for AAV. Mol Ther. Apr. 2016;24(4):663-6.
Sun et al., A Retrospective Study of the Cytokine Profile Changes in Mice with FVIII Inhibitor Development After Adeno-Associated Virus-Mediated Gene Therapy in a Hemophilia A Mouse Model. Hum Gene Ther. Mar. 2018;29(3):381-389. pre-publication edition.
Sun et al., Gene Delivery of Activated Factor VII Using Alternative Adeno-Associated Virus Serotype Improves Hemostasis in Hemophiliac Mice with FVIII Inhibitors and Adeno-Associated Virus Neutralizing Antibodies. Hum Gene Ther. Aug. 2017;28(8):654-666.
Sun et al., Preclinical Development of New Therapy for Glycogen Storage Diseases. Curr Gene Ther. 2015;15(4):338-47.
Suzuki et al., Cochlear gene therapy with ancestral AAV in adult mice: complete transduction of inner hair cells without cochlear dysfunction. Sci Rep. Apr. 3, 2017;7:45524, 11 pages.
Tadokoro et al., Subpial Adeno-associated Virus 9 (AAV9) Vector Delivery in Adult Mice. J Vis Exp. Jul. 13, 2017;(125):55770, 9 pages.

(56) References Cited

OTHER PUBLICATIONS

Talla et al., Complex I subunit gene therapy with NDUFA6 ameliorates neurodegeneration in EAE. Invest Ophthalmol Vis Sci. Jan. 22, 2015;56(2):1129-40.
Tarantal et al., Systemic and Persistent Muscle Gene Expression in Rhesus Monkeys with a Liver De-Targeted Adeno-Associated Virus Vector. Hum Gene Ther. May 2017;28(5):385-391. pre-publication edition.
Tardieu et al., Intracerebral gene therapy in children with mucopolysaccharidosis type IIIB syndrome: an uncontrolled phase 1/2 clinical trial. Lancet Neurol. Sep. 2017;16(9):712-720.
Tervo et al., A Designer AAV Variant Permits Efficient Retrograde Access to Projection Neurons. Neuron. Oct. 19, 2016;92(2):372-382.
Thome et al., Fractalkine Signaling Regulates the Inflammatory Response in an a-Synuclein Model of Parkinson Disease. PLoS One. Oct. 15, 2015;10(10):e0140566, 13 pages.
Thorne et al., Gene Therapy. Adv Biochem Eng Biotechnol. 2018;165:351-399.
Todd et al., Correcting Neuromuscular Deficits With Gene Therapy in Pompe Disease. Ann Neurol. Aug. 2015;78(2):222-34.
Tomlinson et al., Systematic review of levodopa dose equivalency reporting in Parkinson's disease. Mov Disord. Nov. 15, 2010;25(15):2649-53.
Tratschin et al., Adeno-associated virus vector for high-frequency integration, expression, and rescue of genes in mammalian cells. Mol Cell Biol. Nov. 1985;5(11):3251-60.
Tse et al., Mapping and Engineering Functional Domains of the Assembly-Activating Protein of Adeno-associated Viruses. J Virol. Jun. 29, 2018;92(14):e00393-18.
Tse et al., Structure-guided evolution of antigenically distinct adeno-associated virus variants for immune evasion. Proc Natl Acad Sci U S A. Jun. 13, 2017;114(24):E4812-E4821.
Tu et al., Role of capsid proteins in parvoviruses infection. Virol J. Aug. 4, 2015;12:114, 8 pages.
Tysnes et al., Epidemiology of Parkinson's disease. J Neural Transm (Vienna). Aug. 2017;124(8):901-905.
Urabe et al., Scalable generation of high-titer recombinant adeno-associated virus type 5 in insect cells. J Virol. Feb. 2006;80(4):1874-85.
Valdmanis et al., Future of rAAV Gene Therapy: Platform for RNAi, Gene Editing, and Beyond. Hum Gene Ther. Apr. 2017;28(4):361-372. pre-publication edition.
Van Der Loo et al., Progress and challenges in viral vector manufacturing. Hum Mol Genet. Apr. 15, 2016;25(R1):R42-52.
Van Lieshout et al., A Novel Triple-Mutant AAV6 Capsid Induces Rapid and Potent Transgene Expression in the Muscle and Respiratory Tract of Mice. Mol Ther Methods Clin Dev. Apr. 14, 2018;9:323-329.
Van Rompuy et al., Nigral overexpression of alpha-synuclein in the absence of parkin enhances alpha-synuclein phosphorylation but does not modulate dopaminergic neurodegeneration. Mol Neurodegener. Jun. 23, 2015;10:23, 14 pages.
Vandamme et al., Unraveling the Complex Story of Immune Responses to AAV Vectors Trial After Trial. Hum Gene Ther. Nov. 2017;28(11):1061-1074. pre-publication edition.
Varanese et al., Treatment of advanced Parkinson's disease. Parkinsons Dis. Feb. 7, 2011;2010:480260, 9 pages.
Vercauteren et al., Superior In vivo Transduction of Human Hepatocytes Using Engineered AAV3 Capsid. Mol Ther. Jun. 2016;24(6):1042-1049.
Verhelle et al., AAV9 delivered bispecific nanobody attenuates amyloid burden in the gelsolin amyloidosis mouse model. Hum Mol Genet. Apr. 1, 2017;26(7):1353-1364. pre- publication edition.
Voon et al., Impulse control disorders and levodopa-induced dyskinesias in Parkinson's disease: an update. Lancet Neurol. Mar. 2017;16(3):238-250.
Wachter et al., A tool to improve pre-selection for deep brain stimulation in patients with Parkinson's disease. J Neurol. Apr. 2011;258(4):641-6.
Wang et al., AAV gene therapy corrects OTC deficiency and prevents liver fibrosis in aged OTC-knock out heterozygous mice. Mol Genet Metab. Apr. 2017;120(4):299-305.
Wang et al., Adeno-associated virus vector as a platform for gene therapy delivery. Nat Rev Drug Discov. May 2019;18(5):358-378.
Wang et al., Comparative Study of Liver Gene Transfer With AAV Vectors Based on Natural and Engineered AAV Capsids. Mol Ther. Dec. 2015;23(12):1877-87.
Wang et al., Direct brain infusion can be enhanced with focused ultrasound and microbubbles. J Cereb Blood Flow Metab. Feb. 2017;37(2):706-714. pre-publication edition.
Wang et al., Direct interaction of human serum proteins with AAV virions to enhance AAV transduction: immediate impact on clinical applications. Gene Ther. Jan. 2017;24(1):49-59.
Wang et al., Direct interaction of human serum proteins with AAV virions to enhance AAV transduction: immediate impact on clinical applications. Gene Ther. Jan. 2017;24(1):49-59. pre-publication edition.
Wang et al., Human Bocavirus 1 Is a Novel Helper for Adeno-associated Virus Replication. J Virol. Aug. 24, 2017;91(18):e00710-17.
Wang et al., Noninvasive, neuron-specific gene therapy can be facilitated by focused ultrasound and recombinant adeno-associated virus. Gene Ther. Jan. 2015;22(1):104-10.
Wang et al., Productive life cycle of adeno-associated virus serotype 2 in the complete absence of a conventional polyadenylation signal. J Gen Virol. Sep. 2015;96(9):2780-2787.
Wasilko et al., The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32.
Watakabe et al., Comparative analyses of adeno-associated viral vector serotypes 1, 2, 5, 8 and 9 in marmoset, mouse and macaque cerebral cortex. Neurosci Res. Apr. 2015;93:144-57.
Watanabe et al., Protein Phosphatase Inhibitor-1 Gene Therapy in a Swine Model of Nonischemic Heart Failure. J Am Coll Cardiol. Oct. 3, 2017;70(14):1744-1756.
Watson et al., Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Weber-Adrian et al., Gene delivery to the spinal cord using MRI-guided focused ultrasound. Gene Ther. Jul. 2015;22(7):568-77.
Wilson et al., Adeno-associated virus vector-mediated gene therapy can effectively treat CNS and cardiac lesions and induce immune tolerance to the therapeutic enzyme in large animal models of mucopolysaccharidosis type. Molecular Genetics and Metabolism. Feb. 2015;114(2):S126-S127, Abstract 287.
Woodard et al., Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90(21):9878-9888. pre-publication edition.
Wooley et al., A directed evolution approach to select for novel Adeno-associated virus capsids on an HIV-1 producer T cell line. J Virol Methods. Dec. 2017;250:47-54.
Wu et al., Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49, 18 pages.
Wu et al., Mutational analysis of the adeno-associated virus type 2 (AAV2) capsid gene and construction of AAV2 vectors with altered tropism. J Virol. Sep. 2000;74(18):8635-47.
Xiao et al., Disruption of Microtubules Post-Virus Entry Enhances Adeno-Associated Virus Vector Transduction. Hum Gene Ther. Apr. 2016;27(4):309-24. pre-publication edition.
Xie et al., Short DNA Hairpins Compromise Recombinant Adeno-Associated Virus Genome Homogeneity. Mol Ther. Jun. 7, 2017;25(6):1363-1374.
Xie et al., The 2.8 Å Electron Microscopy Structure of Adeno-Associated Virus-DJ Bound by a Heparinoid Pentasaccharide. Mol Ther Methods Clin Dev. Mar. 8, 2017;5:1-12.

(56) References Cited

OTHER PUBLICATIONS

Xie et al., The atomic structure of adeno-associated virus (AAV-2), a vector for human gene therapy. Proc Natl Acad Sci U S A. Aug. 6, 2002;99(16):10405-10.

Xu et al., Quantitative comparison of expression with adeno-associated virus (AAV-2) brain-specific gene cassettes. Gene Ther. Sep. 2001;8(17):1323-32.

Yalvac et al., AAV1.NT-3 gene therapy attenuates spontaneous autoimmune peripheral polyneuropathy. Gene Ther. Jan. 2016;23(1):95-102.

Yamada et al., Parkin gene therapy for alpha-synucleinopathy: a rat model of Parkinson's disease. Hum Gene Ther. Feb. 2005;16(2):262-70.

Yan et al., Human Bocavirus Type-1 Capsid Facilitates the Transduction of Ferret Airways by Adeno-Associated Virus Genomes. Hum Gene Ther. Aug. 2017;28(8):612-625.

Yan et al., Inverted terminal repeat sequences are important for intermolecular recombination and circularization of adeno-associated virus genomes. J Virol. Jan. 2005;79(1):364-79.

Yan et al., Optimization of Recombinant Adeno-Associated Virus-Mediated Expression for Large Transgenes, Using a Synthetic Promoter and Tandem Array Enhancers. Hum Gene Ther. Jun. 2015;26(6):334-46.

Yang et al., Sequential Adeno-Associated Viral Vector Serotype 9-Green Fluorescent Protein Gene Transfer Causes Massive Inflammation and Intense Immune Response in Rat Striatum. Hum Gene Ther. Jul. 2016;27(7):528-43.

Yazdan-Shahmorad et al., Widespread optogenetic expression in macaque cortex obtained with MR-guided, convection enhanced delivery (CED) of AAV vector to the thalamus. J Neurosci Methods. Jan. 1, 2018;293:347-358.

Ye et al., Adeno-Associated Virus Vector Mediated Delivery of the HBV Genome Induces Chronic Hepatitis B Virus Infection and Liver Fibrosis in Mice. PLoS One. Jun. 15, 2015;10(6):e0130052, 11 pages.

Yi et al., Systemic Correction of Murine Glycogen Storage Disease Type IV by an AAV-Mediated Gene Therapy. Hum Gene Ther. Mar. 2017;28(3):286-294. pre-publication edition.

Yun et al., Block of A1 astrocyte conversion by microglia is neuroprotective in models of Parkinson's disease. Nat Med. Jul. 2018;24(7):931-938.

Zeng et al., Probing the Link among Genomic Cargo, Contact Mechanics, and Nanoindentation in Recombinant Adeno-Associated Virus 2. J Phys Chem B. Mar. 2, 2017;121(8):1843-1853. pre-publication edition.

Zerah et al., Intracerebral Gene Therapy Using AAVrh.10-hARSA Recombinant Vector to Treat Patients with Early-Onset Forms of Metachromatic Leukodystrophy: Preclinical Feasibility and Safety Assessments in Nonhuman Primates. Hum Gene Ther Clin Dev. Jun. 2015;26(2):113-24.

Zhao et al., BPV1 E2 protein enhances packaging of full-length plasmid DNA in BPV1 pseudovirions. Virology. Jul. 5, 2000;272(2):382-93.

Zhao et al., Intracerebral adeno-associated virus gene delivery of apolipoprotein E2 markedly reduces brain amyloid pathology in Alzheimer's disease mouse models. Neurobiol Aging. Aug. 2016;44:159-172.

Zharikov et al., shRNA targeting a-synuclein prevents neurodegeneration in a Parkinson's disease model. J Clin Invest. Jul. 1, 2015;125(7):2721-35.

Zhu et al., Soluble FLT1 Gene Therapy Alleviates Brain Arteriovenous Malformation Severity. Stroke. May 2017;48(5):1420-1423, including online supplement information. pre-publication edition.

Zhu et al., Zika virus has oncolytic activity against glioblastoma stem cell. J Exp Med. 2017;214(10):2843-2857. pre-publication edition.

Ziegler et al., Steerable Induction of the Thymosin β4/MRTF-A Pathway via AAV-Based Overexpression Induces Therapeutic Neovascularization. Hum Gene Ther. Oct. 3, 2017. 9 pages. doi: 10.1089/hum.2017.013. pre-publication edition.

Zinn et al., In Silico Reconstruction of the Viral Evolutionary Lineage Yields a Potent Gene Therapy Vector. Cell Rep. Aug. 11, 2015;12(6):1056-68.

Zolotukhin et al., Potential for cellular stress response to hepatic factor VIII expression from AAV vector. Mol Ther Methods Clin Dev. Sep. 28, 2016;3:16063, 8 pages.

Zou et al., Nonstructural Protein NP1 of Human Bocavirus 1 Plays a Critical Role in the Expression of Viral Capsid Proteins. J Virol. Apr. 14, 2016;90(9):4658-4669. pre-publication edition.

* cited by examiner

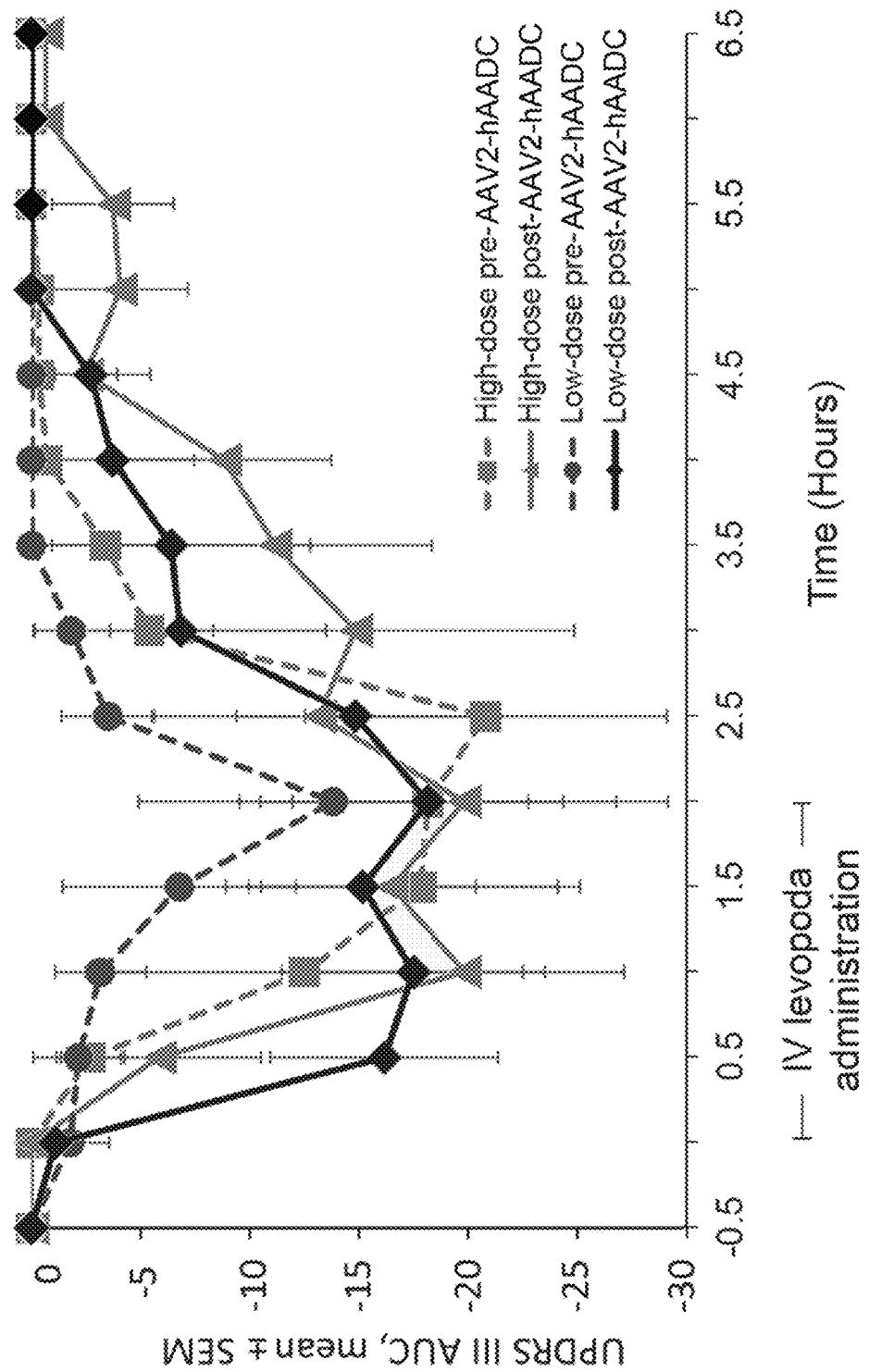

COMPOSITIONS AND METHODS FOR THE TREATMENT OF PARKINSON'S DISEASE

CROSS REFERENCE TO RELATED APPLICATIONS

This application is a 35 U.S.C. § 371 U.S. National Stage Entry of International Application No. PCT/US2019/032384, filed May 15, 2019 and entitled COMPOSITIONS AND METHODS FOR TREATMENT OF PARKINSON'S DISEASE; which claims priority to U.S. Provisional Patent Application No. 62/671,944, filed May 15, 2018 and entitled COMPOSITIONS AND METHODS FOR TREATMENT OF PARKINSON'S DISEASE, U.S. Provisional Patent Application No. 62/681,891, filed Jun. 7, 2018 and entitled COMPOSITIONS AND METHODS FOR TREATMENT OF PARKINSON'S DISEASE, U.S. Provisional Patent Application No. 62/684,384, filed Jun. 13, 2018 and entitled COMPOSITIONS AND METHODS FOR TREATMENT OF PARKINSON'S DISEASE, U.S. Provisional Patent Application No. 62/691,748, filed Jun. 29, 2018 and entitled COMPOSITIONS AND METHODS FOR TREATMENT OF PARKINSON'S DISEASE, U.S. Provisional Patent Application No. 62/698,419, filed Jul. 16, 2018 and entitled COMPOSITIONS AND METHODS FOR TREATMENT OF PARKINSON'S DISEASE, U.S. Provisional Patent Application No. 62/703,137, filed Jul. 25, 2018 and entitled COMPOSITIONS AND METHODS FOR TREATMENT OF PARKINSON'S DISEASE, U.S. Provisional Patent Application No. 62/741,021, filed Oct. 4, 2018, 2018 and entitled COMPOSITIONS AND METHODS FOR TREATMENT OF PARKINSON'S DISEASE, U.S. Provisional Patent Application No. 62/748,119, filed Oct. 19, 2018 and entitled COMPOSITIONS AND METHODS FOR TREATMENT OF PARKINSON'S DISEASE, U.S. Provisional Patent Application No. 62/756,897, filed Nov. 7, 2018 and entitled COMPOSITIONS AND METHODS FOR TREATMENT OF PARKINSON'S DISEASE, U.S. Provisional Patent Application No. 62/789,909, filed Jan. 8, 2019 and entitled COMPOSITIONS AND METHODS FOR TREATMENT OF PARKINSON'S DISEASE, and U.S. Provisional Patent Application No. 62/831,400, filed Apr. 9, 2019 and entitled COMPOSITIONS AND METHODS FOR TREATMENT OF PARKINSON'S DISEASE, the contents of each of which are herein incorporated by reference in their entirety.

REFERENCE TO SEQUENCE LISTING

The present application is being filed along with a Sequence Listing in electronic format. The Sequence Listing is provided as a file entitled 20571025US371_SL.txt, created on Nov. 13, 2020, which is 6,404,916 bytes in size. The information in the electronic format of the sequence listing is incorporated herein by reference in its entirety.

FIELD OF THE DISCLOSURE

The present disclosure relates to methods, formulations and devices for the delivery and therapeutic administration of polynucleotides encoding AADC. The present disclosure relates to methods, formulations and devices for the delivery and therapeutic administration of AAV vectors which include polynucleotides encoding AADC. The present disclosure relates to methods, formulations and devices for the delivery and therapeutic administration of polynucleotides encoding AADC in the treatment of neurological diseases, disorders and conditions, including Parkinson's Disease.

BACKGROUND

Aromatic L-amino acid decarboxylase (AADC) is a homodimeric pyridoxal phosphate-dependent enzyme responsible for the synthesis of dopamine and serotonin. The encoded protein catalyzes the decarboxylation of L-3,4-dihydroxyphenylalanine (L-DOPA or levodopa) to dopamine; L-5-hydroxytryptophan to serotonin; and L-tryptophan to tryptamine. Defects in this gene are the cause of aromatic L-amino-acid decarboxylase deficiency (AADCD), which is an inborn error in neurotransmitter metabolism leading to combined serotonin and catecholamine deficiency that results in severe motor and autonomic dysfunctions.

Parkinson's Disease (PD) is a progressive neurodegenerative disease of the central nervous system (CNS) producing sensory and motor symptoms. Dopamine replacement (i.e., levodopa) has been the standard pharmacotherapy for motor impairment in PD. However, the benefit of dopamine therapy becomes less marked over time, due, in part, to the progressive death of dopamine-generating cells and corresponding loss of AADC activity. Furthermore, systemic administration of high-dose dopamine is complicated by side effects, such as fluctuations in motor performance, dyskinesias, and hallucinations, resulting from dopaminergic stimulation of the mesolimbic system. One strategy to restore dopaminergic function and minimize side effects is the use of gene therapy to deliver AADC directly to a targeted region of the CNS.

The adeno-associated virus (AAV) has emerged as an attractive vector for gene therapy due to its long-term gene expression, the inability to autonomously replicate without a helper virus, the ability to transduce dividing and non-dividing cells, and the lack of pathogenicity from wild-type infections (See e.g., Hadaczek et al. Mol. Ther. 18(8), 1458-1461, August 2010). AAV is a helper-dependent DNA parvovirus which belongs to the genus Dependovirus.

The present disclosure provides methods, formulations and devices for the delivery and therapeutic administration of such improved nucleic acid constructs, e.g., polynucleotides, for use with AAV-derived vectors comprising dopa carboxylase ("DDC") gene sequence which encodes a full-length AADC protein for the purpose of gene therapy in the treatment of Parkinson's Disease.

The nucleic acid constructs described herein comprise at least a 5'-ITR and a 3'-ITR, each or both of which may be derived from an AAV, positioned about a DDC gene sequence, as well as additional components required for gene expression and clone selection.

SUMMARY

The present disclosure presents a method of administering a pharmaceutical composition to a subject. In certain embodiments, the method includes administering to the subject a pharmaceutical composition which includes an adeno-associated virus (AAV) particle which includes an AAV2 capsid and a vector genome, wherein the vector genome includes a nucleotide sequence which has at least 97% identity to SEQ ID NO: 979. In certain embodiments, the vector genome includes a nucleotide sequence which has at least 99% identity to SEQ ID NO: 979. In certain embodiments, the vector genome includes SEQ ID NO: 979.

In certain embodiments, the pharmaceutical composition is administered to the subject by posterior surgical infusion into at least one putamen of the subject; wherein the average total putaminal coverage from the posterior administration is at least 50%. In certain embodiments, the average total putaminal coverage from the posterior administration is 50-65%. In certain embodiments, the average total putaminal coverage from the posterior administration is 50-60%. In certain embodiments, the average total putaminal coverage from the posterior administration is 55-65%. In certain embodiments, the posterior administration of the pharmaceutical composition is bilateral to both the right putamen and the left putamen of the subject during a single procedure. In certain embodiments, the surgical time is 7-10 hours or 7-9 hours. In certain embodiments, the infusion time is 2.5-4.5 hours, 2.5-5.0 hours, 3.0-4.5 hours, 3.0-5.0 hours, 3.5-4.5 hours or 3.5-5.0 hours.

In certain embodiments, the pharmaceutical composition is administered to the subject by transfrontal surgical infusion into at least one putamen of the subject; and wherein the average total putaminal coverage from the posterior administration is 30-50%. In certain embodiments, the average total putaminal coverage from the transfrontal administration is 35-50%. In certain embodiments, the average total putaminal coverage from the transfrontal administration is 40-50%. In certain embodiments, the transfrontal administration of the pharmaceutical composition is bilateral to both the right putamen and the left putamen of the subject during a single procedure.

In certain embodiments, the pharmaceutical composition includes an AAV concentration of between $2.0 \times 10^{12}$ vg/ml and $3.0 \times 10^{12}$ vg/ml. In certain embodiments, the pharmaceutical composition includes an AAV concentration of between $2.4 \times 10^{12}$ vg/ml and $2.8 \times 10^{12}$ vg/ml. In certain embodiments, the pharmaceutical composition includes an AAV concentration of about $2.6 \times 10^{12}$ vg/ml. In certain embodiments, the pharmaceutical composition includes an AAV concentration of $2.6 \times 10^{12}$ vg/ml.

In certain embodiments, the pharmaceutical composition is administered at a volume of up to 1800 μL per putamen. In certain embodiments, the pharmaceutical composition is administered at a volume of up to 1500 μL per putamen. In certain embodiments, the pharmaceutical composition is administered at a volume of up to 1200 μL per putamen. In certain embodiments, the pharmaceutical composition is administered at a volume of up to 900 μL per putamen. In certain embodiments, the pharmaceutical composition is administered at a volume of up to 450 μL per putamen.

In certain embodiments, the total viral dosage from the administration is between $2.0 \times 10^{12}$ vg/ml and $9.4 \times 10^{12}$ vg/ml. In certain embodiments, the total viral dosage from the administration is between $3.5 \times 10^{12}$ vg/ml and $8.0 \times 10^{12}$ vg/ml.

In certain embodiments, the pharmaceutical composition is a formulation which includes sodium chloride, sodium phosphate and pluronic acid F-68, and wherein the formulation has a pH between 7.0-7.5. In certain embodiments, the formulation includes 150-200 mM sodium chloride, 8-12 mM sodium phosphate and 0.001-0.01% w/v pluronic acid F-68, at a pH between 7.2-7.4. In certain embodiments, the formulation includes 180 mM sodium chloride, 10 mM sodium phosphate and 0.001% w/v pluronic acid F-68, at a pH of 7.3.

The present disclosure presents a method of treating a neurological disease in a subject. In certain embodiments, the method includes administering to the subject a pharmaceutical composition according to the administration methods of the present disclosure. In certain embodiments, the method includes administering to the subject a pharmaceutical composition which includes an adeno-associated virus (AAV) particle which includes an AAV2 capsid and a vector genome, wherein the vector genome includes a nucleotide sequence which has at least 97% identity to SEQ ID NO: 979. In certain embodiments, the vector genome includes a nucleotide sequence which has at least 99% identity to SEQ ID NO: 979. In certain embodiments, the vector genome includes SEQ ID NO: 979. In certain embodiments, the neurological disease is Parkinson's Disease.

In certain embodiments, the administration of the pharmaceutical composition produces a therapeutically effective outcome.

In certain embodiments, the therapeutically effective outcome includes an increase in AADC enzyme activity relative to baseline of more than 50%, as measured by PET $^{18}$F-Dopa analysis 2-7 months after administration. In certain embodiments, the increase in AADC enzyme activity relative to baseline is between 50%-85%. In certain embodiments, the increase in AADC enzyme activity relative to baseline is between 60%-85%. In certain embodiments, the increase in AADC enzyme activity relative to baseline is between 70/6-85%.

In certain embodiments, the therapeutically effective outcome includes a reduced UPDRS III score in the "ON" medication state relative to baseline of up to 20%, as measured 6 months after administration. In certain embodiments, the reduction in UPDRS III score in the "ON" medication state relative to baseline is between 15%-20% at 6 months. In certain embodiments, the therapeutically effective outcome includes a reduced UPDRS III score in the "ON" medication state relative to baseline of up to 30%, as measured 12 months after administration. In certain embodiments, the reduction in UPDRS III score in the "ON" medication state relative to baseline is between 20%-30% at 12 months. In certain embodiments, the patient has a baseline UPDRS III "ON" score greater than 10. In certain embodiments, the patient has a baseline UPDRS III "ON" score between 10 and 14. In certain embodiments, the therapeutically effective outcome includes a reduced UPDRS III score in the "OFF" medication state relative to baseline of up to 26%, as measured 6 months after administration. In certain embodiments, the reduction in UPDRS III score in the "OFF" medication state relative to baseline is between 20%-26% at 6 months. In certain embodiments, the therapeutically effective outcome includes a reduced UPDRS III score in the "OFF" medication state relative to baseline of up to 33%, as measured 12 months after administration. In certain embodiments, the reduction in UPDRS III score in the "OFF" medication state relative to baseline is between 25%-33% at 12 months. In certain embodiments, the patient has a baseline UPDRS III "OFF" score greater than 30. In certain embodiments, the patient has a baseline UPDRS III "OFF" score between 30 and 36.5.

In certain embodiments, the therapeutically effective outcome includes an increase in diary ON-time without troublesome dyskinesia of at least 3.0 hours relative to baseline, as measured by Hauser motor diary at 6 months. In certain embodiments, the increase in diary ON-time without troublesome dyskinesia relative to baseline is between 3.0 hours to 3.9 hours at 6 months. In certain embodiments, the therapeutically effective outcome includes an increase in diary ON-time without troublesome dyskinesia of at least 2.5 hours relative to baseline, as measured by Hauser motor diary at 12 months. In certain embodiments, the increase in diary ON-time without troublesome dyskinesia relative to baseline is between 2.5 hours to 3.0 hours at 12 months. In certain embodiments, the therapeutically effective outcome includes a decrease in diary OFF-time of at least 3.0 hours relative to baseline, as measured by Hauser motor diary at 6 months. In certain embodiments, the decrease in diary OFF-time relative to baseline is between 3.0 hours to 3.9 hours at 6 months. In certain embodiments, the therapeutically effective outcome includes a decrease in diary OFF-time of at least 2.5 hours relative to baseline, as measured by Hauser motor diary at 12 months. In certain embodiments, the decrease in diary OFF-time relative to baseline is between 2.5 hours to 3.0 hours at 12 months.

BRIEF DESCRIPTION OF THE DRAWINGS

The foregoing and other objects, features and advantages will be apparent from the following description of particular embodiments of the disclosure, as illustrated in the accompanying drawings. The drawings are not necessarily to scale, emphasis instead being placed upon illustrating the principles of various embodiments of the disclosure.

FIG. 12c shows UPDRS III AUC scores after IV Levodopa administration up to $4.7\times10^{12}$ vg, corresponding with certain embodiments of the present disclosure.

DETAILED DESCRIPTION

I. Compositions of the Disclosure

Adeno-Associated Viruses (AAVs) and AAV Particles

Figure 1:
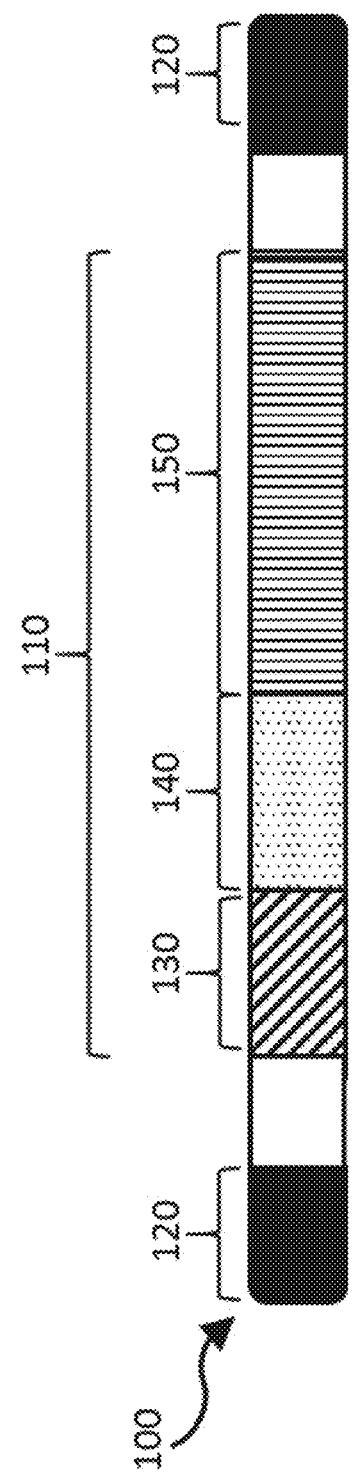
FIG. 1 is a schematic of one embodiment a viral genome of the present disclosure.

Viruses of the Parvoviridae family are small non-enveloped icosahedral capsid viruses characterized by a single stranded DNA genome. Parvoviridae family viruses consist of two subfamilies: Parvovirinae, which infect vertebrates, and Densovirinae, which infect invertebrates. Due to its relatively simple structure, easily manipulated using standard molecular biology techniques, this virus family is useful as a biological tool. The genome of the virus may be modified to contain a minimum of components for the assembly of a functional recombinant virus, or viral particle, which is loaded with or engineered to express or deliver a desired payload, which may be delivered to a target cell, tissue, organ, or organism.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

The Parvoviridae family comprises the Dependovirus genus which includes adeno-associated viruses (AAV) capable of replication in vertebrate hosts including, but not limited to, human, primate, bovine, canine, equine, and ovine species.

The vector genome is a linear, single-stranded DNA (ssDNA) molecule approximately 5,000 nucleotides (nt) in length. The AAV viral genome can comprise a payload region and at least one inverted terminal repeat (ITR) or ITR region. ITRs traditionally flank the coding nucleotide sequences for the non-structural proteins (encoded by Rep genes) and the structural proteins (encoded by capsid genes or Cap genes). While not wishing to be bound by theory, an AAV viral genome typically comprises two ITR sequences. The vector genome comprises a characteristic T-shaped hairpin structure defined by the self-complementary terminal 145 nt of the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In addition to the encoded heterologous payload, AAV particles may comprise the viral genome, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. Chiorini et al., J. Vir. 71: 6823-33 (1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 863547 (2000), the contents of each of which are incorporated herein by reference in their entirety.

In certain embodiments, AAV particles of the present disclosure are recombinant AAV particles which are replication defective, lacking sequences encoding functional Rep and Cap proteins within their viral genome. These defective AAV particles may lack most or all parental coding sequences and essentially carry only one or two AAV ITR sequences and the nucleic acid of interest for delivery to a cell, a tissue, an organ or an organism.

In certain embodiments, the viral genome of the AAV particles of the present disclosure comprise at least one control element which provides for the replication, transcription and translation of a coding sequence encoded therein. Not all of the control elements need always be present as long as the coding sequence is capable of being replicated, transcribed and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

According to the present disclosure, AAV particles for use in therapeutics and/or diagnostics comprise a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV particles of the present disclosure may be produced recombinantly and may be based on adeno-associated virus (AAV) parent or reference sequences. As used herein, a "vector" is any molecule or moiety which transports, transduces or otherwise acts as a carrier of a heterologous molecule such as the nucleic acids described herein.

In addition to single stranded AAV particles (e.g., ssAAVs), the present disclosure also provides for self-complementary AAV (scAAVs) particles. scAAV particles contain DNA strands which anneal together to form double stranded DNA. By skipping second strand synthesis, scAAVs allow for rapid expression in the cell.

In certain embodiments, the AAV particle of the present disclosure is an scAAV.

In certain embodiments, the AAV particle of the present disclosure is an ssAAV.

Methods for producing and/or modifying AAV particles are disclosed in the art such as pseudotyped AAV particles (PCT Patent Publication Nos. WO200028004; WO200123001; WO2004112727; WO 2005005610 and WO 2005072364, the content of each of which is incorporated herein by reference in its entirety).

AAV particles may be modified to enhance the efficiency of delivery. Such modified AAV particles can be packaged efficiently and be used to successfully infect the target cells at high frequency and with minimal toxicity. In some embodiments the capsids of the AAV particles are engineered according to the methods described in US Publication Number US 20130195801, the contents of which are incorporated herein by reference in their entirety.

In certain embodiments, the AAV particles comprising a payload region encoding the polypeptides of the disclosure may be introduced into mammalian cells.

AAV Serotypes

AAV particles of the present disclosure may comprise or be derived from any natural or recombinant AAV serotype. According to the present disclosure, the AAV particles may utilize or be based on a serotype selected from any of the following PHP.B, PHP.A, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3. AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1. AAV223.2. AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15. AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5. AAVCy.5R1, AAVCy.5R2, AAVCy.5R3, AAVCy.5R4, AAVcy.6. AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24. AAVhu.25. AAVhu.27. AAVhu.28. AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh. 14, AAVrh.17. AAVrh.18, AAVrh.19, AAVrh.20, AAVrh.21, AAVrh.22, AAVrh.23, AAVrh.24. AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, ovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07. AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrb.50, AAVrh.43, AAVrh.62. AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2. AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10. AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10. AAV CKd-2. AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, PHP.B (AAV-PHP.B), PHP.A (AAV.PHP.A), G2B-26, G2B-13, TH1.1-32, TH1.1-35, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, and/or AAVG2B5, and variants thereof.

In some embodiments, the AAV serotype may be, or have, a modification as described in United States Publication No. US 20160361439, the contents of which are herein incorporated by reference in their entirety, such as but not limited to, Y252F, Y272F, Y444F, Y500F, Y700F, Y704F, Y730F, Y275F, Y281F, Y508F, Y576F, Y612G, Y673F, and Y720F of the wild-type AAV1, AAV2, AAV3, AAV4, AAV5, AAV6, AAV7, AAV8, AAV9, AAV10, AAV11, AAV12, and hybrids thereof.

In some embodiments, the AAV serotype may be, or have, a mutation as described in U.S. Pat. No. 9,546,112, the contents of which are herein incorporated by reference in their entirety, such as, but not limited to, at least two, but not all the F129L, D418E, K531E, L584F, V598A and H642N mutations in the sequence of AAV6 (SEQ ID NO:4 of U.S. Pat. No. 9,546,112), AAV1 (SEQ ID NO:6 of U.S. Pat. No. 9,546,112), AAV2, AAV3, AAV4, AAV5, AAV7, AAV9, AAV10 or AAV11 or derivatives thereof. In yet another embodiment, the AAV serotype may be, or have, an AAV6 sequence comprising the K531E mutation (SEQ ID NO:5 of U.S. Pat. No. 9,546,112).

In some embodiments, the AAV serotype may be, or have, a mutation in the AAV1 sequence, as described in in United States Publication No. US 20130224836, the contents of which are herein incorporated by reference in their entirety, such as, but not limited to, at least one of the surface-exposed tyrosine residues, preferably, at positions 252, 273, 445, 701, 705 and 731 of AAV1 (SEQ ID NO: 2 of US 20130224836) substituted with another amino acid, preferably with a phenylalanine residue. In certain embodiments, the AAV serotype may be, or have, a mutation in the AAV9 sequence, such as, but not limited to, at least one of the surface-exposed tyrosine residues, preferably, at positions 252, 272, 444, 500, 700, 704 and 730 of AAV2 (SEQ ID NO: 4 of US 20130224836) substituted with another amino acid, preferably with a phenylalanine residue. In certain embodiments, the tyrosine residue at position 446 of AAV9 (SEQ ID NO: 6 US 20130224836) is substituted with a phenylalanine residue.

In some embodiments, the serotype may be AAV2 or a variant thereof, as described in International Publication No.

WO2016130589, herein incorporated by reference in its entirety. The amino acid sequence of AAV2 may comprise N587A, E548A, or N708A mutations. In certain embodiments, the amino acid sequence of any AAV may comprise a V708K mutation.

In some embodiments, the AAV serotype may be, or have, a sequence as described in United States Publication No. US20030138772, the contents of which are herein incorporated by reference in their entirety, such as, but not limited to: AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22). AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39). AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951). AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have, a mutation in the AAV9 sequence as described by N Pulicherla et al. (Molecular Therapy 19(6):1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have, a sequence as described in United States Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). In certain embodiments, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q: Gln) and (2) R590T where arginine (R: Arg) at amino acid 590 is changed to threonine (T; Thr). In certain embodiments, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T: Thr).

In some embodiments, the AAV serotype may be, or have, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or have, a mutation in the AAV2 sequence to generate AAV2G9 as described in International Publication No. WO2014144229 and herein incorporated by reference in its entirety.

In some embodiments, the AAV serotype may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321). AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321). AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321). AAV4-19/rh.55 (SEQ ID NO: 117 of WO2005033321), AAV4-4 (SEQ ID NO: 201 and 218 of WO2005033321). AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321). AAV5-22/rh.58 (SEQ ID No: 27 of WO2005033321). AAV5-3/rh.57 (SEQ ID NO: 105 of WO2005033321), AAV5-3/rh.57 (SEQ ID No: 26 of WO2005033321). AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321). AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321). AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321). AAVhu.56 (SEQ ID NO: 192 of WO2005033321), AAVhu.57 (SEQ ID NO: 193 of WO2005033321), AAVhu.58 (SEQ ID NO: 194 of WO2005033321). AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321). AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321). AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321). AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3. AAVcy.4, AAVcy.5, AAVcy.6, AAVrh.12, AAVrh.17. AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151,154, 158, 161, 162, 165-183, 202, 204-212, 215, 219, 224-236, of WO2005033321, the contents of which are herein incorporated by reference in their entirety.

In some embodiments, the AAV serotype may be, or have, a sequence as described in International Publication No. WO2015168666, the contents of which are herein incorporated by reference in their entirety, such as, but not limited to, AAVrh8R (SEQ ID NO: 9 of WO2015168666). AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131). AAVhEr1.35 (SEQ ID NO:50 of U.S. Pat. No. 9,233,131), AAVhEr1.7 (SEQ ID NO:51 of U.S. Pat. No. 9,233,131). AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of US9233131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131). AAVhEr3.1 (SEQ ID NO:59 of U.S. Pat. No. 9,233,131). AAV2.5T (SEQ ID NO:42 of U.S. Pat. No. 9,233,131), or variants thereof.

In some embodiments, the AAV serotype may be, or have, a sequence as described in United States Patent Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607). AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO:10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295). AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612). AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use may be from a variety of species. In certain embodiments, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In certain embodiments, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In certain embodiments, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments the AAV may be engineered as a hybrid AAV from two or more parental serotypes. In certain embodiments, the AAV may be AAV2G9 which comprises sequences from AAV2 and AAV9. The AAV2G9 AAV serotype may be, or have, a sequence as described in United States Patent Publication No. US20160017005, the contents of which are herein incorporated by reference in its entirety.

In certain embodiments, the AAV may be a serotype generated by the AAV9 capsid library with mutations in amino acids 390-627 (VP1 numbering) as described by Pulicherla et al. (Molecular Therapy 19(6):1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and 1479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T4921, H527N), AAV.59 (T1336C; Y446H), AAV9.61 (A1493T; N4981), AAV9.64 (C1531A, A1617T; L511I), AAV9.65 (C1335T, T1530C, C1568A; A523D), AAV9.68 (C1510A; P5041), AAV9.80 (G1441A, G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV serotype may be, or have, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or have, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: X and X of U.S. Pat. No. 8,734,809), AAV CLv-R9 (SEQ ID NO: X and X of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734,809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809). AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809). AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734,809), or variants or derivatives thereof.

In some embodiments, the AAV serotype may be, or have, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001). AAV CBr-7.1 (SEQ ID NO: 4 and 54 of WO2016065001), AAV CBr-7.2 (SEQ ID NO: 5 and 55 of WO2016065001). AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001). AAV CBr-7.7 (SEQ ID NO: 9 and 59 of WO2016065001). AAV CBr-7.8 (SEQ ID NO: 10 and 60 of WO2016065001). AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001). AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001). AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO201606500 1), AAV4 (SEQ ID NO: 49 and 99 of WO2016065001), AAV5 (SEQ ID NO: 50 and 100 of WO2016065001), or variants or derivatives thereof.

In some embodiments, the AAV serotype may be, or have, a modification as described in United States Publication No. US 20160361439, the contents of which are herein incorporated by reference in their entirety, such as but not limited to, Y252F, Y272F, Y444F, Y500F, Y700F, Y704F, Y730F, Y275F, Y281F, Y508F, Y576F, Y612G, Y673F, and Y720F of the wild-type AAV1, AAV2, AAV3, AAV4, AAV5, AAV6, AAV7, AAV8, AAV9, AAV10, AAV11, AAV12, and hybrids thereof.

In some embodiments, the AAV serotype may be, or have, a mutation as described in U.S. Pat. No. 9,546,112, the contents of which are herein incorporated by reference in their entirety, such as, but not limited to, at least two, but not all the F129L, D418E, K531E, L584F, V598A and H642N mutations in the sequence of AAV6 (SEQ ID NO:4 of U.S. Pat. No. 9,546,112), AAV1 (SEQ ID NO:6 of U.S. Pat. No. 9,546,112), AAV2, AAV3, AAV4, AAV5, AAV7, AAV9, AAV10 or AAV11 or derivatives thereof. In yet another embodiment, the AAV serotype may be, or have, an AAV6 sequence comprising the K531E mutation (SEQ ID NO:5 of U.S. Pat. No. 9,546,112).

In some embodiments, the AAV serotype may be, or have, a mutation in the AAV1 sequence, as described in in United States Publication No. US 20130224836, the contents of which are herein incorporated by reference in their entirety, such as, but not limited to, at least one of the surface-exposed tyrosine residues, preferably, at positions 252, 273, 445, 701, 705 and 731 of AAV1 (SEQ ID NO: 2 of US 20130224836) substituted with another amino acid, preferably with a phenylalanine residue. In certain embodiments, the AAV serotype may be, or have, a mutation in the AAV9 sequence, such as, but not limited to, at least one of the surface-exposed tyrosine residues, preferably, at positions 252, 272, 444, 500, 700, 704 and 730 of AAV2 (SEQ ID NO: 4 of US 20130224836) substituted with another amino acid, preferably with a phenylalanine residue. In certain embodiments, the tyrosine residue at position 446 of AAV9 (SEQ ID NO: 6 US 20130224836) is substituted with a phenylalanine residue.

In some embodiments, the serotype may be AAV2 or a variant thereof, as described in International Publication No. WO2036130589, herein incorporated by reference in its entirety. The amino acid sequence of AAV2 may comprise N587A. E548A, or N708A mutations. In certain embodiments, the amino acid sequence of any AAV may comprise a V708K mutation.

In certain embodiments, the AAV may be a serotype selected from any of those found in Table 1.

In certain embodiments, the AAV may comprise a sequence, fragment or variant thereof, of the sequences in Table 1.

In certain embodiments, the AAV may be encoded by a sequence, fragment or variant as described in Table 1.

TABLE 1

AAV Serotypes

| Serotype | SEQ ID NO | Reference Information |
|---|---|---|
| AAVPHP.B or G2B-26 | 1 | WO2015038958 SEQ ID NO: 8 and 13 |
| AAVPHP.B | 2 | WO2015038958 SEQ ID NO: 9 |
| AAVG2B-13 | 3 | WO2015038958 SEQ ID NO: 12 |
| AAVTH1.1-32 | 4 | WO2015038958 SEQ ID NO: 14 |
| AAVTH1.1-35 | 5 | WO2015038958 SEQ ID NO: 15 |
| AAV1 | 6 | US20150159173 SEQ ID NO: 11, US20150315612 SEQ ID NO: 202 |
| AAV1 | 7 | US20160017295 SEQ ID NO: 1 US20030138772 SEQ ID NO: 64, US20150159173 SEQ ID NO: 27, US20150315612 SEQ ID NO: 219, U.S. Pat. No. 7,198,951 SEQ ID NO: 5 |

TABLE 1-continued

AAV Serotypes

| Serotype | SEQ ID NO | Reference Information |
|---|---|---|
| AAV1 | 8 | US20030138772 SEQ ID NO: 6 |
| AAV1.3 | 9 | US20030138772 SEQ ID NO: 14 |
| AAV10 | 10 | US20030138772 SEQ ID NO: 117 |
| AAV10 | 11 | WO2015121501 SEQ ID NO: 9 |
| AAV10 | 12 | WO2015121501 SEQ ID NO: 8 |
| AAV11 | 13 | US20030138772 SEQ ID NO: 118 |
| AAV12 | 14 | US20030138772 SEQ ID NO: 119 |
| AAV2 | 15 | US20150159173 SEQ ID NO: 7, US20150315612 SEQ ID NO: 211 |
| AAV2 | 16 | US20030138772 SEQ ID NO: 70, US20150159173 SEQ ID NO: 23, US20150315612 SEQ ID NO: 221, US20160017295 SEQ ID NO: 2, U.S. Pat. No. 6,156,303 SEQ ID NO: 4, U.S. Pat. No. 7,198,951 SEQ ID NO: 4, WO2015121501 SEQ ID NO: 1 |
| AAV2 | 17 | U.S. Pat. No. 6,156,303 SEQ ID NO: 8 |
| AAV2 | 18 | US20030138772 SEQ ID NO: 7 |
| AAV2 | 19 | U.S. Pat. No. 6,156,303 SEQ ID NO: 3 |
| AAV2.5T | 20 | U.S. Pat. No. 9,233,131 SEQ ID NO: 42 |
| AAV223.10 | 21 | US20030138772 SEQ ID NO: 75 |
| AAV223.2 | 22 | US20030138772 SEQ ID NO: 49 |
| AAV223.2 | 23 | US20030138772 SEQ ID NO: 76 |
| AAV223.4 | 24 | US20030138772 SEQ ID NO: 50 |
| AAV223.4 | 25 | US20030138772 SEQ ID NO: 73 |
| AAV223.5 | 26 | US20030138772 SEQ ID NO: 51 |
| AAV223.5 | 27 | US20030138772 SEQ ID NO: 74 |
| AAV223.6 | 28 | US20030138772 SEQ ID NO: 52 |
| AAV223.6 | 29 | US20030138772 SEQ ID NO: 78 |
| AAV223.7 | 30 | US20030138772 SEQ ID NO: 53 |
| AAV223.7 | 31 | US20030138772 SEQ ID NO: 77 |
| AAV29.3 | 32 | US20030138772 SEQ ID NO: 82 |
| AAV29.4 | 33 | US20030138772 SEQ ID NO: 12 |
| AAV29.5 | 34 | US20030138772 SEQ ID NO: 83 |
| AAV29.5 (AAVbb.2) | 35 | US20030138772 SEQ ID NO: 13 |
| AAV3 | 36 | US20150159173 SEQ ID NO: 12 |
| AAV3 | 37 | US20030138772 SEQ ID NO: 71, US20150159173 SEQ ID NO: 28, US20160017295 SEQ ID NO: 3, U.S. Pat. No. 7,198,951 SEQ ID NO: 6 |
| AAV3 | 38 | US20030138772 SEQ ID NO: 8 |
| AAV3.3b | 39 | US20030138772 SEQ ID NO: 72 |
| AAV3-3 | 40 | US20150315612 SEQ ID NO: 200 |
| AAV3-3 | 41 | US20150315612 SEQ ID NO: 217 |
| AAV3a | 42 | U.S. Pat. No. 6,156,303 SEQ ID NO: 5 |

TABLE 1-continued

AAV Serotypes

| Serotype | SEQ ID NO | Reference Information |
|---|---|---|
| AAV3a | 43 | U.S. Pat. No. 6,156,303 SEQ ID NO: 9 |
| AAV3b | 44 | U.S. Pat. No. 6,156,303 SEQ ID NO: 6 |
| AAV3b | 45 | U.S. Pat. No. 6,156,303 SEQ ID NO: 10 |
| AAV3b | 46 | U.S. Pat. No. 6,156,303 SEQ ID NO: 1 |
| AAV4 | 47 | US20140348794 SEQ ID NO: 17 |
| AAV4 | 48 | US20140348794 SEQ ID NO: 5 |
| AAV4 | 49 | US20140348794 SEQ ID NO: 3 |
| AAV4 | 50 | US20140348794 SEQ ID NO: 14 |
| AAV4 | 51 | US20140348794 SEQ ID NO: 15 |
| AAV4 | 52 | US20140348794 SEQ ID NO: 19 |
| AAV4 | 53 | US20140348794 SEQ ID NO: 12 |
| AAV4 | 54 | US20140348794 SEQ ID NO: 13 |
| AAV4 | 55 | US20140348794 SEQ ID NO: 7 |
| AAV4 | 56 | US20140348794 SEQ ID NO: 8 |
| AAV4 | 57 | US20140348794 SEQ ID NO: 9 |
| AAV4 | 58 | US20140348794 SEQ ID NO: 2 |
| AAV4 | 59 | US20140348794 SEQ ID NO: 10 |
| AAV4 | 60 | US20140348794 SEQ ID NO: 11 |
| AAV4 | 61 | US20140348794 SEQ ID NO: 18 |
| AAV4 | 62 | US20030138772 SEQ ID NO: 63, US20160017295 SEQ ID NO: 4, US20140348794 SEQ ID NO: 4 |
| AAV4 | 63 | US20140348794 SEQ ID NO: 16 |
| AAV4 | 64 | US20140348794 SEQ ID NO: 20 |
| AAV4 | 65 | US20140348794 SEQ ID NO: 6 |
| AAV4 | 66 | US20140348794 SEQ ID NO: 1 |
| AAV42.2 | 67 | US20030138772 SEQ ID NO: 9 |
| AAV42.2 | 68 | US20030138772 SEQ ID NO: 102 |
| AAV42.3b | 69 | US20030138772 SEQ ID NO: 36 |
| AAV42.3B | 70 | US20030138772 SEQ ID NO: 107 |
| AAV42.4 | 71 | US20030138772 SEQ ID NO: 33 |
| AAV42.4 | 72 | US20030138772 SEQ ID NO: 88 |
| AAV42.8 | 73 | US20030138772 SEQ ID NO: 27 |
| AAV42.8 | 74 | US20030138772 SEQ ID NO: 85 |
| AAV43.1 | 75 | US20030138772 SEQ ID NO: 39 |
| AAV43.1 | 76 | US20030138772 SEQ ID NO: 92 |
| AAV43.12 | 77 | US20030138772 SEQ ID NO: 41 |
| AAV43.12 | 78 | US20030138772 SEQ ID NO: 93 |
| AAV43.20 | 79 | US20030138772 SEQ ID NO: 42 |

TABLE 1-continued

AAV Serotypes

| Serotype | SEQ ID NO | Reference Information |
|---|---|---|
| AAV43.20 | 80 | US20030138772 SEQ ID NO: 99 |
| AAV43.21 | 81 | US20030138772 SEQ ID NO: 43 |
| AAV43.21 | 82 | US20030138772 SEQ ID NO: 96 |
| AAV43.23 | 83 | US20030138772 SEQ ID NO: 44 |
| AAV43.23 | 84 | US20030138772 SEQ ID NO: 98 |
| AAV43.25 | 85 | US20030138772 SEQ ID NO: 45 |
| AAV43.25 | 86 | US20030138772 SEQ ID NO: 97 |
| AAV43.5 | 87 | US20030138772 SEQ ID NO: 40 |
| AAV43.5 | 88 | US20030138772 SEQ ID NO: 94 |
| AAV4-4 | 89 | US20150315612 SEQ ID NO: 201 |
| AAV4-4 | 90 | US20150315612 SEQ ID NO: 218 |
| AAV44.1 | 91 | US20030138772 SEQ ID NO: 46 |
| AAV44.1 | 92 | US20030138772 SEQ ID NO: 79 |
| AAV44.5 | 93 | US20030138772 SEQ ID NO: 47 |
| AAV44.5 | 94 | US20030138772 SEQ ID NO: 80 |
| AAV4407 | 95 | US20150315612 SEQ ID NO: 90 |
| AAV5 | 96 | U.S. Pat. No. 7,427,396 SEQ ID NO: 1 |
| AAV5 | 97 | US20030138772 SEQ ID NO: 114 |
| AAV5 | 98 | US20160017295 SEQ ID NO: 5, U.S. Pat. No. 7,427,396 SEQ ID NO: 2, US20150315612 SEQ ID NO: 216 |
| AAV5 | 99 | US20150315612 SEQ ID NO: 199 |
| AAV6 | 100 | US20150159173 SEQ ID NO: 13 |
| AAV6 | 101 | US20030138772 SEQ ID NO: 65, US20150159173 SEQ ID NO: 29, US20160017295 SEQ ID NO: 6, U.S. Pat. No. 6,156,303 SEQ ID NO: 7 |
| AAV6 | 102 | U.S. Pat. No. 6,156,303 SEQ ID NO: 11 |
| AAV6 | 103 | U.S. Pat. No. 6,156,303 SEQ ID NO: 2 |
| AAV6 | 104 | US20150315612 SEQ ID NO: 203 |
| AAV6 | 105 | US20150315612 SEQ ID NO: 220 |
| AAV6.1 | 106 | US20150159173 |
| AAV6.12 | 107 | US20150159173 |
| AAV6.2 | 108 | US20150159173 |
| AAV7 | 109 | US20150159173 SEQ ID NO: 14 |
| AAV7 | 110 | US20150315612 SEQ ID NO: 183 |
| AAV7 | 111 | US20030138772 SEQ ID NO: 2, US20150159173 SEQ ID NO: 30, US20150315612 SEQ ID NO: 181, US20160017295 SEQ ID NO: 7 |
| AAV7 | 112 | US20030138772 SEQ ID NO: 3 |
| AAV7 | 113 | US20030138772 SEQ ID NO: 1, US20150315612 SEQ ID NO: 180 |
| AAV7 | 114 | US20150315612 SEQ ID NO: 213 |

TABLE 1-continued

AAV Serotypes

| Serotype | SEQ ID NO | Reference Information |
|---|---|---|
| AAV7 | 115 | US20150315612 SEQ ID NO: 222 |
| AAV8 | 116 | US20150159173 SEQ ID NO: 15 |
| AAV8 | 117 | US20150376240 SEQ ID NO: 7 |
| AAV8 | 118 | US20030138772 SEQ ID NO: 4, US20150315612 SEQ ID NO: 182 |
| AAV8 | 119 | US20030138772 SEQ ID NO: 95, US20140359799 SEQ ID NO: 1, US20150159173 SEQ ID NO: 31, US20160017295 SEQ ID NO: 8, U.S. Pat. No. 7,198,951 SEQ ID NO: 7, US20150315612 SEQ ID NO: 223 |
| AAV8 | 120 | US20150376240 SEQ ID NO: 8 |
| AAV8 | 121 | US20150315612 SEQ ID NO: 214 |
| AAV-8b | 122 | US20150376240 SEQ ID NO: 5 |
| AAV-8b | 123 | US20150376240 SEQ ID NO: 3 |
| AAV-8h | 124 | US20150376240 SEQ ID NO: 6 |
| AAV-8h | 125 | US20150376240 SEQ ID NO: 4 |
| AAV9 | 126 | US20030138772 SEQ ID NO: 5 |
| AAV9 | 127 | U.S. Pat. No. 7,198,951 SEQ ID NO: 1 |
| AAV9 | 128 | US20160017295 SEQ ID NO: 9 |
| AAV9 | 129 | US20030138772 SEQ ID NO: 100, U.S. Pat. No. 7,198,951 SEQ ID NO: 2 |
| AAV9 | 130 | U.S. Pat. No. 7,198,951 SEQ ID NO: 3 |
| AAV9 (AAVhu.14) | 131 | U.S. Pat. No. 7,906,111 SEQ ID NO: 3, WO2015038958 SEQ ID NO: 11 |
| AAV9 (AAVhu.14) | 132 | U.S. Pat. No. 7,906,111 SEQ ID NO: 123; WO2015038958 SEQ ID NO: 2 |
| AAVA3.1 | 133 | US20030138772 SEQ ID NO: 120 |
| AAVA3.3 | 134 | US20030138772 SEQ ID NO: 57 |
| AAVA3.3 | 135 | US20030138772 SEQ ID NO: 66 |
| AAVA3.4 | 136 | US20030138772 SEQ ID NO: 54 |
| AAVA3.4 | 137 | US20030138772 SEQ ID NO: 68 |
| AAVA3.5 | 138 | US20030138772 SEQ ID NO: 55 |
| AAVA3,5 | 139 | US20030138772 SEQ ID NO: 69 |
| AAVA3.7 | 140 | US20030138772 SEQ ID NO: 56 |
| AAVA3.7 | 141 | US20030138772 SEQ ID NO: 67 |
| AAV29.3 (AAVbb.1) | 142 | US20030138772 SEQ ID NO: 11 |
| AAVC2 | 143 | US20030138772 SEQ ID NO: 61 |
| AAVCh.5 | 144 | US20150159173 SEQ ID NO: 46, US20150315612 SEQ ID NO: 234 |
| AAVcy.2 (AAV13.3) | 145 | US20030138772 SEQ ID NO: 15 |
| AAV24.1 | 146 | US20030138772 SEQ ID NO: 101 |
| AAVcy.3 (AAV24.1) | 147 | US20030138772 SEQ ID NO: 16 |
| AAV27.3 | 148 | US20030138772 SEQ ID NO: 104 |

TABLE 1-continued

AAV Serotypes

| Serotype | SEQ ID NO | Reference Information |
|---|---|---|
| AAVcy.4 (AAV27.3) | 149 | US20030138772 SEQ ID NO: 17 |
| AAVcy.5 | 150 | US20150315612 SEQ ID NO: 227 |
| AAV7.2 | 151 | US20030138772 SEQ ID NO: 103 |
| AAVcy.5 (AAV7.2) | 152 | US20030138772 SEQ ID NO: 18 |
| AAV16.3 | 153 | US20030138772 SEQ ID NO: 105 |
| AAVcy.6 (AAV16.3) | 154 | US20030138772 SEQ ID NO: 10 |
| AAVcy.5 | 155 | US20150159173 SEQ ID NO: 8 |
| AAVcy.5 | 156 | US20150159173 SEQ ID NO: 24 |
| AAVCy.5R1 | 157 | US20150159173 |
| AAVCy.5R2 | 158 | US20150159173 |
| AAVCy.5R3 | 159 | US20150159173 |
| AAVCy.5R4 | 160 | US20150159173 |
| AAVDJ | 161 | US20140359799 SEQ ID NO: 3, U.S. Pat. No. 7,588,772 SEQ ID NO: 2 |
| AAVDJ | 162 | US20140359799 SEQ ID NO: 2, U.S. Pat. No. 7,588,772 SEQ ID NO: 1 |
| AAVDJ-8 | 163 | U.S. Pat. No. 7,588,772; Grimm et al 2008 |
| AAVDJ-8 | 164 | U.S. Pat. No. 7,588,772; Grimm et al 2008 |
| AAVF5 | 165 | US20030138772 SEQ ID NO: 110 |
| AAVH2 | 166 | US20030138772 SEQ ID NO: 26 |
| AAVH6 | 167 | US20030138772 SEQ ID NO: 25 |
| AAVhE1.1 | 168 | U.S. Pat. No. 9,233,131 SEQ ID NO: 44 |
| AAVhEr1.14 | 169 | U.S. Pat. No. 9,233,131 SEQ ID NO: 46 |
| AAVhEr1.16 | 170 | U.S. Pat. No. 9,233,131 SEQ ID NO: 48 |
| AAVhEr1.18 | 171 | U.S. Pat. No. 9,233,131 SEQ ID NO: 49 |
| AAVhEr1.23 (AAVhEr2.29) | 172 | U.S. Pat. No. 9,233,131 SEQ ID NO: 53 |
| AAVhEr1.35 | 173 | U.S. Pat. No. 9,233,131 SEQ ID NO: 50 |
| AAVhEr1.36 | 174 | U.S. Pat. No. 9,233,131 SEQ ID NO: 52 |
| AAVhEr1.5 | 175 | U.S. Pat. No. 9,233,131 SEQ ID NO: 45 |
| AAVhEr1.7 | 176 | U.S. Pat. No. 9,233,131 SEQ ID NO: 51 |
| AAVhEr1.8 | 177 | U.S. Pat. No. 9,233,131 SEQ ID NO: 47 |
| AAVhEr2.16 | 178 | U.S. Pat. No. 9,233,131 SEQ ID NO: 55 |
| AAVhEr2.30 | 179 | U.S. Pat. No. 9,233,131 SEQ ID NO: 56 |
| AAVhEr2.31 | 180 | U.S. Pat. No. 9,233,131 SEQ ID NO: 58 |
| AAVhEr2.36 | 181 | U.S. Pat. No. 9,233,131 SEQ ID NO: 57 |
| AAVhEr2.4 | 182 | U.S. Pat. No. 9,233,131 SEQ ID NO: 54 |
| AAVhEr3.1 | 183 | U.S. Pat. No. 9,233,131 SEQ ID NO: 59 |
| AAVhu.1 | 184 | US20150315612 SEQ ID NO: 46 |
| AAVhu.1 | 185 | US20150315612 SEQ ID NO: 144 |

TABLE 1-continued

AAV Serotypes

| Serotype | SEQ ID NO | Reference Information |
|---|---|---|
| AAVhu.10 (AAV16.8) | 186 | US20150315612 SEQ ID NO: 56 |
| AAVhu.10 (AAV16.8) | 187 | US20150315612 SEQ ID NO: 156 |
| AAVhu.11 (AAV16.12) | 188 | US20150315612 SEQ ID NO: 57 |
| AAVhu.11 (AAV16.12) | 189 | US20150315612 SEQ ID NO: 153 |
| AAVhu.12 | 190 | US20150315612 SEQ ID NO: 59 |
| AAVhu.12 | 191 | US20150315612 SEQ ID NO: 154 |
| AAVhu.13 | 192 | US20150159173 SEQ ID NO: 16, US20150315612 SEQ ID NO: 71 |
| AAVhu.13 | 193 | US20150159173 SEQ ID NO: 32, US20150315612 SEQ ID NO: 129 |
| AAVhu.136.1 | 194 | US20150315612 SEQ ID NO: 165 |
| AAVhu.140.1 | 195 | US20150315612 SEQ ID NO: 166 |
| AAVhu.140.2 | 196 | US20150315612 SEQ ID NO: 167 |
| AAVhu.145.6 | 197 | US20150315612 SEQ ID No: 178 |
| AAVhu.15 | 198 | US20150315612 SEQ ID NO: 147 |
| AAVhu.15 (AAV33.4) | 199 | US20150315612 SEQ ID NO: 50 |
| AAVhu.156.1 | 200 | US20150315612 SEQ ID No: 179 |
| AAVhu.16 | 201 | US20150315612 SEQ ID NO: 148 |
| AAVhu.16 (AAV33.8) | 202 | US20150315612 SEQ ID NO: 51 |
| AAVhu.17 | 203 | US20150315612 SEQ ID NO: 83 |
| AAVhu.17 (AAV33.12) | 204 | US20150315612 SEQ ID NO: 4 |
| AAVhu.172.1 | 205 | US20150315612 SEQ ID NO: 171 |
| AAVhu.172.2 | 206 | US20150315612 SEQ ID NO: 172 |
| AAVhu.173.4 | 207 | US20150315612 SEQ ID NO: 173 |
| AAVhu.173.8 | 208 | US20150315612 SEQ ID NO: 175 |
| AAVhu.18 | 209 | US20150315612 SEQ ID NO: 52 |
| AAVhu.18 | 210 | US20150315612 SEQ ID NO: 149 |
| AAVhu.19 | 211 | US20150315612 SEQ ID NO: 62 |
| AAVhu.19 | 212 | US20150315612 SEQ ID NO: 133 |
| AAVhu.2 | 213 | US20150315612 SEQ ID NO: 48 |
| AAVhu.2 | 214 | US20150315612 SEQ ID NO: 143 |
| AAVhu.20 | 215 | US20150315612 SEQ ID NO: 63 |
| AAVhu.20 | 216 | US20150315612 SEQ ID NO: 134 |
| AAVhu.21 | 217 | US20150315612 SEQ ID NO: 65 |
| AAVhu.21 | 218 | US20150315612 SEQ ID NO: 135 |
| AAVhu.22 | 219 | US20150315612 SEQ ID NO: 67 |
| AAVhu.22 | 220 | US20150315612 SEQ ID NO: 138 |
| AAVhu.23 | 221 | US20150315612 SEQ ID NO: 60 |
| AAVhu.23.2 | 222 | US20150315612 SEQ ID NO: 137 |

TABLE 1-continued

AAV Serotypes

| Serotype | SEQ ID NO | Reference Information |
|---|---|---|
| AAVhu.24 | 223 | US20150315612 SEQ ID NO: 66 |
| AAVhu.24 | 224 | US20150315612 SEQ ID NO: 136 |
| AAVhu.25 | 225 | US20150315612 SEQ ID NO: 49 |
| AAVhu.25 | 226 | US20150315612 SEQ ID NO: 146 |
| AAVhu.26 | 227 | US20150159173 SEQ ID NO: 17, US20150315612 SEQ ID NO: 61 |
| AAVhu.26 | 228 | US20150159173 SEQ ID NO: 33, US20150315612 SEQ ID NO: 139 |
| AAVhu.27 | 229 | US20150315612 SEQ ID NO: 64 |
| AAVhu.27 | 230 | US20150315612 SEQ ID NO: 140 |
| AAVhu.28 | 231 | US20150315612 SEQ ID NO: 68 |
| AAVhu.28 | 232 | US20150315612 SEQ ID NO: 130 |
| AAVhu.29 | 233 | US20150315612 SEQ ID NO: 69 |
| AAVhu.29 | 234 | US20150159173 SEQ ID NO: 42, US20150315612 SEQ ID NO: 132 |
| AAVhu.29 | 235 | US20150315612 SEQ ID NO: 225 |
| AAVhu.29R | 236 | US20150159173 |
| AAVhu.3 | 237 | US20150315612 SEQ ID NO: 44 |
| AAVhu.3 | 238 | US20150315612 SEQ ID NO: 145 |
| AAVhu.30 | 239 | US20150315612 SEQ ID NO: 70 |
| AAVhu.30 | 240 | US20150315612 SEQ ID NO: 131 |
| AAVhu.31 | 241 | US20150315612 SEQ ID NO: 1 |
| AAVhu.31 | 242 | US20150315612 SEQ ID NO: 121 |
| AAVhu.32 | 243 | US20150315612 SEQ ID NO: 2 |
| AAVhu.32 | 244 | US20150315612 SEQ ID NO: 122 |
| AAVhu.33 | 245 | US20150315612 SEQ ID NO: 75 |
| AAVhu.33 | 246 | US20150315612 SEQ ID NO: 124 |
| AAVhu.34 | 247 | US20150315612 SEQ ID NO: 72 |
| AAVhu.34 | 248 | US20150315612 SEQ ID NO: 125 |
| AAVhu.35 | 249 | US20150315612 SEQ ID NO: 73 |
| AAVhu.35 | 250 | US20150315612 SEQ ID NO: 164 |
| AAVhu.36 | 251 | US20150315612 SEQ ID NO: 74 |
| AAVhu.36 | 252 | US20150315612 SEQ ID NO: 126 |
| AAVhu.37 | 253 | US20150159173 SEQ ID NO: 34, US20150315612 SEQ ID NO: 88 |
| AAVhu.37 (AAV106.1) | 254 | US20150315612 SEQ ID NO: 10, US20150159173 SEQ ID NO: 18 |
| AAVhu.38 | 255 | US20150315612 SEQ ID NO: 161 |
| AAVhu.39 | 256 | US20150315612 SEQ ID NO: 102 |
| AAVhu.39 (AAVLG-9) | 257 | US20150315612 SEQ ID NO: 24 |
| AAVhu.4 | 258 | US20150315612 SEQ ID NO: 47 |

TABLE 1-continued

AAV Serotypes

| Serotype | SEQ ID NO | Reference Information |
| --- | --- | --- |
| AAVhu.4 | 259 | US20150315612 SEQ ID NO: 141 |
| AAVhu.40 | 260 | US20150315612 SEQ ID NO: 87 |
| AAVhu.40 (AAV114.3) | 261 | US20150315612 SEQ ID No: 11 |
| AAVhu.41 | 262 | US20150315612 SEQ ID NO: 91 |
| AAVhu.41 (AAV127.2) | 263 | US20150315612 SEQ ID NO: 6 |
| AAVhu.42 | 264 | US20150315612 SEQ ID NO: 85 |
| AAVhu.42 (AAV127.5) | 265 | US20150315612 SEQ ID NO: 8 |
| AAVhu.43 | 266 | US20150315612 SEQ ID NO: 160 |
| AAVhu.43 | 267 | US20150315612 SEQ ID NO: 236 |
| AAVhu.43 (AAV128.1) | 268 | US20150315612 SEQ ID NO: 80 |
| AAVhu.44 | 269 | US20150159173 SEQ ID NO: 45, US20150315612 SEQ ID NO: 158 |
| AAVhu.44 (AAV128.3) | 270 | US20150315612 SEQ ID NO: 81 |
| AAVhu.44R1 | 271 | US20150159173 |
| AAVhu.44R2 | 272 | US20150159173 |
| AAVhu.44R3 | 273 | US20150159173 |
| AAVhu.45 | 274 | US20150315612 SEQ ID NO: 76 |
| AAVhu.45 | 275 | US20150315612 SEQ ID NO: 127 |
| AAVhu.46 | 276 | US20150315612 SEQ ID NO: 82 |
| AAVhu.46 | 277 | US20150315612 SEQ ID NO: 159 |
| AAVhu.46 | 278 | US20150315612 SEQ ID NO: 224 |
| AAVhu.47 | 279 | US20150315612 SEQ ID NO: 77 |
| AAVhu.47 | 280 | US20150315612 SEQ ID NO: 128 |
| AAVhu.48 | 281 | US20150159173 SEQ ID NO: 38 |
| AAVhu.48 | 282 | US20150315612 SEQ ID NO: 157 |
| AAVhu.48 (AAV130.4) | 283 | US20150315612 SEQ ID NO: 78 |
| AAVhu.48R1 | 284 | US20150159173 |
| AAVhu.48R2 | 285 | US20150159173 |
| AAVhu.48R3 | 286 | US20150159173 |
| AAVhu.49 | 287 | US20150315612 SEQ ID NO: 209 |
| AAVhu.49 | 288 | US20150315612 SEQ ID NO: 189 |
| AAVhu.5 | 289 | US20150315612 SEQ ID NO: 45 |
| AAVhu.5 | 290 | US20150315612 SEQ ID NO: 142 |
| AAVhu.51 | 291 | US20150315612 SEQ ID NO: 208 |
| AAVhu.51 | 292 | US20150315612 SEQ ID NO: 190 |
| AAVhu.52 | 293 | US20150315612 SEQ ID NO: 210 |
| AAVhu.52 | 294 | US20150315612 SEQ ID NO: 191 |
| AAVhu.53 | 295 | US20150159173 SEQ ID NO: 19 |

TABLE 1-continued

AAV Serotypes

| Serotype | SEQ ID NO | Reference Information |
|---|---|---|
| AAVhu.53 | 296 | US20150159173 SEQ ID NO: 35 |
| AAVhu.53 (AAV145.1) | 297 | US20150315612 SEQ ID NO: 176 |
| AAVhu.54 | 298 | US20150315612 SEQ ID NO: 188 |
| AAVhu.54 (AAV145.5) | 299 | US20150315612 SEQ ID No: 177 |
| AAVhu.55 | 300 | US20150315612 SEQ ID NO: 187 |
| AAVhu.56 | 301 | US20150315612 SEQ ID NO: 205 |
| AAVhu.56 (AAV145.6) | 302 | US20150315612 SEQ ID NO: 168 |
| AAVhu.56 (AAV145.6) | 303 | US20150315612 SEQ ID NO: 192 |
| AAVhu.57 | 304 | US20150315612 SEQ ID NO: 206 |
| AAVhu.57 | 305 | US20150315612 SEQ ID NO: 169 |
| AAVhu.57 | 306 | US20150315612 SEQ ID NO: 193 |
| AAVhu.58 | 307 | US20150315612 SEQ ID NO: 207 |
| AAVhu.58 | 308 | US20150315612 SEQ ID NO: 194 |
| AAVhu.6 (AAV3.1) | 309 | US20150315612 SEQ ID NO: 5 |
| AAVhu.6 (AAV3.1) | 310 | US20150315612 SEQ ID NO: 84 |
| AAVhu.60 | 311 | US20150315612 SEQ ID NO: 184 |
| AAVhu.60 (AAV161.10) | 312 | US20150315612 SEQ ID NO: 170 |
| AAVhu.61 | 313 | US20150315612 SEQ ID NO: 185 |
| AAVhu.61 (AAV161.6) | 314 | US20150315612 SEQ ID NO: 174 |
| AAVhu.63 | 315 | US20150315612 SEQ ID NO: 204 |
| AAVhu.63 | 316 | US20150315612 SEQ ID NO: 195 |
| AAVhu.64 | 317 | US20150315612 SEQ ID NO: 212 |
| AAVhu.64 | 318 | US20150315612 SEQ ID NO: 196 |
| AAVhu.66 | 319 | US20150315612 SEQ ID NO: 197 |
| AAVhu.67 | 320 | US20150315612 SEQ ID NO: 215 |
| AAVhu.67 | 321 | US20150315612 SEQ ID NO: 198 |
| AAVhu.7 | 322 | US20150315612 SEQ ID NO: 226 |
| AAVhu.7 | 323 | US20150315612 SEQ ID NO: 150 |
| AAVhu.7 (AAV7.3) | 324 | US20150315612 SEQ ID NO: 55 |
| AAVhu.71 | 325 | US20150315612 SEQ ID NO: 79 |
| AAVhu.8 | 326 | US20150315612 SEQ ID NO: 53 |
| AAVhu.8 | 327 | US20150315612 SEQ ID NO: 12 |
| AAVhu.8 | 328 | US20150315612 SEQ ID NO: 151 |
| AAVhu.9 (AAV3.1) | 329 | US20150315612 SEQ ID NO: 58 |
| AAVhu.9 (AAV3.1) | 330 | US20150315612 SEQ ID NO: 155 |
| AAV-LK01 | 333 | US20150376607 SEQ ID NO: 2 |
| AAV-LK01 | 332 | US20150376607 SEQ ID NO: 29 |
| AAV-LK02 | 333 | US20150376607 SEQ ID NO: 3 |

TABLE 1-continued

AAV Serotypes

| Serotype | SEQ ID NO | Reference Information |
|---|---|---|
| AAV-LK02 | 334 | US20150376607 SEQ ID NO: 30 |
| AAV-LK03 | 335 | US20150376607 SEQ ID NO: 4 |
| AAV-LK03 | 336 | WO2015121501 SEQ ID NO: 12, US20150376607 SEQ ID NO: 31 |
| AAV-LK04 | 337 | US20150376607 SEQ ID NO: 5 |
| AAV-LK04 | 338 | US20150376607 SEQ ID NO: 32 |
| AAV-LK05 | 339 | US20150376607 SEQ ID NO: 6 |
| AAV-LK05 | 340 | US20150376607 SEQ ID NO: 33 |
| AAV-LK06 | 341 | US20150376607 SEQ ID NO: 7 |
| AAV-LK06 | 342 | US20150376607 SEQ ID NO: 34 |
| AAV-LK07 | 343 | US20150376607 SEQ ID NO: 8 |
| AAV-LK07 | 344 | US20150376607 SEQ ID NO: 35 |
| AAV-LK08 | 345 | US20150376607 SEQ ID NO: 9 |
| AAV-LK08 | 346 | US20150376607 SEQ ID NO: 36 |
| AAV-LK09 | 347 | US20150376607 SEQ ID NO: 10 |
| AAV-LK09 | 348 | US20150376607 SEQ ID NO: 37 |
| AAV-LK10 | 349 | US20150376607 SEQ ID NO: 11 |
| AAV-LK10 | 350 | US20150376607 SEQ ID NO: 38 |
| AAV-LK11 | 351 | US20150376607 SEQ ID NO: 12 |
| AAV-LK11 | 352 | US20150376607 SEQ ID NO: 39 |
| AAV-LK12 | 353 | US20150376607 SEQ ID NO: 13 |
| AAV-LK12 | 354 | US20150376607 SEQ ID NO: 40 |
| AAV-LK13 | 355 | US20150376607 SEQ ID NO: 14 |
| AAV-LK13 | 356 | US20150376607 SEQ ID NO: 41 |
| AAV-LK14 | 357 | US20150376607 SEQ ID NO: 15 |
| AAV-LK14 | 358 | US20150376607 SEQ ID NO: 42 |
| AAV-LK15 | 359 | US20150376607 SEQ ID NO: 16 |
| AAV-LK15 | 360 | US20150376607 SEQ ID NO: 43 |
| AAV-LK16 | 361 | US20150376607 SEQ ID NO: 17 |
| AAV-LK16 | 362 | US20150376607 SEQ ID NO: 44 |
| AAV-LK17 | 363 | US20150376607 SEQ ID NO: 18 |
| AAV-LK17 | 364 | US20150376607 SEQ ID NO: 45 |
| AAV-LK18 | 365 | US20150376607 SEQ ID NO: 19 |
| AAV-LK18 | 366 | US20150376607 SEQ ID NO: 46 |
| AAV-LK19 | 367 | US20150376607 SEQ ID NO: 20 |
| AAV-LK19 | 368 | US20150376607 SEQ ID NO: 47 |
| AAV-PAEC | 369 | US20150376607 SEQ ID NO: 1 |
| AAV-PAEC | 370 | US20150376607 SEQ ID NO: 48 |
| AAV-PAEC11 | 371 | US20150376607 SEQ ID NO: 26 |

TABLE 1-continued

AAV Serotypes

| Serotype | SEQ ID NO | Reference Information |
|---|---|---|
| AAV-PAEC11 | 372 | US20150376607 SEQ ID NO: 54 |
| AAV-PAEC12 | 373 | US20150376607 SEQ ID NO: 27 |
| AAV-PAEC12 | 374 | US20150376607 SEQ ID NO: 51 |
| AAV-PAEC13 | 375 | US20150376607 SEQ ID NO: 28 |
| AAV-PAEC13 | 376 | US20150376607 SEQ ID NO: 49 |
| AAV-PAEC2 | 377 | US20150376607 SEQ ID NO: 21 |
| AAV-PAEC2 | 378 | US20150376607 SEQ ID NO: 56 |
| AAV-PAEC4 | 379 | US20150376607 SEQ ID NO: 22 |
| AAV-PAEC4 | 380 | US20150376607 SEQ ID NO: 55 |
| AAV-PAEC6 | 381 | US20150376607 SEQ ID NO: 23 |
| AAV-PAEC6 | 382 | US20150376607 SEQ ID NO: 52 |
| AAV-PAEC7 | 383 | US20150376607 SEQ ID NO: 24 |
| AAV-PAEC7 | 384 | US20150376607 SEQ ID NO: 53 |
| AAV-PAEC8 | 385 | US20150376607 SEQ ID NO: 25 |
| AAV-PAEC8 | 386 | US20150376607 SEQ ID NO: 50 |
| AAVpi.1 | 387 | US20150315612 SEQ ID NO: 28 |
| AAVpi.1 | 388 | US20150315612 SEQ ID NO: 93 |
| AAVpi.2 | 389 | US20150315612 SEQ ID NO: 30 |
| AAVpi.2 | 390 | US20150315612 SEQ ID NO: 95 |
| AAVpi.3 | 391 | US20150315612 SEQ ID NO: 29 |
| AAVpi.3 | 392 | US20150315612 SEQ ID NO: 94 |
| AAVrh.10 | 393 | US20150159173 SEQ ID NO: 9 |
| AAVrh.10 | 394 | US20150159173 SEQ ID NO: 25 |
| AAV44.2 | 395 | US20030138772 SEQ ID NO: 59 |
| AAVrh.10 (AAV44.2) | 396 | US20030138772 SEQ ID NO: 81 |
| AAV42.1B | 397 | US20030138772 SEQ ID NO: 90 |
| AAVrh.12 (AAV42.1b) | 398 | US20030138772 SEQ ID NO: 30 |
| AAVrh.13 | 399 | US20150159173 SEQ ID NO: 10 |
| AAVrh.13 | 400 | US20150159173 SEQ ID NO: 26 |
| AAVrh.13 | 401 | US20150315612 SEQ ID NO: 228 |
| AAVrh.13R | 402 | US20150159173 |
| AAV42.3A | 403 | US20030138772 SEQ ID NO: 87 |
| AAVrh.14 (AAV42.3a) | 404 | US20030138772 SEQ ID NO: 32 |
| AAV42.5A | 405 | US20030138772 SEQ ID NO: 89 |
| AAVrh.17 (AAV42.5a) | 406 | US20030138772 SEQ ID NO: 34 |
| AAV42.5B | 407 | US20030138772 SEQ ID NO: 91 |
| AAVrh.18 (AAV42.5b) | 408 | US20030138772 SEQ ID NO: 29 |
| AAV42.6B | 409 | US20030138772 SEQ ID NO: 112 |

TABLE 1-continued

AAV Serotypes

| Serotype | SEQ ID NO | Reference Information |
|---|---|---|
| AAVrh.19 (AAV42.6b) | 410 | US20030138772 SEQ ID NO: 38 |
| AAVrh.2 | 411 | US20150159173 SEQ ID NO: 39 |
| AAVrh.2 | 412 | US20150315612 SEQ ID NO: 231 |
| AAVrh.20 | 413 | US20150159173 SEQ ID NO: 1 |
| AAV42.10 | 414 | US20030138772 SEQ ID NO: 106 |
| AAVrh.21 (AAV42.10) | 415 | US20030138772 SEQ ID NO: 35 |
| AAV42.11 | 416 | US20030138772 SEQ ID NO: 108 |
| AAVrh.22 (AAV42.11) | 417 | US20030138772 SEQ ID NO: 37 |
| AAV42.12 | 418 | US20030138772 SEQ ID NO: 113 |
| AAVrh.23 (AAV42.12) | 419 | US20030138772 SEQ ID NO: 58 |
| AAV42.13 | 420 | US20030138772 SEQ ID NO: 86 |
| AAVrh.24 (AAV42.13) | 421 | US20030138772 SEQ ID NO: 31 |
| AAV42.15 | 422 | US20030138772 SEQ ID NO: 84 |
| AAVrh.25 (AAV42.15) | 423 | US20030138772 SEQ ID NO: 28 |
| AAVrh.2R | 424 | US20150159173 |
| AAVrh.31 (AAV223.1) | 425 | US20030138772 SEQ ID NO: 48 |
| AAVC1 | 426 | US20030138772 SEQ ID NO: 60 |
| AAVrh.32 (AAVC1) | 427 | US20030138772 SBQ ID NO: 19 |
| AAVrh.32/33 | 428 | US20150159173 SEQ ID NO: 2 |
| AAVrh.33 (AAVC3) | 429 | US20030138772 SEQ ID NO: 20 |
| AAVC5 | 430 | US20030138772 SEQ ID NO: 62 |
| AAVrh.34 (AAVC5) | 431 | US20030138772 SEQ ID NO: 21 |
| AAVF1 | 432 | US20030138772 SEQ ID NO: 109 |
| AAVrh.35 (AAVF1) | 433 | US20030138772 SEQ ID NO: 22 |
| AAVF3 | 434 | US20030138772 SEQ ID NO: 111 |
| AAVrh.36 (AAVF3) | 435 | US20030138772 SEQ ID NO: 23 |
| AAVrh.37 | 436 | US20030138772 SEQ ID NO: 24 |
| AAVrh.37 | 437 | US20150159173 SEQ ID NO: 40 |
| AAVrh.37 | 438 | US20150315612 SEQ ID NO: 229 |
| AAVrh.37R2 | 439 | US20150159173 |
| AAVrh.38 (AAVLG-4) | 440 | US20150315612 SEQ ID NO: 7 |
| AAVrh.38 (AAVLG-4) | 441 | US20150315612 SEQ ID NO: 86 |
| AAVrh.39 | 442 | US20150159173 SEQ ID NO: 20, US20150315612 SEQ ID NO: 13 |
| AAVrh.39 | 443 | US20150159173 SEQ ID NO: 3, US20150159173 SEQ ID NO: 36, US20150315612 SEQ ID NO: 89 |
| AAVrh.40 | 444 | US20150315612 SEQ ID NO: 92 |
| AAVrh.40 (AAVLG-10) | 445 | US20150315612 SEQ ID No: 14 |
| AAVrh.43 (AAVN721-8) | 446 | US20150315612 SEQ ID NO: 43, US20150159173 SEQ ID NO: 21 |

TABLE 1-continued

AAV Serotypes

| Serotype | SEQ ID NO | Reference Information |
|---|---|---|
| AAVrh.43 (AAVN721-8) | 447 | US20150315612 SEQ ID NO: 163, US20150159173 SEQ ID NO: 37 |
| AAVrh.44 | 448 | US20150315612 SEQ ID NO: 34 |
| AAVrh.44 | 449 | US20150315612 SEQ ID NO: 111 |
| AAVrh.45 | 450 | US20150315612 SEQ ID NO: 41 |
| AAVrh.45 | 451 | US20150315612 SEQ ID NO: 109 |
| AAVrh.46 | 452 | US20150159173 SEQ ID NO: 22, US20150315612 SEQ ID NO: 19 |
| AAVrh.46 | 453 | US20150159173 SEQ ID NO: 4, US20150315612 SEQ ID NO: 101 |
| AAVrh.47 | 454 | US20150315612 SEQ ID NO: 38 |
| AAVrh.47 | 455 | US20150315612 SEQ ID NO: 118 |
| AAVrh.48 | 456 | US20150159173 SEQ ID NO: 44, US20150315612 SEQ ID NO: 115 |
| AAVrh.48.1 | 457 | US20150159173 |
| AAVrh.48.1.2 | 458 | US20150159173 |
| AAVrh.48.2 | 459 | US20150159173 |
| AAVrh.48 (AAV1-7) | 460 | US20150315612 SEQ ID NO: 32 |
| AAVrh.49 (AAV1-8) | 461 | US20150315612 SEQ ID NO: 25 |
| AAVrh.49 (AAV1-8) | 462 | US20150315612 SEQ ID NO: 103 |
| AAVrh.50 (AAV2-4) | 463 | US20150315612 SEQ ID NO: 23 |
| AAVrh.50 (AAV2-4) | 464 | US20150315612 SEQ ID NO: 108 |
| AAVrh.51 (AAV2-5) | 465 | US20150315612 SEQ ID No: 22 |
| AAVrh.51 (AAV2-5) | 466 | US20150315612 SEQ ID NO: 104 |
| AAVrh.52 (AAV3-9) | 467 | US20150315612 SEQ ID NO: 18 |
| AAVrh.52 (AAV3-9) | 468 | US20150315612 SEQ ID NO: 96 |
| AAVrh.53 | 469 | US20150315612 SEQ ID NO: 97 |
| AAVrh.53 (AAV3-11) | 470 | US20150315612 SEQ ID NO: 17 |
| AAVrh.53 (AAV3-11) | 471 | US20150315612 SEQ ID NO: 186 |
| AAVrh.54 | 472 | US20150315612 SEQ ID NO: 40 |
| AAVrh.54 | 473 | US20150159173 SEQ ID NO: 49, US20150315612 SEQ ID NO: 116 |
| AAVrh.55 | 474 | US20150315612 SEQ ID NO: 37 |
| AAVrh.55 (AAV4-19) | 475 | US20150315612 SEQ ID NO: 117 |
| AAVrh.56 | 476 | US20150315612 SEQ ID NO: 54 |
| AAVrh.56 | 477 | US20150315612 SEQ ID NO: 152 |
| AAVrh.57 | 478 | US20150315612 SEQ ID NO: 26 |
| AAVrh.57 | 479 | US20150315612 SEQ ID NO: 105 |
| AAVrh.58 | 480 | US20150315612 SEQ ID NO: 27 |
| AAVrh.58 | 481 | US20150159173 SEQ ID NO: 48, US20150315612 SEQ ID NO: 106 |

TABLE 1-continued

| AAV Serotypes | | |
|---|---|---|
| Serotype | SEQ ID NO | Reference Information |
| AAVrh.58 | 482 | US20150315612 SEQ ID NO: 232 |
| AAVrh.59 | 483 | US20150315612 SEQ ID NO: 42 |
| AAVrh.59 | 484 | US20150315612 SEQ ID NO: 110 |
| AAVrh.60 | 485 | US20150315612 SEQ ID NO: 31 |
| AAVrh.60 | 486 | US20150315612 SEQ ID NO: 120 |
| AAVrh.61 | 487 | US20150315612 SEQ ID NO: 107 |
| AAVrh.61 (AAV2-3) | 488 | US20150315612 SEQ ID NO: 21 |
| AAVrh.62 (AAV2-15) | 489 | US20150315612 SEQ ID No: 33 |
| AAVrh.62 (AAV2-15) | 490 | US20150315612 SEQ ID NO: 114 |
| AAVrh.64 | 491 | US20150315612 SEQ ID No: 15 |
| AAVrh.64 | 492 | US20150159173 SEQ ID NO: 43, US20150315612 SEQ ID NO: 99 |
| AAVrh.64 | 493 | US20150315612 SEQ ID NO: 233 |
| AAVRh.64R1 | 494 | US20150159173 |
| AAVRh.64R2 | 495 | US20150159173 |
| AAVrh.65 | 496 | US20150315612 SEQ ID NO: 35 |
| AAVrh.65 | 497 | US20150315612 SEQ ID NO: 112 |
| AAVrh.67 | 498 | US20150315612 SEQ ID NO: 36 |
| AAVrh.67 | 499 | US20150315612 SEQ ID NO: 230 |
| AAVrh.67 | 500 | US20150159173 SEQ ID NO: 47, US20150315612 SEQ ID NO: 113 |
| AAVrh.68 | 501 | US20150315612 SEQ ID NO: 16 |
| AAVrh.68 | 502 | US20150315612 SEQ ID NO: 100 |
| AAVrh.69 | 503 | US20150315612 SEQ ID NO: 39 |
| AAVrh.69 | 504 | US20150315612 SEQ ID NO: 119 |
| AAVrh.70 | 505 | US20150315612 SEQ ID NO: 20 |
| AAVrh.70 | 506 | US20150315612 SEQ ID NO: 98 |
| AAVrh.71 | 507 | US20150315612 SEQ ID NO: 162 |
| AAVrh.72 | 508 | US20150315612 SEQ ID NO: 9 |
| AAVrh.73 | 509 | US20150159173 SEQ ID NO: 5 |
| AAVrh.74 | 510 | US20150159173 SEQ ID NO: 6 |
| AAVrh.8 | 511 | US20150159173 SEQ ID NO: 41 |
| AAVrh.8 | 512 | US20150315612 SEQ ID NO: 235 |
| AAVrh.8R | 513 | US20150159173, WO2015168666 SEQ ID NO: 9 |
| AAVrh.8R A586R mutant | 514 | WO2015168666 SEQ ID NO: 10 |
| AAVrh.8R R533A mutant | 515 | WO2015168666 SEQ ID NO: 11 |
| BAAV (bovine AAV) | 516 | U.S. Pat. No. 9,193,769 SEQ ID NO: 8 |
| BAAV (bovine AAV) | 517 | U.S. Pat. No. 9,193,769 SEQ ID NO: 10 |
| BAAV (bovine AAV) | 518 | U.S. Pat. No. 9,193,769 SEQ ID NO: 4 |

TABLE 1-continued

AAV Serotypes

| Serotype | SEQ ID NO | Reference Information |
|---|---|---|
| BAAV (bovine AAV) | 519 | U.S. Pat. No. 9,193,769 SEQ ID NO: 2 |
| BAAV (bovine AAV) | 520 | U.S. Pat. No. 9,193,769 SEQ ID NO: 6 |
| BAAV (bovine AAV) | 521 | U.S. Pat. No. 9,193,769 SEQ ID NO: 1 |
| BAAV (bovine AAV) | 522 | U.S. Pat. No. 9,193,769 SEQ ID NO: 5 |
| BAAV (bovine AAV) | 523 | U.S. Pat. No. 9,193,769 SEQ ID NO: 3 |
| BAAV (bovine AAV) | 524 | U.S. Pat. No. 9,193,769 SEQ ID NO: 11 |
| BAAV (bovine AAV) | 525 | U.S. Pat. No. 7,427,396 SEQ ID NO: 5 |
| BAAV (bovine AAV) | 526 | U.S. Pat. No. 7,427,396 SEQ ID NO: 6 |
| BAAV (bovine AAV) | 527 | U.S. Pat. No. 9,193,769 SEQ ID NO: 7 |
| BAAV (bovine AAV) | 528 | U.S. Pat. No. 9,193,769 SEQ ID NO: 9 |
| BNP61 AAV | 529 | US20150238550 SEQ ID NO: 1 |
| BNP61 AAV | 530 | US20150238550 SEQ ID NO: 2 |
| BNP62 AAV | 531 | US20150238550 SEQ ID NO: 3 |
| BNP63 AAV | 532 | US20150238550 SEQ ID NO: 4 |
| caprine AAV | 533 | U.S. Pat. No. 7,427,396 SEQ ID NO: 3 |
| caprine AAV | 534 | U.S. Pat. No. 7,427,396 SEQ ID NO: 4 |
| true type AAV (ttAAV) | 535 | WO2015121501 SEQ ID NO: 2 |
| AAAV (Avian AAV) | 536 | U.S. Pat. No. 9,238,800 SEQ ID NO: 12 |
| AAAV (Avian AAV) | 537 | U.S. Pat. No. 9,238,800 SEQ ID NO: 2 |
| AAAV (Avian AAV) | 538 | U.S. Pat. No. 9,238,800 SEQ ID NO: 6 |
| AAAV (Avian AAV) | 539 | U.S. Pat. No. 9,238,800 SEQ ID NO: 4 |
| AAAV (Avian AAV) | 540 | U.S. Pat. No. 9,238,800 SEQ ID NO: 8 |
| AAAV (Avian AAV) | 541 | U.S. Pat. No. 9,238,800 SEQ ID NO: 14 |
| AAAV (Avian AAV) | 542 | U.S. Pat. No. 9,238,800 SEQ ID NO: 10 |
| AAAV (Avian AAV) | 543 | U.S. Pat. No. 9,238,800 SEQ ID NO: 15 |
| AAAV (Avian AAV) | 544 | U.S. Pat. No. 9,238,800 SEQ ID NO: 5 |
| AAAV (Avian AAV) | 545 | U.S. Pat. No. 9,238,800 SEQ ID NO: 9 |
| AAAV (Avian AAV) | 546 | U.S. Pat. No. 9,238,800 SEQ ID NO: 3 |
| AAAV (Avian AAV) | 547 | U.S. Pat. No. 9,238,800 SEQ ID NO: 7 |
| AAAV (Avian AAV) | 548 | U.S. Pat. No. 9,238,800 SEQ ID NO: 11 |
| AAAV (Avian AAV) | 549 | U.S. Pat. No. 9,238,800 SEQ ID NO: 13 |
| AAAV (Avian AAV) | 550 | U.S. Pat. No. 9,238,800 SEQ ID NO: 1 |
| AAV Shuffle 100-1 | 551 | US20160017295 SBQ ID NO: 23 |
| AAV Shuffle 100-1 | 552 | US20160017295 SEQ ID NO: 11 |
| AAV Shuffle 100-2 | 553 | US20160017295 SEQ ID NO: 37 |
| AAV Shuffle 100-2 | 554 | US20160017295 SEQ ID NO: 29 |
| AAV Shuffle 100-3 | 555 | US20160017295 SEQ ID NO: 24 |
| AAV Shuffle 100-3 | 556 | US20160017295 SEQ ID NO: 12 |

TABLE 1-continued

AAV Serotypes

| Serotype | SEQ ID NO | Reference Information |
|---|---|---|
| AAV Shuffle 100-7 | 557 | US20160017295 SEQ ID NO: 25 |
| AAV Shuffle 100-7 | 558 | US20160017295 SEQ ID NO: 13 |
| AAV Shuffle 10-2 | 559 | US20160017295 SEQ ID NO: 34 |
| AAV Shuffle 10-2 | 560 | US20160017295 SEQ ID NO: 26 |
| AAV Shuffle 10-6 | 561 | US20160017295 SEQ ID NO: 35 |
| AAV Shuffle 10-6 | 562 | US20160017295 SEQ ID NO: 27 |
| AAV Shuffle 10-8 | 563 | US20160017295 SEQ ID NO: 36 |
| AAV Shuffle 10-8 | 564 | US20160017295 SEQ ID NO: 28 |
| AAV SM 100-10 | 565 | US20160017295 SEQ ID NO: 41 |
| AAV SM 100-10 | 566 | US20160017295 SEQ ID NO: 33 |
| AAV SM 100-3 | 567 | US20160017295 SEQ ID NO: 40 |
| AAV SM 100-3 | 568 | US20160017295 SEQ ID NO: 32 |
| AAV SM 10-1 | 569 | US20160017295 SEQ ID NO: 38 |
| AAV SM 10-1 | 570 | US20160017295 SEQ ID NO: 30 |
| AAV SM 10-2 | 571 | US20160017295 SEQ ID NO: 10 |
| AAV SM 10-2 | 572 | US20160017295 SEQ ID NO: 22 |
| AAV SM 10-8 | 573 | US20160017295 SEQ ID NO: 39 |
| AAV SM 10-8 | 574 | US20160017295 SEQ ID NO: 31 |
| AAVF1/HSC1 | 575 | WO2016049230 SEQ ID NO: 20 |
| AAVF2/HSC2 | 576 | WO2016049230 SEQ ID NO: 21 |
| AAVF3/HSC3 | 577 | WO2016049230 SEQ ID NO: 22 |
| AAVF4/HSC4 | 578 | WO2016049230 SEQ ID NO: 23 |
| AAVF5/HSC5 | 579 | WO2016049230 SEQ ID NO: 25 |
| AAVF6/HSC6 | 580 | WO2016049230 SEQ ID NO: 24 |
| AAVF7/HSC7 | 581 | WO2016049230 SEQ ID NO: 27 |
| AAVFS/HSC8 | 582 | WO2016049230 SEQ ID NO: 28 |
| AAVF9/HSC9 | 583 | WO2016049230 SEQ ID NO: 29 |
| AAVF11/HSC11 | 584 | WO2016049230 SEQ ID NO: 26 |
| AAVF12/HSC12 | 585 | WO2016049230 SEQ ID NO: 30 |
| AAVF13/HSC13 | 586 | WO2016049230 SEQ ID NO: 31 |
| AAVF14/HSC14 | 587 | WO2016049230 SEQ ID NO: 32 |
| AAVF15/HSC15 | 588 | WO2016049230 SEQ ID NO: 33 |
| AAVF16/HSC16 | 589 | WO2016049230 SEQ ID NO: 34 |
| AAVF17/HSC17 | 590 | WO2016049230 SEQ ID NO: 35 |
| AAVF1/HSC1 | 591 | WO2016049230 SEQ ID NO: 2 |
| AAVF2/HSC2 | 592 | WO2016049230 SEQ ID NO: 3 |
| AAVF3/HSC3 | 593 | WO2016049230 SEQ ID NO: 5 |
| AAVF4/HSC4 | 594 | WO2016049230 SEQ ID NO: 6 |

TABLE 1-continued

AAV Serotypes

| Serotype | SEQ ID NO | Reference Information |
|---|---|---|
| AAVF5/HSC5 | 595 | WO2016049230 SEQ ID NO: 11 |
| AAVF6/HSC6 | 596 | WO2016049230 SEQ ID NO: 7 |
| AAVF7/HSC7 | 597 | WO2016049230 SEQ ID NO: 8 |
| AAVF8/HSC8 | 598 | WO2016049230 SEQ ID NO: 9 |
| AAVF9/HSC9 | 599 | WO2016049230 SEQ ID NO: 10 |
| AAVF11/HSC11 | 600 | WO2016049230 SEQ ID NO: 4 |
| AAVF12/HSC12 | 601 | WO2016049230 SEQ ID NO: 12 |
| AAVF13/HSC13 | 602 | WO2016049230 SEQ ID NO: 14 |
| AAVF14/HSC14 | 603 | WO2016049230 SEQ ID NO: 15 |
| AAVF15/HSC15 | 604 | WO2016049230 SEQ ID NO: 16 |
| AAVF16/HSC16 | 605 | WO2016049230 SEQ ID NO: 17 |
| AAVF17/HSC17 | 606 | WO2016049230 SEQ ID NO: 13 |
| AAV CBr-E1 | 607 | U.S. Pat. No. 8,734,809 SEQ ID NO: 13 |
| AAV CBr-E2 | 608 | U.S. Pat. No. 8,734,809 SEQ ID NO: 14 |
| AAV CBr-E3 | 609 | U.S. Pat. No. 8,734,809 SEQ ID NO: 15 |
| AAV CBr-E4 | 610 | U.S. Pat. No. 8,734,809 SEQ ID NO: 16 |
| AAV CBr-E5 | 611 | U.S. Pat. No. 8,734,809 SEQ ID NO: 17 |
| AAV CBr-e5 | 612 | U.S. Pat. No. 8,734,809 SEQ ID NO: 18 |
| AAV CBr-E6 | 613 | U.S. Pat. No. 8,734,809 SEQ ID NO: 19 |
| AAV CBr-E7 | 614 | U.S. Pat. No. 8,734,809 SEQ ID NO: 20 |
| AAV CBr-E8 | 615 | U.S. Pat. No. 8,734,809 SEQ ID NO: 21 |
| AAV CLv-D1 | 616 | U.S. Pat. No. 8,734,809 SEQ ID NO: 22 |
| AAV CLv-D2 | 617 | U.S. Pat. No. 8,734,809 SEQ ID NO: 23 |
| AAV CLv-D3 | 618 | U.S. Pat. No. 8,734,809 SEQ ID NO: 24 |
| AAV CLv-D4 | 619 | U.S. Pat. No. 8,734,809 SEQ ID NO: 25 |
| AAV CLv-D5 | 620 | U.S. Pat. No. 8,734,809 SEQ ID NO: 26 |
| AAV CLv-D6 | 621 | U.S. Pat. No. 8,734,809 SEQ ID NO: 27 |
| AAV CLv-D7 | 622 | U.S. Pat. No. 8,734,809 SEQ ID NO: 28 |
| AAV CLv-D8 | 623 | U.S. Pat. No. 8,734,809 SEQ ID NO: 29 |
| AAV CLv-E1 | 624 | U.S. Pat. No. 8,734,809 SEQ ID NO: 13 |
| AAV CLv-R1 | 625 | U.S. Pat. No. 8,734,809 SEQ ID NO: 30 |
| AAV CLv-R2 | 626 | U.S. Pat. No. 8,734,809 SEQ ID NO: 31 |
| AAV CLv-R3 | 627 | U.S. Pat. No. 8,734,809 SEQ ID NO: 32 |
| AAV CLv-R4 | 628 | U.S. Pat. No. 8,734,809 SEQ ID NO: 33 |
| AAV CLv-R5 | 629 | U.S. Pat. No. 8,734,809 SEQ ID NO: 34 |
| AAV CLv-R6 | 630 | U.S. Pat. No. 8,734,809 SEQ ID NO: 35 |
| AAV CLv-R7 | 631 | U.S. Pat. No. 8,734,809 SEQ ID NO: 36 |
| AAV CLv-R8 | 632 | U.S. Pat. No. 8,734,809 SEQ ID NO: 37 |

TABLE 1-continued

| AAV Serotypes | | |
|---|---|---|
| Serotype | SEQ ID NO | Reference Information |
| AAV CLv-R9 | 633 | U.S. Pat. No. 8,734,809 SEQ ID NO: 38 |
| AAV CLg-F1 | 634 | U.S. Pat. No. 8,734,809 SBQ ID NO: 39 |
| AAV CLg-F2 | 635 | U.S. Pat. No. 8,734,809 SEQ ID NO: 40 |
| AAV CLg-F3 | 636 | U.S. Pat. No. 8,734,809 SEQ ID NO: 41 |
| AAV CLg-F4 | 637 | U.S. Pat. No. 8,734,809 SEQ ID NO: 42 |
| AAV CLg-F5 | 638 | U.S. Pat. No. 8,734,809 SEQ ID NO: 43 |
| AAV CLg-F6 | 639 | U.S. Pat. No. 8,734,809 SEQ ID NO: 43 |
| AAV CLg-F7 | 640 | U.S. Pat. No. 8,734,809 SEQ ID NO: 44 |
| AAV CLg-F8 | 641 | U.S. Pat. No. 8,734,809 SEQ ID NO: 43 |
| AAV CSp-1 | 642 | U.S. Pat. No. 8,734,809 SEQ ID NO: 45 |
| AAV CSp-10 | 643 | U.S. Pat. No. 8,734,809 SEQ ID NO: 46 |
| AAV CSp-11 | 644 | U.S. Pat. No. 8,734,809 SEQ ID NO: 47 |
| AAV CSp-2 | 645 | U.S. Pat. No. 8,734,809 SEQ ID NO: 48 |
| AAV CSp-3 | 646 | U.S. Pat. No. 8,734,809 SEQ ID NO: 49 |
| AAV CSp-4 | 647 | U.S. Pat. No. 8,734,809 SEQ ID NO: 50 |
| AAV CSp-6 | 648 | U.S. Pat. No. 8,734,809 SEQ ID NO: 51 |
| AAV CSp-7 | 649 | U.S. Pat. No. 8,734,809 SEQ ID NO: 52 |
| AAV CSp-8 | 650 | U.S. Pat. No. 8,734,809 SEQ ID NO: 53 |
| AAV CSp-9 | 651 | U.S. Pat. No. 8,734,809 SEQ ID NO: 54 |
| AAV CHt-2 | 652 | U.S. Pat. No. 8,734,809 SEQ ID NO: 55 |
| AAV CHt-3 | 653 | U.S. Pat. No. 8,734,809 SEQ ID NO: 56 |
| AAV CKd-1 | 654 | U.S. Pat. No. 8,734,809 SEQ ID NO: 57 |
| AAV CKd-10 | 655 | U.S. Pat. No. 8,734,809 SEQ ID NO: 58 |
| AAV CKd-2 | 656 | U.S. Pat. No. 8,734,809 SEQ ID NO: 59 |
| AAV CKd-3 | 657 | U.S. Pat. No. 8,734,809 SEQ ID NO: 60 |
| AAV CKd-4 | 658 | U.S. Pat. No. 8,734,809 SEQ ID NO: 61 |
| AAV CKd-6 | 659 | U.S. Pat. No. 8,734,809 SEQ ID NO: 62 |
| AAV CKd-7 | 660 | U.S. Pat. No. 8,734,809 SEQ ID NO: 63 |
| AAV CKd-8 | 661 | U.S. Pat. No. 8,734,809 SEQ ID NO: 64 |
| AAV CLv-1 | 662 | U.S. Pat. No. 8,734,809 SEQ ID NO: 65 |
| AAV CLv-12 | 663 | U.S. Pat. No. 8,734,809 SEQ ID NO: 66 |
| AAV CLv-13 | 664 | U.S. Pat. No. 8,734,809 SEQ ID NO: 67 |
| AAV CLv-2 | 665 | U.S. Pat. No. 8,734,809 SEQ ID NO: 68 |
| AAV CLv-3 | 666 | U.S. Pat. No. 8,734,809 SEQ ID NO: 69 |
| AAV CLv-4 | 667 | U.S. Pat. No. 8,734,809 SEQ ID NO: 70 |
| AAV CLv-6 | 668 | U.S. Pat. No. 8,734,809 SEQ ID NO: 71 |
| AAV CLv-8 | 669 | U.S. Pat. No. 8,734,809 SEQ ID NO: 72 |
| AAV CKd-B1 | 670 | U.S. Pat. No. 8,734,809 SEQ ID NO: 73 |

TABLE 1-continued

AAV Serotypes

| Serotype | SEQ ID NO | Reference Information |
|---|---|---|
| AAV CKd-B2 | 671 | U.S. Pat. No. 8,734,809 SEQ ID NO: 74 |
| AAV CKd-B3 | 672 | U.S. Pat. No. 8,734,809 SEQ ID NO: 75 |
| AAV CKd-B4 | 673 | U.S. Pat. No. 8,734,809 SEQ ID NO: 76 |
| AAV CKd-B5 | 674 | U.S. Pat. No. 8,734,809 SEQ ID NO: 77 |
| AAV CKd-B6 | 675 | U.S. Pat. No. 8,734,809 SEQ ID NO: 78 |
| AAV CKd-B7 | 676 | U.S. Pat. No. 8,734,809 SEQ ID NO: 79 |
| AAV CKd-B8 | 677 | U.S. Pat. No. 8,734,809 SEQ ID NO: 80 |
| AAV CKd-H1 | 678 | U.S. Pat. No. 8,734,809 SEQ ID NO: 81 |
| AAV CKd-H2 | 679 | U.S. Pat. No. 8,734,809 SEQ ID NO: 82 |
| AAV CKd-H3 | 680 | U.S. Pat. No. 8,734,809 SEQ ID NO: 83 |
| AAV CKd-H4 | 681 | U.S. Pat. No. 8,734,809 SEQ ID NO: 84 |
| AAV CKd-H5 | 682 | U.S. Pat. No. 8,734,809 SEQ ID NO: 85 |
| AAV CKd-H6 | 683 | U.S. Pat. No. 8,734,809 SEQ ID NO: 77 |
| AAV CHt-1 | 684 | U.S. Pat. No. 8,734,809 SEQ ID NO: 86 |
| AAV CLv1-1 | 685 | U.S. Pat. No. 8,734,809 SEQ ID NO: 171 |
| AAV CLv1-2 | 686 | U.S. Pat. No. 8,734,809 SEQ ID NO: 172 |
| AAV CLv1-3 | 687 | U.S. Pat. No. 8,734,809 SEQ ID NO: 173 |
| AAV CLv1-4 | 688 | U.S. Pat. No. 8,734,809 SEQ ID NO: 174 |
| AAV Clv1-7 | 689 | U.S. Pat. No. 8,734,809 SEQ ID NO: 175 |
| AAV Clv1-8 | 690 | U.S. Pat. No. 8,734,809 SEQ ID NO: 176 |
| AAV Clv1-9 | 691 | U.S. Pat. No. 8,734,809 SEQ ID NO: 177 |
| AAV Clv1-10 | 692 | U.S. Pat. No. 8,734,809 SEQ ID NO: 178 |
| AAV.VR-355 | 693 | U.S. Pat. No. 8,734,809 SEQ ID NO: 181 |
| AAV.hu.48R3 | 694 | U.S. Pat. No. 8,734,809 SEQ ID NO: 183 |
| AAV CBr-E1 | 695 | U.S. Pat. No. 8,734,809 SEQ ID NO: 87 |
| AAV CBr-E2 | 696 | U.S. Pat. No. 8,734,809 SEQ ID NO: 88 |
| AAV CBr-E3 | 697 | U.S. Pat. No. 8,734,809 SEQ ID NO: 89 |
| AAV CBr-E4 | 698 | U.S. Pat. No. 8,734,809 SEQ ID NO: 90 |
| AAV CBr-E5 | 699 | U.S. Pat. No. 8,734,809 SEQ ID NO: 91 |
| AAV CBr-e5 | 700 | U.S. Pat. No. 8,734,809 SEQ ID NO: 92 |
| AAV CBr-E6 | 701 | U.S. Pat. No. 8,734,809 SEQ ID NO: 93 |
| AAV CBr-E7 | 702 | U.S. Pat. No. 8,734,809 SEQ ID NO: 94 |
| AAV CBr-E8 | 703 | U.S. Pat. No. 8,734,809 SEQ ID NO: 95 |
| AAV CLv-D1 | 704 | U.S. Pat. No. 8,734,809 SEQ ID NO: 96 |
| AAV CLv-D2 | 705 | U.S. Pat. No. 8,734,809 SEQ ID NO: 97 |
| AAV CLv-D3 | 706 | U.S. Pat. No. 8,734,809 SEQ ID NO: 98 |
| AAV CLv-D4 | 707 | U.S. Pat. No. 8,734,809 SEQ ID NO: 99 |
| AAV CLv-D5 | 708 | U.S. Pat. No. 8,734,809 SEQ ID NO: 100 |

TABLE 1-continued

AAV Serotypes

| Serotype | SEQ ID NO | Reference Information |
|---|---|---|
| AAV CLv-D6 | 709 | U.S. Pat. No. 8,734,809 SEQ ID NO: 101 |
| AAV CLv-D7 | 710 | U.S. Pat. No. 8,734,809 SEQ ID NO: 102 |
| AAV CLv-D8 | 711 | U.S. Pat. No. 8,734,809 SEQ ID NO: 103 |
| AAV CLv-E1 | 712 | U.S. Pat. No. 8,734,809 SEQ ID NO: 87 |
| AAV CLv-R1 | 713 | U.S. Pat. No. 8,734,809 SEQ ID NO: 104 |
| AAV CLv-R2 | 714 | U.S. Pat. No. 8,734,809 SEQ ID NO: 105 |
| AAV CLv-R3 | 715 | U.S. Pat. No. 8,734,809 SEQ ID NO: 106 |
| AAV CLv-R4 | 716 | U.S. Pat. No. 8,734,809 SEQ ID NO: 107 |
| AAV CLv-R5 | 717 | U.S. Pat. No. 8,734,809 SEQ ID NO: 108 |
| AAV CLv-R6 | 718 | U.S. Pat. No. 8,734,809 SEQ ID NO: 109 |
| AAV CLv-R7 | 719 | U.S. Pat. No. 8,734,809 SEQ ID NO: 110 |
| AAV CLv-R8 | 720 | U.S. Pat. No. 8,734,809 SEQ ID NO: 111 |
| AAV CLv-R9 | 721 | U.S. Pat. No. 8,734,809 SEQ ID NO: 112 |
| AAV CLg-F1 | 722 | U.S. Pat. No. 8,734,809 SEQ ID NO: 113 |
| AAV CLg-F2 | 723 | U.S. Pat. No. 8,734,809 SBQ ID NO: 114 |
| AAV CLg-F3 | 724 | U.S. Pat. No. 8,734,809 SEQ ID NO: 115 |
| AAV CLg-F4 | 725 | U.S. Pat. No. 8,734,809 SEQ ID NO: 116 |
| AAV CLg-F5 | 726 | U.S. Pat. No. 8,734,809 SEQ ID NO: 117 |
| AAV CLg-F6 | 727 | U.S. Pat. No. 8,734,809 SEQ ID NO: 117 |
| AAV CLg-F7 | 728 | U.S. Pat. No. 8,734,809 SEQ ID NO: 118 |
| AAV CLg-F8 | 729 | U.S. Pat. No. 8,734,809 SEQ ID NO: 117 |
| AAV CSp-1 | 730 | U.S. Pat. No. 8,734,809 SEQ ID NO: 119 |
| AAV CSp-10 | 731 | U.S. Pat. No. 8,734,809 SEQ ID NO: 120 |
| AAV CSp-11 | 732 | U.S. Pat. No. 8,734,809 SEQ ID NO: 121 |
| AAV CSp-2 | 733 | U.S. Pat. No. 8,734,809 SEQ ID NO: 122 |
| AAV CSp-3 | 734 | U.S. Pat. No. 8,734,809 SEQ ID NO: 123 |
| AAV CSp-4 | 735 | U.S. Pat. No. 8,734,809 SEQ ID NO: 124 |
| AAV CSp-6 | 736 | U.S. Pat. No. 8,734,809 SEQ ID NO: 125 |
| AAV CSp-7 | 737 | U.S. Pat. No. 8,734,809 SEQ ID NO: 126 |
| AAV CSp-8 | 738 | U.S. Pat. No. 8,734,809 SEQ ID NO: 127 |
| AAV CSp-9 | 739 | U.S. Pat. No. 8,734,809 SEQ ID NO: 128 |
| AAV CHt-2 | 740 | U.S. Pat. No. 8,734,809 SEQ ID NO: 129 |
| AAV CHt-3 | 741 | U.S. Pat. No. 8,734,809 SEQ ID NO: 130 |
| AAV CKd-1 | 742 | U.S. Pat. No. 8,734,809 SEQ ID NO: 131 |
| AAV CKd-10 | 743 | U.S. Pat. No. 8,734,809 SEQ ID NO: 132 |
| AAV CKd-2 | 744 | U.S. Pat. No. 8,734,809 SEQ ID NO: 133 |
| AAV CKd-3 | 745 | U.S. Pat. No. 8,734,809 SEQ ID NO: 134 |
| AAV CKd-4 | 746 | U.S. Pat. No. 8,734,809 SEQ ID NO: 135 |

TABLE 1-continued

AAV Serotypes

| Serotype | SEQ ID NO | Reference Information |
|---|---|---|
| AAV CKd-6 | 747 | U.S. Pat. No. 8,734,809 SEQ ID NO: 136 |
| AAV CKd-7 | 748 | U.S. Pat. No. 8,734,809 SEQ ID NO: 137 |
| AAV CKd-8 | 749 | U.S. Pat. No. 8,734,809 SEQ ID NO: 138 |
| AAV CLv-1 | 750 | U.S. Pat. No. 8,734,809 SEQ ID NO: 139 |
| AAV CLv-12 | 751 | U.S. Pat. No. 8,734,809 SEQ ID NO: 140 |
| AAV CLv-13 | 752 | U.S. Pat. No. 8,734,809 SEQ ID NO: 141 |
| AAV CLv-2 | 753 | U.S. Pat. No. 8,734,809 SEQ ID NO: 142 |
| AAV CLv-3 | 754 | U.S. Pat. No. 8,734,809 SEQ ID NO: 143 |
| AAV CLv-4 | 755 | U.S. Pat. No. 8,734,809 SEQ ID NO: 144 |
| AAV CLv-6 | 756 | U.S. Pat. No. 8,734,809 SEQ ID NO: 145 |
| AAV CLv-8 | 757 | U.S. Pat. No. 8,734,809 SEQ ID NO: 146 |
| AAV CKd-B1 | 758 | U.S. Pat. No. 8,734,809 SEQ ID NO: 147 |
| AAV CKd-B2 | 759 | U.S. Pat. No. 8,734,809 SEQ ID NO: 148 |
| AAV CKd-B3 | 760 | U.S. Pat. No. 8,734,809 SEQ ID NO: 149 |
| AAV CKd-B4 | 761 | U.S. Pat. No. 8,734,809 SEQ ID NO: 150 |
| AAV CKd-B5 | 762 | U.S. Pat. No. 8,734,809 SEQ ID NO: 151 |
| AAV CKd-B6 | 763 | U.S. Pat. No. 8,734,809 SEQ ID NO: 152 |
| AAV CKd-B7 | 764 | U.S. Pat. No. 8,734,809 SEQ ID NO: 153 |
| AAV CKd-B8 | 765 | U.S. Pat. No. 8,734,809 SEQ ID NO: 154 |
| AAV CKd-H1 | 766 | U.S. Pat. No. 8,734,809 SEQ ID NO: 155 |
| AAV CKd-H2 | 767 | U.S. Pat. No. 8,734,809 SEQ ID NO: 156 |
| AAV CKd-H3 | 768 | U.S. Pat. No. 8,734,809 SEQ ID NO: 157 |
| AAV CKd-H4 | 769 | U.S. Pat. No. 8,734,809 SEQ ID NO: 158 |
| AAV CKd-H5 | 770 | U.S. Pat. No. 8,734,809 SEQ ID NO: 159 |
| AAV CKd-H6 | 771 | U.S. Pat. No. 8,734,809 SEQ ID NO: 151 |
| AAV CHt-1 | 772 | U.S. Pat. No. 8,734,809 SEQ ID NO: 160 |
| AAV CHt-P2 | 773 | WO2016065001 SEQ ID NO: 1 |
| AAV CHt-P5 | 774 | WO2016065001 SEQ ID NO: 2 |
| AAV CHt-P9 | 775 | WO2016065001 SEQ ID NO: 3 |
| AAV CBr-7.1 | 776 | WO2016065001 SEQ ID NO: 4 |
| AAV CBr-7.2 | 777 | WO2016065001 SEQ ID NO: 5 |
| AAV CBr-7.3 | 778 | WO2016065001 SEQ ID NO: 6 |
| AAV CBr-7.4 | 779 | WO2016065001 SEQ ID NO: 7 |
| AAV CBr-7.5 | 780 | WO2016065001 SEQ ID NO: 8 |
| AAV CBr-7.7 | 781 | WO2016065001 SEQ ID NO: 9 |
| AAV CBr-7.8 | 782 | WO2016065001 SEQ ID NO: 10 |
| AAV CBr-7.10 | 783 | WO2016065001 SEQ ID NO: 11 |
| AAV CKd-N3 | 784 | WO2016065001 SEQ ID NO: 12 |

TABLE 1-continued

| AAV Serotypes | | |
|---|---|---|
| Serotype | SEQ ID NO | Reference Information |
| AAV CKd-N4 | 785 | WO2016065001 SEQ ID NO: 13 |
| AAV CKd-N9 | 786 | WO2016065001 SEQ ID NO: 14 |
| AAV CLv-L4 | 787 | WO2016065001 SEQ ID NO: 15 |
| AAV CLv-L5 | 788 | WO2016065001 SEQ ID NO: 16 |
| AAV CLv-L6 | 789 | WO2016065001 SEQ ID NO: 17 |
| AAV CLv-K1 | 790 | WO2016065001 SEQ ID NO: 18 |
| AAV CLv-K3 | 791 | WO2016065001 SEQ ID NO: 19 |
| AAV CLv-K6 | 792 | WO2016065001 SEQ ID NO: 20 |
| AAV CLv-M1 | 793 | WO2016065001 SEQ ID NO: 21 |
| AAV CLv-M11 | 794 | WO2016065001 SEQ ID NO: 22 |
| AAV CLv-M2 | 795 | WO2016065001 SEQ ID NO: 23 |
| AAV CLv-M5 | 796 | WO2016065001 SEQ ID NO: 24 |
| AAV CLv-M6 | 797 | WO2016065001 SEQ ID NO: 25 |
| AAV CLv-M7 | 798 | WO2016065001 SEQ ID NO: 26 |
| AAV CLv-M8 | 799 | WO2016065001 SEQ ID NO: 27 |
| AAV CLv-M9 | 800 | WO2016065001 SEQ ID NO: 28 |
| AAV CHt-P1 | 801 | WO2016065001 SEQ ID NO: 29 |
| AAV CHt-P6 | 802 | WO2016065001 SEQ ID NO: 30 |
| AAV CHt-P8 | 803 | WO2016065001 SEQ ID NO: 31 |
| AAV CHt-6.1 | 804 | WO2016065001 SEQ ID NO: 32 |
| AAV CHt-6.10 | 805 | WO2016065001 SEQ ID NO: 33 |
| AAV CHt-6.5 | 806 | WO2016065001 SEQ ID NO: 34 |
| AAV CHt-6.6 | 807 | WO2016065001 SEQ ID NO: 35 |
| AAV CHt-6.7 | 808 | WO2016065001 SEQ ID NO: 36 |
| AAV CHt-6.8 | 809 | WO2016065001 SEQ ID NO: 37 |
| AAV CSp-8.10 | 810 | WO2016065001 SEQ ID NO: 38 |
| AAV CSp-8.2 | 811 | WO2016065001 SEQ ID NO: 39 |
| AAV CSp-8.4 | 812 | WO2016065001 SEQ ID NO: 40 |
| AAV CSp-8.5 | 813 | WO2016065001 SEQ ID NO: 41 |
| AAV CSp-8.6 | 814 | WO2016065001 SEQ ID NO: 42 |
| AAV CSp-8.7 | 815 | WO2016065001 SEQ ID NO: 43 |
| AAV CSp-8.8 | 816 | WO2016065001 SEQ ID NO: 44 |
| AAV CSp-8.9 | 817 | WO2016065001 SEQ ID NO: 45 |
| AAV CBr-B7.3 | 818 | WO2016065001 SEQ ID NO: 46 |
| AAV CBr-B7.4 | 819 | WO2016065001 SEQ ID NO: 47 |
| AAV3B | 820 | WO2016065001 SEQ ID NO: 48 |
| AAV4 | 821 | WO2016065001 SEQ ID NO: 49 |
| AAV5 | 822 | WO2016065001 SEQ ID NO: 50 |

TABLE 1-continued

AAV Serotypes

| Serotype | SEQ ID NO | Reference Information |
|---|---|---|
| AAV CHt-P2 | 823 | WO2016065001 SBQ ID NO: 51 |
| AAV CHt-P5 | 824 | WO2016065001 SEQ ID NO: 52 |
| AAV CHt-P9 | 825 | WO2016065001 SEQ ID NO: 53 |
| AAV CBr-7.1 | 826 | WO2016065001 SEQ ID NO: 54 |
| AAV CBr-7.2 | 827 | WO2016065001 SEQ ID NO: 55 |
| AAV CBr-7.3 | 828 | WO2016065001 SEQ ID NO: 56 |
| AAV CBr-7.4 | 829 | WO2016065001 SEQ ID NO: 57 |
| AAV CBr-7.5 | 830 | WO2016065001 SEQ ID NO: 58 |
| AAV CBr-7.7 | 831 | WO2016065001 SEQ ID NO: 59 |
| AAV CBr-7.8 | 832 | WO2016065001 SEQ ID NO: 60 |
| AAV CBr-7.10 | 833 | WO2016065001 SEQ ID NO: 61 |
| AAV CKd-N3 | 834 | WO2016065001 SEQ ID NO: 62 |
| AAV CKd-N4 | 835 | WO2016065001 SEQ ID NO: 63 |
| AAV CKd-N9 | 836 | WO2016065001 SEQ ID NO: 64 |
| AAV CLv-L4 | 837 | WO2016065001 SEQ ID NO: 65 |
| AAV CLv-L5 | 838 | WO2016065001 SEQ ID NO: 66 |
| AAV CLv-L6 | 839 | WO2016065001 SEQ ID NO: 67 |
| AAV CLv-K1 | 840 | WO2016065001 SEQ ID NO: 68 |
| AAV CLv-K3 | 841 | WO2016065001 SEQ ID NO: 69 |
| AAV CLv-K6 | 842 | WO2016065001 SEQ ID NO: 70 |
| AAV CLv-M1 | 843 | WO2016065001 SEQ ID NO: 71 |
| AAV CLv-M11 | 844 | WO2016065001 SEQ ID NO: 72 |
| AAV CLv-M2 | 845 | WO2016065001 SBQ ID NO: 73 |
| AAV CLv-M5 | 846 | WO2016065001 SEQ ID NO: 74 |
| AAV CLv-M6 | 847 | WO2016065001 SEQ ID NO: 75 |
| AAV CLv-M7 | 848 | WO2016065001 SEQ ID NO: 76 |
| AAV CLv-M8 | 849 | WO2016065001 SEQ ID NO: 77 |
| AAV CLv-M9 | 850 | WO2016065001 SEQ ID NO: 78 |
| AAV CHt-P1 | 851 | WO2016065001 SEQ ID NO: 79 |
| AAV CHt-P6 | 852 | WO2016065001 SEQ ID NO: 80 |
| AAV CHt-P8 | 853 | WO2016065001 SEQ ID NO: 81 |
| AAV CHt-6.1 | 854 | WO2016065001 SEQ ID NO: 82 |
| AAV CHt-6.10 | 855 | WO2016065001 SEQ ID NO: 83 |
| AAV CHt-6.5 | 856 | WO2016065001 SEQ ID NO: 84 |
| AAV CHt-6.6 | 857 | WO2016065001 SEQ ID NO: 85 |
| AAV CHt-6.7 | 858 | WO2016065001 SEQ ID NO: 86 |
| AAV CHt-6.8 | 859 | WO2016065001 SEQ ID NO: 87 |
| AAV CSp-8.10 | 860 | WO2016065001 SEQ ID NO: 88 |

TABLE 1-continued

| Serotype | SEQ ID NO | Reference Information |
|---|---|---|
| AAV CSp-8.2 | 861 | WO2016065001 SEQ ID NO: 89 |
| AAV CSp-8.4 | 862 | WO2016065001 SEQ ID NO: 90 |
| AAV CSp-8.5 | 863 | WO2016065001 SEQ ID NO: 91 |
| AAV CSp-8.6 | 864 | WO2016065001 SEQ ID NO: 92 |
| AAV CSp-8.7 | 865 | WO2016065001 SEQ ID NO: 93 |
| AAV CSp-8.8 | 866 | WO2016065001 SEQ ID NO: 94 |
| AAV CSp-8.9 | 867 | WO2016065001 SEQ ID NO: 95 |
| AAV CBr-B7.3 | 868 | WO2016065001 SEQ ID NO: 96 |
| AAV CBr-B7.4 | 869 | WO2016065001 SEQ ID NO: 97 |
| AAV3B | 870 | WO2016065001 SEQ ID NO: 98 |
| AAV4 | 871 | WO2016065001 SEQ ID NO: 99 |
| AAV5 | 872 | WO2016065001 SEQ ID NO: 100 |
| PHP.N/PHP.B-DGT | 873 | WO2017100671 SEQ ID NO: 46 |
| PHP.S/G2A12 | 874 | WO2017100671 SEQ ID NO: 47 |
| AAV9/hu.14 K449R | 875 | WO2017100671 SEQ ID NO: 45 |
| GPV | 992 | U.S. Pat. No. 9,624,274B2 SEQ ID NO: 192 |
| B19 | 993 | U.S. Pat. No. 9,624,274B2 SEQ ID NO: 193 |
| MVM | 994 | U.S. Pat. No. 9,624,274B2 SEQ ID NO: 194 |
| FPV | 995 | U.S. Pat. No. 9,624,274B2 SEQ ID NO: 195 |
| CPV | 996 | U.S. Pat. No. 9,624,274B2 SEQ ID NO: 196 |
| AAV6 | 997 | U.S. Pat. No. 9,546,112B2 SEQ ID NO: 5 |
| AAV6 | 998 | U.S. Pat. No. 9,457,103B2 SEQ ID NO: 1 |
| AAV2 | 999 | U.S. Pat. No. 9,457,103B2 SEQ ID NO: 2 |
| ShH10 | 1000 | U.S. Pat. No. 9,457,103B2 SEQ ID NO: 3 |
| ShH13 | 1001 | U.S. Pat. No. 9,457,103B2 SEQ ID NO: 4 |
| ShH10 | 1002 | U.S. Pat. No. 9,457,103B2 SEQ ID NO: 5 |
| ShH10 | 1003 | U.S. Pat. No. 9,457,103B2 SEQ ID NO: 6 |
| ShH10 | 1004 | U.S. Pat. No. 9,457,103B2 SEQ ID NO: 7 |
| ShH10 | 1005 | U.S. Pat. No. 9,457,103B2 SEQ ID NO: 8 |
| ShH10 | 1006 | U.S. Pat. No. 9,457,103B2 SEQ ID NO: 9 |
| rh74 | 1007 | U.S. Pat. No. 9,434,928B2 SEQ ID NO: 1, US2015023924A1 SEQ ID NO: 2 |
| rh74 | 1008 | U.S. Pat. No. 9,434,928B2 SEQ ID NO: 2, US2015023924A1 SEQ ID NO: 1 |
| AAV8 | 1009 | U.S. Pat. No. 9,434,928B2 SEQ ID NO: 4 |
| rh74 | 1010 | U.S. Pat. No. 9,434,928B2 SEQ ID NO: 5 |
| rh74 (RHM4-1) | 1011 | US2015023924A1 SEQ ID NO: 5, US20160375110A1 SEQ ID NO: 4 |
| rh74 (RHM15-1) | 1012 | US2015023924A1 SEQ ID NO: 6, US20160375110A1 SEQ ID NO: 5 |

TABLE 1-continued

| AAV Serotypes | | |
|---|---|---|
| Serotype | SEQ ID NO | Reference Information |
| rh74 (RHM15-2) | 1013 | US2015023924A1 SEQ ID NO: 7, US20160375110A1 SEQ ID NO: 6 |
| rh74 (RHM15-3/RHM15-5) | 1014 | US2015023924A1 SEQ ID NO: 8, US20160375110A1 SEQ ID NO: 7 |
| rh74 (RHM15-4) | 1015 | US2015023924A1 SEQ ID NO: 9, US20160375110A1 SEQ ID NO: 8 |
| rh74 (RHM15-6) | 1016 | US2015023924A1 SEQ ID NO: 10, US20160375110A1 SEQ ID NO: 9 |
| rh74 (RHM4-1) | 1017 | US2015023924A1 SEQ ID NO: 11 |
| rh74 (RHM15-1) | 1018 | US2015023924A1 SEQ ID NO: 12 |
| rh74 (RHM15-2) | 1019 | US2015023924A1 SEQ ID NO: 13 |
| rh74 (RHM15-3/RHM15-5) | 1020 | US2015023924A1 SEQ ID NO: 14 |
| rh74 (RHM15-4) | 1021 | US2015023924A1 SEQ ID NO: 15 |
| rh74 (RHM15-6) | 1022 | US2015023924A1 SEQ ID NO: 16 |
| AAV2 (comprising lung specific polypeptide) | 1023 | US20160175389A1 SEQ ID NO: 9 |
| AAV2 (comprising lung specific polypeptide) | 1024 | US20160175389A1 SEQ ID NO: 10 |
| Anc80 | 1025 | US20170051257A1 SEQ ID NO: 1 |
| Anc80 | 1026 | US20170051257A1 SEQ ID NO: 2 |
| Anc81 | 1027 | US20170051257A1 SEQ ID NO: 3 |
| Anc80 | 1028 | US20170051257A1 SEQ ID NO: 4 |
| Anc82 | 1029 | US20170051257A1 SEQ ID NO: 5 |
| Anc82 | 1030 | US20170051257A1 SEQ ID NO: 6 |
| Anc83 | 1031 | US20170051257A1 SEQ ID NO: 7 |
| Anc83 | 1032 | US20170051257A1 SEQ ID NO: 8 |
| Anc84 | 1033 | US20170051257A1 SEQ ID NO: 9 |
| Anc84 | 1034 | US20170051257A1 SEQ ID NO: 10 |
| Anc94 | 1035 | US20170051257A1 SEQ ID NO: 11 |
| Anc94 | 1036 | US20170051257A1 SEQ ID NO: 12 |
| Anc113 | 1037 | US20170051257A1 SEQ ID NO: 13 |
| Anc113 | 1038 | US20170051257A1 SEQ ID NO: 14 |
| Anc126 | 1039 | US20170051257A1 SEQ ID NO: 15 |
| Anc126 | 1040 | US20170051257A1 SEQ ID NO: 16 |
| Anc127 | 1041 | US20170051257A1 SEQ ID NO: 17 |
| Anc127 | 1042 | US20170051257A1 SEQ ID NO: 18 |
| Anc80L27 | 1043 | US20170051257A1 SEQ ID NO: 19 |
| Anc80L59 | 1044 | US20170051257A1 SEQ ID NO: 20 |
| Anc80L60 | 1045 | US20170051257A1 SEQ ID NO: 21 |
| Anc80L62 | 1046 | US20170051257A1 SEQ ID NO: 22 |
| Anc80L65 | 1047 | US20170051257A1 SEQ ID NO: 23 |

TABLE 1-continued

| AAV Serotypes | | |
|---|---|---|
| Serotype | SEQ ID NO | Reference Information |
| Anc80L33 | 1048 | US20170051257A1 SEQ ID NO: 24 |
| Anc80L36 | 1049 | US20170051257A1 SEQ ID NO: 25 |
| Anc80L44 | 1050 | US20170051257A1 SEQ ID NO: 26 |
| Anc80L1 | 1051 | US20170051257A1 SEQ ID NO: 35 |
| Anc80L1 | 1052 | US20170051257A1 SEQ ID NO: 36 |
| AAV-X1 | 1053 | U.S. Pat. No. 8,283,151B2 SEQ ID NO: 11 |
| AAV-X1b | 1054 | U.S. Pat. No. 8,283,151B2 SEQ ID NO: 12 |
| AAV-X5 | 1055 | U.S. Pat. No. 8,283,151B2 SEQ ID NO: 13 |
| AAV-X19 | 1056 | U.S. Pat. No. 8,283,151B2 SEQ ID NO: 14 |
| AAV-X21 | 1057 | U.S. Pat. No. 8,283,151B2 SEQ ID NO: 15 |
| AAV-X22 | 1058 | U.S. Pat. No. 8,283,151B2 SEQ ID NO: 16 |
| AAV-X23 | 1059 | U.S. Pat. No. 8,283,151B2 SEQ ID NO: 17 |
| AAV-X24 | 1060 | U.S. Pat. No. 8,283,151B2 SEQ ID NO: 18 |
| AAV-X25 | 1061 | U.S. Pat. No. 8,283,151B2 SEQ ID NO: 19 |
| AAV-X26 | 1062 | U.S. Pat. No. 8,283,151B2 SEQ ID NO: 20 |
| AAV-X1 | 1063 | U.S. Pat. No. 8,283,151B2 SEQ ID NO: 21 |
| AAV-X1b | 1064 | U.S. Pat. No. 8,283,151B2 SEQ ID NO: 22 |
| AAV-X5 | 1065 | U.S. Pat. No. 8,283,151B2 SEQ ID NO: 23 |
| AAV-X19 | 1066 | U.S. Pat. No. 8,283,151B2 SEQ ID NO: 24 |
| AAV-X21 | 1067 | U.S. Pat. No. 8,283,151B2 SEQ ID NO: 25 |
| AAV-X22 | 1068 | U.S. Pat. No. 8,283,151B2 SEQ ID NO: 26 |
| AAV-X23 | 1069 | U.S. Pat. No. 8,283,151B2 SEQ ID NO: 27 |
| AAV-X24 | 1070 | U.S. Pat. No. 8,283,151B2 SEQ ID NO: 28 |
| AAV-X25 | 1071 | U.S. Pat. No. 8,283,151B2 SEQ ID NO: 29 |
| AAV-X26 | 1072 | U.S. Pat. No. 8,283,151B2 SEQ ID NO: 30 |
| AAVrh8 | 1073 | WO2016054554A1 SEQ ID NO: 8 |
| AAVrh8VP2FC5 | 1074 | WO2016054554A1 SEQ ID NO: 9 |
| AAVrh8VP2FC44 | 1075 | WO2016054554A1 SEQ ID NO: 10 |
| AAVrh8VP2ApoB100 | 1076 | WO2016054554A1 SEQ ID NO: 11 |
| AAVrh8VP2RVG | 1077 | WO2016054554A1 SEQ ID NO: 12 |
| AAVrh8VP2Angiopep-2 VP2 | 1078 | WO2016054554A1 SEQ ID NO: 13 |
| AAV9.47VP1.3 | 1079 | WO2016054554A1 SEQ ID NO: 14 |
| AAV9.47VP2ICAMg3 | 1080 | WO2016054554A1 SEQ ID NO: 15 |
| AAV9.47VP2RVG | 1081 | WO2016054554A1 SEQ ID NO: 16 |
| AAV9.47VP2Angiopep-2 | 1082 | WO2016054554A1 SEQ ID NO: 17 |
| AAV9.47VP2A-string | 1083 | WO2016054554A1 SEQ ID NO: 18 |
| AAVrh8VP2FC5 VP2 | 1084 | WO2016054554A1 SEQ ID NO: 19 |

TABLE 1-continued

AAV Serotypes

| Serotype | SEQ ID NO | Reference Information |
|---|---|---|
| AAVrh8VP2FC44 VP2 | 1085 | WO2016054554A1 SEQ ID NO: 20 |
| AAVrh8VP2ApoB100 VP2 | 1086 | WO2016054554A1 SEQ ID NO: 21 |
| AAVrh8VP2RVG VP2 | 1087 | WO2016054554A1 SEQ ID NO: 22 |
| AAVrh8VP2 Angiopep-2 VP2 | 1088 | WO2016054554A1 SEQ ID NO: 23 |
| AAV9.47VP2ICAMg3 VP2 | 1089 | WO2016054554A1 SEQ ID NO: 24 |
| AAV9.47VP2RVG VP2 | 1090 | WO2016054554A1 SEQ ID NO: 25 |
| AAV9.47VP2Angiopep-2 VP2 | 1091 | WO2016054554A1 SEQ ID NO: 26 |
| AAV9.47VP2A-string VP2 | 1092 | WO2016054554A1 SEQ ID NO: 27 |
| rAAV-B1 | 1093 | WO2016054557A1 SEQ ID NO: 1 |
| rAAV-B2 | 1094 | WO2016054557A1 SEQ ID NO: 2 |
| rAAV-B3 | 1095 | WO2016054557A1 SEQ ID NO: 3 |
| rAAV-B4 | 1096 | WO2016054557A1 SEQ ID NO: 4 |
| rAAV-B1 | 1097 | WO2016054557A1 SEQ ID NO: 5 |
| rAAV-B2 | 1098 | WO2016054557A1 SEQ ID NO: 6 |
| rAAV-B3 | 1099 | WO2016054557A1 SEQ ID NO: 7 |
| rAAV-B4 | 1100 | WO2016054557A1 SEQ ID NO: 8 |
| rAAV-L1 | 1101 | WO2016054557A1 SEQ ID NO: 9 |
| rAAV-L2 | 1102 | WO2016054557A1 SEQ ID NO: 10 |
| rAAV-L3 | 1103 | WO2016054557A1 SEQ ID NO: 11 |
| rAAV-L4 | 1104 | WO2016054557A1 SEQ ID NO: 12 |
| rAAV-L1 | 1105 | WO2016054557A1 SEQ ID NO: 13 |
| rAAV-L2 | 1106 | WO2016054557A1 SEQ ID NO: 14 |
| rAAV-L3 | 1107 | WO2016054557A1 SEQ ID NO: 15 |
| rAAV-L4 | 1108 | WO2016054557A1 SEQ ID NO: 16 |
| AAV9 | 1109 | WO2016073739A1 SEQ ID NO: 3 |
| rAAV | 1110 | WO2016081811A1 SEQ ID NO: 1 |
| rAAV | 1113 | WO2016081811A1 SEQ ID NO: 2 |
| rAAV | 1112 | WO2016081811A1 SEQ ID NO: 3 |
| rAAV | 1113 | WO2016081811A1 SEQ ID NO: 4 |
| rAAV | 1114 | WO2016081811A1 SEQ ID NO: 5 |
| rAAV | 1115 | WO2016081811A1 SEQ ID NO: 6 |
| rAAV | 1116 | WO2016081811A1 SEQ ID NO: 7 |
| rAAV | 1117 | WO2016081811A1 SEQ ID NO: 8 |
| rAAV | 1118 | WO2016081811A1 SEQ ID NO: 9 |
| rAAV | 1119 | WO2016081811A1 SEQ ID NO: 10 |
| rAAV | 1120 | WO2016081811A1 SEQ ID NO: 11 |
| rAAV | 1121 | WO2016081811A1 SEQ ID NO: 12 |

TABLE 1-continued

AAV Serotypes

| Serotype | SEQ ID NO | Reference Information |
|---|---|---|
| rAAV | 1122 | WO2016081811A1 SEQ ID NO: 13 |
| rAAV | 1123 | WO2016081811A1 SEQ ID NO: 14 |
| rAAV | 1124 | WO2016081811A1 SEQ ID NO: 15 |
| rAAV | 1125 | WO2016081811A1 SEQ ID NO: 16 |
| rAAV | 1126 | WO2016081811A1 SEQ ID NO: 17 |
| rAAV | 1127 | WO2016081811A1 SEQ ID NO: 18 |
| rAAV | 1128 | WO2016081811A1 SEQ ID NO: 19 |
| rAAV | 1129 | WO2016081811A1 SEQ ID NO: 20 |
| rAAV | 1130 | WO2016081811A1 SEQ ID NO: 21 |
| rAAV | 1131 | WO2016081811A1 SEQ ID NO: 22 |
| rAAV | 1132 | WO2016081811A1 SEQ ID NO: 23 |
| rAAV | 1133 | WO2016081811A1 SEQ ID NO: 24 |
| rAAV | 1134 | WO2016081811A1 SEQ ID NO: 25 |
| rAAV | 1135 | WO2016081811A1 SEQ ID NO: 26 |
| rAAV | 1136 | WO2016081811A1 SEQ ID NO: 27 |
| rAAV | 1137 | WO2016081811A1 SEQ ID NO: 28 |
| rAAV | 1138 | WO2016081811A1 SEQ ID NO: 29 |
| rAAV | 1139 | WO2016081811A1 SEQ ID NO: 30 |
| rAAV | 1140 | WO2016081811A1 SEQ ID NO: 31 |
| rAAV | 1141 | WO2016081811A1 SEQ ID NO: 32 |
| rAAV | 1142 | WO2016081811A1 SEQ ID NO: 33 |
| rAAV | 1143 | WO2016081811A1 SEQ ID NO: 34 |
| rAAV | 1144 | WO2016081811A1 SEQ ID NO: 35 |
| rAAV | 1145 | WO2016081811A1 SEQ ID NO: 36 |
| rAAV | 1146 | WO2016081811A1 SEQ ID NO: 37 |
| rAAV | 1147 | WO2016081811A1 SEQ ID NO: 38 |
| rAAV | 1148 | WO2016081811A1 SEQ ID NO: 39 |
| rAAV | 1149 | WO2016081811A1 SEQ ID NO: 40 |
| rAAV | 1150 | WO2016081811A1 SEQ ID NO: 41 |
| rAAV | 1151 | WO2016081811A1 SEQ ID NO: 42 |
| rAAV | 1152 | WO2016081811A1 SEQ ID NO: 43 |
| rAAV | 1153 | WO2016081811A1 SEQ ID NO: 44 |
| rAAV | 1154 | WO2016081811A1 SEQ ID NO: 45 |
| rAAV | 1155 | WO2016081811A1 SEQ ID NO: 46 |
| rAAV | 1156 | WO2016081811A1 SEQ ID NO: 47 |
| rAAV | 1157 | WO2016081811A1 SEQ ID NO: 48 |
| rAAV | 1158 | WO2016081811A1 SEQ ID NO: 49 |
| rAAV | 1159 | WO2016081811A1 SEQ ID NO: 50 |

TABLE 1-continued

| AAV Serotypes | | |
|---|---|---|
| Serotype | SEQ ID NO | Reference Information |
| rAAV | 1160 | WO2016081811A1 SEQ ID NO: 51 |
| rAAV | 1161 | WO2016081811A1 SEQ ID NO: 52 |
| rAAV | 1162 | WO2016081811A1 SEQ ID NO: 53 |
| rAAV | 1163 | WO2016081811A1 SEQ ID NO: 54 |
| rAAV | 1164 | WO2016081811A1 SEQ ID NO: 55 |
| rAAV | 1165 | WO2016081811A1 SEQ ID NO: 56 |
| rAAV | 1166 | WO2016081811A1 SEQ ID NO: 57 |
| rAAV | 1167 | WO2016081811A1 SEQ ID NO: 58 |
| rAAV | 1168 | WO2016081811A1 SEQ ID NO: 59 |
| rAAV | 1169 | WO2016081811A1 SEQ ID NO: 60 |
| rAAV | 1170 | WO2016081811A1 SEQ ID NO: 61 |
| rAAV | 1171 | WO2016081811A1 SEQ ID NO: 62 |
| rAAV | 1172 | WO2016081811A1 SEQ ID NO: 63 |
| rAAV | 1173 | WO2016081811A1 SEQ ID NO: 64 |
| rAAV | 1174 | WO2016081811A1 SEQ ID NO: 65 |
| rAAV | 1175 | WO2016081811A1 SEQ ID NO: 66 |
| rAAV | 1176 | WO2016081811A1 SEQ ID NO: 67 |
| rAAV | 1177 | WO2016081811A1 SEQ ID NO: 68 |
| rAAV | 1178 | WO2016081811A1 SEQ ID NO: 69 |
| rAAV | 1179 | WO2016081811A1 SEQ ID NO: 70 |
| rAAV | 1180 | WO2016081811A1 SEQ ID NO: 71 |
| rAAV | 1181 | WO2016081811A1 SEQ ID NO: 72 |
| rAAV | 1182 | WO2016081811A1 SEQ ID NO: 73 |
| rAAV | 1183 | WO2016081811A1 SEQ ID NO: 74 |
| rAAV | 1184 | WO2016081811A1 SEQ ID NO: 75 |
| rAAV | 1185 | WO2016081811A1 SEQ ID NO: 76 |
| rAAV | 1186 | WO2016081811A1 SEQ ID NO: 77 |
| rAAV | 1187 | WO2016081811A1 SEQ ID NO: 78 |
| rAAV | 1188 | WO2016081811A1 SEQ ID NO: 79 |
| rAAV | 1189 | WO2016081811A1 SEQ ID NO: 80 |
| rAAV | 1190 | WO2016081811A1 SEQ ID NO: 81 |
| rAAV | 1191 | WO2016081811A1 SEQ ID NO: 82 |
| rAAV | 1192 | WO2016081811A1 SEQ ID NO: 83 |
| rAAV | 1193 | WO2016081811A1 SEQ ID NO: 84 |
| rAAV | 1194 | WO2016081811A1 SEQ ID NO: 85 |
| rAAV | 1195 | WO2016081811A1 SEQ ID NO: 86 |
| rAAV | 1196 | WO2016081811A1 SEQ ID NO: 87 |
| rAAV | 1197 | WO2016081811A1 SEQ ID NO: 88 |

TABLE 1-continued

| AAV Serotypes | | |
|---|---|---|
| Serotype | SEQ ID NO | Reference Information |
| rAAV | 1198 | WO2016081811A1 SEQ ID NO: 89 |
| rAAV | 1199 | WO2016081811A1 SEQ ID NO: 90 |
| rAAV | 1200 | WO2016081811A1 SEQ ID NO: 91 |
| rAAV | 1201 | WO2016081811A1 SEQ ID NO: 92 |
| rAAV | 1202 | WO2016081811A1 SEQ ID NO: 93 |
| rAAV | 1203 | WO2016081811A1 SEQ ID NO: 94 |
| rAAV | 1204 | WO2016081811A1 SEQ ID NO: 95 |
| rAAV | 1205 | WO2016081811A1 SEQ ID NO: 96 |
| rAAV | 1206 | WO2016081811A1 SEQ ID NO: 97 |
| rAAV | 1207 | WO2016081811A1 SEQ ID NO: 98 |
| rAAV | 1208 | WO2016081811A1 SEQ ID NO: 99 |
| rAAV | 1209 | WO2016081811A1 SEQ ID NO: 100 |
| rAAV | 1210 | WO2016081811A1 SEQ ID NO: 101 |
| rAAV | 1211 | WO2016081811A1 SEQ ID NO: 102 |
| rAAV | 1212 | WO2016081811A1 SEQ ID NO: 103 |
| rAAV | 1213 | WO2016081811A1 SEQ ID NO: 104 |
| rAAV | 1214 | WO2016081811A1 SEQ ID NO: 105 |
| rAAV | 1215 | WO2016081811A1 SEQ ID NO: 106 |
| rAAV | 1216 | WO2016081811A1 SEQ ID NO: 107 |
| rAAV | 1217 | WO2016081811A1 SEQ ID NO: 108 |
| rAAV | 1218 | WO2016081811A1 SEQ ID NO: 109 |
| rAAV | 1219 | WO2016081811A1 SEQ ID NO: 110 |
| rAAV | 1220 | WO2016081811AL SEQ ID NO: 111 |
| rAAV | 1221 | WO2016081811A1 SEQ ID NO: 112 |
| rAAV | 1222 | WO2016081811A1 SEQ ID NO: 113 |
| rAAV | 1223 | WO2016081811A1 SEQ ID NO: 114 |
| rAAV | 1224 | WO2016081811A1 SEQ ID NO: 115 |
| rAAV | 1225 | WO2016081811A1 SEQ ID NO: 116 |
| rAAV | 1226 | WO2016081811A1 SEQ ID NO: 117 |
| rAAV | 1227 | WO2016081811A1 SEQ ID NO: 118 |
| rAAV | 1228 | WO2016081811A1 SEQ ID NO: 119 |
| rAAV | 1229 | WO2016081811A1 SEQ ID NO: 120 |
| rAAV | 1230 | WO2016081811A1 SEQ ID NO: 121 |
| rAAV | 1231 | WO2016081811A1 SEQ ID NO: 122 |
| rAAV | 1232 | WO2016081811A1 SEQ ID NO: 123 |
| rAAV | 1233 | WO2016081811A1 SEQ ID NO: 124 |
| rAAV | 1234 | WO2016081811A1 SEQ ID NO: 125 |
| rAAV | 1235 | WO2016081811A1 SEQ ID NO: 126 |

TABLE 1-continued

AAV Serotypes

| Serotype | SEQ ID NO | Reference Information |
|---|---|---|
| rAAV | 1236 | WO2016081811A1 SEQ ID NO: 127 |
| rAAV | 1237 | WO2016081811A1 SEQ ID NO: 128 |
| AAV8 E532K | 1238 | WO2016081811A1 SEQ ID NO: 133 |
| AAV8 E532K | 1239 | WO2016081811A1 SEQ ID NO: 134 |
| rAAV4 | 1240 | WO2016115382A1 SEQ ID NO: 2 |
| rAAV4 | 1243 | WO2016115382A1 SEQ ID NO: 3 |
| rAAV4 | 1242 | WO2016115382A1 SEQ ID NO: 4 |
| rAAV4 | 1243 | WO2016115382A1 SEQ ID NO: 5 |
| rAAV4 | 1244 | WO2016115382A1 SEQ ID NO: 6 |
| rAAV4 | 1245 | WO2016115382A1 SEQ ID NO: 7 |
| rAAV4 | 1246 | WO2016115382A1 SEQ ID NO: 8 |
| rAAV4 | 1247 | WO2016115382A1 SEQ ID NO: 9 |
| rAAV4 | 1248 | WO2016115382A1 SEQ ID NO: 10 |
| rAAV4 | 1249 | WO2016115382A1 SEQ ID NO: 11 |
| rAAV4 | 1250 | WO2016115382A1 SEQ ID NO: 12 |
| rAAV4 | 1251 | WO2016115382A1 SEQ ID NO: 13 |
| rAAV4 | 1252 | WO2016115382A1 SEQ ID NO: 14 |
| rAAV4 | 1253 | WO2016115382A1 SEQ ID NO: 15 |
| rAAV4 | 1254 | WO2016115382A1 SEQ ID NO: 16 |
| rAAV4 | 1255 | WO2016115382A1 SEQ ID NO: 17 |
| rAAV4 | 1256 | WO2016115382A1 SEQ ID NO: 18 |
| rAAV4 | 1257 | WO2016115382A1 SEQ ID NO: 19 |
| rAAV4 | 1258 | WO2016115382A1 SEQ ID NO: 20 |
| rAAV4 | 1259 | WO2016115382A1 SEQ ID NO: 21 |
| AAV11 | 1260 | WO2016115382A1 SEQ ID NO: 22 |
| AAV12 | 1261 | WO2016115382A1 SEQ ID NO: 23 |
| rh32 | 1262 | WO2016115382A1 SEQ ID NO: 25 |
| rh33 | 1263 | WO2016115382A1 SEQ ID NO: 26 |
| rh34 | 1264 | WO2016115382A1 SEQ ID NO: 27 |
| rAAV4 | 1265 | WO2016115382A1 SEQ ID NO: 28 |
| rAAV4 | 1266 | WO2016115382A1 SEQ ID NO: 29 |
| rAAV4 | 1267 | WO2016115382A1 SEQ ID NO: 30 |
| rAAV4 | 1268 | WO2016115382A1 SEQ ID NO: 31 |
| rAAV4 | 1269 | WO2016115382A1 SEQ ID NO: 32 |
| rAAV4 | 1270 | WO2016115382A1 SEQ ID NO: 33 |
| AAV2/8 | 1271 | WO2016131981A1 SEQ ID NO: 47 |
| AAV2/8 | 1272 | WO2016131981A1 SEQ ID NO: 48 |
| ancestral AAV | 1273 | WO2016154344A1 SEQ ID NO: 7 |

TABLE 1-continued

AAV Serotypes

| Serotype | SEQ ID NO | Reference Information |
|---|---|---|
| ancestral AAV variant C4 | 1274 | WO2016154344A1 SEQ ID NO: 13 |
| ancestral AAV variant C7 | 1275 | WO2016154344A1 SEQ ID NO: 14 |
| ancestral AAV variant G4 | 1276 | WO2016154344A1 SEQ ID NO: 15 |
| consensus amino acid sequence of ancestral AAV variants, C4, C7 and G4 | 1277 | WO2016154344A1 SEQ ID NO: 16 |
| consensus amino acid sequence of ancestral AAV variants, C4 and C7 | 1278 | WO2016154344A1 SEQ ID NO: 17 |
| AAV8 (with a AAV2 phospholipase domain) | 1279 | WO2016150403A1 SEQ ID NO: 13 |
| AAV VR-942n | 1280 | US20160289275A1 SEQ ID NO: 10 |
| AAV5-A (M569V) | 1281 | US20160289275A1 SEQ ID NO: 13 |
| AAV5-A (M569V) | 1282 | US20160289275A1 SEQ ID NO: 14 |
| AAV5-A (Y585V) | 1283 | US20160289275A1 SEQ ID NO: 16 |
| AAV5-A (Y585V) | 1284 | US20160289275A1 SEQ ID NO: 17 |
| AAV5-A (L587T) | 1285 | US20160289275A1 SEQ ID NO: 19 |
| AAV5-A (L587T) | 1286 | US20160289275A1 SEQ ID NO: 20 |
| AAV5-A (Y585V/L587T) | 1287 | US20160289275A1 SEQ ID NO: 22 |
| AAV5-A (Y585V/L587T) | 1288 | US20160289275A1 SEQ ID NO: 23 |
| AAV5-B (D652A) | 1289 | US20160289275A1 SEQ ID NO: 25 |
| AAV5-B (D652A) | 1290 | US20160289275A1 SEQ ID NO: 26 |
| AAV5-B (T362M) | 1291 | US20160289275A1 SEQ ID NO: 28 |
| AAV5-B (T362M) | 1292 | US20160289275A1 SEQ ID NO: 29 |
| AAV5-B (Q359D) | 1293 | US20160289275A1 SEQ ID NO: 31 |
| AAV5-B (Q359D) | 1294 | US20160289275A1 SEQ ID NO: 32 |
| AAV5-B (E350Q) | 1295 | US20160289275A1 SEQ ID NO: 34 |
| AAV5-B (E350Q) | 1296 | US20160289275A1 SEQ ID NO: 35 |
| AAV5-B (P533S) | 1297 | US20160289275A1 SEQ ID NO: 37 |
| AAV5-B (P533S) | 1298 | US20160289275A1 SEQ ID NO: 38 |
| AAV5-B (P533G) | 1299 | US20160289275A1 SEQ ID NO: 40 |
| AAV5-B (P533G) | 1300 | US20160289275A1 SEQ ID NO: 41 |
| AAV5-mutation in loop VII | 1301 | US20160289275A1 SEQ ID NO: 43 |
| AAV5-mutation in loop VII | 1302 | US20160289275A1 SEQ ID NO: 44 |
| AAV8 | 1303 | US20160289275A1 SEQ ID NO: 47 |
| Mut A (LK03/AAV8) | 1304 | WO2016181123A1 SEQ ID NO: 1 |
| Mut B (LK03/AAV5) | 1305 | WO2016181123A1 SEQ ID NO: 2 |
| Mut C (AAV8/AAV3B) | 1306 | WO2016181123A1 SEQ ID NO: 3 |
| Mut D (AAV5/AAV3B) | 1307 | WO2016181123A1 SEQ ID NO: 4 |
| Mut E (AAV8/AAV3B) | 1308 | WO2016181123A1 SEQ ID NO: 5 |
| Mut F (AAV3B/AAV8) | 1309 | WO2016181123A1 SEQ ID NO: 6 |

TABLE 1-continued

AAV Serotypes

| Serotype | SEQ ID NO | Reference Information |
|---|---|---|
| AAV44.9 | 1310 | WO2016183297A1 SEQ ID NO: 4 |
| AAV44.9 | 1311 | WO2016183297A1 SEQ ID NO: 5 |
| AAVrh8 | 1312 | WO2016183297A1 SEQ ID NO: 6 |
| AAV44.9 (S470N) | 1313 | WO2016183297A1 SEQ ID NO: 9 |
| rh74 VP1 | 1314 | US20160375110A1 SEQ ID NO: 1 |
| AAV-LK03 (L125I) | 1315 | WO2017015102A1 SEQ ID NO: 5 |
| AAV3B (S663V + T492V) | 1316 | WO2017015102A1 SEQ ID NO: 6 |
| Anc80 | 1317 | WO2017019994A2 SEQ ID NO: 1 |
| Anc80 | 1318 | WO2017019994A2 SEQ ID NO: 2 |
| Anc81 | 1319 | WO2017019994A2 SEQ ID NO: 3 |
| Anc81 | 1320 | WO2017019994A2 SEQ ID NO: 4 |
| Anc82 | 1321 | WO2017019994A2 SEQ ID NO: 5 |
| Anc82 | 1322 | WO2017019994A2 SEQ ID NO: 6 |
| Anc83 | 1323 | WO2017019994A2 SEQ ID NO: 7 |
| Anc83 | 1324 | WO2017019994A2 SEQ ID NO: 8 |
| Anc84 | 1325 | WO2017019994A2 SEQ ID NO: 9 |
| Anc84 | 1326 | WO2017019994A2 SEQ ID NO: 10 |
| Anc94 | 1327 | WO2017019994A2 SEQ ID NO: 11 |
| Anc94 | 1328 | WO2017019994A2 SEQ ID NO: 12 |
| Anc113 | 1329 | WO2017019994A2 SEQ ID NO: 13 |
| Anc113 | 1330 | WO2017019994A2 SEQ ID NO: 14 |
| Anc126 | 1331 | WO2017019994A2 SEQ ID NO: 15 |
| Anc126 | 1332 | WO2017019994A2 SEQ ID NO: 16 |
| Anc127 | 1333 | WO2017019994A2 SEQ ID NO: 17 |
| Anc127 | 1334 | WO2017019994A2 SEQ ID NO: 18 |
| Anc80L27 | 1335 | WO2017019994A2 SEQ ID NO: 19 |
| Anc80L59 | 1336 | WO2017019994A2 SEQ ID NO: 20 |
| Anc80L60 | 1337 | WO2017019994A2 SEQ ID NO: 21 |
| Anc80L62 | 1338 | WO2017019994A2 SEQ ID NO: 22 |
| Anc80L65 | 1339 | WO2017019994A2 SEQ ID NO: 23 |
| Anc80L33 | 1340 | WO2017019994A2 SEQ ID NO: 24 |
| Anc80L36 | 1341 | WO2017019994A2 SEQ ID NO: 25 |
| Anc80L44 | 1342 | WO2017019994A2 SEQ ID NO: 26 |
| Anc80L1 | 1343 | WO2017019994A2 SEQ ID NO: 35 |
| Anc80L1 | 1344 | WO2017019994A2 SEQ ID NO: 36 |
| AAVrh10 | 1345 | WO2017019994A2 SEQ ID NO: 41 |
| Anc110 | 1346 | WO2017019994A2 SEQ ID NO: 42 |
| Anc110 | 1347 | WO2017019994A2 SEQ ID NO: 43 |

TABLE 1-continued

AAV Serotypes

| Serotype | SEQ ID NO | Reference Information |
|---|---|---|
| AAVrh32.33 | 1348 | WO2017019994A2 SEQ ID NO: 45 |
| AAVrh74 | 1349 | WO2017049031A1 SEQ ID NO: 1 |
| AAV2 | 1350 | WO2017053629A2 SEQ ID NO: 49 |
| AAV2 | 1353 | WO2017053629A2 SEQ ID NO: 50 |
| AAV2 | 1352 | WO2017053629A2 SEQ ID NO: 82 |
| Parvo-like virus | 1353 | WO2017070476A2 SEQ ID NO: 1 |
| Parvo-like virus | 1354 | WO2017070476A2 SEQ ID NO: 2 |
| Parvo-like virus | 1355 | WO2017070476A2 SEQ ID NO: 3 |
| Parvo-like virus | 1356 | WO2017070476A2 SEQ ID NO: 4 |
| Parvo-like virus | 1357 | WO2017070476A2 SEQ ID NO: 5 |
| Parvo-like virus | 1358 | WO2017070476A2 SEQ ID NO: 6 |
| AAVrh.10 | 1359 | WO2017070516A1 SEQ ID NO: 7 |
| AAVrh.10 | 1360 | WO2017070516A1 SEQ ID NO: 14 |
| AAV2tYF | 1361 | WO2017070491A1 SEQ ID NO: 1 |
| AAV-SPK | 1362 | WO2017075619A1 SEQ ID NO:28 |
| AAV2.5 | 1363 | US20170128528A1 SEQ ID NO: 13 |
| AAV1.1 | 1364 | US20170128528A1 SEQ ID NO: 15 |
| AAV6.1 | 1365 | US20170128528A1 SEQ ID NO: 17 |
| AAV6.3.1 | 1366 | US20170128528A1 SEQ ID NO: 18 |
| AAV2i8 | 1367 | US20170128528A1 SEQ ID NO: 28 |
| AAV2i8 | 1368 | US20170128528A1 SEQ ID NO: 29 |
| ttAAV | 1369 | US20170128528A1 SEQ ID NO: 30 |
| ttAAV-S312N | 1370 | US20170128528A1 SEQ ID NO: 32 |
| ttAAV-S312N | 1371 | US20170128528A1 SEQ ID NO: 33 |
| AAV6 (Y705, Y731, and T492) | 1372 | WO2016134337A1 SEQ ID NO: 24 |
| AAV2 | 1373 | WO2016134375A1 SEQ ID NO: 9 |
| AAV2 | 1374 | WO2016134375A1 SEQ ID NO: 10 |

In any of the DNA and RNA sequences referenced and/or described herein, the single letter symbol has the following description: A for adenine; C for cytosine: G for guanine; T for thymine; U for Uracil; W for weak bases such as adenine or thymine; S for strong nucleotides such as cytosine and guanine; M for amino nucleotides such as adenine and cytosine: K for keto nucleotides such as guanine and thymine; R for purines adenine and guanine; Y for pyrimidine cytosine and thymine; B for any base that is not A (e.g., cytosine, guanine, and thymine): D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description: G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gin) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

In certain embodiments, the AAV serotype may be, or may have a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 132 and 131 respectively herein). PHP.B (SEQ ID NO: 8 and 9 of WO2015038958 or SEQ ID NO: 1 and 2 herein), G2B-13 (SEQ ID NO: 12 of WO2015038958 or SEQ ID NO: 3 herein), G2B-26 (SEQ ID NO: 13 of WO2015038958 or SEQ ID NO: 1 herein), TH1.1-32 (SEQ ID NO: 14 of WO2015038958 or SEQ ID NO: 4 herein), TH1.1-35 (SEQ ID NO: 15 of WO2015038958 or SEQ ID NO: 5 herein) or variants thereof. Further, any of the targeting peptides or amino acid inserts described in WO2015038958, may be inserted into any parent AAV serotype, such as, but not limited to, AAV9 (SEQ ID NO: 131 for the DNA sequence and SEQ ID NO: 132 for the amino acid sequence). In certain embodiments, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, TLAVPFK (SEQ ID NO: 1 of WO2015038958; herein SEQ ID NO: 876), KFPVALT (SEQ ID NO: 3 of WO2015038958; herein SEQ ID NO: 877). LAVPFK (SEQ ID NO: 31 of WO2015038958; herein SEQ ID NO: 878), AVPFK (SEQ ID NO: 32 of WO2015038958; herein SEQ ID NO: 879), VPFK (SEQ ID NO: 33 of WO2015038958; herein SEQ ID NO: 880), TLAVPF (SEQ ID NO: 34 of WO2015038958; herein SEQ ID NO: 881), TLAVP (SEQ ID NO: 35 of WO2015038958; herein SEQ ID NO: 882), TLAV (SEQ ID NO: 36 of WO2015038958; herein SEQ ID NO: 883), SVSKPFL (SEQ ID NO: 28 of WO2015038958; herein SEQ ID NO: 884), FTLTTPK (SEQ ID NO: 29 of WO2015038958; herein SEQ ID NO: 885), MNATKNV (SEQ ID NO: 30 of WO2015038958; herein SEQ ID NO: 886), QSSQTPR (SEQ ID NO: 54 of WO2015038958; herein SEQ ID NO: 887), ILGTGTS (SEQ ID NO: 55 of WO2015038958; herein SEQ ID NO: 888), TRTNPEA (SEQ ID NO: 56 of WO2015038958; herein SEQ ID NO: 889). NGGTSSS (SEQ ID NO: 58 of WO2015038958; herein SEQ ID NO: 890), or YTLSQGW (SEQ ID NO: 60 of WO2015038958; herein SEQ ID NO: 891). Non-limiting examples of nucleotide sequences that may encode the amino acid inserts include the following, AAGTITCCTGTGGCGTTGACT (for SEQ ID NO: 3 of WO2015038958; herein SEQ ID NO: 892), ACTTTGGCGGTGCCTTITAAG (SEQ ID NO: 24 and 49 of WO2015038958; herein SEQ ID NO: 893), AGTGTGAGTAAGCCTITTTG (SEQ ID NO: 25 of WO2015038958; herein SEQ ID NO: 894), TITACGTTGACGACGCCTAAG (SEQ ID NO: 26 of WO2015038958; herein SEQ ID NO: 895), ATGAATGCTACGAAGAATGTG (SEQ ID NO: 27 of WO2015038958; herein SEQ ID NO: 896), CAGTCGTCGCAGACGCCTAGG (SEQ ID NO: 48 of WO2015038958; herein SEQ ID NO: 897), ATTCTGGGGACTGGTACTTCG (SEQ ID NO: 50 and 52 of WO2015038958; herein SEQ ID NO: 898), ACGCGGACTAATCCTGAGGCT (SEQ ID NO: 51 of WO2015038958; herein SEQ ID NO: 899), AATGGGGGGACTAGTAGTTCT (SEQ ID NO: 53 of WO2015038958; herein SEQ ID NO: 900), or TATACTITGTCGCAGGGTIGG (SEQ ID NO: 59 of WO2015038958; herein SEQ ID NO: 901).

In certain embodiments, the AAV serotype may be, or may have a sequence as described in International Patent Publication WO2017100671, the contents of which are herein incorporated by reference in their entirety, such as, but not limited to, AAV9 (SEQ ID NO: 45 of WO2017100671, herein SEQ ID NO: 875), PHP.N (SEQ ID NO: 46 of WO2017100671, herein SEQ ID NO: 873), PHP.S (SEQ ID NO: 47 of WO2017100671, herein SEQ ID NO: 874), or variants thereof. Further, any of the targeting peptides or amino acid inserts described in WO2017100671 may be inserted into any parent AAV serotype, such as, but not limited to, AAV9 (SEQ ID NO: 127 or SEQ ID NO: 875). In certain embodiments, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, AQTLAVPFKAQ (SEQ ID NO: 1 of WO2017100671; herein SEQ ID NO: 902), AQSVSKPFLAQ (SEQ ID NO: 2 of WO2017100671; herein SEQ ID NO: 903), AQFTLTTPKAQ (SEQ ID NO: 3 in the sequence listing of WO2017100671; herein SEQ ID NO: 904), DGTLAVPFKAQ (SEQ ID NO: 4 in the sequence listing of WO2017100671; herein SEQ ID NO: 905), ESTLAVPFKAQ (SEQ ID NO: 5 of WO2017100671; herein SEQ ID NO: 906), GGTLAVPFKAQ (SEQ ID NO: 6 of WO2017100671; herein SEQ ID NO: 907), AQTLATPFKAQ (SEQ ID NO: 7 and 33 of WO2017100671; herein SEQ ID NO: 908), ATTLATPFKAQ (SEQ ID NO: 8 of WO2017100671; herein SEQ ID NO: 909), DGTLATPFKAQ (SEQ ID NO: 9 of WO2017100671; herein SEQ ID NO: 910), GGTLATPFKAQ (SEQ ID NO: 10 of WO2017100671; herein SEQ ID NO: 911), SGSLAVPFKAQ (SEQ ID NO: 11 of WO2017100671; herein SEQ ID NO: 912), AQTLAQPFKAQ (SEQ ID NO: 12 of WO2017100671; herein SEQ ID NO: 913), AQTLQQPFKAQ (SEQ ID NO: 13 of WO2017100671; herein SEQ ID NO: 914), AQTLSNPFKAQ (SEQ ID NO: 14 of WO2017100671; herein SEQ ID NO: 915), AQTLAVPFSNP (SEQ ID NO: 15 of WO2017100671; herein SEQ ID NO: 916), QGTLAVPFKAQ (SEQ ID NO: 16 of WO2017100671; herein SEQ ID NO: 917), NQTLAVPFKAQ (SEQ ID NO: 17 of WO2017100671; herein SEQ ID NO: 918), EGSLAVPFKAQ (SEQ ID NO: 18 of WO2017100671; herein SEQ ID NO: 919), SGNLAVPFKAQ (SEQ ID NO: 19 of WO2017100671; herein SEQ ID NO: 920), EGTLAVPFKAQ (SEQ ID NO: 20 of WO2017100671; herein SEQ ID NO: 921), DSTLAVPFKAQ (SEQ ID NO: 21 in Table 1 of WO2017100671; herein SEQ ID NO: 922), AVTLAVPFKAQ (SEQ ID NO: 22 of WO2017100671; herein SEQ ID NO: 923), AQTLSTPFKAQ (SEQ ID NO: 23 of WO2017100671; herein SEQ ID NO: 924), AQTLPQPFKAQ (SEQ ID NO: 24 and 32 of WO2017100671; herein SEQ ID NO: 925), AQTLSQPFKAQ (SEQ ID NO: 25 of WO2017100671; herein SEQ ID NO: 926), AQTLQLPFKAQ (SEQ ID NO: 26 of WO2017100671; herein SEQ ID NO: 927), AQTLTMPFKAQ (SEQ ID NO: 27, and 34 of WO2017100671 and SEQ ID NO: 35 in the sequence listing of WO2017100671; herein SEQ ID NO: 928), AQTLTMPFKAQ (SEQ ID NO: 28 of WO2017100671; herein SEQ ID NO: 929), AQYTLSQGWAQ (SEQ ID NO: 29 of WO2017100671; herein SEQ ID NO: 930), AQMNATKNVAQ (SEQ ID NO: 30 of WO2017100671; herein SEQ ID NO: 931), AQVSGGHHSAQ (SEQ ID NO: 31 of WO2017100671; herein SEQ ID NO: 932), AQTLTAPFKAQ (SEQ ID NO: 35 in Table 1 of WO2017100671; herein SEQ ID NO: 933), AQTLSKPFKAQ (SEQ ID NO: 36 of WO2017100671; herein SEQ ID NO: 934), QAVRTSL (SEQ ID NO: 37 of WO2017100671; herein SEQ ID NO: 935), YTLSQGW (SEQ ID NO: 38 of WO2017100671; herein SEQ ID NO: 891), LAKERLS (SEQ ID NO: 39 of WO2017100671; herein SEQ ID NO: 936), TLAVPFK (SEQ ID NO: 40 in the sequence listing of WO2017100671; herein SEQ ID NO: 876), SVSKPFL (SEQ ID NO: 41 of WO2017100671; herein SEQ ID NO: 884), FTLTTPK (SEQ ID NO: 42 of WO2017100671; herein SEQ ID NO: 885), MNSTKNV (SEQ ID NO: 43 of WO2017100671; herein SEQ ID NO: 937), VSGGHHS (SEQ ID NO: 44 of WO2017100671; herein SEQ ID NO: 938), SAQTLAVPFKAQAQ (SEQ ID NO: 48 of WO2017100671; herein SEQ ID NO: 939), SXXXLAVPFKAQAQ (SEQ ID NO: 49 of WO2017100671 wherein X may be any amino acid; herein SEQ ID NO: 940), SAQXXXVPFKAQAQ (SEQ ID NO: 50 of WO2017100671 wherein X may be any amino acid; herein SEQ ID NO: 941), SAQTLXXXFKAQAQ (SEQ ID NO: 51 of WO2017100671 wherein X may be any amino acid; herein SEQ ID NO: 942), SAQTLAVXXXAQAQ (SEQ ID NO: 52 of WO2017100671 wherein X may be any amino acid; herein SEQ ID NO: 943), SAQTLAVPFXXXAQ (SEQ ID NO: 53 of WO2017100671 wherein X may be any amino acid; herein SEQ ID NO: 944), TNHQSAQ (SEQ ID NO: 65 of WO2017100671; herein SEQ ID NO: 945), AQAQTGW (SEQ ID NO: 66 of WO2017100671; herein SEQ ID NO: 946), DGTLATPFK (SEQ ID NO: 67 of WO2017100671; herein SEQ ID NO: 947). DGTLATPFKXX (SEQ ID NO: 68 of WO2017100671 wherein X may be any amino acid; herein SEQ ID NO: 948), LAVPFKAQ (SEQ ID NO: 80 of WO2017100671; herein SEQ ID NO: 949), VPFKAQ (SEQ ID NO: 81 of WO2017100671; herein SEQ ID NO: 950), FKAQ (SEQ ID NO: 82 of WO2017100671; herein SEQ ID NO: 951), AQTLAV (SEQ ID NO: 83 of WO2017100671; herein SEQ ID NO: 952), AQTLAVPF (SEQ ID NO: 84 of WO2017100671; herein SEQ ID NO: 953), QAVR (SEQ ID NO: 85 of WO2017100671; herein SEQ ID NO: 954), AVRT (SEQ ID NO: 86 of WO2017100671; herein SEQ ID NO: 955), VRTS (SEQ ID NO: 87 of WO2017100671; herein SEQ ID NO: 956), RTSL (SEQ ID NO: 88 of WO2017100671; herein SEQ ID NO: 957), QAVRT (SEQ ID NO: 89 of WO2017100671; herein SEQ ID NO: 958), AVRTS (SEQ ID NO: 90 of WO2017100671; herein SEQ ID NO: 959), VRTSL (SEQ ID NO: 91 of WO2017100671; herein SEQ ID NO: 960), QAVRTS (SEQ ID NO: 92 of WO2017100671; herein SEQ ID NO: 961), orAVRTSL (SEQ ID NO: 93 of WO2017100671; herein SEQ ID NO: 962).

Non-limiting examples of nucleotide sequences that may encode the amino acid inserts include the following, GATGGGACTTTGGCGGTGCCTTTTAAGGCACAG (SEQ ID NO: 54 of WO2017100671; herein SEQ ID NO: 963), GATGGGACGTTGGCGGTGCCTTT-TAAGGCACAG (SEQ ID NO: 55 of WO2017100671; herein SEQ ID NO: 964), CAGGCGGT-TAGGACGTCTTTG (SEQ ID NO: 56 of WO2017100671; herein SEQ ID NO: 965), CAGGTCTTCACGGACTCA-GACTATCAG (SEQ ID NO: 57 and 78 of WO2017100671; herein SEQ ID NO: 966), CAAGTAAAACCTCTA-CAAATGTGGTAAAATCG (SEQ ID NO: 58 of WO2017100671; herein SEQ ID NO: 967). ACT-CATCGACCAATACTTGTACTATCTCTAGAAC (SEQ ID NO: 59 of WO2017100671; herein SEQ ID NO: 968), GGAAGTATTCCTTGGTTTTGAACCCA (SEQ ID NO: 60 of WO2017100671; herein SEQ ID NO: 969), GGTCGCGGTTCTTGTTTGTGGAT (SEQ ID NO: 61 of WO2017100671; herein SEQ ID NO: 970), CGACCTT-GAAGCGCATGAACTCCT (SEQ ID NO: 62 of WO2017100671; herein SEQ ID NO: 971), GTAT-TCCTTGGTTTTGAACC-CAACCGGTCTGCGCCTGTGCMNNMNNMNNMN-NMNN MNNMNNTTGGGCACTCTGGTGGTTTGTC (SEQ ID NO: 63 of WO2017100671 wherein N may be A, C, T, or G; herein SEQ ID NO: 972), GTAT-TCCTTGGTTTTGAACC-CAACCGGTCTGCGCMNNMNNMN-NAAAAGGCACCGCC AAAGTTTG (SEQ ID NO: 69 of WO2017100671 wherein N may be A, C, T, or G; herein SEQ ID NO: 973), GTATTCCTTGGTTTTGAACC-CAACCGGTCTGCGCCTGTGCMNNMNNMNN-CACCGCC AAAGTTGGGCACT (SEQ ID NO: 70 of WO2017100671 wherein N may be A, C, T, or G; herein SEQ ID NO: 974), GTATTCCTTGGTTTGAACC-CAACCGGTCTGCGCCTGTGCCT-TAAAMNNMNNMNNC AAAGTTTGGGCACTCTGGTGG (SEQ ID NO: 71 of WO2017100671 wherein N may be A, C, T, or G; herein SEQ ID NO: 975), GTATTCCTTGGTTTTGAACC-CAACCGGTCTGCGCCTGTGCCT-TAAAAGGCACMNNM NNMNNTTGGGCACTCTGGTGGTTFGTG (SEQ ID NO: 72 of WO2017100671 wherein N may be A, C, T, or G; herein SEQ ID NO: 976), AC-TTGGCGGTGCCTTTTAAG (SEQ ID NO: 74 of WO2017100671; herein SEQ ID NO: 893), AGTGTGAGTAAGCCTTITTTG (SEQ ID NO: 75 of WO2017100671; herein SEQ ID NO: 894), TITACGTTGACGACGCCTAAG (SEQ ID NO: 76 of WO2017100671; herein SEQ ID NO: 895), TATACTTTGTCGCAGGGTTGG (SEQ ID NO: 77 of WO2017100671; herein SEQ ID NO: 901), or CTTGCGAAGGAGCGGCTITCG (SEQ ID NO: 79 of WO2017100671; herein SEQ ID NO: 977).

In certain embodiments, the AAV serotype may be, or may have a sequence as described in U.S. Pat. No. 9,624,274, the contents of which are herein incorporated by reference in their entirety, such as, but not limited to, AAV1 (SEQ ID NO: 181 of U.S. Pat. No. 9,624,274), AAV6 (SEQ ID NO: 182 of U.S. Pat. No. 9,624,274), AAV2 (SEQ ID NO: 183 of U.S. Pat. No. 9,624,274), AAV3b (SEQ ID NO: 184 of U.S. Pat. No. 9,624,274), AAV7 (SEQ ID NO: 185 of U.S. Pat. No. 9,624,274), AAV8 (SEQ ID NO: 186 of U.S. Pat. No. 9,624,274), AAV10 (SEQ ID NO: 187 of U.S. Pat. No. 9,624,274), AAV4 (SEQ ID NO: 188 of U.S. Pat. No. 9,624,274), AAV11 (SEQ ID NO: 189 of U.S. Pat. No. 9,624,274), bAAV (SEQ ID NO: 190 of U.S. Pat. No. 9,624,274), AAV5 (SEQ ID NO: 191 of U.S. Pat. No. 9,624,274), GPV (SEQ ID NO: 192 of U.S. Pat. No. 9,624,274; herein SEQ ID NO: 992), B19 (SEQ ID NO: 193 of U.S. Pat. No. 9,624,274; herein SEQ ID NO: 993), MVM (SEQ ID NO: 194 of U.S. Pat. No. 9,624,274; herein SEQ ID NO: 994), FPV (SEQ ID NO: 195 of U.S. Pat. No. 9,624,274; herein SEQ ID NO: 995), CPV (SEQ ID NO: 196 of U.S. Pat. No. 9,624,274; herein SEQ ID NO: 996) or variants thereof. Further, any of the structural protein inserts described in U.S. Pat. No. 9,624,274, may be inserted into, but not limited to, I-453 and I-587 of any parent AAV serotype, such as, but not limited to, AAV2 (SEQ ID NO: 183 of U.S. Pat. No. 9,624,274). The amino acid insert may be, but is not limited to, any of the following amino acid sequences, VNLTWSRASG (SEQ ID NO: 50 of U.S. Pat. No. 9,624,274; herein SEQ ID NO: 1375), EFCINHR-GYWVCGD (SEQ ID NO:55 of U.S. Pat. No. 9,624,274; herein SEQ ID NO: 1376), EDGQVMDVDLS (SEQ ID NO: 85 of U.S. Pat. No. 9,624,274; herein SEQ ID NO:

1377), EKQRNGTLT (SEQ ID NO: 86 of U.S. Pat. No. 9,624,274; herein SEQ ID NO: 1378), TYQCRVTHPHLPRALMR (SEQ ID NO: 87 of U.S. Pat. No. 9,624,274; herein SEQ ID NO: 1379), RHSTTQPRKTKGSG (SEQ ID NO: 88 of U.S. Pat. No. 9,624,274; herein SEQ ID NO: 1380), DSNPRGVSAYLSR (SEQ ID NO: 89 of U.S. Pat. No. 9,624,274; herein SEQ ID NO: 1381), TITCLWDLAPSK (SEQ ID NO: 90 of U.S. Pat. No. 9,624,274; herein SEQ ID NO: 1382), KTKGSGFFVF (SEQ ID NO: 91 of U.S. Pat. No. 9,624,274; herein SEQ ID NO: 1383), THPHLPRALMRS (SEQ ID NO: 92 of U.S. Pat. No. 9,624,274; herein SEQ ID NO: 1384), GETYQCRVTHPHLPRALMRSTK (SEQ ID NO: 93 of U.S. Pat. No. 9,624,274; herein SEQ ID NO: 1385), LPRALMRS (SEQ ID NO: 94 of U.S. Pat. No. 9,624,274; herein SEQ ID NO: 1386), INHRGYWV (SEQ ID NO: 95 of U.S. Pat. No. 9,624,274; herein SEQ ID NO: 1387), CDAGSVRTNAPD (SEQ ID NO: 60 of U.S. Pat. No. 9,624,274; herein SEQ ID NO: 1388), AKAVSNLTESRSESLQS (SEQ ID NO: 96 of U.S. Pat. No. 9,624,274; herein SEQ ID NO: 1389), SLTGDEFKKVLET (SEQ ID NO: 97 of U.S. Pat. No. 9,624,274; herein SEQ ID NO: 1390), REAVAYRFEED (SEQ ID NO: 98 of U.S. Pat. No. 9,624,274; herein SEQ ID NO: 1391), INPEIITLDG (SEQ ID NO: 99 of U.S. Pat. No. 9,624,274; herein SEQ ID NO: 1392), DISVTGAPVITATYL (SEQ ID NO: 100 of U.S. Pat. No. 9,624,274; herein SEQ ID NO: 1393), DISVTGAPVITA (SEQ ID NO: 101 of U.S. Pat. No. 9,624,274; herein SEQ ID NO: 1394), PKTVSNLTESSSESVQS (SEQ ID NO: 102 of U.S. Pat. No. 9,624,274; herein SEQ ID NO: 1395), SLMGDEFKAVLET (SEQ ID NO: 103 of U.S. Pat. No. 9,624,274; herein SEQ ID NO: 1396), QHSVAYTFEED (SEQ ID NO: 104 of U.S. Pat. No. 9,624,274; herein SEQ ID NO: 1397), INPEIITRDG (SEQ ID NO: 105 of U.S. Pat. No. 9,624,274; herein SEQ ID NO: 1398), DISLTGDPVITASYL (SEQ ID NO: 106 of U.S. Pat. No. 9,624,274; herein SEQ ID NO: 1399), DISLTGDPVITA (SEQ ID NO: 107 of U.S. Pat. No. 9,624,274; herein SEQ ID NO: 1400), DQSIDFEIDSA (SEQ ID NO: 108 of U.S. Pat. No. 9,624,274; herein SEQ ID NO: 1401), KNVSEDLPLPTFSPTLLGDS (SEQ ID NO: 109 of U.S. Pat. No. 9,624,274; herein SEQ ID NO: 1402), KNVSEDLPLPT (SEQ ID NO: 110 of U.S. Pat. No. 9,624,274; herein SEQ ID NO: 1403), CDSGRVRTDAPD (SEQ ID NO: 111 of U.S. Pat. No. 9,624,274; herein SEQ ID NO: 1404), FPEHLLVDFLQSLS (SEQ ID NO: 112 of U.S. Pat. No. 9,624,274; herein SEQ ID NO: 1405), DAEFRHDSG (SEQ ID NO: 65 of U.S. Pat. No. 9,624,274; herein SEQ ID NO: 1406), HYAAAQWDFGNTMCQL (SEQ ID NO: 113 of U.S. Pat. No. 9,624,274; herein SEQ ID NO: 1407), YAAQWDFGNTMCQ (SEQ ID NO: 114 of U.S. Pat. No. 9,624,274; herein SEQ ID NO: 1408), RSQKEGLHYT (SEQ ID NO: 115 of U.S. Pat. No. 9,624,274; herein SEQ ID NO: 1409), SSRTPSDKPVAHWANPQAE (SEQ ID NO: 116 of U.S. Pat. No. 9,624,274; herein SEQ ID NO: 1410), SRTPSDKPVAHWANP (SEQ ID NO: 117 of U.S. Pat. No. 9,624,274; herein SEQ ID NO: 1411), SSRTPSDKP (SEQ ID NO: 118 of U.S. Pat. No. 9,624,274; herein SEQ ID NO: 1412), NADGNVDYHMNSVP (SEQ ID NO: 119 of U.S. Pat. No. 9,624,274; herein SEQ ID NO: 1413), DGNVDYHMNSV (SEQ ID NO: 120 of U.S. Pat. No. 9,624,274; herein SEQ ID NO: 1414), RSFKEFLQSSLRALRQ (SEQ ID NO: 121 of U.S. Pat. No. 9,624,274; herein SEQ ID NO: 1415); FKEFLQSSLRA (SEQ ID NO: 122 of U.S. Pat. No. 9,624,274; herein SEQ ID NO: 1416), or QMWAPQWGPD (SEQ ID NO: 123 of U.S. Pat. No. 9,624,274; herein SEQ ID NO: 1417).

In certain embodiments, the AAV serotype may be, or may have a sequence as described in U.S. Pat. No. 9,475,845, the contents of which are herein incorporated by reference in their entirety, such as, but not limited to, AAV capsid proteins comprising modification of one or more amino acids at amino acid positions 585 to 590 of the native AAV2 capsid protein. Further the modification may result in, but not limited to, the amino acid sequence RGNRQA (SEQ ID NO: 3 of U.S. Pat. No. 9,475,845; herein SEQ ID NO: 1418), SSSTDP (SEQ ID NO: 4 of U.S. Pat. No. 9,475,845; herein SEQ ID NO: 1419), SSNTAP (SEQ ID NO: 5 of U.S. Pat. No. 9,475,845; herein SEQ ID NO: 1420), SNSNLP (SEQ ID NO: 6 of U.S. Pat. No. 9,475,845; herein SEQ ID NO: 1421), SSTTAP (SEQ ID NO: 7 of U.S. Pat. No. 9,475,845; herein SEQ ID NO: 1422), AANTAA (SEQ ID NO: 8 of U.S. Pat. No. 9,475,845; herein SEQ ID NO: 1423), QQNTAP (SEQ ID NO: 9 of U.S. Pat. No. 9,475,845; herein SEQ ID NO: 1424), SAQAQA (SEQ ID NO: 10 of U.S. Pat. No. 9,475,845; herein SEQ ID NO: 1425), QANTGP (SEQ ID NO: 11 of U.S. Pat. No. 9,475,845; herein SEQ ID NO: 1426), NATTAP (SEQ ID NO: 12 of U.S. Pat. No. 9,475,845; herein SEQ ID NO: 1427), SSTAGP (SEQ ID NO: 13 and 20 of U.S. Pat. No. 9,475,845; herein SEQ ID NO: 1428), QQNTAA (SEQ ID NO: 14 of U.S. Pat. No. 9,475,845; herein SEQ ID NO: 1429), PSTAGP (SEQ ID NO: 15 of U.S. Pat. No. 9,475,845; herein SEQ ID NO: 1430), NQNTAP (SEQ ID NO: 16 of U.S. Pat. No. 9,475,845; herein SEQ ID NO: 1431), QAANAP (SEQ ID NO: 17 of U.S. Pat. No. 9,475,845; herein SEQ ID NO: 1432), SIVGLP (SEQ ID NO: 18 of U.S. Pat. No. 9,475,845; herein SEQ ID NO: 1433), AASTAA (SEQ ID NO: 19, and 27 of U.S. Pat. No. 9,475,845; herein SEQ ID NO: 1434), SQNTTA (SEQ ID NO: 21 of U.S. Pat. No. 9,475,845; herein SEQ ID NO: 1435), QQDTAP (SEQ ID NO: 22 of U.S. Pat. No. 9,475,845; herein SEQ ID NO: 1436), QTNTGP (SEQ ID NO: 23 of U.S. Pat. No. 9,475,845; herein SEQ ID NO: 1437), QTNGAP (SEQ ID NO: 24 of U.S. Pat. No. 9,475,845; herein SEQ ID NO: 1438), QQNAAP (SEQ ID NO: 25 of U.S. Pat. No. 9,475,845; herein SEQ ID NO: 1439), or AANTQA (SEQ ID NO: 26 of U.S. Pat. No. 9,475,845; herein SEQ ID NO: 1440). In certain embodiments, the amino acid modification is a substitution at amino acid positions 262 through 265 in the native AAV2 capsid protein or the corresponding position in the capsid protein of another AAV with a targeting sequence. The targeting sequence may be, but is not limited to, any of the amino acid sequences, NGRAHA (SEQ ID NO: 38 of U.S. Pat. No. 9,475,845; herein SEQ ID NO: 1441), QPEHSST (SEQ ID NO: 39 and 50 of U.S. Pat. No. 9,475,845; herein SEQ ID NO: 1442), VNTANST (SEQ ID NO: 40 of U.S. Pat. No. 9,475,845; herein SEQ ID NO: 1443), HGPMQKS (SEQ ID NO: 41 of U.S. Pat. No. 9,475,845; herein SEQ ID NO: 1444), PHKPPLA (SEQ ID NO: 42 of U.S. Pat. No. 9,475,845; herein SEQ ID NO: 1445), IKNNEMW (SEQ ID NO: 43 of U.S. Pat. No. 9,475,845; herein SEQ ID NO: 1446), RNLDTPM (SEQ ID NO: 44 of U.S. Pat. No. 9,475,845; herein SEQ ID NO: 1447), VDSHRQS (SEQ ID NO: 45 of U.S. Pat. No. 9,475,845; herein SEQ ID NO: 1448), YDSKTKT (SEQ ID NO: 46 of U.S. Pat. No. 9,475,845; herein SEQ ID NO: 1449), SQLPHQK (SEQ ID NO: 47 of U.S. Pat. No. 9,475,845; herein SEQ ID NO: 1450), STMQQNT (SEQ ID NO: 48 of U.S. Pat. No. 9,475,845; herein SEQ ID NO: 1451), TERYMTQ (SEQ ID NO: 49 of U.S. Pat. No. 9,475,845; herein SEQ ID NO: 1452), DASLSTS (SEQ ID NO: 51 of U.S. Pat. No. 9,475,845; herein SEQ ID NO: 1453), DLPNKKT (SEQ ID NO: 52 of U.S. Pat. No.

9,475,845; herein SEQ ID NO: 1454), DLTAARL (SEQ ID NO: 53 of U.S. Pat. No. 9,475,845; herein SEQ ID NO: 1455), EPHQFNY (SEQ ID NO: 54 of U.S. Pat. No. 9,475,845; herein SEQ ID NO: 1456), EPQSNHT (SEQ ID NO: 55 of U.S. Pat. No. 9,475,845; herein SEQ ID NO: 1457), MSSWPSQ (SEQ ID NO: 56 of U.S. Pat. No. 9,475,845; herein SEQ ID NO: 1458), NPKHNAT (SEQ ID NO: 57 of U.S. Pat. No. 9,475,845; herein SEQ ID NO: 1459), PDGMRTT (SEQ ID NO: 58 of U.S. Pat. No. 9,475,845; herein SEQ ID NO: 1460), PNNNKTT (SEQ ID NO: 59 of U.S. Pat. No. 9,475,845; herein SEQ ID NO: 1461), QSTTHDS (SEQ ID NO: 60 of U.S. Pat. No. 9,475,845; herein SEQ ID NO: 1462), TGSKQKQ (SEQ ID NO: 61 of U.S. Pat. No. 9,475,845; herein SEQ ID NO: 1463), SLKHQAL (SEQ ID NO: 62 of U.S. Pat. No. 9,475,845; herein SEQ ID NO: 1464), SPIDGEQ (SEQ ID NO: 63 of U.S. Pat. No. 9,475,845; herein SEQ ID NO: 1465), WIFPWIQL (SEQ ID NO: 64 and 112 of U.S. Pat. No. 9,475,845; herein SEQ ID NO: 1466), CDCRGDCFC (SEQ ID NO: 65 of U.S. Pat. No. 9,475,845; herein SEQ ID NO: 1467), CNGRC (SEQ ID NO: 66 of U.S. Pat. No. 9,475,845; herein SEQ ID NO: 1468), CPRECES (SEQ ID NO: 67 of U.S. Pat. No. 9,475,845; herein SEQ ID NO: 1469), CTTHWGFTLC (SEQ ID NO: 68 and 123 of U.S. Pat. No. 9,475,845; herein SEQ ID NO: 1470), CGRRAGGSC (SEQ ID NO: 69 of U.S. Pat. No. 9,475,845; herein SEQ ID NO: 1471), CKGGRAKDC (SEQ ID NO: 70 of U.S. Pat. No. 9,475,845; herein SEQ ID NO: 1472), CVPELGHEC (SEQ ID NO: 71 and 115 of U.S. Pat. No. 9,475,845; herein SEQ ID NO: 1473), CRRETAWAK (SEQ ID NO: 72 of U.S. Pat. No. 9,475,845; herein SEQ ID NO: 1474), VSWFSHRYSPFAVS (SEQ ID NO: 73 of U.S. Pat. No. 9,475,845; herein SEQ ID NO: 1475), GYRDGYAGPILYN (SEQ ID NO: 74 of U.S. Pat. No. 9,475,845; herein SEQ ID NO: 1476), XXXYXXX (SEQ ID NO: 75 of U.S. Pat. No. 9,475,845; herein SEQ ID NO: 1477), YXNW (SEQ ID NO: 76 of U.S. Pat. No. 9,475,845; herein SEQ ID NO: 1478), RPLPPLP (SEQ ID NO: 77 of U.S. Pat. No. 9,475,845; herein SEQ ID NO: 1479), APPLPPR (SEQ ID NO: 78 of U.S. Pat. No. 9,475,845; herein SEQ ID NO: 1480), DVFYPYPYASGS (SEQ ID NO: 79 of U.S. Pat. No. 9,475,845; herein SEQ ID NO: 1481), MYWYPY (SEQ ID NO: 80 of U.S. Pat. No. 9,475,845; herein SEQ ID NO: 1482), DITWDQLWDLMK (SEQ ID NO: 81 of U.S. Pat. No. 9,475,845; herein SEQ ID NO: 1483), CWDDXWLC (SEQ ID NO: 82 of U.S. Pat. No. 9,475,845; herein SEQ ID NO: 1484), EWCEYLGGYLRCYA (SEQ ID NO: 83 of U.S. Pat. No. 9,475,845; herein SEQ ID NO: 1485), YXCXXGPXTWXCXP (SEQ ID NO: 84 of U.S. Pat. No. 9,475,845; herein SEQ ID NO: 1486), IEGPTLRQWLAARA (SEQ ID NO: 85 of U.S. Pat. No. 9,475,845; herein SEQ ID NO: 1487), LWXXX (SEQ ID NO: 86 of U.S. Pat. No. 9,475,845; herein SEQ ID NO: 1488), XFXXYLW (SEQ ID NO: 87 of U.S. Pat. No. 9,475,845; herein SEQ ID NO: 1489), SSIISHFRWGLCD (SEQ ID NO: 88 of U.S. Pat. No. 9,475,845; herein SEQ ID NO: 1490), MSRPACPPNDKYE (SEQ ID NO: 89 of U.S. Pat. No. 9,475,845; herein SEQ ID NO: 1491), CLRSGRGC (SEQ ID NO: 90 of U.S. Pat. No. 9,475,845; herein SEQ ID NO: 1492), CHWMFSPWC (SEQ ID NO: 91 of U.S. Pat. No. 9,475,845; herein SEQ ID NO: 1493), WXXF (SEQ ID NO: 92 of U.S. Pat. No. 9,475,845; herein SEQ ID NO: 1494), CSSRLDAC (SEQ ID NO: 93 of U.S. Pat. No. 9,475,845; herein SEQ ID NO: 1495), CLPVASC (SEQ ID NO: 94 of U.S. Pat. No. 9,475,845; herein SEQ ID NO: 1496), CGFECVRQCPERC (SEQ ID NO: 95 of U.S. Pat. No. 9,475,845; herein SEQ ID NO: 1497), CVALCREACGEGC (SEQ ID NO: 96 of U.S. Pat. No. 9,475,845; herein SEQ ID NO: 1498), SWCEPGWCR (SEQ ID NO: 97 of U.S. Pat. No. 9,475,845; herein SEQ ID NO: 1499), YSGKWGW (SEQ ID NO: 98 of U.S. Pat. No. 9,475,845; herein SEQ ID NO: 1500), GLSGGRS (SEQ ID NO: 99 of U.S. Pat. No. 9,475,845; herein SEQ ID NO: 1501), LMLPRAD (SEQ ID NO: 100 of U.S. Pat. No. 9,475,845; herein SEQ ID NO: 1502), CSCFRDVCC (SEQ ID NO: 101 of U.S. Pat. No. 9,475,845; herein SEQ ID NO: 1503), CRDVVSVIC (SEQ ID NO: 102 of U.S. Pat. No. 9,475,845; herein SEQ ID NO: 1504), MARSGL (SEQ ID NO: 103 of U.S. Pat. No. 9,475,845; herein SEQ ID NO: 1505), MARAKE (SEQ ID NO: 104 of U.S. Pat. No. 9,475,845; herein SEQ ID NO: 1506), MSRTMS (SEQ ID NO: 105 of U.S. Pat. No. 9,475,845; herein SEQ ID NO: 1507), KCCYSL (SEQ ID NO: 106 of U.S. Pat. No. 9,475,845; herein SEQ ID NO: 1508), MYWGDSHWLQYWYE (SEQ ID NO: 107 of U.S. Pat. No. 9,475,845; herein SEQ ID NO: 1509), MQLPLAT (SEQ ID NO: 108 of U.S. Pat. No. 9,475,845; herein SEQ ID NO: 1510), EWLS (SEQ ID NO: 109 of U.S. Pat. No. 9,475,845; herein SEQ ID NO: 1511), SNEW (SEQ ID NO: 110 of U.S. Pat. No. 9,475,845; herein SEQ ID NO: 1512), TNYL (SEQ ID NO: 111 of U.S. Pat. No. 9,475,845; herein SEQ ID NO: 1513), WDLAWMFRLPVG (SEQ ID NO: 113 of U.S. Pat. No. 9,475,845; herein SEQ ID NO: 1514), CTVALPGGYVRVC (SEQ ID NO: 114 of U.S. Pat. No. 9,475,845; herein SEQ ID NO: 1515), CVAYCIEHHCWTC (SEQ ID NO: 116 of U.S. Pat. No. 9,475,845; herein SEQ ID NO: 1516), CVFAHNYDYLVC (SEQ ID NO: 117 of U.S. Pat. No. 9,475,845; herein SEQ ID NO: 1517), CVFTSNYAFC (SEQ ID NO: 118 of U.S. Pat. No. 9,475,845; herein SEQ ID NO: 1518), VHSPNKK (SEQ ID NO: 119 of U.S. Pat. No. 9,475,845; herein SEQ ID NO: 1519), CRGDGWC (SEQ ID NO: 120 of U.S. Pat. No. 9,475,845; herein SEQ ID NO: 1520), XRGCDX (SEQ ID NO: 121 of U.S. Pat. No. 9,475,845; herein SEQ ID NO: 1521), PXXX (SEQ ID NO: 122 of U.S. Pat. No. 9,475,845; herein SEQ ID NO: 1522), SGKGPRQITAL (SEQ ID NO: 124 of U.S. Pat. No. 9,475,845; herein SEQ ID NO: 1523), AAAAAAAAAXXXXX (SEQ ID NO: 125 of U.S. Pat. No. 9,475,845; herein SEQ ID NO: 1524), VYMSPF (SEQ ID NO: 126 of U.S. Pat. No. 9,475,845; herein SEQ ID NO: 1525), ATWLPPR (SEQ ID NO: 127 of U.S. Pat. No. 9,475,845; herein SEQ ID NO: 1526), HTMYYHHYQHHL (SEQ ID NO: 128 of U.S. Pat. No. 9,475,845; herein SEQ ID NO: 1527), SEVGCRAGPLQWLCEKYFG (SEQ ID NO: 129 of U.S. Pat. No. 9,475,845; herein SEQ ID NO: 1528), CGLLPVGRPDRNVWRWLC (SEQ ID NO: 130 of U.S. Pat. No. 9,475,845; herein SEQ ID NO: 1529), CKGQCDRFKGLPWEC (SEQ ID NO: 131 of U.S. Pat. No. 9,475,845; herein SEQ ID NO: 1530), SGRSA (SEQ ID NO: 132 of U.S. Pat. No. 9,475,845; herein SEQ ID NO: 1531), WGFP (SEQ ID NO: 133 of U.S. Pat. No. 9,475,845; herein SEQ ID NO: 1532), AEPMPHSLNFSQYLWYT (SEQ ID NO: 134 of U.S. Pat. No. 9,475,845; herein SEQ ID NO: 1533), WAYXSP (SEQ ID NO: 135 of U.S. Pat. No. 9,475,845; herein SEQ ID NO: 1534), IELLQAR (SEQ ID NO: 136 of U.S. Pat. No. 9,475,845; herein SEQ ID NO: 1535), AYTKCSRQWRTCMTTH (SEQ ID NO: 137 of U.S. Pat. No. 9,475,845; herein SEQ ID NO: 1536), PQNSKIPGPTFLDPH (SEQ ID NO: 138 of U.S. Pat. No. 9,475,845; herein SEQ ID NO: 1537), SMEPALPDWWWKMFK (SEQ ID NO: 139 of U.S. Pat. No. 9,475,845; herein SEQ ID NO: 1538), ANTPCGPYTHDCPVKR (SEQ ID NO: 140 of U.S. Pat. No. 9,475,845; herein SEQ ID NO: 1539), TACHQHVRMVRP (SEQ ID NO: 141 of U.S. Pat. No. 9,475,845; herein SEQ ID NO: 1540), VPWMEPAYQRFL (SEQ ID NO: 142 of U.S. Pat. No. 9,475,845; herein SEQ ID NO: 1541), DPRATPGS (SEQ ID NO: 143 of U.S. Pat. No. 9,475,845; herein SEQ ID NO: 1542), FRPNRAQDYNTN (SEQ ID NO: 144 of U.S. Pat. No. 9,475,845; herein SEQ ID NO: 1543), CTKNSYLMC (SEQ ID NO: 145 of U.S. Pat. No. 9,475,845; herein SEQ ID NO: 1544), CXXTXXXGXGC (SEQ ID NO: 146 of U.S. Pat. No. 9,475,845; herein SEQ ID NO: 1545), CPIEDRPMC (SEQ ID NO: 147 of U.S. Pat. No. 9,475,845; herein SEQ ID NO: 1546), HEWSYLAPYPWF (SEQ ID NO: 148 of U.S. Pat. No. 9,475,845; herein SEQ ID NO: 1547), MCPKHPLGC (SEQ ID NO: 149 of U.S. Pat. No. 9,475,845; herein SEQ ID NO: 1548), RMWPSSTVNLSAGRR (SEQ ID NO: 150 of U.S. Pat. No. 9,475,845; herein SEQ ID NO: 1549), SAKTAVSQRVWLPSHRGGEP (SEQ ID NO: 151 of U.S. Pat. No. 9,475,845; herein SEQ ID NO: 1550), KSREHVNNSACPSKRITAAL (SEQ ID NO: 152 of U.S. Pat. No. 9,475,845; herein SEQ ID NO: 1551), EGFR (SEQ ID NO: 153 of U.S. Pat. No. 9,475,845; herein SEQ ID NO: 1552), AGLGVR (SEQ ID NO: 154 of U.S. Pat. No. 9,475,845; herein SEQ ID NO: 1553), GTRQGHTMRLGVSDG (SEQ ID NO: 155 of U.S. Pat. No. 9,475,845; herein SEQ ID NO: 1554), IAGLATPGWSHWLAL (SEQ ID NO: 156 of U.S. Pat. No. 9,475,845; herein SEQ ID NO: 1555), SMSIARL (SEQ ID NO: 157 of U.S. Pat. No. 9,475,845; herein SEQ ID NO: 1556), HTFEPGV (SEQ ID NO: 158 of U.S. Pat. No. 9,475,845; herein SEQ ID NO: 1557), NTSLKRISNKRIRRK (SEQ ID NO: 159 of U.S. Pat. No. 9,475,845; herein SEQ ID NO: 1558), LRIKRKRRKRKKTRK (SEQ ID NO: 160 of U.S. Pat. No. 9,475,845; herein SEQ ID NO: 1559), GGG, GFS, LWS, EGG, LLV, LSP, LBS, AGG, GRR, GGH and GTV.

In certain embodiments, the AAV serotype may be, or may have a sequence as described in United States Publication No. US 20160369298, the contents of which are herein incorporated by reference in their entirety, such as, but not limited to, site-specific mutated capsid protein of AAV2 (SEQ ID NO: 97 of US 20160369298; herein SEQ ID NO: 1560) or variants thereof, wherein the specific site is at least one site selected from sites R447, G453, S578, N587, N587+1, S662 of VP1 or fragment thereof.

Further, any of the mutated sequences described in US 20160369298, may be or may have, but not limited to, any of the following sequences SDSGASN (SEQ ID NO: 1 and SEQ ID NO: 231 of US20160369298; herein SEQ ID NO: 1561), SPSGASN (SEQ ID NO: 2 of US20160369298; herein SEQ ID NO: 1562), SHSGASN (SEQ ID NO: 3 of US20160369298; herein SEQ ID NO: 1563), SRSGASN (SEQ ID NO: 4 of US20160369298; herein SEQ ID NO: 1564), SKSGASN (SEQ ID NO: 5 of US20160369298; herein SEQ ID NO: 1565), SNSGASN (SEQ ID NO: 6 of US20160369298; herein SEQ ID NO: 1566), SGSGASN (SEQ ID NO: 7 of US20160369298; herein SEQ ID NO: 1567), SASGASN (SEQ ID NO: 8, 175, and 221 of US20160369298; herein SEQ ID NO: 1568), SESGTSN (SEQ ID NO: 9 of US20160369298; herein SEQ ID NO: 1569), STTGGSN (SEQ ID NO: 10 of US20160369298; herein SEQ ID NO: 1570), SSAGSTN (SEQ ID NO: 11 of US20160369298; herein SEQ ID NO: 1571), NNDSQA (SEQ ID NO: 12 of US20160369298; herein SEQ ID NO: 1572), NNRNQA (SEQ ID NO: 13 of US20160369298; herein SEQ ID NO: 1573), NNNKQA (SEQ ID NO: 14 of US20160369298; herein SEQ ID NO: 1574), NAKRQA (SEQ ID NO: 15 of US20160369298; herein SEQ ID NO: 1575), NDEHQA (SEQ ID NO: 16 of US20160369298; herein SEQ ID NO: 1576), NTSQKA (SEQ ID NO: 17 of US20160369298; herein SEQ ID NO: 1577), YYLSRTNTPSGTDTQSRLVFSQAGA (SEQ ID NO: 18 of US20160369298; herein SEQ ID NO: 1578), YYLSRTNTDSGTETQSGLDFSQAGA (SEQ ID NO: 19 of US20160369298; herein SEQ ID NO: 1579), YYLSRTNTESGTPTQSALEFSQAGA (SEQ ID NO: 20 of US20160369298; herein SEQ ID NO: 1580), YYLSRTNTHSGTHTQSPLHFSQAGA (SEQ ID NO: 21 of US20160369298; herein SEQ ID NO: 1581), YYLSRTNTSSGTITISHLIFSQAGA (SEQ ID NO: 22 of US20160369298; herein SEQ ID NO: 1582), YYLSRTNTRSGIMTKSSLMFSQAGA (SEQ ID NO: 23 of US20160369298; herein SEQ ID NO: 1583), YYLSRTNTKSGRKTLSNLSFSQAGA (SEQ ID NO: 24 of US20160369298; herein SEQ ID NO: 1584), YYLSRTNDGSGPVTPSKLRFSQRGA (SEQ ID NO: 25 of US20160369298; herein SEQ ID NO: 1585), YYLSRTNAASGHATHSDLKFSQPGA (SEQ ID NO: 26 of US20160369298; herein SEQ ID NO: 1586), YYLSRTNGQAGSLTMSELGFSQVGA (SEQ ID NO: 27 of US20160369298; herein SEQ ID NO: 1587), YYLSRTNSTGGNQTTSQLLFSQLSA (SEQ ID NO: 28 of US20160369298; herein SEQ ID NO: 1588), YFLSRTNNNTGLNTNSTLNFSQGRA (SEQ ID NO: 29 of US20160369298; herein SEQ ID NO: 1589), SKTGADNNNSEYSWTG (SEQ ID NO: 30 of US20160369298; herein SEQ ID NO: 1590), SKTDADNNNSEYSWTG (SEQ ID NO: 31 of US20160369298; herein SEQ ID NO: 1591), SKTEADNNNSEYSWTG (SEQ ID NO: 32 of US20160369298; herein SEQ ID NO: 1592), SKTPADNNNSEYSWTG (SEQ ID NO: 33 of US20160369298; herein SEQ ID NO: 1593), SKTHADNNNSEYSWTG (SEQ ID NO: 34 of US20160369298; herein SEQ ID NO: 1594), SKTQADNNNSEYSWTG (SEQ ID NO: 35 of US20160369298; herein SEQ ID NO: 1595), SKTIADNNNSEYSWTG (SEQ ID NO: 36 of US20160369298; herein SEQ ID NO: 1596), SKTMADNNNSEYSWTG (SEQ ID NO: 37 of US20160369298; herein SEQ ID NO: 1597), SKTRADNNNSEYSWTG (SEQ ID NO: 38 of US20160369298; herein SEQ ID NO: 1598), SKTNADNNNSEYSWTG (SEQ ID NO: 39 of US20160369298; herein SEQ ID NO: 1599), SKTVGRNNNSEYSWTG (SEQ ID NO: 40 of US20160369298; herein SEQ ID NO: 1600), SKTADRNNNSEYSWTG (SEQ ID NO: 41 of US20160369298; herein SEQ ID NO: 1601), SKKLSQNNNSKYSWQG (SEQ ID NO: 42 of US20160369298; herein SEQ ID NO: 1602), SKPTTGNNNSDYSWPG (SEQ ID NO: 43 of US20160369298; herein SEQ ID NO: 1603), STQKNENNNSNYSWPG (SEQ ID NO: 44 of US20160369298; herein SEQ ID NO: 1604), HKDDEGKF (SEQ ID NO: 45 of US20160369298; herein SEQ ID NO: 1605), HKDDNRKF (SEQ ID NO: 46 of US20160369298; herein SEQ ID NO: 1606), HKDDTNKF (SEQ ID NO: 47 of US20160369298; herein SEQ ID NO: 1607), HEDSDKNF (SEQ ID NO: 48 of US20160369298; herein SEQ ID NO: 1608), HRDGADSF (SEQ ID NO: 49 of US20160369298; herein SEQ ID NO: 1609), HGDNKSRF (SEQ ID NO: 50 of US20160369298; herein SEQ ID NO: 1610), KQGSEKTNVDFEEV (SEQ ID NO: 51 of US20160369298; herein SEQ ID NO: 1611), KQGSEKTNVDSEEV (SEQ ID NO: 52 of US20160369298; herein SEQ ID NO: 1612), KQGSEKTNVDVEEV (SEQ ID NO: 53 of US20160369298; herein SEQ ID NO: 1613), KQGSDKTNVDDAGV (SEQ ID NO: 54 of US20160369298; herein SEQ ID NO: 1614), KQGSSKTNVDPREV (SEQ ID NO: 55 of US20160369298; herein SEQ ID NO: 1615), KQGSRKTNVDHKQV (SEQ ID NO: 56 of US20160369298; herein SEQ ID NO: 1616), KQGSKGGNVDTNRV (SEQ ID NO: 57 of US20160369298; herein SEQ ID NO: 1617), KQGSGEANVDNGDV (SEQ ID NO: 58 of US20160369298; herein SEQ ID NO: 1618), KQDAAADNIDYDHV (SEQ ID NO: 59 of US20160369298; herein SEQ ID NO: 1619), KQSGTRSNAAASSV (SEQ ID NO: 60 of US20160369298; herein SEQ ID NO: 1620), KENTNTNDTELTNV (SEQ ID NO: 61 of US20160369298; herein SEQ ID NO: 1621), QRGNNVAATADVNT (SEQ ID NO: 62 of US20160369298; herein SEQ ID NO: 1622), QRGNNEAATADVNT (SEQ ID NO: 63 of US20160369298; herein SEQ ID NO: 1623), QRGNNPAATADVNT (SEQ ID NO: 64 of US20160369298; herein SEQ ID NO: 1624), QRGNNHAATADVNT (SEQ ID NO: 65 of US20160369298; herein SEQ ID NO: 1625), QEENNIAATPGVNT (SEQ ID NO: 66 of US20160369298; herein SEQ ID NO: 1626), QPPNNMAATHEVNT (SEQ ID NO: 67 of US20160369298; herein SEQ ID NO: 1627), QHHNNSAATTIVNT (SEQ ID NO: 68 of US20160369298; herein SEQ ID NO: 1628), QTTNNRAAFNMVET (SEQ ID NO: 69 of US20160369298; herein SEQ ID NO: 1629), QKKNNNAASKKVAT (SEQ ID NO: 70 of US20160369298; herein SEQ ID NO: 1630), QGGNNKAADDAVKT (SEQ ID NO: 71 of US20160369298; herein SEQ ID NO: 1631), QAAKGGAADDAVKT (SEQ ID NO: 72 of US20160369298; herein SEQ ID NO: 1632), QDDRAAAANESVDT (SEQ ID NO: 73 of US20160369298; herein SEQ ID NO: 1633), QQQHDDAAYQRVHT (SEQ ID NO: 74 of US20160369298; herein SEQ ID NO: 1634), QSSSSLAAVSTVQT (SEQ ID NO: 75 of US20160369298; herein SEQ ID NO: 1635), QNNQTTAAIRNVTT (SEQ ID NO: 76 of US20160369298; herein SEQ ID NO: 1636), NYNKKSDNVDFT (SEQ ID NO: 77 of US20160369298; herein SEQ ID NO: 1637), NYNKKSENVDFT (SEQ ID NO: 78 of US20160369298; herein SEQ ID NO: 1638), NYNKKSLNVDFT (SEQ ID NO: 79 of US20160369298; herein SEQ ID NO: 1639), NYNKKSPNVDFT (SEQ ID NO: 80 of US20160369298; herein SEQ ID NO: 1640), NYSKKSHCVDFT (SEQ ID NO: 81 of US20160369298; herein SEQ ID NO: 1641), NYRKTIYVDFT (SEQ ID NO: 82 of US20160369298; herein SEQ ID NO: 1642), NYKEKKDVHFT (SEQ ID NO: 83 of US20160369298; herein SEQ ID NO: 1643), NYGHRAIVQFT (SEQ ID NO: 84 of US20160369298; herein SEQ ID NO: 1644), NYANHQFVVCT (SEQ ID NO: 85 of US20160369298; herein SEQ ID NO: 1645), NYDDDPTGVLLT (SEQ ID NO: 86 of US20160369298; herein SEQ ID NO: 1646), NYDDPTGVLLT (SEQ ID NO: 87 of US20160369298; herein SEQ ID NO: 1647), NFEQQNSVEWT (SEQ ID NO: 88 of US20160369298; herein SEQ ID NO: 1648), SQSGASN (SEQ ID NO: 89 and SEQ ID NO: 241 of US20160369298; herein SEQ ID NO: 1649), NNGSQA (SEQ ID NO: 90 of US20160369298; herein SEQ ID NO: 1650), YYLSRTNTPSGTTTWSRLQFSQAGA (SEQ ID NO: 91 of US20160369298; herein SEQ ID NO: 1651), SKTSADNNNSEYSWTG (SEQ ID NO: 92 of US20160369298; herein SEQ ID NO: 1652), HKDDEEKF (SEQ ID NO: 93, 209, 214, 219, 224, 234, 239, and 244 of US20160369298; herein SEQ ID NO: 1653), KQGSEKTNVDIEEV (SEQ ID NO: 94 of US20160369298; herein SEQ ID NO: 1654), QRGNNQAATADVNT (SEQ ID NO: 95 of US20160369298; herein SEQ ID NO: 1655), NYNKKSVNVDFT (SEQ ID NO: % of US20160369298; herein SEQ ID NO: 1656), SQSGASNYNTPSGTTTQSRLQFSTSADNNNSEYSWTGATKYH (SEQ ID NO: 106 of US20160369298; herein SEQ ID NO: 1657), SASGASNFNSEGGSLTQSSLGFSTDGENNNSDFSWTGATKYH (SEQ ID NO: 107 of US20160369298; herein SEQ ID NO: 1658), SQSGASNYNTPSGTTTQSRLQFSTDGENNNSDFSWTGATKYH (SEQ ID NO: 108 of US20160369298; herein SEQ ID NO: 1659), SASGASNYNTPSGTTTQSRLQFSTSADNNNSEFSWPGATTYH (SEQ ID NO: 109 of US20160369298; herein SEQ ID NO: 1660), SQSGASNFNSEGGSLTQSSLGFSTDGENNNSDFSWTGATKYH (SEQ ID NO: 110 of US20160369298; herein SEQ ID NO: 1661), SASGASNYNTPSGSLTQSSLGFSTDGENNNSDFSWTGATKYH (SEQ ID NO: 111 of US20160369298; herein SEQ ID NO: 1662), SQSGASNYNTPSGTTTQSRLQFSTSADNNNSDFSWTGATKYH (SEQ ID NO: 112 of US20160369298; herein SEQ ID NO: 1663), SGAGASNFNSEGGSLTQSSLGFSTDGENNNSDFSWTGATKYH (SEQ ID NO: 113 of US20160369298; herein SEQ ID NO: 1664), SGAGASN (SEQ ID NO: 176 of US20160369298; herein SEQ ID NO: 1665), NSEGGSLTQSSLGFS (SEQ ID NO: 177, 185, 193 and 202 of US20160369298; herein SEQ ID NO: 1666), TDGENNNSDFS (SEQ ID NO: 178 of US20160369298; herein SEQ ID NO: 1667), SEFSWPGATT (SEQ ID NO: 179 of US20160369298; herein SEQ ID NO: 1668), TSADNNNSDFSWT (SEQ ID NO: 180 of US20160369298; herein SEQ ID NO: 1669), SQSGASNY (SEQ ID NO: 181, 187, and 198 of US20160369298; herein SEQ ID NO: 1670), NTPSGTTTQSRLQFS (SEQ ID NO: 182, 188, 191, and 199 of US20160369298; herein SEQ ID NO: 1671), TSADNNNSEYSWTGATKYH (SEQ ID NO: 183 of US20160369298; herein SEQ ID NO: 1672), SASGASNF (SEQ ID NO: 184 of US20160369298; herein SEQ ID NO: 1673), TDGENNNSDFSWTGATKYH (SEQ ID NO: 186, 189, 194, 197, and 203 of US20160369298; herein SEQ ID NO: 1674), SASGASNY (SEQ ID NO: 190 and SEQ ID NO: 195 of US20160369298; herein SEQ ID NO: 1675), TSADNNNSEFSWPGATTYH (SEQ ID NO: 192 of US20160369298; herein SEQ ID NO: 1676), NTPSGSLTQSSLGFS (SEQ ID NO: 196 of US20160369298; herein SEQ ID NO: 1677), TSADNNNSDFSWTGATKYH (SEQ ID NO: 200 of US20160369298; herein SEQ ID NO: 1678), SGAGASNF (SEQ ID NO: 201 of US20160369298; herein SEQ ID NO: 1679), CTCCAGVVSVVSMRSRVCVNSGCAGCTDHCVVSRNSGTCVMSACACAA (SEQ ID NO: 204 of US20160369298; herein SEQ ID NO: 1680), CTCCAGAGAGGCAACAGACAAGCAGCTACCGCAGATGTCAACACACAA (SEQ ID NO: 205 of US20160369298; herein SEQ ID NO: 1681), SAAGASN (SEQ ID NO: 206 of US20160369298; herein SEQ ID NO: 1682), YFLSRTNTESGSTTQSTLRFSQAG (SEQ ID NO: 207 of US20160369298; herein SEQ ID NO: 1683), SKTSADNNNSDFS (SEQ ID NO: 208, 228, and 253 of US20160369298; herein SEQ ID NO: 1684), KQGSEKTDVDIDKV (SEQ ID NO: 210 of US20160369298; herein SEQ ID NO: 1685), STAGASN (SEQ ID NO: 211 of US20160369298; herein SEQ ID NO: 1686), YFLSRTNTTSGIETQSTLRFSQAG (SEQ ID NO: 212 and SEQ ID NO: 247 of US20160369298; herein SEQ ID NO: 1687), SKTDGENNNSDFS (SEQ ID NO: 213 and SEQ ID NO: 248 of US20160369298; herein SEQ ID NO: 1688), KQGAAADDVEIDGV (SEQ ID NO: 215 and SEQ ID NO: 250 of US20160369298; herein SEQ ID NO: 1689), SEAGASN (SEQ ID NO: 216 of US20160369298; herein SEQ ID NO: 1690), YYLSRTNTPSGTTTQSRLQFSQAG (SEQ ID NO: 217, 232 and 242 of US20160369298; herein SEQ ID NO: 1691), SKTSADNNNSEYS (SEQ ID NO: 218, 233, 238, and 243 of US20160369298; herein SEQ ID NO: 1692), KQGSEKTNVDIEKV (SEQ ID NO: 220, 225 and 245 of US20160369298; herein SEQ ID NO: 1693), YFLSRTNDASGSDTKSTLLFSQAG (SEQ ID NO: 222 of US20160369298; herein SEQ ID NO: 1694), STTPSENNN-SEYS (SEQ ID NO: 223 of US20160369298; herein SEQ ID NO: 1695), SAAGATN (SEQ ID NO: 226 and SEQ ID NO: 251 of US20160369298; herein SEQ ID NO: 16%), YFLSRTNGEAGSATLSELRFSQAG (SEQ ID NO: 227 of US20160369298; herein SEQ ID NO: 1697), HGDDADRF (SEQ ID NO: 229 and SEQ ID NO: 254 of US20160369298; herein SEQ ID NO: 1698), KQGAEKSDVEVDRV (SEQ ID NO: 230 and SEQ ID NO: 255 of US20160369298; herein SEQ ID NO: 1699), KQDSGGDNIDIDQV (SEQ ID NO: 235 of US20160369298; herein SEQ ID NO: 1700), SDA-GASN (SEQ ID NO: 236 of US20160369298; herein SEQ ID NO: 1701), YFLSRTNTEGGHDTQSTLRFSQAG (SEQ ID NO: 237 of US20160369298; herein SEQ ID NO: 1702), KEDGGGSDVAIDEV (SEQ ID NO: 240 of US20160369298; herein SEQ ID NO: 1703), SNAGASN (SEQ ID NO: 246 of US20160369298: herein SEQ ID NO: 1704), and YFLSRTNGEAGSATLSELRFSQPG (SEQ ID NO: 252 of US20160369298; herein SEQ ID NO: 1705). Non-limiting examples of nucleotide sequences that may encode the amino acid mutated sites include the following, AGCVVMDCAGGARSCASCAAC (SEQ ID NO: 97 of US20160369298; herein SEQ ID NO: 1706), AACRACRRSMRSMAGGCA (SEQ ID NO: 98 of US20160369298; herein SEQ ID NO: 1707), CACRRGGACRRCRMSRRSARSTIT (SEQ ID NO: 99 of US20160369298; herein SEQ ID NO: 1708), TATTTCTT-GAGCAGAACAAACRVCVVSRSCGGAMNCVH-SACGMHSTCAVVSCTTVDS TTTTCTCAGSBCRGSGCG (SEQ ID NO: 100 of US20160369298; herein SEQ ID NO: 1709), TCAAMAM-MAVNSRVCSR-SAACAACAACAGTRASTTCTCGTGGMMAGGA (SEQ ID NO: 101 of US20160369298; herein SEQ ID NO: 1710), AAGSAARRCRSCRVSRVARVCRA-TRYCGMSNHCRVMVRSGTC (SEQ ID NO: 102 of US20160369298; herein SEQ ID NO: 1711), CAGVVSVVSMRSRVCVNSGCAGCTDHCVVSRN-SGTCVMSACA (SEQ ID NO: 103 of US20160369298; herein SEQ ID NO: 1712), AACTWCRVSVASMVSVHSDDTGTGSWSTKSACT (SEQ ID NO: 104 of US20160369298; herein SEQ ID NO: 1713), TTGTTGAACATCACCACGTGACGCACGTTC (SEQ ID NO: 256 of US20160369298; herein SEQ ID NO: 1714), TCCCCGTGGTTCTACTACATAATGTGGCCG (SEQ ID NO: 257 of US20160369298; herein SEQ ID NO: 1715), TTCCACACTCCGTTTTGGATAATGTTGAAC (SEQ ID NO: 258 of US20160369298; herein SEQ ID NO: 1716), AGGGACATCCCCAGCTCCATGCTGTGGTCG (SEQ ID NO: 259 of US20160369298; herein SEQ ID NO: 1717), AGGGACAACCCCTCCGACTCGCCCTAATCC (SEQ ID NO: 260 of US20160369298; herein SEQ ID NO: 1718), TCCTAGTAGAAGACACCCTCTCACTGCCCG (SEQ ID NO: 261 of US20160369298; herein SEQ ID NO: 1719), AGTACCATGTACACCCACTCTCCCAGTGCC (SEQ ID NO: 262 of US20160369298; herein SEQ ID NO: 1720), ATATGGACGTFCATGCTGATCACCATACCG (SEQ ID NO: 263 of US20160369298; herein SEQ ID NO: 1721), AGCAGGAGCTCCTTGGCCTCAGCGTGCGAG (SEQ ID NO: 264 of US20160369298; herein SEQ ID NO: 1722), ACAAGCAGCTTCACTATGACAACCACTGAC (SEQ ID NO: 265 of US20160369298; herein SEQ ID NO: 1723), CAGCCTAGGAACTGGCTTCCTGGACCCTGT-TACCGCCAGCAGAGAGTCTCAAMAMM AVN-SRVCSRSAACAACAACAGTRASTTCTCCTGGM-MAGGAGCTACCAAGTACCACC TCAATGGCAGAGACTCTCTGGT-GAATCCCGGACCAGCTATGGCAAGCCACRRGGAC RRCRMSRRSARSTTTTTTCCTCAGAGCGGGGTTCT-CATCTTTGGGAAGSAARRCRSCR VSRVARVCRA-TRYCGMSNHCRVMVRSGTCATGATTACA-GACGAAGAGGAGATCTGG AC (SEQ ID NO: 266 of US20160369298; herein SEQ ID NO: 1724), TGGGACAATGGCGGTCGTCTCTCAGAGTTKTKKT (SEQ ID NO: 267 of US20160369298; herein SEQ ID NO: 1725), AGAGGACCKKTCCTCGATGGTTCATGGTG-GAGTTA (SEQ ID NO: 268 of US20160369298; herein SEQ ID NO: 1726), CCACTTAGGGCCTGGTCGA-TACCGTTCGGTG (SEQ ID NO: 269 of US20160369298; herein SEQ ID NO: 1727), and TCTCGCCC-CAAGAGTAGAAACCCTTCSTTYYG (SEQ ID NO: 270 of US20160369298; herein SEQ ID NO: 1728).

In some embodiments, the AAV serotype may comprise an ocular cell targeting peptide as described in International Patent Publication WO2016134375, the contents of which are herein incorporated by reference in their entirety, such as, but not limited to SEQ ID NO: 9, and SEQ ID NO:10 of WO2016134375. Further, any of the ocular cell targeting peptides or amino acids described in WO2016134375, may be inserted into any parent AAV serotype, such as, but not limited to, AAV2 (SEQ ID NO:8 of WO2016134375; herein SEQ ID NO: 1729), or AAV9 (SEQ ID NO: 11 of WO2016134375; herein SEQ ID NO: 1730). In some embodiments, modifications, such as insertions are made in AAV2 proteins at P34-A35, T138-A139, A139-P140, G453-T454, N587-R588, and/or R588-Q589. In certain embodiments, insertions are made at D384, G385, I560, T561, N562, E563, E564, E565, N704, and/or Y705 of AAV9. The ocular cell targeting peptide may be, but is not limited to, any of the following amino acid sequences, GSTPPPM (SEQ ID NO: 1 of WO2016134375; herein SEQ ID NO: 1731), or GETRAPL (SEQ ID NO: 4 of WO2016134375; herein SEQ ID NO: 1732).

In some embodiments, the AAV serotype may be modified as described in the United States Publication US 20170145405 the contents of which are herein incorporated by reference in their entirety. AAV serotypes may include, modified AAV2 (e.g., modifications at Y444F, Y500F, Y730F and/or S662V), modified AAV3 (e.g., modifications at Y705F, Y73 IF and/or T492V), and modified AAV6 (e.g., modifications at S663V and/or T492V).

In some embodiments, the AAV serotype may be modified as described in the International Publication WO2017083722 the contents of which are herein incorporated by reference in their entirety. AAV serotypes may include. AAV1 (Y705+731F+T492V), AAV2 (Y444+500+730F+T491V), AAV3 (Y705+731F), AAV5, AAV 5 (Y436+693+719F), AAV6 (VP3 variant Y705F/Y731F/T492V), AAV8 (Y733F), AAV9, AAV9 (VP3 variant Y731F), and AAV10 (Y733F).

In some embodiments, the AAV serotype may comprise, as described in International Patent Publication WO2017015102, the contents of which are herein incorporated by reference in their entirety, an engineered epitope comprising the amino acids SPAKFA (SEQ ID NO: 24 of WO2017015102; herein SEQ ID NO: 1733) or NKDKLN (SEQ ID NO:2 of WO2017015102; herein SEQ ID NO: 1734). The epitope may be inserted in the region of amino acids 665 to 670 based on the numbering of the VP1 capsid of AAV8 (SEQ ID NO:3 of WO2017015102) and/or residues 664 to 668 of AAV3B (SEQ ID NO:3).

In certain embodiments, the AAV serotype may be, or may have a sequence as described in International Patent Publication WO2017058892, the contents of which are herein incorporated by reference in their entirety, such as, but not limited to, AAV variants with capsid proteins that may comprise a substitution at one or more (e.g., 2, 3, 4, 5, 6, or 7) of amino acid residues 262-268, 370-379, 451-459, 472-473, 493-500, 528-534, 547-552, 588-597, 709-710, 716-722 of AAV1, in any combination, or the equivalent amino acid residues in AAV2, AAV3, AAV4, AAV5, AAV6, AAV7, AAV8, AAV9, AAV10, AAV11, AAV12, AAVrh8, AAVrh10, AAVrh32.33, bovine AAV or avian AAV. The amino acid substitution may be, but is not limited to, any of the amino acid sequences described in WO2017058892. In certain embodiments, the AAV may comprise an amino acid substitution at residues 256L, 258K, 259Q, 261S, 263A, 264S, 265T, 266G, 272H, 385S, 386Q, S472R, V473D, N500E 547S, 709A, 710N, 716D, 717N, 718N, 720L, A456T, Q457T, N458Q, K459S, T492S, K493A, S586R, S587G, S588N, T589R and/or 722T of AAV1 (SEQ ID NO: 1 of WO2017058892) in any combination, 244N, 246Q, 248R, 249E, 250I, 251K, 252S, 253G, 254S, 255V, 256D, 263Y, 377E, 378N, 453L, 456R, 532Q, 533P, 535N, 536P, 537G, 538T, 539T, 540A, 541T, 542Y, 543L, 546N, 653V, 654P, 656S, 697Q, 698F, 704D, 705S, 706T, 707G, 708E, 709Y and/or 710R of AAV5 (SEQ ID NO:5 of WO2017058892) in any combination, 248R, 316V, 317Q, 318D, 319S, 443N, 530N, 531S, 532Q, 533P, 534A, 535N, 540A, 541 T, 542Y, 543L, 545G, 546N, 697Q, 704D, 706T, 708E, 709Y and/or 710R of AAV5 (SEQ ID NO: 5 of WO2017058892) in any combination, 264S, 266G, 269N, 272H, 457Q, 588S and/or 589I of AAV6 (SEQ ID NO:6 WO2017058892) in any combination, 457T, 459N, 496G, 499N, 500N, 589Q, 590N and/or 592A of AAV8 (SEQ ID NO: 8 WO2017058892) in any combination, 451I, 452N, 453G, 454S, 455G, 456Q, 457N and/or 458Q of AAV9 (SEQ ID NO: 9 WO2017058892) in any combination.

In some embodiments, the AAV may include a sequence of amino acids at positions 155, 156 and 157 of VP1 or at positions 17, 18, 19 and 20 of VP2, as described in International Publication No. WO 2017066764, the contents of which are herein incorporated by reference in their entirety. The sequences of amino acid may be, but not limited to, N-S-S, S-X-S, S-S-Y, N-X-S, N-S-Y, S-X-Y and N-X-Y, where N, X and Y are, but not limited to, independently non-serine, or non-threonine amino acids, wherein the AAV may be, but not limited to AAV1, AAV2, AAV3, AAV4, AAV5, AAV6, AAV7, AAV8, AAV9, AAV10, AAV11 and AAV12. In some embodiments, the AAV may include a deletion of at least one amino acid at positions 156, 157 or 158 of VP1 or at positions 19, 20 or 21 of VP2, wherein the AAV may be, but not limited to AAV1, AAV2, AAV3, AAV4, AAV5, AAV6, AAV7, AAV8, AAV9, AAV10, AAV11 and AAV12.

In certain embodiments, the AAV serotype may be as described in Jackson et al (Frontiers in Molecular Neuroscience 9:154 (2016)), the contents of which are herein incorporated by reference in their entirety. In some embodiments, the AAV serotype is PHP.B or AAV9. In some embodiments, the AAV serotype is paired with a synapsin promoter to enhance neuronal transduction, as compared to when more ubiquitous promoters are used (i.e., CBA or CMV).

In certain embodiments, the AAV may be a serotype generated by Cre-recombination-based AAV targeted evolution (CREATE) as described by Deverman et al., (Nature Biotechnology 34(2):204-209 (2016)), Chan et al., (Nature Neuroscience 20(8):1172-1179 (2017)), and in International Patent Application Publication Nos. WO2015038958 and WO2017100671, the contents of each of which are herein incorporated by reference in their entirety. In certain embodiments, AAV serotypes generated in this manner have improved CNS transduction and/or neuronal and astrocytic tropism, as compared to other AAV serotypes. As non-limiting examples, the AAV serotype may include a targeting peptide such as, but not limited to, PHP.B, PHP.B2, PHP.B3, PHP.A, PHP.S, PHP.N, G2A12, G2A15, G2A3, G2B4, and G2B5.

In certain embodiments, the AAV serotype may be as described in Jackson et al (Frontiers in Molecular Neuroscience 9:154 (2016)), the contents of which are herein incorporated by reference in their entirety.

In some embodiments, the AAV serotype is PHP.B. In some embodiments, the AAV serotype is paired with a synapsin promoter to enhance neuronal transduction, as compared to when more ubiquitous promoters are used (i.e., CBA or CMV).

In some embodiments, the AAV serotype is PHP.N. In certain embodiments, the AAV serotype is a serotype comprising the AAVPHP.N (PHP.N) peptide, or a variant thereof. In certain embodiments the AAV serotypes is a serotype comprising the AAVPHP.B (PHP.B) peptide, or a variant thereof. In certain embodiments, the AAV serotype is a serotype comprising the AAVPHP.A (PHP.A) peptide, or a variant thereof. In certain embodiments, the AAV serotype is a serotype comprising the PHP.S peptide, or a variant thereof. In certain embodiments, the AAV serotype is a serotype comprising the PHP.B2 peptide, or a variant thereof. In certain embodiments, the AAV serotype is a serotype comprising the PHP.B3 peptide, or a variant thereof. In certain embodiments, the AAV serotype is a serotype comprising the G2B4 peptide, or a variant thereof. In certain embodiments, the AAV serotype is a serotype comprising the G2B5 peptide, or a variant thereof. In certain embodiments the AAV capsid is one that allows for blood brain barrier penetration following intravenous administration.

In certain embodiments, the AAV serotype may comprise a capsid amino acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above.

In certain embodiments, the AAV serotype may comprise a capsid nucleic acid sequence with 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of the those described above.

In certain embodiments, the initiation codon for translation of the AAV VP1 capsid protein may be CTG, TTG, or GTG as described in U.S. Pat. No. 8,163,543, the contents of which are herein incorporated by reference in its entirety.

The present disclosure refers to structural capsid proteins (including VP1, VP2 and VP3) which are encoded by capsid (Cap) genes. These capsid proteins form an outer protein structural shell (i.e. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two or three) VP capsid proteins comprising the viral capsid may be produced, some of which may include a Met1/AA1 amino acid (Met+/AA+) and some of which may lack a Met1/AA1 amino acid as a result of Met/AA-clipping (Met–/AA–). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. *Hum Gene Ther Methods.* 2017 Oct. 28(5):255-267; Hwang, et al. N-Terminal Acetylation of Cellular Proteins Creates Specific Degradation Signals. *Science.* 2010 Feb. 19, 327(5968): 973-977; the contents of which are each incorporated herein by reference in its entirety.

According to the present invention, references to capsid proteins is not limited to either clipped (Met–/AA–) or unclipped (Met+/AA+) and may, in context, refer to independent capsid proteins, viral capsids comprised of a mixture of capsid proteins, and/or polynucleotide sequences (or fragments thereof) which encode, describe, produce or result in capsid proteins of the present disclosure. A direct reference to a "capsid protein" or "capsid polypeptide" (such as VP1, VP2 or VP2) may also comprise VP capsid proteins which include a Met1/AA1 amino acid (Met+/AA+) as well as corresponding VP capsid proteins which lack the Met1/AA1 amino acid as a result of Met/AA-clipping (Met–/AA–).

Further according to the present disclosure, a reference to a specific SEQ ID NO: (whether a protein or nucleic acid) which comprises or encodes, respectively, one or more capsid proteins which include a Met1/AA1 amino acid (Met+/AA+) should be understood to teach the VP capsid proteins which lack the Met1/AA1 amino acid as upon review of the sequence, it is readily apparent any sequence which merely lacks the first listed amino acid (whether or not Met1/AA1).

In certain embodiments, reference to a VP1 polypeptide sequence which is 736 amino acids in length and which includes a "Met1" amino acid (Met+) encoded by the AUG/ATG start codon may also be understood to teach a VP1 polypeptide sequence which is 735 amino acids in length and which does not include the "Met1" amino acid (Met–) of the 736 amino acid Met+ sequence. As a second non-limiting example, reference to a VP1 polypeptide sequence which is 736 amino acids in length and which includes an "AA1" amino acid (AA1+) encoded by any NNN initiator codon may also be understood to teach a VP1 polypeptide sequence which is 735 amino acids in length and which does not include the "AA1" amino acid (AA1–) of the 736 amino acid AA1+ sequence.

References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met–/AA1–), and combinations thereof (Met+/AA1+ and Met–/AA1–).

In certain embodiments, an AAV capsid serotype can include VP1 (Met+/AA1+), VP1 (Met–/AA1–), or a combination of VP1 (Met+/AA1+) and VP1 (Met–/AA1–). An AAV capsid serotype can also include VP3 (Met+/AA1+), VP3 (Met–/AA1–), or a combination of VP3 (Met+/AA1+) and VP3 (Met–/AA1–); and can also include similar optional combinations of VP2 (Met+/AA1) and VP2 (Met–/AA1–).

Viral Genome Component: Inverted Terminal Repeats (ITRs)

The AAV particles of the present disclosure comprise a viral genome with at least one ITR region and a payload region. In certain embodiments, the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the disclosure may be comprised of naturally occurring polynucleotide sequences or recombinantly derived polynucleotide sequences.

The ITRs may be derived from the same serotype as the capsid, selected from any of the serotypes listed in Table 1, or a derivative thereof. The ITR may be of a different serotype than the capsid. In certain embodiments, the AAV particle has more than one ITR. In a non-limiting example, the AAV particle has a viral genome comprising two ITRs. In certain embodiments, the ITRs are of the same serotype as one another. In another embodiment, the ITRs are of different serotypes. Non-limiting examples include zero, one or both of the ITRs having the same serotype as the capsid. In certain embodiments both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In certain embodiments, the ITRs are 140-142 nucleotides in length. Non-limiting examples of ITR length are 102, 130, 140, 141, 142, 145 nucleotides in length, and those having at least 95% identity thereto.

Viral Genome Component: Promoters

In certain embodiments, the payload region of the viral genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides of the disclosure in a target cell may require a specific promoter, including but not limited to, a promoter that is species specific, inducible, tissue-specific, or cell cycle-specific (Parr et al., *Nat. Med* 3:1145-9 (1997); the contents of which are herein incorporated by reference in their entirety).

In certain embodiments, the promoter is deemed to be efficient when it drives expression of the polypeptide(s) encoded in the payload region of the viral genome of the AAV particle. In certain embodiments, that polypeptide is AADC.

In certain embodiments, the promoter is a promoter deemed to be efficient when it drives expression in the cell being targeted.

In certain embodiments, the promoter is a promoter having a tropism for the cell being targeted.

In certain embodiments, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. In certain embodiments, the promoter is a weak promoter for sustained expression of a payload in nervous tissues.

In certain embodiments, the promoter drives expression of the polypeptides of the disclosure for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US 20110212529, the contents of which are herein incorporated by reference in their entirety)

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene np2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In certain embodiments, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In certain embodiments, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In certain embodiments, the promoter is a combination of a 382 nucleotide CMV-enhancer sequence and a 260 nucleotide CBA-promoter sequence.

In certain embodiments, the viral genome comprises a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EF1α, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EFIα promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in its entirety) evaluated an HsH construct with a hGUSB promoter, a HSV-1LAT promoter and an NSE promoter and found that the HsH construct showed weaker expression than NSE in mouse brain. Passini and Wolfe (J. Virol. 2001, 12382-12392, the contents of which are herein incorporated by reference in its entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920-nucleotide promoter which are both absent in the liver but NFH is abundant in the sensory proprioceptive neurons, brain, and spinal cord and NFH is present in the heart. SCN8A is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. *Identification of evolutionary conserved, functional noncoding elements n the promoter region of the sodium channel gene SCN8A*, Mamm Genome (2007) 18:723-731; and Raymond et al. *Expression of Alternatively Spliced Sodium Channel α-subunit genes*, Journal of Biological Chemistry (2004) 279(44) 46234-46241; the contents of each of which are herein incorporated by reference in their entireties).

Any of promoters taught by the aforementioned Yu, Soderblom, Gill, Husain, Passini, Xu, Drews or Raymond may be used in the present disclosures.

In certain embodiments, the promoter is not cell specific.

In certain embodiments, the promoter is an ubiquitin c (UBC) promoter. The UBC promoter may have a size of 300-350 nucleotides. In certain embodiments, the UBC promoter is 332 nucleotides.

In certain embodiments, the promoter is a β-glucuronidase (GUSB) promoter. The GUSB promoter may have a size of 350-400 nucleotides. In certain embodiments, the GUSB promoter is 378 nucleotides.

In certain embodiments, the promoter is a neurofilament light (NFL) promoter. The NFL promoter may have a size of 600-700 nucleotides. In certain embodiments, the NFL promoter is 650 nucleotides.

In certain embodiments, the promoter is a neurofilament heavy (NFH) promoter. The NFH promoter may have a size of 900-950 nucleotides. In certain embodiments, the NFH promoter is 920 nucleotides.

In certain embodiments, the promoter is a SCN8A promoter. The SCN8A promoter may have a size of 450-500 nucleotides. In certain embodiments, the SCN8A promoter is 470 nucleotides.

In certain embodiments, the promoter is a frataxin (FXN) promoter. The FXN promoter may also be referred to as the FRDA promoter.

In certain embodiments, the promoter is a phosphoglycerate kinase 1 (PGK) promoter.

In certain embodiments, the promoter is a chicken β-actin (CBA) promoter.

In certain embodiments, the promoter is a cytomegalovirus (CMV) promoter.

In certain embodiments, the promoter is a H1 promoter.

In certain embodiments, the promoter is an engineered promoter.

In certain embodiments, the promoter is a liver or a skeletal muscle promoter. Non-limiting examples of liver promoters include human α-1-antitrypsin (hAAT) and thyroxine binding globulin (TBG). Non-limiting examples of skeletal muscle promoters include Desmin, MCK or synthetic C5-12.

In certain embodiments, the promoter is a RNA pol III promoter. In certain embodiments, the RNA pol III promoter is U6. In certain embodiments, the RNA pol III promoter is H1.

In certain embodiments, the viral genome comprises two promoters. In certain embodiments, the promoters are an EF1α promoter and a CMV promoter.

In certain embodiments, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, McCP2, and GFAP promoter and the 5'UTR/intron may be, but is not limited to, SV40, and CBA-MVM. In certain embodiments, the enhancer, promoter and/or intron used in combination may be: (1) CMV enhancer, CMV promoter, SV40 5'UTR intron: (2) CMV enhancer, CBA promoter, SV 40 5'UTR intron; (3) CMV enhancer, CBA promoter, CBA-MVM 5'UTR intron: (4) UBC promoter; (5) GUSB promoter; (6) NSE promoter: (7) Synapsin promoter: (8) MeCP2 promoter and (9) GFAP promoter.

In certain embodiments, the viral genome comprises an engineered promoter.

In another embodiment, the viral genome comprises a promoter from a naturally expressed protein.

In certain embodiments, a region located approximately ~5 kb upstream of the first exon of the payload in order to allow for expression of the payload with the promoter. (See e.g., Puspasan et al. *Long Range Regulation of Human FXNGene Expression*, PLOS ONE, 2011: the contents of which is herein incorporated by reference in its entirety; a 17 bp region located approximately 4.9 kb upstream of the first exon of the frataxin gene in order to allow for expression with the FRDA promoter).

In certain embodiments, the vector genome may comprise a promoter such as, but not limited to, CMV or U6. In certain embodiments, the promoter for the AAV particles comprising the payload of the present disclosure is a CMV promoter. In certain embodiments, the promoter for the AAV particles comprising the payload of the present disclosure is a U6 promoter.

In certain embodiments, the vector genome may comprise a CMV and a U6 promoter.

In certain embodiments, the vector genome may comprise a CBA promoter.

Viral Genome Component: Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. In certain embodiments, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles of the disclosure to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In certain embodiments, the 5'UTR in the viral genome includes a Kozak sequence.

In certain embodiments, the 5'UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In certain embodiments, the 3' UTR of the viral genome may include an oligo(dT) sequence for templated addition of a poly-A tail.

In certain embodiments, the viral genome may include at least one miRNA seed, binding site or full sequence. microRNAs (or miRNA or miR) are 19-25 nucleotide non-coding RNAs that bind to the sites of nucleic acid targets and down-regulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In certain embodiments, the viral genome may be engineered to include, alter or remove at least one miRNA binding site, sequence or seed region.

Any UTR from any gene known in the art may be incorporated into the viral genome of the AAV particle. These UTRs, or portions thereof, may be placed in the same orientation as in the gene from which they were selected or they may be altered in orientation or location. In certain embodiments, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In certain embodiments, the viral genome of the AAV particle comprises at least one artificial UTRs which is not a variant of a wild type UTR.

In certain embodiments, the viral genome of the AAV particle comprises UTRs which have been selected from a family of transcripts whose proteins share a common function, structure, feature or property.

Viral Genome Component: Polyadenylation Sequence

In certain embodiments, the viral genome of the AAV particles of the present disclosure comprise at least one polyadenylation sequence. The viral genome of the AAV particle may comprise a polyadenylation sequence between the 3' end of the payload coding sequence and the 5' end of the 3'ITR.

In certain embodiments, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407,408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In certain embodiments, the polyadenylation sequence is 50-100 nucleotides in length.

In certain embodiments, the polyadenylation sequence is 50-150 nucleotides in length.

In certain embodiments, the polyadenylation sequence is 50-160 nucleotides in length.

In certain embodiments, the polyadenylation sequence is 50-200 nucleotides in length.

In certain embodiments, the polyadenylation sequence is 60-100 nucleotides in length.

In certain embodiments, the polyadenylation sequence is 60-150 nucleotides in length.

In certain embodiments, the polyadenylation sequence is 60-160 nucleotides in length.

In certain embodiments, the polyadenylation sequence is 60-200 nucleotides in length.

In certain embodiments, the polyadenylation sequence is 70-100 nucleotides in length.

In certain embodiments, the polyadenylation sequence is 70-150 nucleotides in length.

In certain embodiments, the polyadenylation sequence is 70-160 nucleotides in length.

In certain embodiments, the polyadenylation sequence is 70-200 nucleotides in length.

In certain embodiments, the polyadenylation sequence is 80-100 nucleotides in length.

In certain embodiments, the polyadenylation sequence is 80-150 nucleotides in length.

In certain embodiments, the polyadenylation sequence is 80-160 nucleotides in length.

In certain embodiments, the polyadenylation sequence is 80-200 nucleotides in length.

In certain embodiments, the polyadenylation sequence is 90-100 nucleotides in length.

In certain embodiments, the polyadenylation sequence is 90-150 nucleotides in length.

In certain embodiments, the polyadenylation sequence is 90-160 nucleotides in length.

In certain embodiments, the polyadenylation sequence is 90-200 nucleotides in length.

Viral Genome Component: Introns

In certain embodiments, the payload region comprises at least one element to enhance the expression such as one or more introns or portions thereof. Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In certain embodiments, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300400, 300-500, or 400-500.

In certain embodiments, the vector genome comprises at least one element to enhance the transgene target specificity and expression (See e.g., Powell et al. *Viral Expression Cassette Elements to Enhance Transgene Target Specificity and Expression in Gene Therapy*, 2015: the contents of which are herein incorporated by reference in its entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In certain embodiments, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80450, 80-500, 200-300, 200-400, 200-500, 300-400, 300-500, or 400-500.

Viral Genome Component: Filler Sequence

In certain embodiments, the viral genome comprises one or more filler sequences.

In certain embodiments, the viral genome comprises one or more filler sequences in order to have the length of the viral genome be the optimal size for packaging. In certain embodiments, the viral genome comprises at least one filler sequence in order to have the length of the viral genome be about 2.3 kb. In certain embodiments, the viral genome comprises at least one filler sequence in order to have the length of the viral genome be about 4.6 kb.

In certain embodiments, the viral genome is a single stranded (ss) viral genome and comprises one or more filler sequences which have a length about between 0.1 kb-3.8 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, or 3.8 kb. In certain embodiments, the total length filler sequence in the vector genome is 3.1 kb. In certain embodiments, the total length filler sequence in the vector genome is 2.7 kb. In certain embodiments, the total length filler sequence in the vector genome is 0.8 kb. In certain embodiments, the total length filler sequence in the vector genome is 0.4 kb. In certain embodiments, the length of each filler sequence in the vector genome is 0.8 kb. In certain embodiments, the length of each filler sequence in the vector genome is 0.4 kb.

In certain embodiments, the viral genome is a self-complementary (sc) viral genome and comprises one or more filler sequences which have a length about between 0.1 kb-1.5 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, or 1.5 kb. In certain embodiments, the total length filler sequence in the vector genome is 0.8 kb. In certain embodiments, the total length filler sequence in the vector genome is 0.4 kb. In certain embodiments, the length of each filler sequence in the vector genome is 0.8 kb. In certain embodiments, the length of each filler sequence in the vector genome is 0.4 kb In certain embodiments, the viral genome comprises any portion of a filler sequence. The viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of a filler sequence.

In certain embodiments, the viral genome is a single stranded (ss) viral genome and comprises one or more filler sequences in order to have the length of the viral genome be about 4.6 kb. In certain embodiments, the viral genome comprises at least one filler sequence and the filler sequence is located 3' to the 5' ITR sequence. In certain embodiments, the viral genome comprises at least one filler sequence and the filler sequence is located 5' to a promoter sequence. In certain embodiments, the viral genome comprises at least one filler sequence and the filler sequence is located 3' to the polyadenylation signal sequence. In certain embodiments, the viral genome comprises at least one filler sequence and the filler sequence is located 5' to the 3' ITR sequence. In certain embodiments, the viral genome comprises at least one filler sequence, and the filler sequence is located between two intron sequences. In certain embodiments, the viral genome comprises at least one filler sequence, and the filler sequence is located within an intron sequence. In certain embodiments, the viral genome comprises two filler sequences, and the first filler sequence is located 3' to the 5' ITR sequence and the second filler sequence is located 3' to the polyadenylation signal sequence. In certain embodiments, the viral genome comprises two filler sequences, and the first filler sequence is located 5' to a promoter sequence and the second filler sequence is located 3' to the polyadenylation signal sequence. In certain embodiments, the viral genome comprises two filler sequences, and the first filler sequence is located 3' to the 5' ITR sequence and the second filler sequence is located 5' to the 5' ITR sequence.

In certain embodiments, the viral genome is a self-complementary (sc) viral genome and comprises one or more filler sequences in order to have the length of the viral genome be about 2.3 kb. In certain embodiments, the viral genome comprises at least one filler sequence and the filler sequence is located 3' to the 5' ITR sequence. In certain embodiments, the viral genome comprises at least one filler sequence and the filler sequence is located 5' to a promoter sequence. In certain embodiments, the viral genome comprises at least one filler sequence and the filler sequence is located 3' to the polyadenylation signal sequence. In certain embodiments, the viral genome comprises at least one filler sequence and the filler sequence is located 5' to the 3' ITR sequence. In certain embodiments, the viral genome comprises at least one filler sequence, and the filler sequence is located between two intron sequences. In certain embodiments, the viral genome comprises at least one filler sequence, and the filler sequence is located within an intron sequence. In certain embodiments, the viral genome comprises two filler sequences, and the first filler sequence is located 3' to the 5' ITR sequence and the second filler sequence is located 3' to the polyadenylation signal sequence. In certain embodiments, the viral genome comprises two filler sequences, and the first filler sequence is located 5' to a promoter sequence and the second filler sequence is located 3' to the polyadenylation signal sequence. In certain embodiments, the viral genome comprises two filler sequences, and the first filler sequence is located 3' to the 5' ITR sequence and the second filler sequence is located 5' to the 5' ITR sequence.

In certain embodiments, the viral genome may comprise one or more filler sequences between one of more regions of the viral genome. In certain embodiments, the filler region may be located before a region such as, but not limited to, a payload region, an inverted terminal repeat (ITR), a promoter region, an intron region, an enhancer region, a polyadenylation signal sequence region, a multiple cloning site (MCS) region, and/or an exon region. In certain embodiments, the filler region may be located after a region such as, but not limited to, a payload region, an inverted terminal repeat (ITR), a promoter region, an intron region, an enhancer region, a polyadenylation signal sequence region, a multiple cloning site (MCS) region, and/or an exon region. In certain embodiments, the filler region may be located before and after a region such as, but not limited to, a payload region, an inverted terminal repeat (ITR), a promoter region, an intron region, an enhancer region, a polyadenylation signal sequence region, a multiple cloning site (MCS) region, and/or an exon region.

In certain embodiments, the viral genome may comprise one or more filler sequences which bifurcates at least one region of the viral genome. The bifurcated region of the viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of the of the region to the 5' of the filler sequence region. In certain embodiments, the filler sequence may bifurcate at least one region so that 10% of the region is located 5' to the filler sequence and 90% of the region is located 3' to the filler sequence. In certain embodiments, the filler sequence may bifurcate at least one region so that 20% of the region is located 5' to the filler sequence and 80% of the region is located 3' to the filler sequence. In certain embodiments, the filler sequence may bifurcate at least one region so that 30% of the region is located 5' to the filler sequence and 70% of the region is located 3' to the filler sequence. In certain embodiments, the filler sequence may bifurcate at least one region so that 40% of the region is located 5' to the filler sequence and 60% of the region is located 3' to the filler sequence. In certain embodiments, the filler sequence may bifurcate at least one region so that 50% of the region is located 5' to the filler sequence and 50% of the region is located 3' to the filler sequence. In certain embodiments, the filler sequence may bifurcate at least one region so that 60% of the region is located 5' to the filler sequence and 40% of the region is located 3' to the filler sequence. In certain embodiments, the filler sequence may bifurcate at least one region so that 70% of the region is located 5' to the filler sequence and 30% of the region is located 3' to the filler sequence. In certain embodiments, the filler sequence may bifurcate at least one region so that 80% of the region is located 5' to the filler sequence and 20% of the region is located 3' to the filler sequence. In certain embodiments, the filler sequence may bifurcate at least one region so that 90% of the region is located 5' to the filler sequence and 10% of the region is located 3' to the filler sequence.

In certain embodiments, the viral genome comprises a filler sequence after the 5' ITR.

In certain embodiments, the viral genome comprises a filler sequence after the promoter region. In certain embodiments, the viral genome comprises a filler sequence after the payload region. In certain embodiments, the viral genome comprises a filler sequence after the intron region. In certain embodiments, the viral genome comprises a filler sequence after the enhancer region. In certain embodiments, the viral genome comprises a filler sequence after the polyadenylation signal sequence region. In certain embodiments, the viral genome comprises a filler sequence after the MCS region. In certain embodiments, the viral genome comprises a filler sequence after the exon region.

In certain embodiments, the viral genome comprises a filler sequence before the promoter region. In certain embodiments, the viral genome comprises a filler sequence before the payload region. In certain embodiments, the viral genome comprises a filler sequence before the intron region. In certain embodiments, the viral genome comprises a filler sequence before the enhancer region. In certain embodiments, the viral genome comprises a filler sequence before the polyadenylation signal sequence region. In certain embodiments, the viral genome comprises a filler sequence before the MCS region. In certain embodiments, the viral genome comprises a filler sequence before the exon region.

In certain embodiments, the viral genome comprises a filler sequence before the 3' ITR.

In certain embodiments, a filler sequence may be located between two regions, such as, but not limited to, the 5' ITR and the promoter region. In certain embodiments, a filler sequence may be located between two regions, such as, but not limited to, the 5' ITR and the payload region. In certain embodiments, a filler sequence may be located between two regions, such as, but not limited to, the 5' ITR and the intron region. In certain embodiments, a filler sequence may be located between two regions, such as, but not limited to, the 5' ITR and the enhancer region. In certain embodiments, a filler sequence may be located between two regions, such as, but not limited to, the 5' ITR and the polyadenylation signal sequence region. In certain embodiments, a filler sequence may be located between two regions, such as, but not limited to, the 5' ITR and the MCS region.

In certain embodiments, a filler sequence may be located between two regions, such as, but not limited to, the 5' ITR and the exon region.

In certain embodiments, a filler sequence may be located between two regions, such as, but not limited to, the promoter region and the payload region. In certain embodiments, a filler sequence may be located between two regions, such as, but not limited to, the promoter region and the intron region. In certain embodiments, a filler sequence may be located between two regions, such as, but not limited to, the promoter region and the enhancer region. In certain embodiments, a filler sequence may be located between two regions, such as, but not limited to, the promoter region and the polyadenylation signal sequence region. In certain embodiments, a filler sequence may be located between two regions, such as, but not limited to, the promoter region and the MCS region. In certain embodiments, a filler sequence may be located between two regions, such as, but not limited to, the promoter region and the exon region. In certain embodiments, a filler sequence may be located between two regions, such as, but not limited to, the promoter region and the 3' ITR.

In certain embodiments, a filler sequence may be located between two regions, such as, but not limited to, the payload region and the intron region. In certain embodiments, a filler sequence may be located between two regions, such as, but not limited to, the payload region and the enhancer region. In certain embodiments, a filler sequence may be located between two regions, such as, but not limited to, the payload region and the polyadenylation signal sequence region. In certain embodiments, a filler sequence may be located between two regions, such as, but not limited to, the payload region and the MCS region. In certain embodiments, a filler sequence may be located between two regions, such as, but not limited to, the payload region and the exon region.

In certain embodiments, a filler sequence may be located between two regions, such as, but not limited to, the payload region and the Y ITR.

In certain embodiments, a filler sequence may be located between two regions, such as, but not limited to, the intron region and the enhancer region. In certain embodiments, a filler sequence may be located between two regions, such as, but not limited to, the intron region and the polyadenylation signal sequence region. In certain embodiments, a filler sequence may be located between two regions, such as, but not limited to, the intron region and the MCS region. In certain embodiments, a filler sequence may be located between two regions, such as, but not limited to, the intron region and the exon region. In certain embodiments, a filler sequence may be located between two regions, such as, but not limited to, the intron region and the 3' ITR. In certain embodiments, a filler sequence may be located between two regions, such as, but not limited to, the enhancer region and the polyadenylation signal sequence region. In certain embodiments, a filler sequence may be located between two regions, such as, but not limited to, the enhancer region and the MCS region. In certain embodiments, a filler sequence may be located between two regions, such as, but not limited to, the enhancer region and the exon region. In certain embodiments, a filler sequence may be located between two regions, such as, but not limited to, the enhancer region and the 3' ITR.

In certain embodiments, a filler sequence may be located between two regions, such as, but not limited to, the polyadenylation signal sequence region and the MCS region. In certain embodiments, a filler sequence may be located between two regions, such as, but not limited to, the polyadenylation signal sequence region and the exon region. In certain embodiments, a filler sequence may be located between two regions, such as, but not limited to, the polyadenylation signal sequence region and the 3' ITR.

In certain embodiments, a filler sequence may be located between two regions, such as, but not limited to, the MCS region and the exon region. In certain embodiments, a filler sequence may be located between two regions, such as, but not limited to, the MCS region and the 3' ITR.

In certain embodiments, a filler sequence may be located between two regions, such as, but not limited to, the exon region and the 3' ITR.

In certain embodiments, a viral genome may comprise two filler sequences, the first filler sequence may be located between the 5' ITR and promoter region, and the second filler sequence may be located between the promoter region and payload region. In certain embodiments, a viral genome may comprise two filler sequences, the first filler sequence may be located between the 5' ITR and promoter region, and the second filler sequence may be located between the promoter region and intron region. In certain embodiments, a viral genome may comprise two filler sequences, the first filler sequence may be located between the 5' ITR and promoter region, and the second filler sequence may be located between the promoter region and enhancer region. In certain embodiments, a viral genome may comprise two filler sequences, the first filler sequence may be located between the 5' ITR and promoter region, and the second filler sequence may be located between the promoter region and polyadenylation signal sequence region. In certain embodiments, a viral genome may comprise two filler sequences, the first filler sequence may be located between the 5' ITR and promoter region, and the second filler sequence may be located between the promoter region and MCS region. In certain embodiments, a viral genome may comprise two filler sequences, the first filler sequence may be located between the 5' ITR and promoter region, and the second filler sequence may be located between the promoter region and exon region. In certain embodiments, a viral genome may comprise two filler sequences, the first filler sequence may be located between the 5' ITR and promoter region, and the second filler sequence may be located between the promoter region and 3' ITR. In certain embodiments, a viral genome may comprise two filler sequences, the first filler sequence may be located between the 5' ITR and promoter region, and the second filler sequence may be located between the payload region and intron region. In certain embodiments, a viral genome may comprise two filler sequences, the first filler sequence may be located between the 5' ITR and promoter region, and the second filler sequence may be located between the payload region and enhancer region. In certain embodiments, a viral genome may comprise two filler sequences, the first filler sequence may be located between the 5' ITR and promoter region, and the second filler sequence may be located between the payload region and polyadenylation signal sequence region. In certain embodiments, a viral genome may comprise two filler sequences, the first filler sequence may be located between the 5' ITR and promoter region, and the second filler sequence may be located between the payload region and MCS region. In certain embodiments, a viral genome may comprise two filler sequences, the first filler sequence may be located between the 5' ITR and promoter region, and the second filler sequence may be located between the payload region and exon region. In certain embodiments, a viral genome may comprise two filler sequences, the first filler sequence may be located between the 5' ITR and promoter region, and the second filler sequence may be located between the payload region and 3' ITR. In certain embodiments, a viral genome may comprise two filler sequences, the first filler sequence may be located between the 5' ITR and promoter region, and the second filler sequence may be located between the intron region and enhancer region. In certain embodiments, a viral genome may comprise two filler sequences, the first filler sequence may be located between the 5' ITR and promoter region, and the second filler sequence may be located between the intron region and polyadenylation signal sequence region. In certain embodiments, a viral genome may comprise two filler sequences, the first filler sequence may be located between the 5' ITR and promoter region, and the second filler sequence may be located between the intron region and MCS region. In certain embodiments, a viral genome may comprise two filler sequences, the first filler sequence may be located between the 5' ITR and promoter region, and the second filler sequence may be located between the intron region and exon region. In certain embodiments, a viral genome may comprise two filler sequences, the first filler sequence may be located between the 5' ITR and promoter region, and the second filler sequence may be located between the intron region and 3' ITR. In certain embodiments, a viral genome may comprise two filler sequences, the first filler sequence may be located between the 5' ITR and promoter region, and the second filler sequence may be located between the enhancer region and polyadenylation signal sequence region. In certain embodiments, a viral genome may comprise two filler sequences, the first filler sequence may be located between the 5' ITR and promoter region, and the second filler sequence may be located between the enhancer region and MCS region. In certain embodiments, a viral genome may comprise two filler sequences, the first filler sequence may be located between the 5' ITR and promoter region, and the second filler sequence may be located between the enhancer region and exon region. In certain embodiments, a viral genome may comprise two filler sequences, the first filler sequence may be located between the 5' ITR and promoter region, and the second filler sequence may be located between the enhancer region and 3' ITR. In certain embodiments, a viral genome may comprise two filler sequences, the first filler sequence may be located between the 5' ITR and promoter region, and the second filler sequence may be located between the polyadenylation signal sequence region and MCS region. In certain embodiments, a viral genome may comprise two filler sequences, the first filler sequence may be located between the 5' ITR and promoter region, and the second filler sequence may be located between the polyadenylation signal sequence region and exon region. In certain embodiments, a viral genome may comprise two filler sequences, the first filler sequence may be located between the 5' ITR and promoter region, and the second filler sequence may be located between the polyadenylation signal sequence region and 3' ITR. In certain embodiments, a viral genome may comprise two filler sequences, the first filler sequence may be located between the 5' ITR and promoter region, and the second filler sequence may be located between the MCS region and exon region. In certain embodiments, a viral genome may comprise two filler sequences, the first filler sequence may be located between the 5' ITR and promoter region, and the second filler sequence may be located between the MCS region and 3' ITR. In certain embodiments, a viral genome may comprise two filler sequences, the first filler sequence may be located between the 5' ITR and promoter region, and the second filler sequence may be located between the exon region and 3' ITR.

In certain embodiments, a viral genome may comprise two filler sequences, the first filler sequence may be located between the 5' ITR and payload region, and the second filler sequence may be located between the promoter region and payload region. In certain embodiments, a viral genome may comprise two filler sequences, the first filler sequence may be located between the 5' ITR and payload region, and the second filler sequence may be located between the promoter region and intron region. In certain embodiments, a viral genome may comprise two filler sequences, the first filler sequence may be located between the 5' ITR and payload region, and the second filler sequence may be located between the promoter region and enhancer region. In certain embodiments, a viral genome may comprise two filler sequences, the first filler sequence may be located between the 5' ITR and payload region, and the second filler sequence may be located between the promoter region and polyadenylation signal sequence region. In certain embodiments, a viral genome may comprise two filler sequences, the first filler sequence may be located between the 5' ITR and payload region, and the second filler sequence may be located between the promoter region and MCS region. In certain embodiments, a viral genome may comprise two filler sequences, the first filler sequence may be located between the 5' ITR and payload region, and the second filler sequence may be located between the promoter region and exon region. In certain embodiments, a viral genome may comprise two filler sequences, the first filler sequence may be located between the 5' ITR and payload region, and the second filler sequence may be located between the promoter region and 3' ITR. In certain embodiments, a viral genome may comprise two filler sequences, the first filler sequence may be located between the 5' ITR and payload region, and the second filler sequence may be located between the payload region and intron region. In certain embodiments, a viral genome may comprise two filler sequences, the first filler sequence may be located between the 5' ITR and payload region, and the second filler sequence may be located between the payload region and enhancer region. In certain embodiments, a viral genome may comprise two filler sequences, the first filler sequence may be located between the 5' ITR and payload region, and the second filler sequence may be located between the payload region and polyadenylation signal sequence region. In certain embodiments, a viral genome may comprise two filler sequences, the first filler sequence may be located between the 5' ITR and payload region, and the second filler sequence may be located between the payload region and MCS region. In certain embodiments, a viral genome may comprise two filler sequences, the first filler sequence may be located between the 5' ITR and payload region, and the second filler sequence may be located between the payload region and exon region. In certain embodiments, a viral genome may comprise two filler sequences, the first filler sequence may be located between the 5' ITR and payload region, and the second filler sequence may be located between the payload region and 3' ITR. In certain embodiments, a viral genome may comprise two filler sequences, the first filler sequence may be located between the 5' ITR and payload region, and the second filler sequence may be located between the intron region and enhancer region. In certain embodiments, a viral genome may comprise two filler sequences, the first filler sequence may be located between the 5' ITR and payload region, and the second filler sequence may be located between the intron region and polyadenylation signal sequence region. In certain embodiments, a viral genome may comprise two filler sequences, the first filler sequence may be located between the 5' ITR and payload region, and the second filler sequence may be located between the intron region and MCS region. In certain embodiments, a viral genome may comprise two filler sequences, the first filler sequence may be located between the 5' ITR and payload region, and the second filler sequence may be located between the intron region and exon region. In certain embodiments, a viral genome may comprise two filler sequences, the first filler sequence may be located between the 5' ITR and payload region, and the second filler sequence may be located between the intron region and 3' ITR. In certain embodiments, a viral genome may comprise two filler sequences, the first filler sequence may be located between the 5' ITR and payload region, and the second filler sequence may be located between the enhancer region and polyadenylation signal sequence region. In certain embodiments, a viral genome may comprise two filler sequences, the first filler sequence may be located between the 5' ITR and payload region, and the second filler sequence may be located between the enhancer region and MCS region. In certain embodiments, a viral genome may comprise two filler sequences, the first filler sequence may be located between the 5' ITR and payload region, and the second filler sequence may be located between the enhancer region and exon region. In certain embodiments, a viral genome may comprise two filler sequences, the first filler sequence may be located between the 5' ITR and payload region, and the second filler sequence may be located between the enhancer region and 3' ITR. In certain embodiments, a viral genome may comprise two filler sequences, the first filler sequence may be located between the 5' ITR and payload region, and the second filler sequence may be located between the polyadenylation signal sequence region and MCS region. In certain embodiments, a viral genome may comprise two filler sequences, the first filler sequence may be located between the 5' ITR and payload region, and the second filler sequence may be located between the polyadenylation signal sequence region and exon region. In certain embodiments, a viral genome may comprise two filler sequences, the first filler sequence may be located between the 5' ITR and payload region, and the second filler sequence may be located between the polyadenylation signal sequence region and 3' ITR. In certain embodiments, a viral genome may comprise two filler sequences, the first filler sequence may be located between the 5' ITR and payload region, and the second filler sequence may be located between the MCS region and exon region. In certain embodiments, a viral genome may comprise two filler sequences, the first filler sequence may be located between the 5' ITR and payload region, and the second filler sequence may be located between the MCS region and 3' ITR. In certain embodiments, a viral genome may comprise two filler sequences, the first filler sequence may be located between the 5' ITR and payload region, and the second filler sequence may be located between the exon region and 3' ITR.

In certain embodiments, a viral genome may comprise two filler sequences, the first filler sequence may be located between the 5' ITR and intron region, and the second filler sequence may be located between the promoter region and payload region. In certain embodiments, a viral genome may comprise two filler sequences, the first filler sequence may be located between the 5' ITR and intron region, and the second filler sequence may be located between the promoter region and intron region. In certain embodiments, a viral genome may comprise two filler sequences, the first filler sequence may be located between the 5' ITR and intron region, and the second filler sequence may be located between the promoter region and enhancer region. In certain embodiments, a viral genome may comprise two filler sequences, the first filler sequence may be located between the 5' ITR and intron region, and the second filler sequence may be located between the promoter region and polyadenylation signal sequence region. In certain embodiments, a viral genome may comprise two filler sequences, the first filler sequence may be located between the 5' ITR and intron region, and the second filler sequence may be located between the promoter region and MCS region. In certain embodiments, a viral genome may comprise two filler sequences, the first filler sequence may be located between the 5' ITR and intron region, and the second filler sequence may be located between the promoter region and exon region. In certain embodiments, a viral genome may comprise two filler sequences, the first filler sequence may be located between the 5' ITR and intron region, and the second filler sequence may be located between the promoter region and 3' ITR. In certain embodiments, a viral genome may comprise two filler sequences, the first filler sequence may be located between the 5' ITR and intron region, and the second filler sequence may be located between the payload region and intron region. In certain embodiments, a viral genome may comprise two filler sequences, the first filler sequence may be located between the 5' FR and intron region, and the second filler sequence may be located between the payload region and enhancer region. In certain embodiments, a viral genome may comprise two filler sequences, the first filler sequence may be located between the 5' ITR and intron region, and the second filler sequence may be located between the payload region and polyadenylation signal sequence region. In certain embodiments, a viral genome may comprise two filler sequences, the first filler sequence may be located between the 5' ITR and intron region, and the second filler sequence may be located between the payload region and MCS region. In certain embodiments, a viral genome may comprise two filler sequences, the first filler sequence may be located between the 5' ITR and intron region, and the second filler sequence may be located between the payload region and exon region. In certain embodiments, a viral genome may comprise two filler sequences, the first filler sequence may be located between the 5' ITR and intron region, and the second filler sequence may be located between the payload region and 3' ITR. In certain embodiments, a viral genome may comprise two filler sequences, the first filler sequence may be located between the 5' ITR and intron region, and the second filler sequence may be located between the intron region and enhancer region. In certain embodiments, a viral genome may comprise two filler sequences, the first filler sequence may be located between the 5' ITR and intron region, and the second filler sequence may be located between the intron region and polyadenylation signal sequence region. In certain embodiments, a viral genome may comprise two filler sequences, the first filler sequence may be located between the 5' ITR and intron region, and the second filler sequence may be located between the intron region and MCS region. In certain embodiments, a viral genome may comprise two filler sequences, the first filler sequence may be located between the 5' ITR and intron region, and the second filler sequence may be located between the intron region and exon region. In certain embodiments, a viral genome may comprise two filler sequences, the first filler sequence may be located between the 5' ITR and intron region, and the second filler sequence may be located between the intron region and 3' ITR. In certain embodiments, a viral genome may comprise two filler sequences, the first filler sequence may be located between the 5' ITR and intron region, and the second filler sequence may be located between the enhancer region and polyadenylation signal sequence region. In certain embodiments, a viral genome may comprise two filler sequences, the first filler sequence may be located between the 5' ITR and intron region, and the second filler sequence may be located between the enhancer region and MCS region. In certain embodiments, a viral genome may comprise two filler sequences, the first filler sequence may be located between the 5' ITR and intron region, and the second filler sequence may be located between the enhancer region and exon region. In certain embodiments, a viral genome may comprise two filler sequences, the first filler sequence may be located between the 5' ITR and intron region, and the second filler sequence may be located between the enhancer region and 3' ITR. In certain embodiments, a viral genome may comprise two filler sequences, the first filler sequence may be located between the 5' ITR and intron region, and the second filler sequence may be located between the polyadenylation signal sequence region and MCS region. In certain embodiments, a viral genome may comprise two filler sequences, the first filler sequence may be located between the 5' ITR and intron region, and the second filler sequence may be located between the polyadenylation signal sequence region and exon region. In certain embodiments, a viral genome may comprise two filler sequences, the first filler sequence may be located between the 5' ITR and intron region, and the second filler sequence may be located between the polyadenylation signal sequence region and 3' ITR. In certain embodiments, a viral genome may comprise two filler sequences, the first filler sequence may be located between the 5' ITR and intron region, and the second filler sequence may be located between the MCS region and exon region. In certain embodiments, a viral genome may comprise two filler sequences, the first filler sequence may be located between the 5' ITR and intron region, and the second filler sequence may be located between the MCS region and 3' ITR. In certain embodiments, a viral genome may comprise two filler sequences, the first filler sequence may be located between the 5' ITR and intron region, and the second filler sequence may be located between the exon region and 3' ITR.

In certain embodiments, a viral genome may comprise two filler sequences, the first filler sequence may be located between the 5' ITR and enhancer region, and the second filler sequence may be located between the promoter region and payload region. In certain embodiments, a viral genome may comprise two filler sequences, the first filler sequence may be located between the 5' ITR and enhancer region, and the second filler sequence may be located between the promoter region and intron region. In certain embodiments, a viral genome may comprise two filler sequences, the first filler sequence may be located between the 5' ITR and enhancer region, and the second filler sequence may be located between the promoter region and enhancer region. In certain embodiments, a viral genome may comprise two filler sequences, the first filler sequence may be located between the 5' ITR and enhancer region, and the second filler sequence may be located between the promoter region and polyadenylation signal sequence region. In certain embodiments, a viral genome may comprise two filler sequences, the first filler sequence may be located between the 5' ITR and enhancer region, and the second filler sequence may be located between the promoter region and MCS region. In certain embodiments, a viral genome may comprise two filler sequences, the first filler sequence may be located between the 5' ITR and enhancer region, and the second filler sequence may be located between the promoter region and exon region. In certain embodiments, a viral genome may comprise two filler sequences, the first filler sequence may be located between the 5' ITR and enhancer region, and the second filler sequence may be located between the promoter region and 3' ITR. In certain embodiments, a viral genome may comprise two filler sequences, the first filler sequence may be located between the 5' ITR and enhancer region, and the second filler sequence may be located between the payload region and intron region. In certain embodiments, a viral genome may comprise two filler sequences, the first filler sequence may be located between the 5' ITR and enhancer region, and the second filler sequence may be located between the payload region and enhancer region. In certain embodiments, a viral genome may comprise two filler sequences, the first filler sequence may be located between the 5' ITR and enhancer region, and the second filler sequence may be located between the payload region and polyadenylation signal sequence region. In certain embodiments, a viral genome may comprise two filler sequences, the first filler sequence may be located between the 5' ITR and enhancer region, and the second filler sequence may be located between the payload region and MCS region. In certain embodiments, a viral genome may comprise two filler sequences, the first filler sequence may be located between the 5' ITR and enhancer region, and the second filler sequence may be located between the payload region and exon region. In certain embodiments, a viral genome may comprise two filler sequences, the first filler sequence may be located between the 5' ITR and enhancer region, and the second filler sequence may be located between the payload region and 3' ITR. In certain embodiments, a viral genome may comprise two filler sequences, the first filler sequence may be located between the 5' ITR and enhancer region, and the second filler sequence may be located between the intron region and enhancer region. In certain embodiments, a viral genome may comprise two filler sequences, the first filler sequence may be located between the 5' ITR and enhancer region, and the second filler sequence may be located between the intron region and polyadenylation signal sequence region. In certain embodiments, a viral genome may comprise two filler sequences, the first filler sequence may be located between the 5' ITR and enhancer region, and the second filler sequence may be located between the intron region and MCS region. In certain embodiments, a viral genome may comprise two filler sequences, the first filler sequence may be located between the 5' ITR and enhancer region, and the second filler sequence may be located between the intron region and exon region. In certain embodiments, a viral genome may comprise two filler sequences, the first filler sequence may be located between the 5' ITR and enhancer region, and the second filler sequence may be located between the intron region and 3' ITR. In certain embodiments, a viral genome may comprise two filler sequences, the first filler sequence may be located between the 5' ITR and enhancer region, and the second filler sequence may be located between the enhancer region and polyadenylation signal sequence region. In certain embodiments, a viral genome may comprise two filler sequences, the first filler sequence may be located between the 5' ITR and enhancer region, and the second filler sequence may be located between the enhancer region and MCS region. In certain embodiments, a viral genome may comprise two filler sequences, the first filler sequence may be located between the 5' ITR and enhancer region, and the second filler sequence may be located between the enhancer region and exon region. In certain embodiments, a viral genome may comprise two filler sequences, the first filler sequence may be located between the 5' ITR and enhancer region, and the second filler sequence may be located between the enhancer region and 3' ITR. In certain embodiments, a viral genome may comprise two filler sequences, the first filler sequence may be located between the 5' ITR and enhancer region, and the second filler sequence may be located between the polyadenylation signal sequence region and MCS region. In certain embodiments, a viral genome may comprise two filler sequences, the first filler sequence may be located between the 5' ITR and enhancer region, and the second filler sequence may be located between the polyadenylation signal sequence region and exon region. In certain embodiments, a viral genome may comprise two filler sequences, the first filler sequence may be located between the 5' ITR and enhancer region, and the second filler sequence may be located between the polyadenylation signal sequence region and 3' ITR. In certain embodiments, a viral genome may comprise two filler sequences, the first filler sequence may be located between the 5' ITR and enhancer region, and the second filler sequence may be located between the MCS region and exon region. In certain embodiments, a viral genome may comprise two filler sequences, the first filler sequence may be located between the 5' ITR and enhancer region, and the second filler sequence may be located between the MCS region and 3' ITR. In certain embodiments, a viral genome may comprise two filler sequences, the first filler sequence may be located between the 5' ITR and enhancer region, and the second filler sequence may be located between the exon region and 3' ITR.

In certain embodiments, a viral genome may comprise two filler sequences, the first filler sequence may be located between the 5' ITR and polyadenylation signal sequence region, and the second filler sequence may be located between the promoter region and payload region. In certain embodiments, a viral genome may comprise two filler sequences, the first filler sequence may be located between the 5' ITR and polyadenylation signal sequence region, and the second filler sequence may be located between the promoter region and intron region. In certain embodiments, a viral genome may comprise two filler sequences, the first filler sequence may be located between the 5' ITR and polyadenylation signal sequence region, and the second filler sequence may be located between the promoter region and enhancer region. In certain embodiments, a viral genome may comprise two filler sequences, the first filler sequence may be located between the 5' ITR and polyadenylation signal sequence region, and the second filler sequence may be located between the promoter region and polyadenylation signal sequence region. In certain embodiments, a viral genome may comprise two filler sequences, the first filler sequence may be located between the 5' ITR and polyadenylation signal sequence region, and the second filler sequence may be located between the promoter region and MCS region. In certain embodiments, a viral genome may comprise two filler sequences, the first filler sequence may be located between the 5' ITR and polyadenylation signal sequence region, and the second filler sequence may be located between the promoter region and exon region. In certain embodiments, a viral genome may comprise two filler sequences, the first filler sequence may be located between the 5' ITR and polyadenylation signal sequence region, and the second filler sequence may be located between the promoter region and 3' ITR. In certain embodiments, a viral genome may comprise two filler sequences, the first filler sequence may be located between the 5' ITR and polyadenylation signal sequence region, and the second filler sequence may be located between the payload region and intron region. In certain embodiments, a viral genome may comprise two filler sequences, the first filler sequence may be located between the 5' ITR and polyadenylation signal sequence region, and the second filler sequence may be located between the payload region and enhancer region. In certain embodiments, a viral genome may comprise two filler sequences, the first filler sequence may be located between the 5' ITR and polyadenylation signal sequence region, and the second filler sequence may be located between the payload region and polyadenylation signal sequence region. In certain embodiments, a viral genome may comprise two filler sequences, the first filler sequence may be located between the 5' ITR and polyadenylation signal sequence region, and the second filler sequence may be located between the payload region and MCS region. In certain embodiments, a viral genome may comprise two filler sequences, the first filler sequence may be located between the 5' ITR and polyadenylation signal sequence region, and the second filler sequence may be located between the payload region and exon region. In certain embodiments, a viral genome may comprise two filler sequences, the first filler sequence may be located between the 5' ITR and polyadenylation signal sequence region, and the second filler sequence may be located between the payload region and 3' ITR. In certain embodiments, a viral genome may comprise two filler sequences, the first filler sequence may be located between the 5' ITR and polyadenylation signal sequence region, and the second filler sequence may be located between the intron region and enhancer region. In certain embodiments, a viral genome may comprise two filler sequences, the first filler sequence may be located between the 5' ITR and polyadenylation signal sequence region, and the second filler sequence may be located between the intron region and polyadenylation signal sequence region. In certain embodiments, a viral genome may comprise two filler sequences, the first filler sequence may be located between the 5' ITR and polyadenylation signal sequence region, and the second filler sequence may be located between the intron region and MCS region. In certain embodiments, a viral genome may comprise two filler sequences, the first filler sequence may be located between the 5' ITR and polyadenylation signal sequence region, and the second filler sequence may be located between the intron region and exon region. In certain embodiments, a viral genome may comprise two filler sequences, the first filler sequence may be located between the 5' ITR and polyadenylation signal sequence region, and the second filler sequence may be located between the intron region and 3' ITR. In certain embodiments, a viral genome may comprise two filler sequences, the first filler sequence may be located between the 5' ITR and polyadenylation signal sequence region, and the second filler sequence may be located between the enhancer region and polyadenylation signal sequence region. In certain embodiments, a viral genome may comprise two filler sequences, the first filler sequence may be located between the 5' ITR and polyadenylation signal sequence region, and the second filler sequence may be located between the enhancer region and MCS region. In certain embodiments, a viral genome may comprise two filler sequences, the first filler sequence may be located between the 5' ITR and polyadenylation signal sequence region, and the second filler sequence may be located between the enhancer region and exon region. In certain embodiments, a viral genome may comprise two filler sequences, the first filler sequence may be located between the 5' ITR and polyadenylation signal sequence region, and the second filler sequence may be located between the enhancer region and 3' ITR. In certain embodiments, a viral genome may comprise two filler sequences, the first filler sequence may be located between the 5' ITR and polyadenylation signal sequence region, and the second filler sequence may be located between the polyadenylation signal sequence region and MCS region. In certain embodiments, a viral genome may comprise two filler sequences, the first filler sequence may be located between the 5' ITR and polyadenylation signal sequence region, and the second filler sequence may be located between the polyadenylation signal sequence region and exon region. In certain embodiments, a viral genome may comprise two filler sequences, the first filler sequence may be located between the 5' ITR and polyadenylation signal sequence region, and the second filler sequence may be located between the polyadenylation signal sequence region and 3' ITR. In certain embodiments, a viral genome may comprise two filler sequences, the first filler sequence may be located between the 5' ITR and polyadenylation signal sequence region, and the second filler sequence may be located between the MCS region and exon region. In certain embodiments, a viral genome may comprise two filler sequences, the first filler sequence may be located between the 5' ITR and polyadenylation signal sequence region, and the second filler sequence may be located between the MCS region and 3' ITR. In certain embodiments, a viral genome may comprise two filler sequences, the first filler sequence may be located between the 5' ITR and polyadenylation signal sequence region, and the second filler sequence may be located between the exon region and 3' ITR.

In certain embodiments, a viral genome may comprise two filler sequences, the first filler sequence may be located between the 5' ITR and MCS region, and the second filler sequence may be located between the promoter region and payload region. In certain embodiments, a viral genome may comprise two filler sequences, the first filler sequence may be located between the 5' ITR and MCS region, and the second filler sequence may be located between the promoter region and intron region. In certain embodiments, a viral genome may comprise two filler sequences, the first filler sequence may be located between the 5' ITR and MCS region, and the second filler sequence may be located between the promoter region and enhancer region. In certain embodiments, a viral genome may comprise two filler sequences, the first filler sequence may be located between the 5' ITR and MCS region, and the second filler sequence may be located between the promoter region and polyadenylation signal sequence region. In certain embodiments, a viral genome may comprise two filler sequences, the first filler sequence may be located between the 5' ITR and MCS region, and the second filler sequence may be located between the promoter region and MCS region. In certain embodiments, a viral genome may comprise two filler sequences, the first filler sequence may be located between the 5' ITR and MCS region, and the second filler sequence may be located between the promoter region and exon region. In certain embodiments, a viral genome may comprise two filler sequences, the first filler sequence may be located between the 5' ITR and MCS region, and the second filler sequence may be located between the promoter region and 3' ITR. In certain embodiments, a viral genome may comprise two filler sequences, the first filler sequence may be located between the 5' ITR and MCS region, and the second filler sequence may be located between the payload region and intron region. In certain embodiments, a viral genome may comprise two filler sequences, the first filler sequence may be located between the 5' ITR and MCS region, and the second filler sequence may be located between the payload region and enhancer region. In certain embodiments, a viral genome may comprise two filler sequences, the first filler sequence may be located between the 5' ITR and MCS region, and the second filler sequence may be located between the payload region and polyadenylation signal sequence region. In certain embodiments, a viral genome may comprise two filler sequences, the first filler sequence may be located between the 5' ITR and MCS region, and the second filler sequence may be located between the payload region and MCS region. In certain embodiments, a viral genome may comprise two filler sequences, the first filler sequence may be located between the 5' ITR and MCS region, and the second filler sequence may be located between the payload region and exon region. In certain embodiments, a viral genome may comprise two filler sequences, the first filler sequence may be located between the 5' ITR and MCS region, and the second filler sequence may be located between the payload region and 3' ITR. In certain embodiments, a viral genome may comprise two filler sequences, the first filler sequence may be located between the 5' ITR and MCS region, and the second filler sequence may be located between the intron region and enhancer region. In certain embodiments, a viral genome may comprise two filler sequences, the first filler sequence may be located between the 5' ITR and MCS region, and the second filler sequence may be located between the intron region and polyadenylation signal sequence region. In certain embodiments, a viral genome may comprise two filler sequences, the first filler sequence may be located between the 5' ITR and MCS region, and the second filler sequence may be located between the intron region and MCS region. In certain embodiments, a viral genome may comprise two filler sequences, the first filler sequence may be located between the 5' ITR and MCS region, and the second filler sequence may be located between the intron region and exon region. In certain embodiments, a viral genome may comprise two filler sequences, the first filler sequence may be located between the 5' ITR and MCS region, and the second filler sequence may be located between the intron region and 3' ITR. In certain embodiments, a viral genome may comprise two filler sequences, the first filler sequence may be located between the 5' ITR and MCS region, and the second filler sequence may be located between the enhancer region and polyadenylation signal sequence region. In certain embodiments, a viral genome may comprise two filler sequences, the first filler sequence may be located between the 5' ITR and MCS region, and the second filler sequence may be located between the enhancer region and MCS region. In certain embodiments, a viral genome may comprise two filler sequences, the first filler sequence may be located between the 5' ITR and MCS region, and the second filler sequence may be located between the enhancer region and exon region. In certain embodiments, a viral genome may comprise two filler sequences, the first filler sequence may be located between the 5' ITR and MCS region, and the second filler sequence may be located between the enhancer region and 3' ITR. In certain embodiments, a viral genome may comprise two filler sequences, the first filler sequence may be located between the 5' ITR and MCS region, and the second filler sequence may be located between the polyadenylation signal sequence region and MCS region. In certain embodiments, a viral genome may comprise two filler sequences, the first filler sequence may be located between the 5' ITR and MCS region, and the second filler sequence may be located between the polyadenylation signal sequence region and exon region. In certain embodiments, a viral genome may comprise two filler sequences, the first filler sequence may be located between the 5' ITR and MCS region, and the second filler sequence may be located between the polyadenylation signal sequence region and 3' ITR. In certain embodiments, a viral genome may comprise two filler sequences, the first filler sequence may be located between the 5' ITR and MCS region, and the second filler sequence may be located between the MCS region and exon region. In certain embodiments, a viral genome may comprise two filler sequences, the first filler sequence may be located between the 5' ITR and MCS region, and the second filler sequence may be located between the MCS region and 3' ITR. In certain embodiments, a viral genome may comprise two filler sequences, the first filler sequence may be located between the 5' ITR and MCS region, and the second filler sequence may be located between the exon region and 3' ITR.

In certain embodiments, a viral genome may comprise two filler sequences, the first filler sequence may be located between the 5' ITR and exon region, and the second filler sequence may be located between the promoter region and payload region. In certain embodiments, a viral genome may comprise two filler sequences, the first filler sequence may be located between the 5' ITR and exon region, and the second filler sequence may be located between the promoter region and intron region. In certain embodiments, a viral genome may comprise two filler sequences, the first filler sequence may be located between the 5' ITR and exon region, and the second filler sequence may be located between the promoter region and enhancer region. In certain embodiments, a viral genome may comprise two filler sequences, the first filler sequence may be located between the 5' ITR and exon region, and the second filler sequence may be located between the promoter region and polyadenylation signal sequence region. In certain embodiments, a viral genome may comprise two filler sequences, the first filler sequence may be located between the 5' ITR and exon region, and the second filler sequence may be located between the promoter region and MCS region. In certain embodiments, a viral genome may comprise two filler sequences, the first filler sequence may be located between the 5' ITR and exon region, and the second filler sequence may be located between the promoter region and exon region. In certain embodiments, a viral genome may comprise two filler sequences, the first filler sequence may be located between the 5' ITR and exon region, and the second filler sequence may be located between the promoter region and 3' ITR. In certain embodiments, a viral genome may comprise two filler sequences, the first filler sequence may be located between the 5' ITR and exon region, and the second filler sequence may be located between the payload region and intron region. In certain embodiments, a viral genome may comprise two filler sequences, the first filler sequence may be located between the 5' ITR and exon region, and the second filler sequence may be located between the payload region and enhancer region. In certain embodiments, a viral genome may comprise two filler sequences, the first filler sequence may be located between the 5' ITR and exon region, and the second filler sequence may be located between the payload region and polyadenylation signal sequence region. In certain embodiments, a viral genome may comprise two filler sequences, the first filler sequence may be located between the 5' ITR and exon region, and the second filler sequence may be located between the payload region and MCS region. In certain embodiments, a viral genome may comprise two filler sequences, the first filler sequence may be located between the 5' ITR and exon region, and the second filler sequence may be located between the payload region and exon region. In certain embodiments, a viral genome may comprise two filler sequences, the first filler sequence may be located between the 5' ITR and exon region, and the second filler sequence may be located between the payload region and 3' ITR. In certain embodiments, a viral genome may comprise two filler sequences, the first filler sequence may be located between the 5' ITR and exon region, and the second filler sequence may be located between the intron region and enhancer region. In certain embodiments, a viral genome may comprise two filler sequences, the first filler sequence may be located between the 5' ITR and exon region, and the second filler sequence may be located between the intron region and polyadenylation signal sequence region. In certain embodiments, a viral genome may comprise two filler sequences, the first filler sequence may be located between the 5' ITR and exon region, and the second filler sequence may be located between the intron region and MCS region. In certain embodiments, a viral genome may comprise two filler sequences, the first filler sequence may be located between the 5' ITR and exon region, and the second filler sequence may be located between the intron region and exon region. In certain embodiments, a viral genome may comprise two filler sequences, the first filler sequence may be located between the 5' ITR and exon region, and the second filler sequence may be located between the intron region and 3' ITR. In certain embodiments, a viral genome may comprise two filler sequences, the first filler sequence may be located between the 5' ITR and exon region, and the second filler sequence may be located between the enhancer region and polyadenylation signal sequence region. In certain embodiments, a viral genome may comprise two filler sequences, the first filler sequence may be located between the 5' ITR and exon region, and the second filler sequence may be located between the enhancer region and MCS region. In certain embodiments, a viral genome may comprise two filler sequences, the first filler sequence may be located between the 5' ITR and exon region, and the second filler sequence may be located between the enhancer region and exon region. In certain embodiments, a viral genome may comprise two filler sequences, the first filler sequence may be located between the 5' ITR and exon region, and the second filler sequence may be located between the enhancer region and 3' ITR. In certain embodiments, a viral genome may comprise two filler sequences, the first filler sequence may be located between the 5' ITR and exon region, and the second filler sequence may be located between the polyadenylation signal sequence region and MCS region. In certain embodiments, a viral genome may comprise two filler sequences, the first filler sequence may be located between the 5' ITR and exon region, and the second filler sequence may be located between the polyadenylation signal sequence region and exon region. In certain embodiments, a viral genome may comprise two filler sequences, the first filler sequence may be located between the 5' ITR and exon region, and the second filler sequence may be located between the polyadenylation signal sequence region and 3' ITR. In certain embodiments, a viral genome may comprise two filler sequences, the first filler sequence may be located between the 5' ITR and exon region, and the second filler sequence may be located between the MCS region and exon region. In certain embodiments, a viral genome may comprise two filler sequences, the first filler sequence may be located between the 5' ITR and exon region, and the second filler sequence may be located between the MCS region and 3' ITR. In certain embodiments, a viral genome may comprise two filler sequences, the first filler sequence may be located between the 5' ITR and exon region, and the second filler sequence may be located between the exon region and 3' ITR.

In certain embodiments, a viral genome may comprise two filler sequences, the first filler sequence may be located between the promoter region and payload region, and the second filler sequence may be located between the payload region and intron region. In certain embodiments, a viral genome may comprise two filler sequences, the first filler sequence may be located between the promoter region and payload region, and the second filler sequence may be located between the payload region and enhancer region. In certain embodiments, a viral genome may comprise two filler sequences, the first filler sequence may be located between the promoter region and payload region, and the second filler sequence may be located between the payload region and polyadenylation signal sequence region. In certain embodiments, a viral genome may comprise two filler sequences, the first filler sequence may be located between the promoter region and payload region, and the second filler sequence may be located between the payload region and MCS region. In certain embodiments, a viral genome may comprise two filler sequences, the first filler sequence may be located between the promoter region and payload region, and the second filler sequence may be located between the payload region and exon region. In certain embodiments, a viral genome may comprise two filler sequences, the first filler sequence may be located between the promoter region and payload region, and the second filler sequence may be located between the payload region and 3' ITR. In certain embodiments, a viral genome may comprise two filler sequences, the first filler sequence may be located between the promoter region and payload region, and the second filler sequence may be located between the intron region and enhancer region. In certain embodiments, a viral genome may comprise two filler sequences, the first filler sequence may be located between the promoter region and payload region, and the second filler sequence may be located between the intron region and polyadenylation signal sequence region. In certain embodiments, a viral genome may comprise two filler sequences, the first filler sequence may be located between the promoter region and payload region, and the second filler sequence may be located between the intron region and MCS region. In certain embodiments, a viral genome may comprise two filler sequences, the first filler sequence may be located between the promoter region and payload region, and the second filler sequence may be located between the intron region and exon region. In certain embodiments, a viral genome may comprise two filler sequences, the first filler sequence may be located between the promoter region and payload region, and the second filler sequence may be located between the intron region and 3' ITR. In certain embodiments, a viral genome may comprise two filler sequences, the first filler sequence may be located between the promoter region and payload region, and the second filler sequence may be located between the enhancer region and polyadenylation signal sequence region. In certain embodiments, a viral genome may comprise two filler sequences, the first filler sequence may be located between the promoter region and payload region, and the second filler sequence may be located between the enhancer region and MCS region. In certain embodiments, a viral genome may comprise two filler sequences, the first filler sequence may be located between the promoter region and payload region, and the second filler sequence may be located between the enhancer region and exon region. In certain embodiments, a viral genome may comprise two filler sequences, the first filler sequence may be located between the promoter region and payload region, and the second filler sequence may be located between the enhancer region and 3' ITR. In certain embodiments, a viral genome may comprise two filler sequences, the first filler sequence may be located between the promoter region and payload region, and the second filler sequence may be located between the polyadenylation signal sequence region and MCS region. In certain embodiments, a viral genome may comprise two filler sequences, the first filler sequence may be located between the promoter region and payload region, and the second filler sequence may be located between the polyadenylation signal sequence region and exon region. In certain embodiments, a viral genome may comprise two filler sequences, the first filler sequence may be located between the promoter region and payload region, and the second filler sequence may be located between the polyadenylation signal sequence region and 3' ITR. In certain embodiments, a viral genome may comprise two filler sequences, the first filler sequence may be located between the promoter region and payload region, and the second filler sequence may be located between the MCS region and exon region. In certain embodiments, a viral genome may comprise two filler sequences, the first filler sequence may be located between the promoter region and payload region, and the second filler sequence may be located between the MCS region and 3' ITR. In certain embodiments, a viral genome may comprise two filler sequences, the first filler sequence may be located between the promoter region and payload region, and the second filler sequence may be located between the exon region and 3' ITR.

In certain embodiments, a viral genome may comprise two filler sequences, the first filler sequence may be located between the promoter region and intron region, and the second filler sequence may be located between the payload region and intron region. In certain embodiments, a viral genome may comprise two filler sequences, the first filler sequence may be located between the promoter region and intron region, and the second filler sequence may be located between the payload region and enhancer region. In certain embodiments, a viral genome may comprise two filler sequences, the first filler sequence may be located between the promoter region and intron region, and the second filler sequence may be located between the payload region and polyadenylation signal sequence region. In certain embodiments, a viral genome may comprise two filler sequences, the first filler sequence may be located between the promoter region and intron region, and the second filler sequence may be located between the payload region and MCS region. In certain embodiments, a viral genome may comprise two filler sequences, the first filler sequence may be located between the promoter region and intron region, and the second filler sequence may be located between the payload region and exon region. In certain embodiments, a viral genome may comprise two filler sequences, the first filler sequence may be located between the promoter region and intron region, and the second filler sequence may be located between the payload region and 3' ITR. In certain embodiments, a viral genome may comprise two filler sequences, the first filler sequence may be located between the promoter region and intron region, and the second filler sequence may be located between the intron region and enhancer region. In certain embodiments, a viral genome may comprise two filler sequences, the first filler sequence may be located between the promoter region and intron region, and the second filler sequence may be located between the intron region and polyadenylation signal sequence region. In certain embodiments, a viral genome may comprise two filler sequences, the first filler sequence may be located between the promoter region and intron region, and the second filler sequence may be located between the intron region and MCS region. In certain embodiments, a viral genome may comprise two filler sequences, the first filler sequence may be located between the promoter region and intron region, and the second filler sequence may be located between the intron region and exon region. In certain embodiments, a viral genome may comprise two filler sequences, the first filler sequence may be located between the promoter region and intron region, and the second filler sequence may be located between the intron region and 3' ITR. In certain embodiments, a viral genome may comprise two filler sequences, the first filler sequence may be located between the promoter region and intron region, and the second filler sequence may be located between the enhancer region and polyadenylation signal sequence region. In certain embodiments, a viral genome may comprise two filler sequences, the first filler sequence may be located between the promoter region and intron region, and the second filler sequence may be located between the enhancer region and MCS region. In certain embodiments, a viral genome may comprise two filler sequences, the first filler sequence may be located between the promoter region and intron region, and the second filler sequence may be located between the enhancer region and exon region. In certain embodiments, a viral genome may comprise two filler sequences, the first filler sequence may be located between the promoter region and intron region, and the second filler sequence may be located between the enhancer region and 3' ITR. In certain embodiments, a viral genome may comprise two filler sequences, the first filler sequence may be located between the promoter region and intron region, and the second filler sequence may be located between the polyadenylation signal sequence region and MCS region. In certain embodiments, a viral genome may comprise two filler sequences, the first filler sequence may be located between the promoter region and intron region, and the second filler sequence may be located between the polyadenylation signal sequence region and exon region. In certain embodiments, a viral genome may comprise two filler sequences, the first filler sequence may be located between the promoter region and intron region, and the second filler sequence may be located between the polyadenylation signal sequence region and 3' ITR. In certain embodiments, a viral genome may comprise two filler sequences, the first filler sequence may be located between the promoter region and intron region, and the second filler sequence may be located between the MCS region and exon region. In certain embodiments, a viral genome may comprise two filler sequences, the first filler sequence may be located between the promoter region and intron region, and the second filler sequence may be located between the MCS region and 3' ITR. In certain embodiments, a viral genome may comprise two filler sequences, the first filler sequence may be located between the promoter region and intron region, and the second filler sequence may be located between the exon region and 3' ITR In certain embodiments, a viral genome may comprise two filler sequences, the first filler sequence may be located between the promoter region and enhancer region, and the second filler sequence may be located between the payload region and intron region. In certain embodiments, a viral genome may comprise two filler sequences, the first filler sequence may be located between the promoter region and enhancer region, and the second filler sequence may be located between the payload region and enhancer region. In certain embodiments, a viral genome may comprise two filler sequences, the first filler sequence may be located between the promoter region and enhancer region, and the second filler sequence may be located between the payload region and polyadenylation signal sequence region. In certain embodiments, a viral genome may comprise two filler sequences, the first filler sequence may be located between the promoter region and enhancer region, and the second filler sequence may be located between the payload region and MCS region. In certain embodiments, a viral genome may comprise two filler sequences, the first filler sequence may be located between the promoter region and enhancer region, and the second filler sequence may be located between the payload region and exon region. In certain embodiments, a viral genome may comprise two filler sequences, the first filler sequence may be located between the promoter region and enhancer region, and the second filler sequence may be located between the payload region and 3' ITR. In certain embodiments, a viral genome may comprise two filler sequences, the first filler sequence may be located between the promoter region and enhancer region, and the second filler sequence may be located between the intron region and enhancer region. In certain embodiments, a viral genome may comprise two filler sequences, the first filler sequence may be located between the promoter region and enhancer region, and the second filler sequence may be located between the intron region and polyadenylation signal sequence region. In certain embodiments, a viral genome may comprise two filler sequences, the first filler sequence may be located between the promoter region and enhancer region, and the second filler sequence may be located between the intron region and MCS region. In certain embodiments, a viral genome may comprise two filler sequences, the first filler sequence may be located between the promoter region and enhancer region, and the second filler sequence may be located between the intron region and exon region. In certain embodiments, a viral genome may comprise two filler sequences, the first filler sequence may be located between the promoter region and enhancer region, and the second filler sequence may be located between the intron region and 3' ITR. In certain embodiments, a viral genome may comprise two filler sequences, the first filler sequence may be located between the promoter region and enhancer region, and the second filler sequence may be located between the enhancer region and polyadenylation signal sequence region. In certain embodiments, a viral genome may comprise two filler sequences, the first filler sequence may be located between the promoter region and enhancer region, and the second filler sequence may be located between the enhancer region and MCS region. In certain embodiments, a viral genome may comprise two filler sequences, the first filler sequence may be located between the promoter region and enhancer region, and the second filler sequence may be located between the enhancer region and exon region. In certain embodiments, a viral genome may comprise two filler sequences, the first filler sequence may be located between the promoter region and enhancer region, and the second filler sequence may be located between the enhancer region and 3' ITR. In certain embodiments, a viral genome may comprise two filler sequences, the first filler sequence may be located between the promoter region and enhancer region, and the second filler sequence may be located between the polyadenylation signal sequence region and MCS region. In certain embodiments, a viral genome may comprise two filler sequences, the first filler sequence may be located between the promoter region and enhancer region, and the second filler sequence may be located between the polyadenylation signal sequence region and exon region. In certain embodiments, a viral genome may comprise two filler sequences, the first filler sequence may be located between the promoter region and enhancer region, and the second filler sequence may be located between the polyadenylation signal sequence region and 3' ITR. In certain embodiments, a viral genome may comprise two filler sequences, the first filler sequence may be located between the promoter region and enhancer region, and the second filler sequence may be located between the MCS region and exon region. In certain embodiments, a viral genome may comprise two filler sequences, the first filler sequence may be located between the promoter region and enhancer region, and the second filler sequence may be located between the MCS region and 3' ITR. In certain embodiments, a viral genome may comprise two filler sequences, the first filler sequence may be located between the promoter region and enhancer region, and the second filler sequence may be located between the exon region and 3' ITR.

In certain embodiments, a viral genome may comprise two filler sequences, the first filler sequence may be located between the promoter region and polyadenylation signal sequence region, and the second filler sequence may be located between the payload region and intron region. In certain embodiments, a viral genome may comprise two filler sequences, the first filler sequence may be located between the promoter region and polyadenylation signal sequence region, and the second filler sequence may be located between the payload region and enhancer region. In certain embodiments, a viral genome may comprise two filler sequences, the first filler sequence may be located between the promoter region and polyadenylation signal sequence region, and the second filler sequence may be located between the payload region and polyadenylation signal sequence region. In certain embodiments, a viral genome may comprise two filler sequences, the first filler sequence may be located between the promoter region and polyadenylation signal sequence region, and the second filler sequence may be located between the payload region and MCS region. In certain embodiments, a viral genome may comprise two filler sequences, the first filler sequence may be located between the promoter region and polyadenylation signal sequence region, and the second filler sequence may be located between the payload region and exon region. In certain embodiments, a viral genome may comprise two filler sequences, the first filler sequence may be located between the promoter region and polyadenylation signal sequence region, and the second filler sequence may be located between the payload region and 3' ITR. In certain embodiments, a viral genome may comprise two filler sequences, the first filler sequence may be located between the promoter region and polyadenylation signal sequence region, and the second filler sequence may be located between the intron region and enhancer region. In certain embodiments, a viral genome may comprise two filler sequences, the first filler sequence may be located between the promoter region and polyadenylation signal sequence region, and the second filler sequence may be located between the intron region and polyadenylation signal sequence region. In certain embodiments, a viral genome may comprise two filler sequences, the first filler sequence may be located between the promoter region and polyadenylation signal sequence region, and the second filler sequence may be located between the intron region and MCS region. In certain embodiments, a viral genome may comprise two filler sequences, the first filler sequence may be located between the promoter region and polyadenylation signal sequence region, and the second filler sequence may be located between the intron region and exon region. In certain embodiments, a viral genome may comprise two filler sequences, the first filler sequence may be located between the promoter region and polyadenylation signal sequence region, and the second filler sequence may be located between the intron region and 3' ITR. In certain embodiments, a viral genome may comprise two filler sequences, the first filler sequence may be located between the promoter region and polyadenylation signal sequence region, and the second filler sequence may be located between the enhancer region and polyadenylation signal sequence region. In certain embodiments, a viral genome may comprise two filler sequences, the first filler sequence may be located between the promoter region and polyadenylation signal sequence region, and the second filler sequence may be located between the enhancer region and MCS region. In certain embodiments, a viral genome may comprise two filler sequences, the first filler sequence may be located between the promoter region and polyadenylation signal sequence region, and the second filler sequence may be located between the enhancer region and exon region. In certain embodiments, a viral genome may comprise two filler sequences, the first filler sequence may be located between the promoter region and polyadenylation signal sequence region, and the second filler sequence may be located between the enhancer region and 3' ITR. In certain embodiments, a viral genome may comprise two filler sequences, the first filler sequence may be located between the promoter region and polyadenylation signal sequence region, and the second filler sequence may be located between the polyadenylation signal sequence region and MCS region. In certain embodiments, a viral genome may comprise two filler sequences, the first filler sequence may be located between the promoter region and polyadenylation signal sequence region, and the second filler sequence may be located between the polyadenylation signal sequence region and exon region. In certain embodiments, a viral genome may comprise two filler sequences, the first filler sequence may be located between the promoter region and polyadenylation signal sequence region, and the second filler sequence may be located between the polyadenylation signal sequence region and 3' ITR. In certain embodiments, a viral genome may comprise two filler sequences, the first filler sequence may be located between the promoter region and polyadenylation signal sequence region, and the second filler sequence may be located between the MCS region and exon region. In certain embodiments, a viral genome may comprise two filler sequences, the first filler sequence may be located between the promoter region and polyadenylation signal sequence region, and the second filler sequence may be located between the MCS region and 3' ITR. In certain embodiments, a viral genome may comprise two filler sequences, the first filler sequence may be located between the promoter region and polyadenylation signal sequence region, and the second filler sequence may be located between the exon region and 3' ITR.

In certain embodiments, a viral genome may comprise two filler sequences, the first filler sequence may be located between the promoter region and exon region, and the second filler sequence may be located between the payload region and intron region. In certain embodiments, a viral genome may comprise two filler sequences, the first filler sequence may be located between the promoter region and exon region, and the second filler sequence may be located between the payload region and enhancer region. In certain embodiments, a viral genome may comprise two filler sequences, the first filler sequence may be located between the promoter region and exon region, and the second filler sequence may be located between the payload region and polyadenylation signal sequence region. In certain embodiments, a viral genome may comprise two filler sequences, the first filler sequence may be located between the promoter region and exon region, and the second filler sequence may be located between the payload region and MCS region. In certain embodiments, a viral genome may comprise two filler sequences, the first filler sequence may be located between the promoter region and exon region, and the second filler sequence may be located between the payload region and exon region. In certain embodiments, a viral genome may comprise two filler sequences, the first filler sequence may be located between the promoter region and exon region, and the second filler sequence may be located between the payload region and 3' ITR. In certain embodiments, a viral genome may comprise two filler sequences, the first filler sequence may be located between the promoter region and exon region, and the second filler sequence may be located between the intron region and enhancer region. In certain embodiments, a viral genome may comprise two filler sequences, the first filler sequence may be located between the promoter region and exon region, and the second filler sequence may be located between the intron region and polyadenylation signal sequence region. In certain embodiments, a viral genome may comprise two filler sequences, the first filler sequence may be located between the promoter region and exon region, and the second filler sequence may be located between the intron region and MCS region. In certain embodiments, a viral genome may comprise two filler sequences, the first filler sequence may be located between the promoter region and exon region, and the second filler sequence may be located between the intron region and exon region. In certain embodiments, a viral genome may comprise two filler sequences, the first filler sequence may be located between the promoter region and exon region, and the second filler sequence may be located between the intron region and 3' ITR. In certain embodiments, a viral genome may comprise two filler sequences, the first filler sequence may be located between the promoter region and exon region, and the second filler sequence may be located between the enhancer region and polyadenylation signal sequence region. In certain embodiments, a viral genome may comprise two filler sequences, the first filler sequence may be located between the promoter region and exon region, and the second filler sequence may be located between the enhancer region and MCS region. In certain embodiments, a viral genome may comprise two filler sequences, the first filler sequence may be located between the promoter region and exon region, and the second filler sequence may be located between the enhancer region and exon region. In certain embodiments, a viral genome may comprise two filler sequences, the first filler sequence may be located between the promoter region and exon region, and the second filler sequence may be located between the enhancer region and 3' ITR. In certain embodiments, a viral genome may comprise two filler sequences, the first filler sequence may be located between the promoter region and exon region, and the second filler sequence may be located between the polyadenylation signal sequence region and MCS region. In certain embodiments, a viral genome may comprise two filler sequences, the first filler sequence may be located between the promoter region and exon region, and the second filler sequence may be located between the polyadenylation signal sequence region and exon region. In certain embodiments, a viral genome may comprise two filler sequences, the first filler sequence may be located between the promoter region and exon region, and the second filler sequence may be located between the polyadenylation signal sequence region and 3' ITR. In certain embodiments, a viral genome may comprise two filler sequences, the first filler sequence may be located between the promoter region and exon region, and the second filler sequence may be located between the MCS region and exon region. In certain embodiments, a viral genome may comprise two filler sequences, the first filler sequence may be located between the promoter region and exon region, and the second filler sequence may be located between the MCS region and 3' ITR. In certain embodiments, a viral genome may comprise two filler sequences, the first filler sequence may be located between the promoter region and exon region, and the second filler sequence may be located between the exon region and 3' ITR.

In certain embodiments, a viral genome may comprise two filler sequences, the first filler sequence may be located between the promoter region and MCS region, and the second filler sequence may be located between the payload region and intron region. In certain embodiments, a viral genome may comprise two filler sequences, the first filler sequence may be located between the promoter region and MCS region, and the second filler sequence may be located between the payload region and enhancer region. In certain embodiments, a viral genome may comprise two filler sequences, the first filler sequence may be located between the promoter region and MCS region, and the second filler sequence may be located between the payload region and polyadenylation signal sequence region. In certain embodiments, a viral genome may comprise two filler sequences, the first filler sequence may be located between the promoter region and MCS region, and the second filler sequence may be located between the payload region and MCS region. In certain embodiments, a viral genome may comprise two filler sequences, the first filler sequence may be located between the promoter region and MCS region, and the second filler sequence may be located between the payload region and exon region. In certain embodiments, a viral genome may comprise two filler sequences, the first filler sequence may be located between the promoter region and MCS region, and the second filler sequence may be located between the payload region and 3' ITR. In certain embodiments, a viral genome may comprise two filler sequences, the first filler sequence may be located between the promoter region and MCS region, and the second filler sequence may be located between the intron region and enhancer region. In certain embodiments, a viral genome may comprise two filler sequences, the first filler sequence may be located between the promoter region and MCS region, and the second filler sequence may be located between the intron region and polyadenylation signal sequence region. In certain embodiments, a viral genome may comprise two filler sequences, the first filler sequence may be located between the promoter region and MCS region, and the second filler sequence may be located between the intron region and MCS region. In certain embodiments, a viral genome may comprise two filler sequences, the first filler sequence may be located between the promoter region and MCS region, and the second filler sequence may be located between the intron region and exon region. In certain embodiments, a viral genome may comprise two filler sequences, the first filler sequence may be located between the promoter region and MCS region, and the second filler sequence may be located between the intron region and 3' ITR. In certain embodiments, a viral genome may comprise two filler sequences, the first filler sequence may be located between the promoter region and MCS region, and the second filler sequence may be located between the enhancer region and polyadenylation signal sequence region. In certain embodiments, a viral genome may comprise two filler sequences, the first filler sequence may be located between the promoter region and MCS region, and the second filler sequence may be located between the enhancer region and MCS region. In certain embodiments, a viral genome may comprise two filler sequences, the first filler sequence may be located between the promoter region and MCS region, and the second filler sequence may be located between the enhancer region and exon region. In certain embodiments, a viral genome may comprise two filler sequences, the first filler sequence may be located between the promoter region and MCS region, and the second filler sequence may be located between the enhancer region and 3' ITR. In certain embodiments, a viral genome may comprise two filler sequences, the first filler sequence may be located between the promoter region and MCS region, and the second filler sequence may be located between the polyadenylation signal sequence region and MCS region. In certain embodiments, a viral genome may comprise two filler sequences, the first filler sequence may be located between the promoter region and MCS region, and the second filler sequence may be located between the polyadenylation signal sequence region and exon region. In certain embodiments, a viral genome may comprise two filler sequences, the first filler sequence may be located between the promoter region and MCS region, and the second filler sequence may be located between the polyadenylation signal sequence region and 3' ITR. In certain embodiments, a viral genome may comprise two filler sequences, the first filler sequence may be located between the promoter region and MCS region, and the second filler sequence may be located between the MCS region and exon region. In certain embodiments, a viral genome may comprise two filler sequences, the first filler sequence may be located between the promoter region and MCS region, and the second filler sequence may be located between the MCS region and 3' ITR. In certain embodiments, a viral genome may comprise two filler sequences, the first filler sequence may be located between the promoter region and MCS region, and the second filler sequence may be located between the exon region and 3' ITR.

In certain embodiments, a viral genome may comprise two filler sequences, the first filler sequence may be located between the promoter region and 3'ITR, and the second filler sequence may be located between the payload region and intron region. In certain embodiments, a viral genome may comprise two filler sequences, the first filler sequence may be located between the promoter region and 3'ITR, and the second filler sequence may be located between the payload region and enhancer region. In certain embodiments, a viral genome may comprise two filler sequences, the first filler sequence may be located between the promoter region and 3'ITR, and the second filler sequence may be located between the payload region and polyadenylation signal sequence region. In certain embodiments, a viral genome may comprise two filler sequences, the first filler sequence may be located between the promoter region and 3'ITR and the second filler sequence may be located between the payload region and MCS region. In certain embodiments, a viral genome may comprise two filler sequences, the first filler sequence may be located between the promoter region and 3'ITR, and the second filler sequence may be located between the payload region and exon region. In certain embodiments, a viral genome may comprise two filler sequences, the first filler sequence may be located between the promoter region and 3'ITR, and the second filler sequence may be located between the payload region and 3' ITR. In certain embodiments, a viral genome may comprise two filler sequences, the first filler sequence may be located between the promoter region and 3'ITR, and the second filler sequence may be located between the intron region and enhancer region. In certain embodiments, a viral genome may comprise two filler sequences, the first filler sequence may be located between the promoter region and 3'ITR, and the second filler sequence may be located between the intron region and polyadenylation signal sequence region. In certain embodiments, a viral genome may comprise two filler sequences, the first filler sequence may be located between the promoter region and 3'ITR, and the second filler sequence may be located between the intron region and MCS region. In certain embodiments, a viral genome may comprise two filler sequences, the first filler sequence may be located between the promoter region and 3'ITR, and the second filler sequence may be located between the intron region and exon region. In certain embodiments, a viral genome may comprise two filler sequences, the first filler sequence may be located between the promoter region and 3'ITR, and the second filler sequence may be located between the intron region and 3' ITR. In certain embodiments, a viral genome may comprise two filler sequences, the first filler sequence may be located between the promoter region and 3'ITR, and the second filler sequence may be located between the enhancer region and polyadenylation signal sequence region. In certain embodiments, a viral genome may comprise two filler sequences, the first filler sequence may be located between the promoter region and 3'ITR, and the second filler sequence may be located between the enhancer region and MCS region. In certain embodiments, a viral genome may comprise two filler sequences, the first filler sequence may be located between the promoter region and 3'ITR, and the second filler sequence may be located between the enhancer region and exon region. In certain embodiments, a viral genome may comprise two filler sequences, the first filler sequence may be located between the promoter region and 3'ITR, and the second filler sequence may be located between the enhancer region and 3' ITR. In certain embodiments, a viral genome may comprise two filler sequences, the first filler sequence may be located between the promoter region and 3'ITR, and the second filler sequence may be located between the polyadenylation signal sequence region and MCS region. In certain embodiments, a viral genome may comprise two filler sequences, the first filler sequence may be located between the promoter region and 3'ITR, and the second filler sequence may be located between the polyadenylation signal sequence region and exon region. In certain embodiments, a viral genome may comprise two filler sequences, the first filler sequence may be located between the promoter region and 3'ITR, and the second filler sequence may be located between the polyadenylation signal sequence region and 3' ITR. In certain embodiments, a viral genome may comprise two filler sequences, the first filler sequence may be located between the promoter region and 3'ITR, and the second filler sequence may be located between the MCS region and exon region. In certain embodiments, a viral genome may comprise two filler sequences, the first filler sequence may be located between the promoter region and 3'ITR, and the second filler sequence may be located between the MCS region and 3' ITR. In certain embodiments, a viral genome may comprise two filler sequences, the first filler sequence may be located between the promoter region and 3'ITR, and the second filler sequence may be located between the exon region and 3' ITR.

In certain embodiments, a viral genome may comprise two filler sequences, the first filler sequence may be located between the payload region and intron region, and the second filler sequence may be located between the intron region and enhancer region. In certain embodiments, a viral genome may comprise two filler sequences, the first filler sequence may be located between the payload region and intron region, and the second filler sequence may be located between the intron region and polyadenylation signal sequence region. In certain embodiments, a viral genome may comprise two filler sequences, the first filler sequence may be located between the payload region and intron region, and the second filler sequence may be located between the intron region and MCS region. In certain embodiments, a viral genome may comprise two filler sequences, the first filler sequence may be located between the payload region and intron region, and the second filler sequence may be located between the intron region and exon region. In certain embodiments, a viral genome may comprise two filler sequences, the first filler sequence may be located between the payload region and intron region, and the second filler sequence may be located between the intron region and 3' ITR. In certain embodiments, a viral genome may comprise two filler sequences, the first filler sequence may be located between the payload region and intron region, and the second filler sequence may be located between the enhancer region and polyadenylation signal sequence region. In certain embodiments, a viral genome may comprise two filler sequences, the first filler sequence may be located between the payload region and intron region, and the second filler sequence may be located between the enhancer region and MCS region. In certain embodiments, a viral genome may comprise two filler sequences, the first filler sequence may be located between the payload region and intron region, and the second filler sequence may be located between the enhancer region and exon region. In certain embodiments, a viral genome may comprise two filler sequences, the first filler sequence may be located between the payload region and intron region, and the second filler sequence may be located between the enhancer region and 3' ITR. In certain embodiments, a viral genome may comprise two filler sequences, the first filler sequence may be located between the payload region and intron region, and the second filler sequence may be located between the polyadenylation signal sequence region and MCS region. In certain embodiments, a viral genome may comprise two filler sequences, the first filler sequence may be located between the payload region and intron region, and the second filler sequence may be located between the polyadenylation signal sequence region and exon region. In certain embodiments, a viral genome may comprise two filler sequences, the first filler sequence may be located between the payload region and intron region, and the second filler sequence may be located between the polyadenylation signal sequence region and 3' ITR. In certain embodiments, a viral genome may comprise two filler sequences, the first filler sequence may be located between the payload region and intron region, and the second filler sequence may be located between the MCS region and exon region. In certain embodiments, a viral genome may comprise two filler sequences, the first filler sequence may be located between the payload region and intron region, and the second filler sequence may be located between the MCS region and 3' ITR. In certain embodiments, a viral genome may comprise two filler sequences, the first filler sequence may be located between the payload region and intron region, and the second filler sequence may be located between the exon region and 3' ITR.

In certain embodiments, a viral genome may comprise two filler sequences, the first filler sequence may be located between the payload region and enhancer region, and the second filler sequence may be located between the intron region and enhancer region. In certain embodiments, a viral genome may comprise two filler sequences, the first filler sequence may be located between the payload region and enhancer region, and the second filler sequence may be located between the intron region and polyadenylation signal sequence region. In certain embodiments, a viral genome may comprise two filler sequences, the first filler sequence may be located between the payload region and enhancer region, and the second filler sequence may be located between the intron region and MCS region. In certain embodiments, a viral genome may comprise two filler sequences, the first filler sequence may be located between the payload region and enhancer region, and the second filler sequence may be located between the intron region and exon region. In certain embodiments, a viral genome may comprise two filler sequences, the first filler sequence may be located between the payload region and enhancer region, and the second filler sequence may be located between the intron region and 3' ITR. In certain embodiments, a viral genome may comprise two filler sequences, the first filler sequence may be located between the payload region and enhancer region, and the second filler sequence may be located between the enhancer region and polyadenylation signal sequence region. In certain embodiments, a viral genome may comprise two filler sequences, the first filler sequence may be located between the payload region and enhancer region, and the second filler sequence may be located between the enhancer region and MCS region. In certain embodiments, a viral genome may comprise two filler sequences, the first filler sequence may be located between the payload region and enhancer region, and the second filler sequence may be located between the enhancer region and exon region. In certain embodiments, a viral genome may comprise two filler sequences, the first filler sequence may be located between the payload region and enhancer region, and the second filler sequence may be located between the enhancer region and 3' ITR. In certain embodiments, a viral genome may comprise two filler sequences, the first filler sequence may be located between the payload region and enhancer region, and the second filler sequence may be located between the polyadenylation signal sequence region and MCS region. In certain embodiments, a viral genome may comprise two filler sequences, the first filler sequence may be located between the payload region and enhancer region, and the second filler sequence may be located between the polyadenylation signal sequence region and exon region. In certain embodiments, a viral genome may comprise two filler sequences, the first filler sequence may be located between the payload region and enhancer region, and the second filler sequence may be located between the polyadenylation signal sequence region and 3' ITR. In certain embodiments, a viral genome may comprise two filler sequences, the first filler sequence may be located between the payload region and enhancer region, and the second filler sequence may be located between the MCS region and exon region. In certain embodiments, a viral genome may comprise two filler sequences, the first filler sequence may be located between the payload region and enhancer region, and the second filler sequence may be located between the MCS region and 3' ITR. In certain embodiments, a viral genome may comprise two filler sequences, the first filler sequence may be located between the payload region and enhancer region, and the second filler sequence may be located between the exon region and 3' ITR.

In certain embodiments, a viral genome may comprise two filler sequences, the first filler sequence may be located between the payload region and polyadenylation signal sequence region, and the second filler sequence may be located between the intron region and enhancer region. In certain embodiments, a viral genome may comprise two filler sequences, the first filler sequence may be located between the payload region and polyadenylation signal sequence region, and the second filler sequence may be located between the intron region and polyadenylation signal sequence region. In certain embodiments, a viral genome may comprise two filler sequences, the first filler sequence may be located between the payload region and polyadenylation signal sequence region, and the second filler sequence may be located between the intron region and MCS region. In certain embodiments, a viral genome may comprise two filler sequences, the first filler sequence may be located between the payload region and polyadenylation signal sequence region, and the second filler sequence may be located between the intron region and exon region. In certain embodiments, a viral genome may comprise two filler sequences, the first filler sequence may be located between the payload region and polyadenylation signal sequence region, and the second filler sequence may be located between the intron region and 3' ITR. In certain embodiments, a viral genome may comprise two filler sequences, the first filler sequence may be located between the payload region and polyadenylation signal sequence region, and the second filler sequence may be located between the enhancer region and polyadenylation signal sequence region. In certain embodiments, a viral genome may comprise two filler sequences, the first filler sequence may be located between the payload region and polyadenylation signal sequence region, and the second filler sequence may be located between the enhancer region and MCS region. In certain embodiments, a viral genome may comprise two filler sequences, the first filler sequence may be located between the payload region and polyadenylation signal sequence region, and the second filler sequence may be located between the enhancer region and exon region. In certain embodiments, a viral genome may comprise two filler sequences, the first filler sequence may be located between the payload region and polyadenylation signal sequence region, and the second filler sequence may be located between the enhancer region and 3' ITR. In certain embodiments, a viral genome may comprise two filler sequences, the first filler sequence may be located between the payload region and polyadenylation signal sequence region, and the second filler sequence may be located between the polyadenylation signal sequence region and MCS region. In certain embodiments, a viral genome may comprise two filler sequences, the first filler sequence may be located between the payload region and polyadenylation signal sequence region, and the second filler sequence may be located between the polyadenylation signal sequence region and exon region. In certain embodiments, a viral genome may comprise two filler sequences, the first filler sequence may be located between the payload region and polyadenylation signal sequence region, and the second filler sequence may be located between the polyadenylation signal sequence region and 3' ITR. In certain embodiments, a viral genome may comprise two filler sequences, the first filler sequence may be located between the payload region and polyadenylation signal sequence region, and the second filler sequence may be located between the MCS region and exon region. In certain embodiments, a viral genome may comprise two filler sequences, the first filler sequence may be located between the payload region and polyadenylation signal sequence region, and the second filler sequence may be located between the MCS region and 3' ITR. In certain embodiments, a viral genome may comprise two filler sequences, the first filler sequence may be located between the payload region and polyadenylation signal sequence region, and the second filler sequence may be located between the exon region and 3' ITR In certain embodiments, a viral genome may comprise two filler sequences, the first filler sequence may be located between the payload region and MCS region, and the second filler sequence may be located between the intron region and enhancer region. In certain embodiments, a viral genome may comprise two filler sequences, the first filler sequence may be located between the payload region and MCS region, and the second filler sequence may be located between the intron region and polyadenylation signal sequence region. In certain embodiments, a viral genome may comprise two filler sequences, the first filler sequence may be located between the payload region and MCS region, and the second filler sequence may be located between the intron region and MCS region. In certain embodiments, a viral genome may comprise two filler sequences, the first filler sequence may be located between the payload region and MCS region, and the second filler sequence may be located between the intron region and exon region. In certain embodiments, a viral genome may comprise two filler sequences, the first filler sequence may be located between the payload region and MCS region, and the second filler sequence may be located between the intron region and 3' ITR. In certain embodiments, a viral genome may comprise two filler sequences, the first filler sequence may be located between the payload region and MCS region, and the second filler sequence may be located between the enhancer region and polyadenylation signal sequence region. In certain embodiments, a viral genome may comprise two filler sequences, the first filler sequence may be located between the payload region and MCS region, and the second filler sequence may be located between the enhancer region and MCS region. In certain embodiments, a viral genome may comprise two filler sequences, the first filler sequence may be located between the payload region and MCS region, and the second filler sequence may be located between the enhancer region and exon region. In certain embodiments, a viral genome may comprise two filler sequences, the first filler sequence may be located between the payload region and MCS region, and the second filler sequence may be located between the enhancer region and 3' ITR. In certain embodiments, a viral genome may comprise two filler sequences, the first filler sequence may be located between the payload region and MCS region, and the second filler sequence may be located between the polyadenylation signal sequence region and MCS region. In certain embodiments, a viral genome may comprise two filler sequences, the first filler sequence may be located between the payload region and MCS region, and the second filler sequence may be located between the polyadenylation signal sequence region and exon region. In certain embodiments, a viral genome may comprise two filler sequences, the first filler sequence may be located between the payload region and MCS region, and the second filler sequence may be located between the polyadenylation signal sequence region and 3' ITR. In certain embodiments, a viral genome may comprise two filler sequences, the first filler sequence may be located between the payload region and MCS region, and the second filler sequence may be located between the MCS region and exon region. In certain embodiments, a viral genome may comprise two filler sequences, the first filler sequence may be located between the payload region and MCS region, and the second filler sequence may be located between the MCS region and 3' ITR. In certain embodiments, a viral genome may comprise two filler sequences, the first filler sequence may be located between the payload region and MCS region, and the second filler sequence may be located between the exon region and 3' ITR.

In certain embodiments, a viral genome may comprise two filler sequences, the first filler sequence may be located between the payload region and exon region, and the second filler sequence may be located between the intron region and enhancer region. In certain embodiments, a viral genome may comprise two filler sequences, the first filler sequence may be located between the payload region and exon region, and the second filler sequence may be located between the intron region and polyadenylation signal sequence region. In certain embodiments, a viral genome may comprise two filler sequences, the first filler sequence may be located between the payload region and exon region, and the second filler sequence may be located between the intron region and MCS region. In certain embodiments, a viral genome may comprise two filler sequences, the first filler sequence may be located between the payload region and exon region, and the second filler sequence may be located between the intron region and exon region. In certain embodiments, a viral genome may comprise two filler sequences, the first filler sequence may be located between the payload region and exon region, and the second filler sequence may be located between the intron region and 3' ITR. In certain embodiments, a viral genome may comprise two filler sequences, the first filler sequence may be located between the payload region and exon region, and the second filler sequence may be located between the enhancer region and polyadenylation signal sequence region. In certain embodiments, a viral genome may comprise two filler sequences, the first filler sequence may be located between the payload region and exon region, and the second filler sequence may be located between the enhancer region and MCS region. In certain embodiments, a viral genome may comprise two filler sequences, the first filler sequence may be located between the payload region and exon region, and the second filler sequence may be located between the enhancer region and exon region. In certain embodiments, a viral genome may comprise two filler sequences, the first filler sequence may be located between the payload region and exon region, and the second filler sequence may be located between the enhancer region and 3' ITR. In certain embodiments, a viral genome may comprise two filler sequences, the first filler sequence may be located between the payload region and exon region, and the second filler sequence may be located between the polyadenylation signal sequence region and MCS region. In certain embodiments, a viral genome may comprise two filler sequences, the first filler sequence may be located between the payload region and exon region, and the second filler sequence may be located between the polyadenylation signal sequence region and exon region. In certain embodiments, a viral genome may comprise two filler sequences, the first filler sequence may be located between the payload region and exon region, and the second filler sequence may be located between the polyadenylation signal sequence region and 3' ITR. In certain embodiments, a viral genome may comprise two filler sequences, the first filler sequence may be located between the payload region and exon region, and the second filler sequence may be located between the MCS region and exon region. In certain embodiments, a viral genome may comprise two filler sequences, the first filler sequence may be located between the payload region and exon region, and the second filler sequence may be located between the MCS region and 3' ITR. In certain embodiments, a viral genome may comprise two filler sequences, the first filler sequence may be located between the payload region and exon region, and the second filler sequence may be located between the exon region and 3' ITR.

In certain embodiments, a viral genome may comprise two filler sequences, the first filler sequence may be located between the payload region and 3' ITR region, and the second filler sequence may be located between the intron region and enhancer region. In certain embodiments, a viral genome may comprise two filler sequences, the first filler sequence may be located between the payload region and 3' ITR region, and the second filler sequence may be located between the intron region and polyadenylation signal sequence region. In certain embodiments, a viral genome may comprise two filler sequences, the first filler sequence may be located between the payload region and 3' ITR region, and the second filler sequence may be located between the intron region and MCS region. In certain embodiments, a viral genome may comprise two filler sequences, the first filler sequence may be located between the payload region and 3' ITR region, and the second filler sequence may be located between the intron region and exon region. In certain embodiments, a viral genome may comprise two filler sequences, the first filler sequence may be located between the payload region and 3' ITR region, and the second filler sequence may be located between the intron region and 3' ITR. In certain embodiments, a viral genome may comprise two filler sequences, the first filler sequence may be located between the payload region and 3' ITR region, and the second filler sequence may be located between the enhancer region and polyadenylation signal sequence region. In certain embodiments, a viral genome may comprise two filler sequences, the first filler sequence may be located between the payload region and 3' ITR region, and the second filler sequence may be located between the enhancer region and MCS region. In certain embodiments, a viral genome may comprise two filler sequences, the first filler sequence may be located between the payload region and 3' ITR region, and the second filler sequence may be located between the enhancer region and exon region. In certain embodiments, a viral genome may comprise two filler sequences, the first filler sequence may be located between the payload region and 3' ITR region, and the second filler sequence may be located between the enhancer region and 3' ITR. In certain embodiments, a viral genome may comprise two filler sequences, the first filler sequence may be located between the payload region and 3' ITR region, and the second filler sequence may be located between the polyadenylation signal sequence region and MCS region. In certain embodiments, a viral genome may comprise two filler sequences, the first filler sequence may be located between the payload region and 3' ITR region, and the second filler sequence may be located between the polyadenylation signal sequence region and exon region. In certain embodiments, a viral genome may comprise two filler sequences, the first filler sequence may be located between the payload region and 3' ITR region, and the second filler sequence may be located between the polyadenylation signal sequence region and 3' ITR. In certain embodiments, a viral genome may comprise two filler sequences, the first filler sequence may be located between the payload region and 3' ITR region, and the second filler sequence may be located between the MCS region and exon region. In certain embodiments, a viral genome may comprise two filler sequences, the first filler sequence may be located between the payload region and 3' ITR region, and the second filler sequence may be located between the MCS region and 3' ITR. In certain embodiments, a viral genome may comprise two filler sequences, the first filler sequence may be located between the payload region and 3' ITR region, and the second filler sequence may be located between the exon region and 3' ITR.

In certain embodiments, a viral genome may comprise two filler sequences, the first filler sequence may be located between the intron region and enhancer region, and the second filler sequence may be located between the enhancer region and polyadenylation signal sequence region. In certain embodiments, a viral genome may comprise two filler sequences, the first filler sequence may be located between the intron region and enhancer region, and the second filler sequence may be located between the enhancer region and MCS region. In certain embodiments, a viral genome may comprise two filler sequences, the first filler sequence may be located between the intron region and enhancer region, and the second filler sequence may be located between the enhancer region and exon region. In certain embodiments, a viral genome may comprise two filler sequences, the first filler sequence may be located between the intron region and enhancer region, and the second filler sequence may be located between the enhancer region and 3' ITR. In certain embodiments, a viral genome may comprise two filler sequences, the first filler sequence may be located between the intron region and enhancer region, and the second filler sequence may be located between the polyadenylation signal sequence region and MCS region. In certain embodiments, a viral genome may comprise two filler sequences, the first filler sequence may be located between the intron region and enhancer region, and the second filler sequence may be located between the polyadenylation signal sequence region and exon region. In certain embodiments, a viral genome may comprise two filler sequences, the first filler sequence may be located between the intron region and enhancer region, and the second filler sequence may be located between the polyadenylation signal sequence region and 3' ITR. In certain embodiments, a viral genome may comprise two filler sequences, the first filler sequence may be located between the intron region and enhancer region, and the second filler sequence may be located between the MCS region and exon region. In certain embodiments, a viral genome may comprise two filler sequences, the first filler sequence may be located between the intron region and enhancer region, and the second filler sequence may be located between the MCS region and 3' ITR. In certain embodiments, a viral genome may comprise two filler sequences, the first filler sequence may be located between the intron region and enhancer region, and the second filler sequence may be located between the exon region and 3' ITR.

In certain embodiments, a viral genome may comprise two filler sequences, the first filler sequence may be located between the intron region and polyadenylation signal sequence region, and the second filler sequence may be located between the enhancer region and polyadenylation signal sequence region. In certain embodiments, a viral genome may comprise two filler sequences, the first filler sequence may be located between the intron region and polyadenylation signal sequence region, and the second filler sequence may be located between the enhancer region and MCS region. In certain embodiments, a viral genome may comprise two filler sequences, the first filler sequence may be located between the intron region and polyadenylation signal sequence region, and the second filler sequence may be located between the enhancer region and exon region. In certain embodiments, a viral genome may comprise two filler sequences, the first filler sequence may be located between the intron region and polyadenylation signal sequence region, and the second filler sequence may be located between the enhancer region and 3' ITR. In certain embodiments, a viral genome may comprise two filler sequences, the first filler sequence may be located between the intron region and polyadenylation signal sequence region, and the second filler sequence may be located between the polyadenylation signal sequence region and MCS region. In certain embodiments, a viral genome may comprise two filler sequences, the first filler sequence may be located between the intron region and polyadenylation signal sequence region, and the second filler sequence may be located between the polyadenylation signal sequence region and exon region. In certain embodiments, a viral genome may comprise two filler sequences, the first filler sequence may be located between the intron region and polyadenylation signal sequence region, and the second filler sequence may be located between the polyadenylation signal sequence region and 3' ITR. In certain embodiments, a viral genome may comprise two filler sequences, the first filler sequence may be located between the intron region and polyadenylation signal sequence region, and the second filler sequence may be located between the MCS region and exon region. In certain embodiments, a viral genome may comprise two filler sequences, the first filler sequence may be located between the intron region and polyadenylation signal sequence region, and the second filler sequence may be located between the MCS region and 3' ITR. In certain embodiments, a viral genome may comprise two filler sequences, the first filler sequence may be located between the intron region and polyadenylation signal sequence region, and the second filler sequence may be located between the exon region and 3' ITR.

In certain embodiments, a viral genome may comprise two filler sequences, the first filler sequence may be located between the intron region and MCS region, and the second filler sequence may be located between the enhancer region and polyadenylation signal sequence region. In certain embodiments, a viral genome may comprise two filler sequences, the first filler sequence may be located between the intron region and MCS region, and the second filler sequence may be located between the enhancer region and MCS region. In certain embodiments, a viral genome may comprise two filler sequences, the first filler sequence may be located between the intron region and MCS region, and the second filler sequence may be located between the enhancer region and exon region. In certain embodiments, a viral genome may comprise two filler sequences, the first filler sequence may be located between the intron region and MCS region, and the second filler sequence may be located between the enhancer region and 3' ITR. In certain embodiments, a viral genome may comprise two filler sequences, the first filler sequence may be located between the intron region and MCS region, and the second filler sequence may be located between the polyadenylation signal sequence region and MCS region. In certain embodiments, a viral genome may comprise two filler sequences, the first filler sequence may be located between the intron region and MCS region, and the second filler sequence may be located between the polyadenylation signal sequence region and exon region. In certain embodiments, a viral genome may comprise two filler sequences, the first filler sequence may be located between the intron region and MCS region, and the second filler sequence may be located between the polyadenylation signal sequence region and 3' ITR. In certain embodiments, a viral genome may comprise two filler sequences, the first filler sequence may be located between the intron region and MCS region, and the second filler sequence may be located between the MCS region and exon region. In certain embodiments, a viral genome may comprise two filler sequences, the first filler sequence may be located between the intron region and MCS region, and the second filler sequence may be located between the MCS region and 3' ITR. In certain embodiments, a viral genome may comprise two filler sequences, the first filler sequence may be located between the intron region and MCS region, and the second filler sequence may be located between the exon region and 3' ITR.

In certain embodiments, a viral genome may comprise two filler sequences, the first filler sequence may be located between the intron region and exon region, and the second filler sequence may be located between the enhancer region and polyadenylation signal sequence region. In certain embodiments, a viral genome may comprise two filler sequences, the first filler sequence may be located between the intron region and exon region, and the second filler sequence may be located between the enhancer region and MCS region. In certain embodiments, a viral genome may comprise two filler sequences, the first filler sequence may be located between the intron region and exon region, and the second filler sequence may be located between the enhancer region and exon region. In certain embodiments, a viral genome may comprise two filler sequences, the first filler sequence may be located between the intron region and exon region, and the second filler sequence may be located between the enhancer region and 3' ITR. In certain embodiments, a viral genome may comprise two filler sequences, the first filler sequence may be located between the intron region and exon region, and the second filler sequence may be located between the polyadenylation signal sequence region and MCS region. In certain embodiments, a viral genome may comprise two filler sequences, the first filler sequence may be located between the intron region and exon region, and the second filler sequence may be located between the polyadenylation signal sequence region and exon region. In certain embodiments, a viral genome may comprise two filler sequences, the first filler sequence may be located between the intron region and exon region, and the second filler sequence may be located between the polyadenylation signal sequence region and 3' ITR. In certain embodiments, a viral genome may comprise two filler sequences, the first filler sequence may be located between the intron region and exon region, and the second filler sequence may be located between the MCS region and exon region. In certain embodiments, a viral genome may comprise two filler sequences, the first filler sequence may be located between the intron region and exon region, and the second filler sequence may be located between the MCS region and 3' ITR. In certain embodiments, a viral genome may comprise two filler sequences, the first filler sequence may be located between the intron region and exon region, and the second filler sequence may be located between the exon region and 3' ITR.

In certain embodiments, a viral genome may comprise two filler sequences, the first filler sequence may be located between the intron region and 3'ITR, and the second filler sequence may be located between the enhancer region and polyadenylation signal sequence region. In certain embodiments, a viral genome may comprise two filler sequences, the first filler sequence may be located between the intron region and 3'ITR, and the second filler sequence may be located between the enhancer region and MCS region. In certain embodiments, a viral genome may comprise two filler sequences, the first filler sequence may be located between the intron region and 3'ITR, and the second filler sequence may be located between the enhancer region and exon region. In certain embodiments, a viral genome may comprise two filler sequences, the first filler sequence may be located between the intron region and 3'ITR, and the second filler sequence may be located between the enhancer region and 3' ITR. In certain embodiments, a viral genome may comprise two filler sequences, the first filler sequence may be located between the intron region and 3'ITR, and the second filler sequence may be located between the polyadenylation signal sequence region and MCS region. In certain embodiments, a viral genome may comprise two filler sequences, the first filler sequence may be located between the intron region and 3'ITR, and the second filler sequence may be located between the polyadenylation signal sequence region and exon region. In certain embodiments, a viral genome may comprise two filler sequences, the first filler sequence may be located between the intron region and 3'ITR, and the second filler sequence may be located between the polyadenylation signal sequence region and 3' ITR. In certain embodiments, a viral genome may comprise two filler sequences, the first filler sequence may be located between the intron region and 3'ITR, and the second filler sequence may be located between the MCS region and exon region. In certain embodiments, a viral genome may comprise two filler sequences, the first filler sequence may be located between the intron region and 3'ITR, and the second filler sequence may be located between the MCS region and 3' ITR. In certain embodiments, a viral genome may comprise two filler sequences, the first filler sequence may be located between the intron region and 3'ITR, and the second filler sequence may be located between the exon region and 3' ITR.

In certain embodiments, a viral genome may comprise two filler sequences, the first filler sequence may be located between the enhancer region and polyadenylation signal sequence region, and the second filler sequence may be located between the polyadenylation signal sequence region and MCS region. In certain embodiments, a viral genome may comprise two filler sequences, the first filler sequence may be located between the enhancer region and polyadenylation signal sequence region, and the second filler sequence may be located between the polyadenylation signal sequence region and exon region. In certain embodiments, a viral genome may comprise two filler sequences, the first filler sequence may be located between the enhancer region and polyadenylation signal sequence region, and the second filler sequence may be located between the polyadenylation signal sequence region and 3' ITR. In certain embodiments, a viral genome may comprise two filler sequences, the first filler sequence may be located between the enhancer region and polyadenylation signal sequence region, and the second filler sequence may be located between the MCS region and exon region. In certain embodiments, a viral genome may comprise two filler sequences, the first filler sequence may be located between the enhancer region and polyadenylation signal sequence region, and the second filler sequence may be located between the MCS region and 3' ITR. In certain embodiments, a viral genome may comprise two filler sequences, the first filler sequence may be located between the enhancer region and polyadenylation signal sequence region, and the second filler sequence may be located between the exon region and 3' ITR.

In certain embodiments, a viral genome may comprise two filler sequences, the first filler sequence may be located between the enhancer region and MCS region, and the second filler sequence may be located between the polyadenylation signal sequence region and MCS region. In certain embodiments, a viral genome may comprise two filler sequences, the first filler sequence may be located between the enhancer region and MCS region, and the second filler sequence may be located between the polyadenylation signal sequence region and exon region. In certain embodiments, a viral genome may comprise two filler sequences, the first filler sequence may be located between the enhancer region and MCS region, and the second filler sequence may be located between the polyadenylation signal sequence region and 3' ITR. In certain embodiments, a viral genome may comprise two filler sequences, the first filler sequence may be located between the enhancer region and MCS region, and the second filler sequence may be located between the MCS region and exon region. In certain embodiments, a viral genome may comprise two filler sequences, the first filler sequence may be located between the enhancer region and MCS region, and the second filler sequence may be located between the MCS region and 3' ITR. In certain embodiments, a viral genome may comprise two filler sequences, the first filler sequence may be located between the enhancer region and MCS region, and the second filler sequence may be located between the exon region and 3' ITR.

In certain embodiments, a viral genome may comprise two filler sequences, the first filler sequence may be located between the enhancer region and exon region, and the second filler sequence may be located between the polyadenylation signal sequence region and MCS region. In certain embodiments, a viral genome may comprise two filler sequences, the first filler sequence may be located between the enhancer region and exon region, and the second filler sequence may be located between the polyadenylation signal sequence region and exon region. In certain embodiments, a viral genome may comprise two filler sequences, the first filler sequence may be located between the enhancer region and exon region, and the second filler sequence may be located between the polyadenylation signal sequence region and 3' ITR. In certain embodiments, a viral genome may comprise two filler sequences, the first filler sequence may be located between the enhancer region and exon region, and the second filler sequence may be located between the MCS region and exon region. In certain embodiments, a viral genome may comprise two filler sequences, the first filler sequence may be located between the enhancer region and exon region, and the second filler sequence may be located between the MCS region and 3' ITR. In certain embodiments, a viral genome may comprise two filler sequences, the first filler sequence may be located between the enhancer region and exon region, and the second filler sequence may be located between the exon region and 3' ITR.

In certain embodiments, a viral genome may comprise two filler sequences, the first filler sequence may be located between the enhancer region and 3' ITR, and the second filler sequence may be located between the polyadenylation signal sequence region and MCS region. In certain embodiments, a viral genome may comprise two filler sequences, the first filler sequence may be located between the enhancer region and 3' ITR, and the second filler sequence may be located between the polyadenylation signal sequence region and exon region. In certain embodiments, a viral genome may comprise two filler sequences, the first filler sequence may be located between the enhancer region and 3' ITR, and the second filler sequence may be located between the polyadenylation signal sequence region and 3' ITR. In certain embodiments, a viral genome may comprise two filler sequences, the first filler sequence may be located between the enhancer region and 3' ITR, and the second filler sequence may be located between the MCS region and exon region. In certain embodiments, a viral genome may comprise two filler sequences, the first filler sequence may be located between the enhancer region and 3' ITR, and the second filler sequence may be located between the MCS region and 3' ITR. In certain embodiments, a viral genome may comprise two filler sequences, the first filler sequence may be located between the enhancer region and 3' ITR, and the second filler sequence may be located between the exon region and 3' ITR.

In certain embodiments, a viral genome may comprise two filler sequences, the first filler sequence may be located between the polyadenylation signal sequence region and MCS region, and the second filler sequence may be located between the MCS region and exon region. In certain embodiments, a viral genome may comprise two filler sequences, the first filler sequence may be located between the polyadenylation signal sequence region and MCS region, and the second filler sequence may be located between the MCS region and 3' ITR. In certain embodiments, a viral genome may comprise two filler sequences, the first filler sequence may be located between the polyadenylation signal sequence region and MCS region, and the second filler sequence may be located between the exon region and 3' ITR.

In certain embodiments, a viral genome may comprise two filler sequences, the first filler sequence may be located between the polyadenylation signal sequence region and exon region, and the second filler sequence may be located between the MCS region and exon region. In certain embodiments, a viral genome may comprise two filler sequences, the first filler sequence may be located between the polyadenylation signal sequence region and exon region, and the second filler sequence may be located between the MCS region and 3' ITR. In certain embodiments, a viral genome may comprise two filler sequences, the first filler sequence may be located between the polyadenylation signal sequence region and exon region, and the second filler sequence may be located between the exon region and 3' ITR.

In certain embodiments, a viral genome may comprise two filler sequences, the first filler sequence may be located between the polyadenylation signal sequence region and 3' ITR, and the second filler sequence may be located between the MCS region and exon region. In certain embodiments, a viral genome may comprise two filler sequences, the first filler sequence may be located between the polyadenylation signal sequence region and 3' ITR, and the second filler sequence may be located between the MCS region and 3' ITR. In certain embodiments, a viral genome may comprise two filler sequences, the first filler sequence may be located between the polyadenylation signal sequence region and 3' ITR, and the second filler sequence may be located between the exon region and 3' ITR.

In certain embodiments, a viral genome may comprise two filler sequences, the first filler sequence may be located between the MCS region and exon region, and the second filler sequence may be located between the exon region and 3' ITR.

AAV Production

The present disclosure provides methods for the generation of parvoviral particles, e.g. AAV particles, by viral genome replication in a viral replication cell.

In accordance with the disclosure, the viral genome comprising a payload region will be incorporated into the AAV particle produced in the viral replication cell. Methods of making AAV particles are well known in the art and are described in e.g., U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597; Methods In Molecular Biology, ed. Richard, Humana Press, NJ (1995); O'Reilly et al., Baculovirus Expression Vectors, A Laboratory Manual. Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J Vir. 66:6922-30 (1992); Kimbauer et al., Vir., 219:37-44 (1996); Zhao et al., Vir. 272:382-93 (2000); the contents of each of which are herein incorporated by reference in their entirety. In certain embodiments, the AAV particles are made using the methods described in WO2015191508, the contents of which are herein incorporated by reference in their entirety.

Viral replication cells commonly used for production of recombinant AAV particles include but are not limited to 293 cells, COS cells, HeLa cells. KB cells, and other mammalian cell lines as described in U.S. Pat. Nos. 6,156,303, 5,387, 484, 5,741,683, 5,691,176, and 5,688,676: U.S. patent publication No. 2002/0081721, and International Patent Publication Nos. WO 00/47757. WO 00/24916, and WO 96/17947, the contents of each of which are herein incorporated by reference in their entireties.

In some embodiments, the present disclosure provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, and 5) harvesting and purifying the AAV particle comprising a viral genome.

In some embodiments, the present disclosure provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome. In some embodiments, the AAV particle is produced by transient transfection of an adherent HEK293 cell line using three or more bacteria-produced plasmids. In some embodiments, the resulting AAV particles can be purified by ion exchange chromatography, ultracentrifugation or a combination thereof.

In some embodiments, the viral genome of the AAV particle of the disclosure optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes as described in International application No. WO 96/23810; Heim et al., Current Biology 2:178-182 (1996): Heim et al., Proc. Natl. Acad. Sci. USA (1995); or Heim et al., Science 373:663-664 (1995); WO 96/30540, the contents of each of which are incorporated herein by reference in their entireties).

Genome Size

In certain embodiments, the AAV particle which comprises a payload described herein may be single stranded or double stranded vector genome. The size of the vector genome may be small, medium, large or the maximum size. Additionally, the vector genome may comprise a promoter and a polyA tail.

In certain embodiments, the vector genome which comprises a payload described herein may be a small single stranded vector genome. A small single stranded vector genome may be 2.7 to 3.5 kb in size such as about 2.7, 2.8, 2.9, 3.0, 3.1, 3.2, 3.3, 3.4, and 3.5 kb in size. In certain embodiments, the small single stranded vector genome may be 3.2 kb in size. Additionally, the vector genome may comprise a promoter and a polyA tail.

In certain embodiments, the vector genome which comprises a payload described herein may be a small double stranded vector genome. A small double stranded vector genome may be 1.3 to 1.7 kb in size such as about 1.3, 1.4, 1.5, 1.6, and 1.7 kb in size. In certain embodiments, the small double stranded vector genome may be 1.6 kb in size. Additionally, the vector genome may comprise a promoter and a polyA tail.

In certain embodiments, the vector genome which comprises a payload described herein may be a medium single stranded vector genome. A medium single stranded vector genome may be 3.6 to 4.3 kb in size such as about 3.6, 3.7, 3.8, 3.9, 4.0, 4.1, 4.2 and 4.3 kb in size. In certain embodiments, the medium single stranded vector genome may be 4.0 kb in size. Additionally, the vector genome may comprise a promoter and a polyA tail.

In certain embodiments, the vector genome which comprises a payload described herein may be a medium double stranded vector genome. A medium double stranded vector genome may be 1.8 to 2.1 kb in size such as about 1.8, 1.9, 2.0, and 2.1 kb in size. In certain embodiments, the medium double stranded vector genome may be 2.0 kb in size. Additionally, the vector genome may comprise a promoter and a polyA tail.

In certain embodiments, the vector genome which comprises a payload described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. In certain embodiments, the large single stranded vector genome may be 4.7 kb in size. In certain embodiments, the large single stranded vector genome may be 4.8 kb in size. As yet another non-limiting example, the large single stranded vector genome may be 6.0 kb in size. Additionally, the vector genome may comprise a promoter and a polyA tail.

In certain embodiments, the vector genome which comprises a payload described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. In certain embodiments, the large double stranded vector genome may be 2.4 kb in size. Additionally, the vector genome may comprise a promoter and a polyA tail.

Payloads of the Disclosure

The AAV particles of the present disclosure comprise at least one payload region. As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid. Payloads of the present disclosure typically encode polypeptides or fragments or variants thereof.

The payload region may be constructed in such a way as to reflect a region similar to or mirroring the natural organization of an mRNA.

The payload region may comprise a combination of coding and non-coding nucleic acid sequences.

In some embodiments, the AAV payload region may encode a coding or non-coding RNA.

In certain embodiments, the AAV particle comprises a viral genome with a payload region comprising nucleic acid sequences encoding more than one polypeptide of interest. In such an embodiment, a viral genome encoding more than one polypeptide may be replicated and packaged into a viral particle. A target cell transduced with a viral particle comprising more than one polypeptide may express each of the polypeptides in a single cell.

In certain embodiments, the payload region may comprise one or more of the components as shown in FIG. 1. The payload region 110 is located within the viral genome 100. At the 5' and/or the 3' end of the payload region 110 there may be at least one inverted terminal repeat (ITR) 120. Within the payload region, there is a promoter region 130, an intron region 140 and a coding region 150.

Where the AAV particle payload region encodes a polypeptide, the polypeptide may be a peptide or protein. The viral genomes encoding polypeptides described herein may be useful in the fields of human disease, viruses, infections veterinary applications and a variety of in vivo and in vitro settings.

In some embodiments, the AAV particles are useful in the field of medicine for the treatment, prophylaxis, palliation or amelioration of neurological diseases and/or disorders.

In some embodiments, the AAV particles are useful in the field of medicine for the treatment, prophylaxis, palliation or amelioration of Parkinson's Disease.

In some embodiments, the AAV particles are useful in the field of medicine for the treatment, prophylaxis, palliation or amelioration of diseases of the central nervous system.

The Nature of the Polypeptides and Variants

Amino acid sequences encoded by payload regions of the viral genomes of the disclosure may be translated as a whole polypeptide, a plurality of polypeptides or fragments of polypeptides, which independently may be encoded by one or more nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least about 70% homology to a native sequence, and preferably, they will be at least about 80%, more preferably at least about 90% homologous to a native sequence. "Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

Sequence tags or amino acids, such as one or more lysines, can be added to the peptide sequences of the disclosure (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid. [02%]"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present disclosure.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

"Features" when referring to proteins are defined as distinct amino acid sequence-based components of a molecule. Features of the proteins of the present disclosure include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and comprises four or more amino acid residues. Oliva et al. have identified at least 5 classes of protein loops (J. Mol Biol 266 (4): 814-830: 1997).

As used herein when referring to proteins the term "half-loop" refers to a portion of an identified loop having at least half the number of amino acid residues as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins the term "domain" refers to a motif of a polypeptide having one or more identifiable structural or functional characteristics or properties (e.g., binding capacity, serving as a site for protein-protein interactions).

As used herein when referring to proteins the term "half-domain" means portion of an identified domain having at least half the number of amino acid residues as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present disclosure.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present disclosure may be characterized as having both an N-terminus (terminated by an amino acid with a free amino group (NH2)) and a C-terminus (terminated by an amino acid with a free carboxyl group (COOH)). Proteins of the disclosure are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the disclosure, any of several manipulations and/or modifications of these features may be performed by moving, swapping, inverting, deleting, randomizing or duplicating. Furthermore, it is understood that manipulation of features may result in the same outcome as a modification to the molecules of the disclosure. For example, a manipulation which involves deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Payload: AADC Polynucleotide Constructs

According to the present disclosure, aromatic L-amino acid decarboxylase (AADC; also known as dopa decarboxylase and DDC) polynucleotides are provided which function alone or in combination with additional nucleic acid sequence(s) to encode the AADC protein. As used herein an "AADC polynucleotide" is any nucleic acid polymer which encodes an AADC protein and when present in a vector, plasmid or translatable construct, expresses such AADC protein in a cell, tissue, organ or organism.

AADC polynucleotides include precursor molecules which are processed inside the cell. AADC polynucleotides or the processed forms thereof may be encoded in a plasmid, vector, genome or other nucleic acid expression vector for delivery to a cell.

In some embodiments AADC polynucleotides are designed as components of AAV viral genomes and packaged in AAV particles which are processed within the cell to produce the wild type AADC protein.

In some embodiments, the AADC polynucleotide may be the payload of the AAV particle.

As used herein, the wild type AADC protein may be any of the naturally occurring isoforms or variants from the DDC gene. Multiple alternatively spliced transcript variants encoding different isoforms of AADC have been identified. Specifically, the DDC gene produces seven transcript variants that encode six distinct isoforms. DDC transcript variants 1 and 2 both encode AADC isoform 1. In some embodiments, the AADC polynucleotides encode DDC transcript variant 2, thereby encoding a native AADC isoform 1 (NCBI Reference Sequence: NP_000781.1). This sequence is given here:

```
                                    (SEQ ID NO: 978)
MNASEFRRRGKEMVDYVANYMEGIEGRQVYPDVEPGYLRPLIPAAAPQE

PDTFEDIINDVEKIIMPGVTHWHSPYFFAYFPTASSYPAMLADMLCGAI

GCIGFSWAASPACTELETVMMDWLGKMLELPKAFLNEKAGEGGGVIQGS

ASEATLVALLAARTKVIHRLQAASPELTQAAIMEKLVAYSSDQAHSSVE

RAGLIGGVKLKAIPSDGNFAMRASALQEALERDKAAGLIPFFMVATLGT

TTCCSFDNLLEVGPICNKEDIWLHVDAAYAGSAFICPEFRHLLNGVEFA

DSFNFNPHKWLLVNFDCSAMWVKKRTDLIGAFRLDPTYLKHSHQDSGLI

TDYRHWQIPLGRRFRSLKMWFVFRMYGVKGLQAYIRKHVQLSHEFESLV

RQDPRFEICVEVILGLVCFRLKGSNKVNEALLQRINSAKKIHLVPCHLR

DKFVLRFAICSRTVESAHVQRAWEHIKELAADVLRAERE
```

The AADC polynucleotides of the disclosure, may be engineered to contain modular elements and/or sequence motifs assembled to create AADC polynucleotide constructs.

According to the present disclosure, AADC polynucleotides are provided. Such polynucleotides comprise nucleic acid polymers which comprise a region of linked nucleosides encoding one or more isoforms or variants of the AADC protein.

In some embodiments, the AADC polynucleotide comprises a codon optimized transcript encoding an AADC protein.

In some embodiments, the AADC polynucleotide comprises a sequence region encoding one or more wild type isoforms or variants of an AADC protein. Such polynucleotides may also comprise a sequence region encoding any one or more of the following: a 5' ITR, a cytomegalovirus (CMV) Enhancer, a CMV Promoter, an ie1 exon 1, an ie1 intron1, an hbBglobin intron2, an hBglobin exon 3, a 5' UTR, a 3' UTR, an hGH poly(A) signal, and/or a 3' ITR. Such sequence regions are taught herein or may be any of those known in the art.

In some embodiments, the AADC polynucleotide comprises a SEQ ID NO: 979 or a fragment or variant thereof. This AADC polynucleotide sequence is given here:

```
                                    (SEQ ID NO: 979)
5'cctgcaggcagctgcgcgctcgctcgctcactgaggccgcccgggca aagcccgggcgtcgggcgacctttggtcgcccggcctcagtgagcgagc gagcgcgcagagagggagtggccaactccatcactagggggttccttgta gttaatgattaacccgccatgctacttatctacgtagccatgcgtcgac ataacgcgtatatctagacgttacataacttacggtaaatggcccgcct ggctgaccgcccaacgaccccccgcccattgacgtcaataatgacgtatg ttcccatagtaacgccaatagggactttccattgacgtcaatgggtgga gtatttacggtaaactgcccacttggcagtacatcaagtgtatcatatg ccaagtacgccccctattgacgtcaatgacggtaaatggcccgcctggc attatgcccagtacatgacctttatgggactttcctacttggcagtacat ctagtattagtcatcgctattaccatggtgatgcggttttggcagtaca tcaatgggcgtggatagcggtttgactcacggggatttccaagtctcca ccccattgacgtcaatgggagtttgttttggcaccaaaatcaacgggac tttccaaaatgtcgtaacaactccgccccattgacgcaaatgggcggta ggcgtgtacggtgggaggtctatataagcagagctcgtttagtgaaccg tcagatcgcctggagacgccatccacgctgttttgacctccatagaaga caccgggaccgatccagcctccgcggattcgaatcccggccgggaacgg tgcattggaacgcggattccccgtgccaagagtgacgtaagtaccgcct atagagtctataggcccacaaaaaatgctttcttcttttaatatacttt tttgtttatcttatttctaatactttccctaatctctttctttcagggc aataatgatacaatgtatcatgcctctttgcaccattctaaagaataac agtgataatttctgggttaaggcaatagcaatatttctgcatataaata tttctgcatataaattgtaactgatgtaagaggtttcatattgctaata gcagctacaatccagctaccattctgcttttatttatggttgggataa ggctggattattctgagtccaagctaggccctttgctaatcatgttca tacctcttatcttcctcccacagctcctgggcaacgtgctggtctgtgt gctggcccatcactttggcaaagaattgggattcgaacatcgattgaat tccccggggatccaccatgaacgcaagtgaattccgaaggagagggaag gagatggtggattacgtggccaactacatggaaggcattgagggacgcc aggtctaccctgacgtggagcccgggtacctgcggccgctgatccctgc cgctgcccctcaggagccagacacgtttgaggacatcatcaacgacgtt gagaagataatcatgcctggggtgacgcactggcacagcccctacttct tcgcctacttccccactgccagctcgtacccggccatgcttgcggacat gctgtgcggggccattggctgcatcggcttctcctggggcaagcccag catgcacagagctggagactgtgatgatggactggctcgggaagatgct ggaactaccaaaggcattttttgaatgagaaagctggagaaggggagga gtgatccagggaagtgccagtgaagccaccctggtggccctgctggccg ctcggaccaaagtgatccatcggctgcaggcagcgtccccagagctcac acaggccgctatcatggagaagctggtggcttactcatccgatcaggca cactcctcagtggaaagagctgggttaattggtggagtgaaattaaaag ccatcccctcagatggcaacttcgccatgcgtgcgtctgccctgcagga agccctggagagagacaaagcggctggcctgattcctttctttatggtt gccaccctggggaccacaacatgctgctcctttgacaatctcttagaag
```

```
-continued
tcggtcctatctgcaacaaggaagacatatggctgcacgttgatgcagc ctacgcaggcagtgcattcatctgccctgagttccggcaccttctgaat ggagtggagtttgcagattcattcaactttaatccccacaaatggctat tggtgaattttgactgttctgccatgtgggtgaaaaagagaacagactt aacgggagcctttagactggaccccacttacctgaagcacagccatcag gattcagggcttatcactgactaccggcattggcagataccactgggca gaagatttcgctctttgaaaatgtggtttgtatttaggatgtatggagt caaaggactgcaggcttatatccgcaagcatgtccagctgtcccatgag tttgagtcactggtgcgccaggatcccgctttgaaatctgtgtggaag tcattctgggcttgtctgctttcggctaaagggttccaacaaagtgaa tgaagctcttctgcaaagaataaacagtgccaaaaaatccacttggtt ccatgtcacctcagggacaagtttgtcctgcgctttgccatctgttctc gcacggtggaatctgcccatgtgcagcgggcctgggaacacatcaaaga gctggggccgacgtgctgcgagcagagagggagtaggagtgaagccagg acctgcagaagcttgcctcgagcagcgctgctcgagagatctacgggtg gcatccctgtgaccccctcccagtgcctctcctggccctggaagttgcc actccagtgcccaccagccttgtcctaataaaattaagttgcatcattt tgtctgactaggtgtccttctataatattatgggtggaggggggtggt atggagcaaggggcaagttgggaagacaacctgtagggcctgcgggtc tattgggaaccaagctggagtgcagtggcacaatcttggctcactgcaa tctccgcctcctgggttcaagcgattctcctgcctcagcctcccgagtt gttgggattccaggcatgcatgaccaggctcagctaatttttgtttttt tggtagagacgggtttcaccatattggccaggctggtctccaactcct aatctcaggtgatctacccaccttggcctcccaaattgctgggattaca ggcgtgaaccactgctcccttccctgtccttactagatttaaatatgtc gtgcatcgatgctacgtagataagtagcatgggggttaatcattaacta cagaggaaccctagtgatggagttggccactccctctctgcgcgctcg ctcgctcactgaggccgggcgaccaaaggtcgcccgacgcccggcttt gcccgggcggcctcagtgagcgagcgagcgcgcagctgcctgcagg3'
```

In some embodiments, an AADC polynucleotide that comprises a SEQ ID NO: 979 or a fragment or variant thereof is part of an AAV particle comprising an AAV2 capsid serotype.

In certain embodiments, an AADC polynucleotide comprises a ribonucleotide form of SEQ ID NO: 979.

In certain embodiments, the AADC polynucleotide comprises a sequence which has a percent identity to any of SEQ ID NO: 979 or a fragment or variant thereof. The AADC polynucleotide may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to any of SEQ ID NO: 979 or a fragment or variant thereof. The AADC polynucleotide may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to any of SEQ ID NO: 979 or a fragment or variant thereof. In certain embodiments, the AADC polynucleotide comprises a sequence which as 80% identity to any of SEQ ID NO: 979 or a fragment or variant thereof. In certain embodiments, the AADC polynucleotide comprises a sequence which as 85% identity to any of SEQ ID NO: 979 or a fragment or variant thereof. In certain embodiments, the AADC polynucleotide comprises a sequence which as 90% identity to any of SEQ ID NO: 979 or a fragment or variant thereof. In certain embodiments, the AADC polynucleotide comprises a sequence which as 95% identity to any of SEQ ID NO: 979 or a fragment or variant thereof. In certain embodiments, the AADC polynucleotide comprises a sequence which as 99% identity to any of SEQ ID NO: 979 or a fragment or variant thereof.

In some embodiments, the coding region of the AADC polynucleotide is 1440 nucleotides in length. Such an AADC polynucleotide may, for example, be codon optimized over all or a portion of the polynucleotide.

In some embodiments, the AADC polynucleotide comprises any of SEQ ID NO: 979 or a fragment or variant thereof but lacking the 5' and/or 3' ITRs. Such a polynucleotide may be incorporated into a plasmid or vector and utilized to express the encoded AADC protein.

In certain embodiments, the AADC polynucleotides may be produced in insect cells (e.g., Sf9 cells).

In certain embodiments, the AADC polynucleotides may be produced using triple transfection.

In certain embodiments, the AADC polynucleotide may comprise an open reading frame of an AADC mRNA, for example, a codon optimized open reading frame of an AADC mRNA, at least one 5'ITR and at least one 3'ITR where the one or more of the 5'ITRs may be located at the 5'end of the promoter region and one or more 3' ITRs may be located at the 3' end of the poly(A) signal. The AADC mRNA may comprise a promoter region, a 5'untranslated region (UTR), a 3'UTR and a poly(A) signal. The promoter region may include, but is not limited to, enhancer element, a promoter element, a first exon region, a first intron region, a second intron region and a second exon region. In certain embodiments, the enhancer element and the promoter element are derived from CMV. In certain embodiments, the first exon region is ie1 exon 1 or fragments thereof, the first intron region is ie1 intron 1 or fragments thereof, the second intron region is hbBglobin intron 2 or fragments thereof and the second exon region is hbBglobin exon 3 or fragments thereof. As yet another non-limiting example, the poly(A) signal is derived from human growth hormone.

In certain embodiments, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

In certain embodiments, at least one element may be used with the AADC polynucleotides described herein to enhance the transgene target specificity and expression (See e.g., Powell et al. *Viral Expression Cassette Elements to Enhance Transgene Target Specificity and Expression in Gene Therapy*, 2015: the contents of which are herein incorporated by reference in its entirety) such as promoters.

In certain embodiments, the AADC polynucleotide is encoded in a plasmid or vector, which may be derived from an adeno-associated virus (AAV).

In certain embodiments, the AAV particle of the disclosure comprises a recombinant AAV2 with a viral genome encoding a human AADC.

In certain embodiments, the AAV particle of the disclosure is VY-AADC01.

In certain embodiments, the AAV particle of the disclosure is VY-AADC02.

In certain embodiments, the AAV particle of the disclosure has a CAS (Chemical Abstracts Service) Registry Number of 2226647-27-2.

II. Formulation and Delivery

Pharmaceutical Compositions

According to the present disclosure the AAV particles may be prepared as pharmaceutical compositions (e.g. formulations). It will be understood that such compositions necessarily comprise one or more active ingredients and, most often, a pharmaceutically acceptable excipient.

Relative amounts of the active ingredient (e.g. AAV particle), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.0001% and 99% (w/w) of the active ingredient. By way of example, the composition may comprise between 0.0001% and 100%. e.g., between 0.5 and 50%, between 1-30%, between 5-80%, at least 80% (w/w) active ingredient.

In some embodiments, the AAV particle pharmaceutical compositions described herein may comprise at least one payload. In certain embodiments, the pharmaceutical compositions may contain an AAV particle with 1, 2, 3, 4 or 5 payloads.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates, mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients or subjects.

Formulations

Formulations of the present disclosure can include, without limitation, saline, liposomes, lipid nanoparticles, polymers, peptides, proteins, cells transfected with AAV particles (e.g., for transfer or transplantation into a subject) and combinations thereof.

Formulations of the pharmaceutical compositions described herein may be prepared by any method known or hereafter developed in the art of pharmacology. As used herein the term "pharmaceutical composition" refers to compositions comprising at least one active ingredient and optionally one or more pharmaceutically acceptable excipients.

In general, such preparatory methods include the step of associating the active ingredient with an excipient and/or one or more other accessory ingredients. As used herein, the phrase "active ingredient" generally refers either to an AAV particle carrying a payload region encoding the polypeptides of the disclosure or to the end product encoded by a viral genome of by an AAV particle as described herein.

Formulations of the AAV particles and pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In certain embodiments, the AAV particles of the disclosure may be formulated in PBS, in combination with an ethylene oxide/propylene oxide copolymer (also known as pluronic or poloxamer).

In certain embodiments, the AAV particles of the disclosure may be formulated in PBS with 0.001% w/v pluronic acid (F-68) (poloxamer 188) at a pH of about 7.0.

In certain embodiments, the AAV particles of the disclosure may be formulated in PBS with 0.001% w/v pluronic acid (F-68) (poloxamer 188) at a pH of about 7.3.

In certain embodiments, the AAV particles of the disclosure may be formulated in PBS with 0.001% w/v pluronic acid (F-68) (poloxamer 188) at a pH of about 7.4.

In certain embodiments, the AAV particles of the disclosure may be formulated in a solution comprising sodium chloride, sodium phosphate and an ethylene oxide/propylene oxide copolymer.

In certain embodiments, the AAV particles of the disclosure may be formulated in a solution comprising sodium chloride, sodium phosphate dibasic, sodium phosphate monobasic and poloxamer 188/pluronic acid (F-68).

In certain embodiments, the AAV particles of the disclosure may be formulated in a solution comprising about 180 mM sodium chloride, about 10 mM sodium phosphate and about 0.001% w/v poloxamer 188 (i.e. pluronic acid F-68), at a pH of about 7.3. In certain embodiments, the AAV particles of the disclosure may be formulated at a target concentration of $\geq 3.0 \times 10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be formulated at a target concentration of $3.5\text{-}5.5 \times 10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be formulated at a target concentration of $4.5\text{-}5.5\times10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be formulated at a target concentration of $4.9\times10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be formulated at a target concentration of $2.0\text{-}3.5\times10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be formulated at a target concentration of $2.4\text{-}2.8\times10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be formulated at a target concentration of $2.6\times10^{12}$ vg/mL in a solution comprising about 180 mM sodium chloride, about 10 mM sodium phosphate and about 0.001% w/v poloxamer 188, at a pH of about 7.3.

In certain embodiments, the AAV particles of the disclosure may be administered at a target concentration of $2.0\text{-}3.5\times10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be administered at a target concentration of $2.4\text{-}2.8\times10^{12}$ vg/mL in a solution comprising about 180 mM sodium chloride, about 10 mM sodium phosphate and about 0.001% w/v poloxamer 188, at a pH of about 7.3. In certain embodiments, the AAV particles of the disclosure may be administered at a target concentration of $2.6\times10^{12}$ vg/mL in a solution comprising about 180 mM sodium chloride, about 10 mM sodium phosphate and about 0.001% w/v poloxamer 188, at a pH of about 7.3.

The concentration of sodium chloride in the final solution may be 150 mM-200 mM. As non-limiting examples, the concentration of sodium chloride in the final solution may be 150 mM, 160 mM, 170 mM, 180 mM, 190 mM or 200 mM. The concentration of sodium phosphate in the final solution may be 1 mM-50 mM. As non-limiting examples, the concentration of sodium phosphate in the final solution may be 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, or 50 mM. The concentration of poloxamer 188 (pluronic acid (F-68)) may be 0.0001%-1%. As non-limiting examples, the concentration of poloxamer 188 (pluronic acid (F-68)) may be 0.0001%, 0.0005%, 0.001%, 0.005%, 0.01%, 0.05%, 0.1%, 0.5%, or 1% w/v. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In certain embodiments, the AAV particles of the disclosure may be formulated in a solution comprising about 1.05% sodium chloride, about 0.212% sodium phosphate dibasic, heptahydrate, about 0.025% sodium phosphate monobasic, monohydrate, and 0.001% poloxamer 188, at a pH of about 7.4. In certain embodiments, the concentration of AAV particle in this formulated solution may be about 0.001%. The concentration of sodium chloride in the final solution may be 0.1-2.0%, with non-limiting examples of 0.1%, 0.25%, 0.5%, 0.75%, 0.95%, 0.96%, 0.97%, 0.98%, 0.99%, 1.00%, 1.01%, 1.02%, 1.03%, 1.04%, 1.05%, 1.06%, 1.07%, 1.08%, 1.09%, 1.10%, 1.25%, 1.5/a, 1.75%, or 2%. The concentration of sodium phosphate dibasic in the final solution may be 0.100-0.300% with non-limiting examples including 0.100%, 0.125%, 0.150%, 0.175%, 0.200%, 0.210%, 0.211%, 0.212%, 0.213%, 0.214%, 0.215%, 0.225%, 0.250%, 0.275%, 0.300%. The concentration of sodium phosphate monobasic in the final solution may be 0.010-0.050%, with non-limiting examples of 0.010%, 0.015%, 0.020%, 0.021%, 0.022%, 0.023%, 0.024%, 0.025%, 0.026%, 0.027%, 0.028%, 0.029%, 0.030%, 0.035%, 0.040%, 0.045%, or 0.050%. The concentration of poloxamer 188 (pluronic acid (F-68)) may be 0.0001%-1%. As non-limiting examples, the concentration of poloxamer 188 (pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In certain embodiments, the formulation comprises components with the following CAS (Chemical Abstracts Services) Registry Numbers, 7647-14-15 (sodium chloride), 7782-85-6 (sodium phosphate dibasic, heptahydrate), 10049-21-5 (sodium phosphate monobasic, monohydrate), 9003-11-6 (poloxamer 188) and 2226647-27-2 (recombinant adeno-associated virus 2 vector VY-AADC02 human aromatic amino acid decarboxylase-specifying).

In some embodiments, the AAV formulations described herein may contain sufficient AAV particles for expression of at least one expressed functional payload. In certain embodiments, the AAV particles may contain viral genomes encoding 1, 2, 3, 4 or 5 functional payloads.

In certain embodiments, AAV formulations of the present disclosure may be formulated with a target concentration of AAV vectors (vg/mL) and administered at a different target concentration of AAV vectors. In certain embodiments, an AAV formulations may be formulated at a target concentration of AAV vectors (vg/mL) and then concentrated to be administered at a higher target concentration of AAV vectors. In certain embodiments, an AAV formulations may be formulated at a target concentration of AAV vectors (vg/mL) and then diluted to be administered at a lower target concentration of AAV vectors.

According to the present disclosure AAV particles may be formulated for CNS delivery. Agents that cross the brain blood barrier may be used. For example, some cell penetrating peptides that can target molecules to the brain blood barrier endothelium may be used for formulation (e.g., Mathupala, *Expert Opin Ther Pat.*, 2009, 19, 137-140; the content of which is incorporated herein by reference in its entirety).

Excipients and Diluents

The AAV particles of the disclosure can be formulated using one or more excipients or diluents to (1) increase stability; (2) increase cell transfection or transduction; (3) permit the sustained or delayed release of the payload; (4) alter the biodistribution (e.g., target the viral particle to specific tissues or cell types); (5) increase the translation of encoded protein; (6) alter the release profile of encoded protein and/or (7) allow for regulatable expression of the payload of the disclosure.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington; The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In certain embodiments, the AAV particles may be formulated in a hydrogel prior to administration. Hydrogels have a degree of flexibility which is similar to natural tissue as a result of their significant water content.

In another embodiment, a hydrogel may be administered to a subject prior to the administration of an AAV particle formulation. In certain embodiments, the site of administration of the hydrogel may be within 3 inches (e.g., within 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less than 0.1 inches) of the site of administration of the AAV particle formulation.

Inactive Ingredients

In some embodiments, AAV particle formulations may comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients which may be used in the formulations of the present disclosure may be approved by the US Food and Drug Administration (FDA).

In certain embodiments, the AAV particle pharmaceutical compositions comprise at least one inactive ingredient such as, but not limited to, 1,2,6-Hexanetriol; 1,2-Dimyristoyl-Sn-Glycero-3-(Phospho-S-(1-Glycerol)): 1,2-Dimyristoyl-Sn-Glycero-3-Phosphocholine: 1,2-Dioleoyl-Sn-Glycero-3-Phosphocholine; 1,2-Dipalmitoyl-Sn-Glycero-3-(Phospho-Rac-(1-Glycerol)); 1,2-Distearoyl-Sn-Glycero-3-(Phospho-Rac-(1-Glycerol)); 1,2-Distearoyl-Sn-Glycero-3-Phosphocholine; 1-O-Tolylbiguanide; 2-Ethyl-1,6-Hexanediol; Acetic Acid; Acetic Acid, Glacial; Acetic Anhydride; Acetone; Acetone Sodium Bisulfite; Acetylated Lanolin Alcohols; Acetylated Monoglycerides; Acetylcysteine; Acetyltryptophan, DL-; Acrylates Copolymer; Acrylic Acid-Isooctyl Acrylate Copolymer; Acrylic Adhesive 788; Activated Charcoal; Adcote 72A103; Adhesive Tape; Adipic Acid; Aerotex Resin 3730; Alanine; Albumin Aggregated; Albumin Colloidal; Albumin Human; Alcohol; Alcohol, Dehydrated; Alcohol, Denatured; Alcohol. Diluted; Alfadex; Alginic Acid; Alkyl Ammonium Sulfonic Acid Betaine; Alkyl Aryl Sodium Sulfonate; Allantoin; Allyl .Alpha.-Ionone; Almond Oil; Alpha-Terpineol; Alpha-Tocopherol; Alpha-Tocopherol Acetate, Dl-; Alpha-Tocopherol, Dl-; Aluminum Acetate; Aluminum Chlorohydroxy Allantoinate; Aluminum Hydroxide; Aluminum Hydroxide—Sucrose, Hydrated; Aluminum Hydroxide Gel; Aluminum Hydroxide Gel F 500; Aluminum Hydroxide Gel F 5000; Aluminum Monostearate; Aluminum Oxide; Aluminum Polyester; Aluminum Silicate; Aluminum Starch Octenylsuccinate; Aluminum Stearate; Aluminum Subacetate; Aluminum Sulfate Anhydrous; Amerchol C; Amerchol-Cab; Aminomethylpropanol; Ammonia; Ammonia Solution; Ammonia Solution, Strong; Ammonium Acetate; Ammonium Hydroxide; Ammonium Lauryl Sulfate; Ammonium Nonoxynol-4 Sulfate; Ammonium Salt Of C-12-C-15 Linear Primary Alcohol Ethoxylate; Ammonium Sulfate; Ammonyx; Amphoteric-2; Amphoteric-9; Anethole; Anhydrous Citric Acid; Anhydrous Dextrose; Anhydrous Lactose; Anhydrous Trisodium Citrate; Aniseed Oil; Anoxid Sbn; Antifoam; Antipyrine; Apaflurane; Apricot Kernel Oil Peg-6 Esters; Aquaphor; Arginine; Arlacel; Ascorbic Acid; Ascorbyl Palmitate; Aspartic Acid; Balsam Peru; Barium Sulfate; Beeswax; Beeswax, Synthetic; Beheneth-10; Bentonite; Benzalkonium Chloride; Benzenesulfonic Acid; Benzethonium Chloride; Benzododecinium Bromide; Benzoic Acid; Benzyl Alcohol; Benzyl Benzoate; Benzyl Chloride; Betadex; Bibapcitide; Bismuth Subgallate; Boric Acid; Brocrinat; Butane; Butyl Alcohol; Butyl Ester Of Vinyl Methyl Ether/Maleic Anhydride Copolymer (125000 Mw); Butyl Stearate; Butylated Hydroxyanisole; Butylated Hydroxytoluene; Butylene Glycol; Butylparaben; Butyric Acid; C20-40 Pareth-24; Caffeine; Calcium; Calcium Carbonate; Calcium Chloride; Calcium Gluceptate; Calcium Hydroxide; Calcium Lactate; Calcobutrol; Caldiamide Sodium; Caloxetate Trisodium; Calteridol Calcium; Canada Balsam; Caprylic/Capric Triglyceride; Caprylic/Capric/Stearic Triglyceride; Captan; Captisol; Caramel; Carbomer 1342; Carbomer 1382; Carbomer 934; Carbomer 934p; Carbomer 940; Carbomer 941; Carbomer 980; Carbomer 981; Carbomer Homopolymer Type B (Allyl Pentaerythritol Crosslinked); Carbomer Homopolymer Type C (Allyl Pentaerythritol Crosslinked); Carbon Dioxide; Carboxy Vinyl Copolymer; Carboxymethylcellulose; Carboxymethylcellulose Sodium; Carboxypolymethylene; Carrageenan; Carrageenan Salt; Castor Oil; Cedar Leaf Oil; Cellulose; Cellulose, Microcrystalline; Cerasynt-Se; Ceresin; Cetcareth-12; Cetéareth-15; Ceteareth-30; Cetearyl Alcohol/Ceteareth-20; Cetearyl Ethylhexanoate; Ceteth-10; Ceteth-2; Ceteth-20; Ceteth-23; Cetostearyl Alcohol; Cetrimonium Chloride; Cetyl Alcohol; Cetyl Esters Wax; Cetyl Palmitate; Cetylpyridinium Chloride; Chlorobutanol; Chlorobutanol Hemihydrate; Chlorobutanol, Anhydrous; Chlorocresol; Chloroxylenol; Cholesterol; Choleth; Choleth-24; Citrate; Citric Acid; Citric Acid Monohydrate; Citric Acid, Hydrous; Cocamide Ether Sulfate; Cocamine Oxide; Coco Betaine; Coco Diethanolamide; Coco Monoethanolamide; Cocoa Butter; Coco-Glycerides; Coconut Oil; Coconut Oil, Hydrogenated; Coconut Oil/Palm Kernel Oil Glycerides, Hydrogenated; Cocoyl Caprylocaprate; Cola Nitida Seed Extract; Collagen; Coloring Suspension; Corn Oil; Cottonseed Oil; Cream Base; Creatine; Creatinine; Cresol; Croscarmellose Sodium; Crospovidone; Cupric Sulfate; Cupric Sulfate Anhydrous; Cyclomethicone; Cyclomethicone/Dimethicone Copolyol; Cysteine; Cysteine Hydrochloride; Cysteine Hydrochloride Anhydrous; Cysteine, Dl-; D&C Red No. 28; D&C Red No.

33; D&C Red No. 36; D&C Red No. 39; D&C Yellow No. 10; Dalfampridine; Daubert 1-5 Pestr (Matte) 164z; Decyl Methyl Sulfoxide; Dehydag Wax Sx; Dehydroacetic Acid; Dehymuls E; Denatonium Benzoate; Deoxycholic Acid; Dextran; Dextran 40; Dextrin; Dextrose; Dextrose Monohydrate; Dextrose Solution; Diatrizoic Acid; Diazolidinyl Urea; Dichlorobenzyl Alcohol; Dichlorodifluoromethane; Dichlorotetrafluoroethane; Diethanolamine; Diethyl Pyrocarbonate; Diethyl Scbacate; Diethylene Glycol Monoethyl Ether; Diethylhexyl Phthalate; Dihydroxyaluminum Aminoacetate; Diisopropanolamine; Diisopropyl Adipate; Diisopropyl Dilinoleate; Dimethicone 350; Dimethicone Copolyol; Dimethicone Mdx4-4210; Dimethicone Medical Fluid 360; Dimethyl Isosorbide; Dimethyl Sulfoxide; Dimethylaminoethyl Methacrylate-Butyl Methacrylate-Methyl Methacrylate Copolymer; Dimethyldioctadecylammonium Bentonite; Dimethylsiloxane/Methylvinylsiloxane Copolymer; Dinoseb Ammonium Salt; Dipalmitoylphosphatidylglycerol, Dl-; Dipropylene Glycol; Disodium Cocoamphodiacetate; Disodium Laureth Sulfosuccinate; Disodium Lauryl Sulfosuccinate; Disodium Sulfosalicylate; Disofenin; Divinylbenzene Styrene Copolymer; Dmdm Hydantoin; Docosanol; Docusate Sodium; Duro-Tak 280-2516; Duro-Tak 387-2516; Duro-Tak 80-1196; Duro-Tak 87-2070; Duro-Tak 87-2194; Duro-Tak 87-2287; Duro-Tak 87-2296; Duro-Tak 87-2888; Duro-Tak 87-2979; Edetate Calcium Disodium; Edetate Disodium; Edetate Disodium Anhydrous; Edetate Sodium; Edetic Acid; Egg Phospholipids; Entsufon; Entsufon Sodium; Epilactose; Epitetracycline Hydrochloride; Essence Bouquet 9200; Ethanolamine Hydrochloride; Ethyl Acetate; Ethyl Oleate; Ethylcelluloses; Ethylene Glycol; Ethylene Vinyl Acetate Copolymer; Ethylenediamine; Ethylenediamine Dihydrochloride; Ethylene-Propylene Copolymer; Ethylene-Vinyl Acetate Copolymer (28% Vinyl Acetate); Ethylene-Vinyl Acetate Copolymer (9% Vinylacetate); Ethylhexyl Hydroxystearate; Ethylparaben; Eucalyptol; Exametazime; Fat, Edible; Fat, Hard; Fatty Acid Esters; Fatty Acid Pentaerythritol Ester; Fatty Acids; Fatty Alcohol Citrate; Fatty Alcohols; Fd&C Blue No. 1; Fd&C Green No. 3; Fd&C Red No. 4; Fd&C Red No. 40; Fd&C Yellow No. 10 (Delisted); Fd&C Yellow No. 5; Fd&C Yellow No. 6; Ferric Chloride; Ferric Oxide; Flavor 89-186; Flavor 89-259; Flavor Df-119; Flavor Df-1530; Flavor Enhancer; Flavor Fig 827118; Flavor Raspberry Pfc-8407; Flavor Rhodia Pharmaceutical No. Rf 451; Fluorochlorohydrocarbons; Formaldehyde; Formaldehyde Solution; Fractionated Coconut Oil; Fragrance 3949-5; Fragrance 520a; Fragrance 6.007; Fragrance 91-122; Fragrance 9128-Y; Fragrance 93498g; Fragrance Balsam Pine No. 5124; Fragrance Bouquet 10328; Fragrance Chemoderm 6401-B; Fragrance Chemoderm 6411; Fragrance Cream No. 73457; Fragrance Cs-28197; Fragrance Felton 066m; Fragrance Firmenich 47373; Fragrance Givaudan Ess 9090/1c; Fragrance H-6540; Fragrance Herbal 10396; Fragrance Nj-1085; Fragrance P O F1-147; Fragrance Pa 52805; Fragrance Pera Derm D; Fragrance Rbd-9819; Fragrance Shaw Mudge U-7776; Fragrance Tf 044078; Fragrance Ungerer Honeysuckle K 2771; Fragrance Ungerer N5195; Fructose; Gadolinium Oxide; Galactose; Gamma Cyclodextrin; Gelatin; Gelatin, Crosslinked; Gelfoam Sponge; Gellan Gum (Low Acyl); Gelva 737; Gentisic Acid; Gentisic Acid Ethanolamide; Gluceptate Sodium; Gluceptate Sodium Dihydrate; Gluconolactone; Glucuronic Acid; Glutamic Acid, Dl-; Glutathione; Glycerin; Glycerol Ester Of Hydrogenated Rosin; Glyceryl Citrate; Glyceryl Isostearate; Glyceryl Laurate; Glyceryl Monostearate; Glyceryl Oleate; Glyceryl Oleate/ Propylene Glycol; Glyceryl Palmitate; Glyceryl Ricinoleate; Glyceryl Stearate; Glyceryl Stearate-Laureth-23; Glyceryl Stearate/Peg Stearate; Glyceryl Stearate/Peg-100 Stearate; Glyceryl Stearate/Peg-40 Stearate; Glyceryl Stearate-Stearamidoethyl Diethylamine; Glyceryl Trioleate; Glycine; Glycine Hydrochloride; Glycol Distearate; Glycol Stearate; Guanidine Hydrochloride; Guar Gum; Hair Conditioner (18n195-1m); Heptane; Hetastarch; Hexylene Glycol; High Density Polyethylene; Histidine; Human Albumin Microspheres; Hyaluronate Sodium; Hydrocarbon; Hydrocarbon Gel, Plasticized; Hydrochloric Acid; Hydrochloric Acid. Diluted; Hydrocortisone; Hydrogel Polymer; Hydrogen Peroxide; Hydrogenated Castor Oil; Hydrogenated Palm Oil; Hydrogenated Palm/Palm Kernel Oil Peg-6 Esters; Hydrogenated Polybutene 635-690; Hydroxide Ion; Hydroxyethyl Cellulose; Hydroxyethylpiperazine Ethane Sulfonic Acid; Hydroxymethyl Cellulose; Hydroxyoctacosanyl Hydroxystearate; Hydroxypropyl Cellulose; Hydroxypropyl Methylcellulose 2906; Hydroxypropyl-Beta-cyclodextrin; Hypromellose 2208 (15000 Mpa.S); Hypromellose 2910 (15000 Mpa.S); Hypromelloses; Imidurea; Iodine; Iodoxamic Acid; Iofetamine Hydrochloride; Irish Moss Extract; Isobutane; Isoceteth-20; Isoleucine; Isooctyl Acrylate; Isopropyl Alcohol; Isopropyl Isostearate; Isopropyl Myristate; Isopropyl Myristate—Myristyl Alcohol; Isopropyl Palmitate; Isopropyl Stearate; Isostearic Acid; Isostearyl Alcohol; Isotonic Sodium Chloride Solution; Jelene; Kaolin; Kathon Cg; Kathon Cg II; Lactate; Lactic Acid; Lactic Acid, Dl-; Lactic Acid, L-; Lactobionic Acid; Lactose; Lactose Monohydrate; Lactose. Hydrous; Laneth; Lanolin; Lanolin Alcohol—Mineral Oil; Lanolin Alcohols; Lanolin Anhydrous; Lanolin Cholesterols; Lanolin Nonionic Derivatives; Lanolin, Ethoxylated; Lanolin, Hydrogenated; Lauralkonium Chloride; Lauramine Oxide; Laurdimonium Hydrolyzed Animal Collagen; Laureth Sulfate; Laureth-2; Laureth-23; Laureth-4; Lauric Diethanolamide; Lauric Myristic Diethanolamide; Lauroyl Sarcosine; Lauryl Lactate; Lauryl Sulfate; *Lavandula Angustifolia* Flowering Top; Lecithin; Lecithin Unbleached; Lecithin, Egg; Lecithin, Hydrogenated; Lecithin, Hydrogenated Soy; Lecithin, Soybean; Lemon Oil; Leucine; Levulinic Acid; Lidofenin; Light Mineral Oil, Light Mineral Oil (85 Ssu); Limonene, (+/−)-; Lipocol Sc-15; Lysine; Lysine Acetate; Lysine Monohydrate; Magnesium Aluminum Silicate; Magnesium Aluminum Silicate Hydrate; Magnesium Chloride; Magnesium Nitrate; Magnesium Stearate; Maleic Acid; Mannitol; Maprofix; Mebrofenin; Medical Adhesive Modified S-15; Medical Antiform A-F Emulsion; Medronate Disodium; Medronic Acid; Meglumine; Menthol; Metacresol; Metaphosphoric Acid; Methanesulfonic Acid; Methionine; Methyl Alcohol; Methyl Gluceth-10; Methyl Gluceth-20; Methyl Gluceth-20 Sesquistearate; Methyl Glucose Sesquistearate; Methyl Laurate; Methyl Pyrrolidone; Methyl Salicylate; Methyl Stearate; Methylboronic Acid; Methylcellulose (4000 Mpa.S); Methylcelluloses; Methylchloroisothiazolinone; Methylene Blue; Methylisothiazolinone; Methylparaben; Microcrystalline Wax; Mineral Oil; Mono And Diglyceride; Monostearyl Citrate; Monothioglycerol; Multisterol Extract; Myristyl Alcohol; Myristyl Lactate; Myristyl-.Gamma.-Picolinium Chloride; N-(Carbamoyl-Methoxy Peg-40)-1,2-Distearoyl-Cephalin Sodium; N,N-Dimethylacetamide; Niacinamide; Nioxime; Nitric Acid; Nitrogen; Nonoxynol Iodine; Nonoxynol-15; Nonoxynol-9; Norflurane; Oatmeal; Octadecene-1/Maleic Acid Copolymer; Octanoic Acid; Octisalate; Octoxynol-1; Octoxynol-40; Octoxynol-9; Octyldodecanol; Octylphenol Polymethylene; Oleic Acid; Oleth-10/Oleth-5; Oleth-2; Oleth-20; Oleyl Alcohol; Oleyl Oleate; Olive Oil; Oxidronate Disodium; Oxyquinoline; Palm Kernel Oil; Palmitamine Oxide; Parabens; Paraffin; Paraffin, White Soft; Parfum Creme 45/3; Peanut Oil; Peanut Oil, Refined; Pectin; Peg 6-32 Stearate/Glycol Stearate; Peg Vegetable Oil; Peg-100 Stearate; Peg-12 Glyceryl Laurate; Peg-120 Glyceryl Stearate; Peg-120 Methyl Glucose Dioleate; Peg-15 Cocamine; Peg-150 Distearate; Peg-2 Stearate; Peg-20 Sorbitan Isostearate; Peg-22 Methyl Ether/Dodecyl Glycol Copolymer; Peg-25 Propylene Glycol Stearate; Peg-4 Dilaurate; Peg-4 Laurate; Peg-40 Castor Oil; Peg-40 Sorbitan Diisostearate; Peg-45/ Dodecyl Glycol Copolymer; Peg-5 Oleate; Peg-50 Stearate; Peg-54 Hydrogenated Castor Oil; Peg-6 Isostearate; Peg-60 Castor Oil; Peg-60 Hydrogenated Castor Oil; Peg-7 Methyl Ether; Peg-75 Lanolin; Peg-8 Laurate; Peg-8 Stearate; Pegoxol 7 Stearate; Pentadecalactone; Pentaerythritol Cocoate; Pentasodium Pentetate; Pentetate Calcium Trisodium; Pentetic Acid; Peppermint Oil; Perflutren; Perfume 25677; Perfume Bouquet; Perfume E-1991; Perfume Gd 5604; Perfume Tana 90/42 Seba; Perfume W-1952-1; Petrolatum; Petrolatum. White; Petroleum Distillates; Phenol; Phenol, Liquefied; Phenonip; Phenoxyethanol; Phenylalanine; Phenylethyl Alcohol; Phenylmercuric Acetate; Phenylmercuric Nitrate; Phosphatidyl Glycerol, Egg; Phospholipid; Phospholipid, Egg; Phospholipon 90g; Phosphoric Acid; Pine Needle Oil (*Pinus Sylvestris*); Piperazine Hexahydrate; Plastibase-50w; Polacrilin; Polidronium Chloride; Poloxamer 124; Poloxamer 181; Poloxamer 182; Poloxamer 188; Poloxamcr 237; Poloxamer 407; Poly(Bis(P-Carboxyphenoxy)Propane Anhydride); Sebacic Acid; Poly(Dimethylsiloxane/Methylvinylsiloxane/Methylhydrogensiloxane) Dimethylvinyl Or Dimethylhydroxy Or Trimethyl Endblocked; Poly(DI-Lactic-Co-Glycolic Acid), (50;50; Poly (DI-Lactic-Co-Glycolic Acid), Ethyl Ester Terminated, (50; 50; Polyacrylic Acid (250000 Mw); Polybutene (1400 Mw); Polycarbophil; Polyester; Polyester Polyamine Copolymer; Polyester Rayon; Polyethylene Glycol 1000; Polyethylene Glycol 1450; Polyethylene Glycol 1500; Polyethylene Glycol 1540; Polyethylene Glycol 200; Polyethylene Glycol 300; Polyethylene Glycol 300-1600; Polyethylene Glycol 3350; Polyethylene Glycol 400; Polyethylene Glycol 4000; Polyethylene Glycol 540; Polyethylene Glycol 600; Polyethylene Glycol 6000; Polyethylene Glycol 8000; Polyethylene Glycol 900; Polyethylene High Density Containing Ferric Oxide Black (<1%); Polyethylene Low Density Containing Barium Sulfate (20-24%); Polyethylene T; Polyethylene Terephthalates; Polyglactin; Polyglyceryl-3 Oleate; Polyglyceryl-4 Oleate; Polyhydroxyethyl Methacrylate; Polyisobutylene; Polyisobutylene (1100000 Mw); Polyisobutylene (35000 Mw); Polyisobutylene 178-236; Polyisobutylene 241-294; Polyisobutylene 35-39; Polyisobutylene Low Molecular Weight; Polyisobutylene Medium Molecular Weight; Polyisobutylene/Polybutene Adhesive; Polylactide; Polyols; Polyoxyethylene-Polyoxypropylene 1800; Polyoxyethylene Alcohols; Polyoxyethylene Fatty Acid Esters; Polyoxyethylene Propylene; Polyoxyl 20 Cetostearyl Ether; Polyoxyl 35 Castor Oil; Polyoxyl 40 Hydrogenated Castor Oil; Polyoxyl 40 Stearate; Polyoxyl 400 Stearate; Polyoxyl 6 And Polyoxyl 32 Palmitostearate; Polyoxyl Distearate; Polyoxyl Glyceryl Stearate; Polyoxyl Lanolin; Polyoxyl Palmitate; Polyoxyl Stearate; Polypropylene; Polypropylene Glycol; Polyquaternium-10; Polyquaternium-7 (70/30 Acrylamide/Dadmac; Polysiloxane; Polysorbate 20; Polysorbate 40; Polysorbate 60; Polysorbate 65; Polysorbate 80; Polyurethane; Polyvinyl Acetate; Polyvinyl Alcohol; Polyvinyl Chloride; Polyvinyl Chloride-Polyvinyl Acetate Copolymer; Polyvinylpyridine; Poppy Seed Oil; Potash; Potassium Acetate; Potassium Alum; Potassium Bicarbonate; Potassium Bisulfite; Potassium Chloride; Potassium Citrate; Potassium Hydroxide; Potassium Metabisulfite; Potassium Phosphate, Dibasic; Potassium Phosphate, Monobasic; Potassium Soap; Potassium Sorbate; Povidone Acrylate Copolymer; Povidone Hydrogel; Povidone K17; Povidone K25; Povidone K29/32; Povidone K30; Povidone K90; Povidone K90f; Povidone/Eicosene Copolymer; Povidones; Ppg-12/Smdi Copolymer; Ppg-15 Stearyl Ether; Ppg-20 Methyl Glucose Ether Distearate; Ppg-26 Oleate; Product Wat; Proline; Promulgen D; Promulgen G; Propane; Propellant A-46; Propyl Gallate; Propylene Carbonate; Propylene Glycol; Propylene Glycol Diacetate; Propylene Glycol Dicaprylate; Propylene Glycol Monolaurate; Propylene Glycol Monopalmitostearate; Propylene Glycol Palmitostearate; Propylene Glycol Ricinoleate; Propylene Glycol/Diazolidinyl Urea/Methylparaben/Propylparaben; Propylparaben; Protamine Sulfate; Protein Hydrolysate; Pvm/Ma Copolymer; Quaternium-15; Quaternium-15 Cis-Form; Quaternium-52; Ra-2397; Ra-3011; Saccharin; Saccharin Sodium; Saccharin Sodium Anhydrous; Safflower Oil; Sd Alcohol 3a; Sd Alcohol 40; Sd Alcohol 40-2; Sd Alcohol 40b; Sepineo P 600; Serine; Sesame Oil; Shea Butter; Silastic Brand Medical Grade Tubing; Silastic Medical Adhesive, Silicone Type A; Silica, Dental; Silicon; Silicon Dioxide; Silicon Dioxide, Colloidal; Silicone; Silicone Adhesive 4102; Silicone Adhesive 4502; Silicone Adhesive Bio-Psa Q7-4201; Silicone Adhesive Bio-Psa Q7-4301; Silicone Emulsion; Silicone/Polyester Film Strip; Simethicone; Simethicone Emulsion; Sipon Ls 20np; Soda Ash; Sodium Acetate; Sodium Acetate Anhydrous; Sodium Alkyl Sulfate; Sodium Ascorbate; Sodium Benzoate; Sodium Bicarbonate; Sodium Bisulfate; Sodium Bisulfite; Sodium Borate; Sodium Borate Decahydrate; Sodium Carbonate; Sodium Carbonate Decahydrate; Sodium Carbonate Monohydrate; Sodium Cetostearyl Sulfate; Sodium Chlorate; Sodium Chloride; Sodium Chloride Injection; Sodium Chloride Injection, Bacteriostatic; Sodium Cholesteryl Sulfate; Sodium Citrate; Sodium Cocoyl Sarcosinate; Sodium Desoxycholate; Sodium Dithionite; Sodium Dodecylbenzenesulfonate; Sodium Formaldehyde Sulfoxylate; Sodium Gluconate; Sodium Hydroxide; Sodium Hypochlorite; Sodium Iodide; Sodium Lactate; Sodium Lactate, L-; Sodium Laureth-2 Sulfate; Sodium Laureth-3 Sulfate; Sodium Laureth-5 Sulfate; Sodium Lauroyl Sarcosinate; Sodium Lauryl Sulfate; Sodium Lauryl Sulfoacetate; Sodium Metabisulfite; Sodium Nitrate; Sodium Phosphate; Sodium Phosphate Dihydrate; Sodium Phosphate, Dibasic; Sodium Phosphate, Dibasic, Anhydrous; Sodium Phosphate, Dibasic, Dihydrate; Sodium Phosphate, Dibasic, Dodecahydrate; Sodium Phosphate, Dibasic, Heptahydrate; Sodium Phosphate, Monobasic; Sodium Phosphate, Monobasic. Anhydrous; Sodium Phosphate, Monobasic, Dihydrate; Sodium Phosphate, Monobasic, Monohydrate; Sodium Polyacrylate (2500000 Mw); Sodium Pyrophosphate; Sodium Pyrrolidone Carboxylate; Sodium Starch Glycolate; Sodium Succinate Hexahydrate; Sodium Sulfate; Sodium Sulfate Anhydrous; Sodium Sulfate Decahydrate; Sodium Sulfite; Sodium Sulfosuccinated Undecylenic Monoalkylolamide; Sodium Tartrate; Sodium Thioglycolate; Sodium Thiomalate; Sodium Thiosulfate; Sodium Thiosulfate Anhydrous; Sodium Trimetaphosphate; Sodium Xylenesulfonate; Somay 44; Sorbic Acid; Sorbitan; Sorbitan Isostearate; Sorbitan Monolaurate; Sorbitan Monooleate; Sorbitan Monopalmitate; Sorbitan Monostearate; Sorbitan Sesquioleate; Sorbitan Trioleate; Sorbitan Tristearate; Sorbitol; Sorbitol Solution; Soybean Flour; Soybean Oil; Spearmint Oil; Spermaceti; Squalane; Stabilized Oxychloro Complex;

Stannous 2-Ethylhexanoate; Stannous Chloride; Stannous Chloride Anhydrous; Stannous Fluoride; Stannous Tartrate; Starch; Starch 1500, Pregelatinized; Starch, Corn; Stearalkonium Chloride; Stearalkonium Hectorite/Propylene Carbonate; Stearamidoethyl Diethylamine; Steareth-10; Steareth-100; Steareth-2; Steareth-20; Steareth-21; Steareth-40; Stearic Acid; Stearic Diethanolamide; Stearoxytrimethylsilane; Steartrimonium Hydrolyzed Animal Collagen; Stearyl Alcohol; Sterile Water For Inhalation; Styrene/Isoprene/Styrene Block Copolymer; Succimer; Succinic Acid; Sucralose; Sucrose; Sucrose Distearate; Sucrose Polyesters; Sulfacetamide Sodium; Sulfobutylether .Beta.-Cyclodextrin; Sulfur Dioxide; Sulfuric Acid; Sulfurous Acid; Surfactol Qs; Tagatose, D-; Talc; Tall Oil; Tallow Glycerides; Tartaric Acid; Tartaric Acid, Dl-; Tenox; Tenox-2; Tert-Butyl Alcohol; Tert-Butyl Hydroperoxide; Tert-Butylhydroquinone; Tetrakis(2-Methoxyisobutylisocyanide)Copper(I) Tetrafluoroborate; Tetrapropyl Orthosilicate; Tetrofosmin; Theophylline; Thimerosal; Threonine; Thymol; Tin; Titanium Dioxide; Tocopherol; Tocophersolan; Total parenteral nutrition, lipid emulsion; Triacetin; Tricaprylin; Trichloromonofluoromethane; Trideceth-10; Triethanolamine Lauryl Sulfate; Trifluoroacetic Acid; Triglycerides, Medium Chain; Trihydroxystearin; Trilaneth-4 Phosphate; Trilaureth-4 Phosphate; Trisodium Citrate Dihydrate; Trisodium Hedta; Triton 720; Triton X-200; Trolamine; Tromantadine; Tromethamine (TRIS); Tryptophan; Tyloxapol; Tyrosine; Undecylenic Acid; Union 76 Amsco-Res 6038; Urea; Valine; Vegetable Oil; Vegetable Oil Glyceride, Hydrogenated; Vegetable Oil, Hydrogenated; Versetamide; Viscarin; Viscose/Cotton; Vitamin E; Wax, Emulsifying; Wecobee Fs; White Ceresin Wax; White Wax; Xanthan Gum; Zinc; Zinc Acetate; Zinc Carbonate; Zinc Chloride; and Zinc Oxide.

Pharmaceutical composition formulations of AAV particles disclosed herein may include cations or anions. In certain embodiments, the formulations include metal cations such as, but not limited to, $Zn^{2+}$, $Ca^{2+}$, $Cu^{2+}$, $Mn^{2+}$, $Mg^{+}$ and combinations thereof. In certain embodiments, formulations may include polymers and complexes with a metal cation (See e.g., U.S. Pat. Nos. 6,265,389 and 6,555,525, each of which is herein incorporated by reference in its entirety).

Formulations of the disclosure may also include one or more pharmaceutically acceptable salts. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids.

The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418. Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977); the content of each of which is incorporated herein by reference in their entirety.

The term "pharmaceutically acceptable solvate," as used herein, means a compound of the disclosure wherein molecules of a suitable solvent are incorporated in the crystal lattice. A suitable solvent is physiologically tolerable at the dosage administered. Solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

III. Administration and Dosing

Administration

In certain embodiments, the AAV particle may be administered to a subject (e.g., to the CNS of a subject) in a therapeutically effective amount to reduce the symptoms of the disease of the central nervous system (e.g., Parkinson's Disease) of a subject (e.g., determined using a known evaluation method).

The AAV particles of the present disclosure may be administered by any delivery route which results in a therapeutically effective outcome. These include, but are not limited to, enteral (into the intestine), gastroenteral, epidural (into the dura mater), oral (by way of the mouth), transdermal, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraparenchymal (into brain tissue), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), or in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal.

In some embodiments, compositions may be administered in a way which allows them to cross the blood-brain barrier, vascular barrier, or other epithelial barrier. The AAV particles of the present disclosure may be administered in any suitable form, either as a liquid solution or suspension, as a solid form suitable for liquid solution or suspension in a liquid solution. The AAV particles may be formulated with any appropriate and pharmaceutically acceptable excipient.

In certain embodiments, the AAV particles of the present disclosure may be delivered to a subject via a single route administration.

In certain embodiments, the AAV particles of the present disclosure may be delivered to a subject via a multi-site route of administration. A subject may be administered at 2, 3, 4, 5 or more than 5 sites.

In certain embodiments, a subject may be administered the AAV particles of the present disclosure using a bolus infusion.

In certain embodiments, a subject may be administered the AAV particles of the present disclosure using sustained delivery over a period of minutes, hours or days. In certain embodiments, the infusion rate is between 1 to 30 µL/min. In certain embodiments, the infusion rate may be changed depending on the subject, distribution, formulation or another delivery parameter. In certain embodiments, the infusion rate increases through the duration of the administration. In certain embodiments, the infusion rate increases from an initial infusion rate to a final infusion rate through the duration of the administration. In certain embodiments, the initial infusion rate is between 1 to 30 µL/min. In certain embodiments, the final infusion rate is between 1 to 30 µL/min.

In certain embodiments, the AAV particles of the present disclosure may be delivered by intramuscular delivery route. (See, e.g., U.S. Pat. No. 6,506,379; the content of which is incorporated herein by reference in its entirety). Non-limiting examples of intramuscular administration include an intravenous injection or a subcutaneous injection.

In certain embodiments, the AAV particles of the present disclosure may be delivered by oral administration. Non-limiting examples of oral administration include a digestive tract administration and a buccal administration.

In certain embodiments, the AAV particles of the present disclosure may be delivered by intraocular delivery route. A non-limiting example of intraocular administration include an intravitreal injection.

In certain embodiments, the AAV particles of the present disclosure may be delivered by intranasal delivery route. Non-limiting examples of intranasal delivery include administration of nasal drops or nasal sprays.

In some embodiments, the AAV particles that may be administered to a subject by peripheral injections. Non-limiting examples of peripheral injections include intraperitoneal, intramuscular, intravenous, conjunctival or joint injection. It was disclosed in the art that the peripheral administration of AAV particles can be transported to the central nervous system, for example, to the motor neurons (e.g., U.S. Patent Publication Nos. 20100240739; and 20100130594; the content of each of which is incorporated herein by reference in their entirety).

In certain embodiments, the AAV particles may be delivered by injection into the CSF pathway. Non-limiting examples of delivery to the CSF pathway include intrathecal and intracerebroventricular administration.

In certain embodiments, the AAV particles may be delivered by systemic delivery. In certain embodiments, the systemic delivery may be by intravascular administration.

In certain embodiments, the AAV particles of the present disclosure may be administered to a subject by intracranial delivery (See, e.g., U.S. Pat. No. 8,119,611; the content of which is incorporated herein by reference in its entirety).

In some embodiments, the AAV particles of the present disclosure may be administered by injection. In certain embodiments, the AAV particles of the present disclosure may be administered to a subject by injection.

In some embodiments, the AAV particles of the present disclosure may be administered by muscular injection. In certain embodiments, the AAV particles of the present disclosure may be administered to a subject by muscular administration.

In some embodiments, the AAV particles of the present disclosure may be administered by intramuscular administration. In certain embodiments, the AAV particles of the present disclosure may be administered to a subject by intramuscular administration.

In certain embodiments, the AAV particles of the present disclosure are administered to a subject and transduce muscle of a subject. In certain embodiments, the AAV particles are administered by intramuscular administration.

In some embodiments, the AAV particles of the present disclosure may be administered via intraparenchymal injection. In certain embodiments, the AAV particles of the present disclosure may be administered to a subject by intraparenchymal administration.

In some embodiments, the AAV particles of the present disclosure may be administered by intravenous administration. In certain embodiments, the AAV particles of the present disclosure may be administered to a subject by intravenous administration.

In certain embodiments, the AAV particles of the present disclosure may be administered via intravenous delivery.

In certain embodiments, the AAV particles of the present disclosure may be administered via a single dose intravenous delivery. In certain embodiments, the single dose intravenous delivery may be a one-time treatment. In the context of diseases of the central nervous system (e.g., Parkinson's Disease), the single dose intravenous delivery can produce durable relief for subjects with central nervous system (e.g., Parkinson's Disease) and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes: hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In certain embodiments, the AAV particles of the present disclosure may be administered via intravenous delivery to the DRG nociceptive neurons.

In certain embodiments, the AAV particles of the present disclosure may be administered via a single dose intravenous delivery to the DRG nociceptive neurons. In certain embodiments, the single dose intravenous delivery may be a one-time treatment. In the context of diseases of the central nervous system (e.g., Parkinson's Disease), the single dose intravenous delivery can produce durable relief for subjects with diseases of the central nervous system (e.g., Parkinson's Disease) and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In some embodiments, the AAV particles of the present disclosure may be administered by intrathecal injection. In certain embodiments, the AAV particles of the present disclosure may be administered by intrathecal injection.

In certain embodiments, the AAV particle may be administered to the cisterna magna in a therapeutically effective amount to transduce spinal cord motor neurons and/or astrocytes. In certain embodiments, the AAV particle may be administered intrathecally.

In certain embodiments, the AAV particle may be administered using intrathecal infusion in a therapeutically effective amount to transduce spinal cord motor neurons and/or astrocytes.

In some embodiments, the AAV particles of the present disclosure may be administered via a single dose intrathecal injection. In certain embodiments, the single dose intrathecal injection may be a one-time treatment. In the context of diseases of the central nervous system (e.g., Parkinson's Disease), the single dose intrathecal injection can produce durable relief for subjects with diseases of the central nervous system (e.g., Parkinson's Disease) and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In some embodiments, the AAV particles of the present disclosure may be administered via intrathecal injection to the DRG nociceptive neurons.

In some embodiments, the AAV particles of the present disclosure may be administered via a single dose intrathecal injection to the DRG nociceptive neurons. In certain embodiments, the single dose intrathecal injection may be a one-time treatment. In the context of diseases of the central nervous system (e.g., Parkinson's Disease), the single dose intrathecal injection can produce durable relief for subjects with diseases of the central nervous system (e.g., Parkinson's Disease) and/or related symptoms. The relief may last for minutes such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes or more than 59 minutes; hours such as, but not limited to, 1, 2, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more than 48 hours; days such as, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more than 31 days; weeks such as, but not limited to, 1, 2, 3, 4, 5, 6, 7, 8, 9, 10, 11, 12, 13, 14, 15, 16, or more than 16 weeks; months such as, but not limited to, 1, 2, 3, 4, 5, 6, 7, 8, 9, 10, 11, 12, 13, 14, 15, 16, 17, 18, 19, 20, 21, 22, 23, 24, or more than 24 months; years such as, but not limited to, 1, 2, 3, 4, 5, 6, 7, 8, 9, 10, 11, 12, 13, 14, 15, or more than 15 years.

In certain embodiments, the AAV particle described herein is administered via intrathecal (IT) infusion at C1. The infusion may be for 1, 2, 3, 4, 6, 7, 8, 9, 10, 11, 12, 13, 14, 15 or more than 15 hours.

In some embodiments, the AAV particles of the present disclosure may be administered by intraparenchymal injection. In certain embodiments, the AAV particles of the present disclosure may be administered to a subject by intraparenchymal injection.

In certain embodiments, the AAV particle may be administered to the cisterna magna in a therapeutically effective amount to transduce spinal cord motor neurons and/or astrocytes. In certain embodiments, the AAV particle may be administered intraparenchymal injection.

In some embodiments, the AAV particles of the present disclosure may be administered by intraparenchymal injection and intrathecal injection. In certain embodiments, the AAV particles of the present disclosure may be administered via intraparenchymal injection and intrathecal injection.

In some embodiments, the AAV particles of the present disclosure may be administered by subcutaneous injection. In certain embodiments, the AAV particles In certain embodiments, the AAV particles of the present disclosure may be administered to a subject by subcutaneous injection.

In some embodiments, the AAV particles of the present disclosure may be administered topically. In certain embodiments, the AAV particles of the present disclosure may be administered to a subject topically.

In certain embodiments, the AAV particles may be delivered by direct injection into the brain. In certain embodiments, the brain delivery may be by intrastriatal administration.

In certain embodiments, the AAV particles of the present disclosure may be administered via intrastriatal injection.

In certain embodiments, the AAV particles of the present disclosure may be administered via intrastriatal injection and another route of administration described herein.

In certain embodiments, the AAV particles may be delivered by more than one route of administration. As non-limiting examples of combination administrations, AAV particles may be delivered by intrathecal and intracerebroventricular, or by intravenous and intraparenchymal administration.

In certain embodiments, the AAV particle may be administered to the CNS in a therapeutically effective amount to improve function and/or survival for a subject with diseases of the central nervous system (e.g., Parkinson's Disease). In certain embodiments, the vector may be administered by direct infusion into the striatum.

The AAV particle may be administered in a "therapeutically effective" amount, i.e., an amount that is sufficient to alleviate and/or prevent at least one symptom associated with the disease, or provide improvement in the condition of the subject.

Parenteral and Injectable Administration

In some embodiments, pharmaceutical compositions, AAV particles of the present disclosure may be administered parenterally. Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of active ingredients, it is often desirable to slow the absorption of active ingredients from subcutaneous or intramuscular injections. This may be accomplished by the use of liquid suspensions of crystalline or amorphous material with poor water solubility. The rate of absorption of active ingredients depends upon the rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Depot Administration

As described herein, in some embodiments, pharmaceutical compositions, AAV particles of the present disclosure are formulated in depots for extended release. Generally, specific organs or tissues ("target tissues") are targeted for administration.

In some aspects of the disclosure, pharmaceutical compositions, AAV particles of the present disclosure are spatially retained within or proximal to target tissues. Provided are methods of providing pharmaceutical compositions, AAV particles, to target tissues of mammalian subjects by contacting target tissues (which comprise one or more target cells) with pharmaceutical compositions, AAV particles, under conditions such that they are substantially retained in target tissues, meaning that least 10, 20, 30, 40, 50, 60, 70, 80, 85, 90, 95, 96, 97, 98, 99, 99.9, 99.99 or greater than 99.99% of the composition is retained in the target tissues. Advantageously, retention is determined by measuring the amount of pharmaceutical compositions, AAV particles, that enter one or more target cells. For example, at least 1%, 5%, 10%, 20%, 30%, 40%, 50%, 60%, 70%, 80%, 85%, 90%, 95%, 96%, 97%, 98%, 99%, 99.9%, 99.99% or greater than 99.99% of pharmaceutical compositions, AAV particles, administered to subjects are present intracellularly at a period of time following administration. For example, intramuscular injection to mammalian subjects may be performed using aqueous compositions comprising pharmaceutical compositions, AAV particles of the present disclosure and one or more transfection reagents, and retention is determined by measuring the amount of pharmaceutical compositions, AAV particles, present in muscle cells.

Certain aspects of the disclosure are directed to methods of providing pharmaceutical compositions, AAV particles of the present disclosure to a target tissues of mammalian subjects, by contacting target tissues (comprising one or more target cells) with pharmaceutical compositions, AAV particles under conditions such that they are substantially retained in such target tissues. Pharmaceutical compositions, AAV particles comprise enough active ingredient such that the effect of interest is produced in at least one target cell. In some embodiments, pharmaceutical compositions, AAV particles generally comprise one or more cell penetration agents, although "naked" formulations (such as without cell penetration agents or other agents) are also contemplated, with or without pharmaceutically acceptable carriers.

Delivery to the Central Nervous System

In certain embodiments, delivery of the pharmaceutical compositions comprising AAV particles to cells of the central nervous system (e.g., parenchyma) comprises infusion of up to 1 mL. In certain embodiments, delivery of the pharmaceutical compositions comprising AAV particles to cells of the central nervous system (e.g., parenchyma) may comprise infusion of 0.001, 0.002, 0.003, 0.004, 0.005, 0.010, 0.015, 0.020, 0.025, 0.030, 0.040, 0.050, 0.060, 0.070, 0.080, 0.090, 0.1, 0.2, 0.3, 0.4, 0.5, 0.6, 0.7, 0.8, or 0.9 mL.

In certain embodiments, delivery of pharmaceutical composition comprising AAV particles to cells of the central nervous system (e.g., parenchyma) comprises infusion of between about 1 mL to about 120 mL. In certain embodiments, delivery of pharmaceutical composition comprising AAV particles to cells of the central nervous system (e.g., parenchyma) may comprise infusion of 0.1, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 mL. In certain embodiments, delivery of AAV particles to cells of the central nervous system (e.g., parenchyma) comprises infusion of at least 3 mL. In certain embodiments, delivery of AAV particles to cells of the central nervous system (e.g., parenchyma) consists of infusion of 3 mL. In certain embodiments, delivery of AAV particles to cells of the central nervous system (e.g., parenchyma) comprises infusion of at least 10 mL. In certain embodiments, delivery of AAV particles to cells of the central nervous system (e.g., parenchyma) consists of infusion of 10 mL.

In certain embodiments, the volume of the pharmaceutical composition comprising AAV particles delivered to the cells of the central nervous system (e.g., parenchyma) of a subject is 50 µL, 100 µL, 200 µL, 300 µL, 400 µL, 500 µL, 600 µL, 700 µL, 800 µL, 900 µL, 1000 µL, 11001 µL, 1200 µL, 1300 µL, 1400 µL, 1500 µL, 1600 µL, 1700 µL, 1800 µL, 1900 µL, 2000 µL or more than 2000 µL.

In certain embodiments, the volume of the pharmaceutical composition comprising AAV particles delivered to a region in both hemispheres of a subject brain is 50 µL, 100 µL, 200 µL, 300 µL, 400 µL, 500 µL, 600 µL, 700 µL, 800 µL, 900 µL, 1000 µL, 1100 µL, 1200 µL, 1300 µL, 1400 µL, 1500 µL, 1600 µL, 1700 µL, 1800 µL, 1900 µL, 2000 µL or more than 2000 µL.

In certain embodiments, the volume delivered to a region in both hemispheres is 200 µL. In certain embodiments, the volume delivered to a region in both hemispheres is 900 µL. As yet another non-limiting example, the volume delivered to a region in both hemispheres is 1800 µL.

In certain embodiments, the volume delivered to each hemisphere of a subject brain is up to 100 µL, 125 µL, 150 µL, 175 µL, 180 µL, 200 µL, 210 µL, 220 µL, 225 µL, 250 µL, 275 µL, 300 µL, 325 µL, 350 µL, 375, 400 µL, 425 µL, 450 µL, 475 µL, 500 µL, 525 µL, 550 µL, 575 µL, 600 µL, 625 µL, 650 µL, 675 µL, 700 µL, 725 µL, 750 µL, 775 µL, 800 µL, 825 µL, 850 µL, 875 µL, 900 µL, 925 µL, 950 µL, 975 µL, or 1000 µL.

In certain embodiments, the total volume delivered to a subject may be split between one or more administration sites e.g., 1, 2, 3, 4, 5 or more than 5 sites. In certain embodiments, the total volume is split between administration to the left and right putamen. In certain embodiments, the total volume is split between two sites of administration to each of the left and right putamen.

In certain embodiments, the pharmaceutical composition comprising AAV particles is administered using a fenestrated needle. Non-limiting examples of fenestrated needles are described in U.S. Pat. Nos. 8,333,734, 7,135,010, 7,575,572, 7,699,852, 4,411,657, 6,890,319, 6,613,026, 6,726,659, 6,565,572, 6,520,949, 6,382,212, 5,848,996, 5,759,179, 5,674,267, 5,588,960, 5,484,401, 5,199,441, 5,012,818, 4,474,569, 3,766,907, 3,552,394, the contents of each of which are herein incorporated by reference in its entirety.

In certain embodiments, a composition comprises at least one payload described herein and the payloads are components of a viral genome packaged in an AAV particle. The percent (%) ratio of AAV particles comprising the payload to the AAV particles without the payload (also referred herein as empty capsids) in the composition may be 0:100, 1:99, 0:90, 15:85, 25:75, 30:70, 50:50, 70:30, 85:15, 90:10, 99:1 or 100:0. In certain embodiments, the percent ratio of AAV particles comprising the payload to empty capsids is 50:50. In certain embodiments, the percent ratio of AAV particles comprising the payload to empty capsids is 70:30. In certain embodiments, the percent ratio of AAV particles comprising the payload to empty capsids is 85:15. In certain embodiments, the percent ratio of AAV particles comprising the payload to empty capsids is 100:0.

In certain embodiments, the composition described herein comprises at least 1, 5, 10, 15, 20, 25, 30, 35, 40, 45, 50, 51, 52, 53, 54, 55, 60, 65, 70, 75, 80, 81, 82, 83, 84, 85, 86, 87, 88, 89, 90, 91, 92, 93, 94, 95, 96, 97, 98, 99 or greater than 99% AAV particles comprising the payload. In certain embodiments, the composition comprises at least 50% AAV particles comprising the payload. In certain embodiments, the composition comprises at least 52% AAV particles comprising the payload. In certain embodiments, the composition comprises at least 58% AAV particles comprising the payload. In certain embodiments, the composition comprises at least 70% AAV particles comprising the payload. In certain embodiments, the composition comprises at least 83% AAV particles comprising the payload. In certain embodiments, the composition comprises at least 85% AAV particles comprising the payload. In certain embodiments, the composition comprises at least 99% AAV particles comprising the payload. In certain embodiments, the composition comprises 100% AAV particles comprising the payload.

In certain embodiments, the composition described herein comprises 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% AAV particles comprising the payload. In certain embodiments, the composition described herein comprises 50-100% AAV particles comprising the payload. In certain embodiments, the composition described herein comprises 50-60% AAV particles comprising the payload. In certain embodiments, the composition described herein comprises 80-99% AAV particles comprising the payload. In certain embodiments, the composition described herein comprises 80-90% AAV particles comprising the payload. In certain embodiments, the composition described herein comprises 80-95% AAV particles comprising the payload. In certain embodiments, the composition described herein comprises 80-85% AAV particles comprising the payload.

In certain embodiments, the composition described herein comprises less than 1, 5, 10, 15, 20, 25, 30, 35, 40, 45, 50, 51, 52, 53, 54, 55, 60, 65, 70, 75, 80, 81, 82, 83, 84, 85, 86, 87, 88, 89, 90, 91, 92, 93, 94, 95, 96, 97, 98, 99 or 100% empty particles. In certain embodiments, the composition comprises less than 50% empty particles. In certain embodiments, the composition comprises less than 45% empty particles. In certain embodiments, the composition comprises less than 40% empty particles. In certain embodiments, the composition comprises less than 35% empty particles. In certain embodiments, the composition comprises less than 30% empty particles. In certain embodiments, the composition comprises less than 25% empty particles. In certain embodiments, the composition comprises less than 20% empty particles. In certain embodiments, the composition comprises less than 15% empty particles. In certain embodiments, the composition comprises less than 10% empty particles. In certain embodiments, the composition comprises less than 5% empty particles. In certain embodiments, the composition comprises less than 1% empty particles.

In the composition described herein comprises 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% empty particles. In certain embodiments, the composition described herein comprises 30-40% empty particles. In certain embodiments, the composition described herein comprises 30-50% empty particles. In certain embodiments, the composition described herein comprises 30-60% empty particles. In certain embodiments, the composition described herein comprises 30-70% empty particles. In certain embodiments, the composition described herein comprises 30-80% empty particles. In certain embodiments, the composition described herein comprises 30-90% empty particles.

In certain embodiments, the ratio of distribution volume in the parenchyma of an area of a subject to the infusion volume of an area of a subject may be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 or more than 6.0. In certain embodiments, the ratio of distribution volume in the parenchyma to infusion volume was 1.6 in the caudate nucleus. In certain embodiments, the ratio of distribution volume in the parenchyma to infusion volume was 3.1 in the putamen. In certain embodiments, the distribution of the AAV particles in the putamen may be 2-3 times the volume infused.

In certain embodiments, the effectiveness of the dose, route of administration and/or volume of administration may be evaluated using various methods described herein such as, but not limited to, PET imaging, L-DOPA challenge test (e.g., see Forsayeth et al. 2006, Mol. Ther. 14(4): 571-577), UPDRS scores and patient diaries (e.g., Hauser diary). In certain embodiments, a subject may have decreased dyskinesia or periods of decreased dyskinesia after administration of the Pharmaceutical composition comprising AAV particles. In certain embodiments, a subject may have a decrease in Parkinson's Disease related symptoms including limited mobility and dyskinesia. As yet another non-limiting example, a subject may show improvement in off time and motor fluctuations. The improvement may be at least 10%, at least 20%, at least 30%, at least 40%, at least 50%, at least 60%, at least 70%, at least 80%, at least 90% or greater than 90%. The improvement may last for minutes (e.g., 1, 2, 3, 4, 5, 6, 7, 8, 9, 10, 15, 20, 25, 30, 35, 40, 45, 50, 55 or more than 55), hours (e.g., 1, 2, 3, 4, 5, 6, 7, 8, 9, 10, 11, 12, 13, 14, 15, 16, 17, 18, 19, 20, 21, 22, 23 or more than 24), days (e.g., 1, 2, 3, 4, 5, 6 or more than 7), weeks (1, 2, 3, 4, 5, 6, 7 or more than 7), months (1, 2, 3, 4, 5, 6, 7, 8, 9, 10, 11 or more than 11) or years (e.g., 1, 2, 3, 4, 5, 6, 7, 8, 9 or more than 9).

In certain embodiments, the selection of subjects for administration of the AAV particles described herein and/or the effectiveness of the dose, route of administration and/or volume of administration may be evaluated using imaging of the perivascular spaces (PVS) which are also known as Virchow-Robin spaces. PVS surround the arterioles and venules as they perforate brain parenchyma and are filled with cerebrospinal fluid (CSF)/interstitial fluid. PVS are common in the midbrain, BG, and centrum semiovale. While not wishing to be bound by theory, PVS may play a role in the normal clearance of metabolites and have been associated with worse cognition and several disease states including Parkinson's disease. PVS are usually normal in size but they can increase in size in a number of disease states. Potter et al. (Cerebrovasc Dis. 2015 January; 39(4): 224-231: the contents of which are herein incorporated by reference in its entirety) developed a grading method where they studied a full range of PVS and rated basal ganglia, centrum semiovale and midbrain PVS. They used the frequency and range of PVS used by Mac and Lullich et al. (J Neurol Neurosurg Psychiatry. 2004 November; 75(11): 1519-23: the contents of which are herein incorporated by reference in its entirety) and Potter et al. gave 5 ratings to basal ganglia and centrum semiovale PVS: 0 (none), 1 (1-10), 2 (11-20), 3 (21-40) and 4 (>40) and 2 ratings to midbrain PVS: 0 (non-visible) or 1 (visible). The user guide for the rating system by Potter et al. can be found at: www.sbire.ed.ac.uk/documents/epvs-rating-scale-user-guide.pdf.

In certain embodiments, the selection of subjects for administration of the AAV particles described herein and/or the effectiveness of the dose, route of administration and/or volume of administration may be evaluated using positron emission tomography (PET) measurements of neuroimaging biomarkers such as, but not limited to [$^{18}$F]FDOPA. Neuroimaging biomarkers such as [$^{18}$F]FDOPA may be used to identify affected individuals and/or may be used to detect a nigrostriatal defect prior to the onset of clinical manifestations. Further, PET-based criteria may be used to categorize subjects based on their nigrostriatal neuronal integrity (e.g., abnormal, normal or uncertain nigrostriatal neuronal integrity) (Rachette et al. Am J Med Genet B Neuropsychiatr Genet. 2006 Apr. 5; 141B(3): 245-249; the contents of which are herein incorporated by reference in its entirety).

In certain embodiments, a subject who may be administered a dose of the AAV particles described herein may have advanced PD and still respond to levodopa therapy but the subject also experiences medically refractory motor complications (e.g., sever motor fluctuations and/or dyskinesias that occur during levodopa and other dopaminergic therapies despite adjustments in and optimization of medication). The subject may be healthy enough to undergo a neurosurgical procedure which may be determined by methods known in the art. In certain embodiments, the subject may meet the selection criteria for deep brain stimulation (DBS). The subject may have idiopathic PD, younger than 69 years of age, have pronounced responses to levodopa, have medication-refractory symptoms (e.g., motor fluctuation and/or dyskinesia) and/or have little or no cognitive dysfunction.

In certain embodiments, a subject who may be administered a dose of the AAV particles described herein may also suffer from dementia or cognitive impairment.

In certain embodiments, a subject who may be administered a dose of the AAV particles described herein may have been previously treated with the same or similar therapeutic. In another embodiment, a subject may have been treated with a therapeutic which has been shown to reduce the symptoms of Parkinson's Disease.

In certain embodiments, a subject who may be administered a dose of the AAV particles described herein may have failed to derive adequate benefit from standard medical therapy. In certain embodiments, the subject may not have responded to treatment. In certain embodiments, a subject may have residual disability despite treatment.

In certain embodiments, a subject who may be administered a dose of the AAV particles described herein may undergo testing to evaluate the levels of neurotransmitter analytes to determine the effectiveness of the dose. In certain embodiments, CSF neurotransmitters, plasma AADC activity and/or urine VLA may be analyzed.

In certain embodiments, a subject who may be administered a dose of the AAV particles described herein may be videotaped or recorded in order to monitor the progress of the subject during the course of treatment.

Delivery to the Putamen

In certain embodiments, the AAV particles may be administered to the right putamen, the left putamen, or a combination of both the right putamen and the left putamen. The administration may be at one or more sites in the putamen such as, but not limited to, 2 sites, 3 sites, 4 sites or more than 4 sites. In certain embodiments, the AAV particles are delivered to 2 sites in the left putamen and 2 sites in the right putamen.

In certain embodiments, administration occurs by a transfrontal (e.g., top of the head) surgical delivery approach to the putamen. In certain embodiments, the average total putaminal coverage less than 50% with posterior delivery and the surgical time is more than 10 hours. In certain embodiments, the average total putaminal coverage using a transfrontal approach is 20-45%. In certain embodiments, the average total putaminal coverage using a transfrontal approach is 30-45%.

In certain embodiments, administration occurs by a posterior (e.g., back of the head) surgical delivery approach to the putamen. In certain embodiments, the average total putaminal coverage is at least 50% with posterior delivery. In certain embodiments, the average total putaminal coverage is 40-65%, 45-60%, 45-65%, 50-60% 50-65%, 55-60%, 55-65%, or 60-65% with posterior delivery. In certain embodiments, the average posterior putaminal coverage is 50-80%, 50-90%, 60-80%, 60-90%, 65-80%, 65-90%, 70-80%, 70-85%, 70-90%, 75-80%, 75-85%, 75-90%, or 80-90% with posterior delivery.

In certain embodiments, the average total putaminal coverage is at least 50% with posterior delivery and the surgical time is less than 10 hours. In certain embodiments, the average putaminal coverage is 50%-65% with posterior delivery and the surgical time is less than 9 hours. In certain embodiments, the average total putaminal coverage is 50%-65% with posterior delivery and the surgical time is less than 8 hours. In certain embodiments, the average total putaminal coverage is 50%-65% with posterior delivery and the surgical time is less than 7 hours. In certain embodiments, the average total putaminal coverage is 50%-65% with posterior delivery and the surgical time is less than 6 hours. In certain embodiments, the average total putaminal coverage is 50%-65% with posterior delivery and the surgical time is less than 5 hours. In certain embodiments, the average total putaminal coverage is 50%-65% with posterior delivery and the surgical time is less than 4 hours. In certain embodiments, the average total putaminal coverage is 50%-65% with posterior delivery and the surgical time is between 7 and 10 hours.

In certain embodiments, the average total putaminal coverage is at least 50% with posterior delivery, the surgical time is between 7 and 10 hours, and the subject is between 50-60, 55-60, or 57-59 years of age. In certain embodiments, the average total putaminal coverage is 50-65% with posterior delivery, the surgical time is between 7 and 10 hours, and the subject is between 50-60, 55-60, or 57-59 years of age. In certain embodiments, the average total putaminal coverage is 50-60% with posterior delivery, the surgical time is between 7 and 10 hours, and the subject is between 50-60, 55-60, or 57-59 years of age.

In certain embodiments, the administration of the formulation of the AAV particles to a subject provides coverage of the putamen of a subject (e.g., the left and/or right putamen). In one aspect, the administration of the AAV particles may provide at least 8%, 9%, 10%, 13%, 14%, 15%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% coverage to the left and/or right putamen of a subject. In certain embodiments, the coverage is at least 20%. In certain embodiments, the coverage is at least 30%. In certain embodiments, the coverage is at least 40%. In certain embodiments, the coverage is at least 50%. In another aspect, the administration of the AAV particles may provide at least 8%, 9%, 10%, 13%, 14%, 15%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% coverage of the surface area of the left and/or right putamen of a subject. In certain embodiments, the total coverage is at least 20%. In certain embodiments, the total coverage is at least 30%. In certain embodiments, the total coverage is at least 40%. In certain embodiments, the total coverage is at least 50%. In yet another aspect, the administration of the AAV particles may provide 10-40%, 20-40%, 20-30%, 20-35%, 20-50%, 30-40%, 35-40%, 30-60%, 30-70%, 30-80%, 30-90%, 40-70%, 50-55%, 50-60%, 50-65%, 50-70%, 50-75%, 50-80% or 60-90% coverage to the left and/or right putamen of a subject or to the total surface area of the left and/or right putamen of a subject.

In certain embodiments, the administration of the formulation of the AAV particles to a subject provides coverage of the posterior putamen of a subject (e.g., the left and/or right posterior putamen). In one aspect, the administration of the AAV particles may provide at least 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% to the left and/or right posterior putamen of a subject. In certain embodiments, the coverage is at least 20%. In certain embodiments, the coverage is at least 30%. In certain embodiments, the coverage is at least 40%. In certain embodiments, the coverage is at least 50%. In another aspect, the administration of the AAV particles may provide at least 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more than 95% coverage of the surface area of the left and/or right posterior putamen of a subject. In certain embodiments, the total coverage is at least 20%. In certain embodiments, the total coverage is at least 30%. In certain embodiments, the total coverage is at least 40%. In certain embodiments, the total coverage is at least 50%. In yet another aspect, the administration of the AAV particles may provide 10-40%, 20-50%, 30-60%, 30-70%, 30-80%, 30-90%, 40-70%, 50-55%, 50-60%, 50-65%, 50-70%, 50-75%, 50-80%, 60-65%, 60-70%, 60-75%, 60-80%, 60-85% or 60-90% coverage to the left and/or right posterior putamen of a subject or to the total surface area of the left and/or right putamen of a subject.

In certain embodiments, the volume of the pharmaceutical composition comprising AAV particles delivered to the putamen in both hemispheres of a subject brain is 50 µL, 100 µL, 200 µL, 300 µL, 400 µL, 450 µL, 500 µL, 600 µL, 700 µL, 800 µL, 900 µL, 1000 µL, 1100 µL, 1200 µL, 1300 µL, 1400 µL, 1500 µL, 1600 µL, 1700 µL, 1800 µL, 1900 µL, 2000 µL or more than 2000 µL. In certain embodiments, the volume delivered to the putamen in both hemispheres is 100 µL. In certain embodiments, the volume delivered to the putamen in both hemispheres is 200 µL. In certain embodiments, the volume delivered to the putamen in both hemispheres is 300 µL. In certain embodiments, the volume delivered to the putamen in both hemispheres is 450 µL. In certain embodiments, the volume delivered to the putamen in both hemispheres is 900 µL. As yet another non-limiting example, the volume delivered to the putamen both hemispheres is 1800 µL.

In certain embodiments, the volume delivered to the putamen of each hemisphere is up to 100 µL, 125 µL, 150 µL, 175 µL, 180 µL, 200 µL, 210 µL, 220 µL, 225 µL, 250 µL, 275 µL, 300 µL, 325 µL, 350 µL, 375, 400 µL, 425 µL, 450 µL, 475 µL, 500 µL, 525 µL, 550 µL, 575 µL, 600 µL, 625 µL, 650 µL, 675 µL, 700 µL, 725 µL, 750 µL, 775 µL, 800 µL, 825 µL, 850 µL, 875 µL, 900 µL, 925 µL, 950 µL, 975 µL, or 1000 µL.

In certain embodiments, the volume of the pharmaceutical composition comprising AAV particles delivered to a subject is 3600 µL to each putamen. In certain embodiments, the volume of the pharmaceutical composition comprising AAV particles delivered to a subject is up to 3600 µL to each putamen.

In certain embodiments, the volume of the pharmaceutical composition comprising AAV particles delivered to a subject is 1800 µL to each putamen. In certain embodiments, the volume of the pharmaceutical composition comprising AAV particles delivered to a subject is up to 1800 µL to each putamen.

In certain embodiments, the volume of the pharmaceutical composition comprising AAV particles delivered to a subject is 1500 µL to each putamen. In certain embodiments, the volume of the pharmaceutical composition comprising AAV particles delivered to a subject is up to 1500 µL to each putamen.

In certain embodiments, the volume of the pharmaceutical composition comprising AAV particles delivered to a subject is 900 µL to each putamen. In certain embodiments, the volume of the pharmaceutical composition comprising AAV particles delivered to a subject is up to 900 µL to each putamen.

In certain embodiments, the volume of the pharmaceutical composition comprising AAV particles delivered to a subject is 450 µL to each putamen. In certain embodiments, the volume of the pharmaceutical composition comprising AAV particles delivered to a subject is up to 450 µL to each putamen.

In certain embodiments, the AAV particles described herein may be administered using acute bilateral placement of catheters into each putamen. The placement may use magnetic resonance image (MRI)-guided stereotactic neurosurgical techniques known in the art or described herein. Additionally, a contrast agent such as, but not limited to a gadolinium based contrast agent (e.g., PROHANCE®) may be used in the formulation to monitor and confirm the distribution of the formulation. In certain embodiments, AAV particles are administered using a patient-specific infusion strategy based on real-time and post-hoc evaluations of intraparenchymal distribution resulting in changes in infusion volume and technique.

In certain embodiments, a subject may be administered the AAV particles in a bilateral stereotactic CED-assisted step infusion into the putamen (e.g., the post commissural putamen).

In certain embodiments, a subject may be administered the AAV particles of the present disclosure at a dose of $2.3 \times 10^{12}$ vector genomes at a volume of 450 µL per putamen. In certain embodiments, a subject may be administered the AAV particles of the present disclosure at a dose of $2.3 \times 10^{12}$ vector genomes at a volume of up to 450 µL per putamen.

In certain embodiments, a subject may be administered the AAV particles of the present disclosure at a dose of $2.3 \times 10^{12}$ vector genomes at a volume of 900 µL per putamen. In certain embodiments, a subject may be administered the AAV particles of the present disclosure at a dose of $2.3 \times 10^{12}$ vector genomes at a volume of up to 900 µL per putamen.

In certain embodiments, a subject may be administered the AAV particles of the present disclosure at a dose of $2.6 \times 10^{12}$ vector genomes per ml (vg/ml), at a volume of 900 µL per putamen. In certain embodiments, a subject may be administered the AAV particles of the present disclosure at a dose of $2.6 \times 10^{12}$ vector genomes per ml (vg/ml) at a volume of up to 900 µL per putamen.

In certain embodiments, a subject may be administered the AAV particles of the present disclosure at a dose of $2.6 \times 10^{12}$ vector genomes per ml (vg/ml) at a volume of 1500 µL per putamen. In certain embodiments, a subject may be administered the AAV particles of the present disclosure at a dose of $2.6 \times 10^{12}$ vector genomes per ml (vg/ml) at a volume of up to 1500 µL per putamen.

In certain embodiments, a subject may be administered the AAV particles of the present disclosure at a dose of $2.6 \times 10^{12}$ vector genomes per ml (vg/ml) at a volume of 1800 ul per putamen. In certain embodiments, a subject may be administered the AAV particles of the present disclosure at a dose of $2.6 \times 10^{12}$ vector genomes per ml (vg/ml) at a volume of up to 1800 µL per putamen.

In certain embodiments, a subject may be administered the AAV particles of the present disclosure at a dose of $2.6 \times 10^{12}$ vector genomes per ml (vg/ml) at a volume of 3600 µL per putamen. In certain embodiments, a subject may be administered the AAV particles of the present disclosure at a dose of $2.6 \times 10^{12}$ vector genomes per ml (vg/ml) at a volume of up to 3600 µL per putamen. µL.

In certain embodiments, a subject may be administered the AAV particles of the present disclosure at a dose of $4.5 \times 10^{12}$ vector genomes at a volume of 900 µL per putamen. In certain embodiments, a subject may be administered the AAV particles of the present disclosure at a dose of $4.5 \times 10^{12}$ vector genomes at a volume of up to 900 µL per putamen.

In certain embodiments, a subject may be administered the AAV particles of the present disclosure at a dose of $4.6 \times 10^{12}$ vector genomes at a volume of 900 µL per putamen. In certain embodiments, a subject may be administered the AAV particles of the present disclosure at a dose of $4.6 \times 10^{12}$ vector genomes at a volume of up to 900 µL per putamen.

In certain embodiments, a subject may be administered the AAV particles of the present disclosure at a dose of $4.7 \times 10^{12}$ vector genomes at a volume of 900 µL per putamen. In certain embodiments, a subject may be administered the AAV particles of the present disclosure at a dose of $4.7 \times 10^{12}$ vector genomes at a volume of up to 900 µL per putamen.

In certain embodiments, a subject may be administered the AAV particles of the present disclosure at a dose of $1.5 \times 10^{12}$ vector genomes at a volume of 900 µL per putamen. In certain embodiments, a subject may be administered the AAV particles of the present disclosure at a dose of $1.5 \times 10^{12}$ vector genomes at a volume of up to 900 µL per putamen.

In certain embodiments, a subject may be administered the AAV particles of the present disclosure at a dose of $7.5 \times 10^{12}$ vector genomes at a volume of 450 µL per putamen. In certain embodiments, a subject may be administered the AAV particles of the present disclosure at a dose of $7.5 \times 10^{12}$ vector genomes at a volume of up to 450 µL per putamen.

In certain embodiments, a subject may be administered the AAV particles of the present disclosure at a dose of $8.8 \times 10^{12}$ vector genomes at a volume of 900 µL per putamen. In certain embodiments, a subject may be administered the AAV particles of the present disclosure at a dose of $8.8 \times 10^{12}$ vector genomes at a volume of up to 900 µL per putamen.

In certain embodiments, a subject may be administered the AAV particles of the present disclosure at a dose of $9.4 \times 10^{12}$ vector genomes at a volume of 900 µL per putamen. In certain embodiments, a subject may be administered the AAV particles of the present disclosure at a dose of $9.4 \times 10^{12}$ vector genomes at a volume of up to 900 µL per putamen.

In certain embodiments, a subject may be administered the AAV particles of the present disclosure at a dose of $9.4 \times 10^{12}$ vector genomes at a volume of 1200 µL per putamen. In certain embodiments, a subject may be administered the AAV particles of the present disclosure at a dose of $9.4 \times 10^{12}$ vector genomes at a volume of up to 1200 µL per putamen.

In certain embodiments, a subject may be administered the AAV particles of the present disclosure at a dose of $9.4 \times 10^{12}$ vector genomes at a volume of 1500 µL per putamen. In certain embodiments, a subject may be administered the AAV particles of the present disclosure at a dose of $9.4 \times 10^{12}$ vector genomes at a volume of up to 1500 µL per putamen.

In certain embodiments, a subject may be administered the AAV particles of the present disclosure at a dose of $9.4 \times 10^{12}$ vector genomes at a volume of 1800 µL per putamen. In certain embodiments, a subject may be administered the AAV particles of the present disclosure at a dose of $9.4 \times 10^{12}$ vector genomes at a volume of up to 1800 µL per putamen.

In certain embodiments, a subject may be administered the AAV particles of the present disclosure at a dose of $9.4 \times 10^{12}$ vector genomes at a volume of 3600 µL per putamen. In certain embodiments, a subject may be administered the AAV particles of the present disclosure at a dose of $9.4 \times 10^{12}$ vector genomes at a volume of up to 3600 µL per putamen.

In certain embodiments, a subject may be administered the AAV particles of the present disclosure at a dose of $3.72 \times 10^{12}$ vector genomes at a volume of 715 µL per putamen. In certain embodiments, a subject may be administered the AAV particles of the present disclosure at a dose of $3.72 \times 10^{12}$ vector genomes at a volume of up to 900 µL per putamen, up to 1200 µL per putamen, up to 1500 µL per putamen, or up to 1800 µL per putamen.

In certain embodiments, a subject may be administered the AAV particles of the present disclosure at a dose of $8.3 \times 10^{12}$ vector genomes at a volume of 500 μL per putamen. In certain embodiments, a subject may be administered the AAV particles of the present disclosure at a dose of $8.3 \times 10^{12}$ vector genomes at a volume of up to 900 μL per putamen, up to 1200 μL per putamen, up to 1500 μL per putamen, or up to 1800 μL per putamen.

In certain embodiments, a subject may be administered the AAV particles of the present disclosure at a dose of $5.95 \times 10^{12}$ vector genomes at a volume of 1144 μL per putamen. In certain embodiments, a subject may be administered the AAV particles of the present disclosure at a dose of $5.95 \times 10^{12}$ vector genomes at a volume of up to 900 μL per putamen, up to 1200 μL per putamen, up to 1500 μL per putamen, or up to 1800 μL per putamen.

In certain embodiments, a subject may be administered the AAV particles of the present disclosure at a dose of $6.58 \times 10^{12}$ vector genomes at a volume of 1265 μL per putamen. In certain embodiments, a subject may be administered the AAV particles of the present disclosure at a dose of $6.58 \times 10^{12}$ vector genomes at a volume of up to 900 μL per putamen, up to 1200 μL per putamen, up to 1500 μL per putamen, or up to 1800 μL per putamen.

In certain embodiments, a subject may be administered the AAV particles of the present disclosure at a dose of $4.31 \times 10^{12}$ vector genomes at a volume of 829 μL per putamen. In certain embodiments, a subject may be administered the AAV particles of the present disclosure at a dose of $4.31 \times 10^{12}$ vector genomes at a volume of up to 900 μL per putamen, up to 1200 μL per putamen, up to 1500 μL per putamen, or up to 1800 μL per putamen.

In certain embodiments, a subject may be administered the AAV particles of the present disclosure at a dose of $6.45 \times 10^{12}$ vector genomes at a volume of 1240 μL per putamen. In certain embodiments, a subject may be administered the AAV particles of the present disclosure at a dose of $6.45 \times 10^{12}$ vector genomes at a volume of up to 900 μL per putamen, up to 1200 μL per putamen, up to 1500 μL per putamen, or up to 1800 μL per putamen.

In certain embodiments, a subject may be administered the AAV particles of the present disclosure at a dose of $7.80 \times 10^{12}$ vector genomes at a volume of 1500 μL per putamen. In certain embodiments, a subject may be administered the AAV particles of the present disclosure at a dose of $7.80 \times 10^{12}$ vector genomes at a volume of up to 900 μL per putamen, up to 1200 μL per putamen, up to 1500 μL per putamen, or up to 1800 μL per putamen.

In certain embodiments, a subject may be administered the AAV particles with a bilateral surgical infusion into at least one putamen using a posterior (i.e., back of the head) surgical delivery approach. In certain embodiments, a subject may be administered the AAV particles with a transparietal-occipital approach along the long axis of the putamen through the posterior tail. The number of posterior bilateral surgical infusions may be one or more such as, but not limited to, 1 infusion, 2 infusions, 3 infusions, 4 infusions or more than 4 infusions. In certain embodiments, the AAV particles are delivered in the left putamen with one posterior bilateral surgical infusion. In certain embodiments, the AAV particles are delivered in the right putamen with one posterior bilateral surgical infusion. In certain embodiments, the AAV particles are delivered in the left putamen with two posterior bilateral surgical infusions. In certain embodiments, the AAV particles are delivered in the right putamen with two posterior bilateral surgical infusions. In certain embodiments, the AAV particles are delivered in the right and left putamen with two posterior bilateral surgical infusions. In certain embodiments, the AAV particles are delivered in the left putamen with three posterior bilateral surgical infusions. In certain embodiments, the AAV particles are delivered in the right putamen with three posterior bilateral surgical infusions. In certain embodiments, the AAV particles are delivered in the right and left putamen with three posterior bilateral surgical infusions. In certain embodiments, the AAV particles are delivered in the left putamen with four posterior bilateral surgical infusions. In certain embodiments, the AAV particles are delivered in the right putamen with four posterior bilateral surgical infusions. In certain embodiments, the AAV particles are delivered in the right and left putamen with four posterior bilateral surgical infusions.

In certain embodiments, a subject may be administered the AAV particles with a bilateral surgical infusion into at least one putamen using a transfrontal (i.e., top of the head) surgical delivery approach. The number of bilateral surgical infusions may be two or more such as, but not limited to, 2 infusions, 3 infusions, 4 infusions or more than 4 infusions. In certain embodiments, the AAV particles are delivered in the left putamen with 2 posterior bilateral surgical infusions. In certain embodiments, the AAV particles are delivered in the right putamen with 2 posterior bilateral surgical infusions. In certain embodiments, the AAV particles are delivered in the left and right putamen with 2 posterior bilateral surgical infusions.

Delivery to the SNpc and VTA or STN

In certain embodiments, a subject may be administered the AAV particles of the present disclosure safely delivered to substantia nigra pars compacta (SNpc) and ventral tegmental area (VTA) via bilateral infusions, or alternatively, intrastriatally (into the caudate nucleus and putamen), or into the subthalamic nucleus (STN).

Delivery, Dose and Regimen

The present disclosure provides methods of administering AAV particles in accordance with the disclosure to a subject in need thereof. The pharmaceutical, diagnostic, or prophylactic AAV particles and compositions of the present disclosure may be administered to a subject using any amount and any route of administration effective for preventing, treating, managing, or diagnosing diseases, disorders and/or conditions. The exact amount required will vary from subject to subject, depending on the species, age, and general condition of the subject, the severity of the disease, the particular composition, its mode of administration, its mode of activity, and the like. The subject may be a human, a mammal, or an animal. Compositions in accordance with the disclosure are typically formulated in unit dosage form for ease of administration and uniformity of dosage. It will be understood, however, that the total daily usage of the compositions of the present disclosure may be decided by the attending physician within the scope of sound medical judgment. The specific therapeutically effective, prophylactically effective, or appropriate diagnostic dose level for any particular individual will depend upon a variety of factors including the disorder being treated and the severity of the disorder, the activity of the specific payload employed; the specific composition employed; the age, body weight, general health, sex and diet of the patient, the time of administration, route of administration, and rate of excretion of the specific AAV particle employed: the duration of the treatment; drugs used in combination or coincidental with the specific AAV particle employed; and like factors well known in the medical arts.

In certain embodiments, delivery of the AAV particles of the present disclosure results in minimal serious adverse events (SAEs) as a result of the delivery of the AAV particles.

In certain embodiments, the AAV particle may be delivered a multi-dose regimen. The multi-dose regimen may be 2, 3, 4, 5, 6, 7, 8, 9, 10 or more than 10 doses.

In certain embodiments, the AAV particle may be delivered to a subject via a multi-site route of administration. A subject may be administered the AAV particle at 2, 3, 4, 5 or more than 5 sites.

Dosage Levels

In certain embodiments, AAV particle pharmaceutical compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect. It will be understood that the above dosing concentrations may be converted to vg or viral genomes per kg or into total viral genomes administered by one of skill in the art.

In certain embodiments, AAV particle pharmaceutical compositions in accordance with the present disclosure may be administered at about 10 to about 1100 µl/site, about 50 to about 500 µl/site, 50 to about 800 µl/site, 50 to about 800 µl/site, about 100 to about 400 µl/site, about 100 to about 500 µl/site, about 100 to about 700 µl/site, about 120 to about 300 µl/site, about 120 to about 600 µl/site, about 140 to about 200 µl/site, about 140 to about 500 µl/site, about 160 to about 500 µl/site, about 160 to about 450 µl/site, about 180 to about 400 µl/site, about 200 to about 350 µl/site, about 250 to about 300 µl/site, about 250 to about 500 µl/site, about 300 to about 900 µl/site, about 450 to about 900 µl/site, about 400 to about 900 µl/site, about 400 to about 600 µl/site, about 400 to about 500 µl/site, about 600 to about 900 µl/site, about 600 to about 1000 µl/site, about 700 to about 900 µl/site, about 700 to about 1000 µl/site, about 800 to about 900 µl/site, about 800 to about 1000 µl/site, about 850 to about 950 µl/site, about 850 to about 900 µl/site, about 500 to about 1800 µl/site, about 700 to about 1800 µl/site, about 900 to about 1800 µl/site, about 1100 to about 1800 µl/site, about 1200 to about 1800 µl/site, about 1500 to about 1800 µl/site, about 500 to about 1500 µl/site, about 700 to about 1500 µl/site, about 900 to about 1500 µl/site, about 1100 to about 1500 µl/site, about 1200 to about 1500 µl/site, about 500 to about 1200 µl/site, about 700 to about 1200 µl/site, and about 900 to about 1200 µl/site. As non-limiting examples, AAV particles may be administered at 50 µl/site and/or 150 µl/site. In certain embodiments, the AAV particles may be administered at about 400 µl/site. In certain embodiments, the AAV particles may be administered at about 450 µl/site. In certain embodiments, the AAV particles may be administered at about 500 µl/site. In certain embodiments, the AAV particles may be administered at about 700 µl/site. In certain embodiments, the AAV particles may be administered at about 750 µl/site. In certain embodiments, the AAV particles may be administered at about 800 µl/site. In certain embodiments, the AAV particles may be administered at about 850 µl/site. In certain embodiments, the AAV particles may be administered at about 900 µl/site. In certain embodiments, the AAV particles may be administered at about 1000 µl/site. In certain embodiments, the AAV particles may be administered at about 1100 µl/site. In certain embodiments, the AAV particles may be administered at about 1200 µl/site. In certain embodiments, the AAV particles may be administered at about 1300 µl/site. In certain embodiments, the AAV particles may be administered at about 1400 µl/site. In certain embodiments, the AAV particles may be administered at about 1500 µl/site. In certain embodiments, the AAV particles may be administered at about 1600 µl/site. In certain embodiments, the AAV particles may be administered at about 1700 µl/site. In certain embodiments, the AAV particles may be administered at about 1800 µl/site.

In certain embodiments, delivery of the compositions in accordance with the present disclosure to cells comprises a rate of delivery defined by [VG/hour=mL/hour*VG/mL] wherein VG is viral genomes, VG/mL is composition concentration, and mL/hour is rate of prolonged delivery.

In certain embodiments, delivery of compositions in accordance with the present disclosure to cells may comprise a total concentration per subject between about $1 \times 10^6$ VG and about $1 \times 10^{16}$ VG. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $\times 1 \times 10^{11}$, $2 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3 \times 10^{11}$, $4 \times 10^{11}$, $5 \times 10^{11}$, $6 \times 10^{11}$, $7 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.1 \times 10^{12}$, $2.2 \times 10^{12}$, $2.3 \times 10^{12}$, $2.4 \times 10^{12}$, $2.5 \times 10^{12}$, $2.6 \times 10^{12}$, $2.7 \times 10^{12}$, $2.8 \times 10^{12}$, $2.9 \times 10^{12}$, $3 \times 10^{12}$, $3.1 \times 10^{12}$, $3.2 \times 10^{12}$, $3.3 \times 10^{12}$, $3.4 \times 10^{12}$, $3.5 \times 10^{12}$, $3.6 \times 10^{12}$, $3.7 \times 10^{12}$, $3.8 \times 10^{12}$, $3.9 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $5.1 \times 10^{12}$, $5.2 \times 10^{12}$, $5.3 \times 10^{12}$, $5.4 \times 10^{12}$, $5.5 \times 10^{12}$, $5.6 \times 10^{12}$, $5.7 \times 10^{12}$, $5.8 \times 10^{12}$, $5.9 \times 10^{12}$, $6 \times 10^{12}$, $6.1 \times 10^{12}$, $6.2 \times 10^{12}$, $6.3 \times 10^{12}$, $6.4 \times 10^{12}$, $6.5 \times 10^{12}$, $6.6 \times 10^{12}$, $6.7 \times 10^{12}$, $6.8 \times 10^{12}$, $6.9 \times 10^{12}$, $7 \times 10^{12}$, $7.1 \times 10^{12}$, $7.2 \times 10^{12}$, $7.3 \times 10^{12}$, $7.4 \times 10^{12}$, $7.5 \times 10^{12}$, $7.6 \times 10^{12}$, $7.7 \times 10^{12}$, $7.8 \times 10^{12}$, $7.9 \times 10^{12}$, $8 \times 10^{12}$, $8.1 \times 10^{12}$, $8.2 \times 10^{12}$, $8.3 \times 10^{12}$, $8.4 \times 10^{12}$, $8.5 \times 10^{12}$, $8.6 \times 10^{12}$, $8.7 \times 10^{12}$, $8.8 \times 10^{12}$, $8.9 \times 10^{12}$, $9 \times 10^{12}$, $9.1 \times 10^{12}$, $9.2 \times 10^{12}$, $9.3 \times 10^{12}$, $9.4 \times 10^{12}$, $9.5 \times 10^{12}$, $9.6 \times 10^{12}$, $9.7 \times 10^{12}$, $9.8 \times 10^{12}$, $9.9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $6.7 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/subject. In certain embodiments, the concentration of the AAV particle in the composition is $1 \times 10^{13}$ VG/subject. In certain embodiments, the concentration of the AAV particle in the composition is $3 \times 10^{12}$ VG/subject. In certain embodiments, the composition administered to the subject has a concentration of about $2.3 \times 10^{11}$ VG/subject. In certain embodiments, the concentration of the AAV particle in the composition is $3 \times 10^{11}$ VG/subject. In certain embodiments, the concentration of the AAV particle in the composition is $7.2 \times 10^{11}$ VG/subject. In certain embodiments, the concentration of the AAV particle in the composition is $7.5 \times 10^{11}$ VG/subject. In certain embodiments, the composition administered to the subject has a concentration of about $9\times10^{11}$ VG/subject. In certain embodiments, the concentration of the AAV particle in the composition is $1.4\times10^{12}$ VG/subject. In certain embodiments, the concentration of the AAV particle in the composition is $1.5\times10^{12}$ VG/subject. In certain embodiments, the concentration of the AAV particle in the composition is $2.3\times10^{12}$ VG/subject. In certain embodiments, the concentration of the AAV particle in the composition is $4.5\times10^{12}$ VG/subject. In certain embodiments, the concentration of the AAV particle in the composition is $4.6\times10^{12}$ VG/subject. In certain embodiments, the concentration of the AAV particle in the composition is $4.7\times10^{12}$ VG/subject. In certain embodiments, the concentration of the AAV particle in the composition is $4.8\times10^{12}$ VG/subject. In certain embodiments, the concentration of the AAV particle in the composition is $4.9\times10^{12}$ VG/subject. In certain embodiments, the concentration of the AAV particle in the composition is $5\times10^{12}$ VG/subject. In certain embodiments, the concentration of the AAV particle in the composition is $8.8\times10^{12}$ VG/subject. In certain embodiments, the concentration of the AAV particle in the composition is $9.4\times10^{12}$ VG/subject. In certain embodiments, the concentration of the AAV particle in the composition is $3.72\times10^{12}$ VG/subject. In certain embodiments, the concentration of the AAV particle in the composition is $8.3\times10^{12}$ VG/subject. In certain embodiments, the concentration of the AAV particle in the composition is $5.95\times10^{12}$ VG/subject. In certain embodiments, the concentration of the AAV particle in the composition is $6.58\times10^{12}$ VG/subject. In certain embodiments, the concentration of the AAV particle in the composition is $4.31\times10^{12}$ VG/subject. In certain embodiments, the concentration of the AAV particle in the composition is $6.45\times10^{12}$ VG/subject. In certain embodiments, the concentration of the AAV particle in the composition is $7.80\times10^{12}$ VG/subject.

In certain embodiments, delivery of compositions in accordance with the present disclosure to cells may comprise a total concentration per subject between about $1\times10^{6}$ VG/kg and about $1\times10^{16}$ VG/kg. In some embodiments, delivery may comprise a composition concentration of about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $8.1\times10^{11}$, $8.2\times10^{11}$, $8.3\times10^{11}$, $8.4\times10^{11}$, $8.5\times10^{11}$, $8.6\times10^{11}$, $8.7\times10^{11}$, $8.8\times10^{11}$, $8.9\times10^{11}$, $9\times10^{11}$, $1\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, 7, $5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$ 1, $0.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $4\times10^{12}$, $4.1\times10^{12}$, $4.2\times10^{12}$, $4.3\times10^{12}$2, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $2\times10^{13}$, $3\times10^{13}$, $4\times10^{13}$, $5\times10^{13}$, $6\times10^{13}$, $6.7\times10^{13}$, $7\times^{13}$, $8\times10^{13}$, $9\times^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/kg.

In certain embodiments, delivery of AAV particles to cells of the central nervous system (e.g., parenchyma) may comprise a total dose between about $1\times10^{6}$ VG and about $1\times10^{16}$ VG. In some embodiments, delivery may comprise a total dose of about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $1.9\times10^{10}$, $2\times10^{10}$, $3\times10^{10}$, $3.73\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $2.5\times10^{11}$, $3\times10^{11}$, $4\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $0.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $5.1\times10^{12}$, $5.2\times10^{12}$, $5.3\times10^{12}$, $5.4\times10^{12}$, $5.5\times10^{12}$, $5.6\times10^{12}$, $5.7\times10^{12}$, $5.8\times10^{12}$, $5.9\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $7.1\times10^{12}$, $7.2\times10^{12}$, $7.3\times10^{12}$, $7.4\times10^{12}$, $7.5\times10^{12}$, $7.6\times10^{12}$, $7.7\times10^{12}$, $7.8\times10^{12}$, $7.9\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $9.1\times10^{12}$, $9.2\times10^{12}$, $9.3\times10^{12}$, $9.4\times10^{12}$, $9.5\times10^{12}$, $9.6\times10^{12}$, $9.7\times10^{12}$, $9.8\times10^{12}$, $9.9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG. In certain embodiments, the total dose is $1\times10^{13}$ VG. In certain embodiments, the total dose is $2.1\times10^{12}$ VG. In certain embodiments, the total dose is $7.2\times10^{11}$ VG. In certain embodiments, the total dose is $7.5\times10^{11}$ VG. In certain embodiments, the total dose is $9\times10^{11}$ VG. In certain embodiments, the total dose is $1.4\times10^{12}$ VG. In certain embodiments, the total dose is $1.5\times10^{12}$ VG. In certain embodiments, the total dose is $2.3\times10^{12}$ VG. In certain embodiments, the total dose is $4.5\times10^{12}$ VG. In certain embodiments, the total dose is $4.6\times10^{12}$ VG. In certain embodiments, the total dose is $4.7\times10^{12}$ VG. In certain embodiments, the total dose is $4.8\times10^{12}$ VG. In certain embodiments, the total dose is $4.9\times10^{12}$ VG. In certain embodiments, the total dose is $5\times10^{12}$ VG. In certain embodiments, the total dose is $8.8\times10^{12}$ VG. In certain embodiments, the total dose is $9.4\times10^{12}$ VG. In certain embodiments, the total dose is $3.72\times10^{12}$ VG. In certain embodiments, the concentration of the AAV particle in the composition is $8.3\times10^{12}$ VG/subject. In certain embodiments, the total dose is $5.95\times10^{12}$ VG. In certain embodiments, the total dose is $6.58\times10^{12}$ VG. In certain embodiments, the total dose is $4.31\times10^{12}$ VG. In certain embodiments, the total dose is $6.45\times10^{12}$ VG. In certain embodiments, the total dose is $7.80\times10^{12}$ VG.

In certain embodiments, about $10^{5}$ to $10^{6}$ viral genome (unit) may be administered per dose.

In certain embodiments, delivery of the compositions in accordance with the present disclosure to cells may comprise a total concentration between about $1\times10^{6}$ VG/mL and about $1\times10^{16}$ VG/mL. In some embodiments, delivery may comprise a composition concentration of about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $3.1\times10^{11}$, $3.2\times10^{11}$, $3.3\times10^{11}$, $3.4\times10^{11}$, $3.5\times10^{11}$, $3.6 \times 10^{11}$, $3.7 \times 10^{11}$, $3.8 \times 10^{11}$, $3.9 \times 10^{11}$, $4 \times 10^{11}$, $5 \times 10^{11}$, $6 \times 10^{11}$, $7 \times 10^{11}$, $8 \times 10^{11}$, $8.1 \times 10^{11}$, $8.2 \times 10^{11}$, $8.3 \times 10^{11}$, $8.4 \times 10^{11}$, $8.5 \times 10^{11}$, $8.6 \times 10^{11}$, $8.7 \times 10^{11}$, $8.8 \times 10^{11}$, $8.9 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.1 \times 10^{12}$, $2.2 \times 10^{12}$, $2.3 \times 10^{12}$, $2.4 \times 10^{12}$, $2.5 \times 10^{12}$, $2.6 \times 10^{12}$, $2.7 \times 10^{12}$, $2.8 \times 10^{12}$, $2.9 \times 10^{12}$, $3 \times 10^{12}$, $3.1 \times 10^{12}$, $3.2 \times 10^{12}$, $3.3 \times 10^{12}$, $3.4 \times 10^{12}$, $3.5 \times 10^{12}$, $3.6 \times 10^{12}$, $3.7 \times 10^{12}$, $3.8 \times 10^{12}$, $3.9 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $6.7 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/mL. In certain embodiments, the concentration of the AAV particle in the composition is $7.0 \times 10^{11}$ VG/mL. In certain embodiments, the concentration of the AAV particle in the composition is $3.3 \times 10^{11}$ VG/mL. In certain embodiments, the concentration of the AAV particle in the composition is $1 \times 10^{13}$ VG/mL. In certain embodiments, the concentration of the AAV particle in the composition is $3 \times 10^{12}$ VG/mL. In certain embodiments, the concentration of the AAV particle in the composition is $1.1 \times 10^{12}$ VG/mL. In certain embodiments, the concentration of the AAV particle in the composition is $1.7 \times 10^{12}$ VG/mL. In certain embodiments, the concentration of the AAV particle in the composition is $3.7 \times 10^{12}$ VG/mL. In certain embodiments, the concentration of the AAV particle in the composition is $8 \times 10^{11}$ VG/mL. In certain embodiments, the concentration of the AAV particle in the composition is $2.5 \times 10^{12}$ VG/mL. In certain embodiments, the concentration of the AAV particle in the composition is $2.6 \times 10^{12}$ VG/mL. In certain embodiments, the concentration of the AAV particle in the composition is $4.9 \times 10^{12}$ VG/mL. In certain embodiments, the concentration of the AAV particle in the composition is $0.8 \times 10^{12}$ VG/mL. In certain embodiments, the concentration of the AAV particle in the composition is $0.83 \times 10^{12}$ VG/mL. In certain embodiments, the concentration of the AAV particle in the composition is the maximum final dose which can be contained in a vial.

In certain embodiments, delivery of AAV particles to cells of the central nervous system (e.g., parenchyma) may comprise a composition concentration between about $1 \times 10^{6}$ VG/mL and about $1 \times 10^{16}$ VG/mL. In some embodiments, delivery may comprise a composition concentration of about $1 \times 10^{6}$, $2 \times 10^{6}$, $3 \times 10^{6}$, $4 \times 10^{6}$, $5 \times 10^{6}$, $6 \times 10^{6}$, $7 \times 10^{6}$, $8 \times 10^{6}$, $9 \times 10^{6}$, $1 \times 10^{7}$, $2 \times 10^{7}$, $3 \times 10^{7}$, $4 \times 10^{7}$, $5 \times 10^{7}$, $6 \times 10^{7}$, $7 \times 10^{7}$, $8 \times 10^{7}$, $9 \times 10^{7}$, $1 \times 10^{8}$, $2 \times 10^{8}$, $3 \times 10^{8}$, $4 \times 10^{8}$, $5 \times 10^{8}$, $6 \times 10^{8}$, $7 \times 10^{8}$, $8 \times 10^{8}$, $9 \times 10^{8}$, $1 \times 10^{9}$, $2 \times 10^{9}$, $3 \times 10^{9}$, $4 \times 10^{9}$, $5 \times 10^{9}$, $6 \times 10^{9}$, $7 \times 10^{9}$, $8 \times 10^{9}$, $9 \times 10^{9}$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $8.1 \times 10^{11}$, $8.2 \times 10^{11}$, $8.3 \times 10^{11}$, $8.4 \times 10^{11}$, $8.5 \times 10^{11}$, $8.6 \times 10^{11}$, $8.7 \times 10^{11}$, $8.8 \times 10^{11}$, $8.9 \times 10^{11}$, $9 \times 10^{11}$, $1 \times 10^{12}$, $2 \times 10^{12}$, $2.1 \times 10^{12}$, $2.2 \times 10^{12}$, $2.3 \times 10^{12}$, $2.4 \times 10^{12}$, $2.5 \times 10^{12}$, $2.6 \times 10^{12}$, $2.7 \times 10^{12}$, $2.8 \times 10^{12}$, $2.9 \times 10^{12}$, $3 \times 10^{12}$, $3.1 \times 10^{12}$, $3.2 \times 10^{12}$, $3.3 \times 10^{12}$, $3.4 \times 10^{12}$, $3.5 \times 10^{12}$, $3.6 \times 10^{12}$, $3.7 \times 10^{12}$, $3.8 \times 10^{12}$, $3.9 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $5.1 \times 10^{12}$, $5.2 \times 10^{12}$, $5.3 \times 10^{12}$, $5.4 \times 10^{112}$, $5.5 \times 10^{12}$, $5.6 \times 10^{12}$, $5.7 \times 10^{12}$, $5.8 \times 10^{12}$, $5.9 \times 10^{12}$, $6 \times 10^{12}$, $6.1 \times 10^{12}$, $6.2 \times 10^{12}$, $6.3 \times 10^{12}$, $6.4 \times 10^{12}$, $6.5 \times 10^{12}$, $6.6 \times 10^{12}$, $6.7 \times 10^{12}$, $6.8 \times 10^{12}$, $6.9 \times 10^{12}$, $7 \times 10^{12}$, $7.1 \times 10^{12}$, $7.2 \times 10^{12}$, $7.3 \times 10^{12}$, $7.4 \times 10^{12}$, $7.5 \times 10^{12}$, $7.6 \times 10^{12}$, $7.7 \times 10^{12}$, $7.8 \times 10^{12}$, $7.9 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/mL. In certain embodiments, the delivery comprises a composition concentration of $7.0 \times 10^{11}$ VG/mL. In certain embodiments, the delivery comprises a composition concentration of $3.3 \times 10^{11}$ VG/mL. In certain embodiments, the delivery comprises a composition concentration of $1 \times 10^{13}$ VG/mL. In certain embodiments, the delivery comprises a composition concentration of $1.7 \times 10^{12}$ VG/mL. In certain embodiments, the delivery comprises a composition concentration of $8.3 \times 10^{11}$ VG/mL. In certain embodiments, the delivery comprises a composition concentration of $2.1 \times 10^{12}$ VG/mL. In certain embodiments, the delivery comprises a composition concentration of $2.5 \times 10^{12}$ VG/mL. In certain embodiments, the delivery comprises a maximum composition concentration of $2.6 \times 10^{12}$ VG/mL.

Regimen

The desired dosage of the AAV particles of the present disclosure may be delivered only once, three times a day, two times a day, once a day, every other day, every third day, every week, every two weeks, every three weeks, or every four weeks. In certain embodiments, the AAV particles are administered in a single dose. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

The desired dosage of the AAV particles of the present disclosure may be administered as a "pulse dose" or as a "continuous flow". As used herein, a "pulse dose" is a series of single unit doses of any therapeutic administered with a set frequency over a period of time. As used herein, a "continuous flow" is a dose of therapeutic administered continuously for a period of time in a single route/single point of contact, i.e., continuous administration event. A total daily dose, an amount given or prescribed in 24 hour period, may be administered by any of these methods, or as a combination of these methods, or by any other methods suitable for a pharmaceutical administration.

In certain embodiments, delivery of the AAV particles of the present disclosure to a subject provides regulating activity of AADC in a subject. The regulating activity may be an increase in the production of AADC in a subject. The regulating activity can be for at least 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 20 months, 21 months, 22 months, 23 months, 2 years, 3 years, 4 years, 5 years, 6 years, 7 years, 8 years, 9 years, 10 years or more than 10 years.

In some embodiments, the AAV particle of the present disclosure may be administered to a subject using a single dose, one-time treatment. The dose of the one-time treatment may be administered by any methods known in the art and/or described herein. As used herein, a "one-time treatment" refers to a composition which is only administered one time. If needed, a booster dose may be administered to the subject to ensure the appropriate efficacy is reached. A booster may be administered 1 month, 2 months, 3 months, 4 months, 5 months, 6 months, 7 months, 8 months, 9 months, 10 months, 11 months, 12 months, 1 year, 13 months, 14 months, 15 months, 16 months, 17 months, 18 months, 19 months, 20 months, 21 months, 22 months, 23 months, 24 months, 2 years, 3 years, 4 years, 5 years, 6 years, 7 years, 8 years, 9 years, 10 years, or more than 10 years after the one-time treatment.

Delivery Methods

In certain embodiments, the AAV particles or pharmaceutical compositions of the present disclosure may be administered or delivered using the methods for treatment of disease described in U.S. Pat. No. 8,999,948, or International Publication No. WO2014178863, the contents of which are herein incorporated by reference in their entirety.

In certain embodiments, the AAV particles or pharmaceutical compositions of the present disclosure may be administered or delivered using the methods for delivering gene therapy in Alzheimer's Disease or other neurodegenerative conditions as described in US Application No. 20150126590, the contents of which are herein incorporated by reference in their entirety.

In certain embodiments, the AAV particles or pharmaceutical compositions of the present disclosure may be administered or delivered using the methods for delivery of a CNS gene therapy as described in U.S. Pat. Nos. 6,436,708, and 8,946,152, and International Publication No. WO2015168666, the contents of which are herein incorporated by reference in their entirety.

In certain embodiments, the AAV particle comprising an AADC polynucleotide may be administered or delivered using the methods for the delivery of AAV virions described in European Patent Application No. EP1857552, the contents of which are herein incorporated by reference in its entirety.

In certain embodiments, the AAV particle or pharmaceutical compositions of the present disclosure may be administered or delivered using the methods for delivering proteins using AAV particles described in European Patent Application No. EP2678433, the contents of which are herein incorporated by reference in their entirety.

In certain embodiments, the AAV particle comprising an AADC polynucleotide may be administered or delivered using the methods for delivering DNA molecules using AAV particles described in U.S. Pat. No. 5,858,351, the contents of which are herein incorporated by reference in its entirety.

In certain embodiments, the AAV particle or pharmaceutical compositions of the present disclosure may be administered or delivered using the methods for delivering DNA to the bloodstream described in U.S. Pat. No. 6,211,163, the contents of which are herein incorporated by reference in their entirety.

In certain embodiments, the AAV particle or pharmaceutical compositions of the present disclosure may be administered or delivered using the methods for delivering a payload to the central nervous system described in U.S. Pat. No. 7,588,757, the contents of which are herein incorporated by reference in their entirety.

In certain embodiments, the AAV particle may be administered or delivered using the methods for delivering AAV virions described in U.S. Pat. No. 6,325,998, the contents of which are herein incorporated by reference in its entirety.

In certain embodiments, the AAV particle or pharmaceutical compositions of the present disclosure may be administered or delivered using the methods for delivering a payload described in U.S. Pat. No. 8,283,151, the contents of which are herein incorporated by reference in their entirety.

In certain embodiments, the AAV particle or pharmaceutical compositions of the present disclosure may be administered or delivered using the methods for delivering a payload using a glutamic acid decarboxylase (GAD) delivery vector described in International Patent Publication No. WO2001089583, the contents of which are herein incorporated by reference in their entirety.

In certain embodiments, the AAV particle or pharmaceutical compositions of the present disclosure may be administered or delivered using the methods for delivering a payload to neural cells described in International Patent Publication No. WO2012057363, the contents of which are herein incorporated by reference in their entirety.

Delivery to Cells

The present disclosure provides a method of delivering to a cell or tissue any of the above-described AAV particles, comprising contacting the cell or tissue with said AAV particle or contacting the cell or tissue with a formulation comprising said AAV particle, or contacting the cell or tissue with any of the described compositions, including pharmaceutical compositions. The method of delivering the AAV particle to a cell or tissue can be accomplished in vitro, ex vivo, or in vivo.

Delivery to Subjects

The present disclosure additionally provides a method of delivering to a subject, including a mammalian subject, any of the above-described AAV particles comprising administering to the subject said AAV particle, or administering to the subject a formulation comprising said AAV particle, or administering to the subject any of the described compositions, including pharmaceutical compositions.

Combinations

The AAV particles may be used in combination with one or more other therapeutic, prophylactic, research or diagnostic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, research, or diagnostic compositions in combination with agents that may improve their bioavailability, reduce and/or modify their metabolism, inhibit their excretion, and/or modify their distribution within the body.

In certain embodiments, the AAV particles described herein may be administered to a subject who is also undergoing levodopa therapy. In certain embodiments, the subject may have a positive response to levodopa therapy and at least one symptom of PD is reduced. In certain embodiments, the subject may have a response to levodopa therapy where the symptoms of PD experienced by the subject are stable. As yet another non-limiting example, the subject may have a negative response to levodopa therapy where the symptoms of PD experienced by the subject are increasing.

In certain embodiments, the dose of levodopa administered to the subject prior to the AAV articles is 1, 2, 3, 4, 5, 6, 7, 8, 9, 10, 11, 12, 13, 14, 15, 16, 17, 18, 19, 20, 21, 22, 23, 24, 25 or more than 25 mg/kg. In certain embodiments, the dose is 3 mg/kg. In certain embodiments, the dose is 10 mg/kg. As yet another non-limiting example, the dose is 20 mg/kg. The subject's response (e.g., behavioral response) to levodopa may be assessed prior to administration of the AAV particles. Additionally, the subject may be administered levodopa again after the administration of the AADC polynucleotides (e.g., 1 week, 2, weeks, 3 weeks, 1 month, 2 months, 3 months, 4 months, 5 months, 6 months, 7 months, 8 months, 9 months, 10 months, 11 months, 1 year or more than 1 year after the administration of AAV particles). The behavioral response can be re-assessed and compared to the initial response to determine the effects of the AAV particles. The subject may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% behavioral improvement.

In certain embodiments, Levodopa may be administered multiple times after the administration of the AAV particles. Levodopa may be administered on a repeating schedule (e.g., every 5 days, weekly, every 10 days, every 15 days, every 30 days, monthly, bimonthly, every 3 months, every 4 months, every 5 months, every 6 months, every 7 months, every 8 months, every 9 months, every 10 months, every 11 months or yearly) or as symptoms arise. In certain embodiments, 3 years post administration of AADC polynucleotides a subject may have 1-10%, 5-15%, 10-20%, 15-30%, 2040%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive. In certain embodiments, 6 years post administration of AAV particles a subject may have 1-10%, 5-15%, 10-20%, 15-30%, 20-40%, 25-50%, 30-50%, 40-50%, 40-60%, 50-70%, 50-80%, 60-70%, 60-75%, 60-80%, 60-90%, 70-80%, 70-90%, 75-90%, 80-90%, 90-100% of the striatal neurons within the infused region of the putamen to be AADC-immunoreactive. In certain embodiments, 9 years post administration of AADC polynucleotides a subject may have 1-10%, 5-15%, 10-20%, 15-30%, 2040%, 25-50%, 30-50%, 40-50%, 40-60%, 50-70%, 50-80%, 60-70%, 60-75%, 60-80%, 60-90%, 70-80%, 70-90%, 75-90/o, 80-90%, 90-100% of the striatal neurons within the infused region of the putamen to be AADC-immunoreactive.

In certain embodiments, a subject who may be administered the AAV particles described herein have a documented response to levodopa therapy but have medically refractory fluctuations and are considered good surgical candidates. The determination if a subject is a good surgical candidate may be made by the physician treating the subject for PD or the physician administering the AAV particles who takes into consideration the overall risk to benefit ratio for the patient for the surgical intervention required for delivery of the AAV particles.

Measurement of Expression

Expression of payloads from viral genomes may be determined using various methods known in the art such as, but not limited to immunochemistry (e.g., IHC), in situ hybridization (ISH), enzyme-linked immunosorbent assay (ELISA), affinity ELISA, ELISPOT, flow cytometry, immunocytology, surface plasmon resonance analysis, kinetic exclusion assay, liquid chromatography-mass spectrometry (LCMS), high-performance liquid chromatography (HPLC), BCA assay, immunoelectrophoresis, Western blot, SDS-PAGE, protein immunoprecipitation, and/or PCR.

The pharmaceutical compositions of AAV particles described herein may be characterized by one or more of bioavailability, therapeutic window and/or volume of distribution.

Bioavailability

The AAV particles, when formulated into a composition with a delivery agent as described herein, can exhibit an increase in bioavailability as compared to a composition lacking a delivery agent as described herein. As used herein, the term "bioavailability" refers to the systemic availability of a given amount of AAV particle or expressed payload administered to a mammal. Bioavailability can be assessed by measuring the area under the curve (AUC) or the maximum serum or plasma concentration ($C_{max}$) of the composition following. AUC is a determination of the area under the curve plotting the serum or plasma concentration of a compound (e.g., AAV particles or expressed payloads) along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, the contents of which are herein incorporated by reference in its entirety.

The $C_{max}$ value is the maximum concentration of the AAV particle or expressed payload achieved in the serum or plasma of a mammal following administration of the AAV particle to the mammal. The $C_{max}$ value of can be measured using methods known to those of ordinary skill in the art. The phrases "increasing bioavailability" or "improving the pharmacokinetics," as used herein mean that the systemic availability of a first AAV particle or expressed payload, measured as AUC, $C_{max}$, or $C_{min}$ in a mammal is greater, when co-administered with a delivery agent as described herein, than when such co-administration does not take place. In some embodiments, the bioavailability can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

As used herein "therapeutic window" refers to the range of plasma concentrations, or the range of levels of therapeutically active substance at the site of action, with a high probability of eliciting a therapeutic effect. In some embodiments, the therapeutic window of the AAV particle as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the AAV particles as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Biological Effect

In certain embodiments, the biological effect of the AAV particles delivered to the animals may be categorized by analyzing the payload expression in the animals. The payload expression may be determined from analyzing a biological sample collected from a mammal administered the AAV particles of the present disclosure. For example, a protein expression of 50-200 µg/ml for the protein encoded by the AAV particles delivered to the mammal may be seen as a therapeutically effective amount of protein in the mammal.

IV. Methods and Uses of the Compositions of the Disclosure CNS Diseases

The polynucleotides of the present disclosure may be used in the treatment, prophylaxis or amelioration of any disease or disorder characterized by aberrant or undesired target expression. In certain embodiments, the disclosure relates to AAV particles for use in the treatment of Parkinson's disease.

In some embodiments, the AAV particles may be used in the treatment, prophylaxis or amelioration of any disease or disorder characterized by aberrant or undesired target expression wherein the payload, i.e. AADC, is swapped for an alternate payload.

The present disclosure provides a method for treating a disease, disorder and/or condition in a mammalian subject, including a human subject, comprising administering to the subject AAV particles described herein.

In certain embodiments, the disease, disorder and/or condition is a neurological disease, disorder and/or condition. The CNS diseases may be diseases that affect any component of the brain (including the cerebral hemispheres, diencephalon, brain stem, and cerebellum) or the spinal cord.

In some embodiments, viral particles of the present disclosure, through delivery of a functional payload that is a therapeutic product that can modulate the level or function of a gene product in the CNS, may be used to treat a neurodegenerative diseases and/or diseases or disorders that are characteristic with neurodegeneration, neuromuscular diseases, lysosomal diseases, trauma, bone marrow injuries, pain (including neuropathic pain), cancers of the nervous system, demyelinating diseases, autoimmune diseases of the nervous system, neurotoxic syndromes, sleeping disorders, genetic brain disorders and developmental CNS disorders. A functional payload may alleviate or reduce symptoms that result from abnormal level and/or function of a gene product (e.g., an absence or defect in a protein) in a subject in need thereof or that otherwise confers a benefit to a CNS disorder in a subject in need thereof.

As non-limiting examples, therapeutic products delivered by AAV particles of the present disclosure may include, but are not limited to, growth and trophic factors, cytokines, hormones, neurotransmitters, enzymes, anti-apoptotic factors, angiogenic factors, and any protein known to be mutated in pathological disorders such as the "survival of motor neuron" protein (SMN); antisense RNA or RNAi targeting messenger RNAs coding for proteins having a therapeutic interest in any of CNS diseases discussed herein; or microRNAs that function in gene silencing and post-transcriptionally regulation of gene expression in the CNS (e.g., brain specific Mir-128a, See Adlakha and Saini, Molecular cancer, 2014, 13:33). For example, an RNAi targeting the superoxide dismutase enzyme may be packaged by viral particles of the present disclosure, for the treatment of ALS.

The growth and trophic factors may include, but are not limited to brain-derived growth factor (BDNF), epidermal growth factor (EGF), basic Fibroblast growth factor (bFGF), Ciliary neurotrophic factor (CNTF), corticotropin-releasing factor (CRF), Glial cell line derived growth factor (GDNF), Insulin-like growth factor-1 (IGF-1), nerve growth factor (NGF), neurotrophin-3 (NT-3), neurotrophin-4 (NT-4), and vascular endothelial growth factor (VEGF). Cytokines may include interleukin-10 (IL-10), interleukin-6, Interleukin-8, chemokine CXCL12 (SDF-1), TGF-beta, and Growth and differentiation factor (GDF-1/10).

In some embodiments, the neurological disorders may be neurodegenerative disorders including, but not limited to, Alzheimer's Diseases (AD); Amyotrophic lateral sclerosis (ALS); Creutzfeldt-Jakob Disease (CJD); Huntingtin's disease (HD); Friedreich's ataxia (FA); Parkinson Disease (PD): Multiple System Atrophy (MSA): Spinal Muscular Atrophy (SMA), Multiple Sclerosis (MS); Primary progressive aphasia; Progressive supranuclear palsy (PSP); Dementia; Brain Cancer, Degenerative Nerve Diseases. Encephalitis, Epilepsy, Genetic Brain Disorders that cause neurodegeneration, Retinitis pigmentosa (RP), Head and Brain Malformations, Hydrocephalus, Stroke, Prion disease. Infantile neuronal ceroid lipofuscinosis (INCL) (a neurodegenerative disease of children caused by a deficiency in the lysosomal enzyme palmitoyl protein thioesterase-1 (PPT1)), and others.

In some embodiments, viral particles of the present disclosure may be used to treat diseases that are associated with impairments of the growth and development of the CNS, i.e., neurodevelopmental disorders. In some aspects, such neurodevelopmental disorders may be caused by genetic mutations, including but not limited to, Fragile X syndrome (caused by mutations in FMRI gene), Down syndrome (caused by trisomy of chromosome 21), Rett syndrome, Williams syndrome, Angelman syndrome, Smith-Magenis syndrome, ATR-X syndrome, Barth syndrome, Immune dysfunction and/or infectious diseases during infancy such as Sydenham's chorea, Schizophrenia Congenital toxoplasmosis, Congenital rubella syndrome, Metabolic disorders such as diabetes mellitus and phenylketonuria; nutritional defects and/or brain trauma, Autism and autism spectrum.

In some embodiments, viral particles of the present disclosure, may be used to treat a tumor in the CNS, including but not limited to, acoustic neuroma, Astrocytoma (Grades I, II, III and IV), Chordoma, CNS Lymphoma, Craniopharyngioma, Gliomas (e.g., brain stem glioma, ependymoma, optical nerve glioma, subependymoma), Medulloblastoma, Meningioma, Metastatic brain tumors, Oligodendroglioma, Pituitary Tumors, Primitive neuroectodermal (PNET), and Schwannoma.

In some embodiments, the neurological disorders may be functional neurological disorders with motor and/or sensory symptoms which have neurological origin in the CNS. As non-limiting examples, functional neurological disorders may be chronic pain, seizures, speech problems, involuntary movements, and sleep disturbances.

In some embodiments, the neurological disorders may be white matter disorders (a group of diseases that affects nerve fibers in the CNS) including but not limited to, Pelizaeus-Merzbacher disease, Hypomyelination with atrophy of basal ganglia and cerebellum, Aicardi-Goutieres syndrome, Megalencephalic leukoencephalopathy with subcortical cysts, Congenital muscular dystrophies, Myotonic dystrophy. Wilson disease, Lowe syndrome, Sjögren-Larsson syndrome, PIBD or Tay syndrome, Cockayne's disease, cerebrotendinous xanthomatosis, Zellweger syndrome, Neonatal adrenoleukodystrophy, Infantile Refsum disease. Zellweger-like syndrome, Pseudo-Zellweger syndrome, Pseudo-neonatal adrenoleukodystrophy, Bifunctional protein deficiency, X-linked adrenoleukodystrophy and adrenomyeloneuropathy and Refsum disease.

In some embodiments, the neurological disorders may be lysosomal storage disorders (LSDs) caused by the inability of cells in the CNS to break down metabolic end products, including but not limited to Niemann-Pick disease (a LSD resulting from inherited deficiency in acid sphingomyelinase (ASM); Metachromatic leukodystrophy (MLD) (a LSD characterized by accumulation of sulfatides in glial cells and neurons, the result of an inherited deficiency of arylsulfatase A (ARSA)); Globoid-cell leukodystrophy (GLD) (a LSD caused by mutations in galactosylceramidase); Fabry disease (a LSD caused by mutations in the alpha-galactosidase A (GLA) gene); Gaucher disease (caused by mutations in the beta-glucocerebrosidase (GBA) gene); GM1/GM2 gangliosidosis; Mucopolysaccharidoses disorder, Pompe disease; and Neuronal ceroid lipofuscinosis.

In another embodiment, the neurological disease, disorder and/or condition is Friedreich's Ataxia. In certain embodiments, the AAV particle used to treat Friedreich's Ataxia comprises a nucleic acid sequence such as, but not limited to, SEQ ID NO: 979 or a fragment or variant thereof, wherein the payload is replaced by Frataxin or any other payload known in the art for treating Friedreich's Ataxia.

In another embodiment, the neurological disease, disorder and/or condition is Amyotrophic lateral sclerosis (ALS). In certain embodiments the AAV particle used to treat ALS comprises a nucleic acid sequence such as, but not limited to, SEQ ID NO: 979 or a fragment or variant thereof, wherein the payload is replaced by replaced by an shRNA, miRNA, siRNA, RNAi for SOD1 or any other payload known in the art for treating ALS.

In another embodiment, the neurological disease, disorder and/or condition is Huntington's disease. In certain embodiments the AAV particle used to treat Huntington's disease comprises a nucleic acid sequence such as, but not limited to, SEQ ID NO: 979 or a fragment or variant thereof, wherein the payload is replaced by replaced by an shRNA, miRNA, siRNA, RNAi for Htt or any other payload known in the art for treating Huntington's disease.

In another embodiment, the neurological disease, disorder or condition is spinal muscular atrophy (SMA). In another embodiment, the neurological disease, disorder and/or condition is Friedreich's Ataxia. In certain embodiments the AAV particle used to treat SMN comprises a nucleic acid sequence such as, but not limited to, SEQ ID NO: 979 or a fragment or variant thereof, wherein the payload is replaced by Frataxin or any other payload known in the art for treating SMA.

Parkinson's Disease

In certain embodiments, the neurological disease, disorder and/or condition is Parkinson's disease. In certain embodiments the AAV particle used to treat Parkinson's disease comprises a payload such as, but not limited to, SEQ ID NO: 979 or a fragment or variant thereof.

In certain embodiments, the subject is a human patient who has a minimum motor score of about 30 to a maximum score of about 100, about 10 to a maximum score of about 100, about 20 to a maximum score of about 100 in the Unified Parkinson's Disease Rating Scale.

In certain embodiments, the subject has been diagnosed with Parkinson's disease within the past 5 years prior to treatment with the compositions described herein. In certain embodiments, the subject may have been diagnosed with Parkinson's disease within a week, 2 weeks, 3 weeks, 4 weeks, 5 weeks, 6 weeks, 7 weeks, 8 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 1 year, 2 years, 3 years, 4 years or less than 5 years prior to treatment with the compositions described herein.

In certain embodiments, the subject has been diagnosed with Parkinson's disease between 5 and 10 years prior to treatment with the compositions described herein. In certain embodiments, the subject may have been diagnosed with Parkinson's disease 5, 5.5, 6, 6.5, 7, 7.5, 8, 8.5, 9, 9.5 or 10 years prior to treatment with the compositions described herein.

In certain embodiments, the subject has been diagnosed with Parkinson's disease more than 10 years prior to treatment with the compositions described herein. In certain embodiments, the subject may have been diagnosed with Parkinson's disease 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24 or more than 24 years prior to treatment with the compositions described herein.

In certain embodiments, a subject is 50-65 years of age. In certain embodiments, the subject is 50, 51, 52, 53, 54, 55, 56, 57, 58, 59, 60, 61, 62, 63, 64, or 65 years of age. In certain embodiments, the subject is 50 years of age. In certain embodiments, the subject is 51 years of age. In certain embodiments, the subject is 52 years of age. In certain embodiments, the subject is 53 years of age. In certain embodiments, the subject is 54 years of age. In certain embodiments, the subject is 55 years of age. In certain embodiments, the subject is 56 years of age. In certain embodiments, the subject is 57 years of age. In certain embodiments, the subject is 58 years of age. In certain embodiments, the subject is 59 years of age. In certain embodiments, the subject is 60 years of age. In certain embodiments, the subject is 61 years of age. In certain embodiments, the subject is 62 years of age. In certain embodiments, the subject is 63 years of age. In certain embodiments, the subject is 64 years of age. In certain embodiments, the subject is 65 years of age.

In certain embodiments, a subject is 30 to 50 years of age. In certain embodiments, the subject is 30 years of age. In certain embodiments, the subject is 31 years of age. In certain embodiments, the subject is 32 years of age. In certain embodiments, the subject is 33 years of age. In certain embodiments, the subject is 34 years of age. In certain embodiments, the subject is 35 years of age. In certain embodiments, the subject is 36 years of age. In certain embodiments, the subject is 37 years of age. In certain embodiments, the subject is 38 years of age. In certain embodiments, the subject is 39 years of age. In certain embodiments, the subject is 40 years of age. In certain embodiments, the subject is 41 years of age. In certain embodiments, the subject is 42 years of age. In certain embodiments, the subject is 43 years of age. In certain embodiments, the subject is 44 years of age. In certain embodiments, the subject is 45 years of age. In certain embodiments, the subject is 46 years of age. In certain embodiments, the subject is 47 years of age. In certain embodiments, the subject is 48 years of age. In certain embodiments, the subject is 49 years of age. In certain embodiments, the subject is 50 years of age.

In certain embodiments, a subject is 65 to 85 years of age. In certain embodiments, the subject is 65 years of age. In certain embodiments, the subject is 66 years of age. In certain embodiments, the subject is 67 years of age. In certain embodiments, the subject is 68 years of age. In certain embodiments, the subject is 69 years of age. In certain embodiments, the subject is 70 years of age. In certain embodiments, the subject is 71 years of age. In certain embodiments, the subject is 72 years of age. In certain embodiments, the subject is 73 years of age. In certain embodiments, the subject is 74 years of age. In certain embodiments, the subject is 75 years of age. In certain embodiments, the subject is 76 years of age. In certain embodiments, the subject is 77 years of age. In certain embodiments, the subject is 78 years of age. In certain embodiments, the subject is 79 years of age. In certain embodiments, the subject is 80 years of age. In certain embodiments, the subject is 81 years of age. In certain embodiments, the subject is 82 years of age. In certain embodiments, the subject is 83 years of age. In certain embodiments, the subject is 84 years of age. In certain embodiments, the subject is 85 years of age.

In certain embodiments, a subject has seen a change in motor symptoms such as tremors and movements prior to administration of the composition described herein. Non-limiting examples of tremors include, unilateral or bilateral mild tremors, bilateral or midline moderate tremors or intractable tremors. Non-limiting examples of movements include mild bradykinesia, moderate bradykinesia, severe bradykinesia and morning akinesia.

In certain embodiments, a subject may have changes in balance such as, but not limited to, impaired balance, impaired righting reflexes, significant balance disorder or falling.

In certain embodiments, a subject may have a reduced quality of life. In certain embodiments, the subject may have a moderate impact on their quality of life such as experiencing some limitations to activities of daily living. In certain embodiments, the subject may have a quality of life which has been diminished by illness.

In certain embodiments, a subject has seen a change in non-motor symptoms prior to administration of the composition described herein. In certain embodiments, the subject may have mild to moderate cognitive impairment prior to administration to the composition described herein. In certain embodiments, the subject may have significant cognitive impairment such as dementia which may also include behavioral disturbances such as hallucinations.

In certain embodiments, a subject may have a satisfactory response with limited fluctuations on one or more dopaminergic medications prior to administration of the compositions described herein.

In certain embodiments, a subject may have motor fluctuations causing mild to moderate disability on one or more dopaminergic medications prior to administration of the compositions described herein.

In certain embodiments, a subject may have medically refractory motor fluctuations consisting of "wearing off" and/or levodopa-induced dyskinesias causing significant disability prior to administration of the compositions described herein.

In certain embodiments, a subject may have mild symptoms associated with Parkinson's disease such as, but not limited to, no cognitive impairment, diagnosed within the past 5 years, satisfactory response with limited fluctuations on one or more dopaminergic medications, unilateral or bilateral mild tremors, little to no impact on the quality of life, and/or no balance impairment.

In certain embodiments, a subject may have moderate symptoms associated with Parkinson's disease such as, but not limited to, mild to moderate cognitive impairment, first signs of impaired balance and righting reflexes, motor fluctuations causing mild-moderate disability on one or more dopaminergic medications, diagnosed within the past 5 to 10 years, bilateral or midline moderate tremors, moderate bradykinesia and/or subject experiencing some limitations to activities of daily living.

In certain embodiments, a subject may have advanced symptoms associated with Parkinson's disease such as, but not limited to, being diagnosed with Parkinson's more than 10 years, medium refractory motor fluctuations wearing off and/or levodopa-induced dyskinesia causing significant disability, intractable tremors, significant balance disorder and/or falling, significant cognitive impairment (such as dementia with or without behavioral disturbances), sever bradykinesia, quality of life markedly diminished by illness and/or morning akinesia.

In certain embodiments, a subject has been referred to a movement disorder specialist (MDS) but has not undergone deep brain stimulation.

In certain embodiments, a subject is using DUOPA™ in combination with the compositions described herein. In certain embodiments, the subject may have success with using DUOPA™ alone. In certain embodiments, the subject may not have any success or limited success using DUOPA™ alone.

In certain embodiments, a subject is one who was a candidate for surgical intervention including, but not limited to, deep-brain stimulation. In certain embodiments, deep-brain stimulation was suggested due to disabling motor complications despite treatment with optimal anti-Parkinsonian medication.

Theoretic Outcomes

Patient Diaries

In certain embodiments, a subject has an average on-time of 7.5-14 hours based on the subject diary. In certain embodiments, the average on-time is 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, or 14 hours. In certain embodiments, a subject has an average on-time of 10.5 hours based on the subject diary.

In certain embodiments, a subject experiences about 1.5 hours more of diary on-time (without troublesome dyskinesia), as compared to baseline, 6 months after administration of the present disclosure. In certain embodiments, a subject experiences about 1.5 hours more of diary on-time 6 months after administration of the present disclosure at a dose volume of up to 900 μL per putamen and a total dose of $4.7 \times 10^{12}$ vector genome.

In certain embodiments, a subject experiences about 2.2 hours more of diary on-time (without troublesome dyskinesia), as compared to baseline, 6 months after administration of the present disclosure. In certain embodiments, a subject experiences about 2.2 hours more of diary on-time 6 months after administration of the present disclosure at a dose volume of up to 900 μL per putamen and a total dose of $1.5 \times 10^{12}$ vector genome.

In certain embodiments, a subject experiences about 4 hours more of diary on-time (without troublesome dyskinesia), as compared to baseline, 6 months after administration of the present disclosure. In certain embodiments, a subject experiences about 4 hours more of diary on-time 6 months after administration of the present disclosure at a dose volume of up to 900 μL per putamen and a total dose of $1.5 \times 10^{12}$ vector genome.

In certain embodiments, a subject experiences about 1.6 hours more of diary on-time (without troublesome dyskinesia), as compared to baseline, 12 months after administration of the present disclosure. In certain embodiments, a subject experiences about 1.6 hours more of diary on-time 12 months after administration of the present disclosure at a dose volume of up to 450 μL per putamen and a total dose of $7.5 \times 10^{12}$ vector genome.

In certain embodiments, a subject experiences about 1.5 hours more of diary on-time (without troublesome dyskinesia), as compared to baseline, 12 months after administration of the present disclosure. In certain embodiments, a subject experiences about 1.5 hours more of diary on-time 12 months after administration of the present disclosure at a dose volume of up to 900 μL per putamen and a total dose of $4.7 \times 10^{12}$ vector genome.

In certain embodiments, a subject experiences about 3.3 hours more of diary on-time (without troublesome dyskinesia), as compared to baseline, 12 months after administration of the present disclosure. In certain embodiments, a subject experiences about 3.3 hours more of diary on-time 12 months after administration of the present disclosure at a dose volume of up to 900 μL per putamen and a total dose of $1.5 \times 10^{12}$ vector genome.

In certain embodiments, a subject experiences about 4 hours more of diary on-time (without troublesome dyskinesia), as compared to baseline, 12 months after administration of the present disclosure. In certain embodiments, a subject experiences about 4 hours more of diary on-time 12 months after administration of the present disclosure at a dose volume of up to 900 μL per putamen and a total dose of $1.5 \times 10^{12}$ vector genome.

In certain embodiments, a subject experiences about 2.3 hours more of diary on-time (without troublesome dyskinesia), as compared to baseline, 24 months after administration of the present disclosure. In certain embodiments, a subject experiences about 2.3 hours more of diary on-time 24 months after administration of the present disclosure at a dose volume of up to 450 μL per putamen and a total dose of $7.5 \times 10^{12}$ vector genome.

In certain embodiments, a subject experiences about 2.1 hours more of diary on-time (without troublesome dyskinesia), as compared to baseline, 36 months after administration of the present disclosure. In certain embodiments, a subject experiences about 2.1 hours more of diary on-time 36 months after administration of the present disclosure at a dose volume of up to 450 μL per putamen and a total dose of $7.5 \times 10^{12}$ vector genome.

In certain embodiments, a subject has an average off-time of 2-7 hours based on the subject diary. In certain embodiments, the average off-time is 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7. In certain embodiments, a subject has an average off-time of 4.6 hours based on the subject diary.

In certain embodiments, a subject experiences about 1.3 hours less of diary off-time, as compared to baseline, 6 months after administration of the present disclosure. In certain embodiments, a subject experiences about 1.3 hours less of diary off-time 6 months after administration of the present disclosure at a dose volume of up to 900 μL per putamen and a total dose of $4.7 \times 10^{12}$ vector genome.

In certain embodiments, a subject experiences about 1.1 hours less of diary off-time, as compared to baseline, 6 months after administration of the present disclosure. In certain embodiments, a subject experiences about 1.1 hours less of diary off-time 6 months after administration of the present disclosure at a dose volume of up to 900 μL per putamen and a total dose of $1.5 \times 10^{12}$ vector genome.

In certain embodiments, a subject experiences about 0.8 hours less of diary off-time, as compared to baseline, 6 months after administration of the present disclosure. In certain embodiments, a subject experiences about 0.8 hours less of diary off-time 6 months after administration of the present disclosure at a dose volume of up to 450 μL per putamen and a total dose of $7.5 \times 10^{12}$ vector genome.

In certain embodiments, a subject experiences about 2.2 hours less of diary off-time, as compared to baseline, 12 months after administration of the present disclosure. In certain embodiments, a subject experiences about 2.2 hours less of diary off-time 12 months after administration of the present disclosure at a dose volume of up to 900 μL per putamen and a total dose of $1.5 \times 10^{12}$ vector genome.

In certain embodiments, a subject experiences about 1.3 hours less of diary off-time, as compared to baseline, 12 months after administration of the present disclosure. In certain embodiments, a subject experiences about 1.3 hours less of diary off-time 12 months after administration of the present disclosure at a dose volume of up to 450 μL per putamen and a total dose of $7.5 \times 10^{12}$ vector genome.

In certain embodiments, a subject experiences about 1.8 hours less of diary off-time, as compared to baseline, 24 months after administration of the present disclosure. In certain embodiments, a subject experiences about 1.8 hours less of diary off-time 24 months after administration of the present disclosure at a dose volume of up to 450 μL per putamen and a total dose of $7.5 \times 10^{12}$ vector genome.

In certain embodiments, a subject experiences 10% less diary off-time 6 months after administration of the present disclosure. In certain embodiments, a subject experiences 10% less diary off-time 12 months after administration of the present disclosure.

In certain embodiments, a subject experiences 20% less diary off-time 6 months after administration of the present disclosure. In certain embodiments, a subject experiences 20% less diary off-time 12 months after administration of the present disclosure.

In certain embodiments, a subject experiences 30% less diary off-time 6 months after administration of the present disclosure. In certain embodiments, a subject experiences 30% less diary off-time 12 months after administration of the present disclosure.

In certain embodiments, a subject experiences 40% less diary off-time 6 months after administration of the present disclosure. In certain embodiments, a subject experiences 40% less diary off-time 12 months after administration of the present disclosure.

In certain embodiments, a subject experiences 50% less diary off-time 6 months after administration of the present disclosure. In certain embodiments, a subject experiences 50% less diary off-time 12 months after administration of the present disclosure.

In certain embodiments, a subject experiences 60% less diary off-time 6 months after administration of the present disclosure. In certain embodiments, a subject experiences 60% less diary off-time 12 months after administration of the present disclosure.

In certain embodiments, a subject experiences 70% less diary off-time 6 months after administration of the present disclosure. In certain embodiments, a subject experiences 70% less diary off-time 12 months after administration of the present disclosure.

In certain embodiments, a subject experiences 80% less diary off-time 6 months after administration of the present disclosure. In certain embodiments, a subject experiences 80% less diary off-time 12 months after administration of the present disclosure.

In certain embodiments, a subject experiences 90% less diary off-time 6 months after administration of the present disclosure. In certain embodiments, a subject experiences 90% less diary off-time 12 months after administration of the present disclosure.

In certain embodiments, a subject experiences 95% less diary off-time 6 months after administration of the present disclosure. In certain embodiments, a subject experiences 95% less diary off-time 12 months after administration of the present disclosure.

UPDRS and Motor Function

In certain embodiments, a subject's UPDRS-3 (or UPDRS-III) medication score is evaluated prior to administration of the present disclosure. In certain embodiments, the subject's UPDRS-3 (or UPDRS-III) medication score prior to administration of the present disclosure is between 1-40, 1-10, 1-15, 1-20, 1-25, 1-30, 1-35, 1-40, 5-10, 5-15, 5-20, 5-25, 5-30, 5-35, 5-40, 10-15, 10-20, 10-25, 10-30, 10-35, 10-40, 15-20, 15-25, 15-30, 15-35, 15-40, 20-25, 20-30, 20-35, 20-40, 25-30, 25-35, 25-40, 30-35, 30-40, or 35-40. In certain embodiments, the subject's UPDRS-3 (or UPDRS-III) medication score prior to administration of the present disclosure is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In certain embodiments, the subject's UPDRS-3 (or UPDRS-III) medication score prior to administration of the present disclosure is 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15. In certain embodiments, the subjects UPDRS-3 medication score prior to administration of the present disclosure is 13.5.

In certain embodiments, a subject's UPDRS-3 (or UPDRS-11) medication score is reduced after administration of the present disclosure.

A subject's UPDRS-3 (or UPDRS-III) medication score may be reduced by a percentage such as, but not limited to, 10%, 15%, 20%, 25%, 30%, 35%, 40%, 45%, 50%, 55%, 60%, 65%, 70%, 75%, 80%, 85%, 90%, 95% or more than 95%. In certain embodiments, a subject's UPDRS-3 score is reduced 10% after administration of the present disclosure. In certain embodiments, a subject's UPDRS-3 score is reduced 20% after administration of the present disclosure. In certain embodiments, a subject's UPDRS-3 score is reduced 30% after administration of the present disclosure. In certain embodiments, a subject's UPDRS-3 score is reduced 40% after administration of the present disclosure. In certain embodiments, a subject's UPDRS-3 score is reduced 50% after administration of the present disclosure. In certain embodiments, a subject's UPDRS-3 score is reduced 60% after administration of the present disclosure. In certain embodiments, a subject's UPDRS-3 score is reduced 70% after administration of the present disclosure. In certain embodiments, a subject's UPDRS-3 score is reduced 80% after administration of the present disclosure. In certain embodiments, a subject's UPDRS-3 score is reduced 90% after administration of the present disclosure.

A subject's UPDRS-3 (or UPDRS-III) medication score may change by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 points. In certain embodiments, a subject's UPDRS-3 score is changed by 0.4 points. In certain embodiments, a subject's UPDRS-3 score is changed by 1.6 points. In certain embodiments, a subject's UPDRS-3 score is changed by 1.8 points. In certain embodiments, a subject's UPDRS-3 score is changed by 8.6 points. In certain embodiments, a subject's UPDRS-3 score is changed by 9.6 points.

A subject's UPDRS-3 (or UPDRS-III) medication score may increase by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 points. In certain embodiments, a subject's UPDRS-3 score is increased by 0.4 points. In certain embodiments, a subject's UPDRS-3 score is increased by 1.6 points. In certain embodiments, a subject's UPDRS-3 score is increased by 1.8 points. In certain embodiments, a subject's UPDRS-3 score is increased by 8.6 points. In certain embodiments, a subject's UPDRS-3 score is increased by 9.6 points.

A subject's UPDRS-3 (or UPDRS-III) medication score may decrease by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 points. In certain embodiments, a subject's UPDRS-3 score is decreased by 0.4 points. In certain embodiments, a subject's UPDRS-3 score is decreased by 1.6 points. In certain embodiments, a subject's UPDRS-3 score is decreased by 1.8 points. In certain embodiments, a subject's UPDRS-3 score is decrease by 8.6 points. In certain embodiments, a subject's UPDRS-3 score is decreased by 9.6 points.

In certain embodiments, a subject's UPDRS-3 (or UPDRS-III) medication score is reduced by 8.6 at 6 months after administration of the present disclosure at a dose volume of up to 900 μL per putamen and a total dose of $4.7 \times 10^{12}$ vector genome.

In certain embodiments, a subject's UPDRS-3 (or UPDRS-III) medication score is reduced by 9.6 at 6 months after administration of the present disclosure at a dose volume of up to 900 µL per putamen and a total dose of $1.5 \times 10^{12}$ vector genome.

In certain embodiments, a subject's UPDRS-3 (or UPDRS-III) medication score is reduced by 6.8 at 12 months after administration of the present disclosure at a dose volume of up to 900 µL per putamen and a total dose of $4.7 \times 10^{12}$ vector genome.

In certain embodiments, a subject's UPDRS-3 (or UPDRS-III) medication score is reduced by 9.6 at 12 months after administration of the present disclosure at a dose volume of up to 900 µL per putamen and a total dose of $1.5 \times 10^{12}$ vector genome.

In certain embodiments, a subject's response to one or more IV-levodopa administrations is improved after the therapeutic administration of the AADC gene therapy of the present disclosure. In certain embodiments, the concentration of the infusion of IV levodopa is 0.6 mg/mL (i.e. low-dose) or 1.2 mg/mL (i.e. suprathreshold). In certain embodiments, the volume of the IV levodopa infusion is 1 mL/kg. In certain embodiments, the rate of the IV levodopa infusion is 1 mL/kg/hr. In certain embodiments, a subject's UPDRS-3 (or UPDRS-III) medication score in response to IV-levodopa administration is reduced after the therapeutic administration of the AADC gene therapy of the present disclosure. In certain embodiments, a subject's UPDRS-3 (or UPDRS-III) medication score in response to IV-levodopa administration is reduced by at least 30% after the therapeutic administration of the AADC gene therapy of the present disclosure.

In certain embodiments, a subject's time to onset of response to IV levodopa administration (IVL-TOR or TOR) is reduced after the therapeutic administration of the AADC gene therapy of the present disclosure. The IVL-TOR of a subject is defined as the time required to achieve at least 30% reduction in UPDRS-III relative to a baseline (i.e. baseline pre-administration of the AADC gene therapy). In certain embodiments, the IVL-TOR of a subject is reduced by 10-160 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, or 160 minutes after the therapeutic administration of the AADC gene therapy of the present disclosure.

In certain embodiments, a subject's duration of response to IV levodopa administration (IVL-DOR or DOR) is increased after the therapeutic administration of the AADC gene therapy of the present disclosure. The IVL-DOR of a subject is defined as the time a subject maintains at least 30% reduction in UPDRS-III relative to a baseline (i.e. baseline pre-administration of the AADC gene therapy). In certain embodiments, the IVL-DOR of a subject is increased by 10-160 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, or 160 minutes after the therapeutic administration of the AADC gene therapy of the present disclosure.

In certain embodiments, a subject's average amount of Parkinson's disease medication was about 1500 mg per day prior to administration of the present disclosure. In certain embodiments, the Parkinson's disease medication is levodopa.

In certain embodiments, a subject's UPDRS-II score is evaluated prior to administration of the present disclosure. The UPDRS-II score of a subject prior to administration of the present disclosure is between 20 and 50, such as, but not limited to, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

A subject's UPDRS-2 (or UPDRS-II) score may change by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 points.

A subject's UPDRS-2 (or UPDRS-11) score may increase by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 points.

A subject's UPDRS-2 (or UPDRS-II) score may decrease by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9.9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 points. In certain embodiments, a 3.6-point reduction is seen 12 months after administration with the present disclosure. In certain embodiments, a 3.6-point reduction is seen 6 months after administration with the present disclosure.

In certain embodiments, a subject's UPDRS-11 score is decreased by 2 to 4 points after administration of the present disclosure as compared to the UPDRS-II score prior to administration.

In certain embodiments, a subject's UPDRS-II score is decreased by 2 to 3 points 6 months after administration of the present disclosure at a dose volume of up to 900 µL per putamen and a total dose of $1.5 \times 10^{12}$ vector genome, as compared to the UPDRS-II medication score prior to administration.

In certain embodiments, a subject's UPDRS-11 score is decreased by 2 to 3 points 12 months after administration of the present disclosure at a dose volume of up to 900 µL per putamen and a total dose of $1.5 \times 10^{12}$ vector genome, as compared to the UPDRS-II medication score prior to administration.

In certain embodiments, a subject's UPDRS-II score is decreased by 3 to 4 points 6 months after administration of the present disclosure at a dose volume of up to 900 µL per putamen and a total dose of $4.5 \times 10^{12}$ vector genome, as compared to the UPDRS-II medication score prior to administration.

In certain embodiments, the present disclosure is used to improve a subject's motor function.

In certain embodiments, the present disclosure is used to control a subject's motor function and improve their quality of life.

In certain embodiments, the present disclosure is used to reduce the dosage of Parkinson's medication a subject needs to take to improve a subject's motor function.

In certain embodiments, a single administration of the present disclosure into the putamen of a subject provides improved motor function as compared to motor function prior to treatment.

In certain embodiments, a single administration of the present disclosure into the putamen of a subject provides improved motor function and a reduction in the amount of levodopa the subject requires to manage symptoms.

In certain embodiments, a single administration of the present disclosure into the putamen of a subject provides improved motor function and a reduction in the amount of dopaminergic medication the subject requires to manage symptoms.

LED and Medications

In certain embodiments, the amount the daily dose of Parkinson's medication (e.g., Levodopa) is reduced by 10-50% after administration of the present disclosure. In certain embodiments, the reduction is seen 6 months after administration of the present disclosure. In certain embodiments, the reduction is seen 12 months after administration of the present disclosure.

In certain embodiments, the amount the daily dose of Parkinson's medication (e.g., Levodopa) is reduced by 10-20% after administration of the present disclosure. In certain embodiments, the reduction of Parkinson's medication (e.g., Levodopa) is 10%. In certain embodiments, the reduction of Parkinson's medication (e.g., Levodopa) is 11%. In certain embodiments, the reduction of Parkinson's medication (e.g., Levodopa) is 12%. In certain embodiments, the reduction of Parkinson's medication (e.g., Levodopa) is 13%. In certain embodiments, the reduction of Parkinson's medication (e.g., Levodopa) is 14%. In certain embodiments, the reduction of Parkinson's medication (e.g., Levodopa) is 15%. In certain embodiments, the reduction of Parkinson's medication (e.g., Levodopa) is 16%. In certain embodiments, the reduction of Parkinson's medication (e.g., Levodopa) is 17%. In certain embodiments, the reduction of Parkinson's medication (e.g., Levodopa) is 18%. In certain embodiments, the reduction of Parkinson's medication (e.g., Levodopa) is 19%. In certain embodiments, the reduction of Parkinson's medication (e.g., Levodopa) is 20%.

In certain embodiments, a 14% reduction in the amount of the daily dose of Parkinson's medication (e.g., Levodopa) required by a subject to manage symptoms occurs 6 months after administration of the present disclosure at a dose volume of up to 450 µL per putamen and a total dose of $7.5 \times 10^{12}$ vector genome.

In certain embodiments, a 10% reduction in the amount of the daily dose of Parkinson's medication (e.g., Levodopa) required by a subject to manage symptoms occurs 12 months after administration of the present disclosure at a dose volume of up to 450 µL per putamen and a total dose of $7.5 \times 10^{12}$ vector genome.

In certain embodiments, the amount the daily dose of Parkinson's medication (e.g., Levodopa) is reduced by 20-30% after administration of the present disclosure. In certain embodiments, the reduction of Parkinson's medication (e.g., Levodopa) is 20%. In certain embodiments, the reduction of Parkinson's medication (e.g., Levodopa) is 21%. In certain embodiments, the reduction of Parkinson's medication (e.g., Levodopa) is 22%. In certain embodiments, the reduction of Parkinson's medication (e.g., Levodopa) is 23%. In certain embodiments, the reduction of Parkinson's medication (e.g., Levodopa) is 24%. In certain embodiments, the reduction of Parkinson's medication (e.g., Levodopa) is 25%. In certain embodiments, the reduction of Parkinson's medication (e.g., Levodopa) is 26%. In certain embodiments, the reduction of Parkinson's medication (e.g., Levodopa) is 27%. In certain embodiments, the reduction of Parkinson's medication (e.g., Levodopa) is 28%. In certain embodiments, the reduction of Parkinson's medication (e.g., Levodopa) is 29%. In certain embodiments, the reduction of Parkinson's medication (e.g., Levodopa) is 30%.

In certain embodiments, a 27% reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 28% reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 29/6 reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 31% reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 32% reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 33% reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, the amount the daily dose of Parkinson's medication (e.g., Levodopa) is reduced by 30-40% after administration of the present disclosure. In certain embodiments, the reduction of Parkinson's medication (e.g., Levodopa) is 30%. In certain embodiments, the reduction of Parkinson's medication (e.g., Levodopa) is 31%. In certain embodiments, the reduction of Parkinson's medication (e.g., Levodopa) is 32%. In certain embodiments, the reduction of Parkinson's medication (e.g., Levodopa) is 33%. In certain embodiments, the reduction of Parkinson's medication (e.g., Levodopa) is 34%. In certain embodiments, the reduction of Parkinson's medication (e.g., Levodopa) is 35%. In certain embodiments, the reduction of Parkinson's medication (e.g., Levodopa) is 36%. In certain embodiments, the reduction of Parkinson's medication (e.g., Levodopa) is 37%. In certain embodiments, the reduction of Parkinson's medication (e.g., Levodopa) is 38%. In certain embodiments, the reduction of Parkinson's medication (e.g., Levodopa) is 39%. In certain embodiments, the reduction of Parkinson's medication (e.g., Levodopa) is 40%.

In certain embodiments, a 34% reduction in the amount of the daily dose of Parkinson's medication (e.g., Levodopa) required by a subject to manage symptoms occurs 6 months after administration of the present disclosure at a dose volume of up to 900 µL per putamen and a total dose of $1.5 \times 10^{12}$ vector genome.

In certain embodiments, the amount the daily dose of Parkinson's medication (e.g., Levodopa) is reduced by 40-50% after administration of the present disclosure. In certain embodiments, the reduction of Parkinson's medication (e.g., Levodopa) is 40%. In certain embodiments, the reduction of Parkinson's medication (e.g., Levodopa) is 41%. In certain embodiments, the reduction of Parkinson's medication (e.g., Levodopa) is 42%. In certain embodiments, the reduction of Parkinson's medication (e.g., Levodopa) is 43%. In certain embodiments, the reduction of Parkinson's medication (e.g., Levodopa) is 44%. In certain embodiments, the reduction of Parkinson's medication (e.g., Levodopa) is 45%. In certain embodiments, the reduction of Parkinson's medication (e.g., Levodopa) is 46%. In certain embodiments, the reduction of Parkinson's medication (e.g., Levodopa) is 47%. In certain embodiments, the reduction of Parkinson's medication (e.g., Levodopa) is 48%. In certain embodiments, the reduction of Parkinson's medication (e.g., Levodopa) is 49%. In certain embodiments, the reduction of Parkinson's medication (e.g., Levodopa) is 50%.

In certain embodiments, a 42% reduction in the amount of the daily dose of Parkinson's medication (e.g., Levodopa) required by a subject to manage symptoms occurs 6 months after administration of the present disclosure at a dose volume of up to 900 µL per putamen and a total dose of $4.5 \times 10^{12}$ vector genome.

In certain embodiments, the amount the daily dose of Parkinson's medication (e.g., Levodopa) is reduced by 108-641 mg after administration of the present disclosure. In certain embodiments, the reduction is seen 6 months after administration of the present disclosure. In certain embodiments, the reduction is seen 12 months after administration of the present disclosure.

In certain embodiments, the amount the daily dose of Parkinson's medication (e.g., Levodopa) is reduced by 108-339 mg after administration of the present disclosure. In certain embodiments, the reduction of Parkinson's medication (e.g., Levodopa) is 108 mg. In certain embodiments, the reduction of Parkinson's medication (e.g., Levodopa) is 134 mg. In certain embodiments, the reduction of Parkinson's medication (e.g., Levodopa) is 159 mg. In certain embodiments, the reduction of Parkinson's medication (e.g., Levodopa) is 154 mg. In certain embodiments, the reduction of Parkinson's medication (e.g., Levodopa) is 208 mg. In certain embodiments, the reduction of Parkinson's medication (e.g., Levodopa) is 231 mg. In certain embodiments, the reduction of Parkinson's medication (e.g., Levodopa) is 254 mg. In certain embodiments, the reduction of Parkinson's medication (e.g., Levodopa) is 276 mg. In certain embodiments, the reduction of Parkinson's medication (e.g., Levodopa) is 298 mg. In certain embodiments, the reduction of Parkinson's medication (e.g., Levodopa) is 319 mg. In certain embodiments, the reduction of Parkinson's medication (e.g., Levodopa) is 339 mg.

In certain embodiments, a 208 mg reduction in the amount of the daily dose of Parkinson's medication (e.g., Levodopa) required by a subject to manage symptoms occurs 6 months after administration of the present disclosure at a dose volume of up to 450 µL per putamen and a total dose of $7.5 \times 10^{12}$ vector genome.

In certain embodiments, a 108 mg reduction in the amount of the daily dose of Parkinson's medication (e.g., Levodopa) required by a subject to manage symptoms occurs 12 months after administration of the present disclosure at a dose volume of up to 450 µL per putamen and a total dose of $7.5 \times 10^{12}$ vector genome.

In certain embodiments, the amount the daily dose of Parkinson's medication (e.g., Levodopa) is reduced by 339-505 mg after administration of the present disclosure. In certain embodiments, the reduction of Parkinson's medication (e.g., Levodopa) is 339 mg. In certain embodiments, the reduction of Parkinson's medication (e.g., Levodopa) is 358 mg. In certain embodiments, the reduction of Parkinson's medication (e.g., Levodopa) is 377 mg. In certain embodiments, the reduction of Parkinson's medication (e.g., Levodopa) is 396 mg. In certain embodiments, the reduction of Parkinson's medication (e.g., Levodopa) is 413 mg. In certain embodiments, the reduction of Parkinson's medication (e.g., Levodopa) is 430 mg. In certain embodiments, the reduction of Parkinson's medication (e.g., Levodopa) is 446 mg. In certain embodiments, the reduction of Parkinson's medication (e.g., Levodopa) is 462 mg. In certain embodiments, the reduction of Parkinson's medication (e.g., Levodopa) is 477 mg. In certain embodiments, the reduction of Parkinson's medication (e.g., Levodopa) is 491 mg. In certain embodiments, the reduction of Parkinson's medication (e.g., Levodopa) is 505 mg.

In certain embodiments, a 462 mg reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 477 mg reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, a 491 mg reduction in the amount of the daily dose of Parkinson's medication (e.g., Levodopa) required by a subject to manage symptoms occurs 12 months after administration of the present disclosure at a dose volume of up to 900 µL per putamen and a total dose of $1.5 \times 10^{12}$ vector genome.

In certain embodiments, the amount the daily dose of Parkinson's medication (e.g., Levodopa) is reduced by 505-606 mg after administration of the present disclosure. In certain embodiments, the reduction of Parkinson's medication (e.g., Levodopa) is 505 mg. In certain embodiments, the reduction of Parkinson's medication (e.g., Levodopa) is 518 mg. In certain embodiments, the reduction of Parkinson's medication (e.g., Levodopa) is 530 mg. In certain embodiments, the reduction of Parkinson's medication (e.g., Levodopa) is 542 mg. In certain embodiments, the reduction of Parkinson's medication (e.g., Levodopa) is 553 mg. In certain embodiments, the reduction of Parkinson's medication (e.g., Levodopa) is 563 mg. In certain embodiments, the reduction of Parkinson's medication (e.g., Levodopa) is 573 mg. In certain embodiments, the reduction of Parkinson's medication (e.g., Levodopa) is 582 mg. In certain embodiments, the reduction of Parkinson's medication (e.g., Levodopa) is 591 mg. In certain embodiments, the reduction of Parkinson's medication (e.g., Levodopa) is 599 mg. In certain embodiments, the reduction of Parkinson's medication (e.g., Levodopa) is 606 mg.

In certain embodiments, a 553 mg reduction in the amount of the daily dose of Parkinson's medication (e.g., Levodopa) required by a subject to manage symptoms occurs 6 months after administration of the present disclosure at a dose volume of up to 900 µL per putamen and a total dose of $1.5 \times 10^{12}$ vector genome.

In certain embodiments, the amount the daily dose of Parkinson's medication (e.g., Levodopa) is reduced by 606-641 mg after administration of the present disclosure. In certain embodiments, the reduction of Parkinson's medication (e.g., Levodopa) is 606 mg. In certain embodiments, the reduction of Parkinson's medication (e.g., Levodopa) is 612 mg. In certain embodiments, the reduction of Parkinson's medication (e.g., Levodopa) is 618 mg. In certain embodiments, the reduction of Parkinson's medication (e.g., Levodopa) is 623 mg. In certain embodiments, the reduction of Parkinson's medication (e.g., Levodopa) is 628 mg. In certain embodiments, the reduction of Parkinson's medication (e.g., Levodopa) is 632 mg. In certain embodiments, the reduction of Parkinson's medication (e.g., Levodopa) is 635 mg. In certain embodiments, the reduction of Parkinson's medication (e.g., Levodopa) is 637 mg. In certain embodiments, the reduction of Parkinson's medication (e.g., Levodopa) is 639 mg. In certain embodiments, the reduction of Parkinson's medication (e.g., Levodopa) is 641 mg.

In certain embodiments, a 553 mg reduction in the amount of the daily dose of Parkinson's medication (e.g., Levodopa) required by a subject to manage symptoms occurs 6 months after administration of the present disclosure at a dose volume of up to 900 µL per putamen and a total dose of $4.5 \times 10^{12}$ vector genome.

In certain embodiments, a 553 mg reduction in the amount of the daily dose of Parkinson's medication (e.g., Levodopa) required by a subject to manage symptoms occurs 6 months after administration of the present disclosure at a dose volume of up to 900 µL per putamen and a total dose of $4.6 \times 10^{12}$ vector genome.

In certain embodiments, a 553 mg reduction in the amount of the daily dose of Parkinson's medication (e.g., Levodopa) required by a subject to manage symptoms occurs 6 months after administration of the present disclosure at a dose volume of up to 900 µL per putamen and a total dose of $4.7 \times 10^{12}$ vector genome AADC Enzyme Activity In certain embodiments, the putaminal AADC enzyme activity is increased in a subject after administration with the present disclosure. In certain embodiments, the increase is seen for at least 6 months relative to the baseline. Assessment of AADC expression and enzyme activity can be determined using positron emission tomography (PET) using [$^{18}$F]fluoro-L-dihydroxyphenylalanine (or $^{18}$F-DOPA), which reflects the capacity of AADC0 to convert levodopa to dopamine. Unless stated otherwise, putaminal AADC enzyme activity is measured relative to baseline prior to infusion of the AADC gene therapy.

In certain embodiments, the putaminal AADC enzyme activity is increased by 10-20% in a subject after administration of the present disclosure. In certain embodiments, the increase in putaminal AADC enzyme activity is about 10%. In certain embodiments, the increase in putaminal AADC enzyme activity is about 11%. In certain embodiments, the increase in putaminal AADC enzyme activity is about 12%. In certain embodiments, the increase in putaminal AADC enzyme activity is about 13%. In certain embodiments, the increase in putaminal AADC enzyme activity is about 14%. In certain embodiments, the increase in putaminal AADC enzyme activity is about 15%. In certain embodiments, the increase in putaminal AADC enzyme activity is about 16%. In certain embodiments, the increase in putaminal AADC enzyme activity is about 17%. In certain embodiments, the increase in putaminal AADC enzyme activity is about 18%. In certain embodiments, the increase in putaminal AADC enzyme activity is about 19%. In certain embodiments, the increase in putaminal AADC enzyme activity is about 20%.

In certain embodiments, the putaminal AADC enzyme activity is increased by about 13% in a subject after administration of the present disclosure at a dose volume of up to 450 µL per putamen and a total dose of $7.5 \times 10^{11}$ vector genome.

In certain embodiments, the putaminal AADC enzyme activity is increased by 50-60% in a subject after administration of the present disclosure. In certain embodiments, the increase in putaminal AADC enzyme activity is about 50%. In certain embodiments, the increase in putaminal AADC enzyme activity is about 51%. In certain embodiments, the increase in putaminal AADC enzyme activity is about 52%. In certain embodiments, the increase in putaminal AADC enzyme activity is about 53%. In certain embodiments, the increase in putaminal AADC enzyme activity is about 54%. In certain embodiments, the increase in putaminal AADC enzyme activity is about 55%. In certain embodiments, the increase in putaminal AADC enzyme activity is about 56%. In certain embodiments, the increase in putaminal AADC enzyme activity is about 57%. In certain embodiments, the increase in putaminal AADC enzyme activity is about 58%. In certain embodiments, the increase in putaminal AADC enzyme activity is about 59%. In certain embodiments, the increase in putaminal AADC enzyme activity is about 60%.

In certain embodiments, the putaminal AADC enzyme activity is increased by about 56% in a subject after administration of the present disclosure at a dose volume of up to 900 µL per putamen and a total dose of $1.5 \times 10^{12}$ vector genome.

In certain embodiments, the putaminal AADC enzyme activity is increased by 70-85% in a subject after administration of the present disclosure. In certain embodiments, the increase in putaminal AADC enzyme activity is about 70%. In certain embodiments, the increase in putaminal AADC enzyme activity is about 71%. In certain embodiments, the increase in putaminal AADC enzyme activity is about 72%. In certain embodiments, the increase in putaminal AADC enzyme activity is about 73%. In certain embodiments, the increase in putaminal AADC enzyme activity is about 74%. In certain embodiments, the increase in putaminal AADC enzyme activity is about 75%. In certain embodiments, the increase in putaminal AADC enzyme activity is about 76%. In certain embodiments, the increase in putaminal AADC enzyme activity is about 77%. In certain embodiments, the increase in putaminal AADC enzyme activity is about 78%. In certain embodiments, the increase in putaminal AADC enzyme activity is about 79%. In certain embodiments, the increase in putaminal AADC enzyme activity is about 80%.

In certain embodiments, the increase in putaminal AADC enzyme activity is about 81%. In certain embodiments, the increase in putaminal AADC enzyme activity is about 82%. In certain embodiments, the increase in putaminal AADC enzyme activity is about 83%. In certain embodiments, the increase in putaminal AADC enzyme activity is about 84%. In certain embodiments, the increase in putaminal AADC enzyme activity is about 85%.

In certain embodiments, the putaminal AADC enzyme activity is increased by about 79% in a subject after administration of the present disclosure at a dose volume of up to 900 μL per putamen and a total dose of $4.5\times10^{12}$ vector genome.

In certain embodiments, the dopamine level of a subject increased after administration of the present disclosure. In certain embodiments, the amount of dopamine increased by 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, or 95-100%.

mH&Y

For the Modified Hoehn and Yahr scale: Stage 1 is unilateral disease; Stage 2.0 is bilateral disease without impairment of balance (20 month median time to transit): Stage 2.5 is mild bilateral disease with recovery on pull test (62 month median time to transit); Stage 3.0 is mild to moderate bilateral disease with some postural instability and physically independent (25 month median time to transit): Stage 4.0 is severe disability, still able to walk or stand unassisted (24 month median time to transit); and Stage 5.0 is wheelchair bound or bedridden unless aided. In certain embodiments, the unmet medical need includes an improvement in mH&Y stage for an individual patient, or improvement in an average mH&Y stage for a group of patients. In certain embodiments, the mHY stage after administration of a pharmaceutical composition of the present disclosure is reduced relative to a mHY baseline stage prior to the administration of the pharmaceutical composition. In certain embodiments, the mHY stage is reduced 6 months, 12 months, 18 months, 24 months, 30 months, 36 months, 42 months, or 48 months after administration of the pharmaceutical composition of the present disclosure. In certain embodiments, the improvement in mH&Y stage is from Stage 5.0 to Stage 4.0, Stage 5.0 to Stage 3.0, Stage 5.0 to Stage 2.5, Stage 5.0 to Stage 2.0, Stage 4.0 to Stage 3.0, Stage 4.0 to Stage 2.5, Stage 4.0 to Stage 2.0. Stage 4.0 to Stage 1.5, Stage 3.0 to Stage 2.5. Stage 3.0 to Stage 2.0, Stage 3.0 to Stage 1.5, Stage 3.0 to Stage 1.0, Stage 2.5 to Stage 2.0. Stage 2.5 to Stage 1.5, Stage 2.5 to Stage 1.0, Stage 2.0 to Stage 1.5, Stage 2.0 to Stage 1.0, or Stage 1.5 to Stage 1.0. In certain embodiments, the improvement relates to 20 months, 49 months, 82 months, 87 months, 107 months, 111 months, 131 months, or any value therebetween of improvement in disease progression under the mH&Y scale.

UDysRS and Misc

In certain embodiments, the unmet medical need includes an improvement in dyskinesia as assessed using the Unified Dyskinesia Rating Scale (UDysRS) or Hauser motor diaries. In certain embodiments, the unmet medical need includes improvement in required dosage of other PD medications, measured as levodopa and levodopa equivalent dose. In certain embodiments, the unmet medical need includes improvement in patient reaction to dosage of other PD medications, including levodopa. In certain embodiments, the unmet medical need includes improvement in response to IV levodopa assessment after the gene transfer procedure. In certain embodiments, the unmet medical need includes improvement in mood as assessed using the BDI-II. In certain embodiments, the unmet medical need includes improvement in cognitive function as assessed using the Montreal Cognitive Assessment (MoCA) and MDRS-2. In certain embodiments, the unmet medical need includes improvement in compulsive behaviors as assessed using the Questionnaire for Impulsive-Compulsive Disorders in Parkinson's Disease-Rating Scale (QUIP-RS). In certain embodiments, the unmet medical need includes improvement in sleep quality and disturbance as assessed using the Parkinson's Disease Sleep Scale 2 (PDSS-2).

In certain embodiments, the unmet medical need includes improvement Quality of life as assessed using the Parkinson's Disease Questionnaire (PDQ39), Schwab and England scale, Clinical Global Impression (CGI), or Patient Global Impression (PGI). In certain embodiments, the unmet medical need includes improvement in rigidity, and/or resting tremor. In certain embodiments, the unmet medical need includes improvement in disabling motor complications. In certain embodiments, the unmet medical need includes improvement in putamenal coverage upon administration, such as putamenal coverage of more than 50%. In certain embodiments, the unmet medical need includes improved AADC expression and activity in the putamen, as determined using positron emission tomography (PET) using [$^{18}$F] fluoro-L-dihydroxyphenylalanine ($^{18}$F-DOPA). In certain embodiments, the unmet medical need includes other improvements to Parkinson's Disease patients known to those with ordinary skill in the art.

Circadian Rhythm and Sleep-Wake Cycles

Circadian rhythms are physical, mental, and behavioral changes that tend to follow a 24-hour cycle. Circadian rhythms can influence sleep-wake cycles, hormone release, body temperature and other bodily functions. Changes in the circadian rhythm can cause conditions and/or disorder such as, but not limited to sleep disorders (e.g., insomnia), depression, bipolar disorder, seasonal affective disorder, obesity and diabetes.

In certain embodiments, the AAV particles described herein may be used to treat insomnia.

The sleep-wake cycle comprises periods of sleep and periods of wake. Generally, in a 24-hour period the total hours of sleep are less than the total hours of wakefulness. In certain embodiments, the sleep-wake cycle comprises 7-9 hours of sleep and 15-17 hours of wakefulness. In certain embodiments, the sleep-wake cycle comprises 8 hours of sleep and 16 hours of wakefulness. In certain embodiments, the sleep-wake cycle comprises 8-10 hours of sleep and 14-16 hours of wakefulness.

In certain embodiments, the sleep-wake cycle of a subject is improved by administering to the subject the AAV particles described herein.

In certain embodiments, the sleep-wake cycle of a subject is regulated by administering to the subject the AAV particles described herein. In certain embodiments, the regulation may be the correction of more periods of sleep occurring at night and less periods of sleep occurring In certain embodiments, the sleep-wake cycle of a subject administered the AAV particles described herein improves as compared to the sleep-wake cycle of the subject prior to administration of the AAV particles. In certain embodiments, the subject has an increased period of sleep and a decreased period of wakefulness. In certain embodiments, the subject has a decreased period of sleep and an increased period of wakefulness.

In certain embodiments, the sleep-wake cycle of a subject administered the AAV particles described herein is regulated as compared to the sleep-wake cycle of the subject prior to administration of the AAV particles. In certain embodiments, the length of the periods of sleep and the periods of wakefulness may be about the same (e.g., +/−1 hour) for at least 2 days. In certain embodiments, the length of the periods of sleep and the periods of wakefulness if a 24 hours period may be within 10 minutes, 15 minutes, 20 minutes, 25 minutes, 30 minutes, 35 minutes, 40 minutes, 45 minutes, 50 minutes, 55 minutes, 1 hour, 1.5 hours, or 2 hours of the previous 24 hour period.

In certain embodiments, the amount of rapid eye movement (REM) sleep a subject experiences in a 24-hour period is altered after the subject is administered the AAV particles described herein. REM sleep is generally considered an active period of sleep marked by intense brain activity where brain waves are fast and desynchronized. An adult, on average, spends about 20-25% of their total daily sleep period in REM sleep. In certain embodiments, the amount of REM sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of REM sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. In certain embodiments, the amount of REM sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of REM sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In certain embodiments, the amount of non-REM (NREM) sleep a subject experiences in a 24-hour period is altered after the subject is administered the AAV particles described herein. NREM sleep is generally characterized by a reduction in physiological activity since as the brain waves, measured by EEG, get slower and have greater amplitude. NREM has four stages: Stage 1 is the time of drowsiness or transition from being awake to falling asleep where the brain waves and muscle activity begin to slow; Stage 2 is a period of light sleep during which eye movements stop and brain waves become slower with occasional bursts of rapid waves (sometimes called sleep spindles); Stage 3 and Stage 4 (collectively referred to as slow wave sleep) are characterized by the presence of slow brain waves (delta waves) interspersed with smaller faster waves where there are no eye movements. An adult, on average, spends about 75-80% of their total daily sleep period in NREM sleep with about half of their total daily sleep time in NREM stage 2 sleep.

In certain embodiments, the amount of NREM sleep a subject experiences is altered after the subject is administered the AAV particles described herein. In certain embodiments, the amount of NREM sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. In certain embodiments, the amount of NREM sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM sleep is increased by 1-5%, 1-10%, 5-10%, 5-15%, 10-15%, 15-20%, 15-25%, 20-25%, 20-30%, 20-30%, 25-30%, 25-35%, 30-35%, 30-40%, 35-40%, 40-50% or 40-60%.

In certain embodiments, the amount of NREM Stage 1 sleep a subject experiences is altered after the subject is administered the AAV particles described herein. In certain embodiments, the amount of NREM Stage 1 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM Stage 1 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. In certain embodiments, the amount of NREM Stage 1 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM Stage 1 sleep is increased by 1-50, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In certain embodiments, the amount of NREM Stage 2 sleep a subject experiences is altered after the subject is administered the AAV particles described herein. In certain embodiments, the amount of NREM Stage 2 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM Stage 2 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. In certain embodiments, the amount of NREM Stage 2 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM Stage 2 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In certain embodiments, the amount of NREM Stage 3 and 4 sleep a subject experiences is altered after the subject is administered the AAV particles described herein. In certain embodiments, the amount of NREM Stage 3 and 4 sleep is decreased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM Stage 3 and 4 sleep is decreased by 1-10%, 5-10%, 5-15%, 10-15%, 15-20%, 15-25%, 20-25%, 20-30%, 25-30%, 25-35%, 30-35%, 30-40%, 35-40%, 40-50% or 40-60%. In certain embodiments, the amount of NREM Stage 3 and 4 sleep is increased by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65% or more than 65%. In certain embodiments, the amount of NREM Stage 3 and 4 sleep is increased by 1-5%, 1-10%, 5-10%, 5-15%, 10-15%, 15-20%, 15-25%, 20-25%, 20-30%, 25-30%, 25-35%, 30-35%, 30-40%, 35-40%, 40-50% or 40-60%.

In certain embodiments, periods of NREM and REM cycles are more consistent in a subject after the subject is administered the AAV particles described herein. Generally NREM and REM cycles alternate every 90 to 110 minutes four to six times per night.

RMAT

In certain embodiments, the disclosure provides therapeutic agents and treatments which are Regenerative Medicine Therapies (RMAT). A regenerative medicine therapy is a regenerative therapy which is intended to treat, modify, reverse, or cure a serious or life-threatening disease or condition, and which has the potential to address unmet medical needs for such disease or condition (as supported by preliminary clinical evidence). In certain embodiments, the serious or life-threatening disease or condition is a CNS Disease. In certain embodiments, the serious or life-threatening disease or condition is Parkinson's Disease. In certain embodiments, the unmet medical need includes a one-time administrations of polynucleotides encoding AADC which treat, modify, reverse, or cure the disease or condition. In certain embodiments, the unmet medical need includes a one-time administrations of polynucleotides encoding AADC to a patient in a singular procedure which takes less than 9 hours, less than 8 hours, less than 7 hours, less than 6 hours, less than 5 hours, or less than 4 hours. In certain embodiments, the unmet medical need includes a one-time administrations of polynucleotides encoding AADC to a patient which is well-tolerated with no vector-related serious adverse events (SAEs). In certain embodiments, the unmet medical need includes a robust and durable improvement in motor function in a treated patient. In certain embodiments, the unmet medical need includes a substantial reduction in use of daily oral levodopa and other Parkinson's disease medications. In certain embodiments, the unmet medical need includes a substantial improvement in reaction to IV levodopa and other Parkinson's disease medications. In certain embodiments, the unmet medical need includes an improvement in motor function in both OFF and ON medication states, as assessed using the Stand-Walk-Sit test, Modified Hoehn and Yahr (mH&Y) scale (OFF medication state only), UPDRS, or Objective Parkinson's Disease Measurement (OPDM) Dexterity.

V. Kits and Devices

Kits

In certain embodiments, the disclosure provides a variety of kits for conveniently and/or effectively carrying out methods of the present disclosure. Typically, kits will comprise sufficient amounts and/or numbers of components to allow a user to perform multiple treatments of a subject(s) and/or to perform multiple experiments.

Any of the AAV particles of the present disclosure may be comprised in a kit. In some embodiments, kits may further include reagents and/or instructions for creating and/or synthesizing compounds and/or compositions of the present disclosure. In some embodiments, kits may also include one or more buffers. In some embodiments, kits of the disclosure may include components for making protein or nucleic acid arrays or libraries and thus, may include, for example, solid supports.

In some embodiments, kit components may be packaged either in aqueous media or in lyophilized form. The container means of the kits will generally include at least one vial, test tube, flask, bottle, syringe or other container means, into which a component may be placed, and preferably, suitably aliquoted. Where there is more than one kit component, (labeling reagent and label may be packaged together), kits may also generally contain second, third or other additional containers into which additional components may be separately placed. In some embodiments, kits may also comprise second container means for containing sterile, pharmaceutically acceptable buffers and/or other diluents. In some embodiments, various combinations of components may be comprised in one or more vial. Kits of the present disclosure may also typically include means for containing compounds and/or compositions of the present disclosure, e.g., proteins, nucleic acids, and any other reagent containers in close confinement for commercial sale. Such containers may include injection or blow-molded plastic containers into which desired vials are retained.

In some embodiments, kit components are provided in one and/or more liquid solutions. In some embodiments, liquid solutions are aqueous solutions, with sterile aqueous solutions being particularly preferred. In some embodiments, kit components may be provided as dried powder(s). When reagents and/or components are provided as dry powders, such powders may be reconstituted by the addition of suitable volumes of solvent. In some embodiments, it is envisioned that solvents may also be provided in another container means. In some embodiments, labeling dyes are provided as dried powders. In some embodiments, it is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the disclosure. In such embodiments, dye may then be resuspended in any suitable solvent, such as DMSO.

In some embodiments, kits may include instructions for employing kit components as well the use of any other reagent not included in the kit. Instructions may include variations that may be implemented.

Devices

In some embodiments, AAV particles of the present disclosure may be combined with, coated onto or embedded in a device. Devices may include, but are not limited to stents, pumps, and/or other implantable therapeutic device. Additionally, AAV particles may be delivered to a subject while the subject is using a compression device such as, but not limited to, a compression device to reduce the chances of deep vein thrombosis (DVT) in a subject.

The present disclosure provides for devices which may incorporate AAV particles. These devices contain in a stable formulation the AAV particles which may be immediately delivered to a subject in need thereof, such as a human patient.

Devices for administration may be employed to deliver the AAV particles of the present disclosure according to single, multi- or split-dosing regimens taught herein.

Method and devices known in the art for multi-administration to cells, organs and tissues are contemplated for use in conjunction with the methods and compositions disclosed herein as embodiments of the present disclosure. These include, for example, those methods and devices having multiple needles, hybrid devices employing for example lumens or catheters as well as devices utilizing heat, electric current or radiation driven mechanisms.

In some embodiments, AAV particles of the present disclosure may be delivered using a device such as, but not limited to, a stent, a tube, a catheter, a pipe, a straw, needle and/or a duct. Methods of using these devices are described herein and are known in the art.

In certain embodiments, the AAV particles of the present disclosure may be administered to a subject using delivery systems which integrate image guided therapy and integrate imaging such as, but not limited to, laser, MRgFUS, endoscopic and robotic surgery devices.

In certain embodiments, the AAV particles of the present disclosure may be administered to a subject using the CLEARPOINT® neuro intervention system by MRI Interventions, Inc. The CLEARPOINT® neuro intervention system may be used alone or in combination with any of the other administration methods and devices described herein. The CLEARPOINT® neuro intervention system helps to provide stereotactic guidance in the placement and operation of instruments or devices during the planning and operation of neurological procedures.

In certain embodiments, the AAV particles of the present disclosure may be administered to a subject using the NEUROMATE® stereotactic robot system by Renishaw PLC. The NEUROMATE® V system may be used alone or in combination with any of the other administration methods and devices described herein. In certain embodiments, the NEUROMATE® system may be used with head holders, CT image localizers, frame attachments, remote controls and software.

In certain embodiments, the AAV particles of the present disclosure may be administered to a subject using the Elekta MICRODRIVE™ device by Elekta AB. The MICRODRIVE™ device may be used alone or in combination with any of the other administration methods and devices described herein. In certain embodiments, the MICRODRIVE™ device may be used to position electrodes (e.g., for micro electrode recording (MER), macro stimulation and deep brain stimulation (DBS) electrode implantation), implantation of catheters, tubes or DBS electrodes using cross-hair and A-P holders to verify position, biopsies, injections and aspirations, brain lesioning, endoscope guidance and GAMMA KNIFE® radiosurgery.

In certain embodiments, the AAV particles of the present disclosure may be administered to a subject using the AXIIIS® stereotactic miniframe by MONTERIS® Medical, Inc. The AXIIIS® stereotactic miniframe may be used alone or in combination with any of the other administration methods and devices described herein. The AXIIIS® stereotactic miniframe is a trajectory alignment device which may be used for laser coagulation, biopsies, catheter placement, electrode implant, endoscopy, and clot evacuation. The miniframe allows for 360 degree interface and provides access to multiple intracranial targets with a simple adjustment. Further, the miniframe is compatible with MRI.

In certain embodiments, the AAV particles of the present disclosure may be administered to a subject using the INTEGRA™ CRW® system by Integra LifeSciences Corporation. The INTEGRA™ CRW® system may be used alone or in combination with any of the other administration methods and devices described herein. The CRW® system may be used for various applications such as, but not limited to, stereotactic surgery, microsurgery, catheterization and biopsy. The CRW® system is designed to provide accuracy to those who use the system (e.g., thumb lock screws, Vernier scaling, double bolt fixation, and a solid frame).

In certain embodiments, the AAV particles of the present disclosure may be administered to a subject using the EPOCH® solution system by Stereotaxis, Inc. which may include the NIOBE® ES magnetic navigation system, the VDRIVE® robotic navigation system and/or the ODYSSEY® information solution (all by Stereotaxis, Inc.). The EPOCH® 9 solution system may be used alone or in combination with any of the other administration methods and devices described herein. In certain embodiments, the NIOBE® ES magnetic navigation system may be used to accurately contact a subject. In certain embodiments the NIOBE® ES magnetic system may be used with the VDRIVE® robotic navigation system to provide precise movement and stability.

In certain embodiments, the AAV particles of the present disclosure may be administered to a subject using a NeuroStation workstation which uses frameless stereotactic methods to provide image-guidance for applications such as, but not limited to, surgical planning, biopsies, craniotomies, endoscopy, intra-operative ultrasound and radiation therapy.

In certain embodiments, the AAV particles of the present disclosure may be administered to a subject using a robotic stereotaxis system such as, but not limited to the device described in U.S. Pat. No. 5,078,140, the contents of which are herein incorporated by reference in its entirety. The robotic arm of the device may be used to precisely orient the surgical tools or other implements used to conduct a procedure.

In certain embodiments, the AAV particles of the present disclosure may be administered to a subject using an automatic delivery system such as, but not limited to the device described in U.S. Pat. No. 5,865,744, the contents of which are herein incorporated by reference in its entirety. Based on the images gathered by the delivery system, the computer adjusts the administration of the needle to be the appropriate depth for the particular subject.

In certain embodiments, the AAV particles of the present disclosure may be administered to a subject who is simultaneously using during administration, and/or uses for a period of time before and/or after administration a compression device such as, but not limited to, a compression device which reduces the chances of deep vein thrombosis (DVT) in a subject. The compression device may be used for at least 5 minutes, 15 minutes, 30 minutes, 45 minutes, 1 hour, 2 hours, 3 hours, 4 hours, 5 hours, 6 hours, 7 hours, 8 hours, or more than 8 hours before a subject is administered the AAV particles. The compression device may be used for at least 5 minutes, 15 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 2 weeks, 3 weeks or a month after the AAV particles are administered. In certain embodiments, the compression device is used simultaneously during the procedure of the delivery of the AAV particles. In certain embodiments, the compression device is used before the administration of the AAV particles. In certain embodiments, the compression device is used after administration of the AAV particles. In certain embodiments, the compression device is used before, during and after administration of the AAV particles.

Non-limiting examples, of compression devices include ActiveCare+S.F.T. intermittent compression device, ActiveCare+S.F.T pneumatic compression device, DVTlite's Venowave, KCI system compression pump, Aircast VenaFlow system, SCD Express Compression System or Bio Compression Systems, Inc. pneumatic compression therapy equipment (e.g., the pump may be selected from Model SC-2004, Model SC-2004-FC, Model SC-3004, Model SC-3004-FC, Model SC-2008, Model SC-2008-DL, Model SC-3008-T, the BioCryo system, Model IC-BAP-DL or multi-flo DVT combo IC_1545-DL and the garment used with the pump may be a 4 chamber, 8 chamber, BioCryo, Multi-Flo or BioArterial garment).

In certain embodiments, the AAV particles may delivered to a subject using a device to deliver the AAV particles and a head fixation assembly. The head fixation assembly may be, but is not limited to, any of the head fixation assemblies sold by MRI interventions. In certain embodiments, the head fixation assembly may be any of the assemblies described in U.S. Pat. Nos. 8,099,150, 8,548,569 and 9,031,636 and International Patent Publication Nos. WO201108495 and WO2014014585, the contents of each of which are incorporated by reference in their entireties. A head fixation assembly may be used in combination with an MRI compatible drill such as, but not limited to, the MRI compatible drills described in International Patent Publication No. WO2013181008 and US Patent Publication No. US20130325012, the contents of which are herein incorporated by reference in its entirety.

In certain embodiments, the AAV particles may be delivered using a method, system and/or computer program for positioning apparatus to a target point on a subject to deliver the AAV particles. In certain embodiments, the method, system and/or computer program may be the methods, systems and/or computer programs described in U.S. Pat. No. 8,340,743, the contents of which are herein incorporated by reference in its entirety. The method may include: determining a target point in the body and a reference point, wherein the target point and the reference point define a planned trajectory line (PTL) extending through each; determining a visualization plane, wherein the PTL intersects the visualization plane at a sighting point: mounting the guide device relative to the body to move with respect to the PTL, wherein the guide device does not intersect the visualization plane; determining a point of intersection (GPP) between the guide axis and the visualization plane; and aligning the GPP with the sighting point in the visualization plane.

In certain embodiments, the AAV particles may be delivered to a subject using a convention-enhanced delivery device. Non-limiting examples of targeted delivery of drugs using convection are described in US Patent Publication Nos. US20100217228, US20130035574 and US20130035660 and International Patent Publication No. WO2013019830 and WO2008144585, the contents of each of which are herein incorporated by reference in their entireties.

In certain embodiments, a subject may be imaged prior to, during and/or after delivery of the AAV particles. The imaging method may be a method known in the art and/or described herein, such as but not limited to, magnetic resonance imaging (MRI). Images can be captured and analyzed with MP-RAGE and dcMPRAGE. In certain embodiments, imaging may be used to assess therapeutic effect. In certain embodiments, imaging may be used for assisted delivery of AAV particles.

In certain embodiments, the AAV particles may be delivered using an MRI-guided device. Non-limiting examples of MRI-guided devices are described in U.S. Pat. Nos. 9,055,884, 9,042,958, 8,886,288, 8,768,433, 8,396,532, 8,369,930, 8,374,677 and 8,175,677 and US Patent Application No. US20140024927 the contents of each of which are herein incorporated by reference in their entireties. In certain embodiments, the MRI-guided device may be able to provide data in real time such as those described in U.S. Pat. Nos. 8,886,288 and 8,768,433, the contents of each of which is herein incorporated by reference in its entirety. In certain embodiments, the MRI-guided device or system may be used with a targeting cannula such as the systems described in U.S. Pat. Nos. 8,175,677 and 8,374,677, the contents of each of which are herein incorporated by reference in their entireties. As yet another non-limiting example, the MRI-guided device includes a trajectory guide frame for guiding an interventional device as described, for example, in U.S. Pat. No. 9,055,884 and US Patent Application No. US20140024927, the contents of each of which are herein incorporated by reference in their entireties.

In certain embodiments the AAV particles may be delivered using an MRI-compatible tip assembly. Non-limiting examples of MRI-compatible tip assemblies are described in US Patent Publication No. US20140275980, the contents of which is herein incorporated by reference in its entirety.

In certain embodiments, the AAV particles may be delivered using a cannula which is MRI-compatible. Non-limiting examples of MRI-compatible cannulas include those taught in International Patent Publication No. WO2011130107, the contents of which are herein incorporated by reference in its entirety.

In certain embodiments, the AAV particles may be delivered using a catheter which is MRI-compatible. Non-limiting examples of MRI-compatible catheters include those taught in International Patent Publication No. WO2012116265, U.S. Pat. No. 8,825,133 and US Patent Publication No. US20140024909, the contents of each of which are herein incorporated by reference in their entireties.

In certain embodiments, the AAV particles may be delivered using a device with an elongated tubular body and a diaphragm as described in US Patent Publication Nos. US20140276582 and US20140276614, the contents of each of which are herein incorporated by reference in their entireties.

In certain embodiments, the AAV particles may be delivered using an MRI compatible localization and/or guidance system such as, but not limited to, those described in US Patent Publication Nos. US20150223905 and US20150230871, the contents of each of which are herein incorporated by reference in their entireties. In certain embodiments, the MRI compatible localization and/or guidance systems may comprise a mount adapted for fixation to a patient, a targeting cannula with a lumen configured to attach to the mount so as to be able to controllably translate in at least three dimensions, and an elongate probe configured to snugly advance via slide and retract in the targeting cannula lumen, the elongate probe comprising at least one of a stimulation or recording electrode.

In certain embodiments, the AAV particles may be delivered to a subject using a trajectory frame as described in US Patent Publication Nos. US20150031982 and US20140066750 and International Patent Publication Nos. WO2015057807 and WO2014039481, the contents of each of which are herein incorporated by reference in their entireties.

In certain embodiments, the AAV particles may be delivered to a subject using a gene gun.

VI. Definitions

At various places in the present specification, substituents of compounds of the present disclosure are disclosed in groups or in ranges. It is specifically intended that the present disclosure include each and every individual subcombination of the members of such groups and ranges.

About: As used herein, the term "about" means +/−10% of the recited value.

Activity: As used herein, the term "activity" refers to the condition in which things are happening or being done. Compositions described herein may have activity and this activity may involve one or more biological events.

Adeno-associated virus: The term "adeno-associated virus" or "AAV" as used herein refers to members of the dependovirus genus comprising any particle, sequence, gene, protein, or component derived therefrom. The term "AAV particle" as used herein comprises a capsid and a polynucleotide. The AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Administered in combination: As used herein, the term "administered in combination" or "combined administration" means that two or more agents (e.g., AAV) are administered to a subject at the same time or within an interval such that there may be an overlap of an effect of each agent on the patient and/or the subject is at some point in time simultaneously exposed to both. In some embodiments, they are administered within about 60, 30, 15, 10, 5, or 1 minutes of one another or within about 24 hours, 12 hours, 6 hours, 3 hours of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biologically active: As used herein, the phrase "biologically active" refers to a characteristic of any substance (e.g., AAV) that has activity in a biological system and/or organism. For instance, a substance that, when administered to an organism, has a biological effect on that organism, is considered to be biologically active. In particular embodiments, a polynucleotide of the present disclosure may be considered biologically active if even a portion of the polynucleotides is biologically active or mimics an activity considered biologically relevant.

Biological system: As used herein, the term "biological system" refers to a group of organs, tissues, cells, intracellular components, proteins, nucleic acids, molecules (including, but not limited to biomolecules) that function together to perform a certain biological task within cellular membranes, cellular compartments, cells, tissues, organs, organ systems, multicellular organisms, or any biological entity. In some embodiments, biological systems are cell signaling pathways comprising intracellular and/or extracellular cell signaling biomolecules. In some embodiments, biological systems comprise growth factor signaling events within the extracellular/cellular matrix and/or cellular niches.

Biomolecule: As used herein, the term "biomolecule" is any natural molecule which is amino acid-based, nucleic acid-based, carbohydrate-based or lipid-based, and the like.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pairs in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present disclosure, the ability to substitute a T is implied, unless otherwise stated. Perfect complementarity or 100% complementarity refers to the situation in which each nucleotide unit of one polynucleotide strand can form a hydrogen bond with a nucleotide unit of a second polynucleotide strand. Less than perfect complementarity refers to the situation in which some, but not all, nucleotide units of two strands can form hydrogen bonds with each other. For example, for two 20-mers, if only two base pairs on each strand can form hydrogen bonds with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present disclosure. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide, a polynucleotide or polypeptide or may apply to a portion, region or feature thereof.

In certain embodiments, conserved sequences are not contiguous. Those skilled in the art are able to appreciate how to achieve alignment when gaps in contiguous alignment are present between sequences, and to align corresponding residues not withstanding insertions or deletions present.

In certain embodiments, conserved sequences are not contiguous. Those skilled in the art are able to appreciate how to achieve alignment when gaps in contiguous alignment are present between sequences, and to align corresponding residues not withstanding insertions or deletions present.

Delivery: As used herein, "delivery" refers to the act or manner of delivering a compound such as a parvovirus, e.g. an AAV and/or AAV compound, substance, entity, moiety, cargo or payload to a target. Such target may be a cell, tissue, organ, organism, or system (whether biological or production).

Delivery Agent: As used herein, "delivery agent" refers to any agent or substance which facilitates, at least in part, the in vivo and/or in vitro delivery of a polynucleotide and/or one or more substances (including, but not limited to a compounds and/or compositions of the present disclosure, e.g., viral particles or expression vectors) to targeted cells.

Destabilized: As used herein, the term "destabilized," "destabilize," or "destabilizing region" means a region or molecule that is less stable than a starting, reference, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance immunological detection, and the like. Detectable labels may include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Dosing regimen: As used herein, a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, upon single or multiple dose administration to a subject cell, in curing, alleviating, relieving or improving one or more symptoms of a disorder, clinical results, and, as such, an "effective amount" depends upon the context in which it is being applied. For example, in the context of administering an agent that treats Parkinson's Disease, an effective amount of an agent is, for example, an amount sufficient to achieve treatment, as defined herein, of Parkinson's Disease, as compared to the response obtained without administration of the agent.

Encapsulate: As used herein, the term "encapsulate" means to enclose, surround or encase.

Engineered: As used herein, embodiments are "engineered" when they are designed to have a feature or property, whether structural or chemical, that varies from a starting point, wild-type or native molecule. Thus, engineered agents or entities are those whose design and/or production include an act of the hand of man.

Epitope: As used herein, an "epitope" refers to a surface or region on a molecule that is capable of interacting with a biomolecule. For example, a protein may contain one or more amino acids, e.g., an epitope, which interacts with an antibody, e.g., a biomolecule. In some embodiments, when referring to a protein or protein module, an epitope may comprise a linear stretch of amino acids or a three-dimensional structure formed by folded amino acid chains.

Expression: As used herein, "expression" of a nucleic acid sequence refers to one or more of the following events: (1) production of an RNA template from a DNA sequence (e.g., by transcription): (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" includes at least one polynucleotide and/or compound and/or composition of the present disclosure (e.g., a vector, AAV particle, etc.) and a delivery agent.

Fragment: A "fragment." as used herein, refers to a contiguous portion of a whole. For example, fragments of proteins may comprise polypeptides obtained by digesting full-length protein isolated from cultured cells. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. In some embodiments, fragments of an antibody include portions of an antibody subjected to enzymatic digestion or synthesized as such.

Functional: As used herein, a "functional" biological molecule is a biological molecule and/or entity with a structure and in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is typically determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids. In many embodiments, homologous protein may show a large overall degree of homology and a high degree of homology over at least one short stretch of at least 3, 4, 5, 6, 7, 8, 9, 10, 11, 12, 13, 14, 15, 16, 17, 18, 19, 20, 25, 30, 35, 40, 45, 50 or more amino acids. In many embodiments, homologous proteins share one or more characteristic sequence elements. As used herein, the term "characteristic sequence element" refers to a motif present in related proteins. In some embodiments, the presence of such motifs correlates with a particular activity (such as biological activity).

Identity: As used herein, the term "identity" refers to the overall relatedness between polymeric molecules, e.g., between oligonucleotide and/or polynucleotide molecules (e.g. DNA molecules and/or RNA molecules) and/or between polypeptide molecules. Calculation of the percent identity of two polynucleotide sequences, for example, may be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology. Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference in its entirety. For example, the percent identity between two nucleotide sequences can be determined, for example using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988): incorporated herein by reference in its entirety. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

Inhibit expression of a gene: As used herein, the phrase "inhibit expression of a gene" means to cause a reduction in the amount of an expression product of the gene. The expression product may be RNA transcribed from the gene (e.g. mRNA) or a polypeptide translated from mRNA transcribed from the gene. Typically, a reduction in the level of mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated" but carries with it the inference separation was carried out by the hand of man. In certain embodiments, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art. In some embodiments, isolation of a substance or entity includes disruption of chemical associations and/or bonds. In some embodiments, isolation includes only the separation from components with which the isolated substance or entity was previously combined and does not include such disruption.

Modified: As used herein, the term "modified" refers to a changed state or structure of a molecule or entity of the disclosure as compared with a parent or reference molecule or entity. Molecules may be modified in many ways including chemically, structurally, and functionally. In some embodiments, compounds and/or compositions of the present disclosure are modified by the introduction of non-natural amino acids, or non-natural nucleotides.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids). In embodiments wherein mutations comprise the addition and/or substitution of amino acids and/or nucleotides, such additions and/or substitutions may comprise 1 or more amino acid and/or nucleotide residues and may include modified amino acids and/or nucleotides.

Naturally occurring: As used herein, "naturally occurring" means existing in nature without artificial aid or involvement of the hand of man Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid: As used herein, the term "nucleic acid", "polynucleotide" and "oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

Off-target: As used herein, "off target" refers to any unintended effect on any one or more target, gene and/or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid.

Patient: As used herein, "patient" refers to a subject who may seek or be in need of treatment, requires treatment, is receiving treatment, will receive treatment, or a subject who is under care by a trained professional for a particular disease or condition, such as for example Parkinson's Disease.

Payload: As used herein, "payload" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid.

Payload construct: As used herein, "payload construct" is one or more polynucleotide regions encoding or comprising a payload that is flanked on one or both sides by an inverted terminal repeat (ITR) sequence. The payload construct is a template that is replicated in a viral production cell to produce a viral genome.

Payload construct vector: As used herein, "payload construct vector" is a vector encoding or comprising a payload construct, and regulatory regions for replication and expression in bacterial cells.

Payload construct expression vector: As used herein, a "payload construct expression vector" is a vector encoding or comprising a payload construct and which further comprises one or more polynucleotide regions encoding or comprising components for viral expression in a viral replication cell.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers to any ingredient other than the compounds and/or active agents (e.g. as described herein) present in pharmaceutical compositions and having the properties of being substantially nontoxic and non-inflammatory in a subject such as a patient. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspension or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein. As used herein, "pharmaceutically acceptable salts" refers to derivatives or forms of the disclosed compounds wherein the parent compound is modified by converting an existing acid or base moiety to its salt form (e.g., as generated by reacting the free base group with a suitable organic acid). Examples of pharmaceutically acceptable salts include, but are not limited to, mineral or organic acid salts of basic residues such as amines: alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. In some embodiments a pharmaceutically acceptable salt of the present disclosure can be synthesized salt prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile am preferred. Lists of suitable salts am found in Remington's Pharmaceutical Sciences, 17th ed., Mack Publishing Company. Easton, Pa., 1985, p. 1418, Pharmaceutical Salts: Properties, Selection, and Use, P. H. Stahl and C. G. Wenmuth (eds.), Wiley-VCH, 2008, and Berge et al., Journal of Pharmaceutical Science, 66, 1-19 (1977), each of which is incorporated herein by reference in its entirety.

Pharmaceutically acceptable solvate: The term "pharmaceutically acceptable solvate," as used herein, refers to a crystalline form of a compound of the disclosure wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates). N-methylpyrrolidinone (NMP), dimethyl sulfoxide (DMSO). N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition: partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition, such as for example Parkinson's Disease.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand, replicate or increase or cause to grow, expand, replicate or increase. "Proliferative" means having the ability to proliferate. "Anti-proliferative" means having properties counter to or in opposition to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest: As used herein, the terms "proteins of interest" or "desired proteins" include those provided herein and fragments, mutants, variants, and alterations thereof.

Purified: As used herein, "purify," "purified," "purification" means to make substantially pure or clear from unwanted components, material defilement, admixture or imperfection. "Purified" refers to the state of being pure. "Purification" refers to the process of making pure. In some embodiments, a sample can be purified using ion exchange chromotography, ultracentrifugation, or a combination thereof.

Region: As used herein, the term "region" refers to a zone or general area. In some embodiments, when referring to a protein or protein module, a region may comprise a linear sequence of amino acids along the protein or protein module or may comprise a three-dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini. N-termini refer to the end of a protein comprising an amino acid with a free amino group. C-termini refer to the end of a protein comprising an amino acid with a free carboxyl group. N- and/or C-terminal regions may therefore comprise the N- and/or C-termini as well as surrounding amino acids. In some embodiments, N- and/or C-terminal regions comprise from about 3 amino acid to about 30 amino acids, from about 5 amino acids to about 40 amino acids, from about 10 amino acids to about 50 amino acids, from about 20 amino acids to about 100 amino acids and/or at least 100 amino acids. In some embodiments, N-terminal regions may comprise any length of amino acids that includes the N-terminus, but does not include the C-terminus. In some embodiments, C-terminal regions may comprise any length of amino acids, which include the C-terminus, but do not comprise the N-terminus.

In some embodiments, when referring to a polynucleotide, a region may comprise a linear sequence of nucleic acids along the polynucleotide or may comprise a three-dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and 3' termini, 5' termini refer to the end of a polynucleotide comprising a nucleic acid with a free phosphate group. 3' termini refer to the end of a polynucleotide comprising a nucleic acid with a free hydroxyl group. 5' and 3' regions may therefore comprise the 5' and 3' termini as well as surrounding nucleic acids. In some embodiments, 5' and 3' terminal regions comprise from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In some embodiments, 5' regions may comprise any length of nucleic acids that includes the 5' terminus, but does not include the 3' terminus. In some embodiments, 3' regions may comprise any length of nucleic acids, which include the 3' terminus, but does not comprise the 5' terminus.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally. e.g., by DNA replication and transcription of DNA, respectively, or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interference: As used herein, the term "RNA interference" or "RNAi" refers to a sequence specific regulatory mechanism mediated by RNA molecules which results in the inhibition or interference or "silencing" of the expression of a corresponding protein-coding gene.

Sample: As used herein, the term "sample" refers to an aliquot, subset or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. In some embodiments, a sample is or comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Self-complementary viral particle: As used herein, a "self-complementary viral particle" is a particle comprised of at least two components, a protein capsid and a polynucleotide sequence encoding a self-complementary genome enclosed within the capsid.

Sense strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the siRNA strand.

Signal Sequences: As used herein, the phrase "signal sequences" refers to a sequence which can direct the transport or localization.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Small short interfering RNA: As used herein, the term "small/short interfering RNA" or "siRNA" refers to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, the subject may be an infant, neonate, or a child under the age of 12 years old. In some embodiments, the subject may be in utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term typically means within about 2 seconds.

Suffering from: An individual who is "suffering from" a disease, disorder, and/or condition has been diagnosed with or displays one or more symptoms of a disease, disorder, and/or condition such as for example Parkinson's Disease.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present disclosure may be chemical or enzymatic.

Targeting: As used herein, "targeting" means the process of design and selection of nucleic acid sequence that will hybridize to a target nucleic acid and induce a desired effect.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition such as for example Parkinson's Disease. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hour period. It may be administered as a single unit dose.

Transfection: As used herein, the term "transfection" refers to methods to introduce exogenous nucleic acids into a cell. Methods of transfection include, but are not limited to, chemical methods, physical treatments and cationic lipids or mixtures.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition such as for example Parkinson's Disease.

Unmodified: As used herein, "unmodified" refers to any substance, compound or molecule prior to being changed in any way. Unmodified may, but does not always, refer to the wild type or native form of a biomolecule or entity. Molecules or entities may undergo a series of modifications whereby each modified substance, compound, molecule or entity may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly and may be based on and/or may comprise adeno-associated virus (AAV) parent or reference sequence. Such parent or reference AAV sequences may serve as an original, second, third or subsequent sequence for engineering vectors. In non-limiting examples, such parent or reference AAV sequences may comprise any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral construct vector: As used herein, a "viral construct vector" is a vector which comprises one or more polynucleotide regions encoding or comprising Rep and or Cap protein.

Viral construct expression vector: As used herein, a "viral construct expression vector" is a vector which comprises one or more polynucleotide regions encoding or comprising Rep and or Cap that further comprises one or more polynucleotide regions encoding or comprising components for viral expression in a viral replication cell.

Viral genome: As used herein, a "viral genome" is a polynucleotide encoding at least one inverted terminal repeat (ITR), at least one regulatory sequence, and at least one payload. The viral genome is derived by replication of a payload construct from the payload construct expression vector. A viral genome encodes at least one copy of the payload construct.

VII. Equivalents and Scope

Those skilled in the art will recognize, or be able to ascertain using no more than routine experimentation, many equivalents to the specific embodiments in accordance with the disclosure described herein.

In the claims, articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the terms "comprising" and "including" are intended to be open and permit, but do not require, the inclusion of additional elements or steps. When the term "comprising" is used herein, the term "consisting of" is thus also encompassed and disclosed.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used.

Where ranges are given, endpoints are included (including disclosures where a range is said to be "between" endpoint values). Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this disclosure by reference, even if not expressly stated in the citation. In case of conflicting statements of a cited source and the present disclosure, the statement in the present disclosure shall control.

Section and table headings are not intended to be limiting. In addition, the materials, methods, and examples presented herein are illustrative of certain embodiments only and not intended to be limiting.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

EXAMPLES

Example 1. Design of Payloads: AADC Polynucleotides

AADC polynucleotides are designed to comprise at a minimum a nucleic acid sequence encoding an AADC protein.

Once designed, the sequence is engineered or synthesized or inserted in a plasmid or vector and administered to a cell or organism. Suitable plasmids or vectors are any which transduce or transfect the target cell.

Adeno-associated viral (AAV) particles may be used.

Administration results in the processing of the AADC polynucleotide to generate the AADC protein which alters the etiology of the disease, in this case Parkinson's Disease.

In one non-limiting example, plasmids containing an AADC polynucleotide of the disclosure have a CMV promoter and encode AADC. In some embodiments the open reading frame of the AADC protein mRNA is codon optimized.

AADC polynucleotides, listed ITR to ITR, suitable for use in a AAV particles include those in Table 2.

TABLE 2

| ITR to ITR AADC polynucleotides | |
|---|---|
| Construct | SEQ ID NO |
| AADC Polynucleotide | 979 |

The start and stop positions of various regions of the AADC polynucleotides as given are relative to the ITR to ITR AADC polynucleotides described in Table 2. In Table 3, ITR is inverted terminal repeat, MCS is multiple cloning site, CMV is cytomegalovirus, Ie1 is immediate-early 1, hBglobin is human beta-globin, AADC is region encoding the AADC polypeptide, and poly(A) is the polyadenylation signal.

TABLE 3

| Component regions of AADC polynucleotides | | | | |
|---|---|---|---|---|
| | AADC Polynucleotide (SEQ ID NO: 979) | | | |
| Region | Start | Stop | Length of Region | SEQ ID NO of region |
| 5' ITR | 1 | 141 | 141 | 980 |
| MCS | 189 | 206 | 18 | 981 |
| CMV enhancer | 213 | 515 | 303 | 982 |
| CMV promoter | 516 | 719 | 204 | 983 |
| Ie1 exon 1 | 734 | 867 | 134 | 984 |
| Ie1 intron partial | 868 | 899 | 32 | 985 |
| hBglobin intron 2 | 900 | 1246 | 347 | 986 |
| hBglobin exon 3 | 1247 | 1299 | 53 | 987 |
| AADC | 1338 | 2777 | 1440 | 988 |
| MCS | 2820 | 2837 | 18 | 989 |
| Poly(A) | 2838 | 3314 | 477 | 990 |
| 3' ITR | 3386 | 3526 | 141 | 991 |

Example 2. Design of AADC Polynucleotides to Treat Parkinson's Disease

AADC polynucleotides are designed to comprise at a minimum a nucleic acid sequence encoding an AADC protein.

Once designed, the sequence is engineered or synthesized or inserted in a plasmid or vector and administered to a cell or organism. Suitable plasmids or vectors are any which transduce or transfect the target cell.

Adeno-associated viral (AAV) particles may be used.

Administration results in the processing of the AADC polynucleotide to generate the AADC protein which alters the etiology of the disease, in this case Parkinson's Disease.

Example 3. Administration of AAV Particles

AAV particles are infused into the substantia nigra, and in particular, the substantia nigra pars compacta (SNpc) and ventral tegmental area (VTA) of patients having Parkinson's Disease and identified as qualified for treatment according to methods known in the art.

One method of administration contemplated for use in the methods described herein is real-time convection-enhanced delivery (RCD) of AAV particle compositions by co-infusion of gadoteridol (a magnetic resonance (MR) contrast agent) and T1 or 12 magnetic resonance imaging (MRI), which can predict areas of subsequent AADC gene expression. As described in Richardson, et al., 2011, the accuracy of cannula placement and initial infusate distribution may be safely determined by saline infusion without significantly altering the subsequent distribution of the tracer agent (Richardson, et al., 2011, Neurosurgery, 69(1):154-163). T2 RCD provides detection of intraparenchymal convection-enhanced delivery in the uninjured brain and may predict subsequent distribution of a transgene after AAV particle infusion. Subjects undergo saline infusion/T2 acquisition, immediately followed by gadoteridol infusion/T1 acquisition in the putamen and brainstem. Distribution volumes and spatial patterns are analyzed. Gadoteridol and AAV-encoded AADC are co-infused under alternating T2/T1 acquisition in the thalamus, and hyperintense areas are compared with areas of subsequent transgene expression. Ratios of distribution volume to infusion volume are expected to be similar between saline and gadoteridol RCD. Spatial overlap should correlate well between T2 and T1 images. The second infusate will follow a spatiotemporal pattern similar to that of the first, filling the target area before developing extra-target distribution. Areas of AADC expression should correlate well with areas of both T1 and T2 hyperintensity observed during RCD (Richardson, et al., 2011, Neurosurgery, 69(1):154-163).

Convection-enhanced delivery (CED) of macromolecules directly into the brain parenchyma has been known for over two decades. CED is a term that denotes the use of a pressure gradient to generate bulk flow within the brain parenchyma, i.e. convection of macromolecules within the interstitial fluid driven by infusing a solution through a cannula placed directly in the targeted structure. This method allows therapeutic agents to be homogenously distributed through large volumes of brain tissue by bypassing the blood brain barrier and surpassing simple diffusion (Richardson, et al., 2011, Stereotact. Funct. Neurosurg. 89:141-151).

Salegio, et al. recently demonstrated the distribution of nanoparticles of different sizes, including micelles (~15 nm in size), AAV (~20-25 nm) and liposomes (~65 nm), within the CNS of rodents and NHPs (Salegio et al., 2014, Frontiers in Neuroanatomy, vol. 8, article 9: pp. 1-8). Simple injections cannot engage the perivascular system, and specialized infusion cannulae are required, enabling constant pressures to be exerted at the tip of the cannula such that the interstitial hydrostatic pressure is exceeded and infusate can flow out into the tissue. Simple needles generate significant reflux; thus, reflux-resistant cannulas have been developed to counter this tendency. The advent of platforms for MRI-guided convection-enhanced infusions further refined understanding of the mechanics of perivascular flow, and it was demonstrated that perivascular distribution of liposomes was linear with respect to time, the slope of the curve was increased in myelinated regions, and cessation of infusion prevented further expansion in the volume of distribution. (Richardson, et al., 2011, Stereotact. Funct. Neurosurg. 89:141-151; Salegio et al., 2014. Frontiers in Neuroanatomy, vol. 8, article 9: pp. 1-8).

Intraparenchymal rAAV injections are known to result in robust but relatively local transduction. Such local delivery methods are advantageous when attempting gene therapy for neurological disorders that result from neuropathology that is localized to a specific anatomical region or anatomical circuitry such as in the case of Parkinson's disease. However, in treatments requiring more widespread CNS transduction, intraparenchymal injections are impractical. Treatment of neurological disorders attributable to inborn errors of metabolism and/or single-gene defects, or those that affect motor neurons of the spinal cord can require transduction of large proportions of the brain or spinal cord, respectively. Development of less invasive trans-BBB delivery methods for vectors is an extremely important endeavor. Numerous attempts to use molecules that are known to interact with various active transport mechanisms (probably receptor-mediated) to convey proteins across the BBB have been reported with varying results. Given the large number of AAV serotypes available, one or more serotypes may bind a cell-entry receptor capable of transporting the AAV capsid across the BBB (Manfredsson, et al., 2009, AAV9: a potential blood "brain barrier buster." Molecular Therapy 17(3): 403-405).

Vector and Stereotaxic Infusion

A stereotactic approach may be used to surgically deliver the AADC polynucleotides. Although individuals with AADC deficiency lack epinephrine and norepinephrine, these patients should maintain stable blood pressure and heart rates during the surgery. There should be no notable intracerebral hemorrhages in the postoperative computed tomography (CT) or MRI scans. The needle tracts, as shown on the MRI scans, should show accurate injection into the substantia nigra pars compacta (SNpc) and ventral tegmental area (VTA). The patients will be discharged from the hospital about one week after the surgery (Hwu, W. L., et al., 2012. Gene therapy for aromatic L-amino acid decarboxylase deficiency. Sci. Transl. Med Vol. 4, 134ra61).

Subjects of treatment receive the AAV-vector composition vector, safely delivered to substantia nigra pars compacta (SNpc) and ventral tegmental area (VTA) via bilateral infusions, or alternatively, intrastriatally (into the caudate nucleus and putamen), or into the subthalamic nucleus (STN), for example optionally using the FDA-approved SMARTFLOW® neuroventricular cannula (SurgiVision, Inc.) specifically designed for clinical application (including step-tipped design), with or without the aid of the CLEAR-POINT® system to help the treating neurosurgeon(s) target and observe the delivery of the therapeutic agent in the brain (See, for example, San Sebastian, et al., 2014, Mol. Ther. Methods Clin. Dev. 3: 14049; See, for example, Feng and Maguire-Zeiss, 2010, CNS Drugs 24(3):177-192).

For example, during the surgery, two target points are determined in the substantia nigra pars compacta (SNpc) and ventral tegmental area (VTA) that are sufficiently separated from each other in dorsolateral directions and identified on a magnetic resonance image. One burr hole is trepanned in each side of the cranial bone, through which the vector is injected into the two target points via the two-track insertion route. The AAV-vector-containing solution is prepared to a concentration of $1.5 \times 10^{12}$ vector genome/ml, and 50 µL per point of the solution is injected at 1 µL/min; each patient receives $3 \times 10^{11}$ vector genome of the AAV-vector construct.

Neutralizing antibody titers against AAV2 are determined by measuring β-galactosidase activities in HEK293 cells transduced with $5 \times 10^3$ vector genome/cell of AAV2 vectors expressing β-galactosidase in various dilutions of sera.

PET

The AADC expression level in the substantia nigra are assessed on PET imaging with FMT six days before surgery and at one- and six-months after gene transfer. All patients cease taking dopaminergic medications 18 hours before PET and take 2.5 mg/kg of carbidopa orally one hour before FMT injection. Subsequently, 0.12 mCi/kg of FMT in saline is infused into an antecubital vein, and a 90-minute dynamic acquisition sequence is obtained. The PET and magnetic resonance imaging data are co-registered with a fusion processing program (Syntegra Philips, Amsterdam, The Netherlands) to produce the fusion images. Radioactivities within volumes of interest drawn in the nigrostriatal pathway are calculated between 80 and 90 minutes after tracer injection. A change in nigrostriatal pathway FMT uptake from baseline to 24 weeks is assessed using the substantia nigra to striatal ratio of radioactivity.

Statistical Analysis

Values at baseline and 6 months after gene transfer are compared using Student's t-test (paired analyses). A two-sided P value <0.05 is taken to indicate significant differences. Two-way analysis of variance with Bonferroni correction of P values is used for the short-duration response to levodopa. (See, for example, Muramatsu, et al., 2010, "A phase I study of aromatic L-amino acid decarboxylase gene therapy for Parkinson's disease." Mol. Ther. 18:1731-1735).

Safety and tolerability of bilateral administration of AAV-vector compositions using real-time image-guided infusion into the brains of Parkinson's Disease subjects may be monitored for up to or after 9 months post-surgery. Broad coverage of targeted areas (substantia nigra pars compacta (SNpc) and ventral tegmental area (VTA)) and widespread AADC protein distribution in the striatum should be achieved without inducing any adverse effects.

Changes in Growth and Motor Skills

The patients should gain weight and exhibit improvement in their motor scores after gene transfer, within a year, post-treatment. Weight will be measured at 3 to 6 months after gene transfer. All patients initially should have raw scores of zero on the Alberta Infant Motor Scale (AIMS) and very low raw scores for the Peabody Developmental Motor Scale, Second Edition (PDMS-II). After the gene transfer, all of the patients should show continuous increases in their raw scores on these two scales, which indicates that their motor functions have improved. The Comprehensive Developmental Inventory for Infants and Toddlers (CDIIT) covers both cognition and motor development. All of the patients should show low raw CDIIT scores before gene transfer, and the subsequent increase in scores demonstrate improvement in both motor and cognitive functions.

Subjective Improvements after Gene Transfer

To document the symptoms that are more difficult to quantify, spouses, guardians or caretakers of the patients are asked to fill out a questionnaire at the end of the study. The symptoms of the oculogyric crises should lessen, and eye deviations and sleep disruptions, for example, are some mild symptoms of the oculogyric crises that may remain after gene therapy. Subjects may experience increased emotional stability, and/or some improvements in sweating and hyperthermia (a common manifestation of body temperature instability in hot weather). There should be no detectable abnormality in heart rate variability as assessed by 24-hour Holter monitoring either before or after gene transfer. Before gene therapy, patients that were bedridden and showed little spontaneous movement may exhibit less severe ptosis (drooping of the upper eyelid) one to two weeks after the gene transfer. According to previous studies, dyskinesia may occur one month after gene transfer, but upon observation of a decrease in dyskinesia, motor development should start (Hwu, W. L., et al., 2012. Gene therapy for aromatic L-amino acid decarboxylase deficiency. Sci. Transl. Med. Vol. 4, 134ra61). Subjects may exhibit increased head control after three months, sitting with support after six to nine months, sitting up from the prone position after thirteen months, and holding toys and standing with support sixteen months after the gene transfer, for example. Anti-AAV2 antibodies should be negative in the patients before gene therapy, and the titers may increase slightly after gene transfer.

PET Scans and CSF Analyses

PET scans and CSF analyses are completed for the treated patients. Six months after gene transfer, PET scans should reveal that uptake of 6-[18F] fluorodopa (FDOPA) increase from baseline in the combined (right and left) treatment sites. The CSF analysis should reveal increases in the levels of homovanillic acid (HVA, a metabolite of dopamine) and 5-hydroxyindoleacetic acid (HIAA, a metabolite of serotonin). However, the levels of L-DOPA and 3-O-methyldopa may remain elevated (Hwu, W. L., et al., 2012. Gene therapy for aromatic L-amino acid decarboxylase deficiency. Sci. Transl. Med. Vol. 4, 134ra61).

Example 4. Administration of AADC Polynucleotides

AAV particle compositions are infused into the putamen of patients having Parkinson's Disease using the administration methods described in Example 3. The dose, number of patients and volume are outlined in Table 4.

TABLE 4

Study Design

| Study No. | Number of Patients | Dose | Volume |
|---|---|---|---|
| 1 | 6 | $3 \times 10^{11}$ vg | 100 µL per putamen |
| 2 | 6 | $9 \times 10^{11}$ vg | 300 µL per putamen |
| 3 | 10 | $2.3 \times 10^{11}$ vg | 100 µL per putamen |
| 4 | 10 | $7.5 \times 10^{11}$ vg | 100 µL per putamen |
| 5 | 5 | $7.5 \times 10^{11}$ vg | 450 µL per putamen |
| 6 | Up to 20 | $1.4 \times 10^{12}$ vg | Up to 900 µL per putamen |
| 7 | Up to 20 | $4.8 \times 10^{12}$ vg | Up to 900 µL per putamen |
| 8 | Up to 20 | $8.8 \times 10^{12}$ vg | Up to 900 µL per putamen |

During the course of the study the safety and tolerability of the infusion of the AADC polynucleotide (SEQ ID NO: 979)-containing recombinant adeno-associated virus (AAV) vector compositions in human patients diagnosed with Parkinson's Disease is evaluated. Patients are evaluated preoperatively and monthly postoperatively for six months, using multiple measures, including the Global Systonia Scale (GDS) (see Comella, et al., 2003, Movement Disorders, 18(3):303-312), L-DOPA challenge test, UPDRS scores, motor state diaries, and laboratory tests. Using diaries that separate the day into half-hour segments, the caregivers of the patients will record their mobility during the four days before admission and for another four days at six months after admission to the study site. The patient caregivers are trained to rate subject's condition as sleeping, immobile, mobile without troublesome dyskinesias, or mobile with troublesome dyskinesias. The total number of hours spent in each of these categories is calculated, and the differences between the baseline and the six-month scores are compared between the groups. The short-duration response to levodopa is evaluated at baseline and 6 months after gene transfer; subjects take 100 mg of levodopa orally with 25 mg benserazide after 20 hours without dopaminergic medication. Motor symptoms based on GDS and plasma levodopa concentrations are assessed at baseline and 30 minutes, 1, 2, 3, and 4 hours after levodopa intake (See, for example. Muramatsu, et al., 2010, "A phase I study of aromatic L-amino acid decarboxylase gene therapy for Parkinson's disease." *Mol. Ther.* 18:1731-1735).

Example 5. High-Dosage Administration of AAV2-hAADC for Parkinson's Disease 15 patients with advanced Parkinson's Disease and disabling motor fluctuations were administered a single administration of AAV2-hAADC (vector genome comprising SEQ ID NO: 979 in an AAV2 serotype capsid). Objectives of this study included the determination of safety and tolerability of AAV2-hAADC and to test the distribution of ascending dose levels of AAV2-hAADC delivered to the putamen in patients with Parkinson's Disease with a suboptimal levodopa response.

AAV2-hAADC is comprised of recombinant AAV2 carrying the complementary deoxyribonucleic acid of the human AADC gene under the control of the cytomegalovirus immediate early promoter as described in Example 1. Study drug was provided in a sterile formulation of phosphate buffered saline with 0.001% Pluronic acid (F-68), in 0.5 mL aliquots at an initial concentration of $4.9 \times 10^{12}$ vg/mL (with an excipient for dilution to the final dosage concentration).

Patient groups were comprised of patients having Parkinson's Disease and identified as qualified for treatment. The criteria to determine eligibility for participation in the study included: males and females, 40 to 70 years of age (inclusive) fluent in English; diagnosed with idiopathic PD, with bradykinesia, rigidity, and/or resting tremor. Documentation of a robust response to dopaminergic medications, an adequate duration of levodopa therapy to ensure responsiveness, and the absence of signs suggesting atypical parkinsonism; disease duration of ≥5 years: modified Hoehn and Yahr Staging of at least 2.5 in the OFF state; candidate for surgical intervention because of disabling motor complications, as defined by a Unified Parkinson's Disease Rating Scale (UPDRS), Part IV B score of 3 (minimum)-7 (maximum) despite optimal antiparkinsonian medication therapy; and ≥2 cumulative hours of OFF time per day during waking hours within 7 days of the screening visit according to the participant; UPDRS Part III (total motor) score ≥25 and a maximum of 60 in the clinically defined OFF state; unequivocal responsiveness to dopaminergic therapy, including a 30% or greater improvement in the UPDRS III (motor score) between ON and OFF states, as determined after overnight withdrawal of Parkinson's medications: a stable regimen of Parkinson's medications for at least 4 weeks prior to screening examination; stable Parkinson's features and symptoms for at least 4 weeks prior to screening examination; laboratory values prior to surgery as follows: platelets $>100 \times 10^9$/L (transfusion independent), prothrombin time (PT)/partial thromboplastin time (PTT) in normal range and international normalized ratio (INR) ≤1.3, absolute neutrophil count $>1.5 \times 10^9$/L, hemoglobin >10.0 g/dL, aspartate aminotransferase or alanine aminotransferase <2.5× the upper limit of normal, total bilirubin <2.5 mg/dL, serum creatinine ≤1.5 mg/dL, neutralizing adeno-associated virus, serotype 2 (AAV2) antibody titer ≤1:1200, hematocrit >34%; white blood cell count $<12 \times 10^9$/L, and estimated glomerular filtration rate ≥30 mL/min.

Adults meeting any of the following criteria were not eligible for study entry: atypical or secondary parkinsonism, including but not limited to symptoms believed to be due to trauma, brain tumor, infection, cerebrovascular disease, other neurological disease, or to drugs, chemicals, or toxins presence of dementia as defined by a Mattis Dementia Rating Scale—Second Edition (MDRS-2) score of less than 130 at screening; presence or history of psychosis, with the exception of mild, benign hallucinations believed to be related to Parkinson's medications: presence of severe depression as measured by Beck Depression Inventory II (BDI-II) >28 or a history of a major affective disorder within 5 years of screening examination; active suicidal ideation (Columbia-Suicide Severity Rating Scale (C-SSRS) typed 4 or 5) or suicide attempt within 5 years of screening examination; history of substance abuse within 2 years of screening examination, brain imaging abnormalities in the striatum or other regions that would substantially increase risk of surgery; contraindication to magnetic resonance imaging (MRI) and/or gadolinium (e.g., ProHance (gadoteridol)); coagulopathy or inability to temporarily stop any anticoagulation or antiplatelet therapy for at least 2 weeks during the perioperative period; prior stereotactic brain surgery including lesioning procedures, deep brain stimulation, infusion therapies or any other prior brain surgery that could complicate the study procedure and/or negatively impact study evaluations: prior gene transfer, as determined from participant interview: history of stroke, poorly controlled or significant cardiovascular disease, diabetes or any other acute or chronic medical condition that would unreasonably increase the risks of the study procedures; history of malignancy other than treated carcinoma in situ within 3 years of screening evaluation: clinically apparent or laboratory-detected infection (including acute or chronic scalp infection) at the time of screening or baseline evaluations or immediately prior to surgery; prior or current treatment with any investigational agent within 2 months of screening evaluation; inability to comply with the procedures of the protocol, including completion of Hauser Diaries: chronic immunosuppressive therapy, including chronic steroids, immunotherapy, cytotoxic therapy, and chemotherapy; any serious medical condition or abnormal finding on physical examination or laboratory investigation that would substantially increase the risks of the study procedures: any medical condition that is likely to lead to disability during the course of the study and interfere with or confound study assessments (including but not limited to orthopedic conditions, spinal disorders, neuropathy, myelopathy, severe pulmonary or cardiac disease, cognitive decline, and compromised nutritional states); pregnant and lactating women; male or female with reproductive capacity who is unwilling to use barrier contraception for 6 months after surgery, and 2 months after each intravenous (IV) levodopa infusion: participant plans to receive any vaccination within 30 days of surgery; any factors, medical or social, which would likely cause the participant to be unable to follow the study protocol, including geographical inaccessibility; ongoing treatments that might interfere with interpretation of the study outcome including neuroleptic medications, apomorphine, or levodopa infusion therapy (Duopa®); participant plans to participate in any other therapeutic intervention study within 12 months after surgery.

Three patient groups were assembled to be representative of advanced stages of Parkinson's disease population. Baseline characteristics for Group 1, Group 2 and Group 3 are shown in Table 5 (mean values for entire patient groups).

TABLE 5

Baseline Characteristics for Groups 1-3

|  | Group 1 | Group 2 | Group 3 | Groups 2-3 |
|---|---|---|---|---|
| Age (years) | 57.4 | 58.4 | 57.4 | 57.9 |
| PD Duration (years) | 9.9 | 10.1 | 8.5 | 9.3 |
| UPDRS II OFF | 13.6 | 16.0 | 19.8 | 17.9 |
| UPDRS II ON | 3.0 | 3.6 | 5.0 | 4.3 |
| UPDRS III OFF | 37.2 | 35.8 | 38.2 | 37.0 |
| UPDRS III ON | 7.6 | 17.0 | 16.0 | 16.5 |
| Diary OFF (hours) | 4.9 | 4.2 | 4.7 | 4.5 |
| Diary ON (hours) | 10.5 | 10.7 | 10.3 | 10.5 |
| Hoehn & Yahr Stage | 3.0 | 3.0 | 3.4 | 3.2 |
| UDysR Score | 19.2 | 17.4 | 30.2 | 23.8 |
| LED (mg) | 1467.5 | 1635.5 | 1476.5 | 1556.0 |

All participants received a multi-trajectory administration of AAV2-hAADC vector on Day 0. Administration was completed with participants in a supine or prone positioning, with head fixation and multichannel flex coil. Interventional MRI was utilized to monitor intracranial infusion procedures in real time to achieve a targeted delivery of AAV2-hAADC. To enhance MRI visualization of the infusion within the brain, a small quantity of gadoteridol (1-2 mM) was added to the AAV2-hAADC dosing solution immediately prior to administration. The AAV2-hAADC vector was delivered transfrontally (top of the head) into the putamen (one posterior injection and one anterior injection) in a single surgical setting. The delivery was completed via step-tipped SmartFlow™ neuro-ventricular injection and aspiration cannula connected to Medfusion 3500 infusion pumps, guided using skull mounted SmartFrames® with the Clearpoint® neuro-navigational system (MRI Interventions, Inc., Irvine, CA). Convection-Enhanced Delivery (CED) was used, with a stacked delivery and an increasing infusion rate (1-30 μL/min) to maximize distribution of the vector within the target. All participants remained on study regardless of total volume infused. Data was analyzed with and without participants that received less than the intended dose of AAV2-hAADC. Patients were observed post-surgery on an in-patient basis overnight at the minimum.

Concentrations and dosage levels for each patient group are summarized in Table 6.

Patients were treated with ascending dose levels of AAV2-hAADC; Group 1 was administered the lowest total amount and Group 3 was administered the highest total amount of vector genomes. AAV2-hAADC was well tolerated with no vector-related serious adverse events. Outcomes of treatment were evaluated by various methods, including the determination of vector distribution in the putamen, measurement of AADC expression and activity, changes in Parkinson's Disease medications (levodopa equivalent dose), patient-reported diaries, and a quality of life questionnaire.

Figure 2:
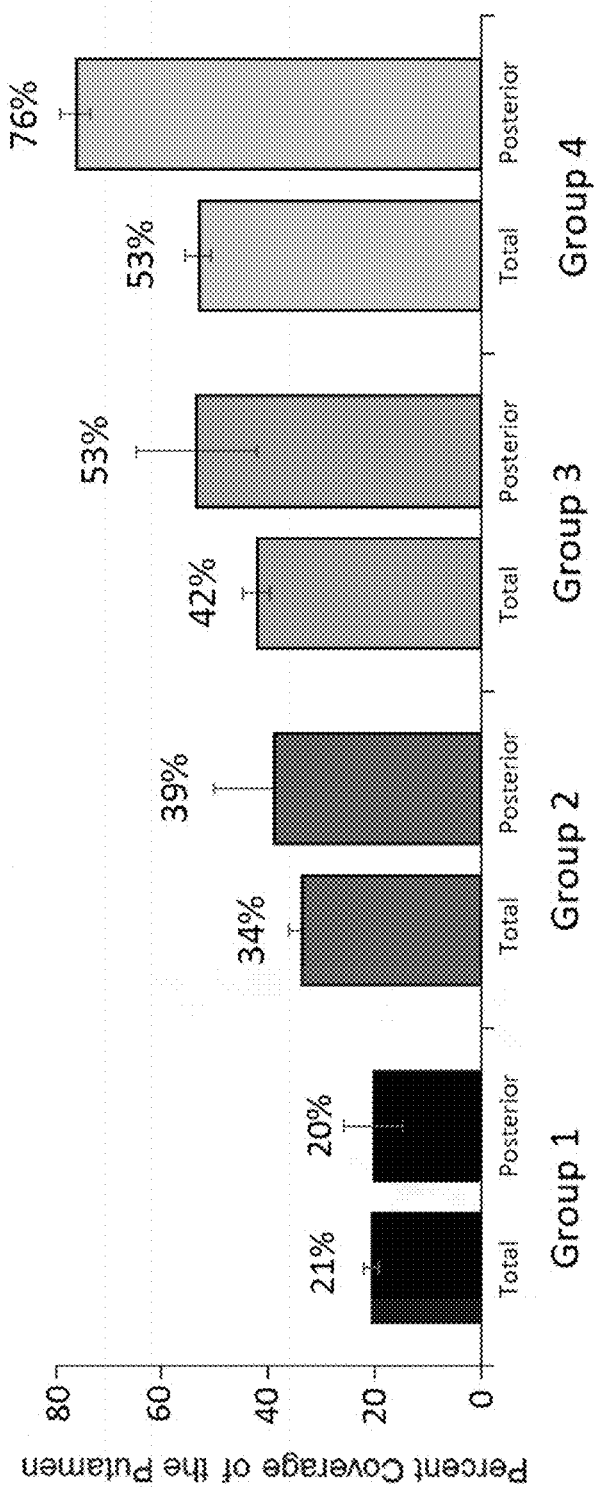
FIG. 2 shows the percent coverage of the putamen corresponding with certain embodiments of the present disclosure, which is represented by average coverage of left and right putamen by volume (total and posterior). Error bars are standard errors.

AAV2-hAADC was co-infused with gadoteridol to allow visualization of the distribution of the vector. Putaminal coverage was measured on the MR images (TIW MR: MP-RAGE; 3 minute acquisition time) acquired during the convection-enhanced delivery procedure. Calculations were made of the total volume of gadoteridol distribution, percentage of putamen covered by gadoteridol, and percentage of gadoteridol distribution contained within the putamen (iPlan Flow software; Brainlab AG, Munich, Germany). FIG. 2 shows that Group 1 had the lowest percentage of coverage, with 20.7% of the putamen covered by the vector. The higher volume administrations covered more of the putamen with Group 2 averaging 33.5% putaminal coverage, and Group 3 averaging 42.3% putaminal coverage.

Figure 3:
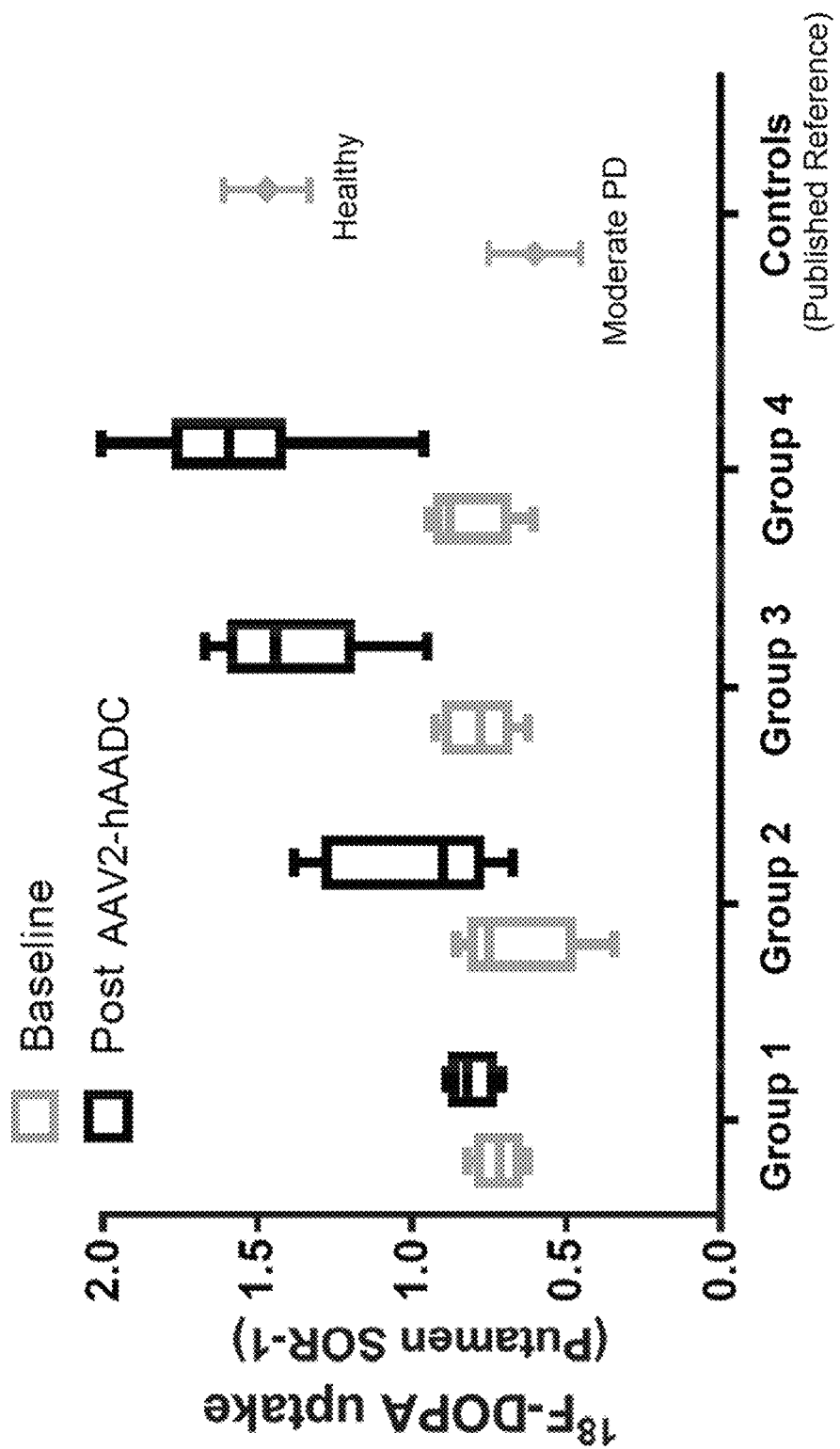
FIG. 3 shows $^{18}$F-DOPA uptake ratios corresponding with certain embodiments of the present disclosure for subjects at 2-7 months post-infusion in comparison to moderate PD control subjects and healthy non-PD subjects. Standardized uptake value ratio (SOR) values are calculated using bilaterally averaged occipital time-activity curve (kBq/mL) region-of-interest values in each subject.
Figure 4:
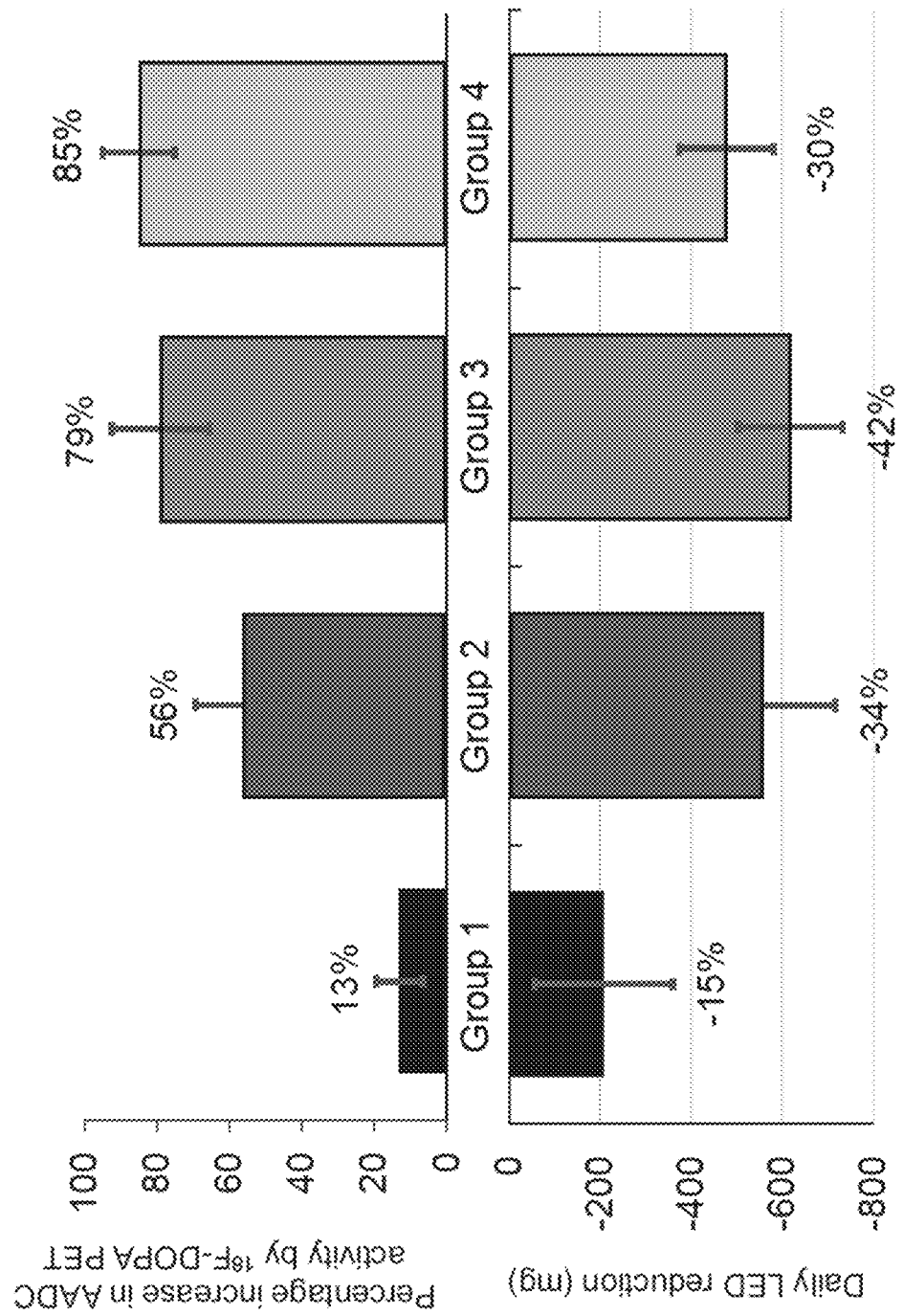
FIG. 4 shows AADC expression and activity in the putamen (top) and levodopa equivalent doses (LEDs) at 6 months as a percentage compared to baseline (bottom), corresponding with certain embodiments of the present disclosure. Error bars are standard errors.

Assessment of AADC expression and activity in the putamen was determined using positron emission tomography (PET) using [$^{18}$F] fluoro-L-dihydroxyphenylalanine (or $^{18}$F-DOPA), which reflects the capacity to convert levodopa to dopamine. Scans were acquired prior to (baseline) and about 6 months after infusion. Carbidopa, 2.5 mg/kg (maximum dose 200 mg), was taken orally 60-90 min prior to $^{18}$F-Dopa administration. $^{18}$F-dopa (~3 mCi) was injected as a bolus in an antecubital vein. Acquisition frames captured 65-75 min after $^{18}$F-Dopa administration were analyzed. Data analysis yielded a putamen-to-occipital-cortex-standardized-uptake-value-ratio, with results expressed as percentage change from baseline. (FIG. 3) All patient groups experienced an increase in AADC enzyme activity at 6 months (FIG. 4). Group 1 experienced a 13.2% increase in AADC enzyme activity, while Group 2 and Group 3 experienced a 56.1% and 79.3% increase, respectively. Group related increases in $^{18}$F-Dopa signal correlated with AAV2-hAADC (gadoteridol) coverage (r=0.84, p=0.0002), suggesting that anatomical coverage of the putamen correlates with the observed increase in AADC activity.

Figure 5:
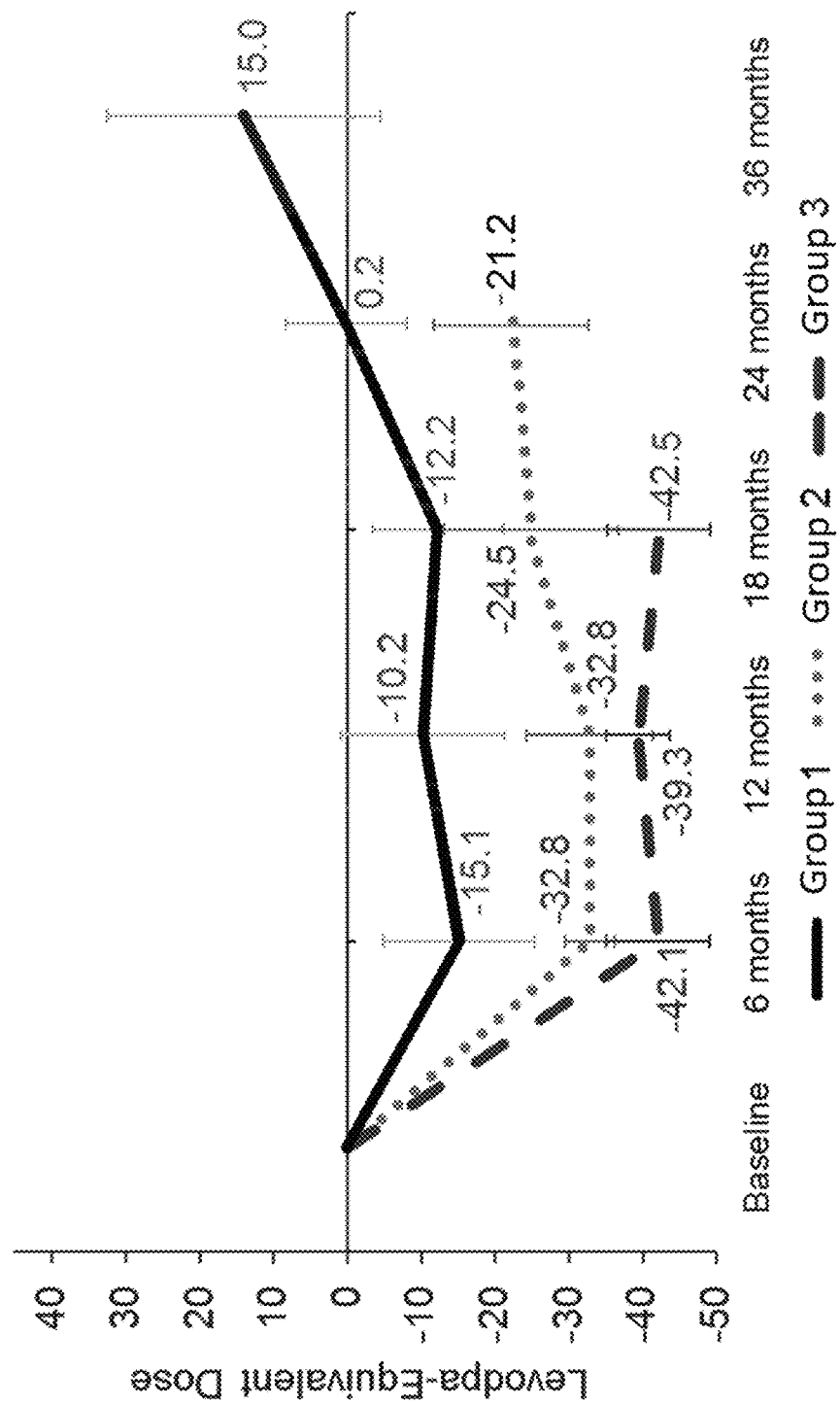
FIG. 5 shows the percentage change in levodopa-equivalent dose as compared to baseline, corresponding with certain embodiments of the present disclosure. Error bars are standard errors.

During the trial, patients of all patient groups were able to reduce their daily doses of oral levodopa and related medications, or levodopa equivalent doses (LEDs), to achieve optimal motor control in response to severe dyskinesia (FIG. 4 and FIG. 5). These changes are summarized in Table 7 (mean values for entire patient groups).

TABLE 6

Groups 1-3 Dosage Levels

| Group | Number of Patients | Maximum Volume administered | Concentration | Maximum Total dose administered |
|---|---|---|---|---|
| 1 | 5 | Up to 450 μL per putamen | $8.3 \times 10^{11}$ vg/ml | $7.5 \times 10^{11}$ vg |
| 2 | 5 | Up to 900 μL per putamen | $8.3 \times 10^{11}$ vg/ml | $1.5 \times 10^{12}$ vg |
| 3 | 5 | Up to 900 μL per putamen | $2.6 \times 10^{12}$ vg/ml | $4.7 \times 10^{12}$ vg |
| — | 0 | Up to 900 μL per putamen | $4.9 \times 10^{12}$ vg/ml | $8.8 \times 10^{12}$ vg |

Patients in Group 1 reduced their Parkinson's disease LEDs from baseline by a mean of 15% at 6 months, 10% at 12 months and 12% at 18 months. Group 2 reduced their Parkinson's disease LEDs by 33% at 6 months and at 12 months, 24.5% at 18 months, and 21.2% at 24 months. Group 3 reduced their Parkinson's disease LEDs by 42% at 6 months, 39.5% at 12 months and 42.5% at 18 months. Percentage calculations are based on average of individual patient change against individual baseline.

TABLE 7

Change from Baseline in Levodopa Equivalent Dose (LED) by Patient Group

|  | Group 1<br>$7.5 \times 10^{11}$ vg<br>(N = 5) | Group 2<br>$1.5 \times 10^{12}$ vg<br>(N = 5) | Group 3<br>$4.7 \times 10^{12}$ vg<br>(N = 5) |
| --- | --- | --- | --- |
| Baseline | 1467.5 (275) | 1635.5 (307.4) | 1476.5 (191.9) |
| 6 Months | −208.0 (151.4) | −553.2 (137.0) | −617.8 (115) |
| 12 Months | −92.5 (191.7) | −627.2 (246.3) | −606.0 (46.7) |
| 18 Months | −176.5 (129.9) | −465.3 (246.0) | −614.1 (87.3) |
| 24 Months | 45.5 (158.8) | −451.9 (249.2) |  |
| 36 Months | 347.5 (404.0) |  |  |

Baseline (BL) LED was similar across patient groups. All patients were treated with carbidopa/levodopa (C/L) at all timepoints. At BL, patients were taking an additional 0 (n=2), 1 (n=5), 2 (n=6), or 3 (n=2) antiparkinsonian medications including dopamine agonists, amantadine, Monoamine Oxidase B (MAO-B) inhibitors, and Catechol-O-methyl transferase (COMT) inhibitors. Six months after AAV2-hAADC administration, 9 patients were receiving the same combination of medications. In the remaining 6 patients for whom there was a change in medication (2 in each patient group) in the combination of antiparkinsonian medications, 2 added amantadine alone, 1 removed a DA agonist, 1 removed a COMT inhibitor, 1 removed amantadine and an MAO-B inhibitor, and 1 removed a DA agonist and added amantadine and an MAO-B inhibitor. At 12 months, 1 patient re-added amantadine and a MAO-B inhibitor and 1, who had no change at 6 months, removed a MAO-B inhibitor. All other patients remained on a stable combination of medications. Percentage change in LED at 12 months was −24% in patients who had no change in medication combination and −33% in patients whose combination was changed. Overall change in LED was significantly correlated with UPDRS III on medication at 12 months (r=0.695, p=0.004). No vector-related serious adverse events (SAEs) have been reported.

Subjects were evaluated clinically at baseline and 3, 6, 12, 24, and 36 months post-AAV2-hAADC infusion. Subjects completed Hauser motor diaries for either 2 or 3 consecutive days. The Unified Parkinson's Disease Rating Scale (UPDRS) was measured at baseline and follow-up visits in the functionally defined off-state, 12 or more hours after the last dose of dopaminergic medication(s), and in the fully on-state (as judged by the patient and investigator 1 hr following the first morning dose). An additional one-half to one carbidopa/levodopa 25/100 tablet was administered if the subject was not fully "on" as judged by the subject and investigator.

Patients recorded in diaries on-time and off-time per day. During patient's on-time, their medicines were considered by the patient to be working and the patient had movement, although not always with good control. During off-time, patient's medicines were considered by the patient to not be working well and the patient experienced feeling rigid, completely frozen, or involuntary shaking. Dyskinesia can affect the patient's arms, legs, torso, or entire body and feels and appears like uncontrolled jerky movements. Because dyskinesia can occur during periods of on-time, patients distinguished between on-time with troublesome dyskinesia, on-time with non-troublesome dyskinesia, and on-time without dyskinesia in their diaries.

Treatment with AAV2-hAADC generated improvements in both diary recorded off-time and diary recorded on-time with troublesome dyskinesia. Treatment also resulted in notable increases in diary-reported "Good ON-Time" (ON-Time without troublesome dyskinesia, which is a combination of diary recorded ON-time without dyskinesia and diary recorded ON-time with non-troublesome dyskinesia). These results are summarized in Table 8.

At baseline, the average Good ON time was 10.5 hours and average OFF time was 4.6 hours. The average amount of Parkinson's disease medications at baseline was 1,526 mg of oral levodopa equivalents per day.

Figure 6:
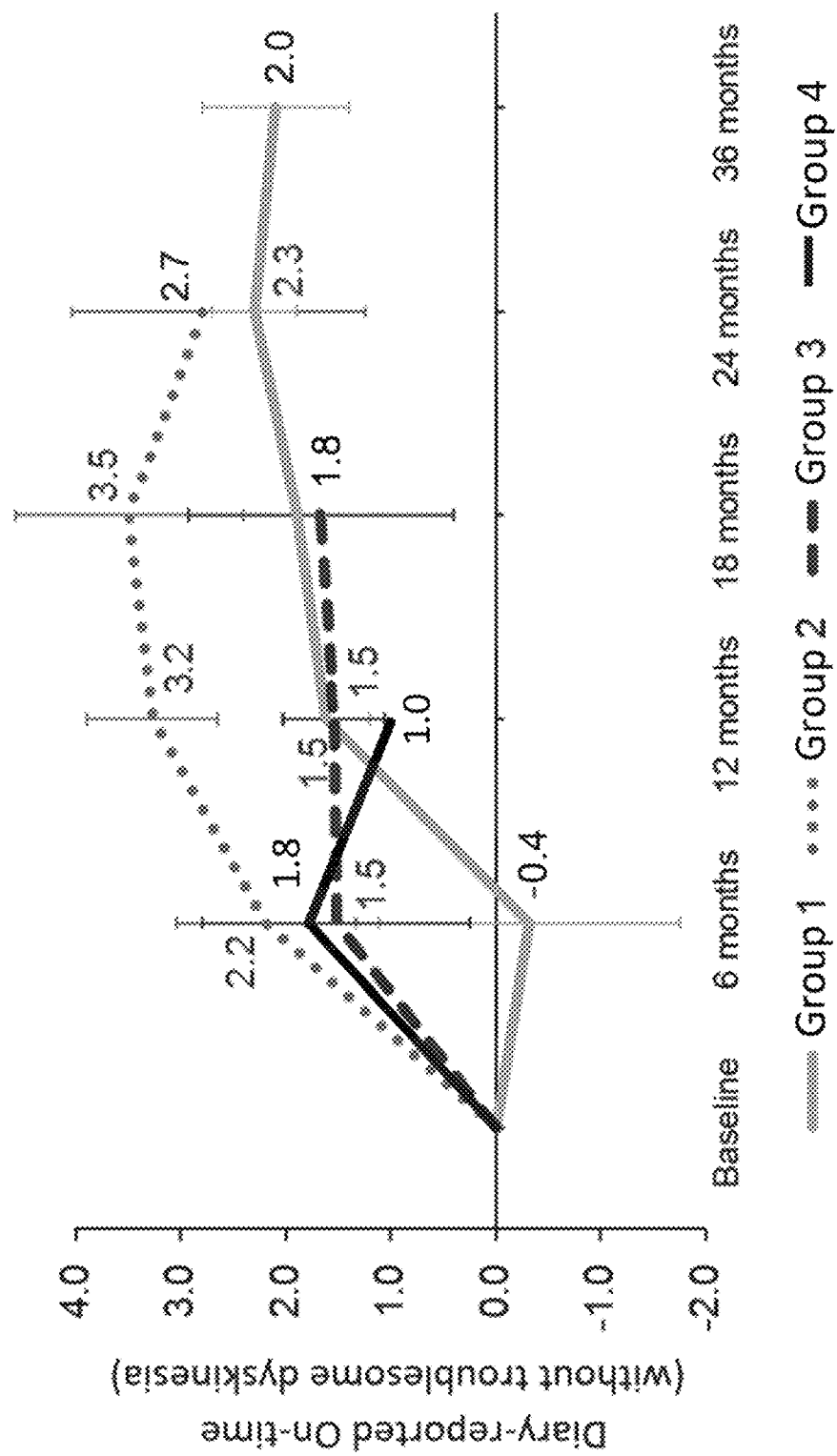
FIG. 6 shows the change in diary reported ON-time without troublesome dyskinesia corresponding with certain embodiments of the present disclosure. Error bars are standard errors.

After administration of the AAV2-hAADC, patients in Groups 1-3 experienced a steady increase in their diary-reported Good ON-Time (On-Time without troublesome dyskinesia) (FIG. 6). Group 1 experienced an average 1.6-hour (15%) improvement over baseline recorded at 12 months post-administration, a 2.3-hour (22%) improvement at 24 months, and a 2.0-hour (19%) improvement at 36 months. Group 2 experienced a 2.2-hour (20.5%) improvement at 6 months, a 3.2-hour (30%) improvement at 12 months, a 3.5-hour (33%) improvement at 18 months, and a 2.7-hour (25%) improvement at 24 months. Group 3 experienced a 1.5-hour (14.5%) improvement at 6 months and at 12 months, and a 1.8-hour (17.5%) improvement at 18 months.

Results from the two highest-dose patient groups (Groups 2 and 3, n=10) were favorable. At baseline, the average Good ON-time was 10.5 hours and average OFF time was 4.5 hours. Groups 2 and 3 experienced a 1.85-hour (17.5%) improvement in Good ON-time at 6 months, a 2.4-hour (22%) improvement at 12 months, and a 2.7-hour (25%) improvement at 18 months. A smaller group of seven patients from Groups 2 and 3 (limited by severity of dyskinesia and minimum OFF time at baseline) had an average baseline Good ON-time of 10.1 hours, with a 1.7-hour (17%) improvement at 6 months, a 2.8-hour (27%) improvement at 12 months and a 2.5-hour (24.5%) improvement at 18 months.

In regards to diary-OFF time, Group 1 had a 1.7-hour (35%) decrease from baseline in diary-OFF time at 36 months. Group 2 had a 2.7-hour (64%) decrease from baseline in diary-OFF time at 18 months, and a 2.2-hour (52%) decrease at 24 months. Group 3 had a 0.6-hour (13%) decrease from baseline in diary-OFF time at 12 months, and a 1.4-hour (30%) decrease from baseline in diary-OFF time at 18 months. Results from the two highest-dose patient groups (Groups 2 and 3, n=10) from an average baseline OFF-time of 4.5 house included a 1.2-hour (27%) decrease in OFF-time at 6 months, a 1.4-hour (31.5%) decrease at 12 months, and a 2.0 hour (46%) decrease at 18 months.

Results from the two highest-dose patient groups (Groups 2 and 3, n=10) was favorable in regards to combined diary-OFF time and ON-time with Troublesome Dyskinesia. At baseline, the average combined diary-OFF time and ON-time with Troublesome Dyskinesia was 5.5 hours. Groups 2 and 3 experienced a 1.9-hour (35%) decrease at 6 months, a 2.4-hour (46%) decrease at 12 months and a 2.6-hour (47%) decrease at 18 months. A smaller group of seven patients from Groups 2 and 3 (limited by severity of dyskinesia and minimum OFF time at baseline) had an average baseline of 5.9 hours, with a 1.7-hour (29%) decrease at 6 months, a 2.8-hour (46%) decrease at 12 months and a 2.5-hour (39%) decrease at 18 months.

Percentage calculations are based on average of individual patient change against individual baseline.

TABLE 8

Diary Recorded On-and Off-Time per 16-Hour Waking Day

| Group 1 (n = 5) | Baseline | 6 months | 12 months | 24 months | 36 months |
|---|---|---|---|---|---|
| Diary Recorded On-time with Troublesome Dyskinesia | 0.6 | 1.7 | 0.4 | 0.2 | 0.2 |
| Diary Recorded On-Time with Non-Troublesome Dyskinesia | 5.4 | 5.3 | 6.7 | 5.8 | 2.6 |
| Diary Recorded On-Time without Dyskinesia | 5.1 | 4.8 | 5.4 | 7.0 | 9.7 |
| Diary Recorded Good On-Time | 10.5 | 10.1 | 12.1 | 12.8 | 12.3 |
| Diary Recorded Off-Time | 4.9 | 4.1 | 3.6 | 3.1 | 3.5 |

| Group 2 (n = 5) | Baseline | 6 months | 12 months | 18 months | 24 months |
|---|---|---|---|---|---|
| Diary Recorded On-time with Troublesome Dyskinesia | 1.1 | 0.0 | 0.1 | 0.4 | 0.0 |
| Diary Recorded On-Time with Non-Troublesome Dyskinesia | 4.9 | 3.2 | 4.2 | 3.3 | 6.4 |
| Diary Recorded On-Time without Dyskinesia | 5.8 | 9.7 | 9.7 | 10.9 | 7.3 |
| Diary Recorded Good On-Time | 10.7 | 12.9 | 13.9 | 14.2 | 13.7 |
| Diary Recorded Off-Time | 4.2 | 3.1 | 2.0 | 1.5 | 2.3 |

| Group 3 ( n = 5) | Baseline | 6 months | 12 months | 18 months |
|---|---|---|---|---|
| Diary Recorded On-time with Troublesome Dyskinesia | 1.0 | 0.8 | 0.0 | 0.6 |
| Diary Recorded On-Time with Non-Troublesome Dyskinesia | 2.2 | 1.7 | 2.1 | 2.2 |
| Diary Recorded On-Time without Dyskinesia | 8.1 | 10.1 | 9.8 | 9.9 |
| Diary Recorded Good On-Time | 10.3 | 11.8 | 11.9 | 12.1 |
| Diary Recorded Off-Time | 4.7 | 3.4 | 4.1 | 3.3 |

Figure 7:
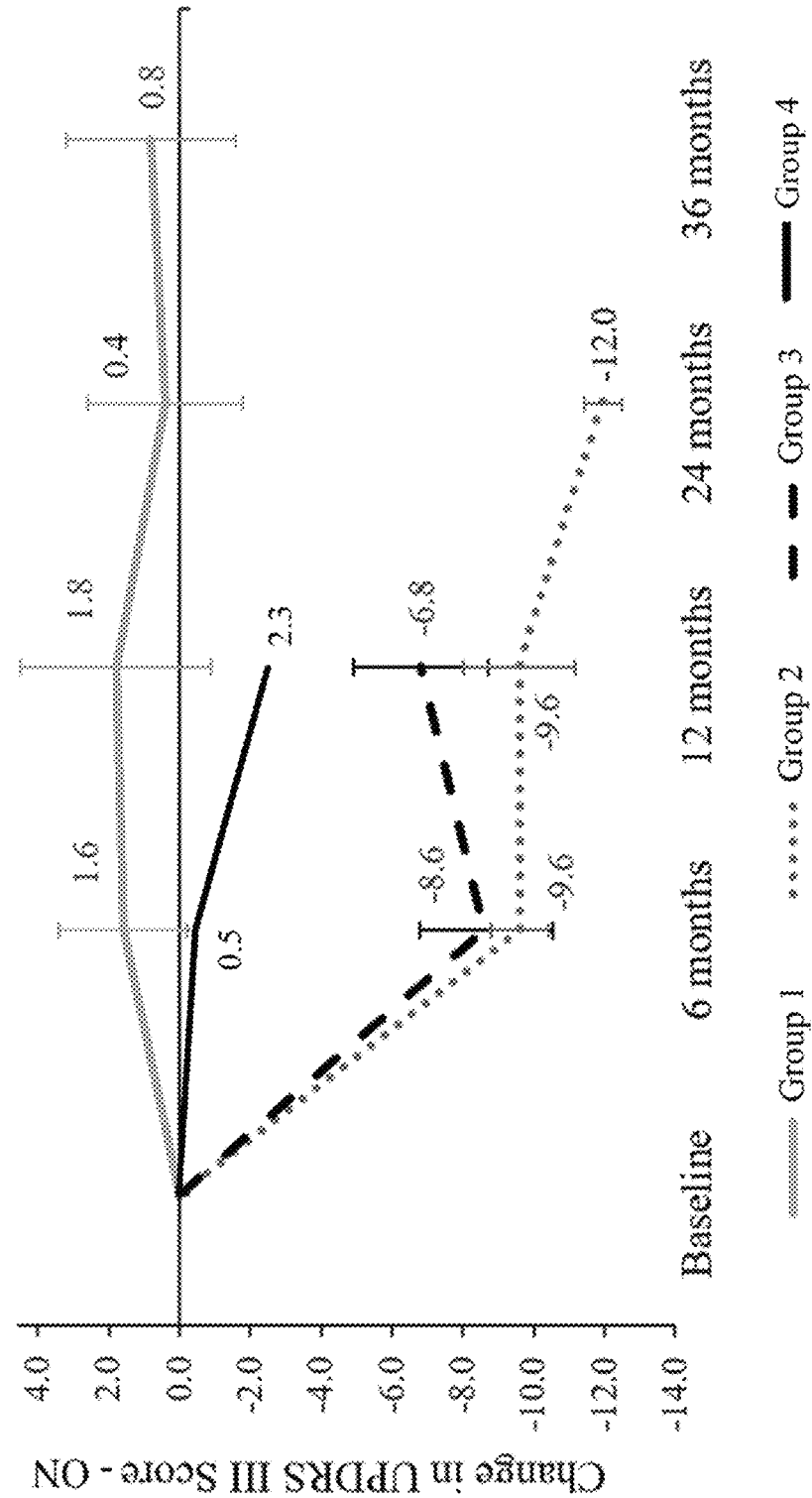
FIG. 7 shows the improvement (reduction) of patient scores on a Unified Parkinson's Disease Rating Scale (UPDRS) Part III, in the patients "ON" medicated state, corresponding with certain embodiments of the present disclosure. Error bars are standard errors.
Figure 8:
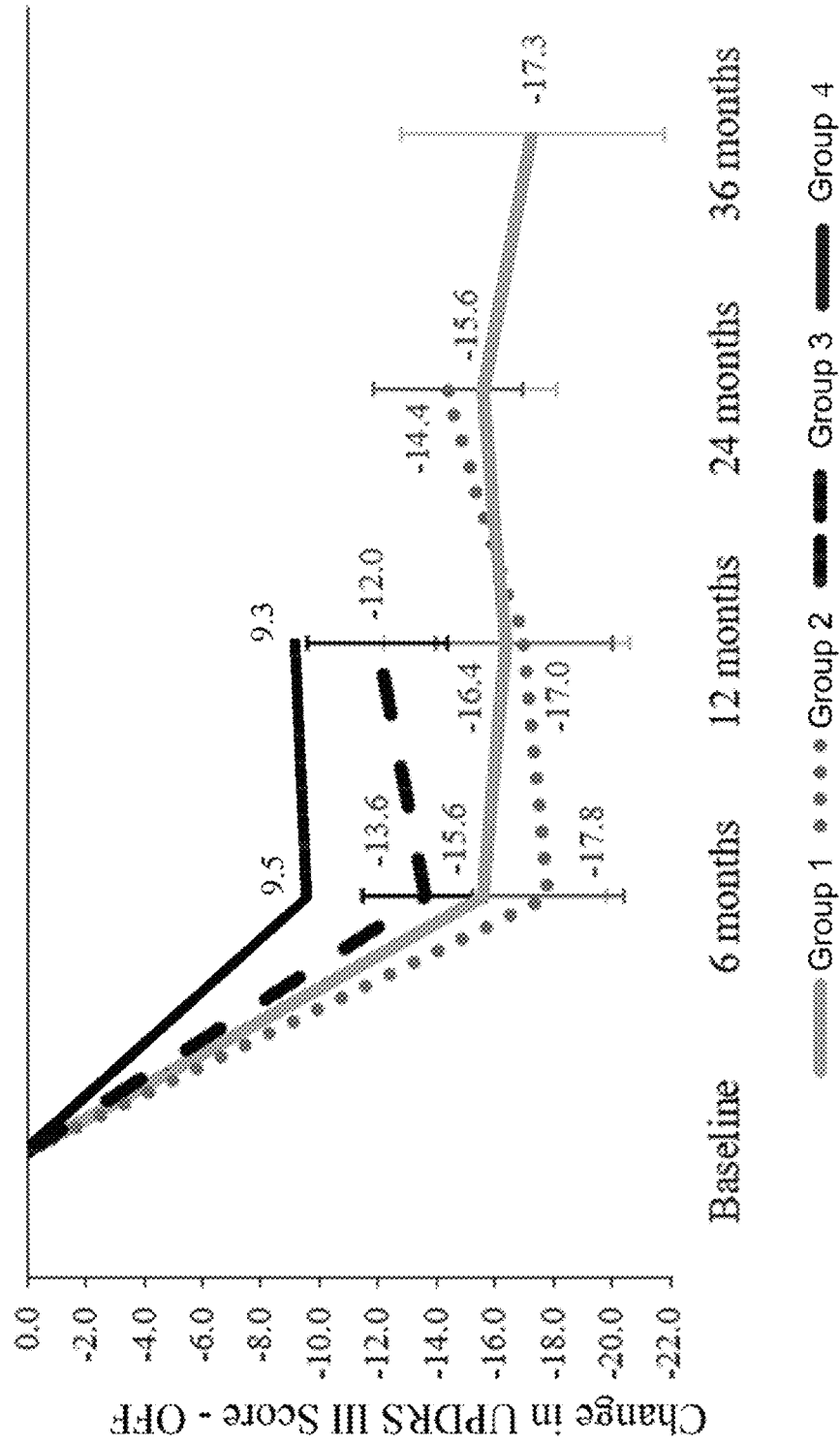
FIG. 8 shows the improvement (reduction) of patient scores on a Unified Parkinson's Disease Rating Scale (UPDRS) Part III, in the patients "OFF" medicated state, corresponding with certain embodiments of the present disclosure. Error bars are standard errors.

Patient motor response was assessed clinically at baseline and every 6 months by the Unified Parkinson's Disease Rating Scale (UPDRS) Part II (Motor Aspects of Experiences of Daily Living) and UPDRS Part III (Motor Examination) (FIG. 7 and FIG. 8).

For UPDRS II, mean±SE UPDRS II off medication scores decreased by 3.4±1.2 points in Group 2 and by 4.4±1.4 points in Group 3 at 12 months.

In regards to UPDRS III scores in the "ON" medication state (FIG. 7), baseline values were as follows: Group 1 (7.6), Group 2 (17.0), and Group 3 (16.0). For Group 1, UPDRS III ON scores were increase from baseline by 1.6 at 6 months, 1.8 at 12 months, 0.4 at 24 months, and 0.8 at 36 months. For Group 2, UPDRS III ON scores were improved from baseline (reduced) by 9.6 at 6 months and 12 months, and 12.0 at 24 months. For Group 3, UPDRS III ON scores were improved from baseline (reduced) by 8.6 at 6 months and 6.8 at 12 months.

In regards to UPDRS III scores in the "OFF" medication state (FIG. 8), baseline values were as follows: Group 1 (37.2), Group 2 (35.8), and Group 3 (38.2). For Group 1, UPDRS III OFF scores were improved from baseline (reduced) by 15.6 at 6 months, 16.4 at 12 months, 15.6 at 24 months, and 17.3 at 36 months (value at 36 months was 19.0 when excluding outlier results). For Group 2, UPDRS III OFF scores were improved from baseline (reduced) by 17.8 at 6 months, 17.0 at 12 months, and 14.4 at 24 months. For Group 3, UPDRS III ON scores were improved from baseline (reduced) by 13.6 at 6 months and 12.0 at 12 months. For the two highest-dose patient groups (Groups 2 and 3, n=10) average baseline value was 37.0, and scores were improved from baseline (reduced) by 15.7 at 6 months and 14.5 at 12 months. For a smaller group of seven patients from Groups 2 and 3 (limited by severity of dyskinesia and minimum OFF time at baseline), the average baseline value was 34.1, and scores were improved from baseline (reduced) by 15.3 at 6 months and 13.7 at 12 months.

Figure 9:
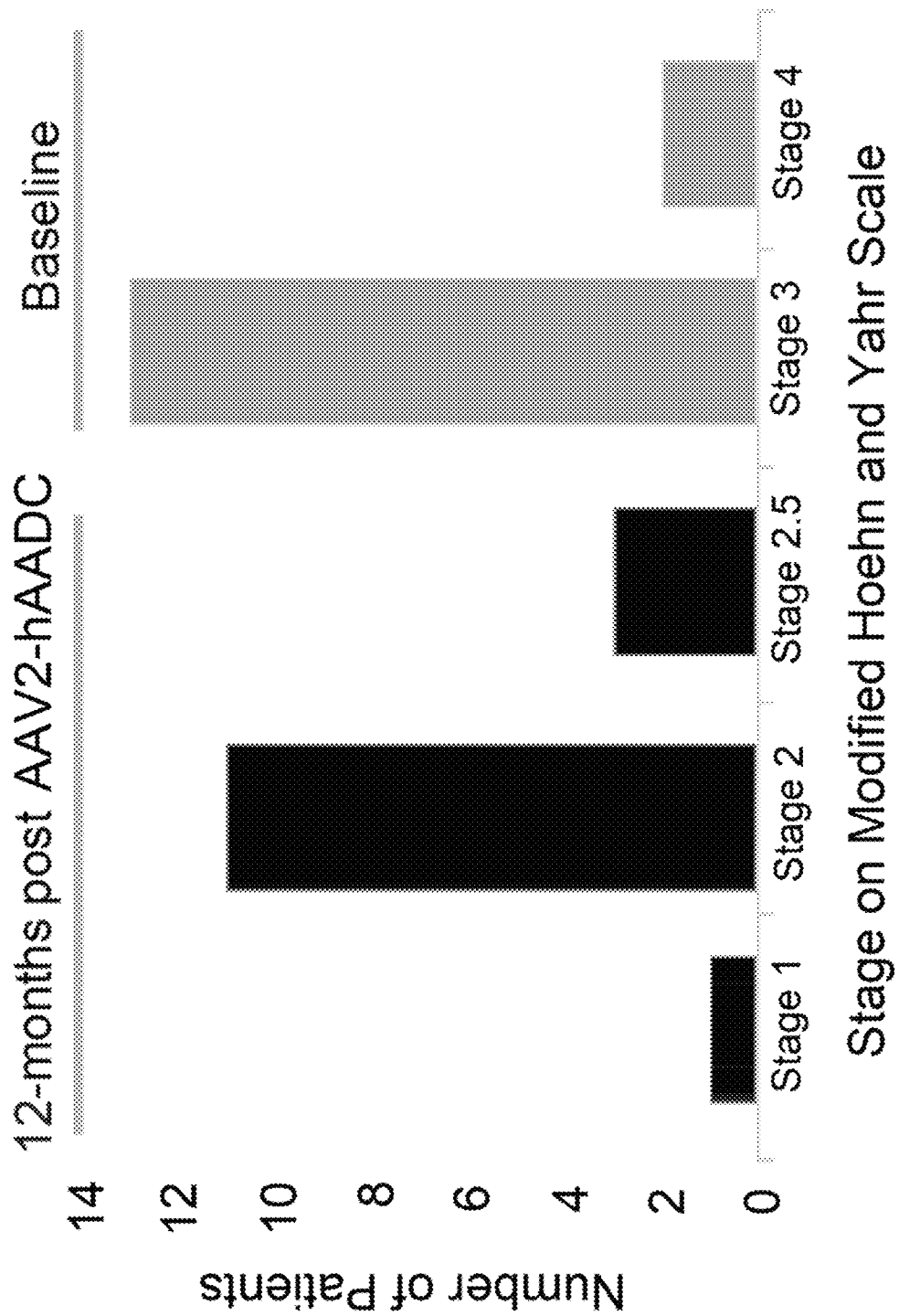
FIG. 9 shows the improvement (reduction) of patient stages under the Modified Hoehn and Yahr (mH&Y) scale from baseline, corresponding with certain embodiments of the present disclosure.

Patient improvement under the Modified Hoehn and Yahr (mH&Y) scale was assessed at 12 months, as compared to baseline values (FIG. 9). At baseline, 13 patients were at Stage 3 and 2 patients were at Stage 4, resulting in an average mH&Y stage of 3.13. At 12 months after administration of AAV2-hAADC, 1 patient was at Stage 1, 11 patients were at Stage 2, and 3 patients were at Stage 2.5, resulting in an average mH&Y stage of 2.03. This reduction of average mH&Y stage from Stage 3.13 to Stage 2.03 correlated with about 87 months (7.25 years) of improvement in disease progression in AAV2-hAADC treated patients after 12 months.

Figure 10:
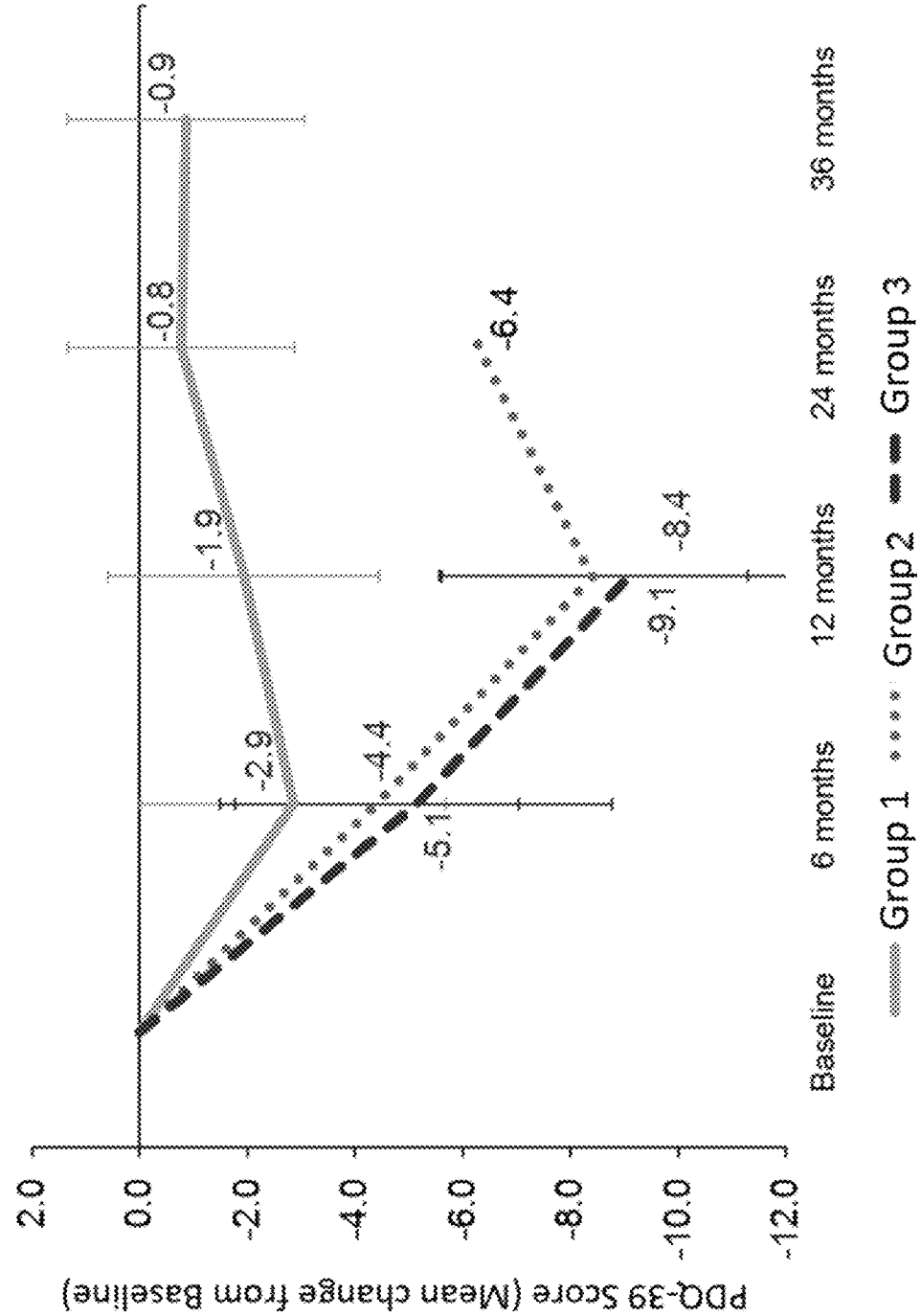
FIG. 10 shows the improvement (reduction) of patients' score on a quality of life assessment (Parkinson's Disease Questionnaire (PDQ-39)), corresponding with certain embodiments of the present disclosure. Error bars are standard errors.

Patient quality of life was assessed using the patient-reported 39-item Parkinson's Disease Questionnaire (PDQ-39), which is a 39-item questionnaire to measure health related quality of life in Parkinson's Disease patients. Administration with AAV2-hAADC improved (reduced) patients' PDQ-39 score by a mean change from baseline to 12 months of 8.4 and 9.1 for Groups 2 and 3, respectively (FIG. 10). The mean improvement in PDQ-39 score for Group 1 was 2.9 at 6 months, 1.9 at 12 months, 0.8 at 24 months and 0.9 at 36 months.

For the two highest-dose patient groups (Groups 2 and 3, n=10), the average PDQ-39 score was improved (reduced) by 4.8 at 6 months and 8.8 at 12 months. For a smaller group of seven patients from Groups 2 and 3 (limited by severity of dyskinesia and minimum OFF time at baseline), the average PDQ-39 score was improved (reduced) by 2.5 at 6 months and 8.8 at 12 months.

The PDQ-39 assessment indicated that AAV2-hAADC treatment improved patient quality of life in a dose-dependent and clinically meaningful fashion.

Figure 11A:
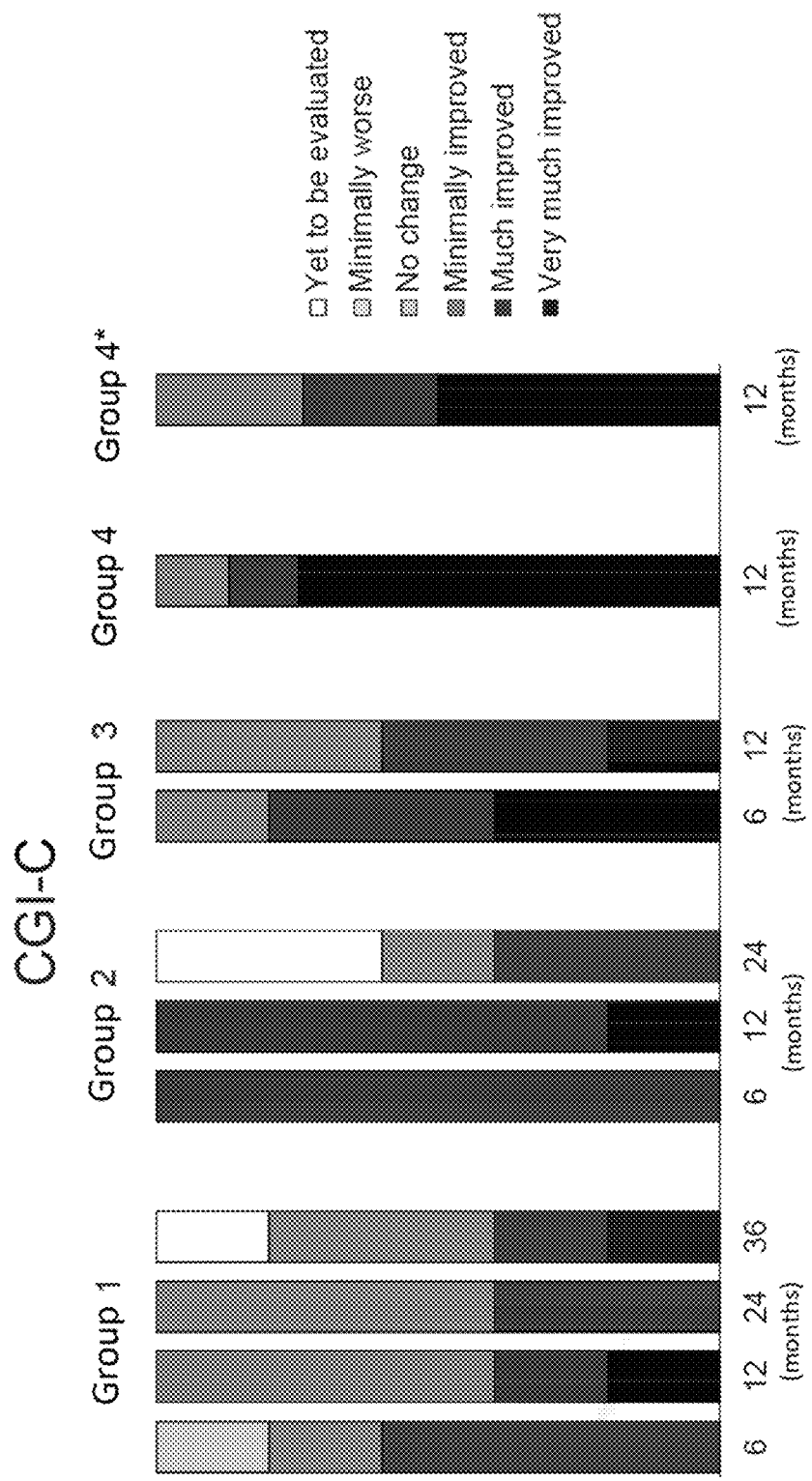
FIG. 11a shows the improvement in patient quality of life, as assessed by the Clinical Global Impression of Change (CGI-C) scale, corresponding with certain embodiments of the present disclosure.
Figure 11B:
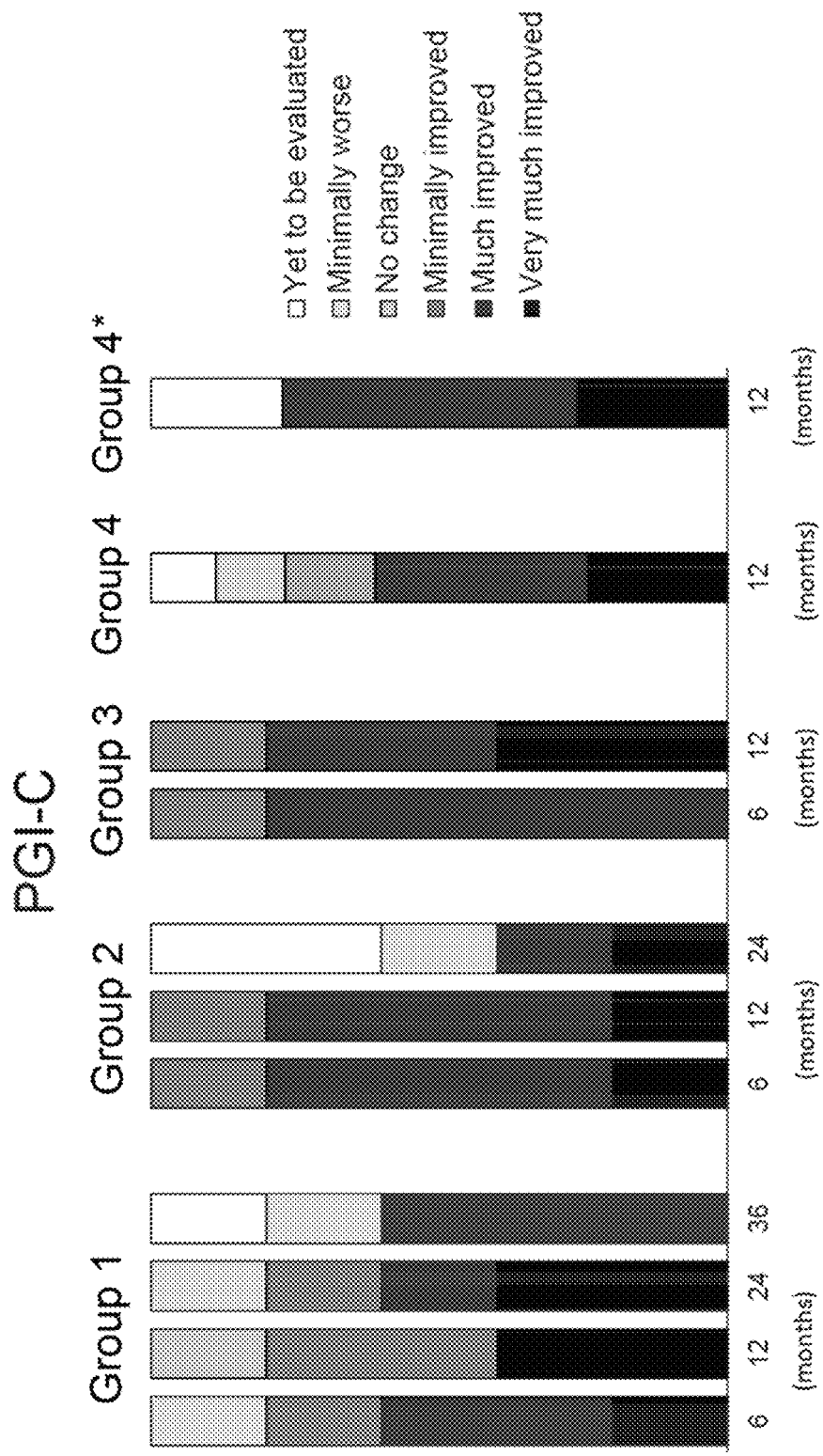
FIG. 11b shows the improvement in patient quality of life, as assessed by the Patient Global Impression of Change (PGI-C) scale, corresponding with certain embodiments of the present disclosure.

Patient quality of life was assessed using the Clinical Global Impression of Change (CGI-C) scale and the Patient Global Impression of Change (PGI-C) scale. CGI-C results are shown in FIG. 11a; PGI-C results are shown in FIG. 11b.

Taken together, these data show AADC enzyme activity is increased and clinically meaningful improvements are obtained by a single administration of AAV2-hAADC at tolerably-high dosage concentrations and volumes.

Without being bound by theory, it is possible that AADC treatment allows for improved conversion of endogenous levodopa in remaining dopaminergic nigrostriatal axons. It is also possible that AADC treatment increases the long-duration response of levodopa, perhaps by allowing more efficient and uniform conversion to dopamine in the putamen.

Example 6. Enhancement of Response to Intravenous Levodopa in Patients with Motor Response Fluctuations Thirteen participants were administered AAV2-hAADC (vector genome comprising SEQ ID NO: 979 in an AAV2 serotype capsid); Group 1: 5 subjects received an average total AADC gene therapy dose of about $7.5 \times 10^{11}$ vector genomes (vg); Group 2: 5 subjects received an average total AADC gene therapy dose of about $1.5 \times 10^{12}$ vg; and Group 3 (n=3): 3 subjects received an average total AADC gene therapy dose of about $4.7 \times 10^{12}$ vg. Patients in a practically defined off state also received an infusion of IV levodopa both before and approximately 6 months after administration of AAV2-hAADC.

On sequential days, patients received either a threshold (0.6 mg/mL; low-dose) or suprathreshold (1.2 mg/mL; high-dose) infusion of IV levodopa dosed at 1 mL/kg/hr for 2 hours. The order and threshold of IV levodopa dosing was randomized and double-blinded (LHLH, LHHL, HLHL, HLLH). Dosage levels and sequences for each participant group are summarized in Table 9.

Oral carbidopa (25 mg) was administered 1-2 hours before, during, and 1-2 hours after the infusion. Participants' motor response was measured by UPDRS III (time to 30% change and duration of 30% responses); bradykinesia was measured by finger tapping rate; and dyskinesia was measured by Abnormal Involuntary Movement Scale (AIMS) scoring. Pharmacokinetics were assessed every 30 minutes after administration of IV levodopa.

Figure 12A:
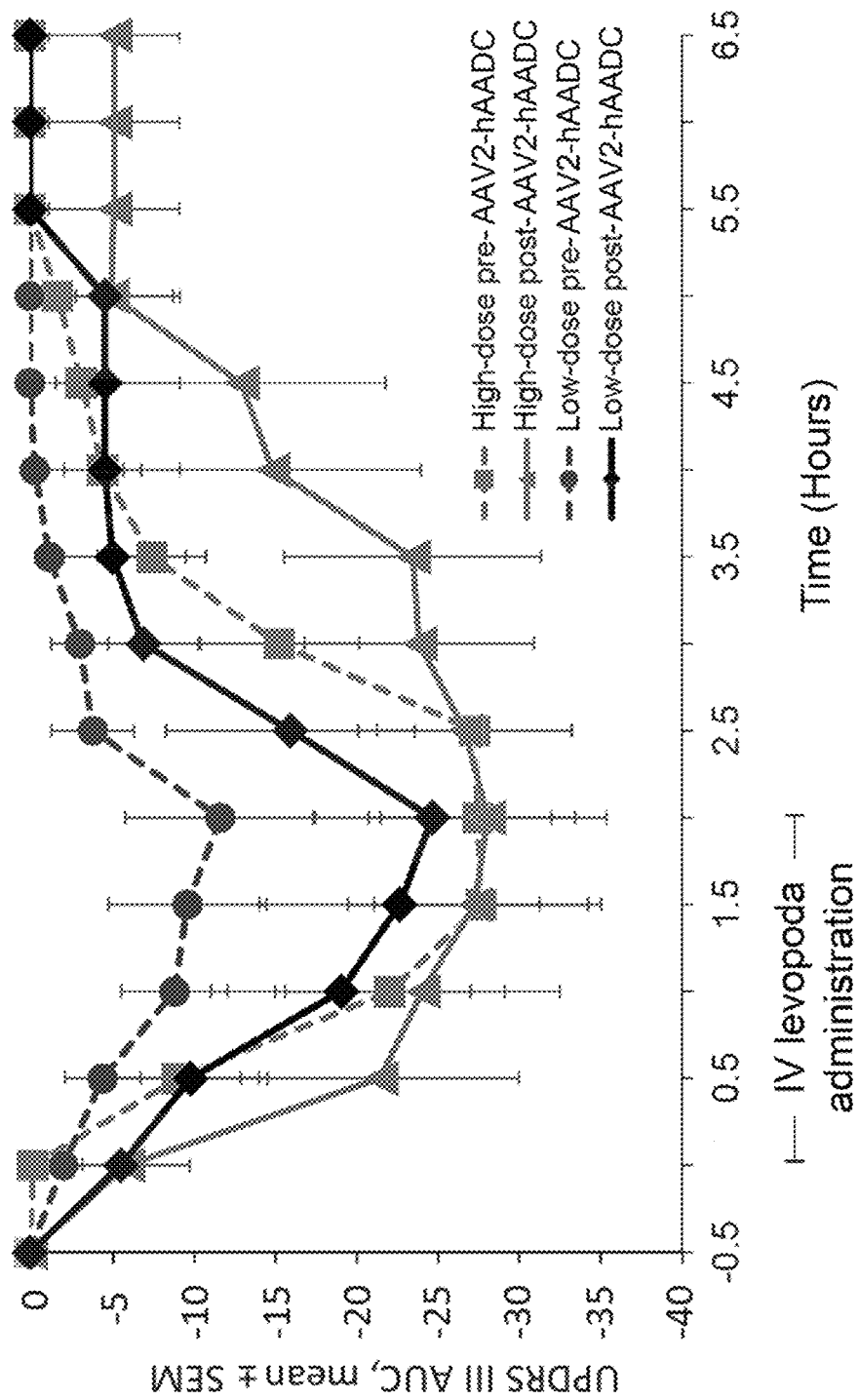
FIG. 12a shows UPDRS III AUC scores after IV Levodopa administration up to $7.5\times10^{11}$ vg, corresponding with certain embodiments of the present disclosure.
Figure 12B:
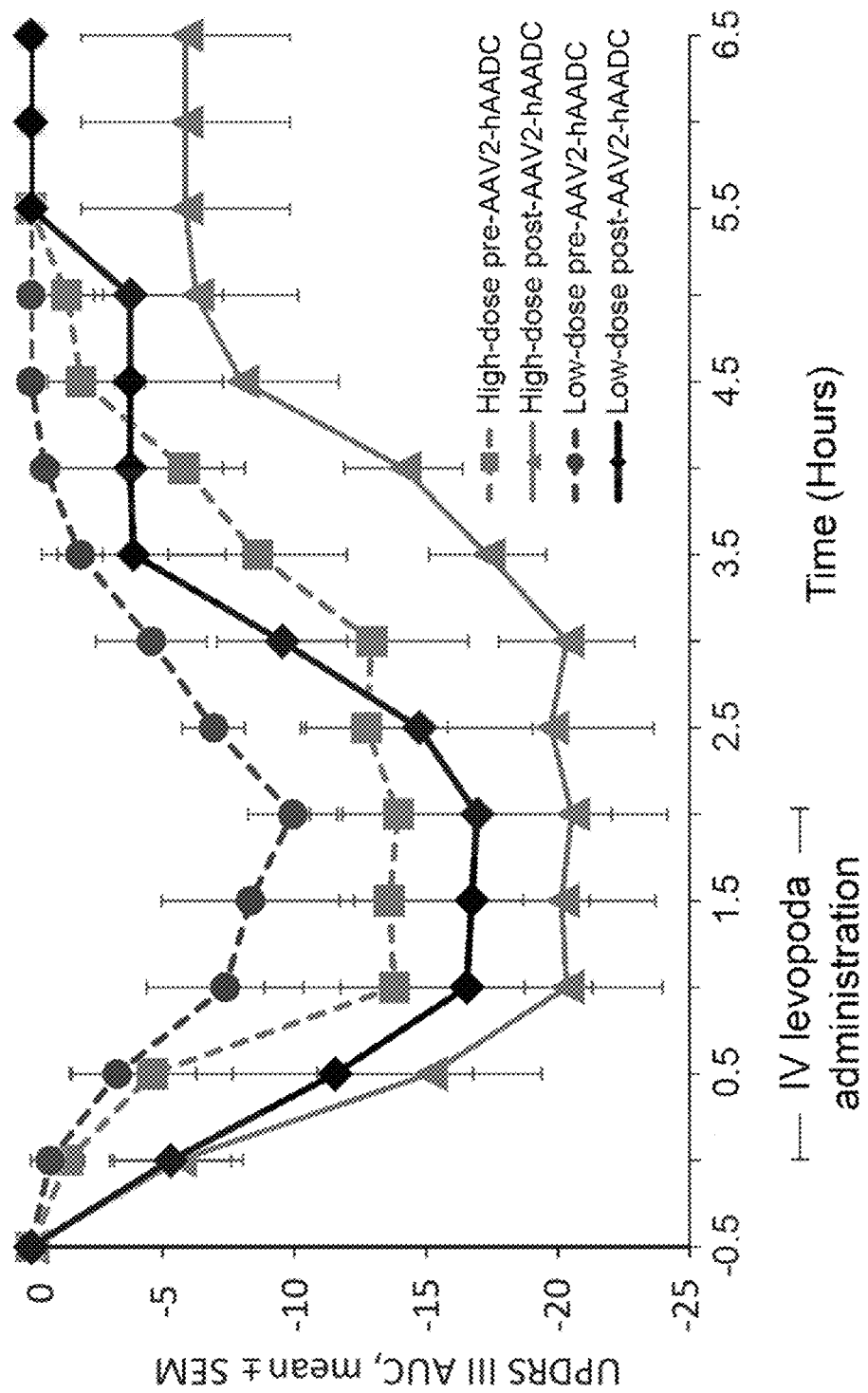
FIG. 12b shows UPDRS III AUC scores after IV Levodopa administration up to $1.5\times10^{12}$ vg, corresponding with certain embodiments of the present disclosure.

Across the three patient groups, the duration and magnitude of change in response to IV levodopa on UPDRS II was analyzed using AUC from the baseline to up to 6.5 hours. Results for Group 1 are shown in FIG. 12a; results for Group 2 are shown in FIG. 12b; and results for Group 3 are shown in FIG. 12c.

For low-dose IV levodopa (threshold), AUC increased by 168% from pre- to 6-months post-AAV2-hAADC administration. For high-dose levodopa (suprathreshold) AUC increased by 67%. Results are summarized in Table 10 (Data are mean (standard error) areas under the curve across subjects, with negative numbers indicating improvement in UPDRS scores).

TABLE 10

UPDRS III AUC Analysis for Threshold and Suprathreshold Infusions of Intravenous Levodopa at Baseline and 6 Months After Administration of AAV2-hAADC

| | | Group 1 $7.5 \times 10^{11}$ vg (N = 5) | Group 2 $1.5 \times 10^{12}$ vg (N = 5) | Group 3 $4.7 \times 10^{12}$ vg (N=3) |
|---|---|---|---|---|
| Threshold (0.6 mg/kg/hr) IV Levodopa | Baseline | −22.1 (9.7) | −21.8 (5.9) | −16.1 (11.4) |
| | Post-AAV2-hAADC | −60.4 (27.5) | −52.0 (19.4) | −51.1 (19.7) |
| Suprathreshold (1.2 mg/kg/hr) IV Levodopa | Baseline | −72.8 (13.1) | −45.0 (13.5) | −41.1 (13.8) |
| | Post-AAV2-hAADC | −111.8 (41.5) | −89.7 (20.4) | −60.7 (25.0) |

Figure 13:
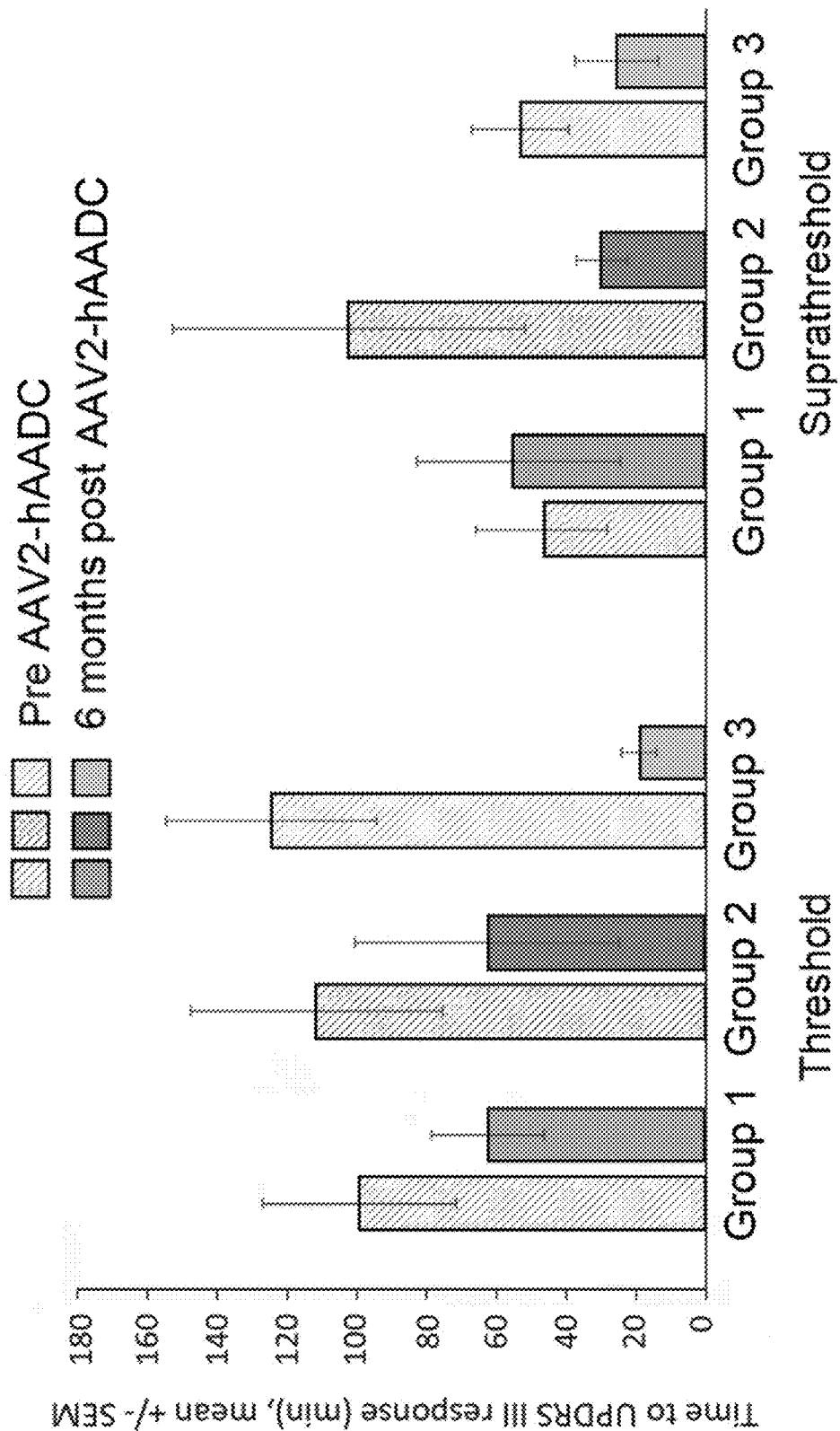
FIG. 13 shows the time (min) to UPDRS III response (≥30% change from pre-dose levels) after IV Levodopa administration, corresponding with certain embodiments of the present disclosure.

The time to onset of response (TOR) to IV levodopa, defined as a ≥30% change from pre-dose, was measured. Results are summarized in Table 11 and shown in FIG. 13. TOR was substantially reduced in both Groups 2 and 3 at both IV levodopa doses. In the low-dose group of Groups 2, the time to onset of response to levodopa is 59 minutes while the time for pre-dose response is 109 minutes. Similarly, in the high-dose group of Group 2, the time to onset of response to levodopa is reduced to 30 minutes from the pre-dose 104 minutes. Similar reductions are observed in Group 3 and low-dose group of Group 1.

TABLE 9

IV Levodopa Dosage Levels

| Group | Total Number of Patients | Maximum Total Dose Administered | Treatment Sequence (number of patients) | | | |
|---|---|---|---|---|---|---|
| | | | LHLH | LHHL | HLHL | HLLH |
| 1 | 5 | $7.5 \times 10^{11}$ vg | 1 | 2 | 0 | 2 |
| 2 | 5 | $1.5 \times 10^{12}$ vg | 1 | 1 | 2 | 1 |
| 3 | 3 | $4.7 \times 10^{12}$ vg | 1 | 1 | 0 | 1 |
| Total | 13 | — | 3 | 4 | 2 | 4 |

TABLE 11

Time (min) to response (UPDRS change from pre-dose >30%)
by levodopa dose and Group (Mean)

|  | Group 1 | | Group 2 | | Group 3 | |
| --- | --- | --- | --- | --- | --- | --- |
|  | Low L-dopa | High L-dopa | Low L-dopa | High L-dopa | Low L-dopa | High L-dopa |
| Pre-dose | 90 | 48 | 109 | 104 | 127 | 53 |
| Post-AADC | 65 | 59 | 59 | 30 | 19 | 36 |

Figure 14:
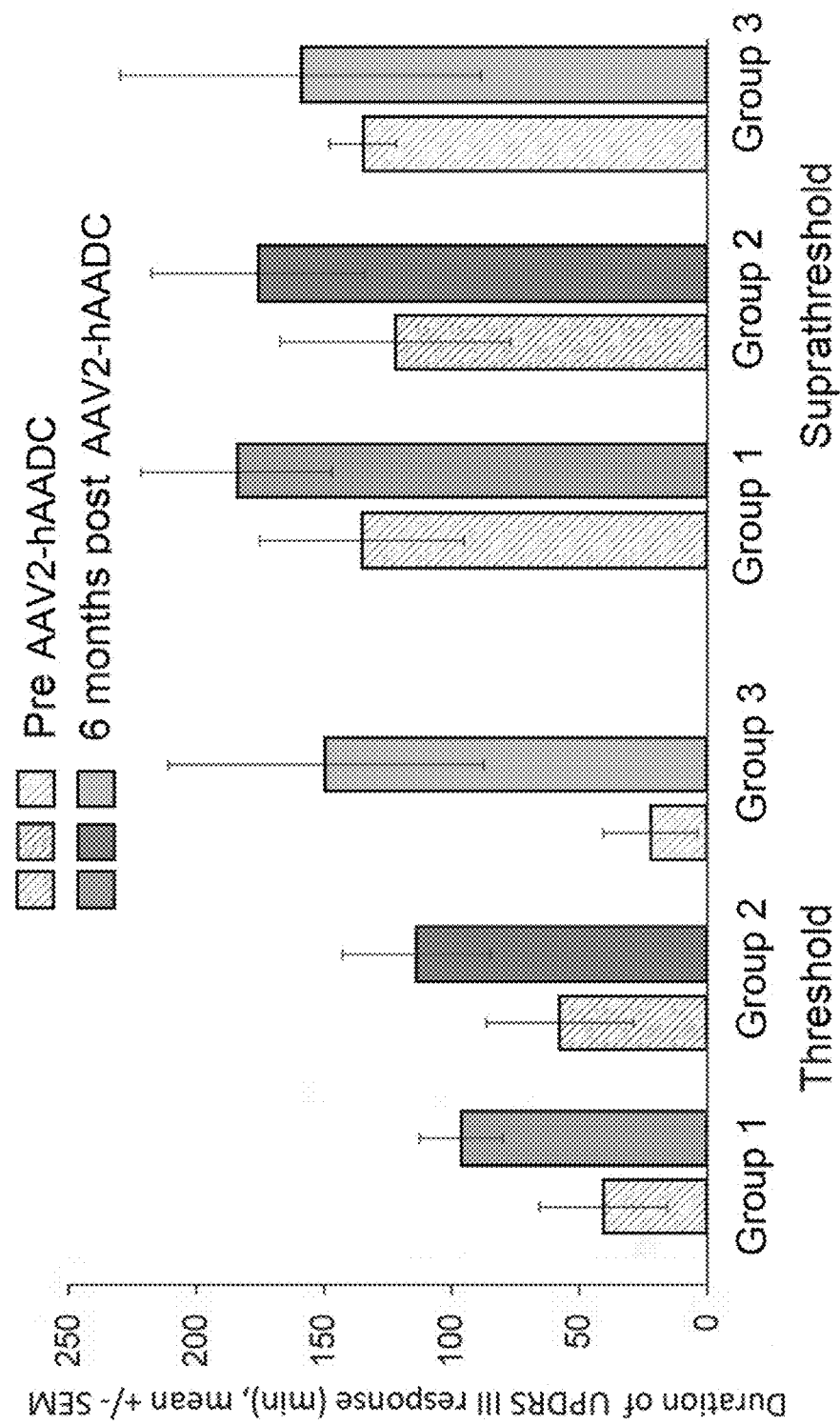
FIG. 14 shows the duration (min) of UPDRS III response (?30% change from pre-dose levels) after IV Levodopa administration, corresponding with certain embodiments of the present disclosure.

The duration of response (DOR) to IV levodopa, defined as maintaining a ≤30% change from pre-dose, was measured. Results are shown in FIG. 14.

Bradykinesia was measured by finger tapping rate. Results are summarized in Table 12.

TABLE 12

Finger Tapping Rate after IV Levodopa

| | Threshold (Low) | | Suprathreshold (High) | |
| --- | --- | --- | --- | --- |
| | Baseline | Post AAV2-BAADC | Baseline | Post AAV2-hAADC |
| AUC, mean (SD) | | | | |
| Group 1 | 20.3 (21.1) | 105.0 (116.0) | 89.8 (72.9) | 217.8 (214.3) |
| Group 2 | 81.5 (80.1) | 161.0 (112.5) | 125.2 (115.0) | 212.7 (113.7) |
| Group 3 | 32.4 (30.9) | 85.0 (79.2) | 60.8 (60.8) | 161.9 (143.8) |
| Peak Response, mean (SD) | | | | |
| Group 1 | 142.4 (22.9) | 165.8 (38.2) | 163.6 (26.1) | 182.6 (39.7) |
| Group 2 | 169.2 (43.1) | 187.4 (47.7) | 173.2 (49.8) | 186.2 (40.8) |
| Group 3 | 140.3 (11.8) | 150.0 (7.9) | 145.3 (5.1) | 156.7 (7.2) |
| Speed of Onset, mean (SD) | | | | |
| Group 1 | 1.2 (8.6) | 6.4 (3.2) | 25.4 (37.8) | 27.8 (23.5) |
| Group 2 | 9.4 (29.7) | 22.6 (24.1) | 14.4 (18.6) | 28.8 (23.6) |
| Group 3 | 0.3 (7.0) | −1.7 (22.5) | 15.7 (23.5) | 7.5 (4.9) |

Dyskinesia was measured by Abnormal Involuntary Movement Scale (AIMS) scoring. Results are summarized in Table 13.

TABLE 13

Finger Tapping Rate after IV Levodopa

| | Threshold (Low) | | Suprathreshold (High) | |
| --- | --- | --- | --- | --- |
| | Baseline | Post AAV2-BAADC | Baseline | Post AAV2-hAADC |
| AUC, mean (SD) | | | | |
| Group 1 | 2.7 (3.2) | 22.5 (14.7) | 9.5 (8.6) | 29.1 (12.1) |
| Group 2 | 7.8 (6.3) | 13.5 (7.3) | 16.6 (7.4) | 27.1 (12.1) |
| Group 3 | 4.0 (6.9) | 12.3 (18.8) | 22.3 (19.6) | 31.0 (37.1) |
| Peak Response, mean (SD) | | | | |
| Group 1 | 2.6 (2.9) | 7.2 (5.4) | 10.4 (4.7) | 11.4 (2.2) |
| Group 2 | 4.8 (3.3) | 7.8 (2.3) | 6.2 (2.2) | 10.2 (4.0) |
| Group 3 | 5.0 (8.7) | 9.3 (9.1) | 7.0 (10.4) | 10.0 (10.6) |
| Speed of Onset, mean (SD) | | | | |
| Group 1 | 0 (0) | 0.8 (1.1) | 3.8 (4.4) | 6.0 (4.2) |
| Group 2 | 1.8 (2.5) | 2.8 (4.4) | 3.0 (4.1) | 5.4 (4.2) |
| Group 3 | 0.3 (0.6) | 2.7 (3.1) | 1.0 (1.7) | 2.7 (3.1) |

Similar patterns of increased AUC after AADC infusion are seen on measures of bradykinesia and dyskinesia. These data suggest that patients treated with AADC showed a marked shift in the response to IV levodopa after AADC administration across three measures of motor response, including faster onset and longer duration of effect. A dose related effect of AADC on response to IV levodopa is also observed.

Example 7. Posterior Administration of AAV2-hAADC for Parkinson's Disease

A single administration of AAV2-hAADC (vector genome comprising SEQ ID NO: 979 in an AAV2 serotype capsid) was administered 8 patients in Patient Group 4 with advanced Parkinson's Disease and disabling motor fluctuations (Disease duration ≥5 years). AAV2-hAADC is comprised of recombinant AAV2 carrying the complementary deoxyribonucleic acid of the human AADC gene under the control of the cytomegalovirus immediate early promoter as described in Example 1. Study drug was provided in a sterile formulation of phosphate buffered saline with 0.001% Pluronic acid (F-68), in 0.5 mL aliquots at an initial concentration of $4.9 \times 10^{12}$ vg/mL (with an excipient for dilution to the final dosage concentration). The criteria to determine eligibility for participation in the study (including exclusion criteria) are similar the study presented in Example 5. Baseline characteristics for Group 4 and Group 4* (n=4, UDysRS ≤30, no impulse control disorder) are shown in Table 14 (mean values).

TABLE 14

Baseline Characteristics for Group 4

|  | Group 4 | Group 4* |
| --- | --- | --- |
| Age (years) | 56.8 | 58.5 |
| PD Duration (years) | 9.2 | 8.2 |
| UPDRS II OFF | 15.3 | 15.0 |
| UPDRS II ON | 3.5 | 3.0 |
| UPDRS III OFF | 34.9 | 36.3 |
| UPDRS III ON | 11.4 | 13.8 |
| Diary OFF (hours) | 6.8 | 7.2 |
| Diary Good ON (hours) | 9.1 | 8.8 |
| Hoehn & Yahr Stage | Stg 2.5 (4); Stg 3 (4) | Stg 3 (4) |
| UDysR Score | 22.8 | 16.0 |
| LED (mg) | 1500.9 | 1187.9 |

Seven participants received a single administration of AAV2-hAADC vector on Day 0, with a target volume of up to 1800 μL per putamen at a concentration of $2.6 \times 10^{12}$ vg/ml (target total dose of up to $9.4 \times 10^{12}$ vg). Clinical concentrations and dosage levels for Patient Group 4 are summarized in Table 15:

TABLE 15

Group 4 Dosage Levels

| Patient | Average Volume Administered | Concentration | Maximum total dose administered |
|---|---|---|---|
| 100.201 | 715 µL per putamen | $2.6 \times 10^{12}$ vg/ml | $3.72 \times 10^{12}$ vg |
| 100.202 | 500 µL per putamen | $8.3 \times 10^{11}$ vg/ml | $8.30 \times 10^{11}$ vg |
| 200.201 | 1144 µL per putamen | $2.6 \times 10^{12}$ vg/ml | $5.95 \times 10^{12}$ vg |
| 200.202 | 1265 µL per putamen | $2.6 \times 10^{12}$ vg/ml | $6.58 \times 10^{12}$ vg |
| 200.204 | 829 µL per putamen | $2.6 \times 10^{12}$ vg/ml | $4.31 \times 10^{12}$ vg |
| 300.201 | 1240 µL per putamen | $2.6 \times 10^{12}$ vg/ml | $6.45 \times 10^{12}$ vg |
| 400.202 | 1500 µL per putamen | $2.6 \times 10^{12}$ vg/ml | $7.80 \times 10^{12}$ vg |
| 400.203 | 1500 µL per putamen | $2.6 \times 10^{12}$ vg/ml | $7.80 \times 10^{12}$ vg |

As shown in Table 15, Participant 100.202 received a lower vector genome concentration than other participants. This was consistent with the planned procedure and not due to safety reasons. Data for Participant 100.202 was general included in resulting averages, with a "sensitivity analyses" also calculated when appropriate to exclude Participant 100.202.

Figure 15:
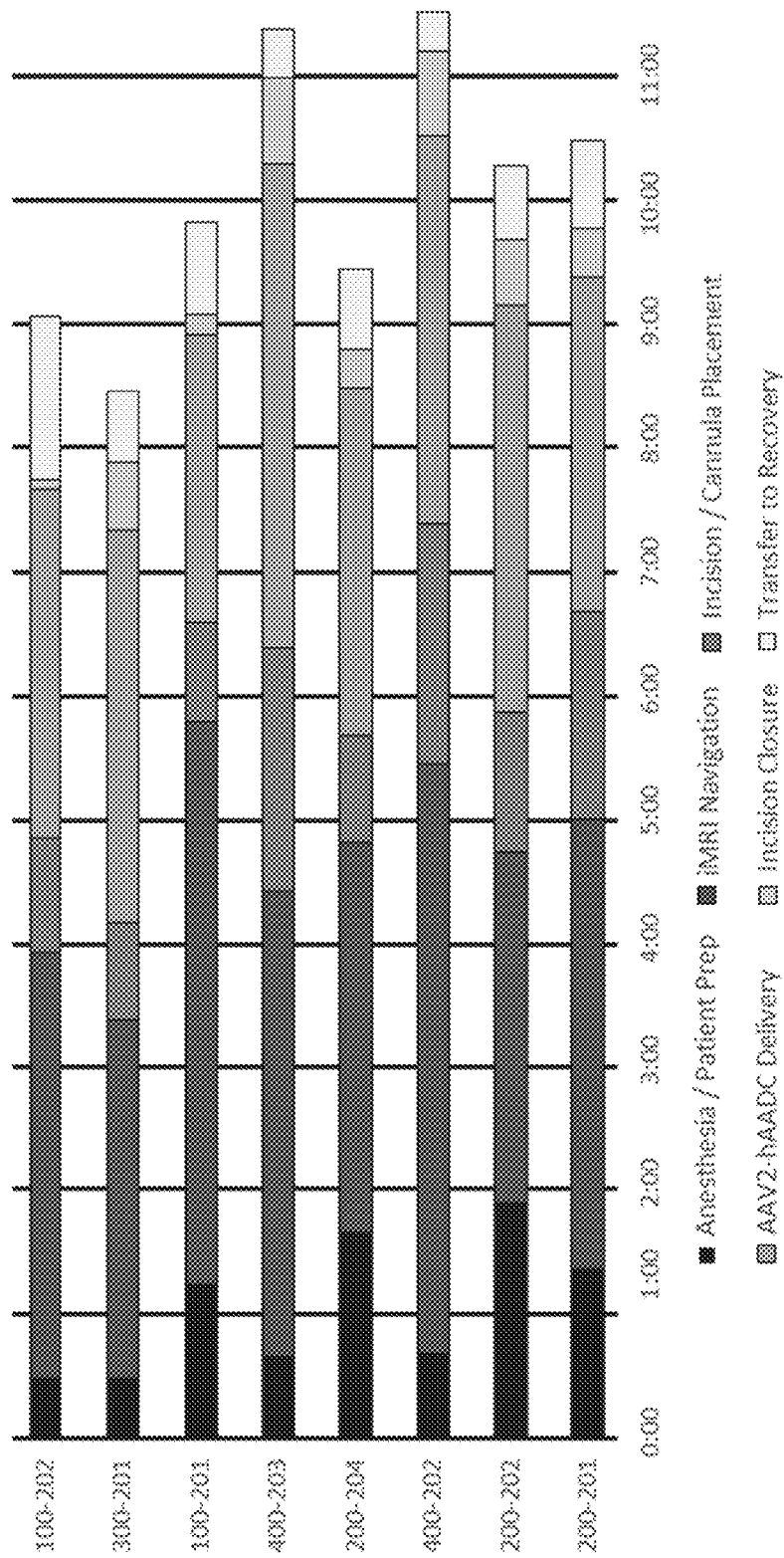
FIG. 15 shows timelines for the delivery of AAV2-hAADC corresponding with certain embodiments of the present disclosure.

Interventional MRI was utilized to monitor intracranial infusion procedures in real time to achieve a targeted delivery of AAV2-hAADC. To enhance MRI visualization of the infusion within the brain, a small quantity of gadoteridol (1-2 mM) was added to the AAV2-hAADC dosing solution immediately prior to administration. The AAV2-hAADC vector was delivered posteriorly (transparietal-occipital approach) to both putamen along the long axis of the putamen (through the posterior tail) in a single surgical setting. The delivery was completed via step-tipped Smart-Flow™ neuro-ventricular injection and aspiration cannula connected to Medfusion 3500 infusion pumps, guided using skull mounted SmartFrames® with the Clearpoint® neuro-navigational system (MRI Interventions, Inc., Irvine, CA). Convection-Enhanced Delivery (CED) was used, with a progressive movement and an increasing infusion rate (1-30 µL/min) to maximize distribution of the vector within the target, and progressive advancement of the cannula tip throughout the CED infusion. The average total time for the delivery procedure (from Anesthesia & Patient Prep to Patient Transfer to Recovery) was about 10 hours (min—8:28; max—11:27). The average times for each step in the delivery procedure are as follows (hour:min): Anesthesia & Patient Prep (1:04); iMRI Navigation (3:37); Incision and Cannula Placement (1:15); AAV2-hAADC Delivery (3:01); Incision Closure (0:25); and Transfer to Recovery (0:39). Timelines for the delivery procedure of each patient are shown in FIG. 15. Average infusion time for Group 4 in Example 7 was about 2 hours less than average infusion time for Groups 1-3 in Example 5.

AAV2-hAADC was well tolerated with no vector-related serious adverse events. Outcomes of treatment were evaluated by various methods, including the determination of vector distribution in the putamen, measurement of AADC expression and activity, changes in Parkinson's Disease medications (levodopa equivalent dose), patient-reported diaries, and a quality of life questionnaire.

AAV2-hAADC was co-infused with gadoteridol to allow visualization of the distribution of the vector. Putaminal coverage was measured on the MR images (MP-RAGE; 3 minute acquisition time) acquired during the convection-enhanced delivery procedure. Calculations were made of the total volume of gadoteridol distribution, percentage of putamen covered by gadoteridol, and percentage of gadoteridol distribution contained within the putamen (iPlan Flow software; Brainlab AG, Munich, Germany). Putamen coverage levels are summarized in Table 16:

TABLE 16

Putamen Coverage Levels

| Patient | Total Putamen Coverage | Posterior Putamen Coverage |
|---|---|---|
| 100.201 | 62.3% | 69.9% |
| 100.202 | 51.1% | 65.9% |
| 200.201 | 53.4% | 67.0% |
| 200.202 | 58.3% | 84.5% |
| 200.204 | 57.4% | 84.9% |
| 300.201 | 57.4% | 84.5% |
| 400.202 | 41.0% | 77.2% |
| 400.203 | 47.1% | 74.2% |

As shown in FIG. 2, average total putaminal coverage for Participant Group 4 was 53.5% (max: 62.3%); and average posterior putaminal coverage was 76.0% (max: 84.9%). Average anterior putaminal coverage was about 30%.

Assessment of AADC expression and activity in the putamen was determined using positron emission tomography (PET) using [$^{18}$F] fluoro-L-dihydroxyphenylalanine (or $^{18}$F-DOPA), which reflects the capacity to convert levodopa to dopamine. Scans were acquired prior to (baseline) and about 2-7 months after infusion, with imaging frames captured 65-75 min after administration of $^{18}$F-DOPA.

$^{18}$F-DOPA PET median standardized uptake value ratios (SOR-1) at baseline were 0.93 (range 0.6 to 1.0) and increased to 1.6 (1.0 to 2.1) following AAV2-hAADC administration (2-7 months), similar F-DOPA uptake to that of healthy adults. This represented a 77% average increase from baseline $^{18}$F-DOPA uptake and was mirrored by a 33% decrease in the need for antiparkinsonian medications. Data from participant 400.202 was shown to include PET artifact attributed to movement during the scan (24.1% change) due to trouble with the analysis of the scan attributed to movement. The remaining participants in Group 4 had an 85% increase from baseline $^{18}$F-DOPA uptake and a 27.8% decrease in the need for antiparkinsonian medications (sustained through 12 months).

Changes in antiparkinsonian medications were allowed in response to increased dyskinesia, other side effects of dopaminergic medications, or reduced need for medication. Antiparkinsonian medications were standardized to levodopa-equivalent doses (LED). Improvements in patient motor function using the posterior trajectory approach were observed with dramatic reductions in patient oral levodopa and equivalent medications, similar to results observed from Groups 2 and 3 in Example 5.

Results are summarized in Table 17 (mean values for entire patient groups).

TABLE 17

Change from Baseline in Levodopa Equivalent Dose (LED) by Patient Group

| | Group 4 (N = 8) | Group 4* (N = 4) |
|---|---|---|
| Baseline | 1500.9 (179.2) | 1187.9 (144.8) |
| 3 Months | −446.2 (100.3) | −457.1 (83.6) |
| 6 Months | −417.1 (92.0) | −240.4 (29.6) |
| 9 Months | −430.5 (86.0) | −244.9 (66.1) |
| 12 Months | −405.4 (116.0) | −157.4 (36.2) |

Treatment with AAV2-hAADC also showed improvement in patient motor function at six months across multiple assessments in a clinically-meaningful manner, including patient self-reported diaries, both on- and off-times and Hauser motor diary on-time without troublesome dyskinesia, Unified Parkinson's Disease Rating Scales, and quality of life measures. Results were consistent with results from Groups 2 and 3 in Example 5.

After administration of the AAV2-hAADC, patients in Group 4 (n=8) experienced an increase in their diary-reported Good ON-Time from a baseline of 9.05 (On-Time without troublesome dyskinesia) (FIG. 6). Group 4 experienced an average improvement (increase) in Good ON-Time over baseline of 2.19 hours at 3 months, 1.82 hours at 6 months, 2.34 at 9 months, and 1.74 hours at 12 months post-administration. Group 4* (n=4) experienced an average improvement (increase) in Good ON-Time over baseline (8.74 hours) of 3.53 hours at 3 months, 3.86 hours at 6 months, 4.49 house at 9 months, and 3.19 hours at 12 months post-administration.

In regards to diary-OFF time, patients in Group 4 (n=8) experienced a decrease in their diary-reported OFF-Time from a baseline of 6.82 house. Group 4 experienced an average improvement (decrease) in OFF time over baseline of 2.52 hours at 3 months, 2.56 hours at 6 months, 3.01 hours at 9 months, and 2.17 hours at 12 months post-administration. Group 4* (n=4) experienced an average improvement (decrease) in OFF time over baseline (7.26) of 3.76 at 3 months, 3.90 hours at 6 months, 4.72 at 9 months, and 3.19 hours at 12 months post-administration.

In regards to UPDRS II scores in the "ON" medication state (n=8), Group 4 had a baseline values of 3.5, and scores were improved from baseline (reduced) by 0.9 at 3 months, 0.0 at 6 months, 1.4 at 9 months and 1.0 at 12 months post-administration. Group 4* (n=4) had a baseline values of 3.0, and scores were improved from baseline (reduced) by 1.5 at 3 months, 1.0 at 6 months, 1.8 at 9 months and 0.8 at 12 months post-administration.

In regards to UPDRS II scores in the "OFF" medication state (n=8), Group 4 had a baseline values of 15.3, and scores were improved from baseline (reduced) by 3.6 at 3 months, 3.8 at 6 months, 3.3 at 9 months and 3.3 at 12 months post-administration. Group 4* (n=4) had a baseline values of 15.0, and scores were improved from baseline (reduced) by 3.0 at 3 months, 4.5 at 6 months, 3.3 at 9 months and 3.5 at 12 months post-administration.

In regards to UPDRS III scores in the "ON" medication state (FIG. 7, n=8), Group 4 had a baseline values of 11.4, and scores were improved from baseline (reduced) by 1.5 at 3 months, 0.5 at 6 months, 0.6 at 9 months and 1.3 at 12 months post-administration. Group 4* (n=4) had a baseline values of 13.8, and scores were improved from baseline (reduced) by 4.0 at 3 months, 2.5 at 6 months, 0.5 at 9 months and 1.5 at 12 months post-administration.

In regards to UPDRS III scores in the "OFF" medication state (FIG. 8, n=8), Group 4 had a baseline values of 34.9, and scores were improved from baseline (reduced) by 8.2 at 3 months, 9.6 at 6 months, 9.5 at 9 months and 9.4 at 12 months post-administration. Group 4* (n=4) had a baseline values of 36.3, and scores were improved from baseline (reduced) by 5.5 at 3 months, 9.5 at 6 months, 9.5 at 9 months and 10.8 at 12 months post-administration.

Patient quality of life was assessed using the patient-reported 39-item Parkinson's Disease Questionnaire (PDQ-39), which is a 39-item questionnaire to measure health related quality of life in Parkinson's Disease patients. Administration with AAV2-hAADC improved (reduced) patients' PDQ-39 score by a mean change from baseline (28.5) of 14.1 at 6 months, 9.6 at 9 months and 7.6 at 12 months post-administration. For Group 4* (n=4), administration with AAV2-hAADC improved (reduced) patients' PDQ-39 score by a mean change from baseline (25.8) of 14.3 at 6 months, 13.4 at 9 months and 12.6 at 12 months post-administration Patient quality of life was assessed using the Clinical Global Impression of Change (CGI-C) scale. Initial CGI-C results are shown in FIG. 11a. At 3 months, 3 patients were "very much improved", 4 patients were "much improved", and 1 patient was "minimally worse". At 6 months, 3 patients were "very much improved", 4 patients were "much improved", and 1 patient was "minimally improved". At 9 months, 3 patients were "very much improved", 3 patients were "much improved", 1 patient was minimally improved, and 1 patient was "no change". At 12 months, 3 patients were "very much improved", 3 patients were "much improved", 1 patient was "no change", and 1 patient was "minimally worse".

Patient quality of life was assessed using the Patient Global Impression of Change (PGI-C) scale. Initial PGI-C results are shown in FIG. 11b. At 3 months, 5 patients were "much improved", 2 patients were "minimally improved", and 1 patient was "no change". At 6 months, 1 patient was "very much improved", 6 patients were "much improved", and 1 patient was "minimally improved". At 9 months, 1 patient was "very much improved" and 7 patients were "much improved". At 12 months, 7 patients were "much improved" and 1 patient was "minimally improved".

Patient improvement under the Modified Hoehn and Yahr (mH&Y) scale was assessed at 3, 6, 9 and 12 months, as compared to baseline values (Table 14). At baseline for Group 4 (n=8), 4 patients were at Stage 3 and 4 patients were at Stage 2.5. At 3 months, 7 patients were at Stage 2 and 1 patient was at Stage 3. At 6 months, 6 patients were at Stage 2 and 2 patients were at Stage 2.5. At 9 months, 7 patients were at Stage 2 and 1 patient was at Stage 2.5. At 12 months, 4 patients were at Stage 2, 3 patients were at Stage 2.5 and 1 patient was at Stage 3. At baseline for Group 4* (n=4), 4 patients were at Stage 3. At 3 months, 3 patients were at Stage 2 and 1 patient was at Stage 3. At 6 months, 2 patients were at Stage 2 and 2 patients were at Stage 2.5. At 9 months, 3 patients were at Stage 2 and 1 patient was at Stage 2.5. At 12 months, 1 patient was at Stage 2, 2 patients were at Stage 2.5 and 1 patient was at Stage 3.

Taken together, these data suggest that iMRI-monitored surgery in combination with posterior administration using progressive CED along the long axis of the putamen allows for the rapid evolution of the neurosurgical delivery of AADC for gene therapy, resulting in reduced surgical time and increased target coverage. This surgical approach resulted in considerably greater distribution within the relatively thin post-commissural region of the putamen, and an ability to progressively advance the tip of the cannula beyond perivascular leakage pathways.

Figure 16:
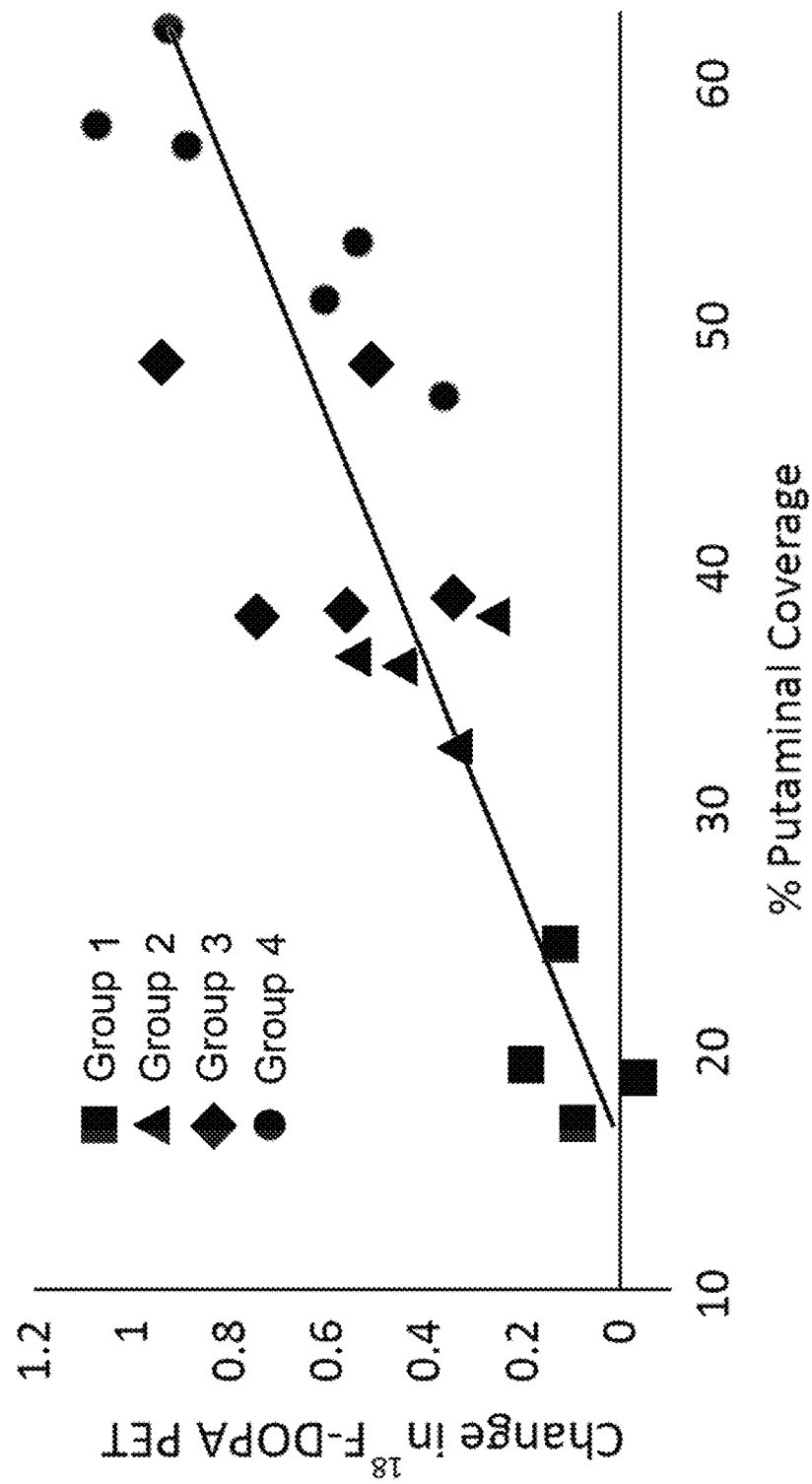
FIG. 16 shows the correlation between $^{18}$F-DOPA uptake and corresponding vector coverage of the putamen of patients, corresponding with certain embodiments of the present disclosure.

Example 8. Correlation Between Increased Vector Coverage and Increase 18F-DOPA Uptake $^{18}$F-DOPA PET median standardized uptake values for Groups 1-4 were correlated with corresponding vector coverage of the putamen of patients in Groups 1-4. Results are shown in FIG. 16. The results show a strong correlation between increased vector coverage and increase $^{18}$F-DOPA uptake.

SEQUENCE LISTING

The patent contains a lengthy sequence listing. A copy of the sequence listing is available in electronic form from the USPTO web site (https://seqdata.uspto.gov/?pageRequest=docDetail&DocID=US12319929B2). An electronic copy of the sequence listing will also be available from the USPTO upon request and payment of the fee set forth in 37 CFR 1.19(b)(3).

We claim:

1. A method of administering a pharmaceutical composition to a subject, the method comprising: administering to the subject the pharmaceutical composition, said pharmaceutical composition comprising an adeno-associated virus (AAV) which comprises an AAV2 capsid and a vector genome, wherein the vector genome comprises a nucleotide sequence which has at least 99% nucleotide sequence identity to SEQ ID NO: 979.

2. The method of claim 1, wherein the nucleotide sequence which has at least 99% nucleotide sequence identity to SEQ ID NO: 979 comprises SEQ ID NO: 980.

3. The method of claim 1, wherein the nucleotide sequence which has at least 99% nucleotide sequence identity to SEQ ID NO: 979 comprises SEQ ID NO: 991.

4. The method of claim 1, wherein the pharmaceutical composition is administered to the subject by posterior surgical infusion into at least one putamen of the subject; and wherein the average total putaminal coverage from the posterior administration is at least 50%.

5. The method of claim 4, wherein the posterior surgical infusion of the pharmaceutical composition is bilateral to both the right putamen and the left putamen of the subject during a single procedure.

6. The method of claim 5, wherein the average total putaminal coverage of the pharmaceutical composition after the posterior surgical infusion is 50-65%.

7. The method of claim 4, wherein surgical time for the posterior surgical infusion is 7-10 hours.

8. The method of claim 4, wherein infusion time for the posterior surgical infusion is 2.5-4.5 hours.

9. The method of claim 1, wherein the pharmaceutical composition is administered to the subject by transfrontal surgical infusion into at least one putamen of the subject; and wherein the average total putaminal coverage from the transfrontal administration is 30-50%.

10. The method of claim 9, wherein the transfrontal surgical infusion of the pharmaceutical composition is bilateral to both the right putamen and the left putamen of the subject during a single procedure.

11. The method of claim 10, wherein the average total putaminal coverage from the transfrontal surgical infusion is 40-50%.

12. The method of claim 1, wherein the pharmaceutical composition comprises an AAV concentration of between $2.0 \times 10^{12}$ vg/ml and $3.0 \times 10^{12}$ vg/ml.

13. The method of claim 1, wherein the pharmaceutical composition comprises an AAV concentration of about $2.6 \times 10^{12}$ vg/ml.

14. The method of claim 1, wherein the pharmaceutical composition is administered at a volume of up to 1800 µL per putamen.

15. The method of claim 1, wherein the pharmaceutical composition is administered at a total viral dosage of $2.0 \times 10^{12}$ vg to $9.4 \times 10^{12}$ vg.

16. The method of claim 1, wherein the pharmaceutical composition is a formulation comprising sodium chloride, sodium phosphate and pluronic acid F-68, and wherein the formulation has a pH between 7.0-7.5.

17. The method of claim 16, wherein the formulation comprises 150-200 mM sodium chloride, 8-12 mM sodium phosphate and 0.001-0.01% w/v pluronic acid F-68, and wherein the formulation has a pH between 7.2-7.4.

18. The method of claim 16, wherein the formulation comprises 180 mM sodium chloride, 10 mM sodium phosphate and 0.001% w/v pluronic acid F-68, and wherein the formulation has a pH of 7.3.

19. A method of treating Parkinson's Disease in a subject, the method comprising: administering to the subject a pharmaceutical composition comprising an adeno-associated virus (AAV) which comprises an AAV2 capsid and a vector genome, wherein the vector genome comprises a nucleotide sequence which has at least 99% nucleotide sequence identity to SEQ ID NO: 979.

* * * * *